United States Patent
Biagetti et al.

(10) Patent No.: US 9,321,776 B2
(45) Date of Patent: Apr. 26, 2016

(54) ISOCHROMENE DERIVATIVES AS PHOSHOINOSITIDE 3-KINASES INHIBITORS

(71) Applicant: CHIESI FARMACEUTICI S.p.A., Parma (IT)

(72) Inventors: Matteo Biagetti, Parma (IT); Anna Maria Capelli, Parma (IT); Alessandro Accetta, Parma (IT); Laura Carzaniga, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 14/573,887

(22) Filed: Dec. 17, 2014

(65) Prior Publication Data

US 2015/0166549 A1    Jun. 18, 2015

(30) Foreign Application Priority Data

Dec. 18, 2013 (EP) ..................... 13197986

(51) Int. Cl.
| | | |
|---|---|---|
| *C07D 487/04* | (2006.01) |
| *C07D 473/38* | (2006.01) |
| *C07D 471/04* | (2006.01) |
| *C07D 495/04* | (2006.01) |
| *C07D 413/14* | (2006.01) |
| *C07D 519/00* | (2006.01) |
| *C07D 473/34* | (2006.01) |
| *C07D 405/12* | (2006.01) |
| *A61K 31/52* | (2006.01) |
| *A61K 45/06* | (2006.01) |
| *A61K 31/506* | (2006.01) |
| *A61K 31/519* | (2006.01) |
| *A61K 31/53* | (2006.01) |
| *A61K 31/5377* | (2006.01) |
| *C07D 417/04* | (2006.01) |
| *C07D 473/16* | (2006.01) |

(52) U.S. Cl.
CPC ............ *C07D 487/04* (2013.01); *A61K 31/506* (2013.01); *A61K 31/519* (2013.01); *A61K 31/52* (2013.01); *A61K 31/53* (2013.01); *A61K 31/5377* (2013.01); *A61K 45/06* (2013.01); *C07D 405/12* (2013.01); *C07D 413/14* (2013.01); *C07D 417/04* (2013.01); *C07D 473/16* (2013.01); *C07D 473/34* (2013.01); *C07D 473/38* (2013.01); *C07D 495/04* (2013.01); *C07D 519/00* (2013.01)

(58) Field of Classification Search
None
See application file for complete search history.

(56) References Cited

FOREIGN PATENT DOCUMENTS

| | | | |
|---|---|---|---|
| EP | 0 585 913 | 3/1994 | |
| JP | 05097841 A | * 4/1993 | ........... C07D 311/76 |
| WO | 2012/151525 | 11/2012 | |

OTHER PUBLICATIONS

Mitra et al., Synthesis and RNase A inhibition study of C2-symmetric bis-isochromenyl sulfones, 2010, Tetrahedron Letters, 51, 2828-2831.*

Extended European Search Report issued in Application No. 13197986.6 issued Sep. 3, 2014.

* cited by examiner

*Primary Examiner* — Kristin Vajda

(74) *Attorney, Agent, or Firm* — Oblon, McClelland, Maier & Neustadt, L.L.P.

(57) ABSTRACT

Compounds of formula (I) described herein are useful for inhibiting phoshoinositide 3-kinases (PI3K) and the treatment of disorders associated with PI3K enzymes.

20 Claims, No Drawings

ISOCHROMENE DERIVATIVES AS PHOSHOINOSITIDE 3-KINASES INHIBITORS

CROSS REFERENCES TO RELATED APPLICATIONS

This application claims priority to European Patent Application No. 13197986.6 filed on Dec. 18, 2013, which is incorporated herein by reference in its entirety.

BACKGROUND OF THE INVENTION

1. Field of the Invention

The present invention relates to compounds inhibiting phosphoinositide 3-kinases (hereinafter PI3K). In particular, the present invention relates to compounds that are isochromene derivatives, methods of preparing such compounds, pharmaceutical compositions containing them and therapeutic use thereof. More particularly, the compounds of the present invention are inhibitors of the activity or function of the Class I of PI3K and more specifically, they are inhibitors of the activity or function of PI3Kα, PI3Kβ, PI3Kδ and/or PI3Kγ isoforms of the Class I PI3K.

Therefore, the compounds of the present invention may be useful in the treatment of many disorders associated with PI3K enzymes mechanisms, such as respiratory diseases including asthma, chronic obstructive pulmonary disease (COPD) and cough; allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; cystic fibrosis; neurodegenerative diseases; pancreatitis; multiorgan failure; kidney diseases; platelet aggregation; cancer; sperm motility; organ transplantation and in particular in transplant rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain, trigeminal neuralgia, and central pain.

2. Discussion of the Background

In biochemistry, a kinase is a type of enzyme that transfers phosphate groups from high-energy donor molecules, such as ATP, to specific substrates, a process referred to as phosphorylation. Specifically, PI3K enzymes are lipid enzyme kinases that can phosphorylate phosphoinositides (PIs) at the 3'-hydroxyl group of the inositol ring (Panayotou et al, Trends Cell Biol 2:358-60 (1992) which is incorporated herein by reference in its entirety). It is well known that PIs, localised in the plasma membranes, can act as second messengers in signaling cascades by docking proteins containing pleckstrin-homology (PH), FYVE, PX and other phospholipid-binding domains (Vanhaesebroeck B et al, Annu. Rev. Biochem 70, 535-602, 2001; Katso R et al, Annu. Rev. Cell Dev. Biol. 17, 615-675, 2001, which are incorporated herein by reference in their entireties).

Therefore, PIs can act as second messengers in many cellular processes including signal transduction, regulation of membrane trafficking and transport, cytoskeleton organization, cell survival and death, and many other functions.

PIs may be bound to the lipid bilayer of the cell membrane via two fatty acids that are attached to the cytosolic inositol ring via a glycerol phosphate linker. PIs inositol ring can be phosphorylated by PI3K enzymes, leading to the regulation of cellular growth, survival and proliferation. For this reason, PIs phosphorylation by PI3K enzymes is one of the most relevant signal transduction events associated with mammalian cell surface receptor activation (Cantley L C, Science 296, 1655-7, 2002; Vanhaesebroeck B et al, Annu. Rev. Biochem 70, 535-602, 2001, which are incorporated herein by reference in their entireties).

The PI3K enzymes have been divided into three classes: Class I PI3K, Class II PI3K and Class III PI3K, on the basis of sequence homology, structure, binding partners, mode of activation, and substrate preference (Vanhaesebroeck B et al, Exp. Cell Res. 253(1), 239-54, 1999; and Leslie N R et al, Chem. Rev. 101(8), 2365-80, 2001, which are incorporated herein by reference in their entireties).

Class I PI3K convert phosphoinositide-(4,5)-diphosphate (PI(4,5)P2) to phosphoinositide-(3,4,5)-triphosphate (PI(3,4,5)P3), which functions as a second messenger. The signaling cascade activated by the increase in intracellular levels of PI(3,4,5)P3 is negatively regulated through the action of 5'-specific and 3'-specific phosphatases (Vanhaesebroeck B et al., Trends Biochem. Sci. 22(7), 267-72, 1997; Katso R et al, Annu. Rev. Cell Dev. Biol. 17, 615-75, 2001; and Toker A, Cell. Mol. Life. Sci. 59(5), 761-79, 2002, which are incorporated herein by reference in their entireties).

Class II PI3K enzymes are the most recently identified class of PI3K and their exact function is still unclear.

Class III PI3K enzymes consists of a single family member which is structurally related to Class I PI3K enzymes and appears to be important in endocytosis and vescicular trafficking. However, there are some evidences showing that Class III PI3K may be relevant in immune cell processes, such as phagocytosis and Toll-like receptor (TLR) signalling.

Class I PI3K enzymes can be further divided in class IA and class IB on the basis of their activation mechanisms.

In more detail, Class IA PI3K enzymes comprise three closely related isoforms: PI3Kα, PI3Kβ and PI3Kδ, while Class IB comprises only the PI3Kγ isoform. These enzymes are heterodimers composed of a catalytic subunit known as p110, with four types: alpha (α), beta (β), delta (δ) and gamma (γ) isoforms, constitutively associated with a regulatory subunit. The first two p110 isoforms (α and β) are ubiquitously expressed and involved in cellular differentiation and proliferation. Consequently, PI3Kα and PI3Kβ enzymes have been extensively studied as targets for the development of new chemotherapeutic agents.

Otherwise, p110δ and p110γ isoforms are mainly expressed in leukocytes and are important in the activation of the immune response, such as leukocytes migration, B and T cells activation and mast cells degranulation. Therefore, PI3Kδ and PI3Kγ isoforms are very relevant in inflammatory respiratory diseases.

Presently, the inhibitors derivatives of PI3K enzymes known in the art could generally inhibit said isoforms (alpha α, beta β, delta δ and gamma γ isoforms) and they could act on the individual roles played in various diseases by said specific isoforms.

Therefore, specific activity assays of Class IA inhibitors for one specific PI3Kα, PI3Kβ, PI3Kδ and PI3Kγ isoform over another have been extensively developed in order to discern the suitable profile for the treatment of disorders associated with PI3K enzymes mechanisms. Such disorders could, for example, include respiratory diseases selected from idiopathic chronic cough, cough-variant asthma, cough associated with thoracic tumour or lung cancer, viral or postviral cough, upper airways cough syndrome (UACS) or post nasal drip cough, or cough associated with gastro-oesophageal reflux disease both acid and non acid, asthma, chronic bronchitis, chronic obstructive pulmonary disease (COPD), interstitial lung disease, idiopathic pulmonary fibrosis (IPF), congestive heart disease, sarcoidosis, infections (such as whooping cough), viral infections including viral respiratory tract infections and viral exacerbation of respiratory diseases; non-viral respiratory infections including aspergillosis and leishmaniasis; allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and central pain.

In view of the number of pathological responses which are mediated by PI3K enzymes, there is a continuing need for inhibitors of PI3K enzymes which can be useful in the treatment of many disorders. Thus, the present invention relates to novel compounds which are inhibitors of PI3Kα, PI3Kβ, PI3Kδ and PI3Kγ isoforms of Class I PI3K enzymes that, for the above reasons, may often have therapeutically desirable characteristics.

Particularly, compounds of the invention may have much more selectivity for the δ isoform or for both the γ and the δ isoforms of PI3K enzyme over other isoforms of the same enzyme.

SUMMARY OF THE INVENTION

Accordingly, it is one object of the present invention to provide novel compounds which inhibit phosphoinositide 3-kinases (hereinafter PI3K).

It is another object of the present invention to provide novel compounds which inhibit phosphoinositide 3-kinases (hereinafter PI3K) and are isochromene derivatives.

It is another object of the present invention to provide novel compounds which are inhibitors of the activity or function of the Class I of PI3K and more specifically, the activity or function of PI3Kα, PI3Kβ, PI3Kδ and/or PI3Kγ isoforms of the Class I PI3K.

It is another object of the present invention to provide novel methods of preparing such compounds.

It is another object of the present invention to provide novel pharmaceutical compositions which contain such a compound.

It is another object of the present invention to provide novel methods of preventing and/or treating certain diseases and conditions by administering such a compound.

These and other objects, which will become apparent during the following detailed description, have been achieved by the inventors' discovery of the compounds of formula (I):

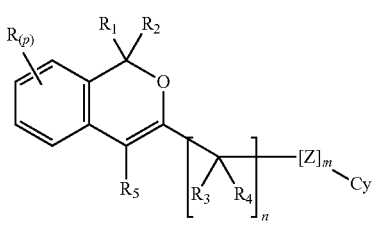

(I)

wherein R, $R_1$, $R_2$, $R_3$, $R_4$, $R_5$, CY, Z, m, n and p are as defined below in the Detailed Description of the Preferred Embodiments, acting as inhibitors of phosphoinositide 3-kinases, to processes for the preparation thereof, pharmaceutical compositions comprising them either alone or in combination with one or more active ingredient, in admixture with one or more pharmaceutically acceptable carrier.

The present invention further provides a suitable device for the delivery of a pharmaceutical composition of a compound of the invention.

In one aspect the present invention provides the use of a compound of the present invention for the manufacture of a medicament.

In a further aspect the present invention provides the use of a compound of the present invention for the preparation of a medicament for the prevention and/or treatment of any disease characterized by phosphoinositide-3-kinase (PI3K) enzyme overactivity and/or wherein an inhibition of PI3K activity is desirable and in particular through the selective inhibition of the delta or of both the delta and the gamma enzyme isoforms over the alfa and beta ones.

Moreover the present invention provides a method for prevention and/or treatment of any disease wherein a PI3K enzyme inhibition is desirable, said method comprises administering to a patient in need of such treatment a therapeutically effective amount of a compound of the present invention.

In particular the compounds of the present invention alone or combined with other active ingredients may be administered for the prevention and/or treatment of a disease of the respiratory tract characterized by inflammatory airway obstruction such as, for example, cough, asthma, COPD and IPF.

It will be apparent to those skilled in the art that the compounds according to the invention might be also represented by the following general formula (I"):

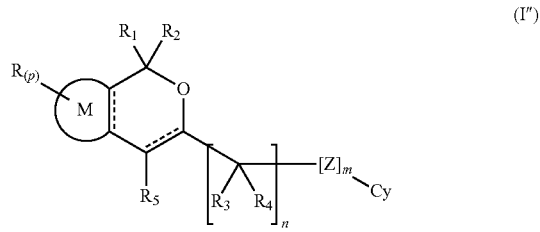

(I")

wherein R, $R_1$, $R_2$, $R_3$, $R_4$, $R_5$, CY, Z, m, n and p are as reported below in the Detailed Description of the Preferred Embodiments, the bond ----- is a double bond and the M residue is an arylene-diyl residue specifically a 1,2-phenylene-diyl radical. Alternative values of the M residue might be 3,4-, 2,3-, or 4,5-thiophene-diyl, 4,5-thiazolediyl; their saturated or partially unsaturated analogues and the like.

Compounds having such alternative values of the M residue are e.g. 5-(1-(4-amino-3-(3-fluoro-5-hydroxyphenyl)-1H-pyrazolo[3,4-d]pyrimidin-1-yl)ethyl)-4-phenyl-7H-thieno[2,3-c]pyran-7-one; 6-(1-(4-amino-3-(3-fluoro-5-hydroxyphenyl)-1H-pyrazolo[3,4-d]pyrimidin-1-yl)ethyl)-7-phenyl-4H-thieno[3,2-c]pyran-4-one; 6-(1-(4-amino-3-(3-fluoro-5-hydroxyphenyl)-1H-pyrazolo[3,4-d]pyrimidin-1-yl)ethyl)-7-phenyl-4H-pyrano[3,4-d]thiazol-4-one;

Hereinbelow in the description of the synthetic routes for the preparation of the compounds according to the present invention (schemes 1 to 9), the M residue will be represented as in the above formula (I"), wherein M is meant to be a 1,2-phenylene-diyl radical.

DETAILED DESCRIPTION OF THE PREFERRED EMBODIMENTS

The invention is directed to a class of compounds acting as inhibitors of Phosphoinositide 3 Kinases (PI3K).

Said class of compounds inhibits the activity or function of the Class I of PI3K and more specifically, they are inhibitors derivatives of the activity or function of PI3Kα, PI3Kβ, PI3Kγ, and/or PI3Kδ isoforms of the Class I PI3K.

The present invention relates to compounds of formula (I):

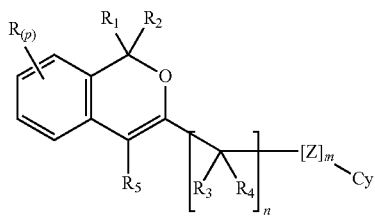

wherein:
each R, when present, is independently selected from the group consisting of:
  $OR_6$;
  $SR_6$
  $S(O)_q-R_8$
  $NR_{10}R_{11}$
  halogen
  $(C_1-C_6)$alkyl;
  $(C_1-C_6)$haloalkyl;
  $(C_3-C_7)$cycloalkyl;
  $(C_5-C_7)$cycloalkenyl;
  $(C_2-C_6)$alkenyl;
  $(C_2-C_6)$alkynyl;
  substituted or unsubstituted aryl; and
  substituted or unsubstituted heteroaryl;
$R_1$ and $R_2$ are both H or are combined to form an oxo group (=O);
$R_3$ and $R_4$ are the same or different and at each occurrence are independently selected from the group consisting of:
  H;
  $(C_1-C_6)$alkyl; and
  $(C_1-C_6)$haloalkyl;
$R_5$ is selected from the group consisting of:
  H;
  $OR_7$;
  $SR_7$
  $S(O)_q-R_9$
  halogen;
  $NR_{12}R_{13}$
  CN;
  $C(O)NR_{12}R_{13}$
  $COOR_{14}$
  $(C_1-C_6)$alkyl;
  $(C_1-C_6)$haloalkyl;
  $(C_1-C_6)$hydroxyalkyl;
  $(C_1-C_6)$aminoalkyl;
  $(C_3-C_7)$cycloalkyl;
  aryl $(C_1-C_3)$alkyl;
  $(C_5-C_7)$cycloalkenyl;
  $(C_2-C_6)$alkenyl;
  $(C_2-C_6)$alkynyl;
  $(C_2-C_6)$aminoalkynyl
  substituted or unsubstituted $(C_3-C_6)$heterocycloalkyl
  substituted or unsubstituted aryl; and
  substituted or unsubstituted heteroaryl;
$R_6$, $R_7$ and $R_{14}$ are the same or different and are at each occurrence independently selected from the group consisting of:
  H;
  $(C_1-C_6)$alkyl;
  $(C_1-C_6)$haloalkyl;
  $(C_1-C_6)$hydroxyalkyl;
  $(C_1-C_6)$aminoalkyl;
  aryl$(C_1-C_6)$alkyl
  $(C_1-C_6)$alkanoyl
  arylcarbonyl; and
  aryl $(C_2-C_4)$alkanoyl
$R_8$ and R are the same or different and are at each occurrence independently selected from the group consisting of
  $(C_1-C_6)$alkyl;
  $(C_1-C_6)$haloalkyl;
  $(C_1-C_6)$hydroxyalkyl;
  $(C_1-C_6)$aminoalkyl;
  substituted or unsubstituted aryl;
  substituted or unsubstituted heteroaryl; and
  $NR_{12}R_{13}$
$R_{10}$, $R_{11}$, $R_{12}$ and $R_{13}$ are the same or different and are at each occurrence independently selected from the group consisting of H, $(C_1-C_6)$aminoalkyl, $(C_1-C_6)$hydroxyalkyl, and $(C_1-C_6)$alkyl, or taken together with the nitrogen atom they are linked to, either $R_{10}$ and $R_{11}$ or $R_{12}$ and $R_{13}$ may form, a 5 to 6 membered heterocyclic radical;
Z, when present, is an atom or a group each time independently selected from the group consisting of O, NH, C(O), NHC(O), C(O)NH, S, S(O), and $S(O)_2$;
m is zero or 1;
n is 1 or 2;
p is zero or an integer ranging from 1 to 3;
q is 1 or 2; and
Cy is selected from the group consisting of:
  substituted or unsubstituted $(C_3-C_6)$heterocycloalkyl group;
  substituted or unsubstituted aryl; and
  substituted or unsubstituted heteroaryl,
or pharmaceutically acceptable salts thereof.

The term "pharmaceutically acceptable salts", as used herein, refers to derivatives of compounds of formula (I) wherein the parent compound is suitably modified by converting any of the free acid or basic group, if present, into the corresponding addition salt with any base or acid conventionally intended as being pharmaceutically acceptable. Suitable examples of said salts may thus include mineral or organic acid addition salts of basic residues such as amino groups, as well as mineral or organic basic addition salts of acid residues such as carboxylic groups.

Cations of inorganic bases which can be suitably used to prepare salts within the invention comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, methane sulfonic acid, camphor sulfonic acid, acetic acid, oxalic acid, maleic acid, fumaric acid, succinic acid and citric acid.

Definitions

The term "halogen atoms" as used herein includes fluorine, chlorine, bromine, and iodine, preferably chlorine or fluorine.

The term "$(C_1\text{-}C_x)$alkyl" where x is an integer greater than 1, refers to straight-chained or branched-chained alkyl groups wherein the number of constituent carbon atoms is in the range 1 to x. Particularly preferred alkyl groups are methyl, ethyl, n-propyl, isopropyl and tert-butyl.

The expressions "$(C_1\text{-}C_x)$haloalkyl" refer to the above defined "$(C_1\text{-}C_x)$alkyl" groups wherein one or more hydrogen atoms are replaced by one or more halogen atoms, which can be the same or different from each other. Examples of said $(C_1\text{-}C_x)$haloalkyl groups may thus include halogenated, polyhalogenated and fully halogenated alkyl groups, e.g. trifluoromethyl or difluoro methyl groups.

By way of analogy, the terms "$(C_1\text{-}C_x)$hydroxyalkyl" or "$(C_1\text{-}C_x)$aminoalkyl" refer to the above defined "$(C_1\text{-}C_x)$alkyl" groups wherein one or more hydrogen atoms are replaced by one or more hydroxy (OH) or amino group respectively.

In the present invention, unless otherwise provided, the definition of aminoalkyl encompasses alkyl groups substituted by one or more ($NR_{10}R_{11}$).

With reference to the substituent $R_{10}$, $R_{11}$, $R_{12}$ and $R_{13}$ as above defined, it is here further explained that when either $R_{10}$ and $R_{11}$ or $R_{12}$ and $R_{13}$ are taken together with the nitrogen atom they are linked to form a 5 to 6 membered heterocyclic radical, at least one further ring carbon atom in the said heterocyclic radical may be replaced by at least one heteroatom or hetero-group (e.g. N, NH, S or O) or may bear an -oxo (=O) substituent group. The said heterocyclic radical might be further optionally substituted on the available points in the ring, namely on a carbon atom, or on a heteroatom or heterogroup available for substitution. Thus, Examples of said heterocycle radicals are 1-pyrrolidinyl, 1-piperidinyl, 1-piperazinyl, 4-morpholinyl, piperazin-4-yl-2-one, 4-methylpiperazine-1-yl.

The term "$(C_3\text{-}C_y)$cycloalkyl", where y is an integer greater than 3, refers to saturated cyclic hydrocarbon groups containing from 3 to y ring carbon atoms. Non-limiting examples include cyclopropyl, cyclobutyl, cyclopentyl, cyclohexyl and cycloheptyl.

The term "aryl$(C_1\text{-}C_x)$alkyl" refers to an aryl ring linked to a straight-chained or branched alkyl groups wherein the number of constituent carbon atoms is in the range 1 to x, e.g. phenylmethyl, phenylethyl or phenylpropyl.

The derived expression "$(C_3\text{-}C_z)$heterocycloalkyl" refers to saturated or partially unsaturated monocyclic $(C_3\text{-}C_z)$cycloalkyl groups, wherein z is an integer greater than 3 in which at least one ring carbon atom is replaced by at least one heteroatom or hetero-group (e.g. N, NH, S or O). Non-limiting examples of $(C_3\text{-}C_z)$heterocycloalkyl are represented by: pyrrolidinyl, imidazolidinyl, thiazolidinyl, piperazinyl, piperidinyl, morpholinyl, thiomorpholinyl, dihydro- or tetrahydro-pyridinyl, tetrahydropyranyl, pyranyl, 2H- or 4H-pyranyl, dihydro- or tetrahydrofuranyl, 1,3-dioxolan-2-yl radicals and the like. $(C_3\text{-}C_z)$heterocycloalkyl groups, as above defined, might be optionally further substituted on the available points in the ring, namely on a carbon atom, or on an heteroatom or hetero-group available for substitution. For example, tetrahydro-pyridinyl groups, when further substituted, might be substituted on the —NH group such as in the following examples: 1-benzyl-1,2,3,6-tetrahydropyridin-4-yl, 1-(cyclopropylmethyl)-1,2,3,6-tetrahydropyridin-4-yl, 1-acetyl-1,2,3,6-tetrahydropyridin-4-yl, and 1-(pyridin-4-ylmethyl)-1,2,3,6-tetrahydropyridin-4-yl.

The term "$(C_2\text{-}C_x)$alkenyl" refers to straight or branched, conjugated or not conjugated, carbon chains with one or more double bonds, in cis or trans configuration, wherein the number atoms is in the range 2 to x.

By way of analogy, the terms "$(C_5\text{-}C_y)$cycloalkenyl", where y is an integer greater than 5, refers to cyclic hydrocarbon groups containing from 5 to y ring carbon atoms and one or two double bonds, wherein the cycloalkenyl might be further optionally substituted by one or more groups, e.g. by amino groups.

The term "$(C_2\text{-}C_x)$alkynyl" refers to straight or branched carbon chains with one or more triple bonds wherein the number atoms is in the range 2 to x.

By way of analogy, the term "$(C_2\text{-}C_x)$aminoalkynyl" refers to the above defined "$(C_2\text{-}C_x)$alkynyl" groups wherein one or more hydrogen atoms are replaced by one or more amino group and wherein the aminogroup might be further optionally substituted by one or more $(C_1\text{-}C_6)$alkyl groups.

The expression "aryl" refers to mono, bi- or tri-cyclic ring systems which have 5 to 20, preferably from 5 to 15 ring atoms, wherein at least one ring is aromatic.

The expression "heteroaryl" refers to mono-, bi- or tricyclic ring systems with 5 to 20, preferably from 5 to 15 ring atoms, in which at least one ring is aromatic and in which at least one ring atom is a heteroatom or heteroaromatic group (e.g. N, NH, S or O).

Examples of suitable aryl or heteroaryl monocyclic ring systems include, for instance, phenyl, thienyl (herein also named thiophen-yl or thiophene-yl), pyrrolyl, pyrazolyl, imidazolyl, isoxazolyl, oxazolyl, isothiazolyl, thiazolyl, pyridinyl, pyrimidinyl, pyrazinyl, furanyl radicals and the like.

Examples of suitable aryl or heteroaryl bicyclic ring systems include naphthalenyl, biphenylenyl, purinyl, pteridinyl, pyrazolopyrimidinyl, benzotriazolyl, quinolinyl, isoquinolinyl, indolyl, isoindolyl, benzothiophenyl, benzodioxinyl, dihydrobenzodioxinyl, indenyl, dihydro-indenyl, dihydrobenzodioxepinyl, benzooxazinyl radicals and the like.

Examples of suitable aryl or heteroaryl tricyclic ring systems include fluorenyl radicals as well as benzocondensed derivatives of the aforementioned heteroaryl bicyclic ring systems.

The term "$(C_1\text{-}C_x)$alkanoyl", refers to alkylcarbonyl groups (e.g. $(C_1\text{-}C_x)$alkyl(CO) where x is an integer greater than 1) wherein the group "alkyl" has the meaning above defined. Non-limiting examples include acetyl, propanoyl, butanoyl.

The expression "arylcarbonyl" refers to aryl-(CO)— groups wherein the group "aryl" has the meaning above defined. Non-limiting example is represented by benzoyl.

The term "aryl $(C_2\text{-}C_x)$alkanoyl" refers to an aryl$(C_2\text{-}C_x)$ alkylcarbonyl group where x is an integer greater than 2 wherein aryl and alkyl have the meaning above defined. Non-limiting examples are represented by phenylacetyl, phenylpropanoyl or phenylbutanoyl radicals;

By way of analogy the expressions "heteroaryl$(C_1\text{-}C_x)$ alkyl" and "$(C_3\text{-}C_y)$cycloalkyl$(C_1\text{-}C_x)$alkyl" refer to a "$(C_1\text{-}C_x)$alkyl" respectively substituted by one or more heteroaryl or $(C_3\text{-}C_y)$cycloalkyl groups, as defined above.

Examples of e.g. aryl$(C_1\text{-}C_6)$alkyl include phenylmethyl herein also named benzyl. Examples of e.g. heteroaryl$(C_1\text{-}C_6)$alkyl include pyridin-4-ylmethyl. Examples of e.g. $(C_3\text{-}C_7)$cycloalkyl$(C_1\text{-}C_6)$alkyl include cyclopropylmethyl.

As used herein, the expression "ring system" refers to mono- or bicyclic ring systems which may be saturated, partially unsaturated or unsaturated, such as aryl, $(C_3\text{-}C_7)$cycloalkyl, $(C_3\text{-}C_6)$heterocycloalkyl or heteroaryl.

It will be apparent to those skilled in the art that compounds of formula (I) can contain at least one stereogenic center when $R_3$ and $R_4$ are different, namely represented in formula (IA) by the carbon atom (*) with an asterisk, and therefore may exist as optical stereoisomers.

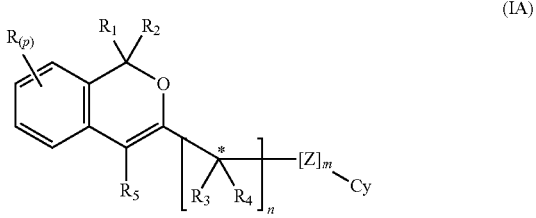

(IA)

Where the compounds according to the present invention have such at least one stereogenic center, they may accordingly exist as enantiomers. Where the compounds according to the invention possess two or more stereogenic centers, they may additionally exist as diastereoisomers. It is to be understood that all such single enantiomers, diastereoisomers and mixtures thereof in any proportion are encompassed within the scope of the present invention. The absolute configuration (R) or (S) for carbon (*), when it is a stereogenic center, is assigned on the basis of Cahn-Ingold-Prelog nomenclature rules based on groups' priorities.

Atropisomers are stereoisomers resulting from hindered rotation about single bonds where the steric strain barrier to rotation is high enough to allow for the isolation of the conformers (Bringmann G et al., Angew. Chemie Int. Ed., 44 (34), 5384-5427, 2005. doi:10.1002/anie.200462661, which is incorporated herein by reference in its entirety).

Oki defined atropisomers as conformers that interconvert with a half-life of more than 1000 seconds at a given temperature (Oki M, Topics in Stereochemistry 14, 1-82, 1983, which is incorporated herein by reference in its entirety).

Atropisomers differ from other chiral compounds in that in many cases they can be equilibrated thermally whereas in the other forms of chirality isomerization is usually only possible chemically.

Separation of atropisomers is possible by chiral resolution methods such as selective crystallization. In an atropo-enantioselective or atroposelective synthesis one atropisomer is formed at the expense of the other. Atroposelective synthesis may be carried out by use of chiral auxiliaries like a Corey Bakshi Shibata (CBS) catalyst, an asymmetric catalyst derived from proline, or by approaches based on thermodynamic equilibration when an isomerization reaction favors one atropisomer over the other.

Racemic forms of compounds of formula (I) as well as the individual atropisomers (substantially free of its corresponding enantiomer) and stereoisomer-enriched atropisomers mixtures are included in the scope of the present invention.

In a preferred embodiment, the present invention is directed to compounds of formula (IA) as above defined wherein n=1, $R_3$ has the same significance as above except H, $R_4$ is H and the absolute configuration of the chiral carbon (*) is (R).

In another embodiment the preferred configuration of the carbon (*) is (S).

In a preferred embodiment, the compounds of formula (I) described in the present invention are present as mixtures of diastereoisomers.

A first preferred group of compounds is that of formula (I) wherein:

$R_1$ and $R_2$ are both H or are combined to form an oxo group (=O);
$R_3$ is selected from H and $(C_1-C_6)$alkyl;
$R_4$ is H;
$R_5$ is selected from H; halogen; $OR_7$; aryl (C1-C3)alkyl; $(C_5-C_7)$cycloalkenyl, $(C_2-C_6)$alkynyl, $(C_2-C_6)$aminoalkynyl, substituted or unsubstituted $(C_3-C_6)$heterocycloalkyl; substituted or unsubstituted aryl and substituted or unsubstituted heteroaryl;
R, $R_7$, m, n, p, Z and CY are as defined above.

A more preferred group of compounds is that of formula (I) wherein:

p is 0 or 1;
R is not present or is selected from the group consisting of halogen and $(C_1-C_6)$alkyl;
$R_1$ and $R_2$ are both H or are combined to form an oxo group (=O);
$R_3$ is selected from H, methyl, ethyl and propyl;
$R_4$ is H;
$R_5$ is selected from H; fluoro; bromo; phenyl; phenylmethyl; 2-, 3- or 4-pyridinyl; 5-thiazolyl; 2-, 3-, 4- or 5-thienyl, 1H-pyrazol-4-yl, 2-, 4-, 5- or 6-pyrimidinyl, cyclohexenyl, prop-1-ynyl, 1,2,3,6-tetrahydropyridin-4-yl, 1,2,5,6-tetrahydropyridin-3-yl, 8-azabicyclo[3.2.1]oct-2-en-3-yl, and 3,6-dihydro-2H-pyran-4-yl, optionally substituted by one or more groups selected from halogen, $(C_1-C_6)$alkyl, $OR_7$, $—S(O)_q—R_9$, $—C(O)NR_{10}R_{11}$, $COOR_{14}$, $(C_1-C_6)$hydroxyalkyl, substituted or unsubstituted $(C_1-C_6)$ aminoalkyl, $(C_1-C_6)$alkanoyl, substituted or unsubstituted $(C_3-C_6)$heterocycloalkyl, aryl$(C_1-C_6)$alkyl, heteroaryl$(C_1-C_6)$alkyl, $(C_3-C_7)$cycloalkyl$(C_1-C_6)$alkyl and $NR_{10}R_{11}$;
$R_7$, $R_9$, $R_{10}$, $R_{11}$, $R_{14}$, m, n, q, Z and CY are as defined above.

An even more preferred group of compounds is that of formula (I) wherein:

p is 0;
R is not present;
$R_1$ and $R_2$ are both H or combined to form an oxo group (=O);
$R_3$ is selected from H, methyl, ethyl and propyl;
$R_4$ is H;
$R_5$ is selected from phenyl; phenylmethyl; 2-, 3- or 4-pyridinyl; 5-thiazolyl, 2-, 3-, 4- or 5-thienyl, 1,2,3,6-tetrahydropyridin-4-yl and 3,6-dihydro-2H-pyran-4-yl, optionally substituted by one or more groups selected from fluoro, bromo, methyl, methoxy, amino, dimethylamino, 4-morpholinosulfonyl, 4-(2-morpholinoethoxy), 4-morpholinomethyl and 4-piperazinomethyl; piperidin-1-ylmethyl, 4-methylpiperazine-1-carbonyl, (2-(dimethylamino)ethyl)-carbonyl, acetyl, phenylmethyl, phenylmethoxy-carbonyl, 4,4,5,5-tetramethyl-1,3-dioxolan-2-yl, pyrrolidin-1-ylmethyl, bis(2-hydroxyethyl)aminomethyl, hydroxymethyl, dimethylaminomethyl, (dimethylamino)propyl, 4-(2-hydroxyethyl)piperazin-1-yl)methyl, piperazin-2-one-1-ylmethyl, cyclopropylmethyl, hydroxycarbonyl, pyridin-4-ylmethyl;
m, n, Z, and CY are as defined above.

A second preferred group of compounds is that of formula (I) wherein:

$R_1$ and $R_2$ are both H or are combined to form an oxo group (=O);
$R_3$ is selected from H, methyl, ethyl and propyl;
$R_4$ is H;
$R_5$ is selected from H; halogen; $OR_7$; aryl $(C_1-C_3)$alkyl; substituted or unsubstituted $(C_3-C_6)$heterocycloalkyl; substituted or unsubstituted aryl and substituted or unsubstituted heteroaryl;

Z, when present, is an atom or a group each time independently selected from O, NH, C(O), NHC(O), C(O)NH, S, S(O) and S(O)$_2$;

CY is an heteroaryl selected from the group of 7H-purin-7-yl; 9H-purin-9-yl; 9H-purin-6-yl; 1H-1-pyrazolo[3,4-d]pyrimidin-1-yl; 1H-pyrazolo[3,4-d]pyrimidin-4-yl; 2H-pyrazolo[3,4-d]pyrimidin-2-yl; 2-, 4-, 5- or 6-pyrimidinyl; and 2-pyrazinyl, pyrrolo[2,3-d]pyrimidin-7-yl, pyrazolo[1,5-a]pyrimidin-3-yl, pyrido[3,2-d]pyrimidin-4-yl, pyrido[2,3-d]pyrimidin-8-yl-5-one, thieno[3,2-d]pyrimidin-4-yl, thieno[2,3-d]pyrimidin-4-yl which are all optionally substituted by one or more groups selected from halogen, $(C_1-C_6)$alkyl, $(C_1-C_6)$haloalkyl, CN, $NR_{10}R_{11}$, optionally substituted aryl and optionally substituted heteroaryl, selected from phenyl, 1H-indazol-4-yl, 1H-indazol-5-yl, 1H-indazol-6-yl, 2-, 3-, 4-, 5-, 6-pyridinyl, 1H-1H-pyrazol-3-yl, pyrazol-4-yl, pyrazol-5-yl, pyrazin-2yl, pyrimidin-5-yl, pyridazin-4-yl and 2-, 4-, 5-thiazolyl;

R, $R_7$, $R_{10}$, $R_{11}$, m, n, p are as defined above

A second more preferred group of compounds is that of formula (I) wherein:

$R_1$ and $R_2$ are combined to form an oxo group (=O);
$R_3$ is selected from H, methyl or ethyl;
$R_4$ is H;
$R_5$ is selected from H; an halogen selected from fluoro and bromo; an aryl which is phenyl; an aryl(C1-C3)alkyl which is phenylmethyl; an heteroaryl selected from 2-, 3- or 4-pyridinyl; 5-thiazolyl, 2-, 3-, 4- or 5-thienyl; a (C3-C6)heterocycloalkyl selected from 1,2,3,6-tetrahydropyridin-4-yl and 3,6-dihydro-2H-pyran-4-yl and 4-cyclohexenyl, which are all optionally substituted by one or more groups selected from fluoro, bromo, methyl, methoxy, dimethylamino, morpholinosulfonyl, morpholinoethoxy, morpholinomethyl and piperazinomethyl; 4-methylpiperazine-1-carbonyl, 4-(2-hydroxyethyl)piperazin-1-yl-methyl, piperazin-2-one-1-yl-methyl, pyridin-4-ylmethyl;

Z, when present, is an atom or a group each time independently selected from O, NH, C(O), NHC(O), C(O)NH, S, S(O) and S(O)$_2$;

CY is a heteroaryl selected from the group of 7H-purin-7-yl; 9H-purin-9-yl; 9H-purin-6-yl; 1H-pyrazolo[3,4-d]pyrimidin-1-yl; 1H-pyrazolo[3,4-d]pyrimidin-4-yl; 2H-pyrazolo[3,4-d]pyrimidin-2-yl; and 2-, 4-, 5- or 6-pyrimidinyl; 2-pyrazinyl which are all optionally substituted by one or more groups selected from Cl, Br, F, I, methyl, trifluoromethyl, CN; NH$_2$; NH—CH$_3$; N(CH$_3$)$_2$; 3-methyl-1H-indazol-5-yl, 1H-indazol-4-yl; 3-fluoro-5-hydroxyphenyl; 1-(3-fluoro-4-hydroxyphenyl); 6-, 5-, 4-hydroxypyridin-3-yl, 6-, 5-methoxypyridin-3-yl, 5-aminopyridin-3-yl, 5-fluoropyridin-3-yl, 5-fluoro-6-hydroxypyridin-3-yl 6-(methylsulfonyl)pyridin-3-yl, 5-hydroxy-6-methylpyridin-3-yl, 6-, 5-(hydroxymethyl)pyridin-3-yl, 2-aminothiazol-5-yl; 2-(acetamino)-(thiazol-5-yl), 2-aminopyrimidin-5-yl, 2-methoxypyrimidin-5-yl, 2-hydroxypyrimidin-5-yl, pyrazin-2-yl, 6-hydroxypyrazin-2-yl and 3-fluoro-4-isopropoxyphenyl;

R, m, n, p are as defined above.

A third more preferred group of compounds is that of formula (I) wherein $R_1$ and $R_2$ are combined to form an oxo group (=O);
$R_3$ is selected from H, methyl or ethyl;
$R_4$ is H;
$R_5$ is selected from substituted or unsubstituted $(C_3-C_6)$ heterocycloalkyl, substituted or unsubstituted aryl; and substituted or unsubstituted heteroaryl; Cy is 1H-pyrazolo[3,4-d]pyrimidin-1-yl, optionally and independently substituted by one or more groups selected from: halogen; —$NR_{12}R_{13}$; $(C_1-C_6)$alkyl, substituted or unsubstituted aryl; and substituted or unsubstituted heteroaryl; or pharmaceutically acceptable salts or solvates thereof.

Even more preferred group of compounds is that of formula (I) wherein $R_1$ and $R_2$ are combined to form an oxo group (=O);
$R_3$ is selected from H, methyl or ethyl;
$R_4$ is H;
$R_5$ is selected from the group of phenyl; 5-thiazolyl; 2-, 3-, 4- or 5-thienyl, 1,2,3,6-tetrahydropyridin-4-yl and 1,2,5,6-tetrahydropyridin-3-yl; optionally substituted by one or more groups selected from $(C_1-C_6)$alkyl, —C(O)$NR_{10}R_{11}$, COOR$_{14}$, substituted or unsubstituted $(C_1-C_6)$aminoalkyl, $(C_1-C_6)$alkanoyl, heteroaryl$(C_1-C_6)$alkyl, $(C_3-C_7)$cycloalkyl $(C_1-C_6)$alkyl and $NR_{10}R_{11}$;

Cy is 1H-pyrazolo[3,4-d]pyrimidin-1-yl, optionally substituted by one or more groups selected independently from halogen; —$NR_{12}R_{13}$, $(C_1-C_6)$alkyl, phenyl and heteroaryl; said phenyl and heteroaryl in their turn further optionally and independently substituted by one or more groups selected from OR$_7$, halogen, —$NR_{12}R_{13}$, —C(O)N $R_{12}R_{13}$, —$NR_7$C (O)$R_9$, $(C_1-C_6)$alkyl, $(C_1-C_6)$-haloalkyl, $(C_1-C_6)$hydroxyalkyl, $R_7$, $R_9$, $R_{10}$, $R_{11}$, $R_{12}$, $R_{13}$, $R_{14}$, m, n, q, and are as defined above or pharmaceutically acceptable salts or solvates thereof A fourth more preferred group of compounds is that of formula (I) wherein $R_1$ and $R_2$ are combined to form an oxo group (=O);
$R_3$ is selected from H, methyl or ethyl;
$R_4$ is H;
$R_5$ is selected from $(C_5-C_7)$cycloalkenyl, $(C_2-C_6)$aminoalkynyl, substituted or unsubstituted $(C_3-C_6)$heterocycloalkyl; substituted or unsubstituted aryl and substituted or unsubstituted heteroaryl;

Cy is 9H-purin-6-yl, optionally substituted by one or more groups independently selected from: halogen; —$NR_{12}R_{13}$; $(C_1-C_6)$alkyl, substituted or unsubstituted aryl; and substituted or unsubstituted heteroaryl;

$R_{12}$, $R_{13}$, m, n, q, and are as defined above;
or pharmaceutically acceptable salts or solvates thereof.

A fifth more preferred group of compounds is that of formula (I) wherein $R_1$ and $R_2$ are combined to form an oxo group (=O);
$R_3$ is selected from H, methyl or ethyl;
$R_4$ is H;
$R_5$ is selected from $(C_5-C_7)$cycloalkenyl, $(C_2-C_6)$aminoalkynyl, substituted or unsubstituted $(C_3-C_6)$heterocycloalkyl; substituted or unsubstituted aryl and substituted or unsubstituted heteroaryl;

Cy is pyrimidin-4-yl, optionally substituted by one or more groups independently selected from: halogen, —$NR_{12}R_{13}$, —CN, $(C_1-C_6)$alkyl, $R_7$, $R_9$, $R_{10}$, $R_{11}$, $R_{12}$, $R_{13}$, $R_{14}$, m, n, q, and are as defined above or pharmaceutically acceptable salts or solvates thereof.

According to specific embodiments, the present invention provides the compounds listed below:

3-(((6-amino-9H-purin-9-yl)methyl)-4-phenyl-1H-isochromen-1-one;
3-(((6-amino-9H-purin-9-yl)methyl)-4-(3-fluorophenyl)-1H-isochromen-1-one;
3-((6-amino-9H-purin-9-yl)methyl)-4-(2-fluorophenyl)-1H-isochromen-1-one;
3-((6-amino-9H-purin-9-yl)methyl)-4-m-tolyl-1H-isochromen-1-one;
3-(1-(6-amino-9H-purin-9-yl)ethyl)-4-phenyl-1H-isochromen-1-one;

3-(1-(6-amino-9H-purin-9-yl)ethyl)-4-m-tolyl-1H-isochromen-1-one;
3-(1-(6-amino-9H-purin-9-yl)ethyl)-4-(3-fluorophenyl)-1H-isochromen-1-one;
3-(1-(6-amino-9H-purin-9-yl)ethyl)-4-(3-(dimethylamino)phenyl)-1H-isochromen-1-one;
3-(1-(6-amino-9H-purin-9-yl)ethyl)-4-(3-(morpholinosulfonyl)phenyl)-1H-isochromen-1-one;
3-((9H-purin-6-ylthio)methyl)-4-phenyl-1H-isochromen-1-one;
3-((9H-purin-6-ylthio)methyl)-4-(2-fluorophenyl)-1H-isochromen-1-one;
3-((9H-purin-6-ylthio)methyl)-4-m-tolyl-1H-isochromen-1-one;
3-(1-(9H-purin-6-ylthio)ethyl)-4-m-tolyl-1H-isochromen-1-one;
3-(1-(9H-purin-6-ylthio)ethyl)-4-(3-fluorophenyl)-1H-isochromen-1-one;
3-(1-(4-amino-1H-pyrazolo[3,4-d]pyrimidin-1-yl)ethyl)-4-(6-methylpyridin-3-yl)-1H-isochromen-1-one;
3-(1-(4-amino-1H-pyrazolo[3,4-d]pyrimidin-1-yl)ethyl)-4-(3-(morpholinosulfonyl)phenyl)-1H-isochromen-1-one;
3-(1-(4-amino-1H-pyrazolo[3,4-d]pyrimidin-1-yl)ethyl)-4-phenyl-1H-isochromen-1-one;
3-(1-(4-amino-1H-pyrazolo[3,4-d]pyrimidin-1-yl)ethyl)-4-(thiazol-5-yl)-1H-isochromen-1-one;
3-(1-(4-amino-1H-pyrazolo[3,4-d]pyrimidin-1-yl)ethyl)-4-(2-methylpyridin-4-yl)-1H-isochromen-1-one;
3-(1-(4-amino-1H-pyrazolo[3,4-d]pyrimidin-1-yl)ethyl)-4-benzyl-1H-isochromen-1-one;
3-((9H-purin-6-ylamino)methyl)-4-(3-fluorophenyl)-1H-isochromen-1-one;
3-(1-(9H-purin-6-ylamino)ethyl)-4-phenyl-1H-isochromen-1-one;
3-(1-(9H-purin-6-ylamino)ethyl)-4-(1,2,3,6-tetrahydropyridin-4-yl)-1H-isochromen-1-one;
3-(1-(9H-purin-6-ylamino)ethyl)-4-(3,6-dihydro-2H-pyran-4-yl)-1H-isochromen-1-one;
3-(1-(9H-purin-6-ylamino)propyl)-4-phenyl-1H-isochromen-1-one;
3-(1-(9H-purin-6-ylamino)ethyl)-4-(4-(2-morpholinoethoxy)phenyl)-1H-isochromen-1-one;
4-amino-8-(1-(1-oxo-4-phenyl-1H-isochromen-3-yl)ethyl)pyrido[2,3-d]pyrimidin-5(8H)-one;
3-(1-(9H-purin-6-ylamino)ethyl)-4-(5-(morpholinomethyl)thiophen-2-yl)-1H-isochromen-1-one;
3-((9H-purin-6-ylamino)methyl)-4-phenyl-1H-isochromen-1-one;
3-((9H-purin-6-ylamino)methyl)-4-(2-fluorophenyl)-1H-isochromen-1-one;
3-((9H-purin-6-ylamino)methyl)-4-m-tolyl-1H-isochromen-1-one;
3-(1-(9H-purin-6-ylamino)ethyl)-4-(3-fluorophenyl)-1H-isochromen-1-one;
3-(1-(9H-purin-6-ylamino)ethyl)-4-m-tolyl-1H-isochromen-1-one;
3-(1-(9H-purin-6-ylamino)ethyl)-4-(3-(dimethylamino)phenyl)-1H-isochromen-1-one;
3-((4-amino-3-(3-fluoro-5-hydroxyphenyl)-1H-pyrazolo[3,4-d]pyrimidin-1-yl)methyl)-4-phenyl-1H-isochromen-1-one;
3-((4-amino-3-(1H-indazol-5-yl)-1H-pyrazolo[3,4-d]pyrimidin-1-yl)methyl)-4-phenyl-1H-isochromen-1-one;
3-((4-amino-3-(3-methyl-1H-indazol-5-yl)-1H-pyrazolo[3,4-d]pyrimidin-1-yl)methyl)-4-phenyl-1H-isochromen-1-one;
3-((4-amino-3-(1H-indazol-6-yl)-1H-pyrazolo[3,4-d]pyrimidin-1-yl)methyl)-4-phenyl-1H-isochromen-1-one;
3-((4-amino-3-(3-fluoro-4-hydroxyphenyl)-1H-pyrazolo[3,4-d]pyrimidin-1-yl)methyl)-4-phenyl-1H-isochromen-1-one;
3-(1-(4-amino-3-(3-fluoro-5-hydroxyphenyl)-1H-pyrazolo[3,4-d]pyrimidin-1-yl)ethyl)-4-phenyl-1H-isochromen-1-one;
3-(1-(4-amino-3-(3-fluoro-5-hydroxyphenyl)-1H-pyrazolo[3,4-d]pyrimidin-1-yl)ethyl)-4-m-tolyl-1H-isochromen-1-one;
3-(1-(4-amino-3-(1H-pyrazol-4-yl)-1H-pyrazolo[3,4-d]pyrimidin-1-yl)ethyl)-4-m-tolyl-1H-isochromen-1-one;
3-(1-(6-amino-9H-purin-9-yl)ethyl)-4-(6-methoxypyridin-3-yl)-1H-isochromen-1-one;
3-((4-amino-3-iodo-1H-pyrazolo[3,4-d]pyrimidin-1-yl)methyl)-4-phenyl-1H-isochromen-1-one;
3-(1-(4-amino-3-iodo-1H-pyrazolo[3,4-d]pyrimidin-1-yl)ethyl)-4-phenyl-1H-isochromen-1-one;
3-(1-(4-amino-3-iodo-1H-pyrazolo[3,4-d]pyrimidin-1-yl)ethyl)-4-m-tolyl-1H-isochromen-1-one;
3-(1-(1H-pyrazolo[3,4-d]pyrimidin-4-ylamino)ethyl)-4-phenyl-1H-isochromen-1-one;
4-amino-6-(1-(1-oxo-4-phenyl-1H-isochromen-3-yl)ethylamino)pyrimidine-5-carbonitrile;
3-(1-(9H-purin-6-ylamino)ethyl)-4-(1-methyl-1,2,3,6-tetrahydropyridin-4-yl)-1H-isochromen-1-one;
3-(1-(4-amino-3-(3-fluoro-5-hydroxyphenyl)-1H-pyrazolo[3,4-d]pyrimidin-1-yl)ethyl)-4-(1-methyl-1,2,3,6-tetrahydropyridin-4-yl)-1H-isochromen-1-one;
3-(1-(4-amino-3-(3-fluoro-5-hydroxyphenyl)-1H-pyrazolo[3,4-d]pyrimidin-1-yl)ethyl)-4-(1-methyl-1,2,3,6-tetrahydropyridin-4-yl)-1H-isochromen-1-one single enantiomer 1;
3-(1-(4-amino-3-(3-fluoro-5-hydroxyphenyl)-1H-pyrazolo[3,4-d]pyrimidin-1-yl)ethyl)-4-(1-methyl-1,2,3,6-tetrahydropyridin-4-yl)-1H-isochromen-1-one single enantiomer 2;
3-(1-(9H-purin-6-ylamino)ethyl)-4-(4-(morpholinomethyl)phenyl)-1H-isochromen-1-one;
3-(1-(4-amino-3-(3-fluoro-5-hydroxyphenyl)-1H-pyrazolo[3,4-d]pyrimidin-1-yl)ethyl)-4-(4-(morpholinomethyl)phenyl)-1H-isochromen-1-one;
3-(1-(4-amino-3-(3-fluoro-5-hydroxyphenyl)-1H-pyrazolo[3,4-d]pyrimidin-1-yl)ethyl)-4-(5-(morpholinomethyl)thiophen-2-yl)-1H-isochromen-1-one;
3-(1-(4-amino-3-(3-fluoro-5-hydroxyphenyl)-1H-pyrazolo[3,4-d]pyrimidin-1-yl)ethyl)-4-(5-(morpholinomethyl)thiophen-2-yl)-1H-isochromen-1-one single enantiomer 1;
3-(1-(4-amino-3-(3-fluoro-5-hydroxyphenyl)-1H-pyrazolo[3,4-d]pyrimidin-1-yl)ethyl)-4-(5-(morpholinomethyl)thiophen-2-yl)-1H-isochromen-1-one single enantiomer 2;
3-(1-(9H-purin-6-ylamino)ethyl)-4-cyclohexenyl-1H-isochromen-1-one;
3-(1-(4-amino-3-(2-aminopyrimidin-5-yl)-1H-pyrazolo[3,4-d]pyrimidin-1-yl)ethyl)-4-phenyl-1H-isochromen-1-one;
3-(1-(4-amino-3-(pyrazin-2-yl)-1H-pyrazolo[3,4-d]pyrimidin-1-yl)ethyl)-4-phenyl-1H-isochromen-1-one;
3-(1-(4-amino-3-(pyridazin-4-yl)-1H-pyrazolo[3,4-d]pyrimidin-1-yl)ethyl)-4-phenyl-1H-isochromen-1-one;
3-(1-(4-amino-3-(pyridin-4-yl)-1H-pyrazolo[3,4-d]pyrimidin-1-yl)ethyl)-4-phenyl-1H-isochromen-1-one;
3-(1-(4-amino-3-(2-methoxypyrimidin-5-yl)-1H-pyrazolo[3,4-d]pyrimidin-1-yl)ethyl)-4-phenyl-1H-isochromen-1-one;

3-(1-(4-amino-3-(2-hydroxypyrimidin-5-yl)-1H-pyrazolo[3,4-d]pyrimidin-1-yl)ethyl)-4-phenyl-1H-isochromen-1-one;

3-(1-(4-amino-3-(5-methoxypyridin-3-yl)-1H-pyrazolo[3,4-d]pyrimidin-1-yl)ethyl)-4-phenyl-1H-isochromen-1-one;

3-(1-(4-amino-3-(pyridin-3-yl)-1H-pyrazolo[3,4-d]pyrimidin-1-yl)ethyl)-4-phenyl-1H-isochromen-1-one;

3-(1-(4-amino-3-(2-aminothiazol-5-yl)-1H-pyrazolo[3,4-d]pyrimidin-1-yl)ethyl)-4-phenyl-1H-isochromen-1-one;

3-(1-(4-amino-3-(6-methoxypyridin-3-yl)-1H-pyrazolo[3,4-d]pyrimidin-1-yl)ethyl)-4-phenyl-1H-isochromen-1-one;

3-(1-(4-amino-3-(6-hydroxypyridin-3-yl)-1H-pyrazolo[3,4-d]pyrimidin-1-yl)ethyl)-4-phenyl-1H-isochromen-1-one;

N-(5-(4-amino-1-(1-(1-oxo-4-phenyl-1H-isochromen-3-yl)ethyl)-1H-pyrazolo[3,4-d]pyrimidin-3-yl)thiazol-2-yl)acetamide;

3-(1-(4-amino-3-(3-fluoro-5-hydroxyphenyl)-1H-pyrazolo[3,4-d]pyrimidin-1-yl)ethyl)-4-(1-methyl-1,2,5,6-tetrahydropyridin-3-yl)-1H-isochromen-1-one;

3-(1-(4-amino-3-(3-fluoro-5-hydroxyphenyl)-1H-pyrazolo[3,4-d]pyrimidin-1-yl)ethyl)-4-(1,2,3,6-tetrahydropyridin-4-yl)-1H-isochromen-1-one;

3-(1-(4-amino-3-(3-fluoro-5-hydroxyphenyl)-1H-pyrazolo[3,4-d]pyrimidin-1-yl)ethyl)-4-(1-(pyridin-4-ylmethyl)-1,2,3,6-tetrahydropyridin-4-yl)-1H-isochromen-1-one;

3-(1-(4-amino-3-(3-fluoro-5-hydroxyphenyl)-1H-pyrazolo[3,4-d]pyrimidin-1-yl)ethyl)-4-(1-(cyclopropylmethyl)-1,2,3,6-tetrahydropyridin-4-yl)-1H-isochromen-1-one;

3-(1-(4-amino-3-(3-fluoro-5-hydroxyphenyl)-1H-pyrazolo[3,4-d]pyrimidin-1-yl)ethyl)-4-(3-((dimethylamino)methyl)phenyl)-1H-isochromen-1-one;

3-(1-(4-amino-3-(3-fluoro-5-hydroxyphenyl)-1H-pyrazolo[3,4-d]pyrimidin-1-yl)ethyl)-4-(3-((dimethylamino)methyl)phenyl)-1H-isochromen-1-one enantiomer 1;

3-(1-(4-amino-3-(3-fluoro-5-hydroxyphenyl)-1H-pyrazolo[3,4-d]pyrimidin-1-yl)ethyl)-4-(3-((dimethylamino)methyl)phenyl)-1H-isochromen-1-one enantiomer 2;

3-(1-(4-amino-3-(3-fluoro-5-hydroxyphenyl)-1H-pyrazolo[3,4-d]pyrimidin-1-yl)ethyl)-4-(5-(piperidin-1-ylmethyl)thiophen-2-yl)-1H-isochromen-1-one;

3-(1-(4-amino-3-(3-fluoro-5-hydroxyphenyl)-1H-pyrazolo[3,4-d]pyrimidin-1-yl)ethyl)-4-(5-(piperidin-1-ylmethyl)thiophen-2-yl)-1H-isochromen-1-one single enantiomer 1;

3-(1-(4-amino-3-(3-fluoro-5-hydroxyphenyl)-1H-pyrazolo[3,4-d]pyrimidin-1-yl)ethyl)-4-(5-(piperidin-1-ylmethyl)thiophen-2-yl)-1H-isochromen-1-one single enantiomer 2;

3-(1-(4-amino-3-(3-fluoro-5-hydroxyphenyl)-1H-pyrazolo[3,4-d]pyrimidin-1-yl)ethyl)-4-(4-(4-methylpiperazine-1-carbonyl)phenyl)-1H-isochromen-1-one;

3-(3-(1-(4-amino-3-(3-fluoro-5-hydroxyphenyl)-1H-pyrazolo[3,4-d]pyrimidin-1-yl)ethyl)-1-oxo-1H-isochromen-4-yl)-N-(2-(dimethylamino)ethyl)benzamide;

4-(1-acetyl-1,2,3,6-tetrahydropyridin-4-yl)-3-(1-(4-amino-3-(5-hydroxypyridin-3-yl)-1H-pyrazolo[3,4-d]pyrimidin-1-yl)ethyl)-1H-isochromen-1-one;

4-(1-acetyl-1,2,3,6-tetrahydropyridin-4-yl)-3-(1-(4-amino-3-(3-fluoro-5-hydroxyphenyl)-1H-pyrazolo[3,4-d]pyrimidin-1-yl)ethyl)-1H-isochromen-1-one;

3-(1-(4-amino-3-(3-fluoro-5-hydroxyphenyl)-1H-pyrazolo[3,4-d]pyrimidin-1-yl)ethyl)-4-(5-(pyrrolidin-1-ylmethyl)thiophen-2-yl)-1H-isochromen-1-one;

3-(1-(4-amino-3-(3-fluoro-5-hydroxyphenyl)-1H-pyrazolo[3,4-d]pyrimidin-1-yl)ethyl)-4-(5-((bis(2-hydroxyethyl)amino)methyl)thiophen-2-yl)-1H-isochromen-1-one;

3-(1-(4-amino-3-(3-fluoro-5-hydroxyphenyl)-1H-pyrazolo[3,4-d]pyrimidin-1-yl)ethyl)-4-(5-(hydroxymethyl)thiophen-2-yl)-1H-isochromen-1-one;

3-(1-(4-amino-3-(3-fluoro-5-hydroxyphenyl)-1H-pyrazolo[3,4-d]pyrimidin-1-yl)ethyl)-4-(5-((4-(2-hydroxyethyl)piperazin-1-yl)methyl)thiophen-2-yl)-1H-isochromen-1-one;

3-(1-(4-amino-3-(3-fluoro-5-hydroxyphenyl)-1H-pyrazolo[3,4-d]pyrimidin-1-yl)ethyl)-4-(5-((4-(2-hydroxyethyl)piperazin-1-yl)methyl)thiophen-2-yl)-1H-isochromen-1-one single enantiomer 1;

3-(1-(4-amino-3-(3-fluoro-5-hydroxyphenyl)-1H-pyrazolo[3,4-d]pyrimidin-1-yl)ethyl)-4-(5-((4-(2-hydroxyethyl)piperazin-1-yl)methyl)thiophen-2-yl)-1H-isochromen-1-one single enantiomer 2;

4-((5-(3-(1-(4-amino-3-(3-fluoro-5-hydroxyphenyl)-1H-pyrazolo[3,4-d]pyrimidin-1-yl)ethyl)-1-oxo-1H-isochromen-4-yl)thiophen-2-yl)methyl)piperazin-2-one;

5-(3-(1-(4-amino-3-(3-fluoro-5-hydroxyphenyl)-1H-pyrazolo[3,4-d]pyrimidin-1-yl)ethyl)-1-oxo-1H-isochromen-4-yl)thiophene-2-carboxylic acid;

3-(1-(4-amino-3-(3-fluoro-5-hydroxyphenyl)-1H-pyrazolo[3,4-d]pyrimidin-1-yl)ethyl)-4-benzyl-1H-isochromen-1-one;

4-(1H-pyrazol-4-yl)-3-(1-(thieno[3,2-d]pyrimidin-4-ylamino)ethyl)-1H-isochromen-1-one 4-(5-(morpholinomethyl)thiophen-2-yl)-3-(1-(thieno[3,2-d]pyrimidin-4-ylamino)ethyl)-1H-isochromen-1-one;

4-amino-6-((1-(4-(5-(morpholinomethyl)thiophen-2-yl)-1-oxo-1H-isochromen-3-yl)ethyl)amino)pyrimidine-5-carbonitrile;

4-phenyl-3-(1-(pyrrolo[2,1-f][1,2,4]triazin-4-ylamino)ethyl)-1H-isochromen-1-one;

4-phenyl-3-(1-(pyrido[3,2-d]pyrimidin-4-ylamino)ethyl)-1H-isochromen-1-one;

3-(1-(4-amino-3-(5-(hydroxymethyl)pyridin-3-yl)-1H-pyrazolo[3,4-d]pyrimidin-1-yl)ethyl)-4-phenyl-1H-isochromen-1-one;

3-(1-(4-amino-3-(6-(hydroxymethyl)pyridin-3-yl)-1H-pyrazolo[3,4-d]pyrimidin-1-yl)ethyl)-4-phenyl-1H-isochromen-1-one;

N-(5-(4-amino-1-(1-(1-oxo-4-phenyl-1H-isochromen-3-yl)ethyl)-1H-pyrazolo[3,4-d]pyrimidin-3-yl)pyridin-3-yl)-4-fluorobenzenesulfonamide;

3-(1-(4-amino-3-(5-aminopyridin-3-yl)-1H-pyrazolo[3,4-d]pyrimidin-1-yl)ethyl)-4-phenyl-1H-isochromen-1-one;

3-(1-(4-amino-3-(2-aminopyrimidin-4-yl)-1H-pyrazolo[3,4-d]pyrimidin-1-yl)ethyl)-4-phenyl-1H-isochromen-1-one;

3-(1-(4-amino-3-(6-hydroxypyrazin-2-yl)-1H-pyrazolo[3,4-d]pyrimidin-1-yl)ethyl)-4-phenyl-1H-isochromen-1-one;

3-(1-(4-amino-3-(5-hydroxypyridin-3-yl)-1H-pyrazolo[3,4-d]pyrimidin-1-yl)ethyl)-4-phenyl-1H-isochromen-1-one;

3-(1-(4-amino-3-(3-fluoro-5-hydroxyphenyl)-1H-pyrazolo[3,4-d]pyrimidin-1-yl)ethyl)-4-(8-methyl-8-azabicyclo[3.2.1]oct-2-en-3-yl)-1H-isochromen-1-one hydrochloride;

3-(1-(4-amino-3-(3-fluoro-4-isopropoxyphenyl)-1H-pyrazolo[3,4-d]pyrimidin-1-yl)ethyl)-4-phenyl-1H-isochromen-1-one;

3-(1-(4-amino-3-(5-fluoropyridin-3-yl)-1H-pyrazolo[3,4-d]pyrimidin-1-yl)ethyl)-4-phenyl-1H-isochromen-1-one;

3-(1-(4-amino-3-(3-chloro-5-fluorophenyl)-1H-pyrazolo[3,4-d]pyrimidin-1-yl)ethyl)-4-phenyl-1H-isochromen-1-one;

3-(1-(4-amino-3-(5-(methylsulfonyl)pyridin-3-yl)-1H-pyrazolo[3,4-d]pyrimidin-1-yl)ethyl)-4-phenyl-1H-isochromen-1-one;

3-(1-(4-amino-3-(6-(methylsulfonyl)pyridin-3-yl)-1H-pyrazolo[3,4-d]pyrimidin-1-yl)ethyl)-4-phenyl-1H-isochromen-1-one;

3-(1-(4-amino-3-(5-fluoro-6-hydroxypyridin-3-yl)-1H-pyrazolo[3,4-d]pyrimidin-1-yl)ethyl)-4-phenyl-1H-isochromen-1-one;

3-(1-(4-amino-3-(5-hydroxy-6-methylpyridin-3-yl)-1H-pyrazolo[3,4-d]pyrimidin-1-yl)ethyl)-4-phenyl-1H-isochromen-1-one;

3-(1-(4-amino-3-(5-(trifluoromethyl)pyridin-3-yl)-1H-pyrazolo[3,4-d]pyrimidin-1-yl)ethyl)-4-phenyl-1H-isochromen-1-one;

3-(1-(4-amino-3-(5-hydroxy-3-sulfur pentafluoride)-1H-pyrazolo[3,4-d]pyrimidin-1-yl)ethyl)-4-phenyl-1H-isochromen-1-one;

5-(4-amino-1-(1-(1-oxo-4-phenyl-1H-isochromen-3-yl)ethyl)-1H-pyrazolo[3,4-d]pyrimidin-3-yl)nicotinonitrile;

3-(1-(4-amino-3-(3-fluoro-5-hydroxyphenyl)-1H-pyrazolo[3,4-d]pyrimidin-1-yl)ethyl)-4-(4-aminocyclohex-1-en-1-yl)-1H-isochromen-1-one;

3-(1-(4-amino-3-(trifluoromethyl)-1H-pyrazolo[3,4-d]pyrimidin-1-yl)ethyl)-4-phenyl-1H-isochromen-1-one;

3-(1-(4-amino-3-methyl-1H-pyrazolo[3,4-d]pyrimidin-1-yl)ethyl)-4-phenyl-1H-isochromen-1-one;

3-(1-(4-amino-7H-pyrrolo[2,3-d]pyrimidin-7-yl)ethyl)-4-phenyl-1H-isochromen-1-one; 3-(1-(2,6-diamino-9H-purin-9-yl)ethyl)-4-phenyl-1H-isochromen-1-one;

4-phenyl-3-(1-(thieno[2,3-d]pyrimidin-4-ylamino)ethyl)-1H-isochromen-1-one;

4-phenyl-3-(1-(thieno[3,2-d]pyrimidin-4-ylamino)ethyl)-1H-isochromen-1-one;

2-amino-N-(1-(1-oxo-4-phenyl-1H-isochromen-3-yl)ethyl)pyrazolo[1,5-a]pyrimidine-3-carboxamide;

3-(1-(4-amino-3-(1H-pyrazol-3-yl)-1H-pyrazolo[3,4-d]pyrimidin-1-yl)ethyl)-4-phenyl-1H-isochromen-1-one;

3-(1-(4-amino-3-(1H-indazol-4-yl)-1H-pyrazolo[3,4-d]pyrimidin-1-yl)ethyl)-4-phenyl-1H-isochromen-1-one;

3-(1-(4-amino-3-(3-amino-1H-indazol-5-yl)-1H-pyrazolo[3,4-d]pyrimidin-1-yl)ethyl)-4-phenyl-1H-isochromen-1-one;

3-(1-(4-amino-3-(3-hydroxy-5-(trifluoromethoxy)phenyl)-1H-pyrazolo[3,4-d]pyrimidin-1-yl)ethyl)-4-phenyl-1H-isochromen-1-one;

3-(1-(6-amino-9H-purin-9-yl)ethyl)-4-(5-(morpholinomethyl)thiophen-2-yl)-1H-isochromen-1-one;

3-(1-(9H-purin-6-ylamino)ethyl)-4-(6-methoxypyridin-3-yl)-1H-isochromen-1-one;

3-(1-(9H-purin-6-ylamino)ethyl)-4-(thiazol-5-yl)-1H-isochromen-1-one;

3-(1-(4-amino-3-(3-fluoro-5-hydroxyphenyl)-2H-pyrazolo[3,4-d]pyrimidin-2-yl)ethyl)-4-phenyl-1H-isochromen-1-one;

3-(1-(4-amino-3-(3-fluoro-5-hydroxyphenyl)-1H-pyrazolo[3,4-d]pyrimidin-1-yl)ethyl)-4-(3-(dimethylamino)phenyl)-1H-isochromen-1-one;

3-(1-(4-amino-3-(3-fluoro-5-hydroxyphenyl)-1H-pyrazolo[3,4-d]pyrimidin-1-yl)ethyl)-4-(thiazol-5-yl)-1H-isochromen-1-one;

3-(1-(4-amino-3-(3-fluoro-5-hydroxyphenyl)-1H-pyrazolo[3,4-d]pyrimidin-1-yl)ethyl)-4-(2-aminothiazol-5-yl)-1H-isochromen-1-one;

3-(1-(9H-purin-6-ylamino)ethyl)-4-(1H-pyrazol-4-yl)-1H-isochromen-1-one;

4-amino-6-((1-(1-oxo-4-(1H-pyrazol-4-yl)-1H-isochromen-3-yl)ethyl)amino)pyrimidine-5-carbonitrile;

3-(1-(9H-purin-6-ylamino)ethyl)-4-(2-aminopyrimidin-5-yl)-1H-isochromen-1-one;

3-(1-(4-amino-3-(3-fluoro-5-hydroxyphenyl)-1H-pyrazolo[3,4-d]pyrimidin-1-yl)ethyl)-4-(4-(piperazin-1-ylmethyl)phenyl)-1H-isochromen-1-one;

3-(1-(9H-purin-6-ylamino)ethyl)-4-(4-(piperazin-1-ylmethyl)phenyl)-1H-isochromen-1-one;

3-(1-(4-amino-1H-pyrazolo[3,4-d]pyrimidin-1-yl)ethyl)-4-(4-(piperazin-1-ylmethyl)phenyl)-1H-isochromen-1-one;

3-(4-amino-1-((4-phenyl-1H-isochromen-3-yl)methyl)-1H-pyrazolo[3,4-d]pyrimidin-3-yl)-5-fluorophenol;

5-(4-amino-1-((4-phenyl-1H-isochromen-3-yl)methyl)-1H-pyrazolo[3,4-d]pyrimidin-3-yl)pyridin-3-ol;

3-(1-(4-amino-3-(3-fluoro-5-hydroxyphenyl)-1H-pyrazolo[3,4-d]pyrimidin-1-yl)ethyl)-4-(morpholinomethyl)-1H-isochromen-1-one;

3-(1-(4-amino-3-(3-fluoro-5-hydroxyphenyl)-1H-pyrazolo[3,4-d]pyrimidin-1-yl)ethyl)-4-(1-benzyl-1,2,3,6-tetrahydropyridin-4-yl)-1H-isochromen-1-one;

3-(1-(4-amino-3-(5-hydroxypyridin-3-yl)-1H-pyrazolo[3,4-d]pyrimidin-1-yl)ethyl)-4-(1-benzyl-1,2,3,6-tetrahydropyridin-4-yl)-1H-isochromen-1-one;

benzyl 4-(3-(1-(4-amino-3-(3-fluoro-5-hydroxyphenyl)-1H-pyrazolo[3,4-d]pyrimidin-1-yl)ethyl)-1-oxo-1H-isochromen-4-yl)-5,6-dihydropyridine-1(2H)-carboxylate;

3-(1-(4-amino-3-(3-fluoro-5-hydroxyphenyl)-1H-pyrazolo[3,4-d]pyrimidin-1-yl)ethyl)-4-(5-(piperazin-1-ylmethyl)thiophen-2-yl)-1H-isochromen-1-one;

3-(1-(4-amino-3-(3-fluoro-5-hydroxyphenyl)-1H-pyrazolo[3,4-d]pyrimidin-1-yl)ethyl)-4-(5-((4-methylpiperazin-1-yl)methyl)thiophen-2-yl)-1H-isochromen-1-one;

3-(1-(4-amino-3-(3-fluoro-5-hydroxyphenyl)-1H-pyrazolo[3,4-d]pyrimidin-1-yl)ethyl)-4-(5-(3-(dimethylamino)propyl)thiophen-2-yl)-1H-isochromen-1-one;

3-(1-(4-amino-3-(3-fluoro-5-hydroxyphenyl)-1H-pyrazolo[3,4-d]pyrimidin-1-yl)ethyl)-4-(3-(3-(dimethylamino)propyl)phenyl)-1H-isochromen-1-one;

3-(1-(4-amino-3-(3-fluoro-5-hydroxyphenyl)-1H-pyrazolo[3,4-d]pyrimidin-1-yl)ethyl)-4-(3-(3-(dimethylamino)propyl)phenyl)-1H-isochromen-1-one single enantiomer 1;

3-(1-(4-amino-3-(3-fluoro-5-hydroxyphenyl)-1H-pyrazolo[3,4-d]pyrimidin-1-yl)ethyl)-4-(3-(3-(dimethylamino)propyl)phenyl)-1H-isochromen-1-one single enantiomer 2;

3-(1-(4-amino-3-(3-fluoro-5-hydroxyphenyl)-1H-pyrazolo[3,4-d]pyrimidin-1-yl)ethyl)-4-(4-(3-(dimethylamino)propyl)phenyl)-1H-isochromen-1-one;

3-(1-(4-amino-3-(3-fluoro-5-hydroxyphenyl)-1H-pyrazolo[3,4-d]pyrimidin-1-yl)ethyl)-4-(4-(3-(dimethylamino)propyl)phenyl)-1H-isochromen-1-one single enantiomer 1;

3-(1-(4-amino-3-(3-fluoro-5-hydroxyphenyl)-1H-pyrazolo[3,4-d]pyrimidin-1-yl)ethyl)-4-(4-(3-(dimethylamino)propyl)phenyl)-1H-isochromen-1-one single enantiomer 2;

3-(1-(4-amino-3-(3-fluoro-5-hydroxyphenyl)-1H-pyrazolo[3,4-d]pyrimidin-1-yl)ethyl)-4-(4-((4-methylpiperazin-1-yl)methyl)phenyl)-1H-isochromen-1-one;

3-(1-(4-amino-3-(3-fluoro-5-hydroxyphenyl)-1H-pyrazolo[3,4-d]pyrimidin-1-yl)ethyl)-4-(4-(pyrrolidin-1-ylmethyl)phenyl)-1H-isochromen-1-one;

3-(1-(4-amino-3-(3-fluoro-5-hydroxyphenyl)-1H-pyrazolo[3,4-d]pyrimidin-1-yl)ethyl)-4-(4-(piperidin-1-ylmethyl)phenyl)-1H-isochromen-1-one;

3-(1-(4-amino-3-(3-fluoro-5-hydroxyphenyl)-1H-pyrazolo[3,4-d]pyrimidin-1-yl)ethyl)-4-(3-((4-methylpiperazin-1-yl)methyl)phenyl)-1H-isochromen-1-one;

3-(1-(4-amino-3-(3-fluoro-5-hydroxyphenyl)-1H-pyrazolo[3,4-d]pyrimidin-1-yl)ethyl)-4-(3-(piperidin-1-ylmethyl)phenyl)-1H-isochromen-1-one;

3-(1-(4-amino-3-(3-fluoro-5-hydroxyphenyl)-1H-pyrazolo[3,4-d]pyrimidin-1-yl)ethyl)-4-(2,2,6,6-tetramethyl-1,2,3,6-tetrahydropyridin-4-yl)-1H-isochromen-1-one;

3-(1-(4-amino-3-(5-hydroxypyridin-3-yl)-1H-pyrazolo[3,4-d]pyrimidin-1-yl)ethyl)-4-(2,2,6,6-tetramethyl-1,2,3,6-tetrahydropyridin-4-yl)-1H-isochromen-1-one;

3-(1-(4-amino-3-(3-fluoro-5-hydroxyphenyl)-1H-pyrazolo[3,4-d]pyrimidin-1-yl)ethyl)-4-(1-(4-(dimethylamino)butanoyl)-1,2,3,6-tetrahydropyridin-4-yl)-1H-isochromen-1-one;

3-(1-(4-amino-3-(3-fluoro-5-hydroxyphenyl)-1H-pyrazolo[3,4-d]pyrimidin-1-yl)ethyl)-4-(1-(2-(dimethylamino)acetyl)-1,2,3,6-tetrahydropyridin-4-yl)-1H-isochromen-1-one;

3-(1-(4-amino-3-(3-fluoro-5-hydroxyphenyl)-1H-pyrazolo[3,4-d]pyrimidin-1-yl)ethyl)-4-(1-(1-methylpiperidine-4-carbonyl)-1,2,3,6-tetrahydropyridin-4-yl)-1H-isochromen-1-one;

3-(1-(4-amino-3-(3-fluoro-5-hydroxyphenyl)-1H-pyrazolo[3,4-d]pyrimidin-1-yl)ethyl)-4-(1-(1-isopropylpiperidin-4-yl)-1,2,3,6-tetrahydropyridin-4-yl)-1H-isochromen-1-one;

3-(1-(4-amino-3-(3-fluoro-5-hydroxyphenyl)-1H-pyrazolo[3,4-d]pyrimidin-1-yl)ethyl)-4-(1-(azetidine-3-carbonyl)-1,2,3,6-tetrahydropyridin-4-yl)-1H-isochromen-1-one;

3-(1-(4-amino-3-(3-fluoro-5-hydroxyphenyl)-1H-pyrazolo[3,4-d]pyrimidin-1-yl)ethyl)-4-(1-(1-methylazetidine-3-carbonyl)-1,2,3,6-tetrahydropyridin-4-yl)-1H-isochromen-1-one;

3-(1-(4-amino-3-(3-chloro-5-hydroxyphenyl)-1H-pyrazolo[3,4-d]pyrimidin-1-yl)ethyl)-4-(1,2,3,6-tetrahydropyridin-4-yl)-1H-isochromen-1-one;

3-(1-(4-amino-3-(3-hydroxy-5-(trifluoromethyl)phenyl)-1H-pyrazolo[3,4-d]pyrimidin-1-yl)ethyl)-4-(1,2,3,6-tetrahydropyridin-4-yl)-1H-isochromen-1-one;

3-(1-(4-amino-3-(3-chloro-5-hydroxyphenyl)-1H-pyrazolo[3,4-d]pyrimidin-1-yl)ethyl)-4-(1-methyl-1,2,3,6-tetrahydropyridin-4-yl)-1H-isochromen-1-one;

3-(1-(4-amino-3-(3-hydroxy-5-(trifluoromethyl)phenyl)-1H-pyrazolo[3,4-d]pyrimidin-1-yl)ethyl)-4-(1-methyl-1,2,3,6-tetrahydropyridin-4-yl)-1H-isochromen-1-one;

3-(1-(4-amino-3-(3-fluoro-5-hydroxyphenyl)-1H-pyrazolo[3,4-d]pyrimidin-1-yl)ethyl)-4-(1-(azetidin-3-yl)-1,2,3,6-tetrahydropyridin-4-yl)-1H-isochromen-1-one;

3-(1-(4-amino-3-(3-fluoro-5-hydroxyphenyl)-1H-pyrazolo[3,4-d]pyrimidin-1-yl)ethyl)-4-(1-(1-(cyclopropylmethyl)azetidin-3-yl)-1,2,3,6-tetrahydropyridin-4-yl)-1H-isochromen-1-one;

3-(1-(4-amino-3-(3-fluoro-5-hydroxyphenyl)-1H-pyrazolo[3,4-d]pyrimidin-1-yl)ethyl)-4-(3-(dimethylamino)prop-1-yn-1-yl)-1H-isochromen-1-one;

3-(1-(4-amino-3-(5-hydroxy-4-methylpyridin-3-yl)-1H-pyrazolo[3,4-d]pyrimidin-1-yl)ethyl)-4-phenyl-1H-isochromen-1-one;

3-(1-(4-amino-3-(5-hydroxy-2-methylpyridin-3-yl)-1H-pyrazolo[3,4-d]pyrimidin-1-yl)ethyl)-4-phenyl-1H-isochromen-1-one;

3-(1-(4-amino-3-(5-hydroxy-6-(trifluoromethyl)pyridin-3-yl)-1H-pyrazolo[3,4-d]pyrimidin-1-yl)ethyl)-4-phenyl-1H-isochromen-1-one;

3-(1-(4-amino-3-(3-fluoro-5-hydroxyphenyl)-1H-pyrazolo[3,4-d]pyrimidin-1-yl)ethyl)-7-methyl-4-phenyl-1H-isochromen-1-one;

3-(1-(4-amino-3-(3-fluoro-5-hydroxyphenyl)-1H-pyrazolo[3,4-d]pyrimidin-1-yl)ethyl)-7-chloro-4-phenyl-1H-isochromen-1-one;

3-(1-(4-amino-3-(3-fluoro-5-hydroxyphenyl)-1H-pyrazolo[3,4-d]pyrimidin-1-yl)ethyl)-6-chloro-4-phenyl-1H-isochromen-1-one;

3-(1-(4-amino-3-(3-fluoro-5-hydroxyphenyl)-1H-pyrazolo[3,4-d]pyrimidin-1-yl)ethyl)-6-fluoro-4-phenyl-1H-isochromen-1-one;

4-(1-acetyl-1,2,3,6-tetrahydropyridin-4-yl)-3-(1-(4-amino-3-(3-fluoro-5-hydroxyphenyl)-1H-pyrazolo[3,4-d]pyrimidin-1-yl)ethyl)-1H-isochromen-1-one single enantiomer 1;

4-(1-acetyl-1,2,3,6-tetrahydropyridin-4-yl)-3-(1-(4-amino-3-(3-fluoro-5-hydroxyphenyl)-1H-pyrazolo[3,4-d]pyrimidin-1-yl)ethyl)-1H-isochromen-1-one single enantiomer 2;

3-(1-(4-amino-3-(3-fluoro-5-hydroxyphenyl)-1H-pyrazolo[3,4-d]pyrimidin-1-yl)ethyl)-4-(thiazol-5-yl)-1H-isochromen-1-one single enantiomer 1;

3-(1-(4-amino-3-(3-fluoro-5-hydroxyphenyl)-1H-pyrazolo[3,4-d]pyrimidin-1-yl)ethyl)-4-(thiazol-5-yl)-1H-isochromen-1-one single enantiomer 2; 3-(1-(4-amino-3-(5-hydroxypyridin-3-yl)-1H-pyrazolo[3,4-d]pyrimidin-1-yl)ethyl)-4-phenyl-1H-isochromen-1-one single enantiomer 1;

3-(1-(4-amino-3-(5-hydroxypyridin-3-yl)-1H-pyrazolo[3,4-d]pyrimidin-1-yl)ethyl)-4-phenyl-1H-isochromen-1-one single enantiomer 2;

3-(1-(4-amino-3-(3-fluoro-5-hydroxyphenyl)-1H-pyrazolo[3,4-d]pyrimidin-1-yl)ethyl)-4-(1-benzyl-1,2,5,6-tetrahydropyridin-3-yl)-1H-isochromen-1-one;

3-(1-(4-amino-3-(3-fluoro-5-hydroxyphenyl)-1H-pyrazolo[3,4-d]pyrimidin-1-yl)ethyl)-4-(1-benzyl-1,2,5,6-tetrahydropyridin-3-yl)-1H-isochromen-1-one single enantiomer 1;

3-(1-(4-amino-3-(3-fluoro-5-hydroxyphenyl)-1H-pyrazolo[3,4-d]pyrimidin-1-yl)ethyl)-4-(1-benzyl-1,2,5,6-tetrahydropyridin-3-yl)-1H-isochromen-1-one single enantiomer 2;

3-(1-(4-amino-3-(3-fluoro-5-hydroxyphenyl)-1H-pyrazolo[3,4-d]pyrimidin-1-yl)ethyl)-4-(pyridin-2-yl)-1H-isochromen-1-one;

3-(1-(4-amino-3-(3-fluoro-5-hydroxyphenyl)-1H-pyrazolo[3,4-d]pyrimidin-1-yl)ethyl)-4-(1,2,5,6-tetrahydropyridin-3-yl)-1H-isochromen-1-one;

3-(1-(4-amino-3-(3-fluoro-5-hydroxyphenyl)-1H-pyrazolo[3,4-d]pyrimidin-1-yl)ethyl)-4-(1-(1-methylpiperidin-4-yl)-1,2,5,6-tetrahydropyridin-3-yl)-1H-isochromen-1-one;

3-(1-(4-amino-3-(3-fluoro-5-hydroxyphenyl)-1H-pyrazolo[3,4-d]pyrimidin-1-yl)ethyl)-4-(1-(azetidin-3-yl)-1,2,5,6-tetrahydropyridin-3-yl)-1H-isochromen-1-one;

3-(1-(4-amino-3-(3-fluoro-5-hydroxyphenyl)-1H-pyrazolo[3,4-d]pyrimidin-1-yl)ethyl)-4-(1-isopropyl-1,2,5,6-tetrahydropyridin-3-yl)-1H-isochromen-1-one;

3-(1-(4-amino-3-(5-hydroxypyridin-3-yl)-1H-pyrazolo[3,4-d]pyrimidin-1-yl)ethyl)-4-(1-methyl-1,2,3,6-tetrahydropyridin-4-yl)-1H-isochromen-1-one;

3-(1-(4-amino-3-(3-fluoro-5-hydroxyphenyl)-1H-pyrazolo[3,4-d]pyrimidin-1-yl)ethyl)-4-phenyl-1H-isochromen-1-one single enantiomer 1;

3-(1-(4-amino-3-(3-fluoro-5-hydroxyphenyl)-1H-pyrazolo[3,4-d]pyrimidin-1-yl)ethyl)-4-phenyl-1H-isochromen-1-one single enantiomer 2;

and pharmaceutical acceptable salts thereof.

The compounds of formula (I) including all the compounds here above listed can be generally prepared according to the procedure outlined in Schemes shown below using generally known methods. The residue M is a 1,2-phenylene-diyl radical optionally substituted by one or more R(p).

When the group Y represents a hydroxy moiety, compound (V) was converted in (VI), where the group X represents a suitable leaving group such as a halide atom, by reaction with a suitable halogenating agent such as $PBr_3$.

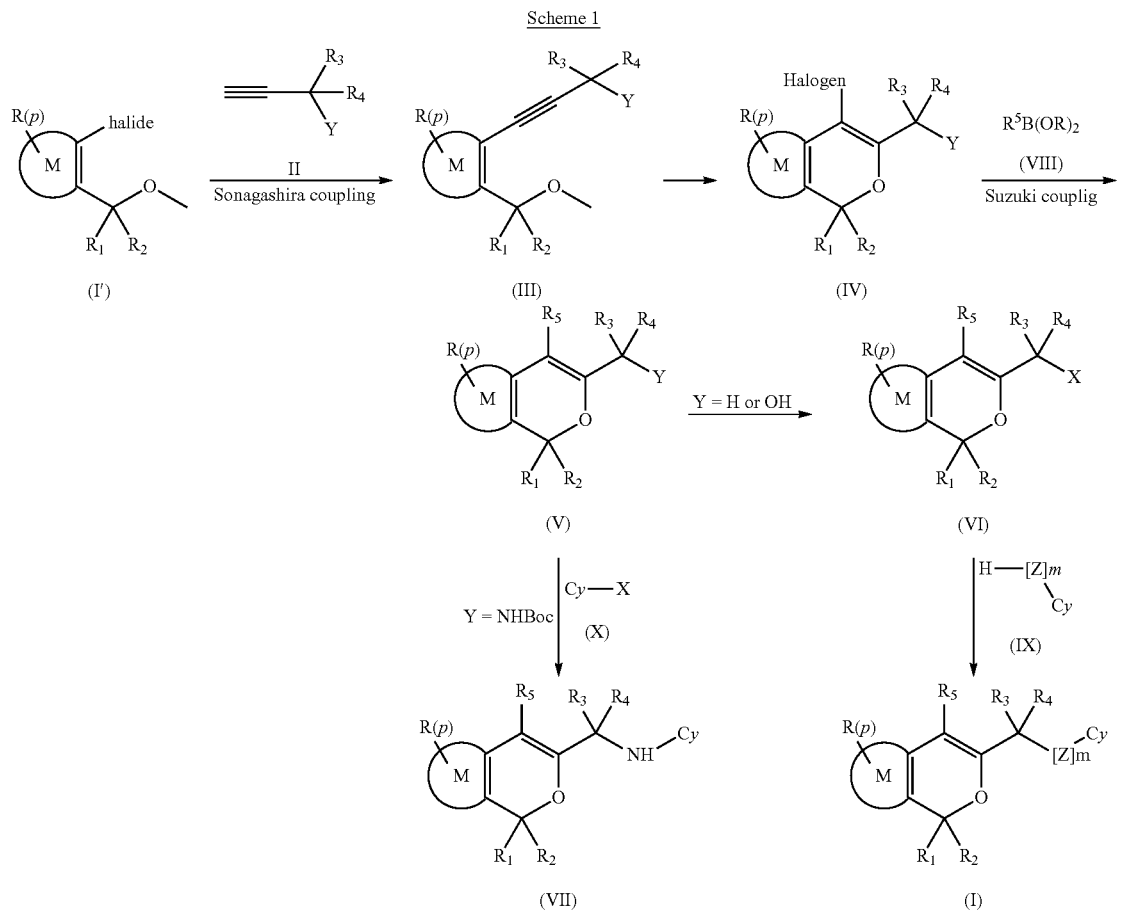

Scheme 1

An alpha-aryl- or alpha-heteroaryl-benzoate ester of formula (I') wherein R1 and R2 are combined to form an oxo group (C=O) was reacted with an alkyne of formula (II) under suitable Sonogashira cross-coupling conditions in presence of a Palladium catalyst as described in "Transition Metals for Organic Synthesis", $2^{nd}$ Ed, 1, 211-229, 2004, which is incorporated herein by reference in its entirety.

Alkyne (II) such as prop-2-yn-1-ol and but-3-yn-2-ol are commercially available or their derivatives such as tert-butyl but-3-yn-2-ylcarbamate can be prepared according to well-known methods.

The intermediate (III) can be cyclised into the corresponding halide of formula (IV) by reaction with $CuBr_2$ in presence of a suitable base according to Li, J H et al, Synthesis 3, 400-406, 2007, which is incorporated herein by reference in its entirety, or using iodine. Compound (IV) can be further converted into (V) by a Suzuki coupling with boronic acid or suitable ester $R_5B(OR)_2$ (VIII). Boronic acid and esters of formula (VIII) are commercially available.

Compounds of formula (VII), corresponding to compounds of formula (I) wherein Z=NH and m=1, may be optionally prepared by the synthetic route illustrated in Scheme 1 from compound of formula (V).

When the group Y represents hydrogen, compound (V) was converted in (VI), where the group X represents a suitable leaving group such as a halide atom, by reaction with N-bromosuccinimide.

Compound (VI) was finally reacted with a nitrogen or sulfur based nucleophile (IX) such as 9H-purin-6-amine, 9H-purine-6-thiol hydrate, tert-butyl 9-trityl-9H-purin-6-yl-carbamate, 1H-pyrazolo[3,4-d]pyrimidin-4-amine to give compound (I).

When group Y represents an amino group protected with a suitable protecting group such as BOC, compound (V) was deprotected under acidic conditions and reacted with the proper halide derivative Cy-Cl (X) to give compound of formula (VII).

This scheme provides a synthetic route for the preparation of the compound of examples 1-35, 43-45, 47, 50, 80-84, 104-110, 115-117, 122-124, 126 and 127.

Using similar methodologies as described in Scheme 1, compound (XII), corresponding to compound (1) wherein m=0 (Z is absent) and Cy is an optionally substituted 1H-pyrazolo[3,4-d]pyrimidinyl, can be synthesized as outlined in Scheme 2 from compound (VI) and commercially available 3-iodo-1H-pyrazolo[3,4-d]pyrimidin-4-amine to give compound (XI) which can be further converted into compound (XII) by mean of a Suzuki coupling. Boronic acid and esters of formula (VIII) are commercially available.

This scheme provides a synthetic route for the preparation of the compound of examples 35-42, 46, 48-49, 51, 54, 58, 63, 72-73, 79, 111, 118-120, 125, 133, 161-165 and 175.

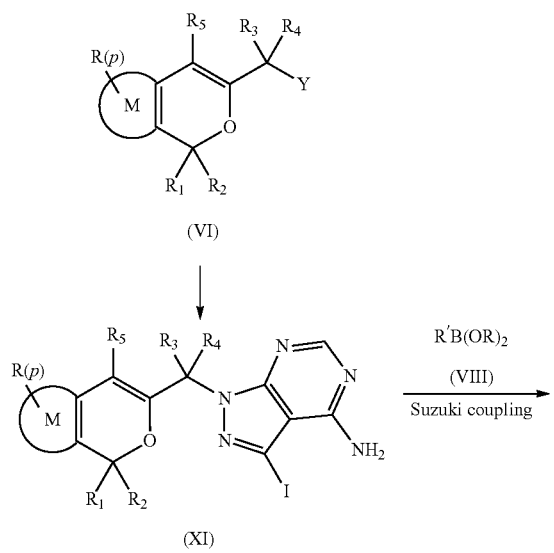

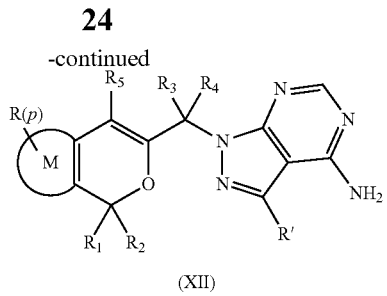

In another embodiment of the present invention, compound (XII) may be prepared according to Scheme 2a either from compound (XI) by mean of Stille, Suzuki cross-coupling reaction (Scheme 2a, step 3a), using a suitable organo tin or organo boron reagent (VIII) and a Palladium catalyst, or from compound (VI) by a nucleophilic substitution using a nitrogen based nucleophile (IXa), such as an optionally substituted 3-iodo-1H-pyrazolo[3,4-d]pyrimidin-4-amine (Scheme 2a, step 4a).). Compound (VI) where X is a suitable leaving group (Lg) such as an halide atom, may be prepared from compound (1V) by a Suzuki, Stille or Sonogashira cross coupling reaction (Scheme 2a, Step 1a) followed by substitution of the hydroxyl moiety with a suitable alogenating agent such as for example PBr₃ (Scheme 2a, step 1b). Some compounds (XII) may contain a protected hydroxyl or amino group which were then removed under well-known procedures (Scheme 2a, step 3b and 4b).

This scheme provides a synthetic route for the preparation of the compound of examples 52-53, 56-57, 59-62, 68-71, 85-103, 112-114, 131-132, 144-149, 152-153, 158-160.

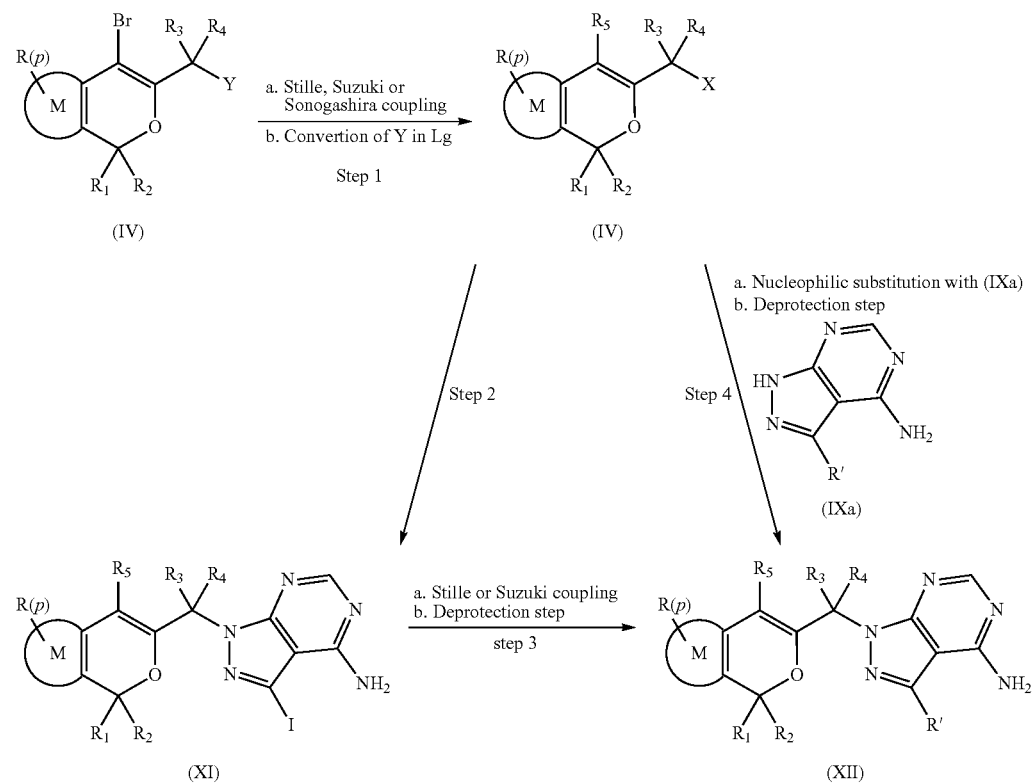

According to Scheme 3, compounds of formula (XIa), wherein R1 and R2 are combined to form an oxo group (C=O), can be prepared in similar way to that of compound (XI), where R5 is a $(C_3-C_6)$heterocycloalkyl group containing a suitable secondary amine —NH. Compound (XIa) may be converted to compound of formula (XIIa), wherein Rx is a suitable substituent as above by mean of sequence of two reactions consisting of an amine derivatisation reaction (step 1), under reductive ammination condition with an appropriate carbonyl compound, or alternatively by mean of an amide coupling with a suitable carboxylic acid, followed by a Suzuki cross-coupling with an appropriate boronic acid (step 2). For the preparation of some compounds (XIIa) the process may be inverted.

This scheme provides a synthetic route for the preparation of the compound of examples 65-66, 150-151, 154-157, 171-174.

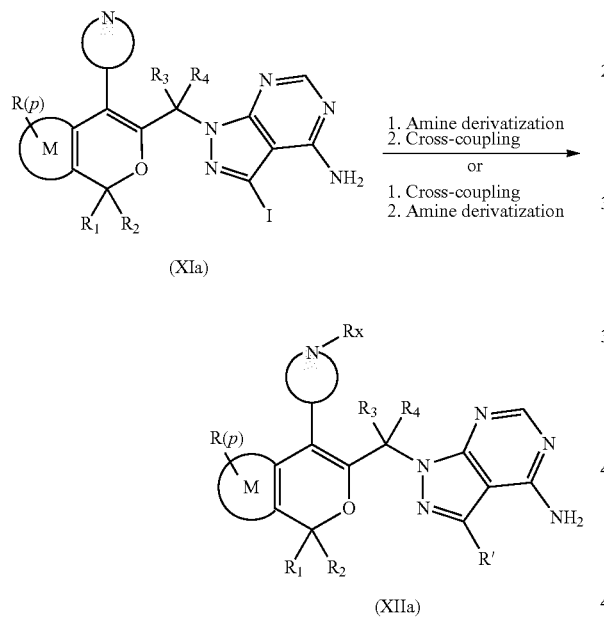

In one embodiment of the present invention compound (Va), wherein R1 and R2 are combined to form an oxo group (C=O) and Y represents an hydroxyl group, and R5 is an aryl or a heteroaryl group A; substituted with an aldehyde moiety, can be prepared from compound (IV) similarly to Scheme 1, either by means of a Suzuki coupling with a suitable boronic acid or ester CHO-A-B(ORz)$_2$, or alternatively, from deprotection of compound (Vb) under acidic condition (Scheme 4, step 1). Compound of formula (Vb) can be prepared from compound (1V) by means of a Suzuki coupling with a suitable boronic acid or ester (RwO)$_2$CH-A-B(ORz)$_2$, containing a protected aldehyde. Compound (Va) can be converted into (XIIb) by reductive amination with a suitable primary or secondary amine (Scheme 4, Step 2a) followed by introduction of suitable leaving group (Lg), such as Bromine atom (Scheme 4, Step 2b), and finally reaction with a suitable nucleophile (IX) (Scheme 4, Step 2c). Compounds (XIIb) may contain a protected hydroxyl group which was then removed under well-known procedures (Scheme 4, Step 2d).

This scheme provides a synthetic route for the preparation of the compound of examples 134-135, 139-142.

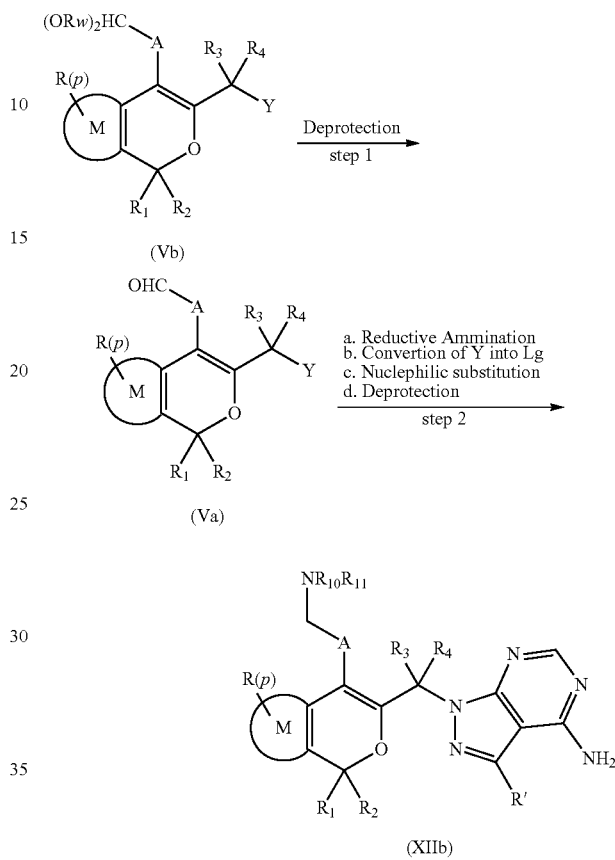

Alternatively, according to Scheme 5, compound (Vb), wherein R1 and R2 are combined to form an oxo group (C=O) and Y represents an hydroxyl group, may be transformed into compound (XIIc), by mean of conversion of Y into a suitable leaving group (Lg), such as a bromine atom (step a), followed by a nucleophilic substitution with a suitable nitrogen based nucleophile (IX) (step b), deprotection of carbonyl moiety under acidic condition (step c) and finally reductive amination with a suitable amine in presence of a reducing agent such as sodium triacetoxyborohydride.

This scheme provides a synthetic route for the preparation of the compound of examples 67, 73-77, 143.

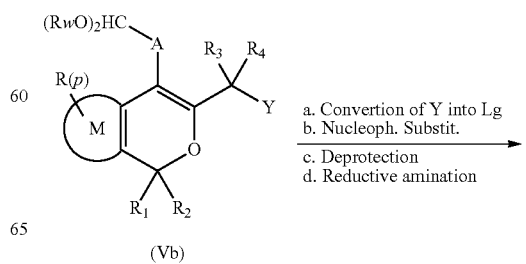

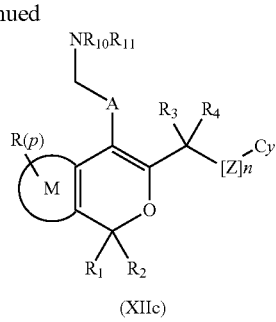

(XIIc)

In another embodiment of the present invention, compound (Va) wherein R1 and R2 are combined to form an oxo group (C=O) and Y represents an hydroxyl group, may be converted into compound (Vc) by mean of a Wittig reaction with a suitable triphenylphosphoium bromide (SCHEME 6, step 1). Compound (Vc) was then converted into compound (XIId) by mean of conversion of Y into a suitable leaving group, such as a bromine atom (Scheme 6, step 2a), followed by a nucleophilic substitution with a suitable nitrogen based nucleophile (IX) (Scheme 6, step 2b) and finally reduction of the double bond with a suitable reducing agent such as triethyl silane in presence of Pd/C.

This scheme provides a synthetic route for the preparation of the compound of examples 137 and 138.

Scheme 6

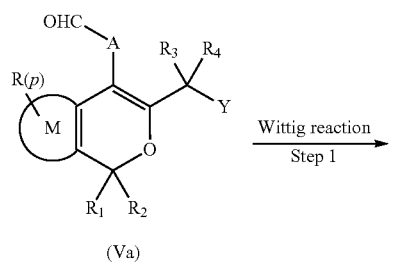

According to Scheme 7, compound (Vd), wherein R1 and R2 are combined to form an oxo group (C=O), wherein R5 is A is an heteroaryl spacer A, may be converted into compound (XIIe) by mean of Pinnick oxidation (Strategic Applications of Named Reactions in Organic Synthesis, Laszlo Kurti, Barbara Czako, Elsevier, Academic Press, 2005, which is incorporated herein by reference in its entirety). Compound (Vd) may be prepared from compound (Vb) according to step a, b and c of Scheme 5. This scheme provides a synthetic route for the preparation of the compound of example 78.

Scheme 7

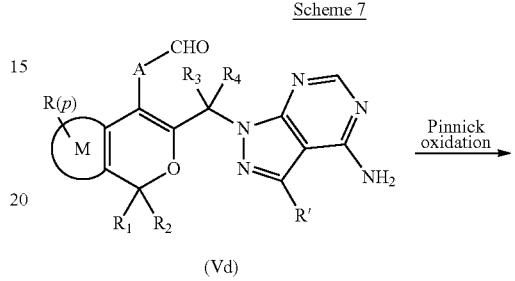

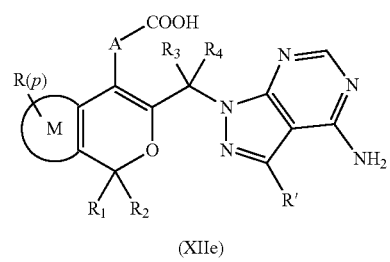

(XIIe)

In one embodiment of the present invention, according to Scheme 8, compounds (XIIf), wherein R1 and R2 are combined to from an oxo group (C=O), can be prepared from compound (Ve). Compound Ve may be converted into an aldehyde by oxonolysis (step a) and then into an amine by reductive amination with a suitable secondary amine such as morpholine in presence of a reducing agent such as sodium triacetoxyborohydride (step b). Y group represents an hydroxyl group and is then converted into a suitable leaving group (Lg) and then displaced by a nitrogen based nucleophile (IX) (step d), followed by a deprotection of hydroxyl moiety (step e). Compound Ve can be prepared by mean of Stille coupling with vinyl tributyl-tin and a Pd catalyst from IV according to Scheme 2, step 1a.

This scheme provides a synthetic route for the preparation of the compound of example 130.

Scheme 8

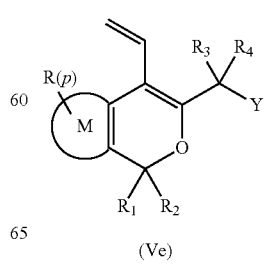

a. Oxonolysis
b. Reductive ammination
c. Convertion of Y into Lg
d. Nuclephilic substitution
e. Deprotection

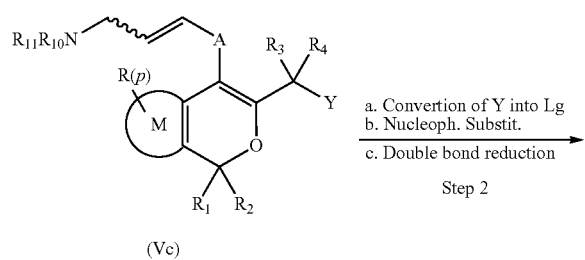

(Vc)

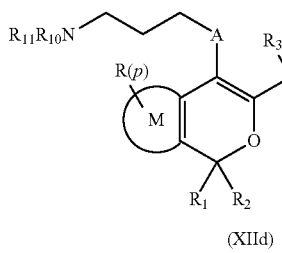

(XIId)

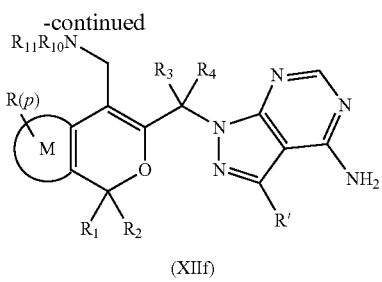

(XIIf)

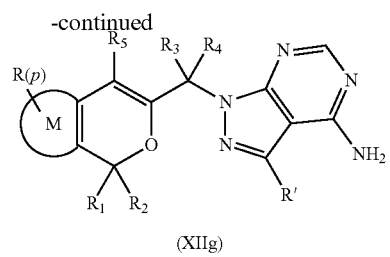

(XIIg)

In one embodiment of the present invention, according to Scheme 9, compound (Vf), wherein R1=R2=R3=R4=H, can be prepared from compound (XIII), such as for example commercially available isochroman-4-one. Compound (XIII) may be converted into chloride (XIV) (Scheme 9, step 1), by reaction with an alogenating agent such as POCl₃. Compound (XIV) may be then converted into (XV) by mean of a Suzuki coupling with a suitable boronic acid (Scheme 9, step 2) and finally to compound (Vf) by reduction with an hydride reagent such as sodium borohydride.

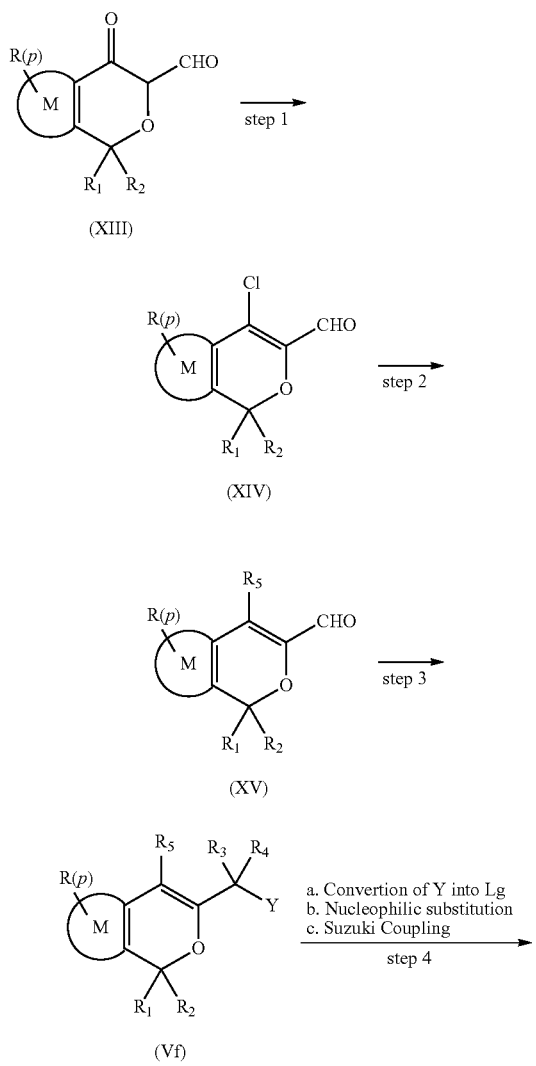

Compound of formula (Vf) may be converted into compound (XIIg), wherein R1=R2=R3=R4=H, by analogy to synthetic procedure reported in Scheme 2a, step 2 and 3, by mean of a conversion of Y into a suitable Lg (Scheme 9, step 4a), followed by a nucleophilic substitution with a suitable nucleophile, such as 3-Iodo-1H-pyrazolo[3,4-d]pyrimidin-4-amine, and finally a Suzuki coupling (Scheme 9, step 4b,c).

This scheme provides a synthetic route for the preparation of the compound of examples 128 and 129.

Enantiomeric pure compounds 46a/b, 49a/b, 67a/b, 68a/b, 76a/b, 137a/b, 138a/b, 166a/b, 167a/b, 168a/b, 169a/b, 176a/b may be prepared from the corresponding racemates by mean of chiral separation of the parent racemate compounds or the eventually protected analogues, followed by a suitable protection step.

The compounds of the present invention are inhibitors of kinase activity, in particular PI3-kinase activity. Generally speaking, compounds which are PI3K inhibitors may be useful in the treatment of many disorders associated with PI3K enzymes mechanisms.

In one embodiment, the disorders that can be treated by the compounds of the present invention include respiratory diseases selected from idiopathic chronic cough, cough-variant asthma, cough associated with thoracic tumour or lung cancer, viral or post-viral cough, upper airways cough syndrome (UACS), or post nasal drip cough, or cough associated with gastro-oesophageal reflux disease (both acid and non acid reflux), asthma, chronic bronchitis, chronic obstructive pulmonary disease (COPD), interstitial lung disease, (such as idiopathic pulmonary fibrosis (IPF)), congestive heart disease, sarcoidosis, infections (such as whooping cough), asthma, chronic obstructive pulmonary disease (COPD) and idiopathic pulmonary fibrosis (IPF)); viral infections (including viral respiratory tract infections and viral exacerbation of respiratory diseases; non-viral respiratory infections including aspergillosis and leishmaniasis; allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and central pain.

In another embodiment, the disorder that can be treated by the compound of the present invention is selected from the group consisting of idiopathic chronic cough, cough-variant asthma, cough associated with thoracic tumour or lung cancer, viral or post-viral cough, upper airways cough syndrome (UACS), post nasal drip cough, cough associated gastro-oesophageal reflux disease (both acid and non acid reflux), asthma, chronic bronchitis, chronic obstructive pulmonary disease (COPD) and interstitial lung disease (such as idiopathic pulmonary fibrosis (IPF).

In a further embodiment, the disorder is selected from the group of asthma, chronic obstructive pulmonary disease (COPD), idiopathic pulmonary fibrosis (IPF), cough and chronic cough.

The methods of treatment of the invention comprise administering a safe and effective amount of a compound of formula (I) or a pharmaceutically acceptable salt thereof to a patient in need thereof. As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects and it can nevertheless be routinely determined by the skilled artisan. The compounds of formula (I) or pharmaceutically acceptable salts thereof may be administered once or according to a dosing regimen wherein a number of doses are administered at varying intervals of time for a given period of time. Typical daily dosages may vary depending upon the particular route of administration chosen.

The present invention also provides pharmaceutical compositions of compounds of formula (I) in admixture with one or more pharmaceutically acceptable carrier or excipient, for example those described in Remington's Pharmaceutical Sciences Handbook, XVII Ed., Mack Pub., N.Y., U.S.A., which is incorporated herein by reference in its entirety.

Administration of the compounds of the present invention and their pharmaceutical compositions may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the present invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, such as suitable carriers, are also known.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention can be administered as the sole active agent or in combination with other pharmaceutical active ingredients including those currently used in the treatment of respiratory disorders, e.g. beta$_2$-agonists, antimuscarinic agents, corticosteroids mitogen-activated kinases (P38 MAP kinases) inhibitors, nuclear factor kappa-B kinase subunit beta inhibitors (IKK2), human neutrophil elastase (HNE) inhibitors, phosphodiesterase 4 (PDE4) inhibitors, leukotriene modulators, non-steroidal anti-inflammatory agents (NSAIDs) and mucus regulators.

The dosages of the compounds of the invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula (I) can be administered for example, at a dosage of 0.001 to 1000 mg/day, preferably 0.1 to 500 mg/day.

When the compounds of formula (I) are administered by inhalation route, they are preferably given at a dosage of 0.001 to 500 mg/day, preferably 0.1 to 200 mg/day.

Other features of the invention will become apparent in the course of the following descriptions of exemplary embodiments which are given for illustration of the invention and are not intended to be limiting thereof.

EXAMPLES

Chemical Names of the compounds were generated with Structure To Name Enterprise 10.0 Cambridge Software.
Abbreviations
Et$_2$O=diethyl ether;
Et$_3$N=triethyl amine;
DCE=1,2-dichloroethane;

TEA=tryethyl amine;
DCC=N,N'-dicyclohexylcarbodiimide;
HOBt=hydroxybenzotriazole;
HATU=(dimethylamino)-N,N-dimethyl(3H-[1,2,3]triazolo[4,5-b]pyridin-3-yloxy)methaniminium hexafluorophosphate;
HBTU=N,N,N',N'-tetramethyl-O-(1H-benzotriazol-1-yl) uronium hexafluorophosphate, O-(Benzotriazol-1-yl)-N,N,N',N'-tetramethyluronium hexafluorophosphate;
EDC=1-ethyl-3-(3-dimethylaminopropyl)carbodiimide hydrochloride;
DMAP=4-dimethylaminopyridine;
DMF=dimethylformamide;
EtOAc=ethyl acetate;
RT=room temperature;
THF=tetrahydrofuran;
DCM=dichloromethane;
MeOH=methyl alcohol;
EtOH=ethylic alcohol;
LHMDS=lithium bis(trimethylsilyl)amide;
m-CPBA=meta-chloroperoxybenzoic acid;
TFA=trifluoroacetic acid;
LC-MS=liquid chromatography/mass spectrometry;
HPLC=high pressure liquid chromatography;
MPLC=medium pressure liquid chromatography;
SFC=supercritical fluid chromatography;
dppf=1,1'-bis(diphenylphosphino) ferrocene;
X-Phos-Pd-G2=cChloro(2-dicyclohexylphosphino-2',4',6'-triisopropyl-1,1'-biphenyl)[2-(2'-amino-1,1'-biphenyl)] palladium(II);
S-Phos-Pd-G2=chloro(2-dicyclohexylphosphino-2',6'-dimethoxy-1,1'-biphenyl)[2-(2'-amino-1,1'-biphenyl)]palladium(II);
DIEA or DIPEA=N,N-diisopropylethylamine;
MeCN=acetonitrile;
MTBE=tert-butyl methyl ether;
Ac2O=acetic anhydride;
AcCl=acetyl chloride;
HBTU=N,N,N',N'-tetramethyl-O-(1H-benzotriazol-1-yl) uronium hexafluorophosphate, O-(benzotriazol-1-yl)-N,N,N',N'-tetramethyluronium hexafluorophosphate;
TBDMSCl=tert-butyl(chloro)dimethylsilane;
DMSO=dimethylsulfoxide;
BoC2O=di-tert-butyl dicarbonate;
UPLC=ultra performance liquid chromatography.

General Experimental Details

NMR Characterization:

$^1$H-NMR spectra were performed on a Varian MR-400 spectrometer operating at 400 MHz (proton frequency), equipped with: a self-shielded z-gradient coil 5 mm 1H/nX broad band probehead for reverse detection, deuterium digital lock channel unit, quadrature digital detection unit with transmitter offset frequency shift, or on Agilent VNMRS-500 or on a Bruker Avance 400 spectrometers. Chemical shift are reported as δ values in ppm relative to trimethyl silane (TMS) as an internal standard. Coupling constants (J values) are given in hertz (Hz) and multiplicities are reported using the following abbreviation (s=singlet, d=doublet, t=triplet, q=quartet, m=multiplet, br=broad, nd=not determined).

LC/UV/MS Analytical Methods.

LC/MS retention times are estimated to be affected by an experimental error of ±0.5 min.

LC/UV/MS—Method 1
LC instrument: HPLC Alliance Waters (or equivalent)
Column: Kinetex 2.6 µm C18 100A 100×4.6 mm (Phenomenex)
Column Temperature (° C.): 50.0
Mobile phases: HCOONH4 0.025M pH3 (A); Acetonitrile (B)
Flow (ml/min): 2.0 (split in MS 1:10)
Stop Time (mins): 17.0
Gradient:

| Time (min) | % A | % B |
|---|---|---|
| 0.00 | 80.0 | 20.0 |
| 10.00 | 20.0 | 80.0 |
| 12.00 | 20.0 | 80.0 |
| 14.00 | 80.0 | 20.0 |
| 17.00 | 80.0 | 20.0 |

UV detection: channel 1 245 nm; channel 2 254 nm
Injection Volume (ul): 5.00
Sample Solvent Acetonitrile
MS instrument: Waters Quattro Micro API (or equivalent)
Polarity ES+
Capillary (kV) 3.20
Cone (V) 20.00
Extractor (V) 2.00
RF Lens (V) 0.3
Polarity ES−
Capillary (kV) 3.20
Cone (V) 20.00
Extractor (V) 3.00
RF Lens (V) 0.3
Source Temperature (° C.) 110
Desolvation Temperature (° C.) 210
Cone Gas Flow (L/Hr) 150
Desolvation Gas Flow (L/Hr) 650
Scan duration (secs): 1.00
Interscan delay (secs): 0.10
Mass range: 125 to 1000

LC/UV/MS—Method 2
LC instrument: Acquity Waters UPLC (or equivalent)
Column: Kinetex 1.7 µM XB-C18 100A 100×2.1 mm (Phenomenex)
Column Temperature (° C.) 50.0
Mobile phases: HCOONH$_4$ 0.025M pH3 (A); Acetonitrile+ 0.1% Formic Acid (B)
Flow (ml/min) 0.65 (split in MS 1:3)
Stop Time (mins) 10.0
Gradient:

| Time (min) | % A | % B |
|---|---|---|
| 0.00 | 80.0 | 20.0 |
| 5.50 | 20.0 | 80.0 |
| 7.50 | 20.0 | 80.0 |
| 8.00 | 80.0 | 20.0 |
| 10.00 | 80.0 | 20.0 |

UV detection: DAD
UV acquisition range (nm): 210-400
Injection Volume (ul)—2.00
Sample solvents: Acetonitrile
MS instrument: Waters ZQ (or equivalent)
Polarity ES+
Capillary (kV) 3.00
Cone (V) 20.00
Extractor (V) 3.00
RF Lens (V) 1.0
Polarity ES−
Capillary (kV) 3.00

Cone (V) 20.00
Extractor (V) 3.00
RF Lens (V) 1.0
Source Temperature (° C.) 110
Desolvation Temperature (° C.) 210
Cone Gas Flow (L/Hr) 150
Desolvation Gas Flow (L/Hr) 650
Mass range: 100 to 950
Scan time (sec): 0.32
LC/UV/MS—Method 3
LC instrument: Acquity Waters UPLC (or equivalent)
Column: Kinetex 1.7 nm PFP 100A 100×2.1 mm (Phenomenex)
Column Temperature (° C.) 55.0
Mobile phases: HCOONH4 0.025M pH3 (A); Acetonitrile (B)
Flow (ml/min) 0.45 (split in MS 1:3)
Stop Time (mins) 10.0
Gradient:

| Time (min) | % A | % B |
|---|---|---|
| 0.00 | 85.0 | 15.0 |
| 5.00 | 55.0 | 45.0 |
| 5.50 | 20.0 | 80.0 |
| 6.50 | 20.0 | 80.0 |
| 7.00 | 85.0 | 15.0 |
| 10.0 | 85.0 | 15.0 |

UV detection: DAD
UV acquisition range (nm): 210-400
Injection Volume (ul)—2.00
Sample solvents: Acetonitrile
MS instrument: Waters ZQ (or equivalent)
Polarity ES+
Capillary (kV) 3.00
Cone (V) 20.00
Extractor (V) 3.00
RF Lens (V) 1.0
Polarity ES−
Capillary (kV) 3.00
Cone (V) 20.00
Extractor (V) 3.00
RF Lens (V) 1.0
Source Temperature (° C.) 110
Desolvation Temperature (° C.) 210
Cone Gas Flow (L/Hr) 150
Desolvation Gas Flow (L/Hr) 650
Mass range: 100 to 950
Scan time (sec): 0.32
LC/UV/MS—Method 4
LC instrument: Acquity Waters UPLC (or equivalent) interfaced with 2996 PDA detector
Column: Acquity UPLC BEH C18 1.7 um 50×2.1 mm
Column Temperature (° C.) 30.0
Mobile phases: 95:5 H2O:ACN+(0.1% HCOOH) (A); 5:95 H2O:ACN+(0.1% HCOOH) (B)
Flow (ml/min) 0.6 (split in MS 1:6)
Stop Time (mins) 3.5
Gradient:

| Time (min) | % A | % B |
|---|---|---|
| 0.00 | 100 | 0 |
| 0.50 | 100 | 0 |
| 2.20 | 0.0 | 100.0 |
| 2.70 | 0.0 | 100.0 |
| 2.90 | 100 | 0 |

UV detection: BPI Detection (Start Wavelength nm 210, End Wavelength nm 400, Sampling Rate spectra/sec=20)
Injection Volume (ul)—1.00
Sample solvents: DMSO:MeOH:ACN ratio 1:3:3
MS instrument: Waters ZQ (or equivalent)
Polarity ES
Capillary (kV) 3.20
Cone (V) 25.00
Extractor (V) 3.00
RF Lens (V) 0.1
Polarity ES−
Capillary (kV) 3.40
Cone (V) 24.00
Extractor (V) 2.00
RF Lens (V) 0.2
Source Temperature (° C.) 130
Desolvation Temperature (° C.) 400
Cone Gas Flow (L/Hr) 80
Desolvation Gas Flow (L/Hr) 800
Mass range: 60 to 1200
Scan time (sec): 0.4
LC/UV/MS—Method 5
LC instrument: Acquity Waters UPLC (or equivalent) interfaced with 2996 PDA detector
Column: Acquity UPLC BEH C18 1.7 um 50×2.1 mm
Column Temperature (° C.) 30.0
Mobile phases: 95:5 H2O:ACN+(0.1% HCOOH) (A); 5:95 H2O:ACN+(0.1% HCOOH) (B)
Flow (ml/min) 0.6 (split in MS 1:6)
Stop Time (mins) 3.5
Gradient:

| Time (min) | % A | % B |
|---|---|---|
| 0.00 | 100 | 0 |
| 0.50 | 100 | 0 |
| 10.0 | 0.0 | 100.0 |
| 11.0 | 0.0 | 100.0 |
| 12.0 | 100 | 0 |

UV detection: BPI Detection (Start Wavelength nm 210, End Wavelength nm 400,
Sampling Rate spectra/sec=20)
Injection Volume (ul)-1.00
Sample solvents: DMSO:MeOH:ACN ratio 1:3:3
MS instrument: Waters ZQ (or equivalent)
Polarity ES
Capillary (kV) 3.20
Cone (V) 25.00
Extractor (V) 3.00
RF Lens (V) 0.1
Polarity ES−
Capillary (kV) 3.40
Cone (V) 24.00
Extractor (V) 2.00
RF Lens (V) 0.2
Source Temperature (° C.) 130
Desolvation Temperature (° C.) 400
Cone Gas Flow (L/Hr) 80
Desolvation Gas Flow (L/Hr) 800

Mass range: 60 to 1200
Scan time (sec): 0.4
LC/UV/MS—Method 6
LC instrument: Acquity Waters UPLC (or equivalent) interfaced with 2996 PDA detector.
Column: Acquity UPLC CSH C18 1.7 um 130A 50×2.1 mm. Column Temperature (° C.) 50.0. Mobile phases: $HCOONH_4$ 0.025M pH 3 (A); ACN+0.1% HCOOH (B). Flow (ml/min) 0.35 (split in MS 1:3). Stop Time (mins) 10
Gradient:

| Time (min) | % A | % B |
|---|---|---|
| 0.00 | 80 | 20 |
| 5.50 | 20 | 80 |
| 7.5 | 20 | 80 |
| 8 | 80 | 20 |
| 10 | 80 | 20 |

UV detection: BPI Detection (Start Wavelength nm 210, End Wavelength nm 400, Sampling Rate spectra/sec=20). Injection Volume (ul)—2.00. Sample solvents: $H_2O$/ACN 80/20
LC/UV/MS—Method 7
LC instrument: Acquity Waters UPLC (or equivalent) interfaced with 2996 PDA detector.
Column: Kinetex 1.7u PFP 100A 100×2.1 mm (Phenomenex). Column Temperature (° C.) 55.0. Mobile phases: $HCOONH_4$ 0.025M pH 3 (A); ACN/MeOH 50/50 (B). Flow (ml/min) 0.45 (split in MS 1:3). Stop Time (mins) 10
Gradient:

| Time (min) | % A | % B |
|---|---|---|
| 0.0 | 85 | 15 |
| 5.0 | 55 | 45 |
| 5.5 | 20 | 80 |
| 6.5 | 20 | 80 |
| 7..0 | 85 | 15 |

UV detection: BPI Detection (Start Wavelength nm 210, End Wavelength nm 400, Sampling Rate spectra/sec=20). Injection Volume (ul)—2.00. Sample solvents: ACN
LC/UV/MS—Method 8
LC instrument: Acquity Waters UPLC (or equivalent) interfaced with 2996 PDA detector.
Column: Kinetex 1.7u PFP 100A 100×2.1 mm (Phenomenex). Column Temperature (° C.) 55° C. Mobile phases: $HCOONH_4$ 0.025M pH 3 (A); ACN/MeOH 85/15 (B). Flow (ml/min) 0.45 (split in MS 1:3). Stop Time (mins) 10
Gradient:

| Time (min) | % A | % B |
|---|---|---|
| 0.0 | 85 | 15 |
| 5.0 | 55 | 45 |
| 5.5 | 20 | 80 |
| 6.5 | 20 | 80 |
| 7..0 | 85 | 15 |

UV detection: BPI Detection (Start Wavelength nm 210, End Wavelength nm 400, Sampling Rate spectra/sec=20). Injection Volume (ul)—2.00. Sample solvents: ACN
LC/UV/MS—Method 9
LC instrument: Acquity Waters UPLC (or equivalent) interfaced with 2996 PDA detector.
Column: Acquity UPLC BEH C18 1.7 um 50×2.1 mm. Column Temperature (° C.) 40.0.
Mobile phases: 95:5 H2O:ACN+(0.1% HCOOH) (A); 5:95 H2O:ACN+(0.1% HCOOH) (B). Flow (ml/min) 1 mL/min. Stop Time (mins) 2. Gradient:

| Time (min) | % A | % B |
|---|---|---|
| 0.00 | 99 | 1 |
| 1.50 | 0.1 | 99.9 |
| 1.90 | 0.1 | 99.9 |
| 2.00 | 99 | 1 |

UV detection: BPI Detection (Start Wavelength nm 210, End Wavelength nm 400, Sampling Rate spectra/sec=20). Injection Volume (ul)-1.00
LC/UV/MS—Method 10
LC instrument: Acquity Waters UPLC (or equivalent) interfaced with 2996 PDA detector.
Column: Acquity UPLC BEH C18 1.7 um 50×2.1 mm. Column Temperature (° C.) 40.0.
Mobile phases: 95:5 H2O:ACN+(0.1% HCOOH) (A); 5:95 H2O:ACN+(0.1% HCOOH) (B). Flow (ml/min) 1 mL/min. Stop Time $(mins)_4$
Gradient:

| Time (min) | % A | % B |
|---|---|---|
| 0.00 | 99 | 1 |
| 3.50 | 0.1 | 99.9 |
| 3.90 | 0.1 | 99.9 |
| 4.00 | 99 | 1 |

UV detection: BPI Detection (Start Wavelength nm 210, End Wavelength nm 400, Sampling Rate spectra/sec=20). Injection Volume (ul)—1.00
LC/UV/MS—Method 11
LC instrument: Acquity Waters UPLC (or equivalent) interfaced with 2996 PDA detector.
Column: Phenomenex Kinetex 1.7 um C8 100*2.1 mm. Column Temperature (° C.) 55.0.
Mobile phases: Ammonium Formate 25 mM pH 3(A): ACN+ 0.1% (B). Flow (ml/min) 0.5 mL/min. Stop Time (mins) 10
Gradient:

| Time (min) | % A | % B |
|---|---|---|
| 0.0 | 99 | 1 |
| 0.5 | 99 | 1 |
| 3.0 | 70 | 30 |
| 6.5 | 50 | 50 |
| 7.5 | 20 | 80 |
| 8.0 | 20 | 80 |
| 8.10 | 99 | 1 |
| 10.0 | 99 | 1 |

UV detection: BPI Detection (Start Wavelength nm 210, End UV detection: BPI Detection (Start Wavelength nm 210, End Wavelength nm 400, Sampling Rate spectra/sec=20). Injection Volume (ul)—1.00
LC/UV/MS—Method 12
LC instrument: UPLC/MS (ES+/ES−) Acquity™ system coupled with coupled with a ZQ mass Spectrometer. Column: Acquity UPLC CSH C18 column (50 mm×2.1 mm i.d. 1.7 μm particle size). Column Temperature (° C.) 40.0. Mobile phases: 0.1% v/v solution of HCOOH in water (A);

0.1% v/v solution of HCOOH in Acetonitrile (B). Flow (ml/min) 1. Stop Time (mins) 2.0

Gradient:

| Time (min) | % A | % B |
|---|---|---|
| 0.00 | 97 | 3 |
| 1.50 | 0.1 | 99.9 |
| 1.90 | 0.1 | 99.9 |
| 2.00 | 97 | 3 |

UV detection range: 210 nm to 350 nm. Acquisition rate Hz=20. Injection mode: Partial Loop with Needle Overfill. DAD-MS Rt offset: 0.01 min LC/UV/MS—Method 13

LC instrument: UPLC/MS (ES+/ES−) Acquity™ system coupled a Waters SQD mass spectrometer. Column: Acquity UPLC CSH C18 column (50 mm×2.1 mm i.d. 1.7 µm particle size). Column Temperature (° C.) 40.0. Mobile phases: 0.1% v/v solution of HCOOH in water (A); 0.1% v/v solution of HCOOH in Acetonitrile (B). Flow (ml/min) 1. Stop Time (mins) 2.0

Gradient:

| Time (min) | % A | % B |
|---|---|---|
| 0.00 | 97 | 3 |
| 1.50 | 0.1 | 99.9 |
| 1.90 | 0.1 | 99.9 |
| 2.00 | 97 | 3 |

UV detection range: 210 nm to 350 nm Acquisition rate Hz=40. Injection mode: Partial Loop with Needle Overfill. DAD-MS Rt offset: 0.01 min LC/UV/MS—Method 14

LC instrument: UPLC/MS (ES+/ES−) Acquity™ system coupled a Waters SQD2 mass spectrometer. Column: Acquity UPLC CSH C18 column (50 mm×2.1 mm i.d. 1.7 µm particle size). Column Temperature (° C.) 40.0. Mobile phases: 0.1% v/v solution of HCOOH in water (A); 0.1% v/v solution of HCOOH in Acetonitrile (B). Flow (ml/min) 1. Stop Time (mins) 2.0

Gradient:

| Time (min) | % A | % B |
|---|---|---|
| 0.00 | 97 | 3 |
| 1.50 | 0.1 | 99.9 |
| 1.90 | 0.1 | 99.9 |
| 2.00 | 97 | 3 |

UV detection range: 210 nm to 350 nm. Acquisition rate Hz=40

Injection mode: Partial Loop with Needle Overfill. DAD-MS Rt offset: 0.01 min

LC/UV/MS—Method 15

LC instrument: UPLC/MS (ES+/ES−) Acquity™ system coupled a Waters SQD2 mass spectrometer. Column: Acquity UPLC BEH C18 column (50 mm×2.1 mm i.d. 1.7 µm particle size). Column Temperature (° C.) 40.0 Mobile phases: H2O+0.1% Ammonia aqueous solution pH 10 (A); Acetonitrile (B). Flow (ml/min)$_1$. Stop Time (mins) 2.0

Gradient:

| Time (min) | % A | % B |
|---|---|---|
| 0.00 | 97 | 3 |
| 1.50 | 0.1 | 99.9 |
| 1.90 | 0.1 | 99.9 |
| 2.00 | 97 | 3 |

UV detection range: 210 nm to 350 nm. Acquisition rate Hz=40. Injection mode: Partial Loop with Needle Overfill. Scan Duration: 0.10 sec LC/UV/MS—Method 16

LC instrument: UPLC/PDA/MS Acquity™ system coupled a Waters SQD mass spectrometer. Column: Acquity UPLC BEH C18 column (50 mm×2.1 mm i.d. 1.7 µm particle size). Column Temperature (° C.) 40.0. Mobile phases: 10 mM ammonium bicarbonate aqueous solution adjusted to pH 10 with ammonia (A); Acetonitrile (B). Flow (ml/min)$_1$. Stop Time (mins) 2.0

Gradient:

| Time (min) | % A | % B |
|---|---|---|
| 0.00 | 97 | 3 |
| 1.50 | 0.1 | 99.9 |
| 1.90 | 0.1 | 99.9 |
| 2.00 | 97 | 3 |

UV detection range: 210 nm to 350 nm. Acquisition rate Hz=40. Injection mode: Partial Loop with Needle Overfill. Scan Duration: 0.10 sec Analytical Chiral for Chiral Compounds The enantiomeric access of chiral compounds are determined by chiral HPLC analysis on a HPLC Agilent 1100 equipped with 6-position switching valve, DAD, and CD detectors. The following methods were used:

Method A1: Column: Chiralpak AD-H (25×0.46 cm), 5 um; Mobile phase: n-Hexane/(2-Propanol+0.1% isopropylamine) 75/25% v/v; Flow rate: 1.0 mL/min; DAD: 220 nm.

Method A2: Column: Whelk O-1 (R,R) (25×0.46 cm), 5 um; Mobile phase: n-Hexane/(Ethanol/Methanol 1/1) 40/60% v/v; Flow rate: 1.0 mL/min; DAD: 220 nm.

Method A3: Column: Chiralpak IA (25×0.46 cm), 5 um; Mobile phase: n-Hexane/(2-Propanol/Methanol 1/1) 60/40% v/v; Flow rate: 1.0 mL/min; DAD: 220 nm.

Method A4: Column: Chiralpak IC (25×0.46 cm), 5 um; Mobile phase: n-Hexane/(2-Propanol/Methanol 1/1+0.1% isopropylamine) 90/10% v/v; Flow rate: 1.0 mL/min; DAD: 220 nm.

Method A5: Column: Chiralpak AD-H (25×0.46 cm), 5 um; Mobile phase: n-Hexane/(2-Propanol+0.1% isopropylamine) 80/20% v/v; Flow rate: 1.0 mL/min; DAD: 220 nm; CD: 240 nm.

Method A6: Column: Whelk O-1 (R,R) (25×0.46 cm), 10 um; Mobile phase: n-Hexane/(2-Propanol+0.1% isopropylamine) 40/60% v/v; Flow rate: 1.0 mL/min; DAD: 220 nm.

Method A7: Column: Whelk O-1 (R,R) (25×0.46 cm), 10 um; Mobile phase: n-Hexane/(Ethanol/Dichloromethane 9/1+0.1% isopropylamine) 40/60% v/v; Flow rate: 1.0 mL/min; DAD: 280 nm.

Method A8: Column: Whelk 0-1 (R,R) (25×0.46 cm), 5 um; Mobile phase: n-Hexane/(Ethanol/Dichloromethane 9/1+0.1% isopropylamine) 70/30% v/v; Flow rate: 1.0 mL/min; DAD: 280 nm.

Method A9: Column: Chiralpak IC (25×0.46 cm), 5 um; Mobile phase: n-Hexane/(Ethanol+0.1% isopropylamine) 70/30% v/v; Flow rate: 0.8 mL/min; DAD: 220 nm.

Method A10: Column: Chiralpak AS-H (25×0.46 cm), 5 um; Mobile phase: n-Hexane/(2-Propanol/Methanol+0.1% isopropylamine) 85/15% v/v; Flow rate: 1.0 mL/min; DAD: 220 nm.

Method A11: Column: Chiralpak AD-H (25×0.46 cm), 5 um; Mobile phase: n-Hexane/(Ethanol/Methanol 1/1+0.1% isopropylamine) 80/20% v/v; Flow rate: 0.8 mL/min; DAD: 220 nm.

Method A12: Column: Chiralpak AD-H (25×0.46 cm), 5 um; Mobile phase: n-Hexane/(Ethanol+0.1% Isopropylamine) 75/25% v/v; Flow rate: 0.8 mL/min; DAD: 220 nm.

Method A13: Column: Whelk O-1 (R,R) (25×0.46 cm), 10 um; Mobile phase: n-Hexane/(Ethanol/Methanol 1/1+0.1% isopropylamine) 75/25% v/v; Flow rate: 1.0 mL/min; DAD: 220 nm.

Method A14: Column: Whelk O-1 (R,R) (25×0.46 cm), 10 um; Mobile phase: n-Hexane/(Ethanol+0.1% isopropylamine) 50/50% v/v; Flow rate: 0.8 mL/min; DAD: 220 nm.

Method A15: Column: Chiralpak IC (25×0.46 cm), 5 um; Mobile phase: n-Hexane/(2-Propanol/Methanol 1/1+0.1% isopropylamine) 60/40% v/v; Flow rate: 1.0 mL/min; DAD: 220 nm.

Method A16: Column: Chiralpak AD-H (25×0.46 cm), 5 um; Mobile phase: n-Hexane/(Ethanol+0.1% isopropylamine) 80/20% v/v; Flow rate: 1.0 mL/min; DAD: 220 nm.

Preparative Reverse-Phase HPLC Conditions
Preparative HPLC—Method 1
Waters Micromass ZQ/Sample manager 2767
Photodiode array detector 2996;
Column: XTerra Prep MS C18 Column (5 μM, 19×150 mm, Waters)
Flow rate: 20 ml/min with MS detection
UV wavelength: 254 nm.
Mobile phase: Solvent A (water:MeCN:HCOOH 95:5:0.05); Solvent B (water:MeCN:HCOOH 5:95:0.05)
Gradient:

| Time (min) | % A | % B |
|---|---|---|
| 0.00 | 100.0 | 0.00 |
| 1.00 | 100 | 0.00 |
| 10.00 | 0.00 | 100.0 |
| 11.00 | 0.00 | 100.0 |
| 12.00 | 100.0 | 0.00 |

Preparative HPLC—Method 2
Column: Waters Symmetry Prep C18 17 um 19×300
Flow: 20 ml/min
Mobile phase: 90% $H_2O$, 10% acetonitrile, 0.05% TFA (A); 10% $H_2O$, 90% acetonitrile, 0.05% TFA (B)
Gradient:

| Time (min) | % A | % B |
|---|---|---|
| 0.00 | 95 | 5 |
| 2.5 | 95 | 5 |
| 22 | 0 | 100 |
| 30 | 0 | 100 |

Preparative HPLC—Method 3
Waters Micromass ZQ/sample manager 2767
Photodiode array detector: 2996
Column: XTERRA Prep MS C18 10 um 19×300
Flow: 20 ml/min
Mobile phases: $H_2O$, 0.1% TFA (A); acetonitrile, 0.1% TFA (B)
Gradient:

| Time (min) | % A | % B |
|---|---|---|
| 0.00 | 90 | 10 |
| 2 | 90 | 10 |
| 23 | 0 | 100 |
| 30 | 0 | 100 |

Conditioning:

| Time (min) | % A | % B |
|---|---|---|
| 30.5 | 90 | 10 |
| 32 | 90 | 10 |

Preparative HPLC—Method 4
Waters Fractionlynx with ZQ MS detector. Column: XSelect CSH Prep. C18 5 um OBD 30×100 mm. Flow rate: 43 ml/min. UV wavelength: 210 nm to 350 nm. Ionization mode: Positive Electrospray (ES+). Mobile phase: Solvent A (H2O+0.1% HCOOH); Solvent B (Acetonitrile)
Gradient:

| Time (min) | % A | % B |
|---|---|---|
| 0.00 | 97.0 | 3.0 |
| 10.00 | 50.0 | 50.0 |
| 10.5 | 0.0 | 100.0 |
| 14.5 | 0.0 | 100.0 |
| 15.0 | 97.0 | 3.0 |

Chiral Preparative HPLC for Chiral Compounds

Chiral resolutions were performed using a Semipreparative Waters 600 system or a Semipreparative Agilent 1100 system. The conditions are reported in the Examples.

Where the preparation of starting materials is not described, these are commercially available, known in the literature, or readily obtainable by those skilled in the art using standard procedures.

Flash chromatography is carried out using an Isolera MPLC system (manufactured by Biotage) using pre-packed silica gel or reverse-phase cartridges (supplied by Biotage).

Many of the compounds described in the following Examples have been prepared from stereochemically pure starting materials, for example 95% ee.

The stereochemistry of the compounds in the Examples, where indicated, has been assigned on the assumption that absolute configuration at resolved stereogenic centers of starting materials is maintained throughout any subsequent reaction conditions.

In the procedures that follow, after each starting material, reference to a compound number is sometimes provided. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

Preparation Of Intermediates

Intermediate A1.
4-Bromo-3-(hydroxymethyl)-1H-isochromen-1-one

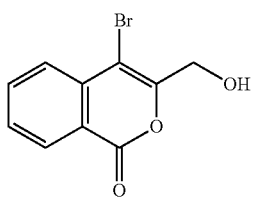 [SMILES: O=c1oc(CO)c(Br)c2ccccc12]

Step 1. Methyl 2-(3-hydroxyprop-1-ynyl)benzoate. (Intermediate 1.1)

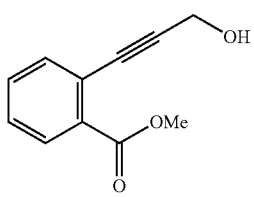 [SMILES: COC(=O)c1ccccc1C#CCO]

Methyl 2-iodobenzoate (25 g, 95 mmol), prop-2-yn-1-ol (8.02 g, 143 mmol) and TEA (26.6 ml, 191 mmol) were added to a deareated mixture of Pd(PPh$_3$)$_4$ (0.220 g, 0.191 mmol), copper(I) iodide (0.073 g, 0.382 mmol) in DMF (60 ml). The resulting mixture was stirred at 90° C. for 5 hrs and then at 40° C. overnight. The reaction mixture was poured into EtOAc (600 ml) and washed with brine (600 ml). Organic phase was then concentrated and the dark oil was rinsed with Et$_2$O (600 ml). The mixture was filtered, and then concentrated to give the title compound as deeply brown oil (13.0 g). This compound was used in the next step without any further purification and characterization.

UPLC-MS: 1.53 min, [M+H-18]+. (Method 4)

Step 2.
4-Bromo-3-(hydroxymethyl)-1H-isochromen-1-one

Methyl 2-(3-hydroxyprop-1-ynyl)benzoate (intermediate 1.1, 6 g, 31.5 mmol), copper(II) bromide (14.09 g, 63.1 mmol) and pyridine (5.10 ml, 63.1 mmol) were reacted in refluxing Acetonitrile (100 ml) for 1 hrs. Solvent was then removed under vacuum, and the crude was rinsed with DCM (200 ml) and filtered. The resulting crude product was purified over a 100 g SNAP Silica column, with a gradient of DCM and Et$_2$O to the title compound (2.5 g, 31%). $^1$H NMR (400 MHz, DMSO-d$_6$) δ ppm 8.21 (dd, 1 H), 7.94-8.05 (m, 1 H), 7.77-7.90 (m, 1 H), 7.64-7.76 (m, 1 H), 5.71 (t, J=6.39 Hz, 1 H), 4.54 (d, J=6.17 Hz, 2 H). UPLC-MS: 3.16 min, [M+H]+. (Method 5).

Intermediate A2.
4-Bromo-3-(1-hydroxyethyl)-1H-isochromen-1-one

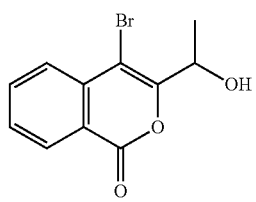

Step 1. Methyl 2-(3-hydroxybut-1-ynyl)benzoate (Intermediate 2.1)

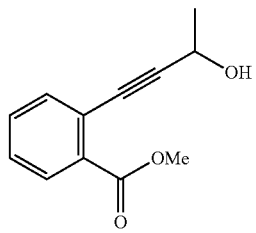

Pd(PPh$_3$)$_4$ (1.9 g, 0.006 eq) and CuI (2.6 g, 0.05 eq) were suspended in DMF (350 ml). Methyl 2-iodobenzoate (70.8 g, 1 eq), but-3-yn-2-ol (32 ml, 1.5 eq), TEA (75 ml, 2 eq) were added under nitrogen atmosphere and the mixture was stirred at 60° C. for 6 hrs and at RT. overnight. The precipitated solid was filtered off, the mother liquors was diluted with a saturated solution of NaCl$_{aqueous}$ and extracted with EtOAc (twice). The collected organic phases were dried over Na$_2$SO$_4$, filtered and concentrated under reduced pressure to give the title compound, as a brownish thick oil (47.7 g).

Step 2.
4-Bromo-3-(1-hydroxyethyl)-1H-isochromen-1-one

Methyl 2-(3-hydroxybut-1-ynyl)benzoate (intermediate 2.1, 20.6 g, 100.98 mmol) was dissolved in DCE (200 ml), CuBr$_2$ (45 g, 201.96 mmol) and dicyclohexylamine hydrochloride (2.2 g, 10.1 mmol) were added at RT. The mixture was heated under nitrogen atmosphere to 65° C. for 2 hrs. The mixture was thus filtered over a Celite® pad and washed with DCM. The mother liquors were concentrated under vacuum and the residue was purified by column chromatography over silica gel (Hex/EtOAc 8:2). The solid residue was triturated with Hex/Et$_2$O (1:1) to give the title compound, as a pale yellow powder (8.7 g, 32%).

$^1$H NMR (400 MHz, DMSO-d6) d ppm 8.20 (d, J=7.50 Hz, 1 H), 7.99 (m, 1 H), 7.85 (d, J=8.38 Hz, 1 H), 7.71 (m, 1 H), 5.66 (d, J=5.29 Hz, 1 H), 5.12 (m, 1 H), 1.38 (d, J=6.62 Hz, 3 H). UPLC-MS: 1.83 min, 267 [M+H]+ (method 1).

Intermediate A3. tert-Butyl 1-(4-bromo-1-oxo-1H-isochromen-3-yl)ethylcarbamate

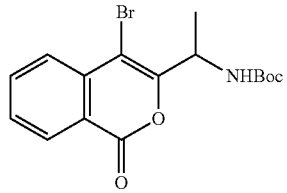 [SMILES: CC(NC(=O)OC(C)(C)C)c1oc(=O)c2ccccc2c1Br]

Step 1. But-3-yn-2-yl methanesulfonate. (intermediate 3.1)

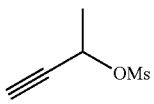

But-3-yn-2-ol (25 ml, 317 mmol) was dissolved in DCM (6 vol) under nitrogen atmosphere. TEA (66 ml, 475.5 mmol) was added and the mixture was cooled to 5° C. Methanesulfonyl chloride (29 ml, 380.4 mmol) was added drop-wise. The reaction was then allowed to warm up to RT and the stirring was continued overnight. The reaction mixture was then poured into water, and extracted with DCM (twice). The collected organic phases were washed with a saturated solution of NaHCO₃, dried over Na₂SO₄ filtered and concentrated under vacuum to give the title compound as a thick oil (34 g).

Step 2. tert-Butyl but-3-yn-2-ylcarbamate. (intermediate 3.2)

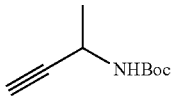

But-3-yn-2-yl methanesulfonate (intermediate 3.1, 34 g) was vigorously stirred in 28-30% aqueous NH₄OH (31 ml) overnight at RT. DCM was added (200 ml) and the phases were separated. The organic phase was dried over Na₂SO₄ and filtered. The residual organic phase was heated to 40° C. until the vapour no longer gave a positive alkali test. The solution was added with TEA (47.7 ml) and di-tert-butyl dicarbonate (50 g, 1 eq) and left on stirring for 20 hrs. The reaction was quenched with water and the product extracted with DCM. The collected organic phases were dried over Na₂SO₄, filtered and concentrated under reduced pressure to give the title compound (26.3 g, 68%).

Step 3. Methyl 2-(3-(tert-butoxycarbonylamino)but-1-ynyl)benzoate. (intermediate 3.3)

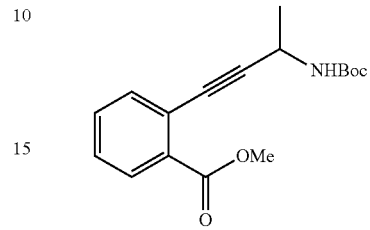

Pd(Ph₃P)₄ (683 mg, 0.591 mmol), CuI (938 mg, 49.2 mmol), methyl 2-iodobenzoate (25.8 g, 98.49 mmol), tert-butyl but-3-yn-2-ylcarbamate (intermediate 3.2, 25 g, 147.75 mmol) in DMF (30 ml) and Et₃N (27 ml) were mixed in DMF (125 ml) and the mixture was heated to 60° C. under nitrogen atmosphere for 12 hrs. The mixture was quenched with water and the product extracted with EtOAc. The collected organic phases were dried over Na₂SO₄, filtered and concentrated under reduced pressure. The residual was purified by column chromatography over silica gel (Hex/EtOAc 9:1) to give the title compound (15.3 g, 51%).

Step 4. tert-Butyl 1-(4-bromo-1-oxo-1H-isochromen-3-yl)ethylcarbamate

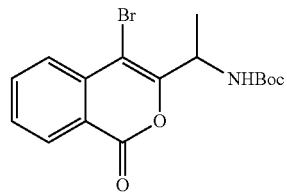 [SMILES: CC(NC(=O)OC(C)(C)C)c1oc(=O)c2ccccc2c1Br]

Methyl 2-(3-(tert-butoxycarbonylamino)but-1-ynyl)benzoate (intermediate 3.3, 5.6 g, 18.48 mmol) was dissolved in DCE (110 ml) under N₂ atmosphere; dicyclohexylamine hydrochloride (401 mg, 1.85 mmol) and CuBr₂ (8.3 g, 37 mmol) were added. The mixture was stirred at 70° C. for 3 hrs and at RT overnight. The mixture was then filtered on a Celite® pad, washed with DCM and the mother liquors were concentrated under vacuum. The crude residue was purified by column chromatography over silica gel (DCM/EtOAc 8:2) and the achieved solid residue triturated with Hexane (4 vol) and Et₂O (few drops) to give the title compound (2.3 g, 34%).

1H NMR (400 MHz, DMSO-d6) d ppm 8.19 (d, J=7.72 Hz, 1 H), 7.92-8.06 (m, 1 H), 7.83 (d, J=7.94 Hz, 1 H), 7.65-7.75

(m, 1 H), 7.58 (d, J=5.73 Hz, 1 H), 4.76-5.13 (m, 1 H), 1.12-1.49 (m, 12 H). UPLC-MS (method 1).

Intermediate A4. 4-bromo-3-(1-hydroxyethyl)-7-methyl-1H-isochromen-1-one

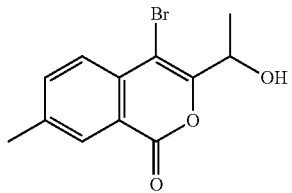 [SMILES: Cc1ccc2c(Br)c(C(C)O)oc(=O)c2c1]

Title compound was prepared following the procedure used for the synthesis of Intermediate A2, from methyl 2-iodo-5-methyl-benzoate (2.0 g, 7.2 mmol) and but-3-yn-2-ol (0.850 ml, 10.87 mmol), to afford title compound (1.04 g, 3.67 mmol, 53%).
UPLC-MS: 0.96 min, 283.1-285.1 [M+H]+, method 13.

Intermediate A5. 4-bromo-7-chloro-3-(1-hydroxyethyl)-1H-isochromen-1-one

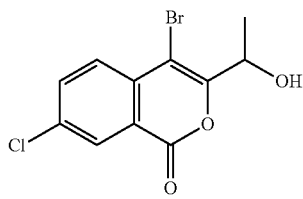 [SMILES: CC(O)c1oc(=O)c2cc(Cl)ccc2c1Br]

Step 1. methyl 5-chloro-2-iodobenzoate (Intermediate A5.1)

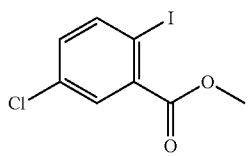

A solution of 5-chloro-2-iodobenzoic acid (3.0 g, 10.62 mmol), $SOCl_2$ (12 mL) and DMF (0.6 mL) was gently warmed with a heat gun until the mixture became homogeneous (15 min). The solution was maintained at 23° C. for additional 30 min and then the solution was concentrated. MeOH (24 mL) was added to the crude residue and the solution was maintained at 23° C. for 30 min. The solution was concentrated and the residue was purified by flash chromatography on Biotage silica gel cartridge (cyclohexane to cyclohexane:EtOAc=85:15) to afford methyl 5-chloro-2-iodobenzoate (3.02 g, 10.20 mmol, 96%).
UPLC-MS: 1.17 min, 296.6 [M+H]+, method 12.

Step 2

Title compound was prepared following the procedure used for the synthesis of Intermediate A2 from methyl 5-chloro-2-iodobenzoate (intermediate A5.1, 3.02 g, 10.18 mmol) and but-3-yn-2-ol (1.2 ml, 15.28 mmol), to afford title compound as a yellow solid (1.4 g, 4.61 mmol).
UPLC-MS: 0.97 min, 302.7-304.7 [M+H]+, method 12.

Intermediate A6. 4-bromo-6-chloro-3-(1-hydroxyethyl)-1H-isochromen-1-one

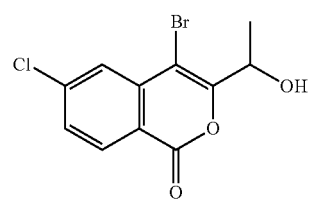 [SMILES: CC(O)c1oc(=O)c2ccc(Cl)cc2c1Br]

Step 1. methyl 4-chloro-2-iodobenzoate (Intermediate A6.1)

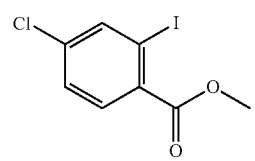

Title compound was prepared following the procedure used for the synthesis of Intermediate A5.1 from 4-chloro-2-iodobenzoic acid (2.00 g, 7.08 mmol) to afford title compound as a white solid (2.07 g, 6.98 mmol, 99%).
UPLC-MS: 1.20 min, 297.0 [M+H]+, method 13.

Step 2

Title compound was prepared following the procedure used for the synthesis of Intermediate A2 from methyl 4-chloro-2-iodobenzoate (intermediate A6.1, 2.07 g, 6.98 mmol) and but-3-yn-2-ol (0.821 ml, 10.47 mmol), to afford title compound as a beige solid (1.388 g, 4.58 mmol)
UPLC-MS: 1.00 min, 303.0-305.0 [M+H]+, method 13.

Intermediate A7. 4-bromo-6-fluoro-3-(1-hydroxyethyl)-1H-isochromen-1-one

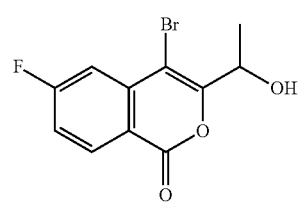 [SMILES: CC(O)c1oc(=O)c2ccc(F)cc2c1Br]

Step 1. methyl 4-fluoro-2-iodobenzoate (Intermediate A7.1)

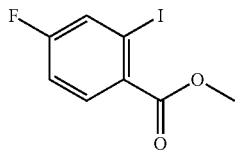

Title compound was prepared following the procedure used for the synthesis of Intermediate A5.1 from 4-fluoro-2-iodobenzoic acid to afford methyl 4-fluoro-2-iodobenzoate (Intermediate A7.1, 1.153 g, 4.11 mmol, 99%).

UPLC-MS: 1.09 min, 281.0 [M+H]+, method 13.

Step 2

Title compound was prepared following the procedure used for the synthesis of Intermediate A2 from methyl 4-fluoro-2-iodobenzoate (intermediate A7.1, 1.153 g, 4.11 mmol) and but-3-yn-2-ol (0.484 ml, 6.176 mmol) to afford title compound (1 g, 3.48 mmol)

UPLC-MS: 0.89 min, 287.0-289.0 [M+H]+, method 13.

Intermediate A8. 4-bromo-3-(1-((tert-butyldimethylsilyl)oxy)ethyl)-1H-isochromen-1-one

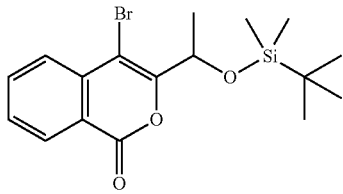 [SMILES: CC(O[Si](C)(C)C(C)(C)C)c1oc(=O)c2ccccc2c1Br]

4-Bromo-3-(1-hydroxyethyl)-1H-isochromen-1-one (intermediate A2, 5 g, 18.658 mmol) was dissolved in DCM (50 ml); imidazole (2.54 g, 37.3 mmol) and tert-butyl(chloro)dimethylsilane (5.624 g, 37.3 mmol) were added and the mixture was stirred at RT for 1 hr. The mixture was washed with brine, the organic phase was dried over sodium sulfate and solvent removed under reduced pressure to afford a crude which was purified by flash chromatography on silica gel Biotage column (cyclohexane:EtOAc=95:5 to 60:40) affording title compound as a white solid (6.5 g, 16.97 mmol, 91%).

UPLC-MS: 1.58 min, 383.3-385.3 [M+H]+, method 13.

Intermediate B1. 3-(1-Hydroxyethyl)-4-phenyl-1H-isochromen-1-one

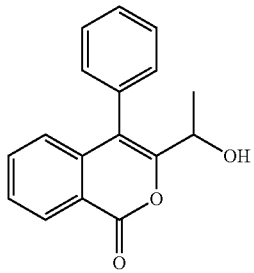 [SMILES: CC(O)c1oc(=O)c2ccccc2c1-c1ccccc1]

4-Bromo-3-(1-hydroxyethyl)-1H-isochromen-1-one (Intermediate A2, 0.77 g, 2.88 mmol), phenylboronic acid (0.63 g, 5.18 mmol), Pd(PPh₃)₄ (0.199 g, 0.173 mmol) and Cs₂CO₃ (1.49 g, 4.6 mmol) were dissolved in DMF (10.7 ml) and heated under microwave irradiation at 120° C. for 20 min. The reaction mixture was then diluted with AcOEt (100 mL) and filtrate. The organic phase was washed twice with 0.5 M HCl$_{aqueous}$, twice with water, sat NaHCO₃ and once with sat NaCl$_{aqueous}$. The resulting organic phase was dried over Na₂SO₄, filtered and concentrated. The crude was finally purified on Biotage Si 50 g Ultra with a gradient of Hexane and EtOAc. The title compound was recovered as dark pink solid (0.53 g, 1.99 mmol, 69.3%) as a dark pink solid.

UPLC-MS: 1.83 min, 267 [M+H]+, method 1.

Intermediate B2. 3-(Hydroxymethyl)-4-phenyl-1H-isochromen-1-one

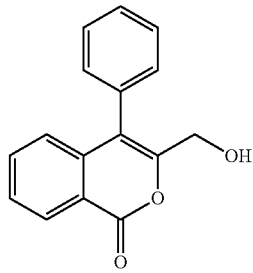 [SMILES: O=c1oc(CO)c(-c2ccccc2)c2ccccc12]

The title compound was made in a similar way as that of the intermediate B1, starting from 4-bromo-3-(hydroxymethyl)-1H-isochromen-1-one (Intermediate A1, 0.8 g, 3.14 mmol), phenylboronic acid (0.467 g, 3.83 mmol), Pd(PPh₃)₄ (0.181 g, 0.379 mmol) and Cs₂CO₃ (3.29 g, 10.11 mmol) to afford the title compound (210 mg, 36%).

UPLC-MS: 1.80 min, 271 [M+H]+, method 4.

Intermediate B3. 4-(3-Fluorophenyl)-3-(hydroxymethyl)-1H-isochromen-1-one

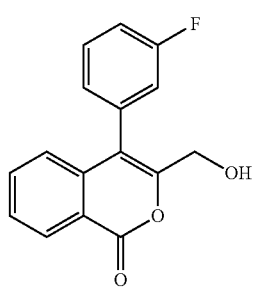 [SMILES: O=c1oc(CO)c(-c2cccc(F)c2)c2ccccc12]

The title compound was made in a similar way as that of the intermediate B2 using 4-bromo-3-(hydroxymethyl)-1H-isochromen-1-one (Intermediate A1, 0.5 g, 1.960 mmol), 3-fluorophenylboronic acid (0.4 g, 2.86 mmol), Pd(PPh₃)₄ (0.136 g, 0.118 mmol) and Cs₂CO₃ (0.96 g, 2.94 mmol) to afford the title compound (0.21 g, 40%).

UPLC-MS: 1.80 min, 271 [M+H]+, method 4.

Intermediate B4. 4-(2-Fluorophenyl)-3-(hydroxymethyl)-1H-isochromen-1-one

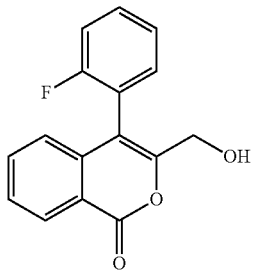 [SMILES: O=c1oc(CO)c(-c2ccccc2F)c2ccccc12]

The title compound was made in a similar way as that of the intermediate B2 using 4-bromo-3-(hydroxymethyl)-1H-isochromen-1-one (Intermediate A1, 0.6 g, 2.352 mmol), 2-fluorophenylboronic acid (0.494 g, 3.53 mmol), Pd(PPh$_3$)$_4$ (0.136 g, 0.118 mmol) and Cs$_2$CO$_3$ (0.77 g, 2.35 mmol) to afford the title compound (0.21 g, 33%).
UPLC-MS: 1.80 min, 271 [M+H]+, method 4.

Intermediate B5. 3-(Hydroxymethyl)-4-m-tolyl-1H-isochromen-1-one

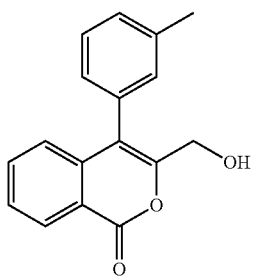 [SMILES: Cc1cccc(-c2c(CO)oc(=O)c3ccccc23)c1]

The title compound was made in a similar way as that of the intermediate B2 using 4-bromo-3-(hydroxymethyl)-1H-isochromen-1-one (Intermediate A1, 0.5 g, 1.96 mmol), m-tolylboronic acid (0.400 g, 2.94 mmol), Pd(PPh$_3$)$_4$ (0.113 g, 0.098 mmol) and Cs$_2$CO$_3$ (0.64 g, 1.96 mmol) to afford the title compound (0.21 g, 40%).
UPLC-MS: 1.89 min, 267 [M+H]+, method 4.

Intermediate B6. 3-(1-Hydroxyethyl)-4-m-tolyl-1H-isochromen-1-one

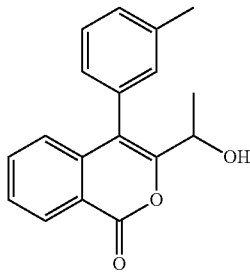 [SMILES: Cc1cccc(-c2c(C(C)O)oc(=O)c3ccccc23)c1]

The title compound was made in a similar way as that of the intermediate B1 using 4-bromo-3-(1-hydroxyethyl)-1H-isochromen-1-one (Intermediate A2, 0.52 g, 1.93 mmol), m-tolylboronic acid (0.45 g, 3.28 mmol), Pd(PPh$_3$)$_4$ (0.11 g, 0.096 mmol) and Cs$_2$CO$_3$ (0.81 g, 2.5 mmol) to afford the title compound (0.3 g, 55%).
UPLC-MS: 5.18 min, 281 [M+H]+, method 5

Intermediate B7. 4-(3-Fluorophenyl)-3-(1-hydroxyethyl)-1H-isochromen-1-one

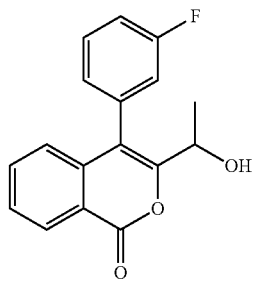 [SMILES: CC(O)c1oc(=O)c2ccccc2c1-c1cccc(F)c1]

The title compound was made in a similar way as that of the intermediate B1 using 4-bromo-3-(1-hydroxyethyl)-1H-isochromen-1-one (Intermediate A2, 0.8 g, 2.97 mmol), 3-fluorophenylboronic acid (0.62 g, 4.46 mmol), Pd(PPh$_3$)$_4$ (0.17 g, 0.149 mmol) and Cs$_2$CO$_3$ (0.97 g, 2.9 mmol) to afford the title compound (0.39 g, 46%).
UPLC-MS: 1.85 min, 285 [M+H]+, method 5.

Intermediate B8. 4-(3-(Dimethylamino)phenyl)-3-(1-hydroxyethyl)-1H-isochromen-1-one

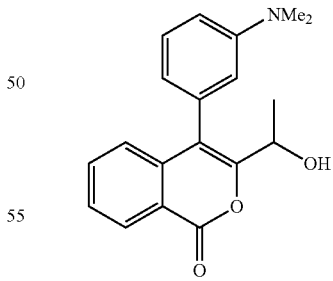

The title compound was made in a similar way as that of the intermediate B1 using 4-bromo-3-(1-hydroxyethyl)-1H-isochromen-1-one (Intermediate A2, 0.5 g, 1.86 mmol), 3-(dimethylamino)phenylboronic acid (0.46 g, 2.79 mmol), Pd(PPh$_3$)$_4$ (0.11 g, 0.093 mmol) and Cs$_2$CO$_3$ (0.78 g, 2.41 mmol) to afford the title compound (0.2 g, 35%).
UPLC-MS: 1.87 min, 350 [M+H+ACN]+, method 4.

Intermediate B9. 3-(1-Hydroxyethyl)-4-(3-(morpholinosulfonyl)phenyl)-1H-isochromen-1-one

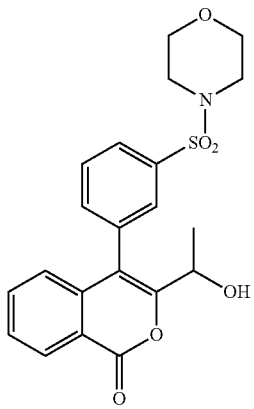

The title compound was made in a similar way as that of the intermediate B1 using 4-bromo-3-(1-hydroxyethyl)-1H-isochromen-1-one (Intermediate A2, 0.3 g, 1.11 mmol), 3-(4-morpholinosulfonyl)phenylboronic acid (0.45 g, 1.67 mmol), Pd(PPh$_3$)$_4$ (0.064 g, 0.056 mmol) and Cs$_2$CO$_3$ (0.47 g, 1.45 mmol) to afford the tile compound (0.163 g, 35%).
UPLC-MS: 1.70 min, 416 [M+H]+, method 4.

Intermediate B10. 3-(1-Hydroxyethyl)-4-(6-methylpyridin-3-yl)-1H-isochromen-1-one

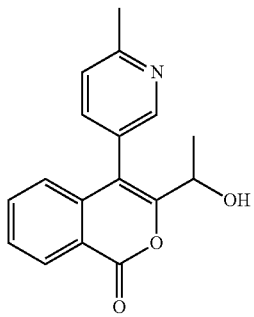 [SMILES: Cc1ccc(-c2c(C(C)O)oc(=O)c3ccccc23)cn1]

The title compound was made in a similar way as that of the intermediate B1 using 4-bromo-3-(1-hydroxyethyl)-1H-isochromen-1-one (Intermediate A2, 0.55 g, 2.04 mmol), 6-methylpyridin-3-ylboronic acid (0.550 g, 2.0 mmol), Pd(PPh$_3$)$_4$ (0.118 g, 0.102 mmol) and Cs$_2$CO$_3$ (1.06 g, 3.27 mmol) to afford the title compound (0.163 g, 28%)
UPLC-MS: 1.25 min, 282 [M+H]+, method 4.

Intermediate B11. 3-(1-Hydroxyethyl)-4-(thiazol-5-yl)-1H-isochromen-1-one

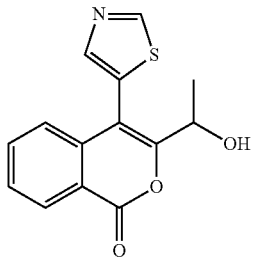 [SMILES: CC(O)c1oc(=O)c2ccccc2c1-c1cncs1]

4-Bromo-3-(1-hydroxyethyl)-1H-isochromen-1-one (Intermediate A2, 0.1 g, 0.372 mmol), 6-methyl-2-(thiazol-5-yl)-1,3,6,2-dioxazaborocane-4,8-dione (0.134 g, 0.56 mmol), Pd(PPh$_3$)$_4$ (0.021 g, 0.019 mmol) and Cs$_2$CO$_3$ (0.182 g, 0.56 mmol) in DMF (1 mL) were heated under microwave irradiation at 120° C. for 1 hrs and 15 min. Then, further 6-methyl-2-(thiazol-5-yl)-1,3,6,2-dioxazaborocane-4,8-dione (0.134 g, 0.56 mmol), Pd(PPh$_3$)$_4$ (0.021 g, 0.019 mmol) and Cs$_2$CO$_3$ (0.182 g, 0.56 mmol) were added and then resulting mixture was reacted for 5 hrs at 100° C. The crude product was purified via reverse phase chromatography with a Biotage C18 30 g SNAP column (Phase A, water 95%, ACN 4.9%, formic acid 0.1%; Phase B ACN 99.9%, formic acid 0.1%) to give the title compound (102 mg).
UPLC-MS: 1.48 min, 274 [M+H]+, method 4

Intermediate B12. tert-Butyl 4-(3-(1-hydroxyethyl)-1-oxo-1H-isochromen-4-yl)-5,6-dihydro-pyridine-1(2H)-carboxylate

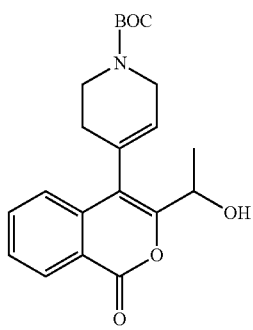 [SMILES: CC(O)c1oc(=O)c2ccccc2c1C1=CCN(C(=O)OC(C)(C)C)CC1]

The title compound was made in a similar way as that of the intermediate B1 using 4-bromo-3-(1-hydroxyethyl)-1H-isochromen-1-one (intermediate A2, 0.55 g, 2.04 mmol), tert-butyl 4-(4,4,5,5-tetramethyl-1,3,2-dioxaborolan-2-yl)-5,6-dihydropyridine-1(2H)-carboxylate (0.79 g, 2.55 mmol), Pd(PPh$_3$)$_4$ (118 mg, 0.102 mmol) and Cs$_2$CO$_3$ (1.0 g, 3.27 mmol) to afford the title compound (0.135 g, 18%) as a yellowish oil.
UPLC-MS: 1.91 min, 371 [M+H]+, method 4

Intermediate B13. 3-(1-Hydroxyethyl)-4-(2-methylpyridin-4-yl)-1H-isochromen-1-one

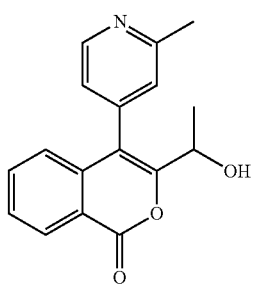 [SMILES: Cc1cc(-c2c(C(C)O)oc(=O)c3ccccc23)ccn1]

The title compound was made in a similar way as that of the intermediate B1 using 4-bromo-3-(1-hydroxyethyl)-1H-isochromen-1-one (Intermediate A2, 0.5 g, 1.86 mmol), 2-methylpyridin-4-ylboronic acid (0.38 g, 2.79 mmol), Pd(PPh$_3$)$_4$ (0.107 g, 0.093 mmol) and Cs$_2$CO$_3$ (0.78 g, 2.41 mmol). The crude was purified via reverse phase chromatography with a Biotage C18 SNAP 30 g column (Phase A, water 95%, ACN 4.9%, formic acid 0.1%; Phase B ACN 99.9%, formic acid 0.1%) to afford the title compound (0.25 g, 48%).

UPLC-MS: 1.20 min, 282 [M+H]+, method 4.

Intermediate B14.
4-Benzyl-3-(1-hydroxyethyl)-1H-isochromen-1-one

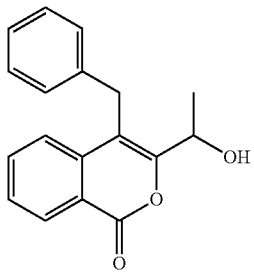 [SMILES: CC(O)c1oc(=O)c2ccccc2c1Cc1ccccc1]

The title compound was made in a similar way as that of the intermediate B1 using 3-(1-hydroxyethyl)-1H-isochromen-1-one (Intermediate A2, 0.6 g, 2.23 mmol), 2-benzyl-4,4,5,5-tetramethyl-1,3,2-dioxaborolane (0.730 g, 3.3 mmol), Pd(PPh$_3$)$_4$ (0.129 g, 0.111 mmol) and Cs$_2$CO$_3$ (1.07 g, 3.12 mmol) to afford the title crude compound (0.62 g) that was used without any further purification.

UPLC-MS: 1.82 min, 281 [M+H]+, method 4.

Intermediate B15. 3-(1-Hydroxyethyl)-4-(4-(2-morpholinoethoxy)phenyl)-1H-isochromen-1-one

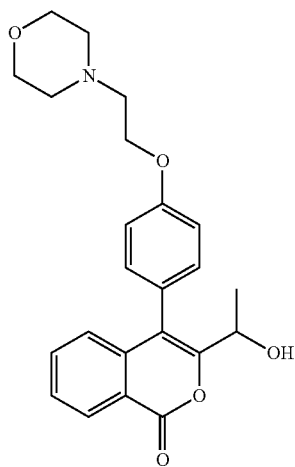 [SMILES: CC(O)c1oc(=O)c2ccccc2c1-c1ccc(OCCN2CCOCC2)cc1]

The title compound was made in a similar way as that of the intermediate B1, using 4-bromo-3-(1-hydroxyethyl)-1H-isochromen-1-one (Intermediate A2, 0.36 g, 1.35 mmol), 4-(2-(4-(4,4,5,5-tetramethyl-1,3,2-dioxaborolan-2-yl)phenoxy)ethyl)-morpholine (0.45 g, 1.35 mmol), Pd(PPh$_3$)$_4$ (0.078 g, 0.068 mmol) and Cs$_2$CO$_3$ (0.53 g, 1.6 mmol). The crude was filtered, diluted with 1M HCl$_{aqueous}$ (3 ml) and purified via reverse phase chromatography with a Biotage C18 SNAP 120 g column (Phase A, water 95%, ACN 4.9%, formic acid 0.1%); Phase B ACN 99.9%, formic acid 0.1%) to afford the title compound (0.179 g, 33%).

UPLC-MS: 1.36 min, 396 [M+H]+, method 4

Intermediate B16. 3-(1-Hydroxyethyl)-4-(5-(morpholinomethyl)thiophen-2-yl)-1H-isochromen-1-one

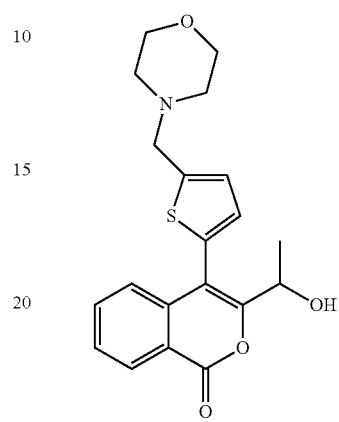

The title compound was made in a similar way as that of the intermediate B1, using 4-bromo-3-(1-hydroxyethyl)-1H-isochromen-1-one (Intermediate A2, 0.4 g, 1.49 mmol), 4-((5-(4,4,5,5-tetramethyl-1,3,2-dioxaborolan-2-yl)thiophen-2-yl)methyl)morpholine (0.598 g, 1.93 mmol), Pd(PPh$_3$)$_4$ (0.086 g, 0.074 mmol) and Cs$_2$CO$_3$ (0.678 g, 2.1 mmol). The crude was purified via reverse phase chromatography with a Biotage C18 SNAP 60 g column (Phase A, water 95%, ACN 4.9%, formic acid 0.1%); Phase B ACN 99.9%, formic acid 0.1%) to afford the title compound (0.26 g, 48%).

UPLC-MS: 1.21 min, 372 [M+H]+, method 4.

Intermediate B17. 3-(1-Hydroxyethyl)-4-(6-methoxypyridin-3-yl)-1H-isochromen-1-one

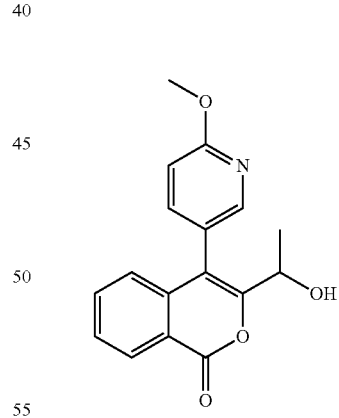

The title compound was made in a similar way as that of the intermediate B1, using 4-bromo-3-(1-hydroxyethyl)-1H-isochromen-1-one (Intermediate A2, 0.6 g, 2.23 mmol), 6-methoxypyridin-3-ylboronic acid (0.443 g, 2.90 mmol), Pd(PPh$_3$)$_4$ (0.206 g, 0.178 mmol) and Cs$_2$CO$_3$ (1.02 g, 3.1 mmol). The crude was purified via reverse phase chromatography on the Biotage 30 g C18 SNAP column (Phase A, water 95%, acetonitrile 4.9%, formic acid 0.1%; Phase B acetonitrile 99.9%, formic acid 0.1%) to afford the title compound (0.25 g, 38%).

UPLC-MS: 1.69 min, 298 [M+H]+, method 4.

Intermediate B18. 4-(3,6-Dihydro-2H-pyran-4-yl)-3-(1-hydroxyethyl)-1H-isochromen-1-one

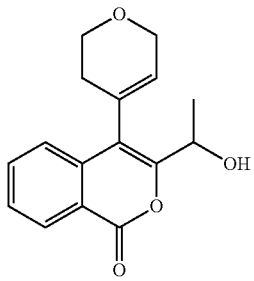 [SMILES: CC(O)c1oc(=O)c2ccccc2c1C1=CCOCC1]

The title compound was made in a similar way as that of the intermediate B1 using 4-bromo-3-(1-hydroxyethyl)-1H-isochromen-1-one (intermediate A2, 0.50 g, 1.86 mmol), 2-(3,6-dihydro-2H-pyran-4-yl)-4,4,5,5-tetramethyl-1,3,2-dioxaborolane (0.51 g, 2.42 mmol), Pd(PPh$_3$)$_4$ (0.11 g, 0.093 mmol) and Cs$_2$CO$_3$ (0.30 mg, 0.93 mmol) to afford the title compound (0.13 g, 26%) as a orange oil.

UPLC-MS: 1.52 min, 273 [M+H]+, method 4

Intermediate B19-23, 32-33 found in the table below may be prepared starting from intermediate A2 and the suitable reagent reported below following similar procedures as for compounds B1.

| Intermediate | Name and Molecular Structure | Reagent | UPLC-MS |
|---|---|---|---|
| B19 | 3-(1-hydroxyethyl)-4-(1-methyl-1,2,3,6-tetrahydropyridin-4-yl)-1H-isochromen-1-one formate | 1-methyl-4-(4,4,5,5-tetramethyl-1,3,2-dioxaborolan-2-yl)-1,2,3,6-tetrahydropyridine | Rt = 1.16 min 285.9 [M + H]+ method 4 |
| B20 | -(1-hydroxyethyl)-4-(4-(morpholinomethyl)phenyl)-1H-isochromen-1-one formate | 4-(4-(4,4,5,5-tetramethyl-1,3,2-dioxaborolan-2-yl)benzyl)morpholine | Rt = 1.28 min 368.9 [M + H]+ method 4. |
| B22 | 4-cyclohexenyl-3-(1-hydroxyethyl)-1H-isochromen-1-one | 2-cyclohexenyl-4,4,5,5-tetramethyl-1,3,2-dioxaborolane | Rt = 1.96 min, 270.9 [M + H]+, method 4. |

| Intermediate | Name and Molecular Structure | | Reagent | UPLC-MS |
|---|---|---|---|---|
| B23 | 3-(1-hydroxyethyl)-4-(1-methyl-1,2,5,6-tetrahydropyridin-3-yl)-1H-isochromen-1-one hydrochloride | | 1-methyl-5-(4,4,5,5-tetramethyl-1,3,2-dioxaborolan-2-yl)-1,2,3,6-tetrahydropyridine | Rt = 0.42 min, 286.1 [M + H]+, method 9. |
| B32 | 4-(2-aminopyrimidin-5-yl)-3-(1-hydroxyethyl)-1H-isochromen-1-one | | 2-aminopyrimidin-5-ylboronic acid | Rt = 1.31 min, 284 [M + H]+, method 4 |
| B33 | tert-butyl 4-(4-(3-(1-hydroxyethyl)-1-oxo-1H-isochromen-4-yl)benzyl)piperazine-1-carboxylate | | tert-butyl 4-(4-(4,4,5,5-tetramethyl-1,3,2-dioxaborolan-2-yl)benzyl)piperazine-1-carboxylate | Rt = 1.56 min, 465 [M + H]+, method 4 |

Intermediate B24. 3-(1-hydroxyethyl)-4-(3-(4,4,5,5-tetramethyl-1,3-dioxolan-2-yl)phenyl)-1H-isochromen-1-one

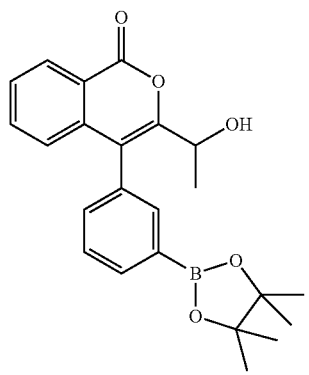 [SMILES: CC(O)c1oc(=O)c2ccccc2c1-c1cccc(B2OC(C)(C)C(C)(C)O2)c1]

4-bromo-3-(1-hydroxyethyl)-1H-isochromen-1-one (Intermediate A2, 4.05 g, 15.05 mmol), 4,4,5,5-tetramethyl-2-(3-(4,4,5,5-tetramethyl-1,3-dioxolan-2-yl)phenyl)-1,3,2-dioxaborolane (Intermediate G2, 5 g, 15.05 mmol), X-Phos-Pd-G2 (1.184 g, 1.505 mmol) and $K_3PO_4 \cdot H_2O$ (9.81 g, 30.1 mmol) were dispersed in THF (42 ml) and deoxygenated under argon, then water (42 mL) was added and the mixture stirred at rt overnight. The reaction was diluted with AcOEt (250 ml) and washed with 0.2 M of $HCl_{aqueous}$ (250 ml), once with saturated $NaCl_{aqueous}$, anhydrified over $Na_2SO_4$ and the solvent removed under reduced pressure. The crude was purified via flash chromatography on silica gel using a Biotage 100G+50 G SNAP with a gradient of hexane and AcOEt to give the title compound (5.4 g, 91%) as dark oil.

UPLC-MS: 1.19 min, 377.2 [(M–$H_2O$)+H]+, method 9

Intermediates B25-30, 35, 36, 43, 50, 51 and 57 found in the table below may be prepared starting from intermediate A2 and the suitable reagent reported below following similar procedures as for compound B24.

| Intermediate | Name and Molecular Structure | Reagent | UPLC-MS |
|---|---|---|---|
| B25 | 3-(1-hydroxyethyl)-4-(5-(piperidin-1-ylmethyl)thiophen-2-yl)-1H-isochromen-1-one hydrochloride | 1-((5-(4,4,5,5-tetramethyl-1,3,2-dioxaborolan-2-yl)thiophen-2-yl)methyl)piperidine | Rt = 0.62 min, 370.0 [M + H]+, method 9 |
| B26 | 3-(1-hydroxyethyl)-4-(4-(4-methylpiperazine-1-carbonyl)phenyl)-1H-isochromen-1-one hydrochloride | (4-methylpiperazin-1-yl)(4-(4,4,5,5-tetramethyl-1,3,2-dioxaborolan-2-yl)phenyl)methanone | Rt = 0.52 min, 393.0 [M + H]+, method 9 |
| B27 | N-(2-(dimethylamino)ethyl)-3-(3-(1-hydroxyethyl)-1-oxo-1H-isochromen-4-yl)benzamide hydrochloride | N-(2-(dimethylamino)ethyl)-3-(4,4,5,5-tetramethyl-1,3,2-dioxaborolan-2-yl)benzamide | Rt = 0.62 min, 370.0 [M + H]+, method 9 |
| B28 | 4-(1-acetyl-1,2,3,6-tetrahydropyridin-4-yl)-3-(1-hydroxyethyl)-1H-isochromen-1-one | 1-(4-(4,4,5,5-tetramethyl-1,3,2-dioxaborolan-2-yl)-5,6-dihydropyridin-1(2H)-yl)ethanone (Intermediate G4) | Rt = 0.67 min, 314.0 [M + H]+, method 9 |

| Intermediate | Name and Molecular Structure | | Reagent | UPLC-MS |
|---|---|---|---|---|
| B29 | 3-(1-hydroxyethyl)-4-(5-(4,4,5,5-tetramethyl-1,3-dioxolan-2-yl)thiophen-2-yl)-1H-isochromen-1-one | 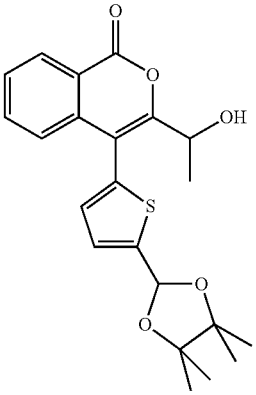 [SMILES: CC(O)c1oc(=O)c2ccccc2c1-c1ccc(C2OC(C)(C)C(C)(C)O2)s1] | 4,4,5,5-tetramethyl-2-(5-(4,4,5,5-tetramethyl-1,3-dioxolan-2-yl)thiophen-2-yl)-1,3,2-dioxaborolane (Intermediate G5) | Rt = 1.18 min, 402.2 [M + H]+, method 9 |
| B30 | benzyl (4-(3-(1-hydroxyethyl)-1-oxo-1H-isochromen-4-yl)cyclohex-3-en-1-yl)carbamate | 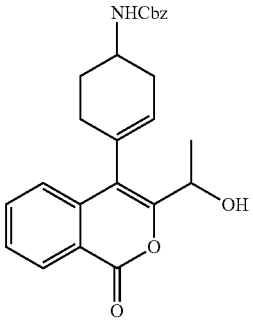 [SMILES: CC(O)c1oc(=O)c2ccccc2c1C1=CCC(NC(=O)OCc2ccccc2)CC1] | benzyl (4-(4,4,5,5-tetramethyl-1,3,2-dioxaborolan-2-yl)cyclohex-3-en-1-yl)carbamate (intermediate G13) | Rt = 1.09 min, 420 [M + H]+, method 9. |
| B35 | benzyl 4-(3-(1-hydroxyethyl)-1-oxo-1H-isochromen-4-yl)-5,6-dihydropyridine-1(2H)-carboxylate | 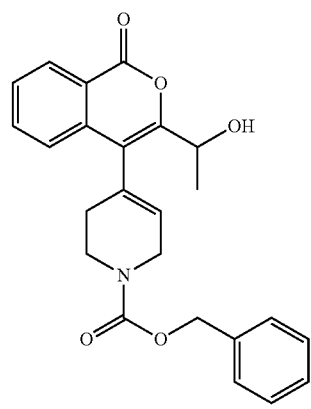 | benzyl 4-(4,4,5,5-tetramethyl-1,3,2-dioxaborolan-2-yl)-5,6-dihydropyridine-1(2H)-carboxylate | Rt = 1.18 min, 383.2 [M + H]+, method 9 |
| B36 | 4-(1-benzyl-1,2,3,6-tetrahydropyridin-4-yl)-3-(1-hydroxyethyl)-1H-isochromen-1-one hydrochloride | 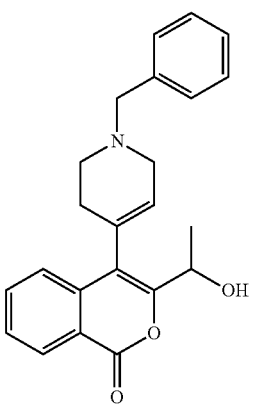 [SMILES: CC(O)c1oc(=O)c2ccccc2c1C1=CCN(Cc2ccccc2)CC1] | 1-benzyl-4-(4,4,5,5-tetramethyl-1,3,2-dioxaborolan-2-yl)-1,2,3,6-tetrahydropyridine | Rt = 1.31 min, 362.2 [M + H]+, method 4 |

-continued

| Intermediate | Name and Molecular Structure | Reagent | UPLC-MS |
|---|---|---|---|
| B43 | 3-(1-hydroxyethyl)-4-(4-(4,4,5,5-tetramethyl-1,3-dioxolan-2-yl)phenyl)-1H-isochromen-1-one | 4,4,5,5-tetramethyl-2-(4-(4,4,5,5-tetramethyl-1,3-dioxolan-2-yl)phenyl)-1,3,2-dioxaborolane | Rt = 2.14 min, 402.2 375 [M + H − H$_2$O]+, method 9. |
| B50 | 3-(1-hydroxyethyl)-4-(2,2,6,6-tetramethyl-1,2,3,6-tetrahydropyridin-4-yl)-1H-isochromen-1-one hydrochloride | 2,2,6,6-tetramethyl-4-(4,4,5,5-tetramethyl-1,3-dioxaborolan-2-yl)-1,2,3,6-tetrahydropyridine | Rt = 0.54 min, 327.9 [M + H]+, method 9. |
| B51 | benzyl 3-(3-(1-hydroxyethyl)-1-oxo-1H-isochromen-4-yl)-8-azabicyclo[3.2.1]oct-2-ene-8-carboxylate | (8-((benzyloxy)carbonyl)-8-azabicyclo[3.2.1]oct-2-en-3-yl)boronic acid (Intermediate G21) | Rt = 1.10 min, 432 [M + H]+, method 9. |
| B57 | 4-(1-benzyl-1,2,5,6-tetrahydropyridin-3-yl)-3-(1-hydroxyethyl)-1H-isochromen-1-one hydrochloride | 1-benzyl-5-(4,4,5,5-tetramethyl-1,3,2-dioxaborolan-2-yl)-1,2,3,6-tetrahydropyridine | Rt = 0.52 min, 362.3 [M + H]+, method 13 |

Intermediate B31. tert-butyl (5-(3-(1-bromoethyl)-1-oxo-1H-isochromen-4-yl)thiazol-2-yl)carbamate

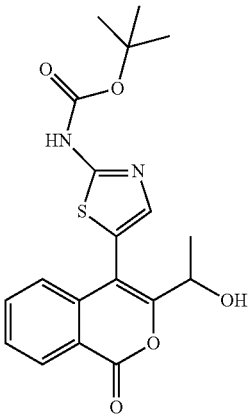 [SMILES: CC(O)c1oc(=O)c2ccccc2c1-c1cnc(NC(=O)OC(C)(C)C)s1]

To a solution of 4-bromo-3-(1-hydroxyethyl)-1H-isochromen-1-one (Intermediate A2, 500 mg, 1.858 mmol), Pd-bis(diphenyphosphine) chloride (130 mg, 0,186 mmol), cesium fluoride (847 mg, 5.57 mmol) in 1,4-dioxane (5 ml), commercially available tert-butyl (5-(tributylstannyl)thiazol-2-yl)carbamate (1.182 g, 2.42 mmol) was added and the mixture stirred at RT for 4 hrs and at 80 deg for 1 hr. The reaction was partitioned between NH₄Cl (100 ml) and AcOEt (30 ml), organic phase was washed with Brine, dried and evaporated in vacuo. The crude was purified via reverse phase chromatography with a Biotage C18 SNAP 30 g column (Phase A, water 95%, ACN 4.9%, formic acid 0.1%); Phase B ACN 95%, water 5%, formic acid 0.1%) to give the title compound (255 mg, 35.3%)

¹H NMR (400 MHz, DMSO-d₆) δ ppm 8.24-8.35 (m, 1 H), 7.82-7.93 (m, 1 H), 7.53-7.76 (m, 8 H), 7.38-7.47 (m, 1 H), 7.10-7.23 (m, 1 H), 6.82-6.99 (m, 1 H), 5.46-5.70 (m, 1 H), 4.12-4.33 (m, 1 H), 1.48 (s, 4 H), 1.26-1.39 (m, 11 H)

Intermediate B34. (4-phenyl-1H-isochromen-3-yl)methanol

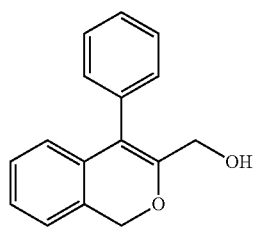 [SMILES: OCC1=C(c2ccccc2)c2ccccc2CO1]

4-phenyl-1H-isochromene-3-carbaldehyde (Intermediate G21, 410 mg, 1.735 mmol) suspended in MeOH (1 ml) was added dropwise to a solution of sodium tetrahydroborate (65.7 mg, 1.735 mmol) in MeOH (17.3 ml) at RT. The mixture was partitioned between AcOEt/NH4Cl 5% (2 ml/2 ml), the organic phase was separated, anhydrified over Na₂SO₄ and evaporated in vacuo to give a crude that underwent next step without any further purification.

1H NMR (400 MHz, DMSO-d6) d ppm 7.34-7.48 (m, 3 H), 7.21-7.29 (m, 2 H), 7.05-7.19 (m, 3 H), 6.37-6.56 (m, 1 H), 5.09 (s, 2 H), 4.85-4.96 (t, 1 H), 3.74-3.85 (d, 2 H)

Intermediate B37. 5-(3-(1-hydroxyethyl)-1-oxo-1H-isochromen-4-yl)thiophene-2-carbaldehyde

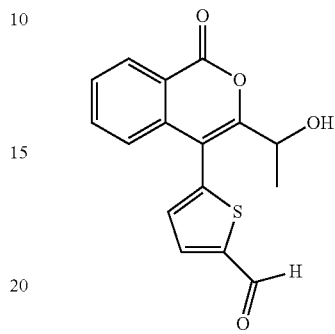

3-(1-hydroxyethyl)-4-(5-(4,4,5,5-tetramethyl-1,3-dioxolan-2-yl)thiophen-2-yl)-1H-isochromen-1-one (Intermediate B29, 940 mg, 2.347 mmol) was dissolved in 20 ml of MeCN and 20 ml of HCl 1M were added. The clear yellow solution was stirred overnight at rt. The mixture was diluted with 50 ml of water and 200 ml of EtOAc were added. then stirred for 20 min. Phases were separated and the organic one was washed again with 100 ml of NaHCO₃ sat. sol. Phases were separated again and the organic one was dried over sodium sulfate, filtered and concentrated to dryness to leave 5-(3-(1-hydroxyethyl)-1-oxo-1H-isochromen-4-yl)thiophene-2-carbaldehyde (700 mg, 2.331 mmol, 99% yield) as a yellow fluffy solid UPLC-MS: 0.83 min, 300.98 [M+H]+, method 9.

Intermediate B38. benzyl 4-((5-(3-(1-hydroxyethyl)-1-oxo-1H-isochromen-4-yl)thiophen-2-yl)methyl)piperazine-1-carboxylate

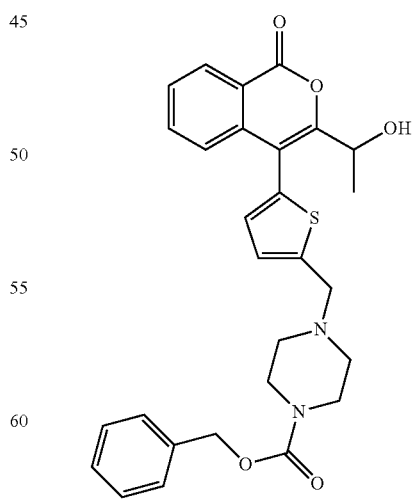

In a 250 ml round bottomed flask 5-(3-(1-hydroxyethyl)-1-oxo-1H-isochromen-4-yl)thiophene-2-carbaldehyde (Intermediate B37) (780 mg, 2.60 mmol) was dissolved in 30 ml of DCM then acetic acid (0.446 ml, 7.79 mmol) and benzyl piperazine-1-carboxylate (1.503 ml, 7.79 mmol) were added. After few minutes sodium triacetoxyhydroborate (2.75 g, 12.99 mmol) was added and the mixture was stirred at r.t. The mixture was poured into 100 ml of DCM and 100 NaHCO$_3$ sat. sol. then phases were separated and the organic one was concentrated to dryness to leave a brown oil that was immediately purified by chromatography eluting with Hexane\EtOAc mixtures to leave the title compound (903 mg, 1.790 mmol, 68.9% yield) as a yellow oil.

UPLC-MS: 0.79 min, 505.12 [M+H]+, method 9

Intermediate B39. 3-(1-hydroxyethyl)-4-(5-((4-methylpiperazin-1-yl)methyl)thiophen-2-yl)-1H-isochromen-1-one

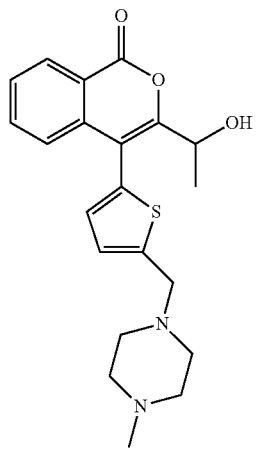 [SMILES: CC(O)c1oc(=O)c2ccccc2c1-c1ccc(CN2CCN(C)CC2)s1]

The title compound was made in a similar way as that of intermediate B38, from 5-(3-(1-hydroxyethyl)-1-oxo-1H-isochromen-4-yl)thiophene-2-carbaldehyde (Intermediate B37) (800 mg, 2.66 mmol),), 1-methylpiperazine (913 μl, 7.99 mmol) to give the title compound (412 mg, 1.072 mmol, 40.2% yield) as a yellow oil.

UPLC-MS: 0.56 min, 385.13 [M+H]+, method 9.

Intermediate B40. 4-(5-(3-(dimethylamino)prop-1-en-1-yl)thiophen-2-yl)-3-(1-hydroxyethyl)-1H-isochromen-1-one

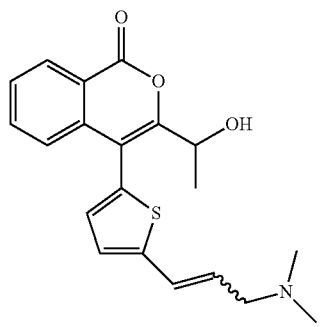 [SMILES: CC(O)c1oc(=O)c2ccccc2c1-c1ccc(C=CCN(C)C)s1]

In a 100 ml 3-necked round bottomed flask (2-(dimethylamino)ethyl)-triphenylphosphonium bromide (1569 mg, 3.79 mmol) was loaded and suspended under Argon in 15 ml of Dioxane. Potassium bis(trimethylsilyl)amide solution 0.5 M in toluene (6.0 ml, 3.03 mmol) was added drop wise and a yellow\orange color appeared. The mixture was further stirred for 20 min then 5-(3-(1-hydroxyethyl)-1-oxo-1H-isochromen-4-yl)thiophene-2-carbaldehyde (Intermediate B37, 455 mg, 1.515 mmol) dissolved in 5 ml of dioxane was added. The mixture was further stirred at rt for 2 h then poured into 100 ml of NH$_4$Cl sat. sol. and 200 ml of EtOAc. Phases were separated and the organic one was dried over sodium sulfate. Solvents were removed and the crude was purified by chromatography eluting with DCM\20% MeOH in DCM mixtures to leave 4-(5-(3-(dimethylamino)prop-1-en-1-yl)thiophen-2-yl)-3-(1-hydroxyethyl)-1H-isochromen-1-one (220 mg, 0,619 mmol, 40.9% yield) as a yellow oil.

UPLC-MS: 0.62 min, 356.15 [M+H]+, method 9

Intermediate B41. 5 3-(3-(1-hydroxyethyl)-1-oxo-1H-isochromen-4-yl)benzaldehyde

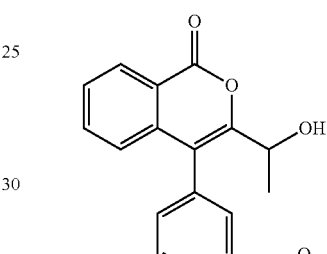

The title compound was made in a similar way as that of the Intermediate B37, from 3-(1-hydroxyethyl)-4-(3-(4,4,5,5-tetramethyl-1,3-dioxolan-2-yl)phenyl)-1H-isochromen-1-one (Intermediate B24, 1.268 mmol, 500 mg) to give the title compound (400 mg, 1.359 mmol, 107%) as a yellow oil.

UPLC-MS: 0.86 min, [M+H]+, method 10.

Intermediate B42. 4-(3-(3-(dimethylamino)prop-1-en-1-yl)phenyl)-3-(1-hydroxyethyl)-1H-isochromen-1-one

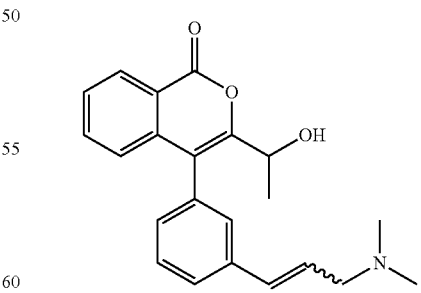

The title compound was made in a similar way as that of the compound of intermediate B40, from 3-(3-(1-hydroxyethyl)-1-oxo-1H-isochromen-4-yl)benzaldehyde (Intermediate B41, 373 mg, mmol) and (2-(dimethylamino)ethyl)triphenylphosphonium bromide (3.17 mmol, 1.313 mg) to give the title compound (280 mg, 0.801 mmol, 63.2% yield) as a yellow oil.
UPLC-MS: 1.09 min, 350.20 [M+H]+, method 10.

Intermediate 44. 4-(3-(1-hydroxyethyl)-1-oxo-1H-isochromen-4-yl)benzaldehyde

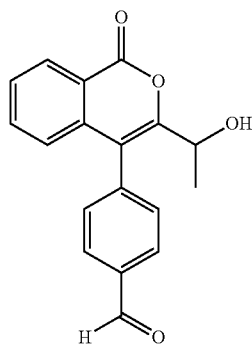 [SMILES: CC(O)c1oc(=O)c2ccccc2c1-c1ccc(C=O)cc1]

The title compound was made in a similar way as that of the compound of intermediate B37, from 3-(1-hydroxyethyl)-4-(4-(4,4,5,5-tetramethyl-1,3-dioxolan-2-yl)phenyl)-1H-isochromen-1-one (intermediate B43, 1.83 g, 4.64 mmol) to give the title compound (1.12 g, 3.81 mmol, 82% yield) as a yellow oil.
UPLC-MS: 1.42 min, 277.17 [M+H—H$_2$O]+, method 10.

Intermediate B45. 4-(4-(3-(dimethylamino)prop-1-en-1-yl)phenyl)-3-(1-hydroxyethyl)-1H-isochromen-1-one

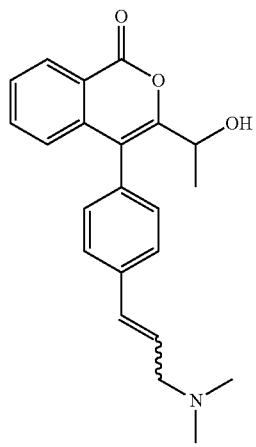 [SMILES: CC(O)c1oc(=O)c2ccccc2c1-c1ccc(C=CCN(C)C)cc1]

The title compound was made in a similar way as that of the compound of intermediate B40, from 4-(3-(1-hydroxyethyl)-1-oxo-1H-isochromen-4-yl)benzaldehyde (Intermediate B44, 480 mg, 1.63 mmol) and (2-(dimethylamino)ethyl)triphenylphosphonium bromide (4.08 mmol, 1.69 mg), to give the title compound (210 mg, 0,601 mmol, 36.8% yield) as a yellow oil.
UPLC-MS: 0.49 min, 350.21 [M+H]+, method 9.

Intermediate B46. 3-(1-hydroxyethyl)-4-(4-((4-methylpiperazin-1-yl)methyl)phenyl)-1H-isochromen-1-one

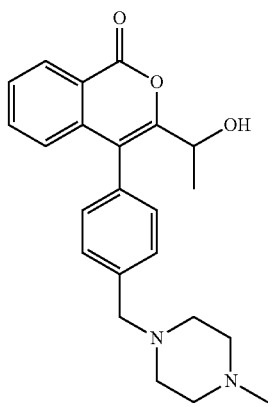 [SMILES: CC(O)c1oc(=O)c2ccccc2c1-c1ccc(CN2CCN(C)CC2)cc1]

The title compound was made in a similar way as that of the compound of intermediate B38, from 4-(3-(1-hydroxyethyl)-1-oxo-1H-isochromen-4-yl)benzaldehyde (Intermediate B44, 320 mg, 1.087 mmol), and 1-methylpiperazine (373 µl, 3.26 mmol), to give the desired product leave 3-(1-hydroxyethyl)-4-(4-((4-methylpiperazin-1-yl)methyl)phenyl)-1H-isochromen-1-one (428 mg, 1.131 mmol, 104% yield) as yellow oil.
UPLC-MS: 0.52 min, 379.33 [M+H]+, method 9.

Intermediate B47. 3-(1-hydroxyethyl)-4-(4-(pyrrolidin-1-ylmethyl)phenyl)-1H-isochromen-1-one

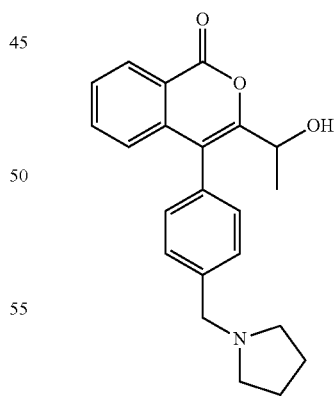

The title compound was made in a similar way as that of the compound of example B37, from 4-(3-(1-hydroxyethyl)-1-oxo-1H-isochromen-4-yl)benzaldehyde (Intermediate B44, 320 mg, 1.087 mmol), and pyrrolidine (232 mg, 3.26 mmol), to give the title compound (353 mg, 1.010 mmol, 93% yield) as yellow oil.
UPLC-MS: 0.55 min, 350.25 [M+H]+, method 9

Intermediate B48. 3-(1-hydroxyethyl)-4-(4-(piperidin-1-ylmethyl)phenyl)-1H-isochromen-1-one

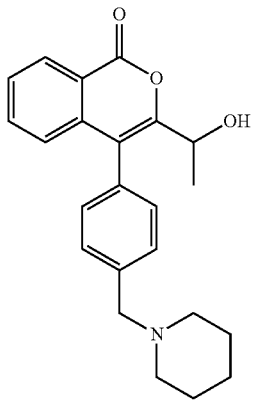 [SMILES: CC(O)c1oc(=O)c2ccccc2c1-c1ccc(CN2CCCCC2)cc1]

The title compound was made in a similar way as that of the compound of Intermediate B37, from 4-(3-(1-hydroxyethyl)-1-oxo-1H-isochromen-4-yl)benzaldehyde (Intermediate B44, 650 mg, 2.209 mmol) and piperidine (654 μl, 6.63 mmol), to give the title compound (720 mg, 1.981 mmol, 90% yield) as a yellow oil.

UPLC-MS: 0.58 min, 364.25 [M+H]+, method 9

Intermediate B49. 3-(1-hydroxyethyl)-4-(3-((4-methylpiperazin-1-yl)methyl)phenyl)-1H-isochromen-1-one

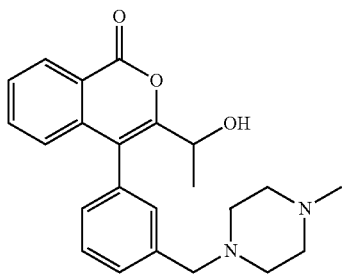 [SMILES: CC(O)c1oc(=O)c2ccccc2c1-c1cccc(CN2CCN(C)CC2)c1]

The title compound was made in a similar way as that of the compound of Intermediate B37, from 3-(3-(1-hydroxyethyl)-1-oxo-1H-isochromen-4-yl)benzaldehyde (Intermediate B42, 530 mg, 1.801 mmol), and 1-METHYLPIPERAZINE (617 μl, 5.40 mmol), to give the title compound (341 mg, 0.900 mmol, 50% yield) as a yellow oil.

UPLC-MS: 0.57 min, 379.28 [M+H]+, method 9

Intermediate B52. benzyl (3-(3-(1-hydroxyethyl)-1-oxo-1H-isochromen-4-yl)prop-2-yn-1-yl)(methyl)carbamate

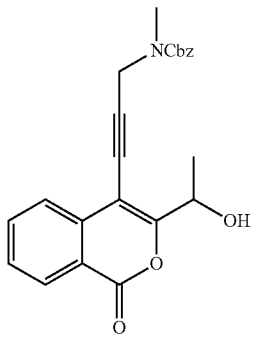 [SMILES: CC(O)c1oc(=O)c2ccccc2c1C#CCN(C)C(=O)OCc1ccccc1]

To a solution of 4-bromo-3-(1-hydroxyethyl)-1H-isochromen-1-one (Intermediate A2, 2.65 g, 9.84 mmol) in dry DMF (30 ml), benzyl methyl(prop-2-yn-1-yl)carbamate (Intermediate G22, 4 g, 19.68 mmol), copper(I) iodide (0.562 g, 2.95 mmol), tetrakis(triphenylphosphine)palladium(0) (1.946 ml, 1.476 mmol), benzyl methyl(prop-2-yn-1-yl)carbamate (4 g, 19.68 mmol) and triethylamine (4.04 ml, 29.5 mmol) were added. The resulting suspension was heated to 95° C. overnight. Then, solvent was removed under reduced pressure. The product was purified by Biotage Si 10 g with a gradient of heptane and EtOAc affording the title compound (3.524 g, 9.00 mmol, 91% yield) a yellowish oil.

UPLC-MS: 1.08 min, 392 [M+H]+, method 9

Intermediate B53. 3-(1-hydroxyethyl)-7-methyl-4-phenyl-1H-isochromen-1-one

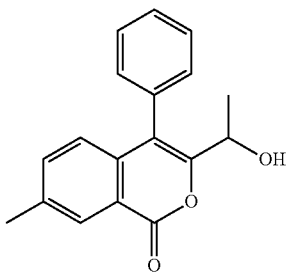 [SMILES: Cc1ccc2c(-c3ccccc3)c(C(C)O)oc(=O)c2c1]

To a solution of 4-bromo-3-(1-hydroxyethyl)-7-methyl-1H-isochromen-1-one (intermediate A4, 1.04 g, 3.67 mmol) in Dioxane/H$_2$O (5:1) (60 ml), phenylboronic acid (0.67 g, 5.51 mmol) and Na$_2$CO$_3$ (0.779 g, 7.34 mmol) were added followed by Pd(dppf)Cl$_2$ (0.269 g, 0.367 mmol) and the resulting mixture was heated at 90° C. for 2 hrs. 1N HCl was added (pH≈2) and the mixture was partitioned between EtOAc and water. The organic phase was washed twice with brine and dried over sodium sulfate. The solvent was removed under vacuum and the crude was purified by flash column chromatography on Biotage silica gel cartridge (cyclohexane:EtOAc=95:5 to 40:60) to afford title compound as a yellow oil (0.835 g, 2.98 mmol, 81%).

UPLC-MS: 1.12 min, 281.2 [M+H]+, method 13

Intermediate B54. 7-chloro-3-(1-hydroxyethyl)-4-phenyl-1H-isochromen-1-one

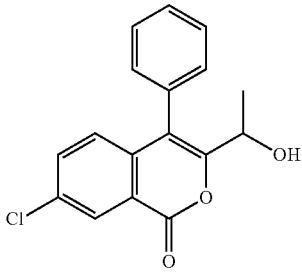 [SMILES: CC(O)c1oc(=O)c2cc(Cl)ccc2c1-c1ccccc1]

The title compound was made in a similar way of that of Intermediate B53 from 4-bromo-7-chloro-3-(1-hydroxyethyl)-1H-isochromen-1-one (intermediate A5, 1.4 g, 4.61 mmol) and phenylboronic acid (0.844 g, 6.92 mmol) to afford title compound as a yellow foam (0.540 g) which was used without any additional purification.

UPLC-MS: 1.11 min, 300.8 [M+H]+, method 12

Intermediate B55. 6-chloro-3-(1-hydroxyethyl)-4-phenyl-1H-isochromen-1-one

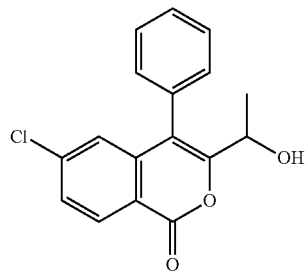 [SMILES: CC(O)c1oc(=O)c2ccc(Cl)cc2c1-c1ccccc1]

The title compound was made in a similar way of that of Intermediate B53 from 4-bromo-6-chloro-3-(1-hydroxyethyl)-1H-isochromen-1-one (intermediate A6, 0.973 g, 3.205 mmol) and phenylboronic acid (0.586 g, 4.808 mmol) to yield title compound as a white foam (0.430 g, 1.43 mmol, 45%).

UPLC-MS: 1.12 min, 301.1 [M+H]+, method 13

Intermediate B56. 6-fluoro-3-(1-hydroxyethyl)-4-phenyl-1H-isochromen-1-one

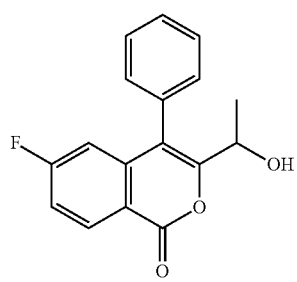 [SMILES: CC(O)c1oc(=O)c2ccc(F)cc2c1-c1ccccc1]

The title compound was made in a similar way of that of Intermediate B53 from 4-bromo-6-fluoro-3-(1-hydroxyethyl)-1H-isochromen-1-one (intermediate A7, 0.95 g, 3.31 mmol) and phenylboronic acid (0.605 g, 4.96 mmol) to afford title compound (0.736 g) which was used without any additional purification.

UPLC-MS: 1.04 min, 285.2 [M+H]+, method 13

Intermediate B58. 3-(1-hydroxyethyl)-4-(pyridin-2-yl)-1H-isochromen-1-one

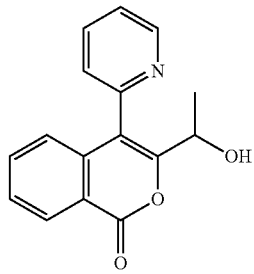 [SMILES: CC(O)c1oc(=O)c2ccccc2c1-c1ccccn1]

Step 1. 3-(1-((tert-butyldimethylsilyl)oxy)ethyl)-4-(pyridin-2-yl)-1H-isochromen-1-one (Intermediate B58.1)

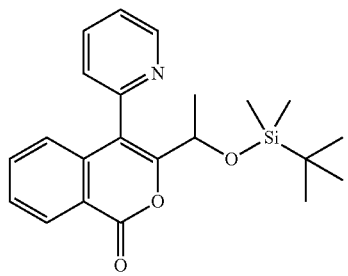 [SMILES: CC(O[Si](C)(C)C(C)(C)C)c1oc(=O)c2ccccc2c1-c1ccccn1]

To a degassed solution of 4-bromo-3-(1-((tert-butyldimethylsilyl)oxy)ethyl)-1H-isochromen-1-one (intermediate A8, 2 g, 5.22 mmol) in toluene (30 ml) $PdCl_2(PPh_3)_2$ (0.183 g, 0.261 mmol) was added followed by 2-(tributylstannyl)pyridine (4.55 ml, 10.44 mmol) and the resulting mixture was heated to reflux overnight. The mixture was allowed to cool to RT and then and filtered through a celite pad. The solvent was removed in vacuo, the crude was dissolved in AcOEt and an aqueous sat. sol of KF was added and the mixture was stirred for 2 hrs. The organic phase was separated, dried over sodium sulfate and evaporated to dryness. The crude was purified by flash chromatography on silica gel Biotage cartridge (cyclohexane to cyclohexane:EtOAc=20:80) to afford 3-(1-((tert-butyldimethylsilyl)oxy)ethyl)-4-(pyridin-2-yl)-1H-isochromen-1-one as a pale yellow oil (Intermediate B58.1, 0.508 g, 1.33 mmol).

UPLC-MS: 1.42 min, 382.4 [M+H]+, method 13

Step 2.

1.0 M TBAF in THF (1.43 mL, 1.43 mmol) was added dropwise to a solution of 3-(1-((tert-butyldimethylsilyl)oxy)ethyl)-4-(pyridin-2-yl)-1H-isochromen-1-one (intermediate B58.1, 0.394 g, 1.3 mmol) in THF (15 ml). The resulting mixture was stirred at RT for 2 hrs. The mixture was diluted with DCM and water was added. The mixture was extracted twice with DCM, the combined organic layers were dried over sodium sulfate and evaporated to dryness. The crude was purified by flash chromatography on silica gel Biotage car- Intermediate B59. 3-(1-hydroxyethyl)-4-(morpholinomethyl)-1H-isochromen-1-one

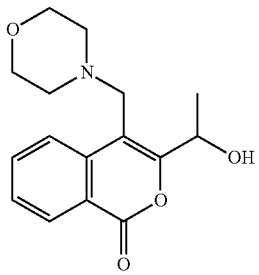 [SMILES: CC(O)c1oc(=O)c2ccccc2c1CN1CCOCC1]

Step 1. 3-(1-((tert-butyldimethylsilyl)oxy)ethyl)-4-vinyl-1H-isochromen-1-one (Intermediate B59.1)

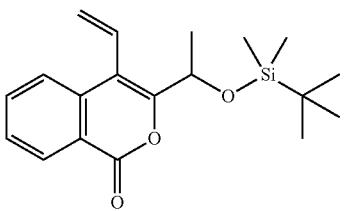 [SMILES: C=Cc1c(C(C)O[Si](C)(C)C(C)(C)C)oc(=O)c2ccccc12]

To a degassed solution of 4-bromo-3-(1-((tert-butyldimethylsilyl)oxy)ethyl)-1H-isochromen-1-one (intermediate A8, 6 g, 15.7 mmol) in toluene (120 ml), PdCl$_2$(PPh$_3$)$_2$ (0.6 g, 079 mmol) was added followed by tributyl(1-ethoxyvinyl)tin (5 ml, 17.2 mmol) and the resulting mixture was heated to reflux overnight. Additional PdCl$_2$(PPh$_3$)$_2$ (0.6 g) was added at room temperature, and the mixture was refluxed for 30 minutes. The mixture was cooled to room temperature, then filtered through a celite pad. The filtrate was evaporated to dryness and the crude was purified by flash chromatography on Biotage silica gel cartridges (cyclohexane to cyclohexane:EtOAc=80:20) to afford 3-(1-((tert-butyldimethylsilyl)oxy)ethyl)-4-vinyl-1H-isochromen-1-one as a pale yellow oil (Intermediate B59.1, 5.8 g).

UPLC-MS: 1.51 min, 331.1 [M+H]+, method 12.

Step. 2. 3-(1-((tert-butyldimethylsilyl)oxy)ethyl)-1-oxo-1H-isochromene-4-carbaldehyde (intermediate B59.2)

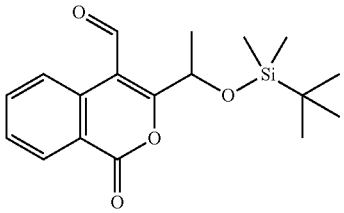 [SMILES: CC(O[Si](C)(C)C(C)(C)C)c1oc(=O)c2ccccc2c1C=O]

A slow stream of O3 in O2 was passed through a −78° C. cooled solution of 3-(1-((tert-butyldimethylsilyl)oxy)ethyl)-4-vinyl-1H-isochromen-1-one (intermediate B59.1, 2.967 g of crude) in DCM (100 ml) for 1.5 hrs. The excess of O3 was purged by N$_2$ bubbling, then a solution of PPh$_3$ (2.316 g, 8.83 mmol) in DCM (20 ml) was added. The solution was allowed to reach 25° C. and it was stirred overnight. The solvent was removed in vacuo and the crude material was purified by flash chromatography on Biotage silica gel cartridge (cyclohexane to cyclohexane:EtOAc=90:10) to afford 3-(1-((tert-butyldimethylsilyl)oxy)ethyl)-1-oxo-1H-isochromene-4-carbaldehyde (Intermediate B59.2, 1.453 g, 4.38 mmol).

UPLC-MS: 1.43 min, 333.1 [M+H]+, method 12.

Step 3. 3-(1-((tert-butyldimethylsilyl)oxy)ethyl)-4-(morpholinomethyl)-1H-isochromen-1-one (Intermediate B59.3)

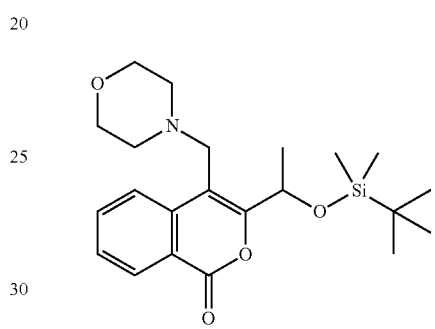

To a solution of 3-(1-((tert-butyldimethylsilyl)oxy)ethyl)-1-oxo-1H-isochromene-4-carbaldehyde (Intermediate B59.2, 0.5 g, 1.5 mmol) and morpholine (0.12 ml, 1.35 mmol) in DCM (20 ml), dry Na$_2$SO$_4$ was added and the mixture stirred RT for 10 min. Sodium triacetoxyborohydride (0.286 g, 2.25 mmol) and acetic acid (0.09 ml, 1.5 mmol) were added and the reaction mixture was stirred for 24 h at RT. The reaction was quenched by the addition of 2M HCl (3 ml), the heterogeneous mixture was filtered and the filtrate was purified by flash chromatography on silica NH cartridge (cyclohexane:EtOAc=90:10 to 80:20) affording 3-(1-((tert-butyldimethylsilyl)oxy)ethyl)-4-(morpholinomethyl)-1H-isochromen-1-one (Intermediate B59.3, 0.183 g, 0.45 mmol, 30%).

UPLC-MS: 1.27 min, 404.5 [M+H]+, method 14.

Step. 4

3-(1-((tert-butyldimethylsilyl)oxy)ethyl)-4-(morpholinomethyl)-1H-isochromen-1-one (Intermediate B59.3, 0.203 g, 0.503 mmol) was dissolved in THF (7 mL); TBAF (1.0 M solution in THF, 0.33 ml, 0.33 mmol) was added drop-wise and the resulting mixture was stirred at room temperature for 2 hrs. Water (10 ml) was added and the mixture was extracted twice with DCM; the combined organic layers were dried over sodium sulfate and evaporated to dryness. The crude was purified by reverse phase flash chromatography on C18 Biotage cartridge ((H$_2$O:CH$_3$CN=95:5 to 80:20, with 0.1% HCOOH) to afford the title compound (0.145 g). The product was used in the next step without further purifications.

UPLC-MS: 0.41 min, 290.4 [M+H]+, method 14.

Intermediate C1.
3-(Bromomethyl)-4-phenyl-1H-isochromen-1-one

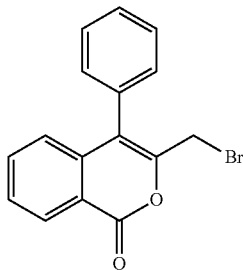 [SMILES: O=c1oc(CBr)c(-c2ccccc2)c2ccccc12]

Triphenylphosphine (250 mg, 0.953 mmol) was added to a solution of 3-(hydroxymethyl)-4-phenyl-1H-isochromen-1-one (intermediate B2, 185 mg, 0.733 mmol) and perbromomethane (316 mg, 0.953 mmol) in DCM (3.7 ml, 57.5 mmol), and the resulting mixture was stirred at RT for 3 days, adding the reagents several times to achieve completion (overall 4 equivalents). The reaction was taken up with MeOH then concentrated under reduced pressure. The crude was purified over a Biotage Silica 50 g SNAP cartridge with a gradient of hexane and EtOAc to give the title compound (0.11 g, 47.6%).
UPLC-MS: 2.21 min, 358 [M+H+ACN]+, method 4.

Intermediate C2. 3-(Bromomethyl)-4-(2-fluorophenyl)-1H-isochromen-1-one

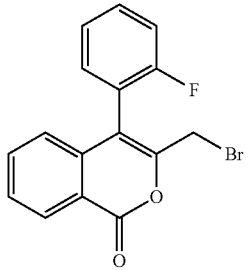 [SMILES: O=c1oc(CBr)c(-c2ccccc2F)c2ccccc12]

Triphenylphosphine (0.127 g, 0.488 mmol)) was added to a solution of 4-(2-fluorophenyl)-3-(hydroxymethyl)-1H-isochromen-1-one (intermediate B4, 40 mg, 0.148 mmol) and perbromomethane (0.161 g, 0.488 mmol) in DCM (0.7 ml, 57.5 mmol), and the resulting mixture was stirred at RT for 24 hrs. The reaction was taken up with MeOH then concentrated under reduced pressure. The crude was purified over a Biotage Silica 10 g SNAP cartridge with a gradient of hexane and EtOAc to give the title compound (37 mg, 75%).
UPLC-MS: 2.21 min, 358 [M+H+ACN]+, method 4.

Intermediate C3.
3-(Bromomethyl)-4-m-tolyl-1H-isochromen-1-one

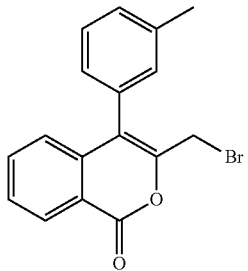 [SMILES: Cc1cccc(-c2c(CBr)oc(=O)c3ccccc23)c1]

Triphenylphosphine (270 mg, 1.030 mmol) and perbromomethane (342 mg, 1.030 mmol) were added to a solution of 3-(hydroxymethyl)-4-m-tolyl-1H-isochromen-1-one (intermediate B5, 211 mg, 0.792 mmol) in DMF (2 ml), and the resulting mixture was stirred at RT. The reaction was then purified via reverse phase chromatography with a Biotage C18 30 g SNAP column (Phase A, water 95%, ACN 4.5%, formic acid 0.5%; Phase B ACN 99.5%, formic acid 0.5%) to give the title compound (192 mg, 73.6%).
UPLC-MS: 2.32 min, 372 [M+H+ACN]+, method 4

Intermediate C4. 3-(Bromomethyl)-4-(3-fluorophenyl)-1H-isochromen-1-one

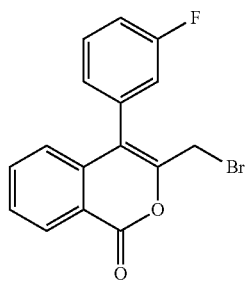 [SMILES: O=c1oc(CBr)c(-c2cccc(F)c2)c2ccccc12]

Triphenylphosphine (265 mg, 1.01 mmol) and perbromomethane (335 mg, 1.010 mmol) were added to a solution of 4-(3-fluorophenyl)-3-(hydroxymethyl)-1H-isochromen-1-one (intermediate B3, 210 mg, 0.777 mmol) in DCM (6.5 ml) and the mixture was stirred overnight at RT. Further triphenylphosphine (265 mg, 1.010 mmol) and perbromomethane (335 mg, 1.01 mmol) were then added and left on stirring at RT for 6 hrs. The reaction was then diluted with MeOH (1 ml) and straightforward purified on 50 g Biotage silica cartridge eluting with a gradient of Hexane and EtOAc to give the title compound (154 mg, 59.5%) as a yellow solid.
UPLC-MS: 2.20 min, 334.6 [M+H]+, method 4

Intermediate C5. 3-(1-Bromoethyl)-4-m-tolyl-1H-isochromen-1-one

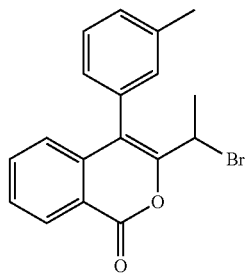 [SMILES: Cc1cccc(-c2c(C(C)Br)oc(=O)c3ccccc23)c1]

Triphenylphosphine (365 mg, 1.39 mmol) and perbromomethane (461 mg, 1.39 mmol) was added to a solution of 3-(1-hydroxyethyl)-4-m-tolyl-1H-isochromen-1-one (intermediate B6, 300 mg, 1.07 mmol) in DCM (2.2 ml), and the resulting mixture was stirred at RT. The reaction product was then purified on the silica Biotage SNAP 50 g, eluting with a gradient of hexane and EtOAc to give the title compound (67 mg, 18.3%).
UPLC-MS: 2.39 min, 386 [M+H+ACN]+, method 4.

Intermediate C6. 3-(1-Bromoethyl)-4-(3-fluorophenyl)-1H-isochromen-1-one

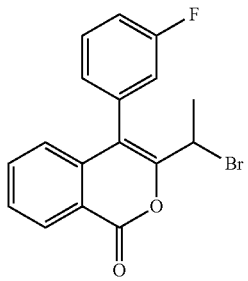 [SMILES: CC(Br)c1oc(=O)c2ccccc2c1-c1cccc(F)c1]

1 M PBr₃ in DCM (2.3 ml, 2.332 mmol) was added to a solution of 4-(3-fluorophenyl)-3-(1-hydroxyethyl)-1H-isochromen-1-one (intermediate B7, 390 mg, 1.372 mmol) in DCM (7.8 ml) and the mixture stirred at RT for 2 hrs. The reaction mixture was then evaporated under reduced pressure and purified on a silica Biotage SNAP 100 g, eluting with a gradient of hexane and EtOAc to give the title (227 mg, 47.7%).

UPLC-MS: 2.27 min, 348 [M+H]+, method 4

Intermediate C7. 3-(1-Bromoethyl)-4-phenyl-1H-isochromen-1-one

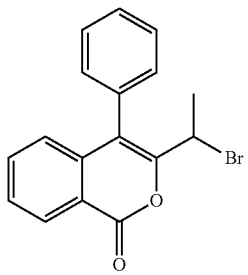 [SMILES: CC(Br)c1oc(=O)c2ccccc2c1-c1ccccc1]

The title compound was made in a similar way as that of the intermediate C6, using 3-(1-hydroxyethyl)-4-phenyl-1H-isochromen-1-one (Intermediate B1, 2.6 g, 9.76 mmol), 1M PBr₃ in DCM (17.5 ml, 17.5 mmol) (30 ml) at RT. The crude was purified with Biotage Silica SNAP 100 g with a gradient of hexane and AcOEt to give the title compound (1.64 g, 51%).

UPLC-MS: 2.28 min, 331 [M+H+ACN]+, method 4

Intermediate C8. 3-(1-Bromoethyl)-4-(3-(dimethylamino)phenyl)-1H-isochromen-1-one

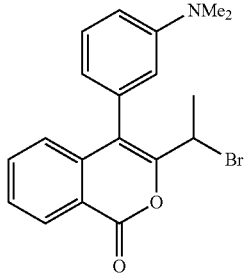 [SMILES: CC(Br)c1oc(=O)c2ccccc2c1-c1cccc(N(C)C)c1]

The title compound was made in a similar way as that of the intermediate C6, using 4-(3-(dimethylamino)phenyl)-3-(1-hydroxyethyl)-1H-isochromen-1-one (intermediate B8, 200 mg, 0.64 mmol), 1M PBr₃ (1.1 ml, 1.1 mmol) in DCM (2 ml) at RT. The crude was purified with Biotage Silica SNAP 50 g with a gradient of DCM and MeOH to give the title compound (300 mg).

UPLC-MS: 6.9 min, 292 [M-Br]+, method 2.

Intermediate C9. 3-(1-Bromoethyl)-4-(3-(morpholinosulfonyl)phenyl)-1H-isochromen-1-one

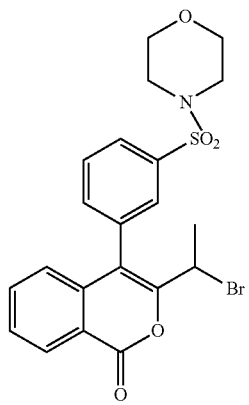

The title compound was made in a similar way as that of the intermediate C6, using 3-(1-hydroxyethyl)-4-(3-(morpholinosulfonyl)phenyl)-1H-isochromen-1-one (intermediate B9, 163 mg, 0.392 mmol), 1M PBr₃ (0.68 ml, 0.667 mmol) in DCM (3.2 ml) at RT. The crude was tritured with DMF to give the title compound (93 mg, 49%). The solution was purified via reverse phase chromatography with a Biotage C18 SNAP 30 g column (Phase A, water 95%, ACN 4.9%, formic acid 0.1%); Phase B ACN 99.9%, formic acid 0.1%) to give further compound (68 mg, 36.2%).

UPLC-MS: 5.75 min, 479 [M+H]+, method 5.

Intermediate C10. 3-(1-Bromoethyl)-4-(6-methylpyridin-3-yl)-1H-isochromen-1-one hydrobromide

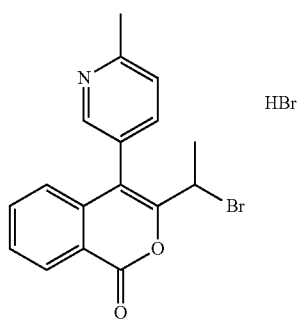 [SMILES: Cc1ccc(-c2c(C(C)Br)oc(=O)c3ccccc23)cn1 ; Br]

The title compound was made in a similar way as that of the intermediate C6, using 3-(1-hydroxyethyl)-4-(6-methylpyridin-3-yl)-1H-isochromen-1-one intermediate B10 (163 mg, 0.579 mmol), 1M PBr₃ (0.87 mL, 0.87 mmol) in a mixture of DCM (2 ml) and DMF (3 ml) at RT. The crude was purified via reverse phase chromatography with a Biotage C18 SNAP 60 g column (Phase A, water 95%, ACN 4.9%, formic acid 0.1%); Phase B ACN 99.9%, formic acid 0.1%). The aqueous fractions were added of 50% HBr$_{aqueous}$ and concentrated under reduced pressure to give the title compound (320 mg).

UPLC-MS: 1.73 min, 344 [M+H]+, method 4.

Intermediate C11. tert-Butyl 4-(3-(1-bromoethyl)-1-oxo-1H-isochromen-4-yl)-5,6-dihydropyridine-1(2H)-carboxylate

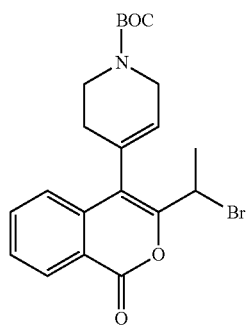 [SMILES: CC(Br)c1oc(=O)c2ccccc2c1C1=CCN(C(=O)OC(C)(C)C)CC1]

1M PBr$_3$ (0.36 ml, 0.363 mmol) in DCM was added dropwise to a solution of tert-butyl 4-(3-(1-hydroxyethyl)-1-oxo-1H-isochromen-4-yl)-5,6-dihydropyridine-1(2H)-carboxylate (intermediate B12, 135 mg, 0.363 mmol) in DCM (5 ml). Reaction mixture was then dried under reduced pressure and dissolved in DCM (5 ml). Di-tert-butyl dicarbonate (0.34 ml, 1.454 mmol) and DMAP (89 mg, 0.727 mmol) were added simultaneously, and the mixture stirred overnight at RT. Reaction mixture was straightforward purified on Biotage SNAP 50 g silica cartridge with a gradient of hexane and EtOAc give the title compound (100 mg, 63.3%) as a yellowish oil.

UPLC-MS: 2.30 min, 435 [M+H]+, method 4.

Intermediate C12. 3-(1-Bromoethyl)-4-(thiazol-5-yl)-1H-isochromen-1-one

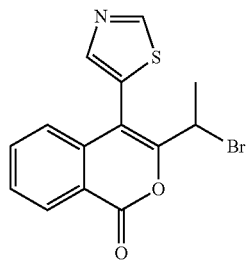 [SMILES: CC(Br)c1oc(=O)c2ccccc2c1-c1cncs1]

1M PBr$_3$ (0.5 ml, 0.50 mmol) in DCM was added dropwise to of 3-(1-hydroxyethyl)-4-(thiazol-5-yl)-1H-isochromen-1-one (Intermediate B11, 102 mg, 0.372 mmol) in DCM (4 ml) and ACN (2 ml) at RT. Reaction mixture was then concentrated under reduced pressure and straightforward purified on Biotage Silica SNAP 12 g cartridge with a gradient of hexane and EtOAc to give the title compound (56 mg, 45%).

UPLC-MS: 1.90 min, 337 [M+H]+, method 4.

Intermediate C13. 4-Benzyl-3-(1-bromoethyl)-1H-isochromen-1-one

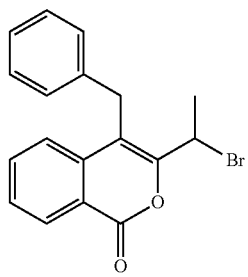 [SMILES: CC(Br)c1oc(=O)c2ccccc2c1Cc1ccccc1]

1 M PBr$_3$ in DCM (0.105 mL, 1.105 mmol) was added to 4-benzyl-3-(1-hydroxyethyl)-1H-isochromen-1-one (Intermediate B14, 625 mg, 2.230 mmol) in DCM (2 ml) at RT. Reaction mixture was straightforward purified on Biotage SNAP 25 g silica cartridge with a gradient of hexane and EtOAc to give the title compound (22 mg, 2.9%).

UPLC-MS: 2.19 min, 345 [M+H]+, method 4.

Intermediate C14. 3-(1-Bromoethyl)-4-(2-methylpyridin-4-yl)-1H-isochromen-1-one

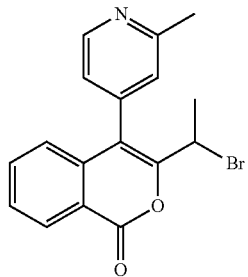 [SMILES: Cc1cc(-c2c(C(C)Br)oc(=O)c3ccccc23)ccn1]

1 M PBr$_3$ in DCM (846 µL, 0.846 mmol) was added to of 3-(1-hydroxyethyl)-4-(2-methylpyridin-4-yl)-1H-isochromen-1-one (intermediate B13, 140 mg, 0.498 mmol) in DCM at RT. Reaction mixture was concentrated under reduced pressure and straightforward purified via reverse phase chromatography with a Biotage C18 SNAP 60 g column (Phase A, water 95%, ACN 4.5%, formic acid 0.5%); Phase B ACN 99.5%, formic acid 0.5%) to give the title compound (80 mg, 45%).

UPLC-MS: 1.60 min, 345 [M+H+ACN]+, method 4.

Intermediate C15. 3-(1-Bromoethyl)-4-(4-(2-morpholinoethoxy)phenyl)-1H-isochromen-1-one hydrobromide

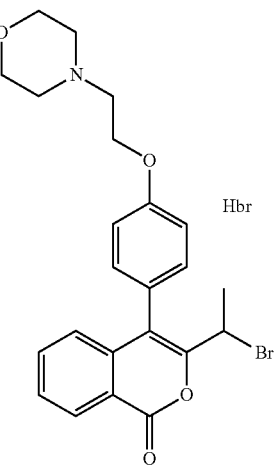

1 M PBr₃ in DCM (1.82 mL, 1.82 mmol) was added to 3-(1-hydroxyethyl)-4-(4-(2-morpholinoethoxy)phenyl)-1H-isochromen-1-one (Intermediate B15, 180 mg, 0.455 mmol) in DCM (2 ml) at RT. The reaction mixture was then was diluted with Et₂O and filtered. The residue was further washed with Et₂O and finally dried to give the title compound (150 mg, 61%) as a pink-red solid.

UPLC-MS: 1.58 min, 457 [M+H+ACN]+, method 4.

Intermediate C16. 3-(1-Bromoethyl)-4-(5-(morpholinomethyl)thiophen-2-yl)-1H-isochromen-1-one hydrobromide

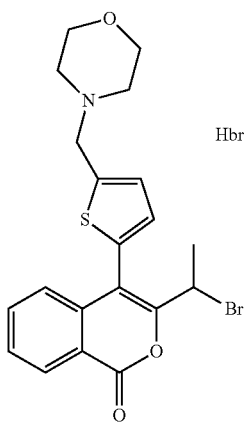 [SMILES: CC(Br)c1oc(=O)c2ccccc2c1-c1ccc(CN2CCOCC2)s1]

1M PBr₃ in DCM (1.82 mL, 1.82 mmol) was added to 3-(1-hydroxyethyl)-4-(5-(morpholinomethyl)thiophen-2-yl)-1H-isochromen-1-one (intermediate B16, 258 mg, 0.695 mmol) in DCM (2.6 ml) at RT. The reaction mixture concentrated under reduced pressure and the crude was crystallized from boiling DCM/MeOH 4/1 (5 ml) to give the title compound as colourless solid (138 mg, 38.6%)

UPLC-MS: 3.60 min, 354 [M-Br]+, method 5.

Intermediate C17. 3-(1-Bromoethyl)-4-(6-methoxypyridin-3-yl)-1H-isochromen-1-one

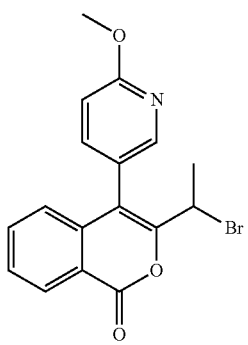 [SMILES: COc1ccc(-c2c(C(C)Br)oc(=O)c3ccccc23)cn1]

1M PBr₃ in DCM (1.80 mL, 1.80 mmol) was added 3-(1-hydroxyethyl)-4-(6-methoxypyridin-3-yl)-1H-isochromen-1-one (intermediate B17, 225 mg, 0.76 mmol) in DCM (9 ml) at RT. The reaction mixture was straightforward purified on Biotage SNAP 25 g silica cartridge with a gradient of hexane and EtOAc to give the title compound (105 mg, 38.5%).

UPLC-MS: 2.12 min, 361 [M+H]+, method 4.

Intermediate C18. 3-(1-Chloroethyl)-4-phenyl-1H-isochromen-1-one

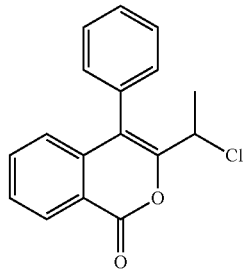 [SMILES: CC(Cl)c1oc(=O)c2ccccc2c1-c1ccccc1]

3-(1-Hydroxyethyl)-4-phenyl-1H-isochromen-1-one (intermediate B1, 300 mg, 1.27 mmol), Methane sulfonyl chloride (516 mg, 4.51 mmol), TEA (0.62 mmol, 4.5 ml) were reacted in DCM (10 ml) at RT. Solvent was then removed under reduced pressure to give the title compound (180 mg). This was used in next step without any further purification.

UPLC-MS: 2.25 min, 285 [M+H]+, method 4.

Intermediate C19. 3-(1-bromoethyl)-4-(3,6-dihydro-2H-pyran-4-yl)-1H-isochromen-1-one

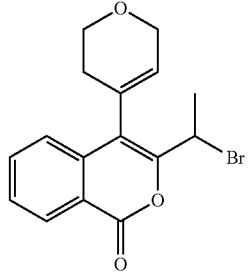 [SMILES: CC(Br)c1oc(=O)c2ccccc2c1C1=CCOCC1]

1 M PBr₃ in DCM (1.43 mL, 1.43 mmol) was added to 4-(3,6-dihydro-2H-pyran-4-yl)-3-(1-hydroxyethyl)-1H-isochromen-1-one (intermediate B18, 130 mg, 0.477 mmol) in DCM (2 mL) and stirred for 2 hrs at RT, then the reaction mixture was adsorbed on silica pad and straightforward purified on Biotage silica cartridge eluting with a gradient of hexane and AcOEt to give the title compound (94 mg, 58.7%) as an off white solid.

UPLC-MS: 1.98 min, 377 [M+H]+, method 4.

Intermediate C20. 3-(1-Bromopropyl)-4-phenyl-1H-isochromen-1-one

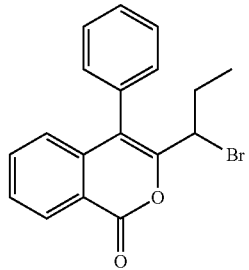 [SMILES: CCC(Br)c1oc(=O)c2ccccc2c1-c1ccccc1]

Step 1. Methyl 2-(pent-1-ynyl)benzoate (intermediate C20.1)

Pent-1-yne (5.6 mL, 57.2 mmol) was added to methyl 2-iodobenzoate (5.6 mL, 38.2 mmol), copper(I) iodide (1.0 g, 5.72 mmol) and Pd(PPh₃)₄ (1.3 g, 1.14 mmol) in DMF (5 mL) and Et₃N (1 mL) at RT for 3 hrs. The reaction was partitioned between Et₂O and 0.1 M HCl$_{aqueous}$. The resulting organic phase was washed with 0.1 M HCl$_{aqueous}$, NaHCO₃$_{aqueous}$ and brine. Organic phase was then anhydrified over Na₂SO₄ and dried under reduced pressure to give methyl 2-(pent-1-ynyl)benzoate (7.8 g) as a dark oil. The crude will be used in the next step without further purification.

UPLC-MS: 2.14 min, 202 [M+H]+, method 4.

Step 2. 4-Iodo-3-propyl-1H-isochromen-1-one (intermediate C20.2)

Methyl 2-(pent-1-ynyl)benzoate (intermediate C20.1, 3 g, 14.83 mmol), iodine (11.29 g, 44.5 mmol) and sodium bicarbonate (3.74 g, 44.5 mmol) were reacted in Acetonitrile (50 mL) for 20 min. at RT. The reaction mixture was diluted with Et₂O and washed with 20% Na₂S₂O₃$_{aqueous}$ and brine. The organic phase was then dried over Na₂SO₄ and concentrated under reduced pressure. The crude was dissolved in Et₂O and purified over a silica pad to give the title compound (3.54 g, 76%) as a brown oil.

UPLC-MS: 2.27 min, 315 [M+H]+, method 4.

Step 3. 4-Phenyl-3-propyl-1H-isochromen-1-one (intermediate C20.3)

4-Iodo-3-propyl-1H-isochromen-1-one (intermediate C20.2, 0.80 g, 2.55 mmol), phenylboronic acid (0.39 g, 3.18 mmol), Pd(PPh₃)₄ (0.15 g, 0.127 mmol) and Cs₂CO₃ (1.16 g, 3.57 mmol) were reacted in DMF (10 ml) at 80° C. for 3 hrs. The reaction was the partitioned between AcOEt and 1 M HCl$_{aqueous}$, washed with 1 M HCl$_{aqueous}$ brine, dried over Na₂SO₄ and concentrated under reduced pressure. The resulting crude was purified on a silica 500 Biotage cartridge eluting with a gradient of Hexane and AcOEt to give the title compound (0.11 g, 15.9%) as a yellowish oil.

UPLC-MS: 2.35 min, 265 [M+H]+, method 4.

Step 4. 3-(1-Bromopropyl)-4-phenyl-1H-isochromen-1-one

4-Phenyl-3-propyl-1H-isochromen-1-one (intermediate C20.3, 107 mg, 0.405 mmol), N-bromosuccinimide (86 mg, 0.486 mmol), benzoyl peroxide (25 mg, 0.1 mmol) were reacted in CCl₄ (2 mL) at 100° C. for 2 hrs. The reaction mixture was then purified on Biotage 50 g silica gel cartridge with a gradient of hexane and EtOAc to give the title compound (101 mg, 72.7%) as a yellowish oil.

UPLC-MS: 2.37 min, 344 [M+H]+, method 4.

Intermediates C21-48 found in the table below may be prepared starting from suitable intermediate (Int.) reported below following similar procedures as for compound C6.

| Intermediate & Name | Molecular Structure | Int. | UPLC-MS Or ¹H-NMR |
|---|---|---|---|
| Intermediate C21<br>3-(1-bromoethyl)-4-(1-methyl-1,2,3,6-tetrahydropyridin-4-yl)-1H-isochromen-1-one hydrobromide | | B19 | Rt = 1.39 min, 349.7 [M + H]+, method 4. |
| Intermediate C22<br>3-(1-bromoethyl)-4-(4-(morpholinomethyl)phenyl)-1H-isochromen-1-one hydrobromide | | B20 | Rt = 1.57 min, 429.9 [M + H]+, method 4 |

-continued

| Intermediate & Name | Molecular Structure | Int. | UPLC-MS Or ¹H-NMR |
|---|---|---|---|
| Intermediate C24<br>3-(1-bromoethyl)-4-cyclohexenyl-1H-isochromen-1-one | | B22 | Rt = 2.43 min, 334.7 [M + H]+,<br>method 4. |
| Intermediate C25<br>3-(1-bromoethyl)-4-(1-methyl-1,2,5,6-tetrahydropyridin-3-yl)-<br>1H-isochromen-1-one hydrobromide | | B23 | Rt = 0.64 min, 350.0 [M + H]+,<br>method 9. |
| Intermediate C26<br>3-(1-bromoethyl)-4-(3-(4,4,5,5-tetramethyl-1,3-dioxolan-2-<br>yl)phenyl)-1H-isochromen-1-one | | B24 | Rt = 1.49 min, 459.1 [M + H]+,<br>method 9 |
| Intermediate C27<br>3-(1-bromoethyl)-4-(5-(piperidin-1-ylmethyl)thiophen-2-yl)-1H-<br>isochromen-1-one hydrobromide | | B25 | Rt = 0.82 min, 484.0 [M + H]+,<br>method 9 |

-continued

| Intermediate & Name | Molecular Structure | Int. | UPLC-MS Or ¹H-NMR |
|---|---|---|---|
| Intermediate C28<br>3-(1-bromoethyl)-4-(4-(4-methylpiperazine-1-carbonyl)phenyl)-1H-isochromen-1-one hydrobromide | 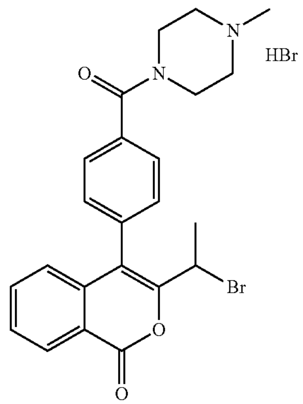 [SMILES: CC(Br)c1oc(=O)c2ccccc2c1-c1ccc(C(=O)N2CCN(C)CC2)cc1 ; Br] | B26 | Rt = 0.74 min, 457.0 [M + H]+, method 9 |
| Intermediate C29<br>3-(3-(1-bromoethyl)-1-oxo-1H-isochromen-4-yl)-N-(2-(dimethylamino)ethyl)benzamide hydrobromide | 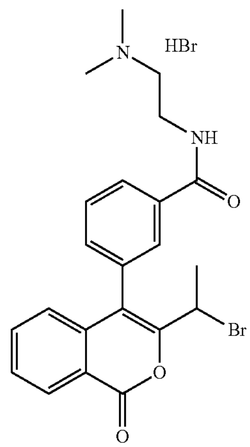 [SMILES: CC(Br)c1oc(=O)c2ccccc2c1-c1cccc(C(=O)NCCN(C)C)c1 ; Br] | B27 | Rt = 0.77 min, 445.0 [M + H]+, method 9 |
| Intermediate C30<br>4-(1-acetyl-1,2,3,6-tetrahydropyridin-4-yl)-3-(1-bromoethyl)-1H-isochromen-1-one | 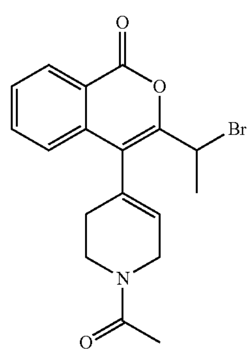 [SMILES: CC(=O)N1CC=C(c2c(C(C)Br)oc(=O)c3ccccc23)CC1] | B28 | Rt = 0.95 min, 378.0 [M + H]+, method 9 |
| Intermediate C31<br>3-(1-bromoethyl)-4-(5-(4,4,5,5-tetramethyl-1,3-dioxolan-2-yl)thiophen-2-yl)-1H-isochromen-1-one | 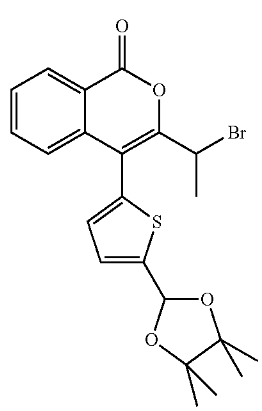 [SMILES: CC(Br)c1oc(=O)c2ccccc2c1-c1ccc(C2OC(C)(C)C(C)(C)O2)s1] | B29 | Rt = 1.47 min, 465.1 [M + H]+, method 9 |

-continued

| Intermediate & Name | Int. | UPLC-MS Or ¹H-NMR |
|---|---|---|
| Intermediate C32<br>benzyl (4-(3-(1-bromoethyl)-1-oxo-1H-isochromen-4-yl)cyclohex-3-en-1-yl)carbamate | B30 | Rt = 1.32 min, 482 [M + H]+, method 9 |
| Intermediate C33<br>tert-butyl (5-(3-(1-bromoethyl)-1-oxo-1H-isochromen-4-yl)thiazol-2-yl)carbamate | B31 | ¹H NMR (400 MHz, DMSO-$d_6$) δ ppm 8.26-8.34 (m, 1 H), 7.88-7.94 (m, 1 H), 7.73-7.80 (m, 1 H), 7.38-7.48 (m, 1 H), 6.89-6.97 (m, 1 H), 4.67-5.10 (m, 1 H), 1.81-1.94 (m, 3 H), 1.33 (s, 9 H). |
| Intermediate C34<br>4-(2-aminopyrimidin-5-yl)-3-(1-bromoethyl)-1H-isochromen-1-one | B32 | ¹H NMR (400 MHz, DMSO-$d_6$) δ ppm 8.17-8.34 (m, 3 H), 7.80-7.94 (m, 1 H), 7.59-7.75 (m, 1 H), 7.13-7.23 (m, 1 H), 6.94-7.08 (m, 2 H), 4.96-5.16 (m, 1 H), 1.90 (d, J = 6.62 Hz, 3 H) |
| Intermediate C35<br>tert-butyl 4-(4-(3-(1-bromoethyl)-1-oxo-1H-isochromen-4-yl)benzyl)piperazine-1-carboxylate | B33 | ¹H NMR (400 MHz, DMSO-$d_6$) δ ppm 8.19-8.32 (m, 1 H), 7.19-7.73 (m, 6 H), 6.93-7.02 (m, 1 H), 4.73-4.92 (m, 1 H), 3.60 (s, 2 H), 3.36 (br. s., 4 H), 2.39 (br. s., 4 H), 1.89 (d, J = 6.62 Hz, 3 H), 1.27-1.40 (s, 9 H) |
| Intermediate C36<br>3-(bromomethyl)-4-phenyl-1H-isochromene | B34 | Rt = 1.41 min, 302 [M + H]+, method 9. |

-continued

| Intermediate & Name | Int. | UPLC-MS Or ¹H-NMR |
|---|---|---|
| Intermediate C37<br>3-(1-(4-amino-3-iodo-1H-pyrazolo[3,4-d]pyrimidin-1-yl)ethyl)-4-(1-benzyl-1,2,3,6-tetrahydropyridin | B36 | Rt = 0.85 min, 426.1 [M + H]+, method 9 |
| Intermediate C38<br>benzyl 4-(3-(1-bromoethyl)-1-oxo-1H-isochromen-4-yl)-5,6-dihydropyridine-1(2H)-carboxylate | B35 | Rt = 1.25 min, 470.1 [M + H]+, method 9. |
| Intermediate C39<br>3-(1-bromoethyl)-4-(2,2,6,6-tetramethyl-1,2,3,6-tetrahydropyridin-4-yl)-1H-isochromen-1-one hydrobromide | B50 | Rt = 0.80 min, 389.8 [M ]+ and 391.8 [M + 2]+, method 9 |
| Intermediate C40<br>benzyl 3-(3-(1-bromoethyl)-1-oxo-1H-isochromen-4-yl)-8-azabicyclo[3.2.1]oct-2-ene-8-carboxylate | B51 | Rt = 1.37 min, 494 [M + H]+, method 9. |

-continued

| Intermediate & Name | Molecular Structure | Int. | UPLC-MS Or ¹H-NMR |
|---|---|---|---|
| Intermediate C41<br>benzyl (3-(3-(1-bromoethyl)-1-oxo-1H-isochromen-4-yl)prop-2-yn-1-yl)(methyl)carbamate | | B52 | Rt = 1.32 min, 454 [M + H]+, method 9 |
| Intermediate C42<br>3-(1-bromoethyl)-7-methyl-4-phenyl-1H-isochromen-1-one | | B53 | Rt = 1.37 min, 342.8-344.8 [M + H]+, method 12 |
| Intermediate C43<br>3-(1-bromoethyl)-7-chloro-4-phenyl-1H-isochromen-1-one | | B54 | Rt = 1.44 min, 363.1-365.1 [M + H]+, method 13 |
| Intermediate C44<br>3-(1-bromoethyl)-6-chloro-4-phenyl-1H-isochromen-1-one | | B55 | Rt = 1.43 min, 363.1-365.1 [M + H]+, method 13 |
| Intermediate C45<br>3-(1-bromoethyl)-6-fluoro-4-phenyl-1H-isochromen-1-one | | B56 | Rt = 1.35 min, 347.1-349.1 [M + H]+, method 13 |

| Intermediate & Name | Molecular Structure | Int. | UPLC-MS Or ¹H-NMR |
|---|---|---|---|
| Intermediate C46<br>4-(1-benzyl-1,2,5,6-tetrahydropyridin-3-yl)-3-(1-bromoethyl)-1H-isochromen-1-one hydrobromide | | B57 | Rt = 0.69 min, 424.3-426.3 [M + H]+, method 13 |
| Intermediate C47<br>3-(1-bromoethyl)-4-(pyridin-2-yl)-1H-isochromen-1-one | | B58 | Rt = 1.03 min, 330.2-332.2 [M + H]+, method 13. |
| Intermediate C48<br>3-(1-bromoethyl)-4-(morpholinomethyl)-1H-isochromen-1-one hydrobromide | | B59 | Rt = 0.71 min, 352.2-354.2 [M + H]+, method 13. |

Intermediate and compound D1. 3-((4-Amino-3-iodo-1H-pyrazolo[3,4-d]pyrimidin-1-yl)methyl)-4-phenyl-1H-isochromen-1-one

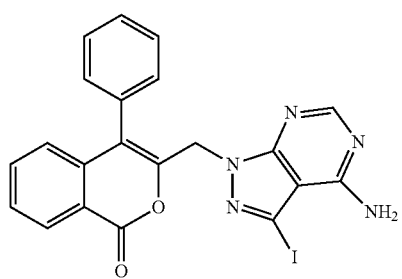 [SMILES: Nc1ncnc2c1c(I)nn2Cc1oc(=O)c2ccccc2c1-c1ccccc1]

Commercially available 3-iodo-1H-pyrazolo[3,4-d]pyrimidin-4-amine (124 mg, 0.476 mmol) was added to a solution of 3-(bromomethyl)-4-phenyl-1H-isochromen-1-one (intermediate C1, 100 mg, 0.317 mmol) in DMF (1 mL). K$_2$CO$_3$ (65.8 mg, 0.476 mmol) was added and the resulting mixture was stirred at 50° C. for 2 hrs. The resulting crude was straightforward purified via reverse phase chromatography with a Biotage C18 SNAP 30 g column (Phase A, water 95%, ACN 5%, formic acid 0.01%); Phase B ACN 95%, water 5%, formic acid 0.01%) to give the title compound (138 mg, 88%).

UPLC-MS: 1.92 min, 496 [M+H]+, method 4.

Intermediate D2a and D2b. 3-(1-(4-Amino-3-iodo-1H-pyrazolo[3,4-d]pyrimidin-1-yl)ethyl)-4-phenyl-1H-isochromen-1-one and 3-(1-(4-amino-3-iodo-2H-pyrazolo[3,4-d]pyrimidin-2-yl)ethyl)-4-phenyl-1H-isochromen-1-one

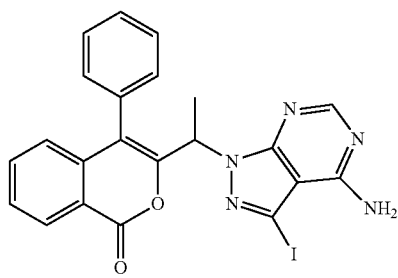

-continued

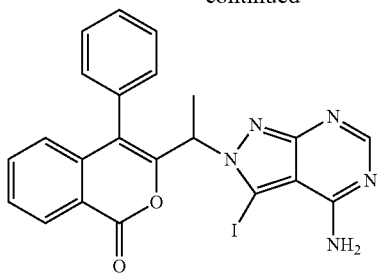

Commercially available 3-iodo-1H-pyrazolo[3,4-d]pyrimidin-4-amine (270 mg, 1.033 mmol) and 3-(1-bromoethyl)-4-phenyl-1H-isochromen-1-one (intermediate C7, 500 mg, 1.519 mmol) were dissolved in DMF (4 mL). $K_2CO_3$ (315 mg, 2.278 mmol) was added and the resulting mixture was stirred at 80° C. for 1 hr. The mixture was poured into water (50 ml) and extracted with AcOEt (10 ml×3). Organic phases were dried and evaporated under reduced pressure. The crude was purified via reverse phase chromatography with a Biotage C18 SNAP 60 g column (Phase A, water 95%, ACN 4.9%, formic acid 0.1%); Phase B ACN 95%, water 5%, formic acid 0.1%) to give 3-(1-(4-Amino-3-iodo-1H-pyrazolo[3,4-d]pyrimidin-1-yl)ethyl)-4-phenyl-1H-isochromen-1-one (intermediate D2a, 78 mg, 10%) and 3-(1-(4-amino-3-iodo-2H-pyrazolo[3,4-d]pyrimidin-2-yl)ethyl)-4-phenyl-1H-isochromen-1-one (intermediate D2b, 20 mg, 2.6%).

Intermediate D2a. UPLC-MS: 1.85 min, 510 [M+H]+, method 4.

Intermediate D2b. UPLC-MS: 1.95 min, 510 [M+H]+, method 4.

Intermediate and compound D3. 3-(1-(4-Amino-3-iodo-1H-pyrazolo[3,4-d]pyrimidin-1-yl)ethyl)-4-m-tolyl-1H-isochromen-1-one

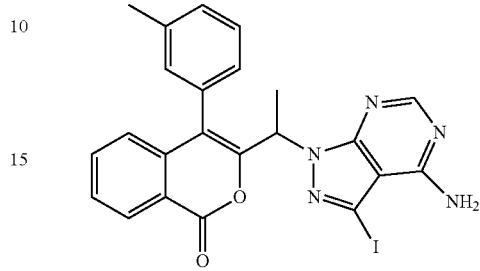

The title compound was made in a way similar to that of intermediate D2, from commercially available 3-iodo-1H-pyrazolo[3,4-d]pyrimidin-4-amine (125 mg, 0.481 mmol) and $K_2CO_3$ (66.4 mg, 0.481 mmol) and a solution of 3-(1-bromoethyl)-4-m-tolyl-1H-isochromen-1-one (intermediate C5, 110 mg, 0.320 mmol) in DMF (1.1 mL) to give the title compound (120 mg, 71.5%).

UPLC-MS: 5.87 min, 523 [M+H]+, method 5.

Intermediates D4-D22, D29-34 found in the table below may be prepared starting from suitable intermediate (Int.) reported below and 3-iodo-1H-pyrazolo[3,4-d]pyrimidin-4-amine following similar procedures as for compound D2.

| Intermediate & Name | | Int. | UPLC-MS |
|---|---|---|---|
| Intermediate D4<br>3-(1-(4-amino-3-iodo-1H-pyrazolo[3,4-d]pyrimidin-1-yl)ethyl)-4-(1-methyl-1,2,3,6-tetrahydropyridin-4-yl)-1H-isochromen-1-one hydrochloride | | C21 | Rt = 1.37 min, 528.7 [M + H]+, method 4 |
| Intermediate D5<br>3-(1-(4-amino-3-iodo-1H-pyrazolo[3,4-d]pyrimidin-1-yl)ethyl)-4-(4-(morpholinomethyl)phenyl)-1H-isochromen-1-one hydrochloride | | C22 | Rt = 1.52 min, 608.9 [M + H]+, method 4. |

-continued

| Intermediate & Name | | Int. | UPLC-MS |
|---|---|---|---|
| Intermediate D6<br>3-(1-(4-amino-3-iodo-1H-pyrazolo[3,4-d]pyrimidin-1-yl)ethyl)-4-(5-(morpholinomethyl)thiophen-2-yl)-1H-isochromen-1-one hydrochloride | 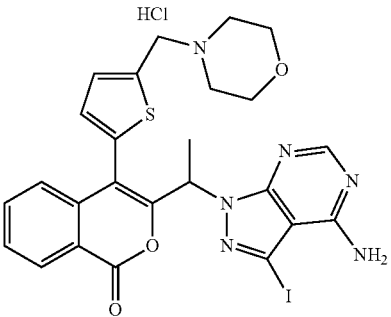 [SMILES: Cl ; CC(c1oc(=O)c2ccccc2c1-c1ccc(CN2CCOCC2)s1)n1nc(I)c2c(N)ncnc21] | C23 | Rt = 1.45 min, 614.8 [M + H]+, method 4. |
| Intermediate D7<br>3-(1-(4-amino-3-iodo-1H-pyrazolo[3,4-d]pyrimidin-1-yl)ethyl)-4-(1-methyl-1,2,5,6-tetrahydropyridin-3-yl)-1H-isochromen-1-one hydrochloride | 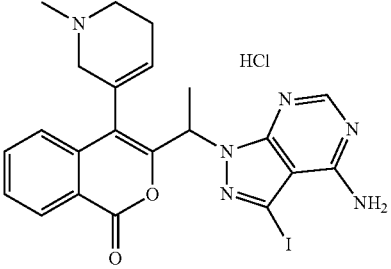 [SMILES: CC(c1oc(=O)c2ccccc2c1C1=CCCN(C)C1)n1nc(I)c2c(N)ncnc21 ; Cl] | C25 | Rt = 0.67 min, 529.0 [M + H]+, method 9 |
| Intermediate D8<br>3-(1-(4-amino-3-iodo-1H-pyrazolo[3,4-d]pyrimidin-1-yl)ethyl)-4-(3-(4,4,5,5-tetramethyl-1,3-dioxolan-2-yl)phenyl)-1H-isochromen-1-one | 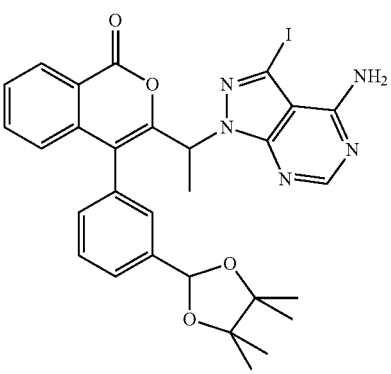 [SMILES: CC(c1oc(=O)c2ccccc2c1-c1cccc(C2OC(C)(C)C(C)(C)O2)c1)n1nc(I)c2c(N)ncnc21] | C26 | Rt = 1.27 min, 638.1 [M + H]+, method 9 |
| Intermediate D9<br>3-(1-(4-amino-3-iodo-1H-pyrazolo[3,4-d]pyrimidin-1-yl)ethyl)-4-(5-(piperidin-1-ylmethyl)thiophen-2-yl)-1H-isochromen-1-one hydrochloride | 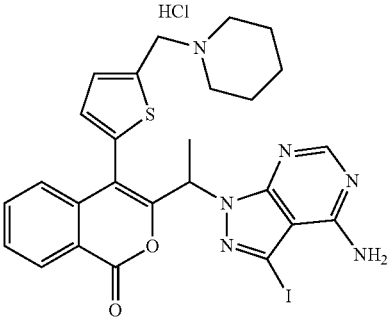 [SMILES: Cl ; CC(c1oc(=O)c2ccccc2c1-c1ccc(CN2CCCCC2)s1)n1nc(I)c2c(N)ncnc21] | C27 | Rt = 0.76 min, 613.0 [M + H]+, method 9 |

-continued

| Intermediate & Name | | Int. | UPLC-MS |
|---|---|---|---|
| Intermediate D10<br>3-(1-(4-amino-3-iodo-1H-pyrazolo[3,4-d]pyrimidin-1-yl)ethyl)-4-(4-(4-methylpiperazine-1-carbonyl)phenyl)-1H-isochromen-1-one hydrochloride | 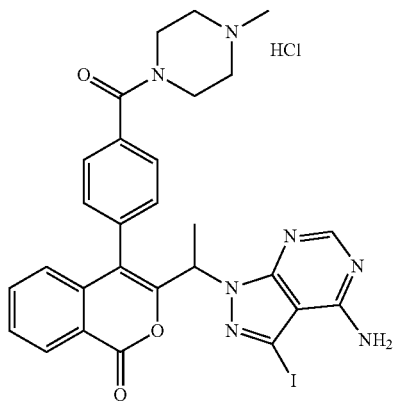 [SMILES: CC(c1oc(=O)c2ccccc2c1-c1ccc(C(=O)N2CCN(C)CC2)cc1)n1nc(I)c2c(N)ncnc21 ; Cl] | C28 | Rt = 0.68 min, 636.0 [M + H]+, method 9 |
| Intermediate D11<br>3-(3-(1-(4-amino-3-iodo-1H-pyrazolo[3,4-d]pyrimidin-1-yl)ethyl)-1-oxo-1H-isochromen-4-yl)-N-(2-(dimethylamino)ethyl)benzamide hydrochloride | 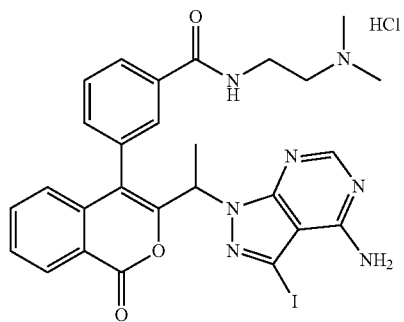 [SMILES: CC(c1oc(=O)c2ccccc2c1-c1cccc(C(=O)NCCN(C)C)c1)n1nc(I)c2c(N)ncnc21 ; Cl] | C29 | Rt = 0.69 min, 624.0 [M + H]+, method 9 |
| Intermediate D12<br>4-(1-acetyl-1,2,3,6-tetrahydropyridin-4-yl)-3-(1-(4-amino-3-iodo-1H-pyrazolo[3,4-d]pyrimidin-1-yl)ethyl)-1H-isochromen-1-one | 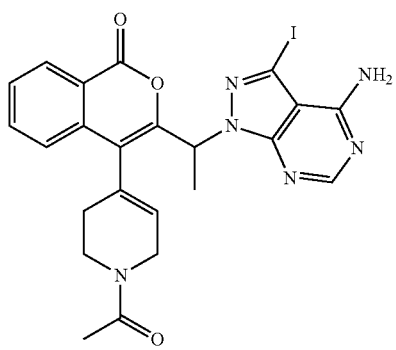 [SMILES: CC(=O)N1CC=C(c2c(C(C)n3nc(I)c4c(N)ncnc43)oc(=O)c3ccccc23)CC1] | C30 | Rt = 0.81 min, 557.0 [M + H]+, method 9 |
| Intermediate D13<br>3-(1-(4-amino-3-iodo-1H-pyrazolo[3,4-d]pyrimidin-1-yl)ethyl)-4-(5-(4,4,5,5-tetramethyl-1,3-dioxolan-2-yl)thiophen-2-yl)-1H-isochromen-1-one | 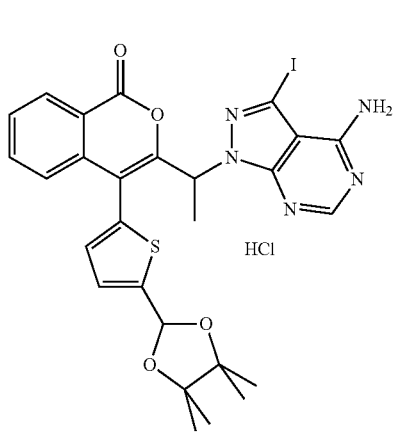 [SMILES: CC(c1oc(=O)c2ccccc2c1-c1ccc(C2OC(C)(C)C(C)(C)O2)s1)n1nc(I)c2c(N)ncnc21 ; Cl] | C31 | Rt = 1.25 min, 644.1 [M + H]+, method 9 |

-continued

| Intermediate & Name | Int. | UPLC-MS |
|---|---|---|
| Intermediate D14<br>tert-butyl 4-(3-(1-(4-amino-3-iodo-1H-pyrazolo[3,4-d]pyrimidin-1-yl)ethyl)-1-oxo-1H-isochromen-4-yl)-5,6-dihydropyridine-1(2H)-carboxylate | C11 | Rt = 1.21 min, 615.0 [M + H]+, method 9 |
| Intermediate D15<br>3-(1-(4-amino-3-iodo-1H-pyrazolo[3,4-d]pyrimidin-1-yl)ethyl)-4-benzyl-1H-isochromen-1-one | C13 | Rt = 1.06 min, 524.0 [M + H]+, method 9 |
| Intermediate D16<br>3-(1-(4-amino-3-iodo-1H-pyrazolo[3,4-d]pyrimidin-1-yl)ethyl)-4-(3-(dimethylamino)phenyl)-1H-isochromen-1-one | C8 | Rt = 1.97 min, 553 [M + H]+, method 4. |
| Intermediate D17<br>3-(1-(4-amino-3-iodo-1H-pyrazolo[3,4-d]pyrimidin-1-yl)ethyl)-4-(thiazol-5-yl)-1H-isochromen-1-one3 | C12 | Rt = 1.67 min, 516.6 [M + H]+, method 4. |
| Intermediate D18<br>tert-butyl (5-(3-(1-(4-amino-3-iodo-1H-pyrazolo[3,4-d]pyrimidin-1-yl)ethyl)-1-oxo-1H-isochromen-4-yl)thiazol-2-yl)carbamate | C33 | Rt = 0.91 min, 1.03 min (mixture of atropodiastereoisomers 50:50), 632 [M + H]+, method 9. |

| Intermediate & Name | Int. | UPLC-MS |
|---|---|---|
| Intermediate D19<br>tert-butyl 4-(4-(3-(1-(4-amino-3-iodo-1H-pyrazolo[3,4-d]pyrimidin-1-yl)ethyl)-1-oxo-1H-isochromen-4-yl)benzyl)piperazine-1-carboxylate | C35 | Rt = 1.57 min, 708 [M + H]+, method 4. |
| Intermediate D20<br>3-iodo-1-((4-phenyl-1H-isochromen-3-yl)methyl)-1H-pyrazolo[3,4-d]pyrimidin-4-amine | C36 | UPLC-MS 1.17 min, 482 [M + H]+, method 9. |
| Intermediate D21<br>3-(1-(4-amino-3-iodo-1H-pyrazolo[3,4-d]pyrimidin-1-yl)ethyl)-4-(1-benzyl-1,2,3,6-tetrahydropyridin-4-yl)-1H-isochromen-1-one hydrochloride | C37 | Rt = 0.83 min, 605.0 [M + H]+, method 9. |
| Intermediate D22<br>benzyl 4-(3-(1-(4-amino-3-iodo-1H-pyrazolo[3,4-d]pyrimidin-1-yl)ethyl) 1-oxo-1H-isochromen-4-yl)-5,6-dihydropyridine-1(2H)-carboxylate | C38 | Rt = 1.25 min, 644.1 [M + H]+, method 6 |

-continued

| Intermediate & Name | Int. | UPLC-MS |
|---|---|---|
| Intermediate D29<br>3-(1-(4-amino-3-iodo-1H-pyrazolo[3,4-d]pyrimidin-1-yl)ethyl)-7-methyl-4-phenyl-1H-isochromen-1-one | C42 | Rt = 1.18 min, 524.2 [M + H]+, method 13 |
| Intermediate D30<br>3-(1-(4-amino-3-iodo-1H-pyrazolo[3,4-d]pyrimidin-1-yl)ethyl)-7-chloro-4-phenyl-1H-isochromen-1-one | C43 | Rt = 1.24 min, 544.1 [M + H]+, method 14 |
| Intermediate D31<br>3-(1-(4-amino-3-iodo-1H-pyrazolo[3,4-d]pyrimidin-1-yl)ethyl)-6-chloro-4-phenyl-1H-isochromen-1-one | C44 | Rt = 1.23 min, 544.1 [M + H]+, method 13 |
| Intermediate D32<br>3-(1-(4-amino-3-iodo-1H-pyrazolo[3,4-d]pyrimidin-1-yl)ethyl)-6-fluoro-4-phenyl-1H-isochromen-1-one | C45 | Rt = 1.12 min, 528.1 [M + H]+, method 13 |
| Intermediate D33<br>3-(1-(4-amino-3-iodo-1H-pyrazolo[3,4-d]pyrimidin-1-yl)ethyl)-4-(1-benzyl-1,2,5,6-tetrahydropyridin-3-yl)-1H-isochromen-1-one hydrochloride | C46 | Rt = 0.65 min, 605.3 [M + H]+, method 13 |

| Intermediate & Name | | Int. | UPLC-MS |
|---|---|---|---|
| Intermediate D34<br>3-(1-(4-amino-3-iodo-1H-pyrazolo[3,4-d]pyrimidin-1-yl)ethyl)-4-(pyridin-2-yl)-1H-isochromen-1-one | 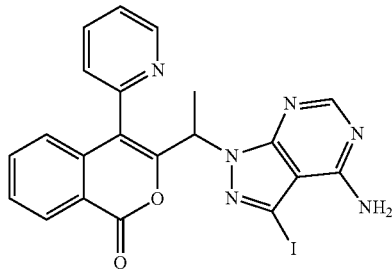 [SMILES: CC(c1oc(=O)c2ccccc2c1-c1ccccn1)n1nc(I)c2c(N)ncnc21] | C47 | Rt = 0.81 min, 511.3 [M + H]+, method 13 |

Intermediate D23. 3-(1-(4-amino-3-iodo-1H-pyrazolo[3,4-d]pyrimidin-1-yl)ethyl)-4-(1,2,3,6-tetrahydropyridin-4-yl)-1H-isochromen-1-one hydrochloride

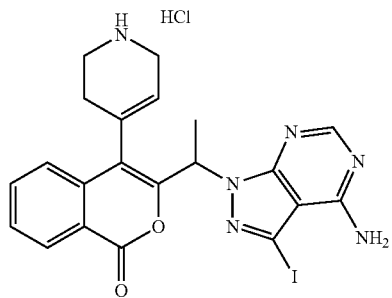 [SMILES: Cl ; CC(c1oc(=O)c2ccccc2c1C1=CCNCC1)n1nc(I)c2c(N)ncnc21]

Tert-butyl 4-(3-(1-(4-amino-3-iodo-1H-pyrazolo[3,4-d]pyrimidin-1-yl)ethyl)-1-oxo-1H-isochromen-4-yl)-5,6-dihydropyridine-1(2H)-carboxylate (Intermediate D14, 1.5 g, 2.441 mmol) was suspended in 1,4-Dioxane (5 ml) and 4 M HCl in dioxane (15.26 ml, 61.0 mmol) was added. The mixture was stirred at rt for 4 h, then volatiles were removed under reduced pressure to give title compound (1.56 g) as a light pink powder.

UPLC-MS: 0.47 min, 515 [M+H]+, method 9

Intermediate D24. 3-(1-(4-amino-3-iodo-1H-pyrazolo[3,4-d]pyrimidin-1-yl)ethyl)-4-(1-(1-isopropylpiperidin-4-yl)-1,2,3,6-tetrahydropyridin-4-yl)-1H-isochromen-1-one formate

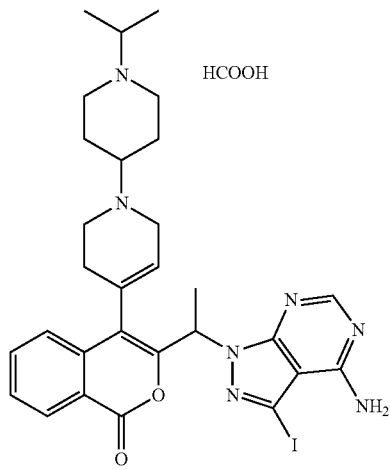 [SMILES: CC(C)N1CCC(N2CC=C(c3c(C(C)n4nc(I)c5c(N)ncnc54)oc(=O)c4ccccc34)CC2)CC1 ; "HCOOH"]

A mixture of 3-(1-(4-amino-3-iodo-1H-pyrazolo[3,4-d]pyrimidin-1-yl)ethyl)-4-(1,2,3,6-tetrahydropyridin-4-yl)-1H-isochromen-1-one hydrochloride (Intermediate D23, 0.1 g, 0.182 mmol), 1-isopropylpiperidin-4-one (0.064 ml, 0.438 mmol), DIPEA (0.032 ml, 0.182 mmol) and a spatula of sodium sulfate in DCM (3 ml) was stirred at rt for 10 min. Acetic acid (0.061 mL, 1.09 mmol) was then added followed by sodium triacetoxyborohydride (154 mg, 0.726 mmol). The resulting suspension was stirred for 3 hrs at rt, then the reaction was quenched by the addition of 2 N HCl. The heterogeneous mixture was concentrated under reduced pressure. Purification by RP-flash chromatography (Biotage 30 g C18 column, gradient elution from 100:0 to 60:40 A/B in 15 CV; A: water/MeCN 95/5+0.01% HCOOH, B: water/MeCN 5/95+0.01% HCOOH) yielded title compound (99.8 mg, 0.146 mmol, 80% yield) as a light yellow powder.

UPLC-MS: 0.71 min, 640 [M+H]+, method 9

Intermediate D25. 3-(1-(4-amino-3-iodo-1H-pyrazolo[3,4-d]pyrimidin-1-yl)ethyl)-4-(1-(4-(dimethylamino)butanoyl)-1,2,3,6-tetrahydropyridin-4-yl)-1H-isochromen-1-one formate

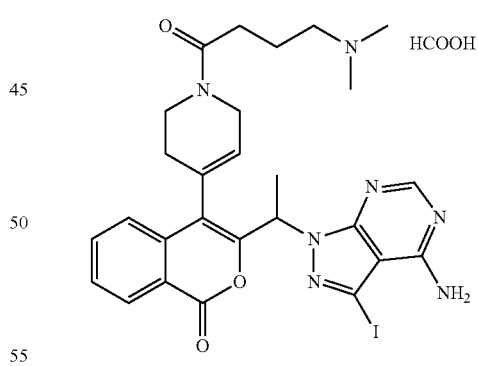

DIPEA (0.253 ml, 1.452 mmol) was added at 0° C. to a stirred suspension of 3-(1-(4-amino-3-iodo-1H-pyrazolo[3,4-d]pyrimidin-1-yl)ethyl)-4-(1,2,3,6-tetrahydropyridin-4-yl)-1H-isochromen-1-one hydrochloride (Intermediate D23, 0.200 g, 0.363 mmol), HATU (0.166 g, 0.436 mmol) and 4-dimethylaminobutyric acid hydrochloride (0.073 g, 0.436 mmol) in THF/DMF 5:1 (6 mL). The mixture was stirred at 0° C. for 15 min, then at rt for further 45 min. The reaction mixture was poured into saturated aqueous sodium bicarbonate and extracted with DCM. The collected organic phases were concentrated under reduced pressure and the crude purified by RP-flash chromatography (Biotage 30 g C18 column, gradient elution from 100:0 to 70:30 A/B in 15 CV; A: water/MeCN 95/5+0.01% HCOOH, B: water/MeCN 5/95+0.01% HCOOH) to give title compound (0.153 g, 0.227 mmol, 62.6% yield) as a white powder.

UPLC-MS: 0.67 min, 628 [M+H]+, method 9

Intermediate D26. 3-(1-(4-amino-3-iodo-1H-pyrazolo[3,4-d]pyrimidin-1-yl)ethyl)-4-(1-(2-(dimethylamino)acetyl)-1,2,3,6-tetrahydropyridin-4-yl)-1H-isochromen-1-one formate

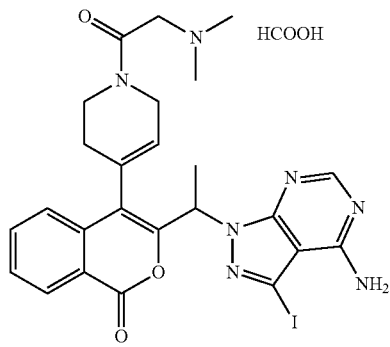 [SMILES: CC(c1oc(=O)c2ccccc2c1C1=CCN(C(=O)CN(C)C)CC1)n1nc(I)c2c(N)ncnc21 ; "HCOOH"]

Title compound was prepared following the procedure used for the synthesis of Intermediate D25, from 3-(1-(4-amino-3-iodo-1H-pyrazolo[3,4-d]pyrimidin-1-yl)ethyl)-4-(1,2,3,6-tetrahydropyridin-4-yl)-1H-isochromen-1-one hydrochloride (Intermediate Intermediate D23, 0.200 g, 0.363 mmol) and 2-(dimethylamino)acetic acid (0.045 g, 0.436 mmol) to give the title compound (0.127 g, 0.197 mmol, 54.2% yield) as a white powder.

UPLC-MS: 0.64 min, 600 [M+H]+, method 9

Intermediate D27. 3-(1-(4-amino-3-iodo-1H-pyrazolo[3,4-d]pyrimidin-1-yl)ethyl)-4-(1-(1-methylpiperidine-4-carbonyl)-1,2,3,6-tetrahydropyridin-4-yl)-1H-isochromen-1-one formate

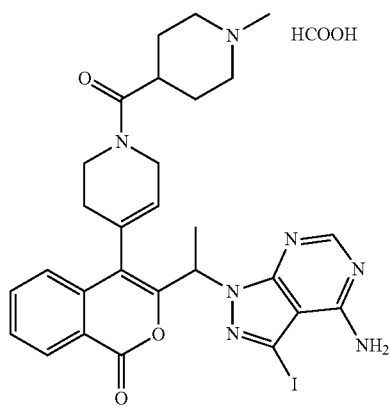 [SMILES: CC(c1oc(=O)c2ccccc2c1C1=CCN(C(=O)C2CCN(C)CC2)CC1)n1nc(I)c2c(N)ncnc21 ; "HCOOH"]

Title compound was prepared following the procedure used for the synthesis of Intermediate D25, from 3-(1-(4-amino-3-iodo-1H-pyrazolo[3,4-d]pyrimidin-1-yl)ethyl)-4-(1,2,3,6-tetrahydropyridin-4-yl)-1H-isochromen-1-one hydrochloride (Intermediate D23, 0.200 g, 0.363 mmol), and 1-methylpiperidine-4-carboxylic acid (0.062 g, 0.436 mmol) to give the title compound (99.4 mg, 0.145 mmol, 39.9% yield) as a white powder.

UPLC-MS: 0.65 min, 640 [M+H]+, method 9

Intermediate D28. tert-butyl 3-(4-(3-(1-(4-amino-3-iodo-1H-pyrazolo[3,4-d]pyrimidin-1-yl)ethyl)-1-oxo-1H-1-isochromen-4-yl)-1,2,3,6-tetrahydropyridine-1-carbonyl)azetidine-1-carboxylate

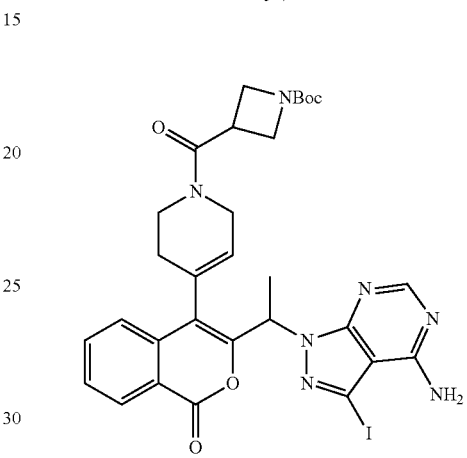

Title compound was prepared following the procedure used for the synthesis of Intermediate D25, from 3-(1-(4-amino-3-iodo-1H-pyrazolo[3,4-d]pyrimidin-1-yl)ethyl)-4-(1,2,3,6-tetrahydropyridin-4-yl)-1H-isochromen-1-one hydrochloride (Intermediate D23, 0.200 g, 0.363 mmol), and Boc-azetidine-3-carboxylic acid (0.088 g, 0.436 mmol) to give the title compound (0.252 g, 0.361 mmol, 99% yield).

UPLC-MS: 1.04 min, 698 [M+H]+, method 9

Intermediate E1. tert-butyl 1-(1-oxo-4-phenyl-1H-isochromen-3-yl)ethylcarbamate

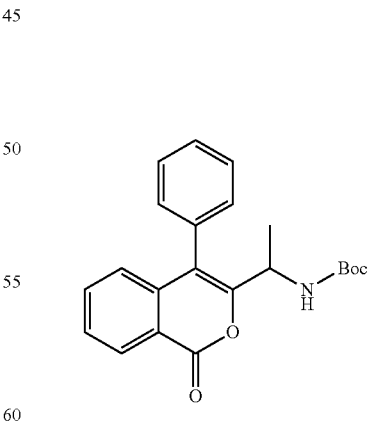

The title compound was made in a way similar to that of intermediate B1 from tert-butyl 1-(4-bromo-1-oxo-1H-isochromen-3-yl)ethylcarbamate (Intermediate A3, 500 mg, 1.358 mmol), phenylboronic acid (215 mg, 1.765 mmol), to give the title compound (112 mg, 22.6%) as a yellowish oil.

UPLC-MS: 2.24 min, 731.0 [2M+H]+, method 4.

Intermediate E2.
3-(1-aminoethyl)-4-phenyl-1H-isochromen-1-one hydrochloride

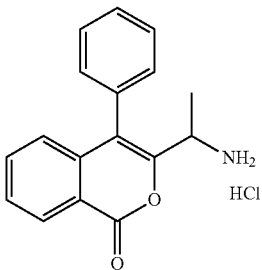 [SMILES: CC(N)c1oc(=O)c2ccccc2c1-c1ccccc1 ; Cl]

tert-butyl 1-(1-oxo-4-phenyl-1H-isochromen-3-yl)ethylcarbamate (Intermediate E1, 112 mg, 0.306 mmol) was dissolved in DCM (3 ml), then a solution of 4M HCl in dioxane (3 ml, 12.00 mmol) was added and the mixture stirred rt for 4 h. The reaction was quenched by the addition of Et$_2$O (50 mL) and the mixture dried under reduced pressure to afford the title compound.
UPLC-MS: 1.43 min, 265.8 [M+H]+, method 4.

Intermediate E3. 3-(1-aminoethyl)-4-(5-(morpholinomethyl)thiophen-2-yl)-1H-isochromen-1-one dihydrochloride

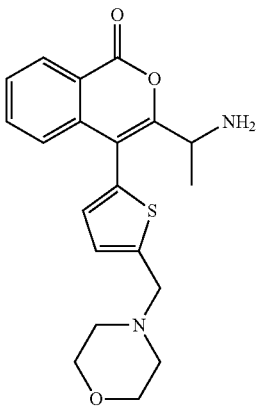 [SMILES: CC(N)c1oc(=O)c2ccccc2c1-c1ccc(CN2CCOCC2)s1]

The title compound was made in a way similar to that of intermediate B1 from tert-butyl (1-(4-bromo-1-oxo-1H-isochromen-3-yl)ethyl)carbamate (Intermediate A3, 1 g, 2.72 mmol), 4-((5-(4,4,5,5-tetramethyl-1,3,2-dioxaborolan-2-yl)thiophen-2-yl)methyl)morpholine (0.840 g, 2.72 mmol), to give (prior to drying a small amount of 1M HCl$_{aqueous}$ was added) the title compound (587 mg, 71.2%) as yellowish solid.
UPLC-MS: 0.39 min, 354.1 [(M+H)—NH$_3$)]+, method 9

Intermediate E4. 3-(1-aminoethyl)-4-(1H-pyrazol-4-yl)-1H-isochromen-1-one dihydrochloride

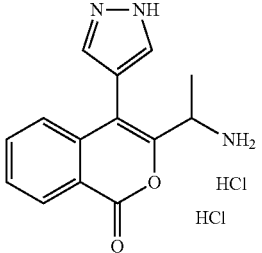 [SMILES: CC(N)c1oc(=O)c2ccccc2c1-c1cn[nH]c1 ; Cl ; Cl]

The title compound was made in a way similar to that of intermediate B1 from tert-butyl 1-(4-bromo-1-oxo-1H-isochromen-3-yl)ethylcarbamate (intermediate A3, 500 mg, 1.358 mmol), 1H-pyrazol-4-ylboronic acid (198 mg, 1.765 mmol). After purification the collected fractions were added with 37% HCl$_{aqueous}$ (1 ml) and concentrated to give the title compound (158 mg, 35.5% yield).
UPLC-MS: 1.44 min, 256, 511 [M+H]+, method 3.

Intermediate F1. 3-(1-(4-amino-3-(3-fluoro-5-hydroxyphenyl)-1H-pyrazolo[3,4-d]pyrimidin-1-yl)ethyl)-4-(3-(4,4,5,5-tetramethyl-1,3-dioxolan-2-yl)phenyl)-1H-isochromen-1-one

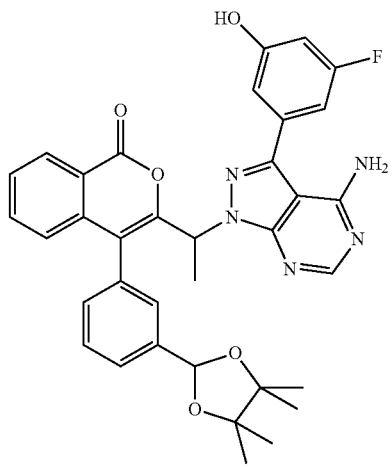 [SMILES: CC(c1oc(=O)c2ccccc2c1-c1cccc(C2OC(C)(C)C(C)(C)O2)c1)n1nc(-c2cc(O)cc(F)c2)c2c(N)ncnc21]

3-(1-(4-amino-3-iodo-1H-pyrazolo[3,4-d]pyrimidin-1-yl)ethyl)-4-(3-(4,4,5,5-tetramethyl-1,3-dioxolan-2-yl)phenyl)-1H-isochromen-1-one (Intermediate D8, 1.14 g, 1.788 mmol), (3-fluoro-5-hydroxyphenyl)boronic acid (0.558 g, 3.58 mmol), K$_2$CO$_3$ (0.494 g, 3.58 mmol) and PdCl$_2$(dppf) (0.196 g, 0.268 mmol) were reacted in dioxane (30 ml) overnight at 120° C. The reaction was diluted with DCM (100 ml), filtered to remove solids, and the filtrate evaporated under reduced pressure. The crude was purified via flash chromatography on silica gel using a Biotage 100G SNAP with a gradient of DCM and MeOH to give the title compound (819 mg, 73.7%) as brown pale solid.
UPLC-MS: 1.23 min, 622.2 [M+H]+, method 9

Intermediate F2. 3-(3-(1-(4-amino-3-(3-fluoro-5-hydroxyphenyl)-1H-pyrazolo[3,4-d]pyrimidin-1-yl)ethyl)-1-oxo-1H-isochromen-4-yl)benzaldehyde

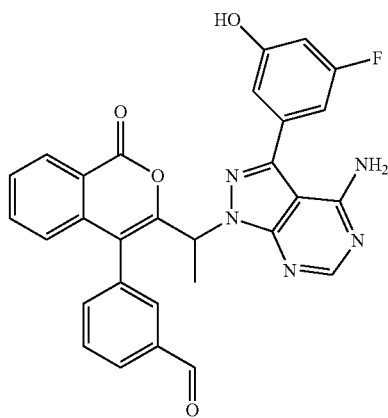 [SMILES: CC(c1oc(=O)c2ccccc2c1-c1cccc(C=O)c1)n1nc(-c2cc(O)cc(F)c2)c2c(N)ncnc21]

3-(1-(4-amino-3-(3-fluoro-5-hydroxyphenyl)-1H-1-pyrazolo[3,4-d]pyrimidin-1-yl)ethyl)-4-(3-(4,4,5,5-tetramethyl-1,3-dioxolan-2-yl)phenyl)-1H-isochromen-1-one (Intermediate F1, 819 mg, 1.317 mmol) was dissolved in MeCN (10 mL) and 2M HCl$_{aqueous}$ (30 mL) and the mixture stirred at rt for 3 h. The reaction was diluted with DCM (300 mL) and washed with water (200 mL). Aqueous layer was extracted twice with DCM, the combined organic fractions were dried through a phase separator and solvent evaporated under reduced pressure to give the title compound (598 mg, 87% yield).

UPLC-MS: 0.97 min, 522.1 [M+H]+, method 9

Intermediate F3 and example 3-(1-(4-amino-3-(3-fluoro-5-hydroxyphenyl)-1H-pyrazolo[3,4-d]pyrimidin-1-yl)ethyl)-4-(5-(4,4,5,5-tetramethyl-1,3-dioxolan-2-yl)thiophen-2-yl)-1H-isochromen-1-one

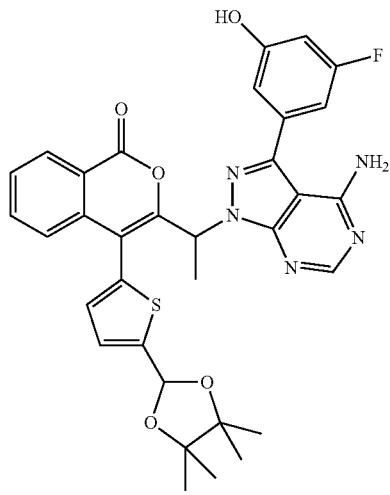 [SMILES: CC(c1oc(=O)c2ccccc2c1-c1ccc(C2OC(C)(C)C(C)(C)O2)s1)n1nc(-c2cc(O)cc(F)c2)c2c(N)ncnc21]

The title compound was made in a way similar to that of intermediate of intermediate F1, from 3-(1-(4-amino-3-iodo-1H-pyrazolo[3,4-d]pyrimidin-1-yl)ethyl)-4-(5-(4,4,5,5-tetramethyl-1,3-dioxolan-2-yl)thiophen-2-yl)-1H-isochromen-1-one (Intermediate D13, 385 mg, 0.598 mmol), (3-fluoro-5-hydroxyphenyl)boronic acid (187 mg, 1.197 mmol) to give the title compound (254 mg, 67.6%) as yellowish solid.

UPLC-MS: 5.13 min, 627.9 [M+H]+, method 6

Intermediate F4. 5-(3-(1-(4-amino-3-(3-fluoro-5-hydroxyphenyl)-1H-pyrazolo[3,4-d]pyrimidin-1-yl)ethyl)-1-oxo-1H-isochromen-4-yl)thiophene-2-carbaldehyde

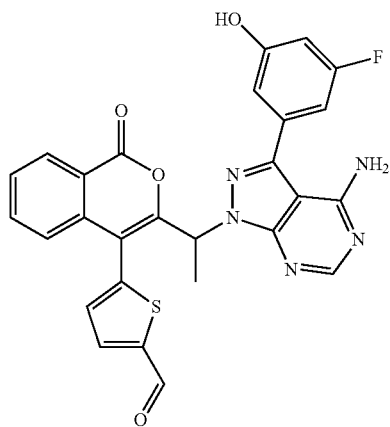 [SMILES: CC(c1oc(=O)c2ccccc2c1-c1ccc(C=O)s1)n1nc(-c2cc(O)cc(F)c2)c2c(N)ncnc21]

The title compound was made in a way similar to that of intermediate F2, from 3-(1-(4-amino-3-(3-fluoro-5-hydroxyphenyl)-1H-pyrazolo[3,4-d]pyrimidin-1-yl)ethyl)-4-(5-(4,4,5,5-tetramethyl-1,3-dioxolan-2-yl)thiophen-2-yl)-1H-isochromen-1-one (Intermediate F3, 254 mg, 0.405 mmol) in MeCN (4 mL)/2M HCl$_{aqueous}$ (4 mL) to give the title compound (201 mg, 94%) as yellowish solid.

UPLC-MS: 1.73 min, 528.1 [M+H]+, method 9.

Intermediate F5. 3-(1-(4-amino-3-(3-(benzyloxy)-5-fluorophenyl)-1H-pyrazolo[3,4-d]pyrimidin-1-yl)ethyl)-4-(3-(4,4,5,5-tetramethyl-1,3-dioxolan-2-yl)phenyl)-1H-isochromen-1-one

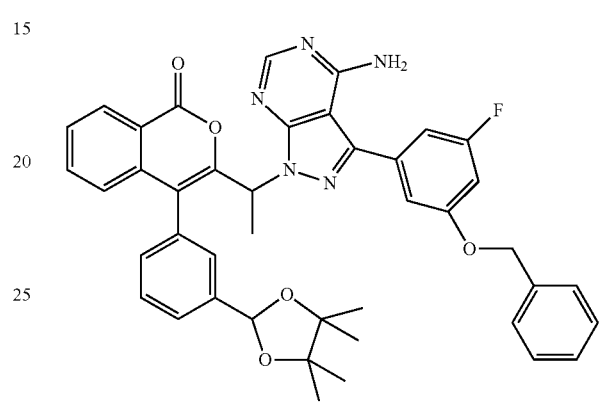

In a 100 ml round bottomed flask 3-(3-(benzyloxy)-5-fluorophenyl)-1H-pyrazolo[3,4-d]pyrimidin-4-amine (Intermediate G18, 400 mg, 1,194 mmol) was dissolved in 7 ml of dry DMF then K$_2$CO$_3$ (254 mg, 1.837 mmol) was added. After stirring for 5 min a solution of 3-(1-bromoethyl)-4-(3-(4,4,5,5-tetramethyl-1,3-dioxolan-2-yl)phenyl)-1H-isochromen-1-one (Intermediate C26, 420 mg, 0,918 mmol) in 7 ml of dry DMF was added and the clear brown mixture was heated at 60° C. for 30 min. The mixture was cooled to r.t. then 30 ml of HCl 0.5 M and 50 ml of EtOAc were added and stirred for 15 min. Phases were separated and the crude material was purified by chromatography eluting with DCM\MeOH (80/20) in DCM to give the title compound (820 mg) as a brown oil. This material was used in the next step without any further purification.

UPLC-MS: 1.48 min, 712.28 [M+H]+, method 9

Intermediate F6. 3-(3-(1-(4-amino-3-(3-(benzyloxy)-5-fluorophenyl)-1H-pyrazolo[3,4-d]pyrimidin-1-yl)ethyl)-1-oxo-1H-isochromen-4-yl)benzaldehyde

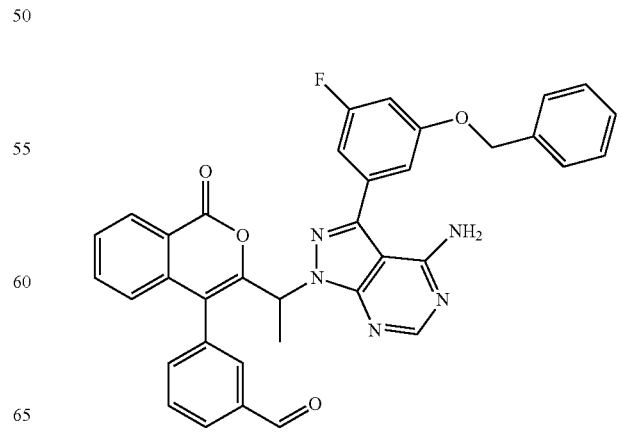

3-(1-(4-amino-3-(3-(benzyloxy)-5-fluorophenyl)-1H-pyrazolo[3,4-d]pyrimidin-1-yl)ethyl)-4-(3-(4,4,5,5-tetramethyl-1,3-dioxolan-2-yl)phenyl)-1H-isochromen-1-one (intermediate F5, 654 mg, 0,919 mmol) was dissolved in MeCN, then 2M HCl was added and the mixture was stirred overnight. DCM (25 ml) and water (25 ml) were added then phases were separated and the aqueous phase was washed again with 10 ml of DCM. The collected organic phases were concentrated to give the title compound (490 mg, 0.801 mmol, 87% yield) as a brown oil.

UPLC-MS: 1.28 min, 612.15 [M+H]+, method 9

Intermediate G1. 3-(3-fluoro-5-methoxyphenyl)-1H-pyrazolo[3,4-d]pyrimidin-4-amine

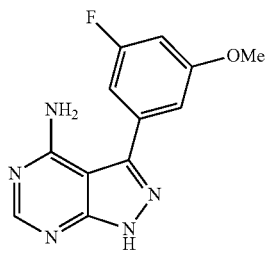 [SMILES: COc1cc(F)cc(-c2n[nH]c3ncnc(N)c23)c1]

3-iodo-1H-pyrazolo[3,4-d]pyrimidin-4-amine (1.52 g, 5.82 mmol), 3-fluoro-5-methoxyphenylboronic acid (1.4 g, 8.24 mmol), Pd(dppf)Cl$_2$ (0.18 g, 0.246 mmol) and 8.7 mL of 1M NaOH$_{aqueous}$ (8.73 mmol) were reacted in DMF (13 mL) under Ar at 120° C. for 48 hrs. The reaction was quenched by the addition of 1M HCl$_{aqueous}$ (10 mL), dried under reduced pressure and the dark crude oil purified via flash chromatography on silica gel using a Biotage 100G SNAP with a gradient of DCM and iPrOH to give the title compound (275 mg, 18.2%) as yellowish solid.

UPLC-MS: 0.54 min, 260.0 [M+H]+, method 9

Intermediate G2. 4,4,5,5-tetramethyl-2-(3-(4,4,5,5-tetramethyl-1,3-dioxolan-2-yl)phenyl)-1,3,2-dioxaborolane

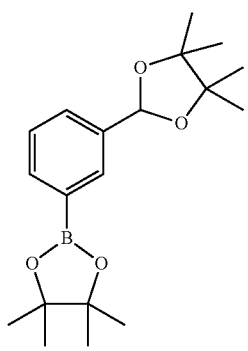

(3-formylphenyl)boronic acid (5 g, 33.3 mmol), 2,3-dimethylbutane-2,3-diol (19.70 g, 167 mmol) and p-toluensulfonic acid monohydrate (0.317 g, 1.667 mmol) were dissolved in toluene (278 mL) and refluxed with a Dean-Stark equipment for 3 h until reaction completion. The mixture was dried under reduced pressure and the residue diluted with AcOEt (250 mL) and washed three times with abundant water, once with saturated NaCl$_{aqueous}$ (250 mL), anhydrified over Na$_2$SO$_4$ and the solvent removed under reduced pressure. The crude was purified via flash chromatography on silica gel using a Biotage 100G+50G SNAP with a gradient of hexane and AcOEt to give the title compound (8.5 g, 77%) as white solid.

1H NMR (400 MHz, DMSO-d6) d ppm 7.72 (s, 1 H), 7.63 (d, J=7.06 Hz, 1 H), 7.55 (d, J=7.50 Hz, 1 H), 7.31-7.44 (m, 1 H), 5.91 (s, 1 H), 1.24-1.37 (s, 18 H), 1.18 (s, 6 H).

Intermediate G3. 4-(4,4,5,5-tetramethyl-1,3,2-dioxaborolan-2-yl)-1,2,3,6-tetrahydropyridine hydrochloride

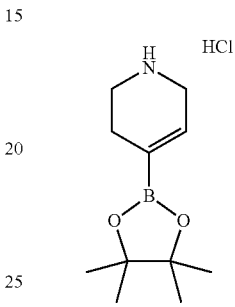

tert-butyl 4-(4,4,5,5-tetramethyl-1,3,2-dioxaborolan-2-yl)-5,6-dihydropyridine-1(2H)-carboxylate (2 g, 6.47 mmol) was suspended in MTBE (8.1 mL) and 2M HCl in Et$_2$O (24 mL). The reaction was stirred rt overnight, the white precipitate formed collected by filtration and washed with Et$_2$O to give the title compound (1.434 g, 90%).

UPLC-MS: 0.51 min, 210.3 [M+H]+, method 9.

Intermediate G4. 1-(4-(4,4,5,5-tetramethyl-1,3,2-dioxaborolan-2-yl)-5,6-dihydropyridin-1(2H)-yl)ethanone

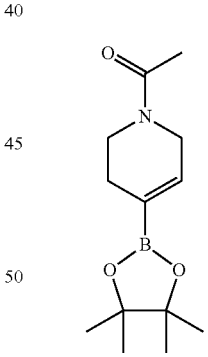

4-(4,4,5,5-tetramethyl-1,3,2-dioxaborolan-2-yl)-1,2,3,6-tetrahydropyridine hydrochloride (Intermediate G3, 1.4 g, 5.70 mmol) was suspended in DCM (15 mL) at 0° C., then TEA (2.384 ml, 17.10 mmol) and AcCl (0.405 ml, 5.70 mmol) were added The reaction was allowed to warm up to rt and stirred for further 30 min, then the reaction volume was reduced to 1/3 of the initial volume and the residue diluted with AcOEt (150 ml). Organic phase was washed twice with water, once with 0.2 M HCl$_{aqueous}$ and once with saturated NaCl$_{aqueous}$, anhydrified over Na$_2$SO$_4$ and solvent removed under reduced pressure to give the title compound (1.24 g, 87% yield) as yellowish solid.

UPLC-MS: 0.83 min, 252.3 [M+H]+, method 9.

Intermediate G5. 4,4,5,5-tetramethyl-2-(5-(4,4,5,5-tetramethyl-1,3-dioxolan-2-yl)thiophen-2-yl)-1,3,2-dioxaborolane

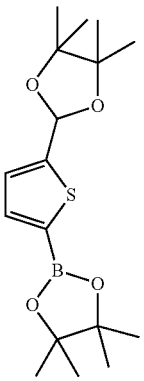 [SMILES: CC1(C)OB(c2ccc(C3OC(C)(C)C(C)(C)O3)s2)OC1(C)C]

The title compound was made in a similar way as that of the compound of intermediate G2, from (5-formylthiophen-2-yl)boronic acid (2.5 g, 16.03 mmol) to give the desired product (3.93 g, 72.5%) as off-white solid.

$^1$H NMR (400 MHz, DMSO-d6) d ppm 7.38 (d, J=3.53 Hz, 1 H), 7.22 (s, 1 H), 6.11 (s, 1 H), 0.98-1.52 (m, 24 H).

Intermediate G6. N-(5-bromopyridin-3-yl)-4-fluorobenzenesulfonamide

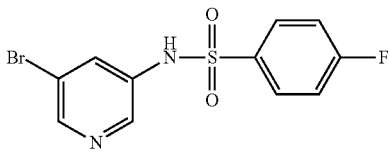 [SMILES: O=S(=O)(Nc1cncc(Br)c1)c1ccc(F)cc1]

To a solution of 5-bromopyridin-3-amine (3 g, 17.34 mmol) in absolute EtOH (15 ml), 4-fluorobenzene-1-sulfonyl chloride (0.989 g, 5.08 mmol) was added and the reaction was stirred overnight. Ethanol was removed under reduced pressure and residue was diluted with DCM (40 ml) and washed once with sat. NaHCO$_3$. Organic phase was dried over Na$_2$SO$_4$, filtered and concentrated. Product was straightforward purified via reverse phase chromatography with a Biotage C18 30 g column (Phase A, water 95%, ACN 5%, formic acid 0.1%); Phase B ACN 95%, water 5%, formic acid 0.1%) to give the title compound (158 mg, 24.4% yield) as yellow pale solid.

UPLC-MS: 0.96 min, 331 [M+H]+, method 9.

Intermediate G7. tert-butyl 5-bromopyridin-3-ylcarbamate

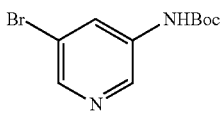

To a solution of 5-bromopyridin-3-amine (3 g, 17.34 mmol) in dry DCM (25 ml), di-tert-butyl dicarbonate (3.78 g, 17.34 mmol) was added under stirring. The resulting solution was cooled to 0° C. and a solution of sodium bis(trimethylsilyl)amide 1 M in THF (17.34 ml, 17.34 mmol) was added dropwise over 20 min. The solution was stirred overnight. Then, solution was diluted with DCM (40 mL) and washed once with sat. NaHCO$_3$. Organic phase was dried over Na$_2$SO$_4$, filtered and concentrated. Crude was finally purified on Biotage Si 50 g with a gradient of hexane and EtOAc. The title compound was recovered (2.60 g, 54.9% yield) as a white solid.

UPLC-MS: 1.07 min, 273 [M+H]+, method 9.

Intermediate G8. 4-Chloro-2-amino(biscarbamate)-pyrimidine

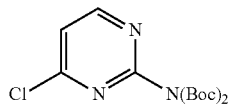

To a solution of 4-chloropyrimidin-2-amine (1.0 g, 7.72 mmol) in dry DCM (30 ml), N,N-dimethylpyridin-4-amine (0.094 g, 0.772 mmol) and N-ethyl-N,N-isopropylpropan-2-amine (2.494 g, 19.30 mmol) were added. After 10 min, di-tert-butyl dicarbonate (1.685 g, 7.72 mmol) was added and the resulting solution was stirred overnight. Reaction was diluted with DCM (40 mL) and washed once with sat NaHCO$_3$. The resulting organic phase was dried over Na$_2$SO$_4$, filtered and concentrated. The crude was finally purified on Biotage Si 50 g with a gradient of hexane and EtOAc. The title compound was recovered (0.53 g, 69.3%) as a white solid.

UPLC-MS: 1.24 min, 330 [M+H]+, method 9.

Intermediate G9. 4-fluoro-N-(5-(trimethylstannyl)pyridin-3-yl)benzenesulfonamide

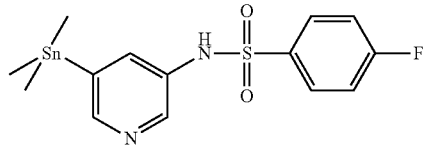 [SMILES: [CH3][Sn]([CH3])([CH3])[c]1cncc(NS(=O)(=O)c2ccc(F)cc2)c1]

To a solution of N-(5-bromopyridin-3-yl)-4-fluorobenzenesulfonamide (intermediate G6, 158 mg, 0.477 mmol) in dry dioxane (6 ml), 1,1,1,2,2,2-hexamethyldistannane (0.340 ml, 1.637 mmol) and Pd(PPh$_3$)$_4$ (105 mg, 0.091 mmol) were added. The solution was heated to 100° C. and stirred overnight. Solvent was removed under vacuum and crude was finally purified on Biotage Si 10 g with a gradient of hexane and EtOAc. The title compound was recovered (165 mg, 83% yield) as a white solid.

UPLC-MS: 0.99 min, 417 [M+H]+, method 9.

Intermediate G10. tert-butyl (5-(trimethylstannyl)pyridin-3-yl)carbamate

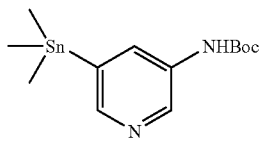 [SMILES: CC(C)(C)OC(=O)Nc1cnc[c]([Sn]([CH3])([CH3])[CH3])c1]

The title compound was made in a similar way as that of intermediate G9 using tert-butyl (5-bromopyridin-3-yl)carbamate (Intermediate G7, 600 mg, 2.197 mmol), 1,1,1,2,2,2-hexamethyldistannane (0.820 ml, 3.95 mmol) to afford the title compound (165 mg, 0.398 mmol, 83% yield) as a white solid.

UPLC-MS: 0.82 min, 359 [M+H]+, method 9.

Intermediate G11. 4-trimethylstannyl-2-amino-(bis-carbamate)-pyrimidine

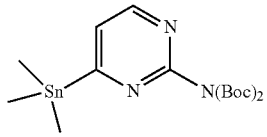

The title compound was made in a similar way as that of intermediate G9 using 4-Chloro-2-amino(biscarbamate)-pyrimidine (Intermediate G8, 400 mg, 1.21 mmol), 1,1,1,2,2,2-hexamethyldistannane (0.503 ml, 2.43 mmol) to afford the title compound (398 mg, 69.8%) as a white solid.

UPLC-MS: 1.42 min, 460 [M+H-Boc]+, method 9.

Intermediate G12. 4-(((benzyloxy)carbonyl)amino)cyclohex-1-en-1-yl trifluoromethanesulfonate

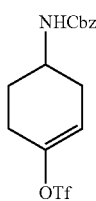

To a solution of sodium bis(trimethylsilyl)amide 1 M in THF (22.24 ml, 22.24 mmol) in dry THF (25 mL), previously cooled to −78° C., a solution of benzyl (4-oxocyclohexyl)carbamate (2.5 g, 10.11 mmol) in dry THF (25 mL) was slowly added. The solution was stirred for 30 min at −78° C. and then a solution of 1,1,1-trifluoro-N-phenyl-N-(trifluoromethylsulfonyl)methanesulfonamide (7.58 g, 21.23 mmol) in dry THF (25 mL) was added. The reaction was stirred at −78° C. for 10 min and then allowed to reach room temperature. Reaction was diluted with diethyl ether (200 mL) and organic layer was washed with 1 M NaOH aqueous solution (100 mL). Organic phases were dried over $Na_2SO_4$, filtered and solvent was removed under reduced pressure. The product was purified by Biotage Si 50 g with a gradient of heptane and EtOAc to give the titled compound (1.43 g, 3.77 mmol, 37.3% yield) as a white solid.

UPLC-MS: 1.25 min, 380 [M+H]+, method 9

Intermediate G13. benzyl (4-(4,4,5,5-tetramethyl-1,3,2-dioxaborolan-2-yl)cyclohex-3-en-1-yl)carbamate

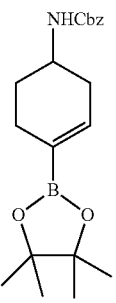

To a solution of 4-(((benzyloxy)carbonyl)amino)cyclohex-1-en-1-yl trifluoromethanesulfonate (1.4 g, 3.69 mmol) in dry DMF, 4,4,4',4',5,5,5',5'-octamethyl-2,2'-bi(1,3,2-dioxaborolane) (intermediate G12, 0.984 g, 3.88 mmol), Pd(dppf)$Cl_2 \cdot CH_2Cl_2$ (0.904 g, 1.107 mmol) and potassium acetate (1.07 g, 11.07 mmol) were added and the reaction was stirred overnight at 80° C. DMF was removed and residue was diluted in ethyl acetate (200 mL). Organic phase was washed with brine (100 mL) then dried over $Na_2SO_4$, filtered and solvent was removed under reduced pressure. The product was purified by Biotage Si 50 g with a gradient of heptane and EtOAc to give the title compound (0.984 g, 15%) as a yellow oil.

UPLC-MS: 1.28 min, 358 [M+H]+, method 9.

Intermediate G14. 3-iodo-N,1-bis(tetrahydro-2H-pyran-2-yl)-1H-pyrazolo[3,4-d]pyrimidin-4-amine

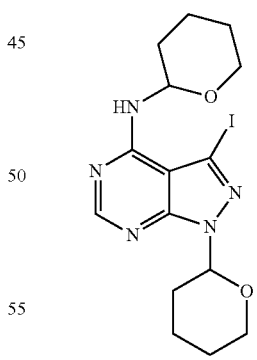

to a solution of 3-iodo-1H-pyrazolo[3,4-d]pyrimidin-4-amine (1 g, 3.83 mmol) in dry DMF (15 mL), 3,4-dihydro-2H-Pyran (1.103 ml, 11.49 mmol) and 4-methylbenzenesulfonic acid monohydrate (0.208 ml, 0.958 mmol) were added. The solution was stirred for 5 days at 90° C. Solvent was removed and product was purified by Biotage Si 25 g with a gradient of heptane and ethyl acetate to give the title compound (320 mg, 19.5% yield).

UPLC-MS: 0.68 min, 430 [M+H]+, method 9

Intermediate G15. N,1-bis(tetrahydro-2H-pyran-2-yl)-3-(trifluoromethyl)-1H-pyrazolo[3,4-d]pyrimidin-4-amine

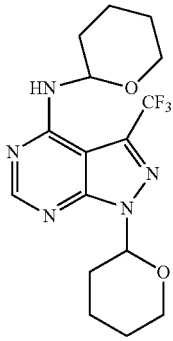 [SMILES: FC(F)(F)c1nn(C2CCCCO2)c2ncnc(NC3CCCCO3)c12]

To a solution of 3-iodo-N,1-bis(tetrahydro-2H-pyran-2-yl)-1H-pyrazolo[3,4-d]pyrimidin-4-amine (Intermediate G14, 322 mg, 0.75 mmol, 31.6% yield) in dry DMF 6 (mL), copper(I) iodide (429 mg, 2.250 mmol) and methyl 2,2-difluoro-2-(fluorosulfonyl)acetate (0.096 ml, 0.750 mmol) were added and solution was stirred for 18 hrs at 80° C. DMF was removed under reduced pressure and product was purified by Biotage Si 25 g with a gradient of heptane and EtOAc to give the title compound (88 mg, 31.6% yield).

UPLC-MS: (mixture of diastereoisomers) 1.16 and 1.18 min, 372 [M+H]+, method 9.

Intermediate G16. 3-(trifluoromethyl)-1H-pyrazolo[3,4-d]pyrimidin-4-amine

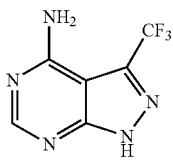

To a solution of N,1-bis(tetrahydro-2H-pyran-2-yl)-3-(trifluoromethyl)-1H-pyrazolo[3,4-d]pyrimidin-4-amine (intermediate G15, 88 mg, 0.237 mmol) in EtOH (5 mL), water (0.5 mL) was added. Then 2,2,2-trifluoroacetic acid (0.3 ml, 0.237 mmol) was added and the mixture was stirred at 80° C. overnight. Solvent was removed to give the title compound (45 mg, 93%) as a yellow solid.

UPLC-MS:0.47 min, 204 [M+H]+, method 9.

Intermediate G17. 3-Methoxyphenylsulphur pentafluoride-5-boronic acid

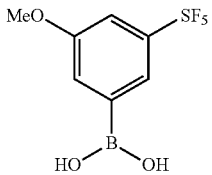

Step 1. 2-(3-methoxy-5-(pentafluoro-16-sulfanyl)phenyl)-4,4,5,5-tetramethyl-1,3,2-dioxaborolane (intermediate G17.1)

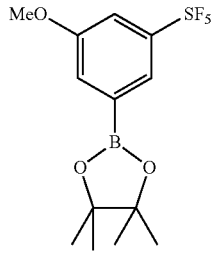

To a solution of 3-Methoxyphenylsulphur pentafluoride (0.5 g, 2.135 mmol) in dry THF (10 mL), 4,4'-di-tert-butyl-2,2'-bipyridine (0.115 g, 0.427 mmol), 4,4,4',4',5,5,5',5'-octamethyl-2,2'-bi(1,3,2-dioxaborolane) (0.488 g, 1.922 mmol) and Ir₂(COD)₂OMe₂ (0.142 g, 0.214 mmol) were added and the solution was stirred overnight at 80° C. Solvent was removed and product was purified by Biotage Si 25 g with a gradient of heptane and EtOAc to give 2-(3-methoxy-5-(pentafluoro-16-sulfanyl)phenyl)-4,4,5,5-tetramethyl-1,3,2-dioxaborolane (intermediate G17.1, 621 mg, 81% yield) as a yellow solid

Step 2

To a solution of 2-(3-methoxy-5-(pentafluoro-16-sulfanyl)phenyl)-4,4,5,5-tetramethyl-1,3,2-dioxaborolane (Intermediate G17.1, 621 mg, 1.724 mmol) in THF (6 ml), 6 N aqueous HCl was added and the solution stirred for 3 hrs. Solvent was removed and the product was straightforward purified via reverse phase chromatography with a Biotage C18 SNAP column (Phase A, water 95%, ACN 5%, formic acid 0.1%); (Phase B ACN 95%, water 5%, formic acid 0.1%) to give the titled compound (245 mg, 51.1% yield) as a white solid.

UPLC-MS: 0.71 min, 279 [M+H]+, method 9.

Intermediate G18. 3-(3-(benzyloxy)-5-fluorophenyl)-1H-pyrazolo[3,4-d]pyrimidin-4-amine

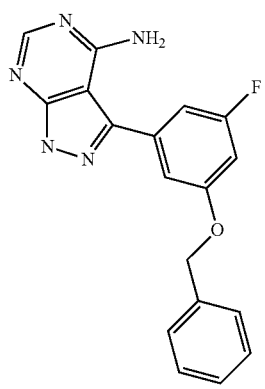 [SMILES: Nc1ncnc2[nH]nc(-c3cc(F)cc(OCc4ccccc4)c3)c12]

3-iodo-1H-pyrazolo[3,4-d]pyrimidin-4-amine (6.10 mmol 1.591 g), (3-(benzyloxy)-5-fluorophenyl)boronic acid (4.06 mmol 1.0 g), dppf (0,610 mmol, 338 mg) Potassium phosphate anhydrous (10.16 mmol, 2.157 g) were suspended in dioxane and the mixture was heated at 180 C for 25 min in a Mw reactor then poured in 100 ml of water. The mixture was stirred overnight then filtered on a buchner funnel washing with 30 ml of water. The crude material was purified by chromatography eluting with DCM\ MeOH (80/20) in DCM to give the title compound (450 mg, 1.342 mmol, 33% yield) as a beige solid.

UPLC-MS: 1.42 min, 336.15 [M+H]+, method 10

Intermediate G19. 4-(trimethylstannyl)-1H-indazole

To a solution of 4-iodo-1H-indazole (500 mg, 2.049 mmol) in 1,4-dioxane (500 ml) 1,1,1,2,2,2-hexamethyldistannane (1.0 g, 3.07 mmol), and Pd(Ph₃P)₄ (237 mg, 0,250 mmol) were added and the mixture stirred at 80° C. for 18 hrs. The crude was purified via reverse phase chromatography with a Biotage C18 60 g SNAP column (Phase A, water 95%, ACN 5%, formic acid 0.1%); Phase B ACN 95%, water 5%, formic acid 0.1%) to give the title compound (576 mg, 66%).

1H NMR (400 MHz, DMSO-d6) □ ppm 12.82-13.13 (bs, 1H), 7.99 (s, 1H), 7.45-7.52 (m, 1H), 7.24-7.32 (m, 1H), 7.20 (s, 1H), 0.11-0.58 (m, 9H).

Intermediate G20.
4-phenyl-1H-isochromene-3-carbaldehyde

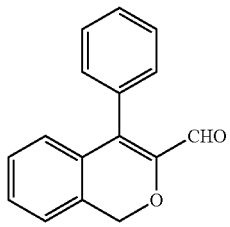 [SMILES: O=CC1=C(c2ccccc2)c2ccccc2CO1]

Step 1. 4-chloro-1H-isochromene-3-carbaldehyde (Intermediate G20.1)

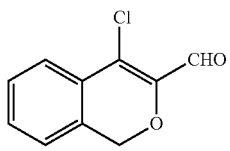 [SMILES: O=CC1=C(Cl)c2ccccc2CO1]

To commercially available isochroman-4-one (900 mg, 6.07 mmol) in DCM (18 ml), DMF (0.706 ml) and POCl₃ (1.699 ml, 18.23 mmol) were added in sequence under Nitrogen at r.t. The mixture was refluxed for 6 h and kept at r.t overnight. The reaction mixture was diluted with DCM (15 ml), washed with water and sat NaCl, then anhydrified over Na₂SO₄ and evaporated in vacuo. The resulting crude was purified via reverse phase chromatography with a Biotage C18 SNAP 30 g column (Phase A, water 95%, ACN 5%, formic acid 0.1%); Phase B ACN 95%, water 5%, formic acid 0.1%) to give 4-chloro-1H-isochromene-3-carbaldehyde (Intermediate G20.1, 716 mg, 60.6% yield)

1H NMR (400 MHz, DMSO-d6) d ppm 10.02 (s, 1H), 7.61-7.81 (m, 1H), 7.42-7.58 (m, 2H), 7.20-7.40 (m, 1H), 5.21 (s, 2H). UPLC-MS: 0.94 min, 195 [M+H]+, method 9

Step 2

X-phos Pd G2 (116 mg, 0,147 mmol) and phenylboronic acid (538 mg, 4.41 mmol) were sealed in a closed vessel equipped with a magnetic bar and oxygen removed by Ar/vacuum cycle. A degassed solution of 4-chloro-1H-isochromene-3-carbaldehyde (Intermediate G20.1, 716 mg, 3.68 mmol) in THF (8 ml) was added followed by a degassed solution of K₃PO₄H₂O (1,795 ml, 7.36 mmol) in water (8 ml) and the resulting mixture stirred at rt overnight. The reaction mixture was partitioned between 1M HCl (15 ml) and the same amount of AcOEt. The organic layer was anhydrified over Na₂SO₄, evaporated in vacuo and purified via reverse phase chromatography with a Biotage C18 SNAP 120 g column (Phase A, water 95%, ACN 5%, formic acid 0.1%); Phase B ACN 95%, water 5%, formic acid 0.1%) to give the title compound (821 mg, 94% yield).

UPLC-MS: 1.12 min, 237 [M+H]+, method 9.

Intermediate G21. benzyl 3-(4,4,5,5-tetramethyl-1,3, 2-dioxaborolan-2-yl)-8-azabicyclo[3.2.1]oct-2-ene-8-carboxylate

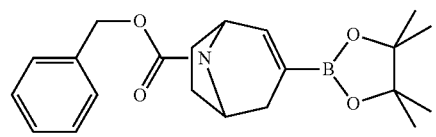 [SMILES: CC1(C)OB(C2=CC3CCC(C2)N3C(=O)OCc2ccccc2)OC1(C)C]

Step a. (1R,5S)-tert-butyl 3-(((trifluoromethyl)sulfonyl)oxy)-8-azabicyclo[3.2.1]oct-2-ene-8-carboxylate (Intermediate G21.1)

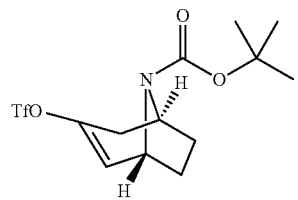 [SMILES: CC(C)(C)OC(=O)N1[C@H]2CC[C@@H]1C=C(OS(=O)(=O)C(F)(F)F)C2]

To a solution of sodium bis(trimethylsilyl)amide 1M IN THF (12.43 ml, 12.43 mmol) in dry THF (10 ml), previously cooled to −78° C., a solution of (1R,5S)-tert-butyl 3-oxo-8-azabicyclo[3.2.1]octane-8-carboxylate (2 g, 8.88 mmol) in dry THF (10 ml) was slowly added and resulting solution was stirred 1 h at −78 C. Then, a solution of 1,1,1-trifluoro-N-phenyl-N-(trifluoromethylsulfonyl)methane-sulfonamide (3.49 g, 9.77 mmol) in dry THF (10 ml) was slowly added and the reaction was stirred 30 min at −78 C and 1 h at room temperature. Ethyl acetate was added (100 mL) and organic phase was washed with 1 M aqueous NaOH solution. Organic phase was collected, dried, filtered and solvent removed under reduced pressure. The product was purified by Biotage Si 50 g with a gradient of heptane and EtOAc affording (1R,5S)-tert-butyl 3-(((trifluoromethyl)sulfonyl)oxy)-8-azabicyclo[3.2.1]oct-2-ene-8-carboxylate (2.93 g, 8.20 mmol, 92% yield) as a white amorphous solid.
UPLC-MS: 1.30 min, 258 [M+H-Boc]+, method 9

Step b. (1R,5S)-tert-butyl 3-(((trifluoromethyl)sulfonyl)oxy)-8-azabicyclo[3.2.1]oct-2-ene-8-carboxylate (Intermediate G21.2)

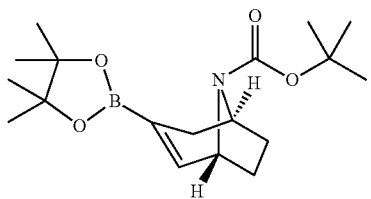 [SMILES: CC(C)(C)OC(=O)N1[C@H]2CC[C@@H]1C=C(B1OC(C)(C)C(C)(C)O1)C2]

To a solution of (1R,5S)-tert-butyl 3-(((trifluoromethyl)sulfonyl)oxy)-8-azabicyclo[3.2.1]oct-2-ene-8-carboxylate (Intermediate G21.1, 2.93 g, 8.20 mmol) in dry DMF (29 ml), 4,4,4',4',5,5,5',5'-octamethyl-2,2'-bi(1,3,2-dioxaborolane) (2.290 g, 9.02 mmol), potassium acetate (2.414 g, 24.60 mmol) and Pd(dppf)Cl$_2$·CH$_2$Cl$_2$ (2.009 g, 2.460 mmol) were added and the reaction heated to 80 C overnight. Solvent was removed and target compound was purified by silica gel flash chromatography (Snap 50 g heptane: ethyl acetate from 100:0 to 7:3) affording (1R,5S)-tert-butyl 3-(((trifluoromethyl)sulfonyl)oxy)-8-azabicyclo[3.2.1]oct-2-ene-8-carboxylate (Intermediate G21.2, 1.93 g, 5.76 mmol, 70.2% yield) as a white solid.
UPLC-MS: 1.34 min, 280 [M+H-tBu]+, method 9

Step c

To a solution of tert-butyl 3-(4,4,5,5-tetramethyl-1,3,2-dioxaborolan-2-yl)-8-azabicyclo[3.2.1]oct-2-ene-8-carboxylate (Intermediate G21.2, 1.93 g, 5.76 mmol) in dry Dioxane (20 ml), 4 M hydrogen chloride 1,4 dioxane (5.76 ml, 23.03 mmol) was added and the solution was stirred for 1 h. Then, solvent was removed. Crude was dissolved in dry DCM (20.00 ml), N-(benzyloxycarbonyloxy)succinimide (1.964 ml, 6.91 mmol) and triethylamine (3.14 ml, 23.03 mmol) were added and the suspension was stirred for 1 h. Then, solvent was removed and the product was purified by Biotage Si 25 g with a gradient of heptane and EtOAc affording the title compound (810 mg, 2.194 mmol, 38.1% yield) as a white solid.
UPLC-MS: 1.30 min, 258 [M+H-Boc]+, method 9

Intermediate G22. benzyl methyl(prop-2-yn-1-yl)carbamate

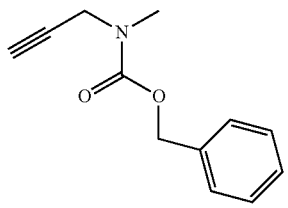

To a solution of N-methylprop-2-yn-1-amine (3.05 ml, 36.2 mmol) in THF (50 ml) and NaHCO$_3$ sat. aqueous solution (50.0 ml), N-(benzyloxycarbonyloxy)succinimide (11.31 ml, 39.8 mmol) was added and the reaction was stirred overnight. Then, organic layers were extracted with ethyl acetate (2×100 mL). Organic phases were collected, dried, filtered and solvent was removed under reduced pressure. The product was purified by Biotage Si 10 g with a gradient of heptane and EtOAc affording the title compound (5 g, 24.60 mmol, 68.0% yield) as a colorless oil.
UPLC-MS: 0.95 min, 204 [M+H]+, method 9

Intermediate G23.
5-methoxy-4-methylpyridin-3-yl)boronic acid

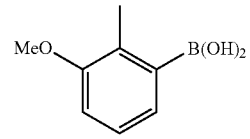

To a solution 3-bromo-5-methoxy-4-methylpyridine (0.5 g, 2.475 mmol) in dry 1,4-Dioxane (5 ml), 4,4,4',4',5,5,5',5'-octamethyl-2,2'-bi(1,3,2-dioxaborolane) (0.691 g, 2.72 mmol), Pd(dppf)Cl$_2$·CH$_2$Cl$_2$ (0.606 g, 0.742 mmol) and potassium acetate (0.729 g, 7.42 mmol) were added and the solution was heated to 80° C. The reaction was stirred overnight. Then, solvent was removed and residue dissolved in THF (5.00 ml) and 12 N aqueous hydrogen chloride (4.12 ml, 49.5 mmol) was added and stirred for 3 h. Then, solvent was removed and the product was purified by C-18 flash chromatography (eluent ((H$_2$O/ACN)) 95:5+0.1% HCOOH}:{(ACN/H$_2$O) 95:5+HCOOH 0.1%} from 95:5 to 0:100 affording the title compound as a white solid (350 mg, 2.096 mmol, 85%)
UPLC-MS: 0.14 min, 168 [M+H]+, method 9

Intermediate G24.
(5-methoxy-2-methylpyridin-3-yl)boronic acid

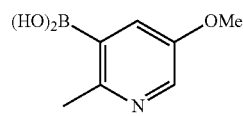

To a solution 3-bromo-5-methoxy-2-methylpyridine (500 mg, 2.475 mmol) in dry 1,4-Dioxane (5 ml), 4,4,4',4',5,5,5',5'-octamethyl-2,2'-bi(1,3,2-dioxaborolane) (691 mg, 2.72 mmol), Pd(dppf)Cl$_2$·CH$_2$Cl$_2$ (606 mg, 0.742 mmol) and potassium acetate (729 mg, 7.42 mmol) were added and the solution was heated to 80° C. The reaction was stirred overnight. Then, solvent was removed and residue dissolved in THF (5.00 ml) and 12 N aqueous hydrogen chloride (4.12 ml, 49.5 mmol) was added and stirred for 3 hrs. Then, solvent was removed and the product was purified by C-18 flash chromatography (eluent ((H$_2$O/ACN)) 95:5+0.1% HCOOH}:{(ACN/H$_2$O) 95:5+HCOOH 0.1%} from 95:5 to 0:100 affording the title (350 mg, 2.096 mmol, 85% yield) as a white solid.
UPLC-MS: 0.13 min, 168 [M+H]+, method 9

Intermediate G25. (5-(benzyloxy)-6-(trifluoromethyl)pyridin-3-yl)boronic acid

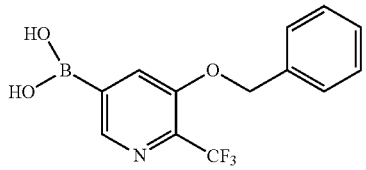 [SMILES: OB(O)c1cnc(C(F)(F)F)c(OCc2ccccc2)c1]

Step a. 3-(benzyloxy)-5-bromo-2-iodopyridine (Intermediate G25.1)

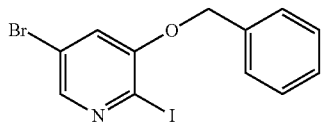 [SMILES: Brc1cnc(I)c(OCc2ccccc2)c1]

To a solution of 5-bromo-2-iodopyridin-3-ol (0.700 g, 2.334 mmol, prepared according to *Bioorg. Med. Chem. Lett.* 2013, 2, 6784, which is incorporated herein by reference in its entirety) in dry THF (10 ml), previously cooled to 0° C., benzyl alcohol (0.728 ml, 7.00 mmol), triphenylphosphine (PPh₃) (2.095 ml, 7.00 mmol) and diisopropyl azodicarboxylate (1.287 ml, 6.54 mmol) were added. The reaction was stirred for 4 h at room temperature. Solvent was removed and the product was purified by Biotage Si 50 g with a gradient of heptane and EtOAc 3-(benzyloxy)-5-bromo-2-iodopyridine (Intermediate G25.1, 835 mg, 2.141 mmol, 92% yield) as a white foam.

UPLC-MS: min, [M+H]+, method 9

Step b. 3-(benzyloxy)-5-bromo-2-(trifluoromethyl) pyridine (Intermediate G25.2)

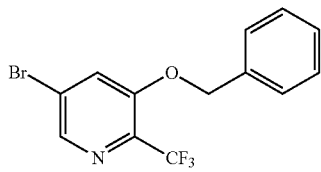

To a solution of 3-(benzyloxy)-5-bromo-2-iodopyridine (Intermediate G25.1, 800 mg, 2.051 mmol) in dry DMF (10 ml), copper(I) iodide (2344 mg, 12.31 mmol) and methyl 2,2-difluoro-2-(fluorosulfonyl)acetate (0.522 ml, 4.10 mmol) were added and the suspension was stirred overnight at 80° C. Then, solid was filtered off over celite pad and solvent was removed. The product was purified by Biotage Si 25 g with a gradient of heptane and EtOAc affording 3-(benzyloxy)-5-bromo-2-(trifluoromethyl)pyridine (Intermediate G25.2, 320 mg, 0.964 mmol, 47.0% yield) as a white solid.

UPLC-MS: 1.30 min, 330 [M+H]+, method 9

Step c

To a solution of 3-(benzyloxy)-5-bromo-2-(trifluoromethyl)pyridine (Intermediate G25.2, 521 mg, 1.569 mmol) in dry 1,4 dioxane (10 ml), 4,4,4',4',5,5,5',5'-octamethyl-2,2'-bi (1,3,2-dioxaborolane) (438 mg, 1.726 mmol), [1,1'-bis (diphenylphosphino)-ferrocene]dichloropalladium(II) (344 mg, 0.471 mmol) and potassium acetate (462 mg, 4.71 mmol) were added and the suspension was stirred at 90° C. overnight. Then, HCl 4 N was added (10 mL) and the solution was stirred overnight. The solvent was removed under reduced pressure and crude was purified by C18 flash chromatography Snap 30 g eluent ((H₂O/ACN)) 95:5+0.1% HCOOH}:{ (ACN/H₂O) 95:5+HCOOH 0.1%} from 95:5 to 0:100 affording the title compound (400 mg, 1.347 mmol, 86% yield) a white solid.

UPLC-MS: 0.97 min, 298 [M+H]+, method 9.

Preparation of Compounds

Example 1

3-((6-Amino-9H-1-purin-9-yl)methyl)-4-phenyl-1H-isochromen-1-one

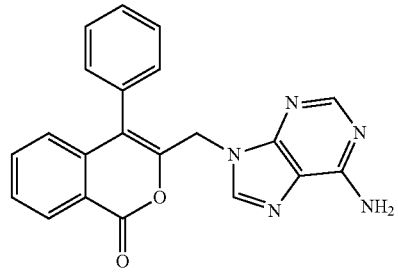 [SMILES: Nc1ncnc2c1ncn2Cc1oc(=O)c2ccccc2c1-c1ccccc1]

3-(Bromomethyl)-4-phenyl-1H-isochromen-1-one (Intermediate Cl, 35 mg, 0.111 mmol), commercially available 9H-purin-6-amine (30.0 mg, 0.222 mmol) and K₂CO₃ (30.7 mg, 0.222 mmol) were dissolved in DMF (1 ml) and stirred 5 min. at RT and then 10 min at 50° C. 2M HCl$_{aqueous}$ (0.5 ml) was then added and the resulting mixture was straightforward purified via reverse phase chromatography with a Biotage C18 SNAP column (Phase A, water 95%, ACN 5%, formic acid 0.1%); Phase B ACN 95%, water 5%, formic acid 0.1%) to give the title compound (19 mg, 46.3%) as a colourless solid.

$^1$H NMR (400 MHz, DMSO-d₆) δ ppm 8.16-8.27 (m, 1 H), 8.09 (s, 2 H), 7.74-7.86 (m, 1 H), 7.47-7.70 (m, 6 H), 7.14-7.30 (m, 2 H), 6.94-7.06 (m, 1 H), 5.09 (s, 2 H).

UPLC-MS: 2.01 min, 370.3 [M+H]+, method 2.

Example 2

3-((6-Amino-9H-purin-9-yl)methyl)-4-(3-fluorophenyl)-1H-isochromen-1-one

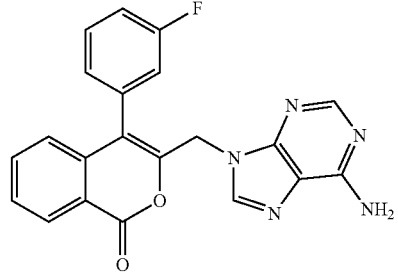 [SMILES: Nc1ncnc2c1ncn2Cc1oc(=O)c2ccccc2c1-c1cccc(F)c1]

The title compound was made in a similar way as that of the compound of example 1, using 3-(bromomethyl)-4-(3-fluorophenyl)-1H-isochromen-1-one (intermediate C4, 50 mg, 0.150 mmol), commercially available 9H-purin-6-amine (40.6 mg, 0.300 mmol) and $K_2CO_3$ (41.5 mg, 0.300 mmol) to give the title compound (36.4 mg, 62.6%) as a colourless solid.

$^1$H NMR (400 MHz, DMSO-$d_6$) δ ppm 8.14-8.22 (m, 1 H) 8.07 (d, J=9.70 Hz, 2 H) 7.74-7.84 (m, 1 H) 7.51-7.70 (m, 2 H) 7.37-7.46 (m, 1 H) 7.27-7.36 (m, 2 H) 7.11 (bs, 2 H) 6.89-7.04 (m, 1 H) 5.07 (s, 2 H). UPLC-MS: 2.09 min, 388.3 [M+H]+, method 2.

Example 3

3-((6-Amino-9H-purin-9-yl)methyl)-4-(2-fluorophenyl)-1H-isochromen-1-one

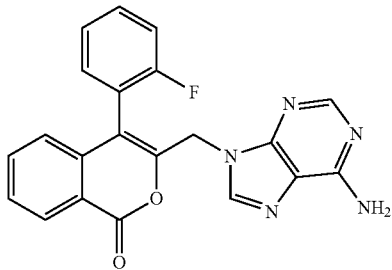 [SMILES: Nc1ncnc2c1ncn2Cc1oc(=O)c2ccccc2c1-c1ccccc1F]

The title compound was made in a similar way as that of the compound of example 1, using 3-(bromomethyl)-4-(2-fluorophenyl)-1H-isochromen-1-one (intermediate C2, 60 mg, 0.180 mmol), 9H-purin-6-amine (48.7 mg, 0.360 mmol) and $K_2CO_3$ (49.8 mg, 0.360 mmol) to give the title compound (45 mg, 64.5%).

$^1$H NMR (400 MHz, DMSO-$d_6$) δ 8.15-8.24 (m, 1H), 7.97-8.08 (m, 2H), 7.75-7.84 (m, 1H), 7.51-7.72 (m, 3H), 7.34-7.47 (m, 2H), 6.86-7.28 (m, 3H), 4.34 (s, 2H). UPLC-MS: 1.92 min, 384.4 [M+H]+, Method 2.

Example 4

3-((6-Amino-9H-purin-9-yl)methyl)-4-m-tolyl-1H-isochromen-1-one

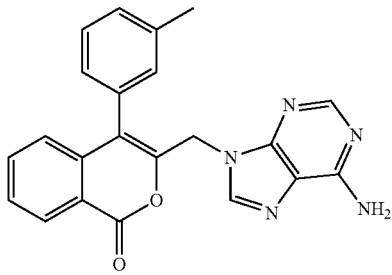 [SMILES: Cc1cccc(-c2c(Cn3cnc4c(N)ncnc43)oc(=O)c3ccccc23)c1]

The title compound was made in a similar way as that of the compound of example 1, using 3-(bromomethyl)-4-m-tolyl-1H-1-isochromen-1-one (Intermediate C3, 64 mg, 0.190 mmol), 9H-purin-6-amine (52.5 mg, 0.39 mmol) and $K_2CO_3$ (53.7 mg, 0.39 mmol) to give the title compound (35 mg, 47%).

$^1$H NMR (400 MHz, DMSO-$d_6$) δ ppm 8.17-8.27 (m, 1 H), 8.00-8.14 (m, 2 H), 7.75-7.86 (m, 1 H), 7.57-7.71 (m, 1 H), 7.40-7.50 (m, 1 H), 7.27-7.38 (m, 3 H), 7.11-7.25 (s, 2 H), 6.96-7.09 (m, 1 H), 4.95 (s, 2 H), 2.37 (s, 3 H). UPLC-MS: 2.37 min, 384.3 [M+H]+, method 2.

Example 5

3-(1-(6-Amino-9H-1-purin-9-yl)ethyl)-4-phenyl-1H-isochromen-1-one

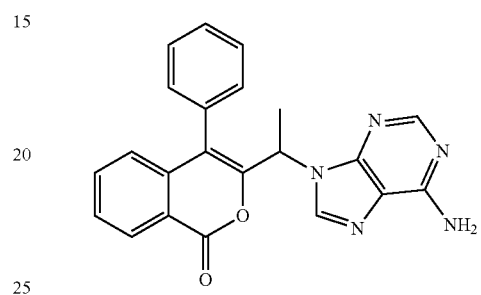

The title compound was made in a similar way as that of the compound of example 1, using 3-(1-bromoethyl)-4-phenyl-1H-isochromen-1-one (intermediate C7, 70 mg, 0.213 mmol), 9H-purin-6-amine (57.5 mg, 0.425 mmol) and $K_2CO_3$ (58.8 mg, 0.425 mmol) to give the title compound (31 mg, 38%).

$^1$H NMR (400 MHz, DMSO-$d_6$) δ ppm 8.40 (s, 1 H), 8.14-8.27 (m, 1 H), 8.10 (s, 1 H), 7.37-7.85 (m, 7 H), 7.17-7.24 (bs, 2 H), 6.88-6.98 (m, 1 H), 5.33-5.49 (m, 1 H), 4.03-4.20 (m, 1 H), 1.75-1.91 (d, 3 H). UPLC-MS: 2.35 min, 384.4 [M+H]+, method 2.

Example 6

3-(1-(6-Amino-9H-purin-9-yl)ethyl)-4-m-tolyl-1H-isochromen-1-one

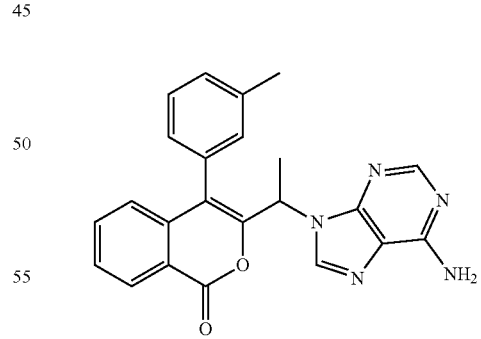

The title compound was made in a similar way as that of the compound of example 1, using 3-(1-bromoethyl)-4-m-tolyl-1H-isochromen-1-one (intermediate C5, 80 mg, 0.23 mmol), 9H-purin-6-amine (63 mg, 0.46 mmol) and $K_2CO_3$ (64.4 mg, 0.46 mmol) to give the title compound (50 mg, 54%).

$^1$H NMR (400 MHz, DMSO-$d_6$) δ ppm 8.27-8.38 (m, 1 H), 8.16-8.25 (m, 1 H), 8.00-8.09 (m, 1 H), 7.72-7.83 (m, 1 H), 7.57-7.67 (m, 1 H), 7.36-7.51 (m, 1 H), 7.28-7.36 (m, 1 H), 7.11-7.26 (m, 4 H), 6.88-7.01 (m, 1 H), 5.35-5.52 (m, 1 H), 2.32 (s, 3 H), 1.71-1.92 (m, 3 H). UPLC-MS: 3.32 min, 398 [M+H]+, method 2.

Example 7

3-(1-(6-Amino-9H-purin-9-yl)ethyl)-4-(3-fluorophenyl)-1H-isochromen-1-one

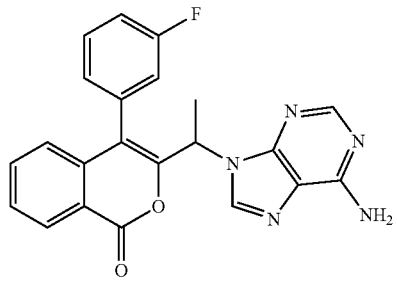 [SMILES: CC(c1oc(=O)c2ccccc2c1-c1cccc(F)c1)n1cnc2c(N)ncnc21]

The title compound was made in a similar way as that of the compound of example 1, using 3-(1-bromoethyl)-4-(3-fluorophenyl)-1H-isochromen-1-one (intermediate C6, 70 mg, 0.202 mmol), 9H-purin-6-amine (54.5 mg, 0.403 mmol) and K$_2$CO$_3$ (55.7 mg, 0.403 mmol) to give the title compound (30 mg, 37.1%).
$^1$H NMR (400 MHz, DMSO-d$_6$) δ ppm 8.20-8.10 (m, 3H), 7.95 (s, 1H), 7.80-7.74 (m, 2H), 7.65-7.60 (m, 2H), 7.37-7.20 (m, 3H), 6.95-6.85 (m, 1H), 5.50-5.40 (m, 1H), 1.85-1.82 (m, 3H). UPLC-MS: 2.89 min, 402 [M+H]+, method 2.

Example 8

3-(1-(6-Amino-9H-purin-9-yl)ethyl)-4-(3-(dimethylamino)phenyl)-1H-isochromen-1-one

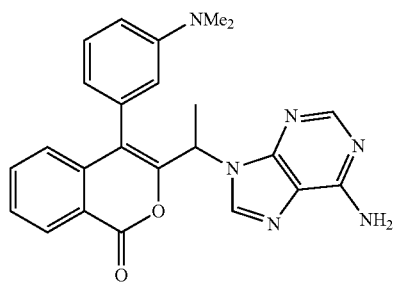 [SMILES: CC(c1oc(=O)c2ccccc2c1-c1cccc(N(C)C)c1)n1cnc2c(N)ncnc21]

The title compound was made in a similar way as that of the compound of example 1, using 3-(1-bromoethyl)-4-(3-(dimethylamino)phenyl)-1H-isochromen-1-one (intermediate C8, 86 mg, 0.231 mmol), 9H-purin-6-amine (46.8 mg, 0.347 mmol) and K$_2$CO$_3$ (47.9 mg, 0.347 mmol) to give the title compound (36 mg, 37%). The resulting mixture was straightforward purified via reverse phase chromatography with a Biotage C18 SNAP column (Phase A, water 95%, ACN 5%, formic acid 0.1%); Phase B ACN 95%, water 5%, formic acid 0.1%). The resulting product was further purified by Preparative HPLC (method 1) to give the title compound (12 mg, 12%).
$^1$H NMR (400 MHz, DMSO-d$_6$) δ ppm 8.38 (s, 1 H), 8.12-8.24 (m, 1 H), 8.03 (s, 1 H), 7.73-7.84 (m, 1 H), 7.54-7.67 (m, 1 H), 7.27-7.42 (m, 1 H), 7.14-7.25 (bs, 2 H), 6.97-7.07 (m, 1 H), 6.87-6.91 (m, 1 H), 6.79-6.86 (m, 1 H), 6.62-6.71 (m, 1 H), 5.42-5.62 (m, 1 H), 2.86 and 2.98 (2 s, 6 H, 3 H each), 1.75-1.90 (m, 3 H). UPLC-MS: 4.68 min, 427 [M+H]+, method 1.

Example 9

3-(1-(6-Amino-9H-purin-9-yl)ethyl)-4-(3-(morpholinosulfonyl)phenyl)-1H-isochromen-1-one

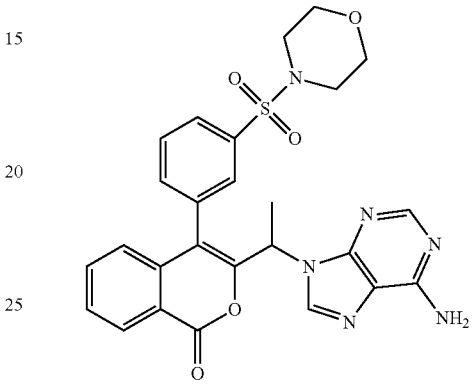

The title compound was made in a similar way as that of the compound of example 1, using 3-(1-bromoethyl)-4-(3-(morpholinosulfonyl)phenyl)-1H-isochromen-1-one (intermediate C9, 68 mg, 0.142 mmol), 9H-purin-6-amine (57.6 mg, 0.426 mmol) and K$_2$CO$_3$ (29.5 mg, 0.213 mmol) to give the title compound (30 mg, 37.1%). The resulting mixture was straightforward purified via reverse phase chromatography with a Biotage C18 SNAP column (Phase A, water 95%, ACN 5%, formic acid 0.1%); Phase B ACN 95%, water 5%, formic acid 0.1%) The resulting product was further purified by Preparative HPLC (method 2) to give the chemically pure compound (10 mg, 13%) and a batch with lower purity (9 mg, 12%).
$^1$H NMR (400 MHz, DMSO-d$_6$) δ ppm 8.45-8.35 (m, 1H), 8.30-8.20 (m, 1H), 8.05-7.65 (m, 6H), 7.45 (br s, 2H), 6.90 (t, 1H), 5.30-5.45 (m, 1H), 3.60-2.6 (m, 8H), 1.80-1.55 (m, 1H). UPLC-MS: 3.59 min, 533 [M+H]+, method 1

Example 10

3-((9H-Purin-6-ylthio)methyl)-4-phenyl-1H-isochromen-1-one

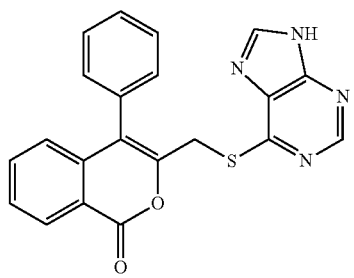 [SMILES: O=c1oc(CSc2ncnc3[nH]cnc23)c(-c2ccccc2)c2ccccc12]

3-(Bromomethyl)-4-phenyl-1H-isochromen-1-one (Intermediate C1, 35 mg, 0.111 mmol), 9H-purine-6-thiol hydrate (18.9 mg, 0.111 mmol) and K₂CO₃ (15.35 mg, 0.111 mmol) were dissolved in DMF (1 ml) and stirred at RT for 1 hrs 30 min. The reaction mixture was then diluted with water (10 ml) and 0.1 N HCl$_{aqueous}$ (1 ml). The mixture was extracted with EtOAc and the collected organic phases were dried over Na₂SO₄, filtered and concentrated under reduced pressure. The crude was purified by Preparative HPLC (method 2) to give the title compound (24 mg, 56%).

¹H NMR (400 MHz, DMSO-d₆) δ ppm 8.51 (s, 1 H), 8.33-8.44 (m, 1 H), 8.19-8.30 (m, 1 H), 7.73-7.85 (m, 1 H), 7.59-7.68 (m, 1 H), 7.48-7.60 (m, 3 H), 7.35-7.43 (m, 2 H), 6.91-7.05 (m, 1 H), 4.46 (s, 2 H). UPLC-MS: 2.80 min, 387.3 [M+H]+, method 2.

Example 11

3-((9H-Purin-6-ylthio)methyl)-4-(2-fluorophenyl)-1H-isochromen-1-one

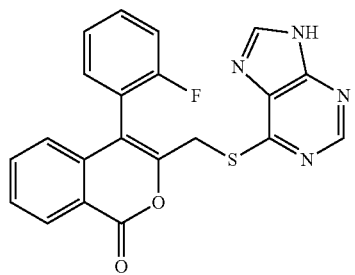 [SMILES: O=c1oc(CSc2ncnc3[nH]cnc23)c(-c2ccccc2F)c2ccccc12]

The title compound was made in a similar way as that of the compound of example 10, 3-(bromomethyl)-4-(2-fluorophenyl)-1H-isochromen-1-one (intermediate C2, 37 mg, 0.111 mmol), 9H-purine-6-thiol hydrate (18.90 mg, 0.111 mmol) and K₂CO₃ (15.35 mg, 0.111 mmol) to give the title compound (33 mg, 73.5%).

¹H NMR (400 MHz, DMSO-d₆) δ ppm 8.41 (m, 2 H) 8.19-8.24 (m, 1 H) 7.71-7.83 (m, 1 H) 7.51-7.66 (m, 2 H) 7.25-7.51 (m, 3 H) 6.81-7.02 (m, 1 H) 4.27-4.66 (s, 2 H).
UPLC-MS: 2.68 min, 405.3 [M+H]+, method 2.

Example 12

3-((9H-Purin-6-ylthio)methyl)-4-m-tolyl-1H-isochromen-1-one

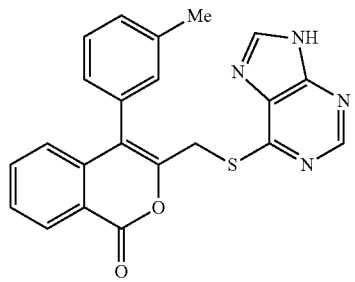 [SMILES: Cc1cccc(-c2c(CSc3ncnc4[nH]cnc34)oc(=O)c3ccccc23)c1]

The title compound was made in a similar way as that of the compound of example 10, 3-(bromomethyl)-4-m-tolyl-1H-isochromen-1-one (intermediate C3, 64 mg, 0.194 mmol), 9H-purine-6-thiol hydrate (33 mg, 0.194 mmol) and K₂CO₃ (27 mg, 0.111 mmol) to give the title compound (64 mg, 82%).

¹H NMR (400 MHz, DMSO-d₆) δ 13.01-13.77 (bs, 1H), 8.46 (s, 1H), 8.37 (s, 1H), 8.15-8.22 (m, 1H), 7.71-7.79 (m, 1H), 7.55-7.62 (m, 1H), 7.35-7.42 (m, 1H), 7.24-7.29 (m, 1H), 7.10-7.17 (m, 2H), 6.93-6.99 (m, 1H), 4.11-4.56 (m, 2H), 2.28 (s, 3H). UPLC-MS: 3.15 min, 401.3 [M+H]+, method 2.

Example 13

3-(1-(9H-Purin-6-ylthio)ethyl)-4-m-tolyl-1H-isochromen-1-one

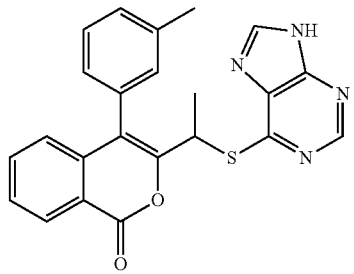 [SMILES: Cc1cccc(-c2c(C(C)Sc3ncnc4[nH]cnc34)oc(=O)c3ccccc23)c1]

The title compound was made in a similar way as that of the compound of example 10, 3-(1-bromoethyl)-4-m-tolyl-1H-isochromen-1-one (intermediate C5, 67 mg, 0.195 mmol), 9H-purine-6-thiol hydrate (33.2 mg, 0.195 mmol)) and K₂CO₃ (27 mg, 0.111 mmol) to give to give the title compound (70 mg, 87%)

¹H NMR (400 MHz, DMSO-d₆) δ 13.5 (bs, 1H), 8.45-8.39 (m, 2H), 8.26-8.21 9m, 1H), 7.80-7.75 (m, 1H), 7.65-7.60 (m, 1H), 7.50-7.20 (m, 3H), 7.10-6.95 (m, 2H), 5.40-5.30 (m, 1H), 2.45 (s, 1.5H), 2.20 (2, 1.5H), 1.72-1.67 (m, 3H). UPLC-MS: 3.32 min, 415.4 [M+H]+, method 2.

Example 14

3-(1-(9H-Purin-6-ylthio)ethyl)-4-(3-fluorophenyl)-1H-isochromen-1-one

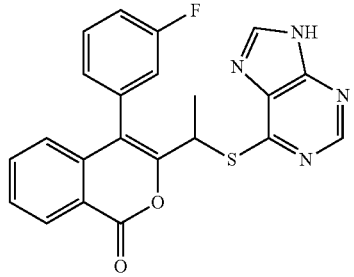 [SMILES: CC(Sc1ncnc2[nH]cnc12)c1oc(=O)c2ccccc2c1-c1cccc(F)c1]

The title compound was made in a similar way as that of the compound of example 10, 3-(1-bromoethyl)-4-(3-fluorophenyl)-1H-isochromen-1-one (intermediate C6, 70 mg, 0.202 mmol), 9H-purine-6-thiol hydrate (34.3 mg, 0.202 mmol) and K₂CO₃ (27.9 mg, 0.202 mmol). The resulting mixture was straightforward purified via reverse phase chromatography with a Biotage C18 SNAP column (Phase A, water 95%, ACN 5%, formic acid 0.1%); Phase B ACN 95%, water 5%, formic acid 0.1%) to give the title compound (53 mg, 63%).

$^1$H NMR (400 MHz, DMSO-$d_6$) δ ppm 13.24-13.73 (bs, 1 H), 8.34-8.46 (m, 2 H), 8.25 (d, 1 H), 7.72-7.86 (m, 1 H), 7.65 (d, 2 H), 7.33 (d, 3 H), 7.06 (m, 1 H), 6.98 (m, 1 H), 5.33 (m, 1 H), 1.72 (t, 3 H). UPLC-MS: 3.04 min, 419.4 [M+H]+, method 2.

Example 15

3-(1-(4-Amino-1H-pyrazolo[3,4-d]pyrimidin-1-yl)ethyl)-4-(6-methylpyridin-3-yl)-1H-isochromen-1-one

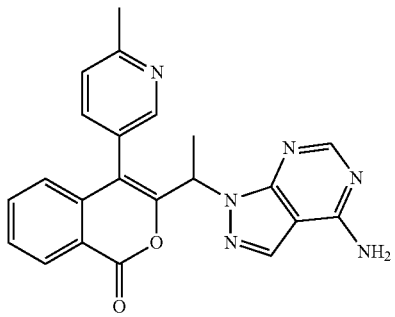 [SMILES: Cc1ccc(-c2c(C(C)n3ncc4c(N)ncnc43)oc(=O)c3ccccc23)cn1]

3-(1-Bromoethyl)-4-(6-methylpyridin-3-yl)-1H-isochromen-1-one hydrobromide (intermediate C10, 120 mg, 0.282 mmol), 1H-pyrazolo[3,4-d]pyrimidin-4-amine (76 mg, 0.565 mmol), and K$_2$CO$_3$ (117 mg, 0.847 mmol) were stirred in DMF (1.5 ml) at 50° C. for 2.5 hrs. The reaction mixture was diluted with 1M HCl$_{aqueous}$ (2 ml) and purified via reverse phase chromatography with a Biotage C18 SNAP column (Phase A, water 95%, ACN 5%, formic acid 0.1%); Phase B ACN 95%, water 5%, formic acid 0.1%) to give the title compound as colourless solid (16.7 mg, 15%).

$^1$H NMR (400 MHz, DMSO-$d_6$) δ ppm 8.49 (br s, 0.5 H), 8.23-8.20 (m, 1H), 8.12 (br s, 0.5 H), 8.09 (br s, 1H), 8.01 (br s, 1H), 7.80-7.62 (m, 4H), 7.42-7.38 (m, 1.51H), 7.25-7.23 (m, 0.5 H) 6.90-6.88 (d, 1H), 5.65-5.55 (m, 1H), 2.54 (m, 3H), 1.81 (t, 3H). UPLC-MS: 1.04 min, 399.4 [M+H]+, method 2.

Example 16. 3-(1-(4-Amino-1H-pyrazolo[3,4-d]pyrimidin-1-yl)ethyl)-4-(3-(morpholinosulfonyl)phenyl)-1H-isochromen-1-one

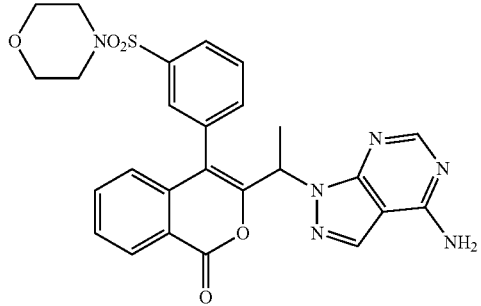

The title compound was made in a similar way as that of the compound of example 15, 3-(1-bromoethyl)-4-(3-(morpholinosulfonyl)phenyl)-1H-isochromen-1-one (intermediate C9, 90 mg, 0.188 mmol), 1H-pyrazolo[3,4-d]pyrimidin-4-amine (50.8 mg, 0.376 mmol) and K$_2$CO$_3$ (52 mg, 0.376 mmol) in DMF (1 ml) at 80° C. for 2 hrs to give the title compound (54 mg, 54%).

$^1$H NMR (400 MHz, DMSO-$d_6$) δ ppm 8.20-8.16 (m, 1H), 8.03 (s, 1H), 7.98 (s, 0.5 H), 7.89 (s, 0.5 H), 7.82-7.69 (m, 4 H), 7.61-7.57 (m, 1H), 7.50-7.46 (m, 1H), 6.81-6.7 (m, 1H), 5.70-5.60 (q, 0.5 H), 5.50-5.40 (q, 0.5H), 3.64-3.46 (m, 4H), 3.04-2.74 (m, 4H), 1.80 (d, 0.5 H), 1.71 (d, 0.5 H). UPLC-MS: 1.98 min, 533.4 [M+H]+, method 2.

Example 17

3-(1-(4-Amino-1H-pyrazolo[3,4-d]pyrimidin-1-yl)ethyl)-4-phenyl-1H-isochromen-1-one

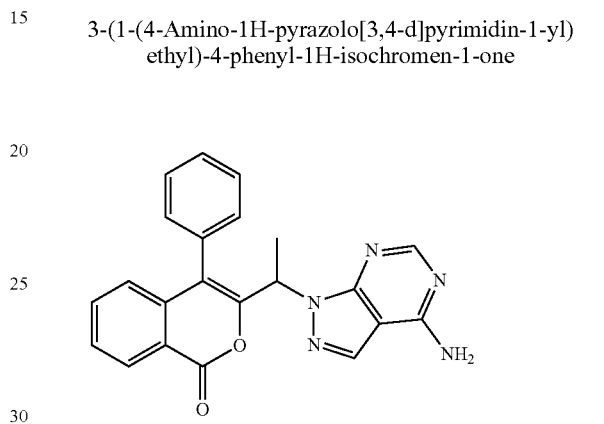

The title compound was made in a similar way as that of the compound of example 15, 3-(1-bromoethyl)-4-phenyl-1H-isochromen-1-one (intermediate C7, 70 mg, 0.213 mmol), 1H-pyrazolo[3,4-d]pyrimidin-4-amine (40.2 mg, 0.298 mmol) and K$_2$CO$_3$ (41.1 mg, 0.298 mmol) in DMF (1 ml) at 80° C. for 4 hrs to give the title compound (28 mg, 34%).

$^1$H NMR (400 MHz, DMSO-$d_6$) δ ppm 8.22 (d, 1 H), 8.14 (s, 1 H), 8.10 (s, 1 H), 8.02 (s, 1 H), 7.72-7.81 (m, 1 H), 7.50-7.66 (m, 3 H), 7.41-7.49 (m, 2 H), 7.34-7.40 (m, 1 H), 7.11 (d, 1 H), 6.90 (d, 1 H), 5.60 (d, 1 H), 1.79 (d, 3 H). UPLC-MS: 4.77 min, 384.2 [M+H]+, method 3.

Example 18

3-(1-(4-Amino-1H-pyrazolo[3,4-d]pyrimidin-1-yl)ethyl)-4-(thiazol-5-yl)-1H-isochromen-1-one

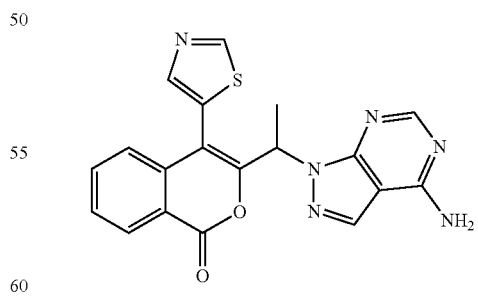

The title compound was made in a similar way as that of the compound of example 15, 3-(1-bromoethyl)-4-(thiazol-5-yl)-1H-isochromen-1-one (intermediate C12, 56 mg, 0.17 mmol), 1H-pyrazolo[3,4-d]pyrimidin-4-amine (45 mg, 0.33 mmol) and K$_2$CO$_3$ (46 mg, 0.33 mmol) in DMF (1 ml) at 80° C. for 3 hrs to give the title compound (35 mg, 54%).

¹H NMR (400 MHz, DMSO-d₆) δ ppm 9.30 (s, 1 H), 8.22 (d, 1 H), 8.14 (s, 1 H), 8.10 (s, 1 H), 8.04 (s, 1 H), 7.83 (s, 2 H), 7.63-7.69 (m, 2 H), 7.05 (d, 1 H), 5.75 (d, 1 H), 1.81 (d, 3 H). UPLC-MS: 3.09 min, 391.2 [M+H]+, method 3.

Example 19

3-(1-(4-Amino-1H-pyrazolo[3,4-d]pyrimidin-1-yl)ethyl)-4-(2-methylpyridin-4-yl)-1H-isochromen-1-one

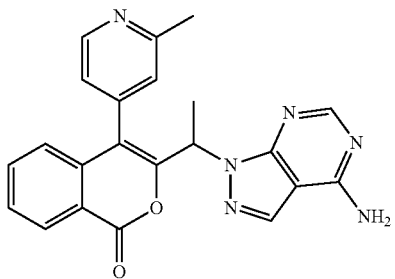 [SMILES: Cc1cc(-c2c(C(C)n3ncc4c(N)ncnc43)oc(=O)c3ccccc23)ccn1]

The title compound was made in a similar way as that of the compound of example 15, 3-(1-bromoethyl)-4-(2-methylpyridin-4-yl)-1H-isochromen-1-one (intermediate C14, 98 mg, 0.285 mmol), 1H-pyrazolo[3,4-d]pyrimidin-4-amine (57.7 mg, 0.43 mmol) and K₂CO₃ (59 mg, 0.42 mmol) in DMF (2 ml) at 50° C. for 6 hrs to give the title compound (3.4 mg, 3%).

¹H NMR (400 MHz, DMSO-d₆) δ ppm 8.57 (d, 0.5 H), 8.38 (d, 0.5H), 8.25-8.22 (m, 1H), 8.11 (s, 0.5H), 8.05 (s, 0.5H), 8.01 (d, 1H), 7.80-7.62 (m, 4H), 7.27-7.25 (m, 1H), 6.90-6.87 (m, 1.5H), 6.68 (br s, 0.5H), 5.70-5.60 (m, 1H), 3.15-3.05 (m, 1H) 1.81-1.75 (m, 3 H), 1.18 (t, 3H). UPLC-MS: 3.02 min, 399.3 [M+H]+, method 3.

Example 20

3-(1-(4-Amino-1H-pyrazolo[3,4-d]pyrimidin-1-yl)ethyl)-4-benzyl-1H-isochromen-1-one

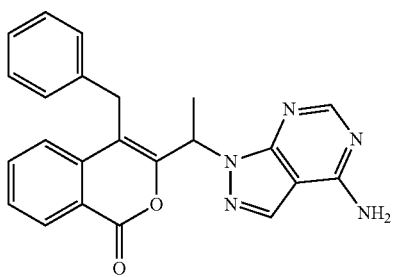 [SMILES: CC(c1oc(=O)c2ccccc2c1Cc1ccccc1)n1ncc2c(N)ncnc21]

The title compound was made in a similar way as that of the compound of example 15, 4-benzyl-3-(1-bromoethyl)-1H-isochromen-1-one (intermediate C13, 22 mg, 0.064 mmol), 1H-pyrazolo[3,4-d]pyrimidin-4-amine (12.99 mg, 0.096 mmol), and K₂CO₃ (13.29 mg, 0.096 mmol) in DMF (1 ml) at 55° C. for 2 hrs to give the title compound (9 mg, 35%).

¹H NMR (400 MHz, DMSO-d₆) δ ppm 8.15-8.23 (m, 1 H), 8.08-8.13 (m, 2 H), 7.70-8.22 (m, 4 H), 6.97-7.24 (m, 6 H), 6.20-6.31 (m, 1 H), 4.18-4.44 (m, 2 H), 1.78-1.89 (m, 3 H). UPLC-MS: 4.55 min, 398.1 [M+H]+, method 3.

Example 21

3-((9H-Purin-6-ylamino)methyl)-4-(3-fluorophenyl)-1H-isochromen-1-one

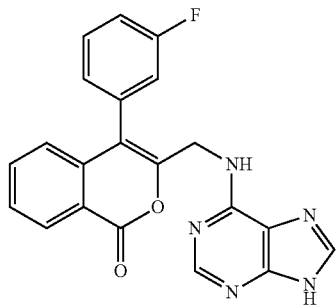 [SMILES: O=c1oc(CNc2ncnc3[nH]cnc23)c(-c2cccc(F)c2)c2ccccc12]

Tert-butyl 9-trityl-9H-purin-6-ylcarbamate (93 mg, 0.195 mmol) and 50% dispersion in mineral oil NaH (9.4 mg, 0.195 mmol) were dissolved in DMF (0.2 ml) at 0° C. A solution of 3-(bromomethyl)-4-(3-fluorophenyl)-1H-isochromen-1-one (intermediate C4, 50 mg, 0.150 mmol) in DMF (0.6 mL) was then added. The reaction mixture was stirred at 0° C. for 5 min and at RT for 15 min. The reaction mixture was then diluted with EtOAc (20 mL) and washed with 0.2 M HCl_{aqueous}, sat NaCl_{aqueous} dried over Na₂SO₄ and concentrated under reduced pressure to give the crude yellow oil. The crude was reacted with TFA (1.5 ml) in DCM (2 ml) for 1 hrs. Then it was diluted with DCM and dried under reduced pressure to give an yellow oil. This was purified via reverse phase chromatography with a Biotage C18 30 g SNAP column (Phase A, water 95%, ACN 5%, formic acid 0.1%); Phase B ACN 95%, water 5%, formic acid 0.1%) to give the title compound (20 mg, 34.4%) as colourless solid.

¹H NMR (400 MHz, DMSO-d₆) δ 8.08-8.23 (m, 4 H), 7.72-7.81 (m, 1H), 7.51-7.63 (m, 2H), 7.25-7.38 (m, 3H), 6.97 (d, 1H), 3.35-3.43 (m, 2H). UPLC-MS: 2.25 min, 388.3 [M+H]+, method 2.

Example 22

3-(1-(9H-Purin-6-ylamino)ethyl)-4-phenyl-1H-isochromen-1-one

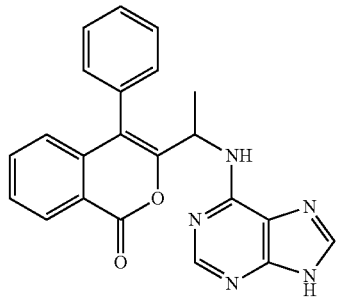 [SMILES: CC(Nc1ncnc2[nH]cnc12)c1oc(=O)c2ccccc2c1-c1ccccc1]

The title compound was made in a similar way as that of the compound of example 21, from tert-butyl 9-trityl-9H-purin- 6-ylcarbamate (139 mg, 0.292 mmol), 3-(1-bromoethyl)-4-phenyl-1H-isochromen-1-one (intermediate C7, 80 mg, 0.243 mmol) and 50% dispersion in mineral oil NaH (16.3 mg, 0.340 mmol) in DMF to give the title compound (16 mg, 17.2%) as yellowish solid.

$^1$H NMR (400 MHz, DMSO-$d_6$) δ ppm 13.08 (s, 1 H), 8.10 (m, 3 H), 7.85-7.95 (m, 1 H), 7.72-7.81 (m, 1 H), 7.46-7.64 (m, 5 H), 7.30-7.43 (m, 1 H), 6.85-6.99 (m, 1 H), 4.78-5.22 (m, 1 H), 1.51 (d, 3 H). UPLC-MS: 2.52 min, 384.5 [M+H]+, method 2.

Example 22a (Enantiomer 1) and Example 22b (Enantiomer 2)

3-(1-(9H-Purin-6-ylamino)ethyl)-4-phenyl-1H-isochromen-1-one single enantiomer

Racemate 3-(1-(9H-purin-6-ylamino)ethyl)-4-phenyl-1H-isochromen-1-one (example 22, 0.145 g, 0.378 mmol) was dissolved in Ethanol/Methanol 1/1 (34 mL) and submitted to chiral resolution by Chiral preparative chromatography. Conditions: Column: Chiralpak AD-H (25×2.0 cm), 5 μ; Mobile phase: n-Hexane/(2-Propanol+0.1% isopropylamine) 75/25% v/v; Flow rate: 19 ml/min; DAD detection: 220 nm; Injection: 19 mg (each injection).

The fractions containing the first eluted enantiomer were evaporated to afford compound 22a (first eluted enantiomer, 0.052 g, 0.135 mmol). Chiral HPLC (Method A1): Rt=6.0 min, ee>99%;

$^1$H NMR (400 MHz, DMSO-$d_6$) δ ppm 12.92 (br. s., 1 H), 8.06-8.27 (m, 3 H), 7.86-7.94 (m, 1 H), 7.73-7.81 (m, 1 H), 7.48-7.64 (m, 5 H), 7.37-7.43 (m, 1 H), 6.95 (d, 1H), 5.06 (br. s., 1 H), 1.53 (d, 3 H). UPLC-MS: 0.85 min, 384.2 [M+H]+, method 13.

The fractions containing the second eluted enantiomer were evaporated to afford compound 22b (second eluted enantiomer, 0.032 g, 0.083 mmol), Chiral HPLC (Method A1): Rt=13.0 min, ee>99%;

$^1$H NMR (400 MHz, DMSO-$d_6$) δ ppm 12.78 (br. s., 1 H), 8.09-8.24 (m, 3 H), 7.82-7.90 (m, 1 H), 7.74-7.81 (m, 1 H), 7.49-7.64 (m, 5 H), 7.38-7.44 (m, 1 H), 6.95 (d, 1H), 5.06 (br. s., 1 H), 1.53 (d, 3 H). UPLC-MS: 0.83 min, 384.2 [M+H]+, method 13.

Example 23

3-(1-(9H-Purin-6-ylamino)ethyl)-4-(1,2,3,6-tetrahydropyridin-4-yl)-1H-isochromen-1-one hydrochloride

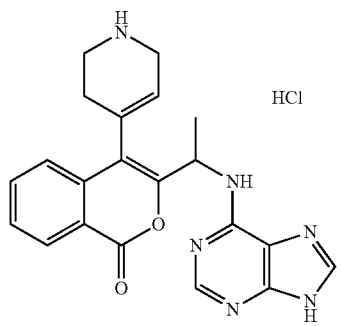 [SMILES: CC(Nc1ncnc2[nH]cnc12)c1oc(=O)c2ccccc2c1C1=CCNCC1 ; Cl]

The title compound was made in a similar way as that of the compound of example 21, from tert-butyl 9-trityl-9H-purin-6-ylcarbamate (71 mg, 0.149 mmol) and tert-butyl 4-(3-(1-bromoethyl)-1-oxo-1H-isochromen-4-yl)-5,6-dihydropyridine-1(2H)-carboxylate (intermediate C11, 54 mg, 0.124 mmol) and 50% dispersion in mineral oil NaH (18 mg, 0.34 mmol) in DMF. This was purified via reverse phase chromatography with a Biotage C18 SNAP column (Phase A, water 95%, ACN 5%, formic acid 0.1%); Phase B ACN 95%, water 5%, formic acid 0.1%). Fractions containing the required product were collected, 1 M HCl$_{aqueous}$ (5 ml) was added and concentrated under reduced pressure to give the title compound (24 mg, 45%) as colourless solid.

1H NMR (400 MHz, DMSO-$d_6$) δ ppm 9.3-9.0 (m, 2 H), 8.5-8.3 (m, 1 H), 8.20-8.14 (m, 1H), 7.89-7.85 (m, 1H), 7.7-760 (m, 2 H), 6.05-5.92 (m, 1H), 5.60-5.40 (m, 1 H), 3.79-3.25 (m, 6 H), 1.61-1.59 (m, 3 H). UPLC-MS: 2.29 min, 389.5 [M+H]+, method 3.

Example 24

3-(1-(9H-Purin-6-ylamino)ethyl)-4-(3,6-dihydro-2H-pyran-4-yl)-1H-isochromen-1-one

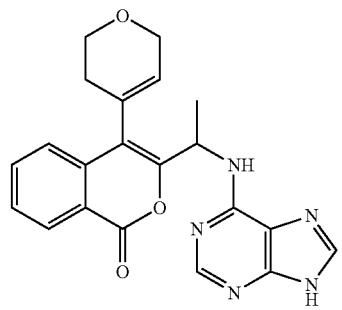 [SMILES: CC(Nc1ncnc2[nH]cnc12)c1oc(=O)c2ccccc2c1C1=CCOCC1]

The title compound was made in a similar way as that of the compound of example 21, from tert-butyl 9-trityl-9H-purin-6-ylcarbamate (214 mg, 0.449 mmol) and 3-(1-bromoethyl)-4-(3,6-dihydro-2H-pyran-4-yl)-1H-isochromen-1-one (intermediate C19, 94 mg, 0.280 mmol) and 50% dispersion in mineral oil NaH (18 mg, 0.34 mmol) in DMF. This was purified via reverse phase chromatography with a Biotage C18 SNAP column (Phase A, water 95%, ACN 5%, formic acid 0.1%); Phase B ACN 95%, water 5%, formic acid 0.1%). Fractions containing the required product were collected, 1 M HCl$_{aqueous}$ (5 ml) was added and concentrated under reduced pressure to give the title compound (6.3 mg, 5.8%) as colourless solid.

$^1$H NMR (400 MHz, DMSO-$d_6$) δ ppm 12.94 (s, 0.8 H), 12.08 (s, 0.2 H), 8.20-8.12 (m, 3H), 7.89-7.84 (m, 2 H), 7.63-7.45 (m, 3 H), 5.98-5.94 (m, 1 H), 5.75-5.50 (m, 1 H). 4.30-4.21 (m, 2H), 3.96-3.90 (m, 2 H), 2.23-2.26 (m, 2 H), 1.59-1.55 (m, 3 H). UPLC-MS: 3.29 min, 390 [M+H]+, method 3.

Example 25

3-(1-(9H-Purin-6-ylamino)propyl)-4-phenyl-1H-isochromen-1-one

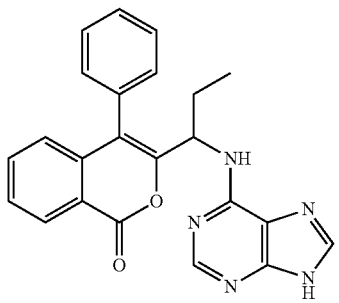 [SMILES: CCC(Nc1ncnc2[nH]cnc12)c1oc(=O)c2ccccc2c1-c1ccccc1]

The title compound was made in a similar way as that of the compound of example 21, from tert-butyl 9-trityl-9H-purin-6-ylcarbamate (167 mg, 0.350 mmol), 3-(1-bromopropyl)-4-phenyl-1H-isochromen-1-one (intermediate C20, 100 mg, 0.291 mmol) and 50% dispersion in mineral oil NaH (21 mg, 0.870 mmol) in DMF at 55° C. The crude was purified via reverse phase chromatography with a column stacking of two Biotage C18 30 g SNAP column (Phase A, water 95%, ACN 5%, formic acid 0.1%); Phase B ACN 95%, water 5%, formic acid 0.1%) and further purified by Preparative HPLC (method 1) to give the title compound (2.8 mg, 2.4%) as a colourless solid.

$^1$H NMR (400 MHz, DMSO-$d_6$) δ ppm 12.64-13.09 (bs, 1 H), 8.05-8.26 (m, 3 H), 7.70-7.88 (m, 2 H), 7.46-7.63 (m, 5 H), 7.36 (d, 1 H), 6.92 (d, 1 H), 4.66-5.08 (m, 1 H), 1.83-2.03 (m, 2 H), 0.84 (t, 3 H). UPLC-MS: 5.04 min, 398.5 [M+H]+, method 3.

Example 26

3-(1-(9H-Purin-6-ylamino)ethyl)-4-(4-(2-morpholinoethoxy)phenyl)-1H-isochromen-1-one formate

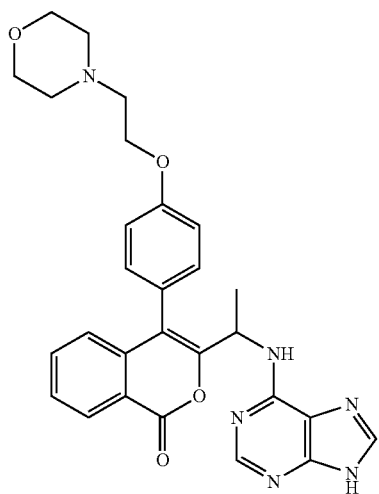 [SMILES: CC(Nc1ncnc2[nH]cnc12)c1oc(=O)c2ccccc2c1-c1ccc(OCCN2CCOCC2)cc1]

The title compound was made in a similar way as that of the compound of example 21, from tert-butyl 9-trityl-9H-purin-6-ylcarbamate (140 mg, 0.29 mmol), 3-(1-bromoethyl)-4-(4-(2-morpholinoethoxy)phenyl)-1H-isochromen-1-one hydrobromide (intermediate C15, 100 mg, 0.185 mmol) and 50% dispersion in mineral oil NaH (27 mg, 0.550 mmol) in DMF at 65° C. to give the title compound (16.9 mg, 16.3%) as a colourless solid.

$^1$H NMR (400 MHz, DMSO-$d_6$) δ ppm 12.77-13.04 (bs, 1 H), 8.15 (m, 4 H), 7.82-7.92 (m, 1 H), 7.71-7.81 (m, 1 H), 7.52-7.62 (m, 1 H), 7.34-7.52 (m, 1 H), 7.22-7.35 (m, 1H), 7.11 (m, 2 H), 6.80-7.02 (m, 1 H), 4.80-5.28 (m, 1 H), 4.17 (m, 2 H), 3.51-3.76 (m, 4 H), 2.75 (m, 2 H), 2.51-2.60 (m, 4 H), 1.50 (d, J=7.06 Hz, 3 H). UPLC-MS: 3.94 min, 513.1 [M+H]+, method 3.

Example 27

4-Amino-8-(1-(1-oxo-4-phenyl-1H-isochromen-3-yl)ethyl)pyrido[2,3-d]pyrimidin-5(8H)-one

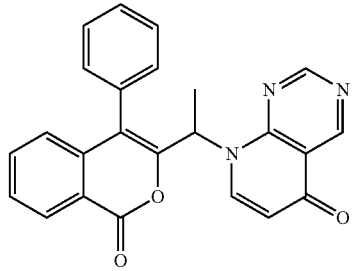 [SMILES: CC(c1oc(=O)c2ccccc2c1-c1ccccc1)n1ccc(=O)c2cncnc21]

3-(1-Bromoethyl)-4-phenyl-1H-isochromen-1-one (intermediate C7, 50 mg, 0.15 mmol), 4-aminopyrido[2,3-d]pyrimidin-5(8H)-one (37 mg, 0.23 mmol), potassium carbonate (31.5 mg, 0.23 mmol) were reacted in DMF (0.5 ml) at 80° C. The crude was purified via reverse phase chromatography with a Biotage C18 30 g SNAP column (Phase A, water 95%, ACN 5%, formic acid 0.1%); Phase B ACN 95%, water 5%, formic acid 0.1%) to give the title compound (32 mg, 51%).

$^1$H NMR (400 MHz, DMSO-$d_6$) δ ppm 9.48-9.56 (m, 1 H), 8.16-8.27 (m, 1 H), 8.06-8.13 (m, 2 H), 7.98-8.04 (m, 1 H), 7.72-7.81 (m, 1 H), 7.58-7.66 (m, 1 H), 7.46-7.57 (m, 1 H), 7.33-7.44 (m, 3 H), 7.07-7.16 (m, 1 H), 6.85-6.94 (m, 1 H), 6.13-6.20 (m, 2H), 1.51-1.81 (m, 3 H). UPLC-MS: 4.7 min, 411.1 [M+H]+, method 5.

Example 28

3-(1-(9H-Purin-6-ylamino)ethyl)-4-(5-(morpholinomethyl)thiophen-2-yl)-1H-isochromen-1-one

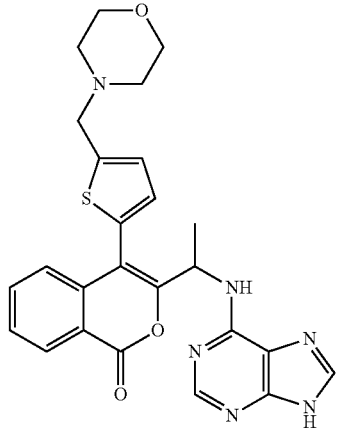 [SMILES: CC(Nc1ncnc2[nH]cnc12)c1oc(=O)c2ccccc2c1-c1ccc(CN2CCOCC2)s1]

tert-Butyl 9-trityl-9H-purin-6-ylcarbamate (102 mg, 0.213 mmol) was added to a solution of 50% dispersion in mineral oil NaH (5.12 mg, 0.213 mmol) in N,N-dimethylformamide (0.5 ml) and the mixture was stirred at RT for 30 min. 3-(1-Bromoethyl)-4-(5-(morpholinomethyl)thiophen-2-yl)-1H-isochromen-1-one hydrobromide (intermediate C16, 100 mg, 0.194 mmol) was suspended in DMF (0.5 ml, 0.194 mmol) and reacted with 50% dispersion in mineral oil NaH (5.1 mg, 0.213 mmol) at RT for 15 min. The resulting solution was added to the previous prepared mixture and left on stirring at 60° C. for 1 hrs, at RT for 3 hrs and then at 80° C. for 3 hrs. The reaction mixture was poured into brine and extracted with EtOAc. The collected organic phases were dried and concentrated. The resulting crude material was purified under reverse phase chromatography using a Biotage C18 60 g SNAP cartridge. The collected fractions were added with 37% HCl$_{aqueous}$ (1 ml) and concentrated. The resulting material was further purified under reverse phase chromatography using a Biotage C18 30 g SNAP cartridge. The resulting material was finally purified on silica with a gradient of DCM and 2-propanol, modified with 0.5% TEA, to give the title compound (9 mg, 9.5%).

$^{1}$H NMR (400 MHz, DMSO-d$_{6}$) δ ppm 12.64-13.05 (bs, 1 H), 8.36-8.44 (m, 1 H), 8.11-8.19 (m, 1 H), 8.01-8.10 (m, 2 H), 7.86-7.99 (m, 1 H), 7.74-7.83 (m, 1 H), 7.47-7.63 (m, 1 H), 7.12-7.22 (m, 1 H), 6.98-7.11 (m, 2 H), 5.11-5.34 (m, 1 H), 3.35-3.79 (m, 6 H), 2.33-2.42 (m, 4 H), 1.41-1.57 (m, 3 H). UPLC-MS: 3.43 min, 489.1 [M+H]+, method 3.

Example 29

3-((9H-Purin-6-ylamino)methyl)-4-phenyl-1H-isochromen-1-one

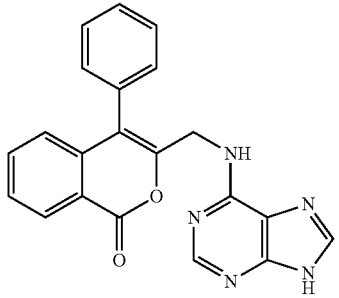 [SMILES: O=c1oc(CNc2ncnc3[nH]cnc23)c(-c2ccccc2)c2ccccc12]

Step 1. tert-Butyl (1-oxo-4-phenyl-1H-isochromen-3-yl)methyl(9-trityl-9H-purin-6-yl)carbamate

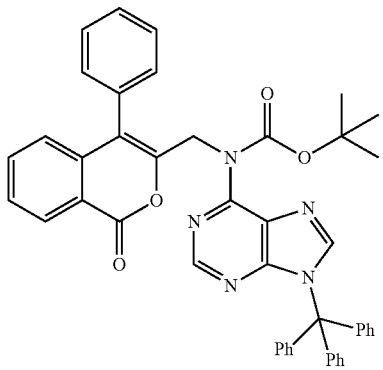 [SMILES: CC(C)(C)OC(=O)N(Cc1oc(=O)c2ccccc2c1-c1ccccc1)c1ncnc2c1ncn2C(c1ccccc1)(c1ccccc1)c1ccccc1]

tert-Butyl 9-trityl-9H-purin-6-ylcarbamate (63.6 mg, 0.133 mmol) in DMF (0.1 ml) was added to a suspension of 50% dispersion in mineral oil NaH (5.33 mg, 0.133 mmol) in DMF (0.1 ml) at 0° C. 3-(bromomethyl)-4-phenyl-1H-isochromen-1-one (intermediate C1, 35 mg, 0.111 mmol) in DMF (0.2 ml) was added and the resulting mixture was allowed to warm to RT. The reaction mixture was then poured into water and extracted with EtOAc. The collected organic phases were dried and concentrated under reduced pressure and the resulting crude (80 mg) was used in the next step without any further purification and characterization.

Step 2 tert-Butyl (1-oxo-4-phenyl-1H-isochromen-3-yl)methyl (9-trityl-9H-purin-6-yl)carbamate (80 mg, 0.112 mmol) was dissolved in DCM (0.7 ml) and TFA (1 mL) at RT for 45 min. Solvent was then removed and the crude was straightforward purified by Preparative HPLC (method 1) to the title compound (17 mg, 40.9%).

$^{1}$H NMR (400 MHz, DMSO-d$_{6}$) δ 12.51-13.14 (bs, 1 H), 8.15-8.25 (m, 1 H), 8.04-8.13 (m, 2 H), 7.92-8.04 (bs, 1 H), 7.68-7.77 (m, 1 H), 7.54-7.61 (m, 1 H), 7.38-7.54 (m, 5 H), 6.91-7.00 (m, 1 H), 4.54 (s, 2 H). UPLC-MS: 2.17 min, 370.3 [M+H]+, method 2.

Example 30

3-((9H-Purin-6-ylamino)methyl)-4-(2-fluorophenyl)-1H-isochromen-1-one

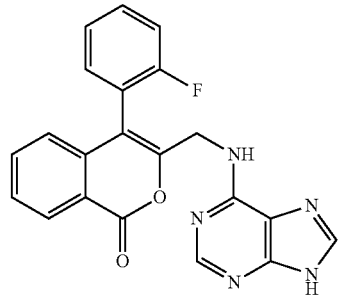 [SMILES: O=c1oc(CNc2ncnc3[nH]cnc23)c(-c2ccccc2F)c2ccccc12]

The title compound was made in a similar way as that of the compound of example 29, from tert-butyl 9-trityl-9H-purin-6-ylcarbamate (60 mg, 0.180 mmol), 3-(bromomethyl)-4-(2-fluorophenyl)-1H-isochromen-1-one (intermediate C2, 99 mg, 0.207 mmol) to give the title compounds (35 mg, 50%).

$^{1}$H NMR (400 MHz, DMSO-d$_{6}$) δ 12.78-12.99 (bs, 1 H), 7.93-8.23 (m, 4 H), 7.68-7.84 (m, 1 H), 7.27-7.63 (m, 5 H), 6.88-7.00 (m, 1 H), 4.44 (s, 2 H). UPLC-MS: 2.08 min, 388.3 [M+H]+, method 2.

Example 31

3-((9H-Purin-6-ylamino)methyl)-4-m-tolyl-1H-isochromen-1-one

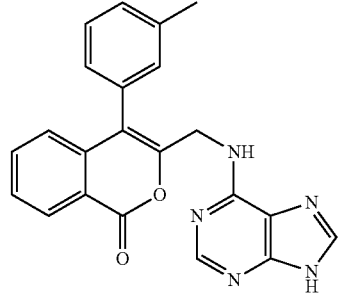 [SMILES: Cc1cccc(-c2c(CNc3ncnc4[nH]cnc34)oc(=O)c3ccccc23)c1]

The title compound was made in a similar way as that of the compound of example 29, from tert-butyl 9-trityl-9H-purin-6-ylcarbamate (102 mg, 0.214 mmol), 3-(bromomethyl)-4-m-tolyl-1H-isochromen-1-one (intermediate C3, 64 mg, 0.194 mmol) to give the title compound (33 mg, 39%).

¹H NMR (400 MHz, DMSO-d₆) δ ppm 12.91 (bs, 1 H) 7.91-8.27 (m, 4 H) 7.74 (t, 1 H) 7.57 (t, 1 H) 7.33-7.42 (m, 1 H) 7.13-7.30 (m, 3 H) 6.97 (d, 1 H) 4.39 (s, 2 H) 2.36 (s, 3H). UPLC-MS: 2.51 min, 384.3 [M+H]+, method 2.

Example 32

3-(1-(9H-purin-6-ylamino)ethyl)-4-(3-fluorophenyl)-1H-isochromen-1-one

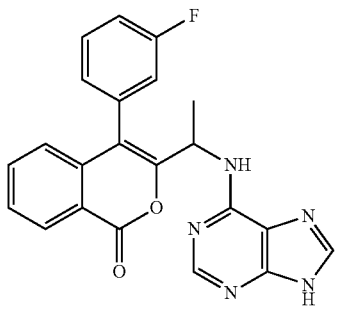 [SMILES: CC(Nc1ncnc2[nH]cnc12)c1oc(=O)c2ccccc2c1-c1cccc(F)c1]

The title compound was made in a similar way as that of the compound of example 29, from tert-butyl 9-trityl-9H-purin-6-ylcarbamate (132 mg, 0.276 mmol), 3-(1-bromoethyl)-4-(3-fluorophenyl)-1H-isochromen-1-one (intermediate C6, 87 mg, 0.251 mmol) to give the title compound (23 mg, 28%).

¹H NMR (400 MHz, DMSO-d₆) δ ppm 12.82-13.02 (bs, 1 H), 8.02-8.27 (m, 3 H), 7.86-8.01 (m, 1 H), 7.73-7.83 (m, 1 H), 7.52-7.66 (m, 2 H), 7.15-7.45 (m, 3 H), 6.88-7.00 (m, 1 H), 4.89-5.18 (m, 1 H), 1.56 (m, 3 H). UPLC-MS: 2.59 min, 402.4 [M+H]+, method 2.

Example 33

3-(1-(9H-Purin-6-ylamino)ethyl)-4-m-tolyl-1H-isochromen-1-one

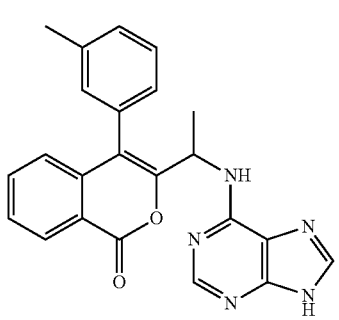 [SMILES: Cc1cccc(-c2c(C(C)Nc3ncnc4[nH]cnc34)oc(=O)c3ccccc23)c1]

The title compound was made in a similar way as that of the compound of example 29, from tert-butyl 9-trityl-9H-purin-6-ylcarbamate (138 mg, 0.28 mmol), 3-(1-bromoethyl)-4-m-tolyl-1H-isochromen-1-one (intermediate C5, 90 mg, 0.26 mmol) to give the title compounds (36 mg, 35%).

¹H NMR (400 MHz, DMSO-d₆) δ ppm 12.79-13.01 (m, 1 H), 8.05-8.31 (m, 3 H), 7.81-7.98 (m, 1 H), 7.68-7.80 (m, 1 H), 7.50-7.66 (m, 1 H), 7.25-7.48 (m, 3 H), 7.11-7.21 (m, 1 H), 6.88-7.00 (m, 1 H), 4.95-5.21 (m, 1 H), 2.35 (m, 3 H), 1.44-1.58 (m, 3H). UPLC-MS: 3.49 min, 398.1 [M+H]+, method 2.

Example 34

3-(1-(9H-Purin-6-ylamino)ethyl)-4-(3-(dimethylamino)phenyl)-1H-isochromen-1-one

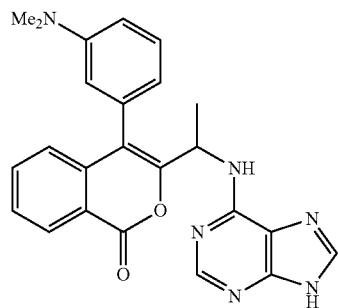 [SMILES: CC(Nc1ncnc2[nH]cnc12)c1oc(=O)c2ccccc2c1-c1cccc(N(C)C)c1]

The title compound was made in a similar way as that of the compound of example 28, from tert-butyl 9-trityl-9H-purin-6-ylcarbamate (127 mg, 0.26 mmol), 3-(1-bromoethyl)-4-(3-(dimethylamino)phenyl)-1H-isochromen-1-one (intermediate C8, 90 mg, 0.242 mmol) to give the title compounds (6 mg, 6%).

¹H NMR (400 MHz, DMSO-d₆) δ ppm 12.61-13.18 (bs, 1 H), 8.53 (s, 1 H), 8.13 (m, 3H), 7.75 (m, 1 H), 7.60 (m, 1 H), 7.28-7.39 (m, 1 H), 6.97-7.10 (m, 1 H), 6.72-6.88 (m, 2 H), 6.57-6.71 (m, 1 H), 4.91-5.28 (m, 1 H), 2.78 (s, 3 H), 2.97 (s, 3 H), 1.43-1.58 (m, 3 H). UPLC-MS: 4.75 min, 427 [M+H]+, method 1.

Example 35

3-((4-Amino-3-(3-fluoro-5-hydroxyphenyl)-1H-pyrazolo[3,4-d]pyrimidin-1-yl)methyl)-4-phenyl-1H-isochromen-1-one

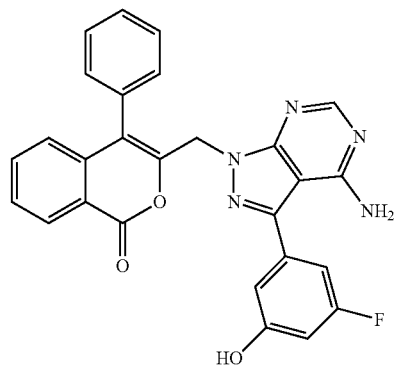 [SMILES: Nc1ncnc2c1c(-c1cc(O)cc(F)c1)nn2Cc1oc(=O)c2ccccc2c1-c1ccccc1]

3-((4-amino-3-iodo-1H-pyrazolo[3,4-d]pyrimidin-1-yl)methyl)-4-phenyl-1H-isochromen-1-one (intermediate D1, 50 mg, 0.101 mmol), 3-fluoro-5-hydroxyphenylboronic acid (32 mg, 0.201 mmol), Cs₂CO₃ (69 mg, 0.202 mmol), Pd(PPh₃)₄ (9.3 mg, 8.0 umol), were reacted in DMF (0.5 mL) at 110° C. under mw irradiation. The resulting crude was straightforward purified via reverse phase chromatography using a Biotage C18 30 g SNAP with a gradient of water and acetonitrile to give the title compound (6 mg, 12%).

$^1$H NMR (400 MHz, DMSO-d$_6$) δ ppm 10.5 (br s, 1 H), 8.54 (s, 1H), 8.24 (s, 1 H), 8.22-8.20 (m, 1 H), 7.83-7.79 (m, 1 H), 7.66-7.62 (m, 1 H), 7.55-7.47 (m, 6 H), 7.04-7.02 (m, 1H), 6.89 (br s, 1 H), 6.84-6.82 (m, 1 H), 6.66-6.64 (m, 1 H), 5.26 (s, 2 H). UPLC-MS: 5.56 min, 479.9 [M+H]+, method 1.

Examples 36-42, 46, 48-49, 63, 111, 118-120 and 125 found in the table below may be prepared starting from suitable reagents reported below following similar procedures as for compound 35.

| Ex. | Name | Structure | reagent | UPLC-MS and $^1$H-NMR |
|---|---|---|---|---|
| 36 | 3-((4-Amino-3-(1H-indazol-5-yl)-1H-pyrazolo[3,4-d]pyrimidin-1-yl)methyl)-4-phenyl-1H-isochromen-1-one | 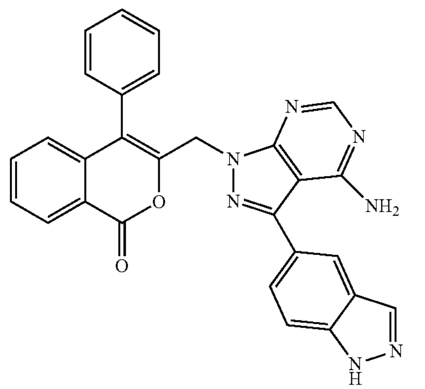 [SMILES: Nc1ncnc2c1c(-c1ccc3[nH]ncc3c1)nn2Cc1oc(=O)c2ccccc2c1-c1ccccc1] | Int. D1 and 1H-indazol-5-ylboronic acid | $^1$H NMR (400 MHz, DMSO-d$_6$) δ ppm 13.04-13.32 (m, 1 H), 8.15-8.27 (m, 3 H), 7.99-8.04 (m, 1 H), 7.77-7.84 (m, 1 H), 7.37-7.74 (m, 9 H), 6.98-7.07 (m, 1 H), 5.35 (s, 2 H). UPLC-MS: 3.46 min, 500.1 [M + H]+, method 2. |
| 37 | 3-((4-Amino-3-(3-methyl-1H-indazol-5-yl)-1H-pyrazolo[3,4-d]pyrimidin-1-yl)methyl)-4-phenyl-1H-isochromen-1-one | 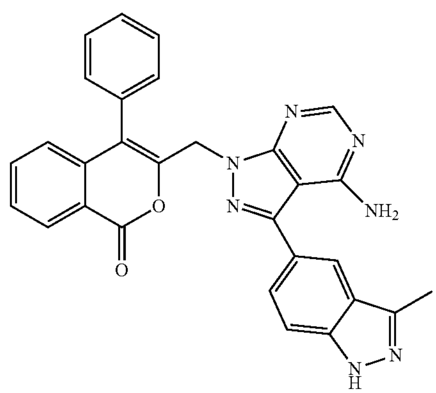 [SMILES: Cc1n[nH]c2ccc(-c3nn(Cc4oc(=O)c5ccccc5c4-c4ccccc4)c4ncnc(N)c34)cc12] | Int. D1 and 3-methyl-1H-indazol-5-ylboronic acid | $^1$H NMR (400 MHz, DMSO-d$_6$) δ ppm 12.80 (brs, 1 H), 8.28 (s, 1H), 8.21 9 d, 1 H), 7.94 (s, 1 H), 7.82-7.78 (m, 1 H), 7.70-7.50 (m, 8 H), 7.03 (d, 1 H), 5.30 (s, 2 H), 2.55 (s, 3 H). UPLC-MS: 3.46 min, 500.1 [M + H]+, method 2 |
| 38 | 3-((4-Amino-3-(1H-indazol-6-yl)-1H-pyrazolo[3,4-d]pyrimidin-1-yl)methyl)-4-phenyl-1H-isochromen-1-one | 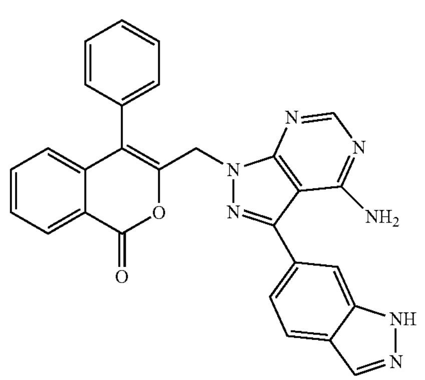 [SMILES: Nc1ncnc2c1c(-c1ccc3cn[nH]c3c1)nn2Cc1oc(=O)c2ccccc2c1-c1ccccc1] | 1H-indazol-6-ylboronic acid | $^1$H NMR (400 MHz, DMSO-d$_6$) δ ppm 13.33 (s, 1 H), 8.24-8.28 (m, 1 H), 8.19-8.23 (m, 1 H), 8.10-8.18 (m, 1 H), 7.89-7.94 (m, 1 H), 7.78-7.84 (m, 1 H), 7.72-7.77 (m, 1 H), 7.59-7.68 (m, 2 H), 7.45-7.58 (m, 5 H), 7.38-7.44 (m, 1 H), 6.93-7.15 (m, 1 H), 5.10 (s, 2 H). UPLC-MS: 4.82 min. 486.1 [M + H]+, method 3. |

-continued

| Ex. | Name | Structure | reagent | UPLC-MS and ¹H-NMR |
|---|---|---|---|---|
| 39 | 3-((4-Amino-3-(3-fluoro-4-hydroxyphenyl)-1H-pyrazolo[3,4-d]pyrimidin-1-yl)methyl)-4-phenyl-1H-isochromen-1-one | 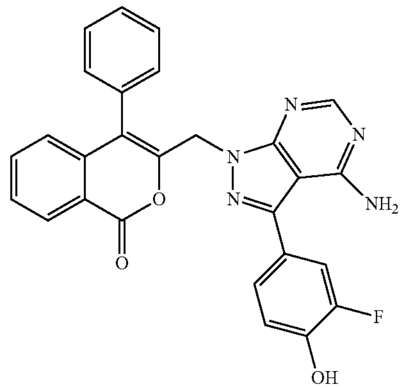 [SMILES: Nc1ncnc2c1c(-c1ccc(O)c(F)c1)nn2Cc1oc(=O)c2ccccc2c1-c1ccccc1] | Int. D1 and 1-(3-fluoro-4-hydroxyphenyl)boronic acid | ¹H NMR (400 MHz, DMSO-d₆) δ ppm 10.07 (s, 1 H), 8.10-8.25 (m, 2 H), 7.72-7.84 (m, 1 H), 7.57-7.68 (m, 1 H), 7.39-7.54 (m, 5 H), 7.28-7.37 (m, 1 H), 7.18-7.28 (m, 1 H), 6.93-7.14 (m, 3 H), 5.13 (s, 2 H). UPLC-MS: 4.90 min. 480.0 [M + H]+, method 3. |
| 40 | 3-(1-(4-Amino-3-(3-fluoro-5-hydroxyphenyl)-1H-pyrazolo[3,4-d]pyrimidin-1-yl)ethyl)-4-phenyl-1H-isochromen-1-one | 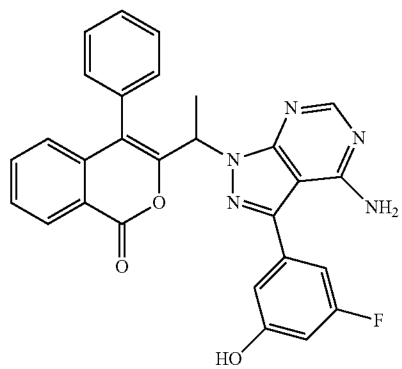 [SMILES: CC(c1oc(=O)c2ccccc2c1-c1ccccc1)n1nc(-c2cc(O)cc(F)c2)c2c(N)ncnc21] | Int. D1 and 3-fluoro-5-hydroxyphenylboronc acid | ¹H NMR (400 MHz, DMSO-d₆) δ ppm 10.37 (s, 1 H), 8.12-8.32 (m, 1 H), 8.09 (s, 1 H), 7.70-7.82 (m, 1 H), 7.59-7.67 (m, 1 H), 7.48-7.56 (m, 1 H), 7.32-7.48 (m, 3 H), 7.08-7.19 (m, 1 H), 6.90 (s, 2 H), 6.79-6.86 (m, 1 H), 6.61-6.70 (m, 1 H), 5.66-5.77 (m, 1 H), 1.83 (d, 3 H). UPLC-MS: 3.85 min, 493.8 [M + H]+, method 2. |
| 41 | 3-(1-(4-Amino-3-(3-fluoro-5-hydroxyphenyl)-1H-pyrazolo[3,4-d]pyrimidin-1-yl)ethyl)-4-m-tolyl-1H-isochromen-1-one | 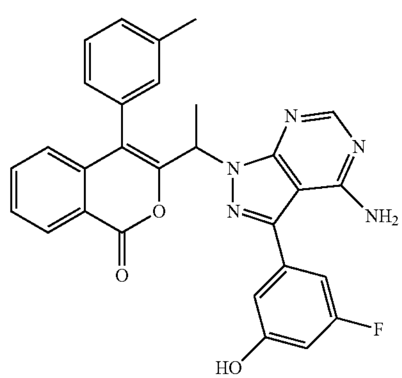 [SMILES: Cc1cccc(-c2c(C(C)n3nc(-c4cc(O)cc(F)c4)c4c(N)ncnc43)oc(=O)c3ccccc23)c1] | Int. D3 and 3-fluoro-5-hydroxyphenylboronic acid | ¹H NMR (400 MHz, DMSO-d₆) δ ppm 10.15 (s, 1 H), 8.18-8.25 (m, 1 H), 8.06-8.13 (m, 1 H), 7.71-7.80 (m, 1 H), 7.58-7.67 (m, 2 H), 7.12-7.47 (m, 5 H), 6.85-6.94 (m, 2 H), 6.76-6.84 (m, 1 H), 6.60-6.69 (m, 1 H), 5.62-5.86 (m, 1 H), 2.35 (s, 3 H), 1.76-1.88 (m, 3 H). UPLC-MS: 6.28 min, 508.0 [M + H]+, method 1. |
| 42 | 3-(1-(4-Amino-3-(1H-pyrazol-4-yl)-1H-pyrazolo[3,4-d]pyrimidin-1-yl)ethyl)-4-m-tolyl-1H-isochromen-1-one | 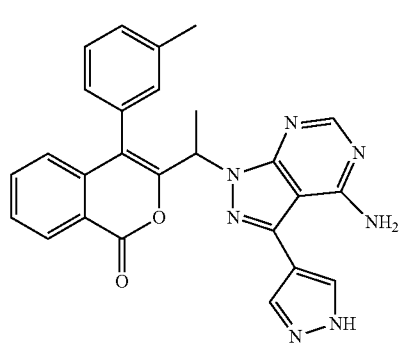 [SMILES: Cc1cccc(-c2c(C(C)n3nc(-c4cn[nH]c4)c4c(N)ncnc43)oc(=O)c3ccccc23)c1] | Int. D3 and 1H-pyrazol-4-ylboronic acid | ¹H NMR (400 MHz, DMSO-d₆) δ ppm 8.22 (ddd, 1 H), 8.09-8.11 (m, 1 H), 8.08-8.15 (bs, 2 H), 7.71-7.81 (m, 1 H), 7.54-7.67 (m, 1 H), 7.30-7.46 (m, 1 H), 6.84-7.28 (m, 6 H), 6.71 (s, 1 H), 5.60-5.79 (m, 1 H), 2.13 and 2.36 (s, 3 H), 1.70-1.89 (m, 3 H). UPLC-MS: 2.55 min, 464.5 [M + H]+, method 2. |

| Ex. | Name | Structure | reagent | UPLC-MS and ¹H-NMR |
|---|---|---|---|---|
| 46 | 3-(1-(4-amino-3-(3-fluoro-5-hydroxyphenyl)-1H-pyrazolo[3,4-d]pyrimidin-1-yl)ethyl)-4-(1-methyl-1,2,3,6-tetrahydropyridin-4-yl)-1H-isochromen-1-one hydrochloride | 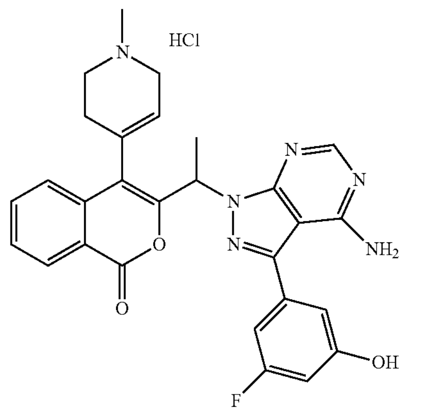 [SMILES: CC(c1oc(=O)c2ccccc2c1C1=CCN(C)CC1)n1nc(-c2cc(O)cc(F)c2)c2c(N)ncnc21 ; Cl] | Int. D4 and 3-fluoro-5-hydroxyphenylboronic acid | ¹H NMR (400 MHz, DMSO-$d_6$) ppm ppm 10.18-11.44 (m, 2 H), 8.34-8.56 (m, 1 H), 8.11-823 (m, 1 H), 7.80-8.01 (m, 2 H), 7.46-7.70 (m, 1 H), 7.02-8.78 (m, 2 H), 6.83-7.01 (m, 2 H), 6.67-6.79 (m, 1 H), 5.46-6.42 (m, 1 H), 2.90-3.01 (m, 3 H), 2.53-4.30 (m, 6 H), 1.83-2.02 (m, 3 H). UPLC-MS: 5.88 min. 513.1 [M + H]+, method 7 |
| 48 | 3-(1-(4-amino-3-(3-fluoro-5-hydroxyphenyl)-1H-pyrazolo[3,4-d]pyrimidin-1-yl)ethyl)-4-(4-(morpholinomethyl)phenyl)-1H-isochromen-1-one hydrochloride | 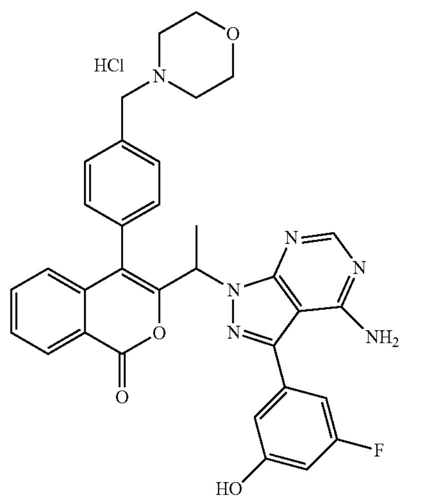 | Int. D5 and 3-fluoro-5-hydroxyphenylboronic acid | ¹H NMR (400 MHz, DMSO-$d_6$) ppm 10.41-10.62 (m, 1 H), 10.14-10.35 (m, 1 H), 8.24 (d, J = 7.94 Hz, 1 H), 8.12 (s, 1 H), 7.44-7.83 (m, 6 H), 7.22 (d, J = 7.94 Hz, 1 H), 6.90 (m, 2 H), 6.83 (d,J = 8.82 Hz, 1 H), 6.68 (d, J = 11.03 Hz, 1 H), 5.74 (d, J = 7.06 Hz, 1 H), 4.39 (br.s., 2 H), 4.01 (d, J = 11.47 Hz, 2 H), 3.75 (m 2 H), 3.05-3.31 (m, 2 H), 1.83 (d, J = 7.06 Hz, 3 H). UPLC-MS; 5.52 min, 631.1 [M + H]+, method 7. |
| 49 | 3-(1-(4-amino-3-(3-fluoro-5-hydroxyphenyl)-1H-pyrazolo[3,4-d]pyrimidin-1-yl)ethyl)-4-(5-(morpholinomethyl)thiophen-2-yl)-1H-isochromen-1-one hydrochloride | 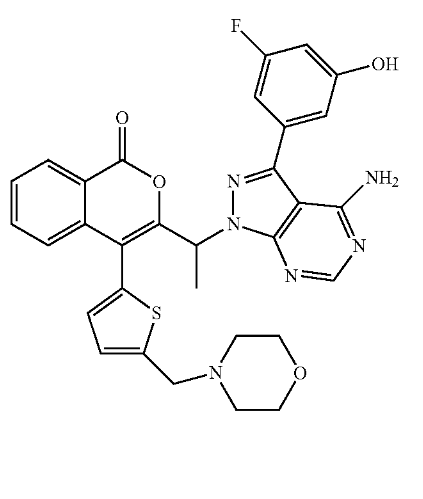 [SMILES: CC(c1oc(=O)c2ccccc2c1-c1ccc(CN2CCOCC2)s1)n1nc(-c2cc(O)cc(F)c2)c2c(N)ncnc21] | Int. D6 and 3-fluoro-5-hydroxyphenylboronic acid | ¹H NMR (400 MHz, DMSO-$d_6$) ppm 10.50-10.68 (m, 1 H), 10.13-10.29 (m, 1 H), 8.22 (s, 1 H), 8.15 (s, 1 H), 7.78-7.89 (m, 1 H), 7.67 (s, 1 H), 7.31-7.45 (m, 1 H), 7.17 (d, J = 8.38 Hz, 3 H), 6.91 (s, 1 H), 6.78-6.86 (m, 1 H), 6.62-6.71 (m, 1 H), 5.85-6.00 (m, 1 H), 4.52-4.71 (m, 2 H), 3.88-4.12 (m, 2 H), 3.64-3.83 (m, 2 H), 3.00-3.21 (m, 4 H), 1.86 (d, J = 7.06 Hz, 3 H). UPLC-MS: 6.31 min, 599.2 [M + H]+, method 7. |

| Ex. | Name | Structure | reagent | UPLC-MS and ¹H-NMR |
|---|---|---|---|---|
| 63 | 3-(1-(4-amino-3-(3-fluoro-5-hydroxyphenyl)-1H-pyrazolo[3,4-d]pyrimidin-1-yl)ethyl)-4-(1-methyl-1,2,5,6-tetrahydropyridin-3-yl)-1H-isochromen-1-one hydrochloride | 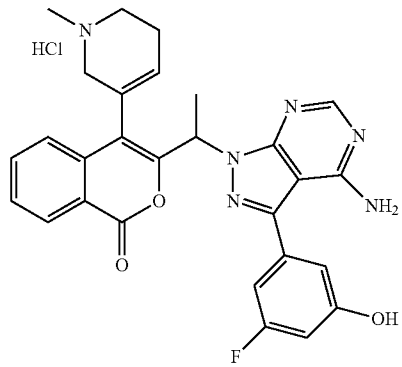 [SMILES: CC(c1oc(=O)c2ccccc2c1C1=CCCN(C)C1)n1nc(-c2cc(O)cc(F)c2)c2c(N)ncnc21 ; Cl] | Int. D7 and 3-fluoro-5-hydroxyphenylboronic acid | ¹H NMR (400 MHz, DMSO-$d_6$) δ ppm 10.17-10.97 (m, 1H), 8.31-8.40 (m, 1H), 8.10-8.24 (m, 1H), 7.79-7.94(m, 1H), 6.62-7.72 (m, 1H), 6.82-7.00 (m, 1H), 6.65-6.75 (m, 1H), 6.14-6.30 (m, 1H), 3.17-4.14 (m, 6H), 2.69-3.06 (m, 4H), 1.74-1.98 (m, 3H). UPLC-MS: 2.30 min, 513.1 [M + H]+, method 6. |
| 111 | 3-(1-(4-amino-3-(1H-pyrazol-3-yl)-1H-pyrazolo[3,4-d]pyrimidin-1-yl)ethyl)-4-phenyl-1H-isochromen-1-one | 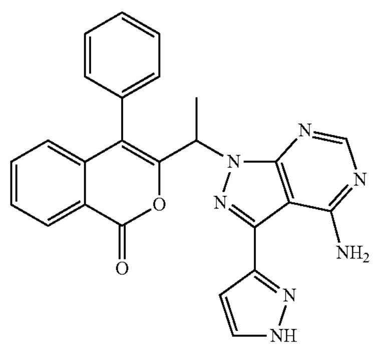 [SMILES: CC(c1oc(=O)c2ccccc2c1-c1ccccc1)n1nc(-c2cc[nH]n2)c2c(N)ncnc21] | Int. D2 and 1H-pyrazol-3-ylboronic acid hydrate | ¹H NMR (400 MHz, DMSO-$d_6$) ppm 13.50 (br.s., 1 H), 10.32 (br.s., 1 H), 8.91 (br.s., 1 H), 8.27 (s, 1 H), 8.22 (d, J = 7.50 Hz, 1 H), 8.00 (s, 1 H), 7.75-7.84 (m, 1 H), 7.61-7.67 (m, 1 H), 7.55 (d, J = 8.82 Hz, 1 H), 7.36-7.50 (m, 3 H), 7.22 (d, J = 7.50 Hz, 1 H), 6.91 (d, J = 7.94 Hz, 1 H), 6.84 (s, 1 H), 5.72 (d, J = 7.06 Hz, 1 H), 1.88 (d, J = 7.50 Hz, 3 H). UPLC-MS: 6.48 min, 450 [M + H]+, method 7 |
| 118 | 3-(1-(4-amino-3-(3-fluoro-5-hydroxyphenyl)-2H-pyrazolo[3,4-d]pyrimidin-2-yl)ethyl)-4-phenyl-1H-isochromen-1-one | 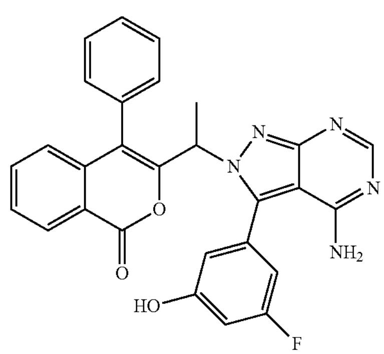 | Int. D2a and 3-fluoro-5-hydroxyphenylboronic acid | ¹H NMR (400 MHz, DMSO-$d_6$) δ ppm 9.97-10.24 (m, 1 H), 8.12-8.30 (m, 1 H), 7.89-8.06 (m, 1 H), 7.49-7.78 (m, 2 H), 7.19-7.40 (m, 3 H), 6.68-6.87 (m, 4 H), 6.50-6.63 (m, 2 H), 4.41-4.67 (m, 1 H), 2.76-2.93 (m, 3 H). UPLC-MS: 4.94 min, 571 [M + H]+, method 7. |
| 119 | 3-(1-(4-amino-3-(3-fluoro-5-hydroxyphenyl)-1H-pyrazolo[3,4-d]pyrimidin-1-yl)ethyl)-4-(3-(dimethylamino)phenyl)-1H-isochromen-1-one | 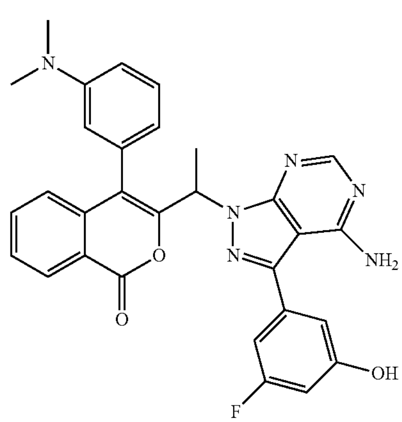 [SMILES: CC(c1oc(=O)c2ccccc2c1-c1cccc(N(C)C)c1)n1nc(-c2cc(O)cc(F)c2)c2c(N)ncnc21] | Int. D16 and 3-fluoro-5-hydroxyphenylboronic acid | ¹H NMR (400 MHz, DMSO-$d_6$) δ ppm ¹H NMR (400 MHz, METHANOL-$d_4$) ppm 8.30 (dd, J = 7.94, 0.88 Hz, 1 H), 6.61-8.09 (m, 14 H), 5.87-6.20 (m, 1 H), 2.93 (s, 3 H), 2.69 (s, 6 H), 1.91 (d, 3 H) UPLC-MS: 6.11 min. 537 [M + H]+, method 7. |

| Ex. | Name | Structure | reagent | UPLC-MS and $^1$H-NMR |
|---|---|---|---|---|
| 120 | 3-(1-(4-amino-3-(3-fluoro-5-hydroxyphenyl)-1H-pyrazolo[3,4-d]pyrimidin-1-yl)ethyl)-4-(thiazol-5-yl)-1H-isochromen-1-one | 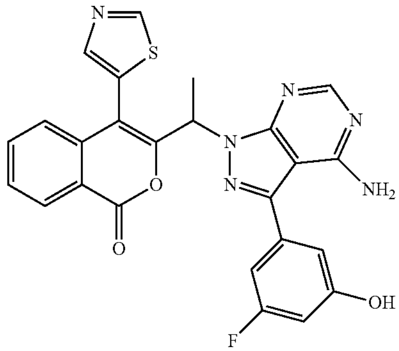 [SMILES: CC(c1oc(=O)c2ccccc2c1-c1cncs1)n1nc(-c2cc(O)cc(F)c2)c2c(N)ncnc21] | Int. D17 and 3-fluoro-5-hydroxyphenylboronic acid | $^1$H NMR (400 MHz, DMSO-d$_6$) δ ppm 10.32 (s, 1 H), 9.40 (s, 1 H), 8.18-8.29 (m, 1 H), 8.14 (s, 1 H), 7.75-7.94 (m, 2 H), 7.59-7.70 (m, 1 H), 7.16-7.51 (m, 2 H), 6.79-7.12 (m, 3 H), 6.56-6.73 (m, 1 H), 5.78-5.96 (m, 1 H), 1.72-1.94 (m, 3 H). UPLC-MS: 4.93 min, 501 [M + H]+, method 7. |
| 125 | 3-(1-(4-amino-3-(3-fluoro-5-hydroxyphenyl)-1H-pyrazolo[3,4-d]pyrimidin-1-yl)ethyl)-4-(4-(piperazin-1-ylmethyl)phenyl)-1H-isochromen-1-one dihydrochloride | 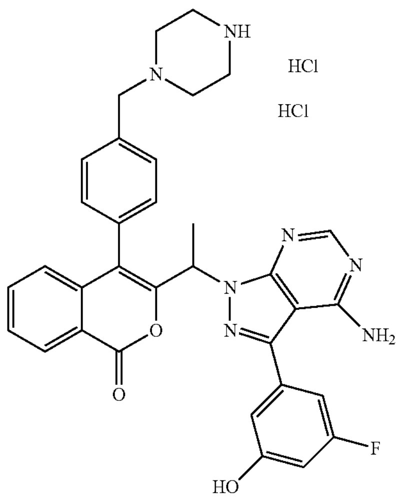 [SMILES: CC(c1oc(=O)c2ccccc2c1-c1ccc(CN2CCNCC2)cc1)n1nc(-c2cc(O)cc(F)c2)c2c(N)ncnc21 ; Cl ; Cl] | Int. D19 and 3-fluoro-5-hydroxyphenylboronic acid | $^1$H NMR (400 MHz, METHANOL-d$_4$) □ ppm 8.34 (s, 1 H), 8.30 (d, J = 7.06 Hz, 1 H), 7.57-7.76 (m, 5 H), 7.52 (d, J = 7.50 Hz, 1 H), 7.39 (d, J = 7.94 Hz, 1 H), 7.01 (d, J = 7.50 Hz, 1 H), 6.88-6.96 (m, 2 H), 6.66-6.77 (m, 1 H), 5.86 (d, J = 7.06 Hz, 1 H), 4.05-4.33 (bs, 2 H), 3.50 (br.s., 4 H), 3.00-3.26 (m, 4 H), 2.00 (d, J = 7.06 Hz, 3 H). UPLC-MS: 5.51 min, 592 [M + H]+, method 7. |

Example 43

3-(1-(1H-pyrazolo[3,4-d]pyrimidin-4-ylamino)ethyl)-4-phenyl-1H-isochromen-1-one

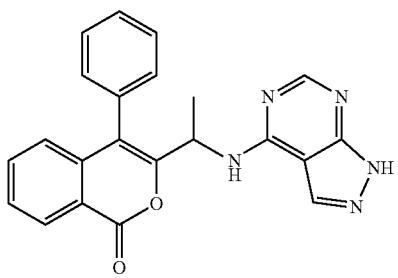

3-(1-aminoethyl)-4-phenyl-1H-isochromen-1-one hydrochloride (Intermediate E1, 141 mg, 0.136 mmol), 4-chloro-1H-pyrazolo[3,4-d]pyrimidine (42.0 mg, 0.272 mmol) and DIEA (95 μL, 0.543 mmol) were stirred at 80° C. for 3 hrs in tert-butanol (800 μL). The reaction was quenched by the addition of 1 mL of 1M HCl$_{aqueous}$ and the resulting crude was straightforward purified via reverse phase chromatography using a Biotage C18 30 g SNAP with a gradient of water and acetonitrile to give the title compound (29 mg, 56%).

$^1$H NMR (400 MHz, DMSO-d$_6$) δ ppm 13.10-13.60 (bs, 1 H), 8.46-8.70 (m, 1 H), 8.15-8.30 (m, 2 H), 8.05-8.13 (m, 1 H), 7.68-7.85 (m, 1 H), 7.47-7.65 (m, 5 H), 7.32-7.43 (m, 1 H), 6.85-7.06 (m, 1 H), 4.92-5.13 (m, 1 H), 1.42-1.63 (m, 3 H). UPLC-MS: 4.69 min, 384.1 [M+H]+, method 3.

Example 44

4-amino-6-(1-(1-oxo-4-phenyl-1H-isochromen-3-yl)ethylamino)pyrimidine-5-carbonitrile

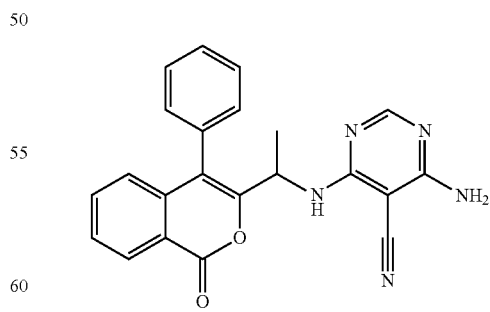

The title compound was made in a similar way as that of the compound of example 43, from (Intermediate E1, 52 mg, 0.172 mmol) and 4-amino-6-chloropyrimidine-5-carbonitrile (53.3 mg, 0.345 mmol), to give the title compound (30 mg, 19.8%).

$^1$H NMR (400 MHz, DMSO-d$_6$) δ ppm 8.17-8.25 (m, 1 H), 7.89 (s, 1 H), 7.72-7.79 (m, 1 H), 7.57-7.63 (m, 1 H), 7.40-7.56 (m, 5 H), 7.31-7.38 (m, 1 H), 7.15-7.27 (m, 2 H), 6.86-6.94 (m, 1 H), 4.79-5.00 (m, 1 H), 1.43 (d, J=7.06 Hz, 3 H). UPLC-MS: 4.88 min, 384.1 [M+H]+, method 3.

Example 45

3-(1-(9H-purin-6-ylamino)ethyl)-4-(1-methyl-1,2,3,6-tetrahydropyridin-4-yl)-1H-isochromen-1-one hydrochloride

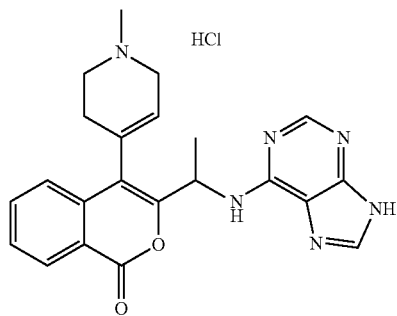

3-(1-bromoethyl)-4-(1-methyl-1,2,3,6-tetrahydropyridin-4-yl)-1H-isochromen-1-one hydrobromide (C21, 100 mg, 0.233 mmol), tert-butyl 9-trityl-9H-purin-6-ylcarbamate (120 mg, 0.251 mmol) and NaH (33.6 mg, 0.699 mmol) were reacted under nitrogen at 65° C. for 2 hrs. The reaction was diluted with 15 mL of EtOAc, washed three times with 10 mL of 0.1M HCl$_{aqueous}$, once with saturated NaCl$_{aqueous}$ and the solvent evaporated to give an oil. The crude was dissolved in TFA/DCM (3 mL+3 mL) and stirred for 3 h at rt and quenched by the addition of 1M HCl$_{aqueous}$ (1 mL). The resulting mixture was straightforward purified via reverse phase chromatography using a Biotage C18 30 g SNAP with a gradient of water and acetonitrile. The combined fractions from flash chromatography were added with 1M HCl$_{aqueous}$ (5 mL) and dried under reduced pressure to give the title compound as a yellow solid (13.6 mg, 13.3% yield) as a yellow solid.

$^1$H NMR (400 MHz, DMSO-d$_6$) δ ppm 10.77 (br. s., 1 H), 8.31-8.55 (m, 2 H), 8.08-8.26 (m, 1 H), 7.72-8.02 (m, 2 H), 7.42-7.72 (m, 2 H), 5.86-6.06 (m, 1 H), 5.53 (br. s., 1 H), 4.00-4.40 (m, 4), 2.48-2.98 (m, 5 H), 1.61 (d, J=7.06 Hz, 3 H). UPLC-MS: 3.89 min, 403.1 [M+H]+, method 7.

Example 46a (Enantiomer 1) and Example 46b (Enantiomer 2)

3-1-(4-amino-3-(3-fluoro-5-hydroxyphenyl)-1H-pyrazolo[3,4-d]pyrimidin-1-yl)ethyl)-4-(1-methyl-1,2,3,6-tetrahydropyridin-4-yl)-1H-isochromen-1-one hydrochloride single enantiomer Racemate 3-(1-(4-amino-3-(3-fluoro-5-hydroxyphenyl)-1H-pyrazolo[3,4-d]pyrimidin-1-yl)ethyl)-4-(1-methyl-1,2,3,6-tetrahydropyridin-4-yl)-1H-isochromen-1-one hydrochloride (example 46, 0.250 g, 0.456 mmol) was dissolved in Ethanol/Methanol 1/1 (18 ml) and submitted to chiral resolution by Chiral preparative chromatography: two methods were identified to obtain each enantiomer respectively and both methods were applied. First method conditions: Column: Chiralpak IA (25×2.0 cm), 5 μm; Mobile phase: n-Hexane/(2-Propanol/Methanol 1/1) 60/40% v/v; Flow rate: 18 ml/min; DAD detection: 220 nm; Loop: 750 μl; Injection: 10 mg/injection. Second method conditions: Column: Whelk 0-1 (25×2.0 cm), 10 μm; Mobile phase: n-Hexane/(2-Propanol/Methanol 1/1) 65/35% v/v; Flow rate: 18 ml/min; DAD detection: 220 nm; Loop: 750 μl; Injection: 10 mg/injection.

The fractions containing the first eluted enantiomer obtained with the first method (second eluted with the second method) were evaporated, 1.25M HCl in MeOH was added and the volatiles were removed under reduced pressure to afford compound 46a (49 mg, 0.089 mmol). Chiral HPLC (Method A3): Rt=6.1 min, ee=93%;

$^1$H NMR (400 MHz, DMSO-d$_6$) δ ppm 10.10-11.00 (m, 2 H), 8.23-8.45 (m, 1 H), 8.10-8.23 (m, 1 H), 7.79-8.01 (m, 2 H), 7.45-7.72 (m, 1 H), 7.02-8.78 (m, 2 H), 6.82-7.01 (m, 2 H), 6.65-6.76 (m, 1 H), 5.43-6.35 (m, 2 H), 2.91-3.04 (m, 3 H), 2.54-4.22 (m, 6 H), 1.82-2.04 (m, 3 H). UPLC-MS: 0.58 min, 513.3 [M+H]+, method 13.

The fractions containing the second eluted enantiomer obtained with the first method (first eluted with the second method) were evaporated, 1.25M HCl in MeOH was added and the volatiles were removed under reduced pressure to afford compound 46b (45 mg, 0.082 mmol). Chiral HPLC (Method A3): Rt=7.7 min, ee>99%;

$^1$H NMR (400 MHz, DMSO-d$_6$) δ ppm 10.08-11.44 (m, 2 H), 8.32-8.56 (m, 1 H), 8.13-8.23 (m, 1 H), 7.80-8.03 (m, 2 H), 7.48-7.74 (m, 1 H), 7.02-8.78 (m, 2 H), 6.84-7.01 (m, 2 H), 6.69-6.79 (m, 1 H), 5.47-6.42 (m, 2 H), 2.90-3.03 (m, 3 H), 2.55-4.29 (m, 6 H), 1.85-2.04 (m, 3 H). UPLC-MS: 0.58 min, 513.3 [M+H]+, method 13.

Example 47

3-(1-(9H-purin-6-ylamino)ethyl)-4-(4-(morpholinomethyl)phenyl)-1H-isochromen-1-one hydrochloride

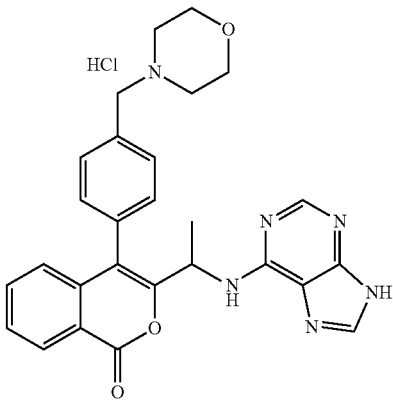

The title compound was made in a similar way as that of the compound of example 21, from 3-(1-bromoethyl)-4-(4-(morpholinomethyl)phenyl)-1H-isochromen-1-one hydrobromide (C22, 100 mg, 0.196 mmol), to give the title compound (5.8 mg, 5.7%).

$^1$H NMR (400 MHz, DMSO-d$_6$) δ ppm 10.43-11.09 (m, 1 H), 8.22 (d, J=7.94 Hz, 3 H), 7.27-7.93 (m, 7 H), 6.95 (d, J=8.38 Hz, 1 H), 4.80-5.18 (m, 1 H), 4.44 (br. s., 2 H), 3.67-4.15 (m, 6 H), 3.18 (m, 2 H), 1.56 (d, J=7.06 Hz, 3 H). UPLC-MS: 5.69 min, 483.1 [M+H]+, method 7.

Example 49a (Enantiomer 1) and Example 49b (Enantiomer 2)

3-(1-(4-amino-3-(3-fluoro-5-hydroxyphenyl)-1H-pyrazolo[3,4-d]pyrimidin-1-yl)ethyl)-4-(5-(morpholinomethyl)thiophen-2-yl)-1H-isochromen-1-one hydrochloride single enantiomer Racemate 3-(1-(4-amino-3-(3-fluoro-5-hydroxyphenyl)-1H-pyrazolo[3,4-d]pyrimidin-1-yl)ethyl)-4-(5-(morpholinomethyl)thiophen-2-yl)-1H-isochromen-1-one hydrochloride (example 49, 0.137 g, 0.21 mmol) was dissolved in Ethanol (7 ml) and submitted to chiral resolution by Chiral preparative chromatography. Conditions: Column: Whelk O-1 (R,R) (25×2.0 cm), 10 μm; Mobile phase: n-Hexane/(Ethanol/Methanol 1/1) 40/60% v/v; Flow rate: 18 ml/min; DAD detection: 220 nm; Loop: 750 μl; Injection: 15 mg (each injection).

The first eluted enantiomer was further purified by Preparative HPLC—Method 4; the residue was treated with 1.25M HCl in MeOH and the volatiles ware removed under vacuum to afford compound 49a (first eluted enantiomer, 27.8 mg, 0.044 mmol). Chiral HPLC (Method A2): Rt=8.2 min, ee=96.8%;

1H NMR (400 MHz, DMSO-d$_6$) δ ppm 11.10 (br. s., 1 H), 10.29 (br. s., 1 H), 8.17-8.27 (m, 2 H), 7.79-7.90 (m, 1 H), 7.65-7.71 (m, 1 H), 7.41-7.49 (m, 1 H), 6.96-7.22 (m, 2H), 6.90-6.94 (m, 1 H), 6.83-6.88 (m, 1 H), 6.74-8.17 (m, 2 H), 6.71 (dt, 1 H), 5.91-5.98 (m, 1 H), 4.62 (br. s., 2 H), 3.60-4.14 (m, 4 H), 3.25-3.43 (m, 2 H), 3.02-3.20 (m, 2 H), 1.87 (d, 3 H). UPLC-MS: 0.63 min, 599.2 [M+H]+, method 13

The fractions containing the second eluted enantiomer were evaporated, 1.25M HCl in MeOH was added and the volatiles were removed under vacuum to afford compound 49b (second eluted enantiomer, 33 mg, 0.052 mmol). Chiral HPLC (Method A2): Rt=9.5 min, ee=98.2%;

1H NMR (400 MHz, DMSO-d6) δ ppm 11.28 (br. s., 1 H), 10.30 (br. s., 1 H), 8.20-8.26 (m, 2 H), 7.79-7.90 (m, 1 H), 7.65-7.71 (m, 1 H), 7.42-7.50 (m, 1 H), 6.96-7.22 (m, 2 H), 6.90-6.94 (m, 1 H), 6.83-6.88 (m, 1 H), 6.74-8.17 (m, 2 H), 6.71 (dt, 1 H), 5.90-5.98 (m, 1 H), 4.61 (br. s., 2 H), 3.41-4.10 (m, 4 H), 3.24-3.42 (m, 2 H), 3.01-3.20 (m, 2 H), 1.87 (d, 3 H). UPLC-MS: 0.65 min, 599.1 [M+H]+, method 12.

Example 50

3-(1-(9H-purin-6-ylamino)ethyl)-4-cyclohexenyl-1H-isochromen-1-one

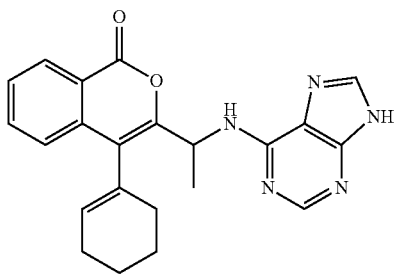 [SMILES: CC(Nc1ncnc2[nH]cnc12)c1oc(=O)c2ccccc2c1C1=CCCCC1]

The title compound was made in a similar way as that of the compound of example 21, from 3-(1-bromoethyl)-4-cyclohexenyl-1H-isochromen-1-one (Intermediate C24, 88 mg, 0.264 mmol), to give the title compound (4.7 mg, 4.6%) as a white solid.

$^1$H NMR (400 MHz, DMSO-d$_6$) δ ppm 12.71-13.16 (bs, 1 H), 8.02-8.29 (m, 3 H), 7.75-7.94 (m, 2 H), 7.31-7.66 (m, 2 H), 5.37-5.93 (m, 2 H), 1.88-2.29 (m, 4 H), 1.64-1.87 (m, 4 H), 1.43-1.61 (m, 3 H). UPLC-MS: 6.34 min, 388.2 [M+H]+, method 7.

Example 51

3-(1-(4-amino-3-(2-aminopyrimidin-5-yl)-1H-pyrazolo[3,4-d]pyrimidin-1-yl)ethyl)-4-phenyl-1H-isochromen-1-one

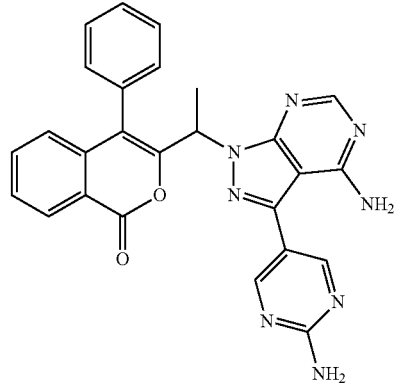 [SMILES: CC(c1oc(=O)c2ccccc2c1-c1ccccc1)n1nc(-c2cnc(N)nc2)c2c(N)ncnc21]

3-(1-(4-amino-3-iodo-1H-pyrazolo[3,4-d]pyrimidin-1-yl)ethyl)-4-phenyl-1H-isochromen-1-one (Intermediate D2a, 60 mg, 0.118 mmol), K$_2$CO$_3$ (32.6 mg, 0.236 mmol), 2-aminopyrimidin-5-ylboronic acid (32.7 mg, 0.236 mmol) and Pd(dppf)Cl$_2$ (4.31 mg, 5.89 μmol) were reacted in 2 ml of dioxane, purged with argon and heated overnight at 120° C. The reaction was quenched by the addition of 1M HCl$_{aqueous}$ (2 ml) and the resulting mixture was straightforward purified via reverse phase chromatography using a Biotage C18 30 g SNAP with a gradient of water and acetonitrile (prior to drying 2 ml of 1M HCl$_{aqueous}$ were added) to give the title compound (16.2 mg, 28.9%) as a yellow solid.

$^1$H NMR (400 MHz, DMSO-d$_6$) δ ppm 8.47 (s, 2 H), 8.22 (s, 2 H), 7.86-8.05 (m, 1 H), 7.77 (m, 1 H), 7.63 (m, 1 H), 7.53 (m, 1 H), 7.42 (m, 3 H), 7.20-7.33 (m, 1 H), 7.06-7.18 (m, 1 H), 6.89 (d, J=7.94 Hz, 1 H), 5.74 (d, J=7.06 Hz, 1 H), 1.85 (d, J=7.06 Hz, 3H). UPLC-MS: 4.56 min, 477.1 [M+H]+, method 7.

Example 52

3-(1-(4-amino-3-(pyrazin-2-yl)-1H-pyrazolo[3,4-d]pyrimidin-1-yl)ethyl)-4-phenyl-1H-isochromen-1-one

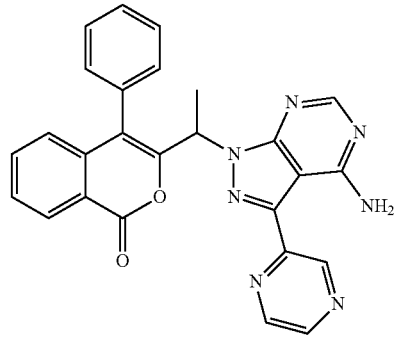 [SMILES: CC(c1oc(=O)c2ccccc2c1-c1ccccc1)n1nc(-c2cnccn2)c2c(N)ncnc21]

3-(1-(4-amino-3-iodo-1H-pyrazolo[3,4-d]pyrimidin-1-yl)ethyl)-4-phenyl-1H-isochromen-1-one (Intermediate D2a, 60 mg, 0.118 mmol), 2-(tributylstannyl)pyrazine (0.072 mL, 0.236 mmol), Pd(PPh$_3$)$_4$, (13.61 mg, 0.012 mmol) and LiCl (4.99 mg, 0.118 mmol) were reacted in dioxane (1.2 mL), purged under argon and heated at 120° C. overnigth. The reaction was quenched by the addition of 1M HCl$_{aqueous}$ (2 ml), and the solids collected by filtration. The solid crude was straightforward purified via reverse phase chromatography using a Biotage C18 30 g SNAP with a gradient of water and acetonitrile (prior to drying 5 mL of 2M HCl$_{aqueous}$ was added). The resulting white solid was triturated in Et$_2$O. to give (13.5 mg, 24.8%) the title compound.

$^1$H NMR (400 MHz, DMSO-d$_6$) δ ppm 9.27-9.50 (m, 1 H), 9.00-9.13 (m, 1 H), 8.75-8.83 (m, 1 H), 8.66-8.75 (m, 1 H), 8.40-8.61 (m, 1 H), 8.18-8.30 (m, 1 H), 7.97-8.15 (m, 2 H), 7.73-7.85 (m, 1 H), 7.35-7.69 (m, 5 H), 7.17-7.31 (m, 1 H), 6.78-6.97 (m, 1 H), 5.66-5.84 (m, 1 H), 1.73-2.00 (m, 3 H). UPLC-MS: 6.04 min, 462.1 [M+H]+, method 7.

Example 53

3-(1-(4-amino-3-(pyridazin-4-yl)-1H-pyrazolo[3,4-d]pyrimidin-1-yl)ethyl)-4-phenyl-1H-isochromen-1-one

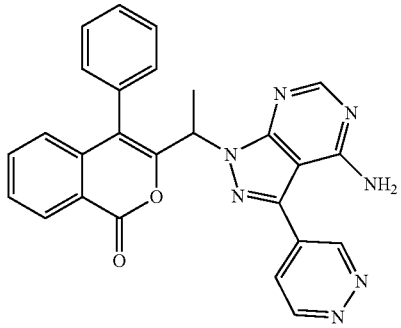 [SMILES: CC(c1oc(=O)c2ccccc2c1-c1ccccc1)n1nc(-c2ccnnc2)c2c(N)ncnc21]

The title compound was made in a similar way as that of the compound of example 52, from 3-(1-(4-amino-3-iodo-1H-pyrazolo[3,4-d]pyrimidin-1-yl)ethyl)-4-phenyl-1H-isochromen-1-one (Intermediate D2a, 60 mg, 0.118 mmol) and 4-(tributylstannyl)pyridazine (87 mg, 0.236 mmol) to give the title compound (34.5 mg, 63.5%).

$^1$H NMR (400 MHz, DMSO-d$_6$) δ ppm 9.46 (dd, J=2.21, 1.32 Hz, 1 H), 9.38 (dd, J=5.51, 1.10 Hz, 1 H), 8.15-8.29 (m, 2 H), 7.91 (dd, J=5.29, 2.65 Hz, 1 H), 7.77 (m, 2 H), 7.63 (m, 1 H), 7.48-7.57 (m, 1 H), 7.35-7.47 (m, 3 H), 7.17 (d, J=7.50 Hz, 1 H), 6.89 (d, J=7.94 Hz, 1 H), 5.80 (d, J=7.06 Hz, 1 H), 1.88 (d, J=7.06 Hz, 3 H). UPLC-MS: 4.80 min, 462.1 [M+H]+, method 7.

Example 54

3-(1-(4-amino-3-(pyridin-4-yl)-1H-pyrazolo[3,4-d]pyrimidin-1-yl)ethyl)-4-phenyl-1H-isochromen-1-one

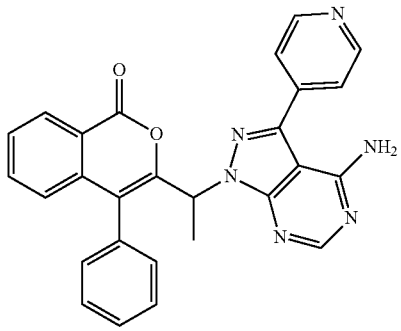 [SMILES: CC(c1oc(=O)c2ccccc2c1-c1ccccc1)n1nc(-c2ccncc2)c2c(N)ncnc21]

The title compound was made in a similar way as that of the compound of example 51, from 3-(1-(4-amino-3-iodo-1H-pyrazolo[3,4-d]pyrimidin-1-yl)ethyl)-4-phenyl-1H-isochromen-1-one (Intermediate D2a, 60 mg, 0.118 mmol), pyridin-4-ylboronic acid (29.0 mg, 0.236 mmol) to give the title compound (10 mg, 18.4%).

$^1$H NMR (400 MHz, DMSO-d$_6$) δ ppm 8.89 (d, J=6.17 Hz, 2 H), 8.21 (s, 2 H), 7.98 (d, J=5.29 Hz, 2 H), 7.70-7.82 (m, 1 H), 7.58-7.66 (m, 1 H), 7.48-7.58 (m, 1 H), 7.34-7.47 (m, 4 H), 7.16 (d, J=7.06 Hz, 1 H), 6.89 (d, J=8.38 Hz, 1 H), 5.70-5.91 (m, 1 H), 1.87 (d, J=7.06 Hz, 3 H). UPLC-MS: 5.34 min, 461.1 [M+H]+, method 7.

Example 55

3-(1-(4-amino-3-(2-methoxypyrimidin-5-yl)-1H-pyrazolo[3,4-d]pyrimidin-1-yl)ethyl)-4-phenyl-1H-isochromen-1-one

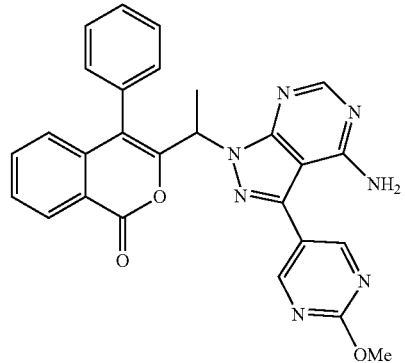 [SMILES: COc1ncc(-c2nn(C(C)c3oc(=O)c4ccccc4c3-c3ccccc3)c3ncnc(N)c23)cn1]

The title compound was made in a similar way as that of the compound of example 51, from 3-(1-(4-amino-3-iodo-1H-pyrazolo[3,4-d]pyrimidin-1-yl)ethyl)-4-phenyl-1H-isochromen-1-one (Intermediate D2a, 60 mg, 0.118 mmol), 2-methoxypyrimidin-5-ylboronic acid (36.3 mg, 0.236 mmol), to give the title compound (36 mg, 62.2%) as a yellowish solid.

$^1$H NMR (400 MHz, DMSO-d$_6$) δ ppm 8.74 (s, 2 H), 8.17-8.27 (m, 1 H), 8.12 (s, 1 H), 7.71-7.83 (m, 1 H), 7.58-7.66 (m, 1 H), 7.49-7.57 (m, 1 H), 7.32-7.48 (m, 3 H), 7.11-7.28 (m, 2 H), 6.74-6.96 (m, 1 H), 5.63-5.82 (m, 1 H), 4.00 (s, 3 H), 1.85 (d, J=7.06 Hz, 3 H). UPLC-MS: 6.20 min, 492.2 [M+H]+, method 7.

Example 56

3-(1-(4-amino-3-(2-hydroxypyrimidin-5-yl)-1H-pyrazolo[3,4-d]pyrimidin-1-yl)ethyl)-4-phenyl-1H-isochromen-1-one

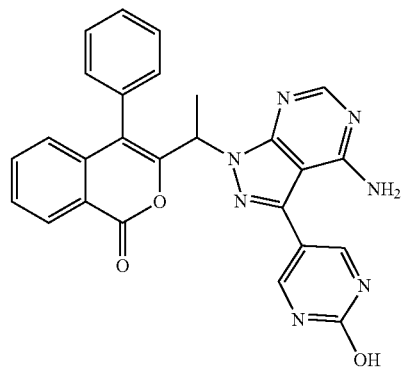 [SMILES: CC(c1oc(=O)c2ccccc2c1-c1ccccc1)n1nc(-c2cnc(O)nc2)c2c(N)ncnc21]

3-(1-(4-amino-3-(2-methoxypyrimidin-5-yl)-1H-pyrazolo[3,4-d]pyrimidin-1-yl)ethyl)-4-phenyl-1H-isochromen-1-one (Example 55, 23.3 mg, 0.047 mmol) was dissolved in HBr 33% in CH₃COOH (1 ml, 0.047 mmol) and stirred at rt for 1 h. The reaction was then diluted with water (3 mL) and the resulting mixture purified via reverse phase chromatography using a Biotage C18 30 g SNAP with a gradient of water and acetonitrile to give the title compound (20 mg, 88%) as a white solid.

¹H NMR (400 MHz, DMSO-d₆) δ ppm 8.29-8.54 (m, 2 H), 8.17-8.26 (m, 1 H), 7.98-8.11 (m, 1 H), 7.72-7.81 (m, 1 H), 7.58-7.66 (m, 1 H), 7.49-7.57 (m, 1 H), 7.33-7.47 (m, 3 H), 7.11-7.23 (m, 3 H), 6.79-6.94 (m, 1 H), 5.27-5.79 (m, 1 H), 1.71-1.87 (m, 3H). UPLC-MS: 4.67 min (40%) and 4.71 min (60%), 478.2 [M+H]+, method 7.

Example 57

3-(1-(4-amino-3-(5-methoxypyridin-3-yl)-1H-pyrazolo[3,4-d]pyrimidin-1-yl)ethyl)-4-phenyl-1H-isochromen-1-one

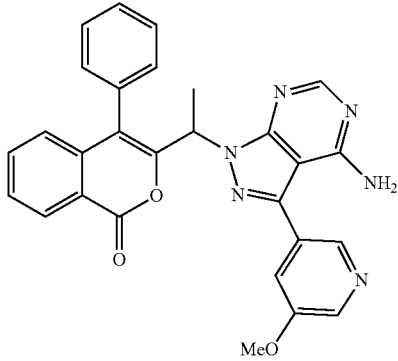 [SMILES: COc1cncc(-c2nn(C(C)c3oc(=O)c4ccccc4c3-c3ccccc3)c3ncnc(N)c23)c1]

The title compound was made in a similar way as that of the compound of example 52, from 3-(1-(4-amino-3-iodo-1H-pyrazolo[3,4-d]pyrimidin-1-yl)ethyl)-4-phenyl-1H-isochromen-1-one (Intermediate D2a, 60 mg, 0.118 mmol) and 3-methoxy-5-(tributylstannyl)pyridine (94 mg, 0.236 mmol) to give the title compound (31.3 mg, 54.2%).

¹H NMR (400 MHz, DMSO-d₆) δ ppm 8.32-8.47 (m, 2 H), 8.18-8.25 (m, 1 H), 8.05-8.16 (m, 1 H), 7.72-7.82 (m, 1 H), 7.32-7.67 (m, 6 H), 7.15-7.23 (m, 1 H), 6.96-7.11 (m, 1 H), 6.81-6.93 (m, 1 H), 5.59-5.83 (m, 1 H), 3.95 (s, 3 H), 1.76-1.92 (m, 3 H).
UPLC-MS: 6.29 min, 491.3 [M+H]+, method 7.

Example 58

3-(1-(4-amino-3-(pyridin-3-yl)-1H-pyrazolo[3,4-d]pyrimidin-1-yl)ethyl)-4-phenyl-1H-isochromen-1-one

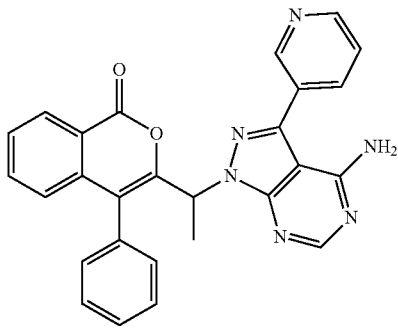 [SMILES: CC(c1oc(=O)c2ccccc2c1-c1ccccc1)n1nc(-c2cccnc2)c2c(N)ncnc21]

The title compound was made in a similar way as that of the compound of example 51, from 3-(1-(4-amino-3-iodo-1H-pyrazolo[3,4-d]pyrimidin-1-yl)ethyl)-4-phenyl-1H-isochromen-1-one (Intermediate D2a, 60 mg, 0.118 mmol), pyridin-3-ylboronic acid (29.0 mg, 0.236 mmol), to give the title compound (42.7 mg, 79%) as yellowish solid.

1H NMR (400 MHz, DMSO-d6) δ ppm 8.94 (s, 1 H), 8.83 (d, J=3.97 Hz, 1 H), 8.17-8.36 (m, 3 H), 7.78 (m, 3 H), 7.63 (t, 1 H), 7.50-7.57 (m, 1 H), 7.35-7.48 (m, 3 H), 7.29 (s, 2 H), 7.04 (m, 1 H), 6.90 (d, J=7.94 Hz, 1 H), 5.80 (d, J=7.06 Hz, 1 H), 1.78-1.95 (m, 3 H). UPLC-MS: 6.06 min, 461.3 [M+H]+, method 7.

Example 59

3-(1-(4-amino-3-(2-aminothiazol-5-yl)-1H-pyrazolo[3,4-d]pyrimidin-1-yl)ethyl)-4-phenyl-1H-isochromen-1-one hydrochloride

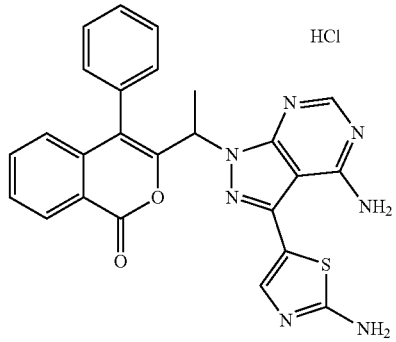 [SMILES: CC(c1oc(=O)c2ccccc2c1-c1ccccc1)n1nc(-c2cnc(N)s2)c2c(N)ncnc21 ; Cl]

The title compound was made in a similar way as that of the compound of example 52, from 3-(1-(4-amino-3-iodo-1H-pyrazolo[3,4-d]pyrimidin-1-yl)ethyl)-4-phenyl-1H-isochromen-1-one (Intermediate D2a, 47.7 mg, 0.094 mmol) and 4-(tributylstannyl)thiazol-2-ylcarbamate (92 mg, 0.187 mmol) to give the title compound (24 mg, 49.5%).

¹H NMR (400 MHz, DMSO-d₆) δ ppm 8.78-9.18 (m, 1 H), 8.13-8.27 (m, 2 H), 7.71-8.04 (m, 2 H), 7.59-7.69 (m, 1 H), 7.50-7.58 (m, 2 H), 7.36-7.49 (m, 3 H), 7.15 (d, J=7.50 Hz, 1 H), 6.90 (d, J=7.94 Hz, 1 H), 5.70 (d, J=7.06 Hz, 1 H), 1.82 (d, J=7.06 Hz, 3H). UPLC-MS: 5.84 min, 482.1 [M+H]+, method 7.

Example 60

3-(1-(4-amino-3-(6-methoxypyridin-3-yl)-1H-pyrazolo[3,4-d]pyrimidin-1-yl)ethyl)-4-phenyl-1H-isochromen-1-one

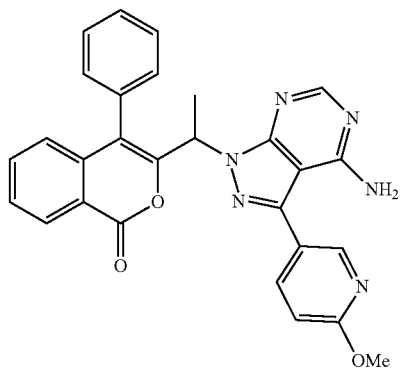 [SMILES: COc1ccc(-c2nn(C(C)c3oc(=O)c4ccccc4c3-c3ccccc3)c3ncnc(N)c23)cn1]

The title compound was made in a similar way as that of the compound of example 52, from 3-(1-(4-amino-3-iodo-1H-pyrazolo[3,4-d]pyrimidin-1-yl)ethyl)-4-phenyl-1H-isochromen-1-one (Intermediate D2a, 60 mg, 0.118 mmol) and 2-methoxy-5-(tributylstannyl)pyridine (94 mg, 0.236 mmol) to give the title compound (35.1 mg, 60.7%).

$^1$H NMR (400 MHz, DMSO-$d_6$) δ ppm 8.30-8.44 (m, 1 H), 8.07-8.24 (m, 2 H), 7.85-7.99 (m, 1 H), 7.71-7.82 (m, 1 H), 7.51-7.66 (m, 3 H), 7.28-7.48 (m, 4 H), 7.09-7.23 (m, 1 H), 6.80-7.05 (m, 2 H), 5.47-5.80 (m, 1 H), 3.93 (s, 3 H), 1.85 (d, J=7.50 Hz, 3 H). UPLC-MS: 6.44 min, 491.2 [M+H]+, method 7.

Example 61

3-(1-(4-amino-3-(6-hydroxypyridin-3-yl)-1H-pyrazolo[3,4-d]pyrimidin-1-yl)ethyl)-4-phenyl-1H-isochromen-1-one

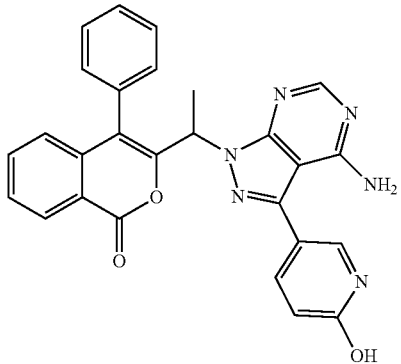 [SMILES: CC(c1oc(=O)c2ccccc2c1-c1ccccc1)n1nc(-c2ccc(O)nc2)c2c(N)ncnc21]

3-(1-(4-amino-3-(6-methoxypyridin-3-yl)-1H-pyrazolo[3,4-d]pyrimidin-1-yl)ethyl)-4-phenyl-1H-isochromen-1-one (Example 60, 28 mg, 0.057 mmol) was dissolved in HBr 33% in CH$_3$COOH (2 ml, 36.8 mmol) and stirred at 60° C. for 4 hr. The reaction was then diluted with 3 ml of water and the resulting mixture purified via reverse phase chromatography using a Biotage C18 30 g SNAP with a gradient of water and acetonitrile to give the title compound (6.9 mg, 25.4%) as yellowish solid.

$^1$H NMR (400 MHz, DMSO-$d_6$) δ ppm 8.11-8.30 (m, 2 H), 7.77 (t, J=7.06 Hz, 2 H), 7.32-7.68 (m, 8 H), 7.14 (d, J=7.50 Hz, 1 H), 6.89 (d, J=7.94 Hz, 1 H), 6.48 (d, J=9.70 Hz, 1 H), 5.72 (d, J=7.06 Hz, 1 H), 1.84 (d, J=7.06 Hz, 3 H). UPLC-MS: 5.18 min, 477.2 [M+H]+, method 7.

Example 62

N-(5-(4-amino-1-(1-(1-oxo-4-phenyl-1H-isochromen-3-yl)ethyl)-1H-pyrazolo[3,4-d]pyrimidin-3-yl)thiazol-2-yl)acetamide

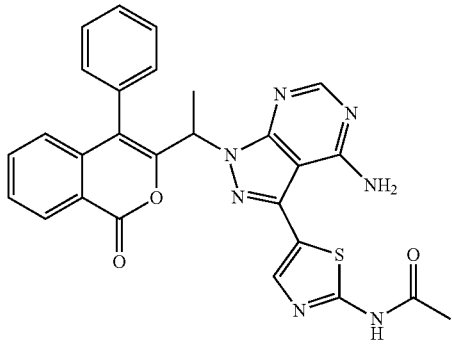 [SMILES: CC(=O)Nc1ncc(-c2nn(C(C)c3oc(=O)c4ccccc4c3-c3ccccc3)c3ncnc(N)c23)s1]

3-(1-(4-amino-3-(2-aminothiazol-5-yl)-1H-pyrazolo[3,4-d]pyrimidin-1-yl)ethyl)-4-phenyl-1H-isochromen-1-one hydrochloride (Example 59, 23 mg, 0.044 mmol) was dissolved in TEA (124 µL, 0.888 mmol)/Ac$_2$O (419 µL, 4.44 mmol) and stirred at rt for 1 h. The reaction mixture was quenched by the addition of 1M HCl (1 ml) and purified via reverse phase chromatography using a Biotage C18 30 g SNAP with a gradient of water and acetonitrile to give the title compound (2.3 mg, 9.9%) as yellowish solid.

1H NMR (400 MHz, DMSO-d6) δ ppm 8.16-8.20 (d, 1 H, J=8.0 Hz), 8.04 (s, 1 H), 7.73 (d, 2H, J=8.0 Hz), 7.73 (d, 1H, J=8.0 Hz), 7.54-7.58 (m, 2H), 7.33-7.44 (m, 5H), 6.83-6.89 (m, 1H), 5.65 (q, 1H, J=8.0 Hz), 2.14 (s, 3H), 1.79 (d, 3H, J=8.0 Hz). UPLC-MS: 3.81 min, 524.1 [M+H]+, method 6.

Example 64

3-(1-(4-amino-3-(3-fluoro-5-hydroxyphenyl)-1H-pyrazolo[3,4-d]pyrimidin-1-yl)ethyl)-4-(1,2,3,6-tetrahydropyridin-4-yl)-1H-isochromen-1-one hydrochloride

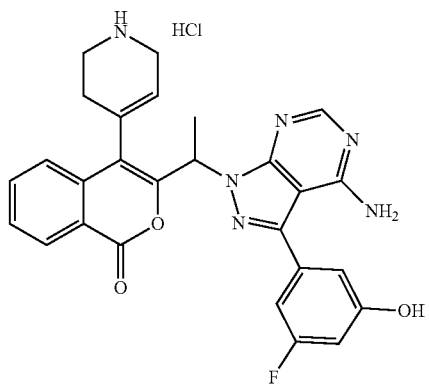 [SMILES: Cl ; CC(c1oc(=O)c2ccccc2c1C1=CCNCC1)n1nc(-c2cc(O)cc(F)c2)c2c(N)ncnc21]

Step 1. 4-(3-(1-(4-amino-3-iodo-1H-pyrazolo[3,4-d]pyrimidin-1-yl)ethyl)-1-oxo-1H-isochromen-4-yl)-5,6-dihydropyridine-1(2H)-carboxylate

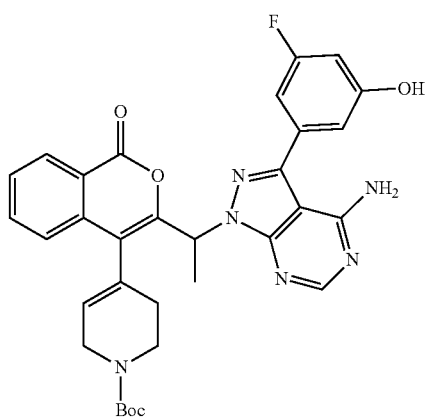 [SMILES: CC(c1oc(=O)c2ccccc2c1C1=CCN(C(=O)OC(C)(C)C)CC1)n1nc(-c2cc(O)cc(F)c2)c2c(N)ncnc21]

Tert-butyl 4-(3-(1-(4-amino-3-iodo-1H-pyrazolo[3,4-d]pyrimidin-1-yl)ethyl)-1-oxo-1H-isochromen-4-yl)-5,6-dihydropyridine-1(2H)-carboxylate (Intermediate D14, 120 mg, 0.195 mmol), 3-fluoro-5-hydroxyphenylboronic acid (67.0 mg, 0.430 mmol), Pd(dppf)Cl₂ (21.44 mg, 0.029 mmol) and K₂CO₃ (59.4 mg, 0.430 mmol) were reacted in 3.2 mL of dioxane under argon at 120° C. overnight. The reaction mixture was diluted with AcOEt (100 mL) and washed with 0.5M HCl_aqueous (100 ml), washed with saturated NaCl_aqueous, anhydrified over Na₂SO₄ and evaporate to dryness. The crude was purified via flash chromatography on silica gel using a Biotage 25G SNAP with a gradient of heptane and AcOEt to give 4-(3-(1-(4-amino-3-iodo-1H-pyrazolo[3,4-d]pyrimidin-1-yl)ethyl)-1-oxo-1H-isochromen-4-yl)-5,6-dihydropyridine-1(2H)-carboxylate (83 mg, 71%) as solid.

UPLC-MS: 1.19 min, 599.0 [M+H]+, method 9

Step 2

A solution of 4-(3-(1-(4-amino-3-iodo-1H-pyrazolo[3,4-d]pyrimidin-1-yl)ethyl)-1-oxo-1H-isochromen-4-yl)-5,6-dihydropyridine-1(2H)-carboxylate (150 mg, 0.244 mmol) in of dioxane (2.4 ml) and 4M HCl in dioxane (2.4 ml) were reacted at rt for 3 h, then Et₂O was added and the yellowish precipitate was collected by filtration to afford the title compound (135 mg, 99%).

¹H NMR (400 MHz, DMSO-d₆) δ ppm 10.13-10.36 (bs, 1 H), 8.96-9.35 (bs, 2 H), 8.38 (s, 1 H), 8.29 (s, 1 H), 8.08-8.21 (m, 1 H), 7.83-7.96 (m, 1 H), 7.66 (m, 2 H), 6.95 (m, 2 H), 6.62-6.75 (m, 1 H), 6.18 (m, 1 H), 6.01-6.09 (m, 1 H), 3.66-3.83 (m, 2 H), 2.96-3.38 (m, 2 H), 2.56-2.74 (m, 2 H), 1.79-2.00 (d, 3 H). UPLC-MS: 2.17 min, 499.0 [M+H]+, method 6

Example 65

3-(1-(4-amino-3-(3-fluoro-5-hydroxyphenyl)-1H-pyrazolo[3,4-d]pyrimidin-1-yl)ethyl)-4-(1-(pyridin-4-ylmethyl)-1,2,3,6-tetrahydropyridin-4-yl)-1H-isochromen-1-one hydrochloride

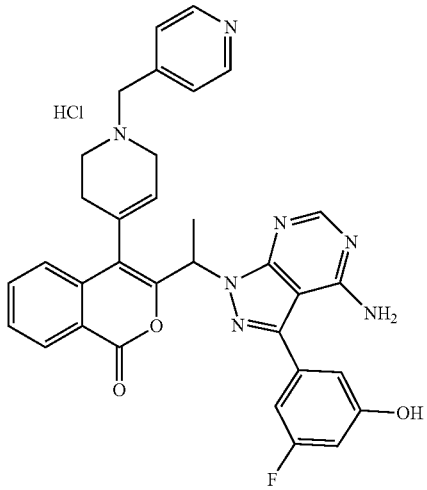 [SMILES: CC(c1oc(=O)c2ccccc2c1C1=CCN(Cc2ccncc2)CC1)n1nc(-c2cc(O)cc(F)c2)c2c(N)ncnc21 ; Cl]

3-(1-(4-amino-3-(3-fluoro-5-hydroxyphenyl)-1H-pyrazolo[3,4-d]pyrimidin-1-yl)ethyl)-4-(1,2,3,6-tetrahydropyridin-4-yl)-1H-isochromen-1-one hydrochloride (example 64, 37 mg, 0.064 mmol), isonicotinaldehyde (8.89 mg, 0.083 mmol) and DIEA (11.15 μl, 0.064 mmol) were dissolved in DCM (1.23 ml) followed by a spatula tip of anhydrous Na₂SO₄, and the mixture stirred rt for 10 min prior to add AcOH (10.97 μl, 0.192 mmol) and NaBH(OAc)₃ (27.1 mg, 0.128 mmol). The resulting mixture was stirred for 1 h at rt, then quenched with 2M HCl_aqueous (1 ml), filtered to remove insoluble materials, and the filtrate purified via reverse phase chromatography using a Biotage C18 60 g SNAP with a gradient of water and acetonitrile to give (prior to drying a small amount of 1M HClaqueous was added) the title compound (10.6 mg, 26.5%) as white solid.

1H NMR (400 MHz, DMSO-d6) δ ppm 11.56-11.67 (m, br 1H), 10.20-10.34 (m, br 1H), 8.78-8.82 (m, 2H), 8.10-8.30 (m, 2H), 7.74-8.00 (m, 3H), 7.48-7.68 (m, 2H), 6.82-6.97 (m, 2H), 6.67-7.73 (m, 1H), 6.15-7.73 (m, 1H), 6.15-6.35 (m, 1H), 5.97-6.10 (m, 1H), 4.50-4.68 (m, 2H), 3.90-3.97 (m, 3H), 3.35-3.50 (m, 2H), 3.04-3.27 (m, 1H), 2.52-2.68 (m, 1H), 1.81-1.99 (m, 3H). UPLC-MS: 2.34 min, 590.0 [M+H]+, method 6.

Example 66

3-(1-(4-amino-3-(3-fluoro-5-hydroxyphenyl)-1H-pyrazolo[3,4-d]pyrimidin-1-yl)ethyl)-4-(1-(cyclopropylmethyl)-1,2,3,6-tetrahydropyridin-4-yl)-1H-isochromen-1-one hydrochloride

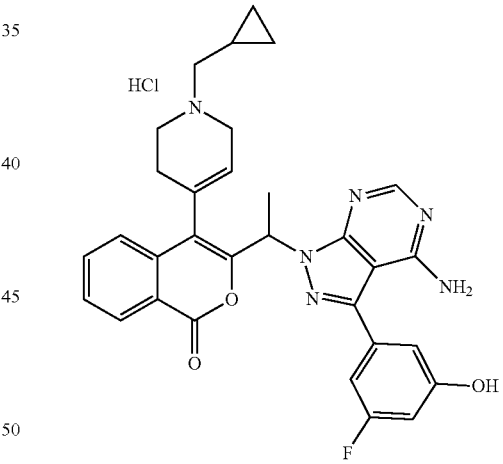

The title compound was made in a similar way as that of the compound of example 65, from 3-(1-(4-amino-3-(3-fluoro-5-hydroxyphenyl)-1H-pyrazolo[3,4-d]pyrimidin-1-yl) ethyl)-4-(1,2,3,6-tetrahydropyridin-4-yl)-1H-isochromen-1-one hydrochloride (example 64, 50 mg, 0.086 mmol) and cyclopropanecarbaldehyde (7.26 mg, 0.104 mmol) to give the title compound (28 mg, 55.1% yield) as a white solid.

1H NMR (400 MHz, DMSO-d6) δ ppm 10.09-10.51 (m, 2H br), 8.27-8.43 (m, 1H), 8.12-8.26 (m, 1H) 7.80-7.95 (m, 1H), 7.61-7.70 (m, 1H), 6.82-6.98 (m, 2H), 6.64-6.73 (m, 1H), 6.04-6.30 (m, 2H), 3.85-4.17 (m, 3H), 3.71-3.82 (m, 1H), 3.23-3.33 (m, 1H), 3.08-3.22 (m, 2H), 2.71-2.96 (m, 2H), 2.52-2.65 (m, 1H), 1.82-2.04 (m, 3H), 1.17-1.27 (m,

Example 67

3-(1-(4-amino-3-(3-fluoro-5-hydroxyphenyl)-1H-pyrazolo[3,4-d]pyrimidin-1-yl)ethyl)-4-(3-((dimethylamino)methyl)phenyl)-1H-isochromen-1-one hydrochloride

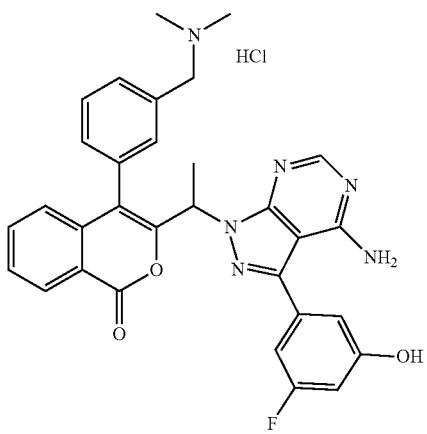 [SMILES: CC(c1oc(=O)c2ccccc2c1-c1cccc(CN(C)C)c1)n1nc(-c2cc(O)cc(F)c2)c2c(N)ncnc21 ; Cl]

3-(3-(1-(4-amino-3-(3-fluoro-5-hydroxyphenyl)-1H-pyrazolo[3,4-d]pyrimidin-1-yl)ethyl)-1-oxo-1H-isochromen-4-yl)benzaldehyde (Intermediate F2, 598 mg, 1.147 mmol), AcOH (131 µl, 2.293 mmol) and 2M dimethylamine (1.15 ml) solution in THF were dissolved in DCM (23 ml) followed by a spoon of anhydrous $Na_2SO_4$, and the mixture stirred rt for 15 min prior to add $NaB(OAc)_3H$ (1215 mg, 5.73 mmol). The resulting mixture was stirred at rt until complete conversion, then quenched with 1M $HCl_{aqueous}$ (5 ml), filtered to remove insoluble materials, and the filtrate purified via reverse phase chromatography using a Biotage C18 60 g SNAP with a gradient of water and acetonitrile to give (prior to drying a small amount of 1M HCl aqueous was added) the title compound (460 mg, 68.3% yield) as white solid.

1H NMR (400 MHz, DMSO-d6) d ppm 10.74 (br. s., 1 H), 10.59 (br. s., 1 H), 10.31 (br. s., 2 H), 8.33 (s, 1 H), 8.19-8.29 (m, 3 H), 7.48-7.85 (m, 11 H), 7.41 (t, J=7.50 Hz, 1 H), 7.04 (d, J=7.94 Hz, 1 H), 6.78-6.97 (m, 6 H), 6.66-6.77 (m, 2 H), 5.85 (q, J=7.06 Hz, 1 H), 5.60-5.75 (m, 1 H), 4.07-4.44 (m, 4 H), 2.78 (t, J=4.41 Hz, 6 H), 2.72 (d, J=4.85 Hz, 3 H), 2.65 (d, J=4.85 Hz, 3 H), 1.77-1.94 (m, 6 H). UPLC-MS: 2.52 min, 551.1 [M+11]+, method 6.

Example 67a (Enantiomer 1) and Example 67b (Enantiomer 2)

3-(1-(4-amino-3-(3-fluoro-5-hydroxyphenyl)-1H-pyrazolo[3,4-d]pyrimidin-1-yl)ethyl)-4-(3-((dimethylamino)methyl)phenyl)-1H-isochromen-1-one Racemate 3-(1-(4-amino-3-(3-fluoro-5-hydroxyphenyl)-1H-pyrazolo[3,4-d]pyrimidin-1-yl)ethyl)-4-(3-((dimethylamino)methyl)phenyl)-1H-isochromen-1-one hydrochloride (example 67, 0.558 g, 0.95 mmol) was dissolved in 10 ml of Ethanol and submitted to chiral resolution by Chiral preparative chromatography. Conditions: Column: Chiralpak AD-H (25×3 cm), 5 um; Mobile phase: n-Hexane/(Ethanol+ 0.1% isopropylamine) 75/25% v/v; Flow rate: 32 ml/min; DAD detection: 220 nm; Loop: 540 µl; Injection: 30 mg (each injection).

The fractions containing the first eluted enantiomer were evaporated to dryness to afford compound 67a (0.214 g, 0.39 mmol). Chiral HPLC (Method A12): Rt=7.1 min, ee>99%.

$^1$H NMR (500 MHz, DMSO-d6) δ ppm 10.19 (s, 1 H), 8.18-8.29 (m, 1 H), 8.03-8.12 (m, 1 H), 7.72-7.83 (m, 1 H), 7.57-7.68 (m, 1 H), 7.22-7.52 (m, 4 H), 6.75-7.01 (m, 5 H), 6.66 (d, 1 H), 5.64-5.80 (m, 1 H), 3.06-3.57 (m, 2 H), 1.93-2.28 (m, 6 H), 1.81 (d, 3 H). UPLC-MS: 0.63-0.065 min, 551.4 [M+H]+, method 13.

The fractions containing the second eluted enantiomer were evaporated to dryness to afford compound 67b (second eluted enantiomer, 0.200 g, 0.37 mmol). Chiral HPLC (Method A12): Rt=11.0 min, ee=98.4%.

$^1$H NMR (500 MHz, DMSO-d6) δ ppm 10.19 (s, 1 H), 8.18-8.29 (m, 1 H), 8.03-8.12 (m, 1 H), 7.72-7.83 (m, 1 H), 7.57-7.68 (m, 1 H), 7.22-7.52 (m, 4 H), 6.75-7.01 (m, 5H), 6.66 (d, 1 H), 5.64-5.80 (m, 1 H), 3.06-3.57 (m, 2 H), 1.93-2.28 (m, 6 H), 1.81 (d, 3 H). UPLC-MS: 0.62-0.65 min, 551.4 [M+H]+, method 13.

Example 68

3-(1-(4-amino-3-(3-fluoro-5-hydroxyphenyl)-1H-pyrazolo[3,4-d]pyrimidin-1-yl)ethyl)-4-(5-(piperidin-1-ylmethyl)thiophen-2-yl)-1H-isochromen-1-one hydrochloride

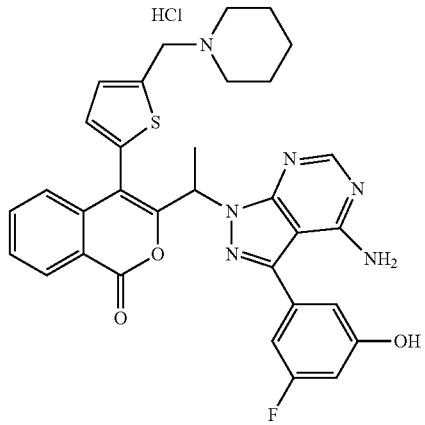 [SMILES: CC(c1oc(=O)c2ccccc2c1-c1ccc(CN2CCCCC2)s1)n1nc(-c2cc(O)cc(F)c2)c2c(N)ncnc21 ; Cl]

3-(1-(4-amino-3-iodo-1H-pyrazolo[3,4-d]pyrimidin-1-yl)ethyl)-4-(5-(piperidin-1-ylmethyl)thiophen-2-yl)-1H-isochromen-1-one hydrochloride (Intermediate D9, 100 mg, 0.154 mmol), 3-fluoro-5-hydroxyphenylboronic acid (48.1 mg, 0.308 mmol), S-Phos-Pd-G2 (11.10 mg, 0.015 mmol) and $K_3PO_4$ (151 mg, 0.462 mmol) were reacted in THF (1.2 ml) and water (0.3 ml) under argon at 80° C. under mw irradiation for 30 min The reaction was quenched by the addition of 1M $HCl_{aqueous}$ (2 ml) and the mixture purified via reverse phase chromatography using a Biotage C18 60 g SNAP with a gradient of water and acetonitrile to give (prior to drying a small amount of 1M HCl aqueous was added) the title compound (70 mg, 71.7% yield) as yellowish solid.

¹H NMR (400 MHz, DMSO-d₆) δ ppm 10.11-10.46 (bs, 2 H), 8.15-8.31 (m, 2 H), 7.77-8.03 (m, 1 H), 7.67 (t, J=7.50 Hz, 1 H), 7.43 (br. s., 1 H), 7.18 (d, J=7.94 Hz, 2 H), 6.92 (s, 1 H), 6.85 (d, J=8.82 Hz, 1 H), 6.70 (d, J=11.03 Hz, 1 H), 5.94 (d, J=7.06 Hz, 1 H), 4.53 (d, J=3.53 Hz, 2 H), 3.38 (m, H), 2.87 (d, J=11.47 Hz, 2 H), 1.61-1.99 (m, 8 H), 1.37 (d, J=11.91 Hz, 1 H). UPLC-MS: 2.82 min, 597.0 [M+H]+, method 6.

Example 68a (Enantiomer 1) and Example 68b (Enantiomer 2)

3-(1-(4-amino-3-(3-fluoro-5-hydroxyphenyl)-1H-pyrazolo[3,4-d]pyrimidin-1-yl)ethyl)-4-(5-(piperidin-1-ylmethyl)thiophen-2-yl)-1H-isochromen-1-one hydrochloride single enantiomers Racemate 3-(1-(4-amino-3-(3-fluoro-5-hydroxyphenyl)-1H-pyrazolo[3,4-d]pyrimidin-1-yl)ethyl)-4-(5-(piperidin-1-ylmethyl)thiophen-2-yl)-1H-isochromen-1-one hydrochloride (example 68, 0.053 g, 0.0837 mmol) was dissolved in 3.5 ml of Ethanol and submitted to chiral resolution by Chiral preparative chromatography. Conditions: Column: Whelk O-1 (R,R) (25×2 cm), 10 um; Mobile phase: n-Hexane/(Ethanol+0.1% isopopylamine) 55/45% v/v; Flow rate: 14 ml/min; DAD detection: 220 nm; Loop: 500 μl; Injection: 7.5 mg (each injection).

The fractions containing the first eluted enantiomer were evaporated to dryness, 1M HCl was added and volatiles were removed under reduced pressure. The residue was purified by reverse phase flash chromatography on C18 cartridge (H2O:CH₃CN=95:5 to 50:50, with 0.1% HCOOH); before drying 2 mL of 1N HCl were added and the volatiles were removed under reduced pressure to afford compound 68a as a white solid (first eluted enantiomer, 0.0149 g, 0.0235 mmol). Chiral HPLC (Method A14): Rt=8.4 min, ee=99%.

¹H NMR (400 MHz, DMSO-d₆) δ ppm 10.21-10.48 (m, 2 H), 8.20-8.29 (m, 2 H), 7.82-7.90 (m, 1 H), 7.65-7.72 (m, 1 H), 7.41-7.48 (m, 1 H), 7.00-7.33 (m, 2 H), 6.90-6.95 (m, 1 H), 6.83-6.89 (m, 1 H), 6.71 (dt, 1 H), 6.65-8.50 (m, 2 H), 5.91-5.99 (m, 1H), 4.49-4.61 (m, 2 H), 3.26-3.88 (m, 2 H), 2.80-2.96 (m, 2 H), 1.66-1.93 (m, 8 H), 1.30-1.47 (m, 1 H). UPLC-MS: 0.68 min, 597.5 [M+H]+, method 13.

The fractions containing the second eluted enantiomer were evaporated to dryness, 1M HCl was added and the volatiles were removed under reduced pressure. The residue was purified by reverse phase flash chromatography on C18 cartridge (H₂O:CH₃CN=95:5 to 50:50, with 0.1% HCOOH); before drying 2 ml of 1N HCl were added and the volatiles were removed under reduced pressure to afford compound 68b as a white solid (second eluted enantiomer, 0.013 g, 0.02 mmol). Chiral HPLC (Method A14): Rt=10.1 min, ee=97.8%.

¹H NMR (400 MHz, DMSO-d₆) δ ppm 10.21-10.62 (m, 2 H), 8.20-8.30 (m, 2 H), 7.82-7.90 (m, 1 H), 7.65-7.72 (m, 1 H), 7.40-7.50 (m, 1 H), 7.00-7.33 (m, 2 H), 6.90-6.95 (m, 1 H), 6.83-6.89 (m, 1 H), 6.71 (dt, 1 H), 6.65-8.50 (m, 2 H), 5.91-5.99 (m, 1 H), 4.48-4.61 (m, 2 H), 3.24-4.00 (m, 2 H), 2.80-2.96 (m, 2 H), 1.66-1.94 (m, 8 H), 1.30-1.47 (m, 1 H). UPLC-MS: 0.67 min, 597.5 [M+H]+, method 13.

Examples 69-71, 85-86, 93-102, 113-114, 121, 128-129, 131-132, 146-149, 152-153, 159-160 found in the table below may be prepared starting from suitable reagents reported below following similar procedures as for compound 68.

The procedures for Examples 99, 101, 159 and 160 required a further deprotection step consisting of a reaction in dry dichloromethane (5 ml) with a molar excess of 1 M boron tribromide in DCM at room temperature, followed by quenching with EtOH at 0° C. and finally a suitable chromoatographic purification step.

| Ex. | Name | Structure | Reagents | UPLC-MS and ¹H NMR |
|---|---|---|---|---|
| 69 | 3-(1-(4-amino-3-(3-fluoro-5-hydroxyphenyl)-1H-pyrazolo[3,4-d]pyrimidin-1-yl)ethyl)-4-(4-(4-methylpiperazine-1-carbonyl)phenyl)-1H-isochromen-1-one hydrochloride | 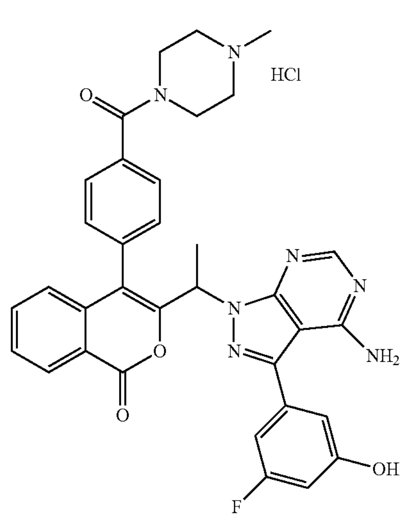 [SMILES: CC(c1oc(=O)c2ccccc2c1-c1ccc(C(=O)N2CCN(C)CC2)cc1)n1nc(-c2cc(O)cc(F)c2)c2c(N)ncnc21 ; Cl] | D10, and 3-fluoro-5-hydroxyphenylboronic acid | ¹H NMR (400 MHz, DMSO-d₆) δ ppm 10.60-10.87 (vs, 1 H), 9.95-10.31 (bs, 1 H), 8.21 (d, J = 7.94 Hz, 1 H), 8.14 (s, 1 H), 7.69-7.79 (m, 1 H), 7.50-7.67 (m, 3 H), 7.42 (d, J = 7.50 Hz, 1 H), 7.14 (d, J = 7.94 Hz, 1 H), 6.86-6.95 (m, 2 H), 6.81 (d, J = 8.82 Hz, 1 H), 6.67 (d, J = 10.58 Hz, 1 H), 5.75 (d, J = 7.06 Hz, 1 H), 3.43 (m, 5 H), 2.91-3.17 (m, 3 H), 2.79 (s, 3 H), 1.81 (d, J = 7.06 Hz, 3 H). UPLC-MS: 2.54 min, 620.0 [M + H]+, method 6. |

| Ex. | Name | Structure | Reagents | UPLC-MS and ¹H NMR |
|---|---|---|---|---|
| 70 | 3-(3-(1-(4-amino-3-(3-fluoro-5-hydroxyphenyl)-1H-pyrazolo[3,4-d]pyrimidin-1-yl)ethyl)-1-oxo-1H-isochromen-4-yl)-N-(2-(dimethylamino)ethyl)benzamide hydrochloride | 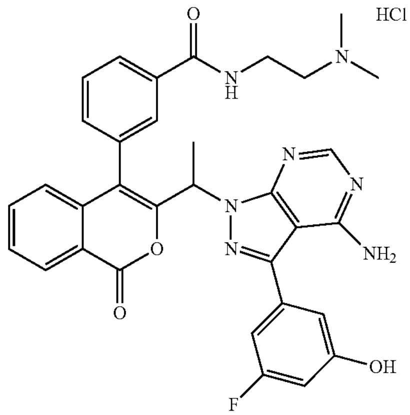 [SMILES: CC(c1oc(=O)c2ccccc2c1-c1cccc(C(=O)NCCN(C)C)c1)n1nc(-c2cc(O)cc(F)c2)c2c(N)ncnc21 ; Cl] | D11, and 3-fluoro-5-hydroxy-phenyl-boronic acid | ¹H NMR (400 MHz, DMSO-$d_6$) δ ppm 10.12-10.54 (bs, 2 H), 9.97 (bs, 2 H), 8.89 (s, 1 H), 8.66 (s, 1 H), 8.25 (dd, J = 7.72, 3.75 Hz, 2 H), 8.21 (s, 1 H), 8.11 (s, 1 H), 7.99 (d, J = 7.50 Hz, 2 H), 7.93 (s, 1 H), 7.73-7.82 (m, 2 H), 7.59-7.71 (m, 4 H), 7.50 (t, 1 H), 7.33 (s, 1 H), 7.29 (m, 1 H), 6.79-6.94 (m, 6 H), 6.70 (dd, J = 11.03, 1.76 Hz, 2 H), 5.72 (d, J = 7.06 Hz, 2 H), 3.66 (m, 4 H), 3.18-3.32 (m, 4 H), 2.84 (t, J = 4.19 Hz, 12 H), 1.85 (dd, J = 15.44, 7.06 Hz, 6 H). UPLC-MS: 2.54 min, 608.1 [M + H]+, method 6. |
| 71 | 4-(1-acetyl-1,2,3,6-tetrahydropyridin-4-yl)-3-(1-(4-amino-3-(5-hydroxypyridin-3-yl)-1H-pyrazolo[3,4-d]pyrimidin-1-yl)ethyl)-1H-isochromen-1-one | 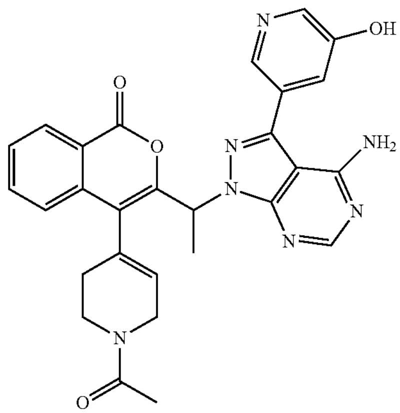 [SMILES: CC(=O)N1CC=C(c2c(C(C)n3nc(-c4cncc(O)c4)c4c(N)ncnc43)oc(=O)c3ccccc23)CC1] | D12 and 5-(4,4,5,5-tetramethyl-1,3,2-dioxa-borolan-2-yl)pyridin-3-ol | ¹H NMR (400 MHz, DMSO-d6) d ppm 11.24 (br.s., 1 H), 8.27-8.53 (m, 3 H), 8.09-8.25 (m, 1 H), 7.84-7.93 (m, 2 H), 7.79 (m, 2 H), 7.56-7.70 (m, 1 H), 7.39-7.50 (m, 1 H), 6.29 (dd, J = 6.84, 2.87 Hz, 1 H), 5.32 (br.s., 1 H), 4.07-4.34 (m, 6 H), 2.08 (s, 3 H), 1.77-1.96 (m, 3 H). UPLC-MS: 2.15 min, 523.9 [M + H]+, method 6. |
| 85 | 3-(1-(4-amino-3-(5-(hydroxymethyl)pyridin-3-yl)-1H-pyrazolo[3,4-d]pyrimidin-1-yl)ethyl)-4-phenyl-1H-isochromen-1-one | 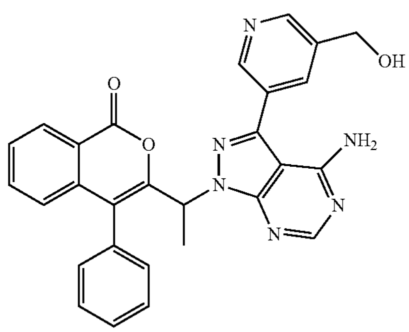 [SMILES: CC(c1oc(=O)c2ccccc2c1-c1ccccc1)n1nc(-c2cncc(CO)c2)c2c(N)ncnc21] | D2a and (5-(4,4,5,5-tetramethyl-1,3,2-dioxa-borolan-2-yl)pyridin-3-yl)methanol | ¹H NMR (400 MHz, DMSO-d6) d ppm 8.86 (s, 1 H), 8.79 (s, 1 H), 8.17-8.39 (m, 3 H), 7.82-8.03 (bs, 1 H), 7.71-7.82 (m, 1 H), 7.60-7.67 (m, 1 H), 7.50-7.60 (m, 1 H), 7.34-7.50 (m, 3 H), 7.16 (d, J = 7.50 Hz, 1 H), 6.90 (d, J = 7.94 Hz, 1 H), 5.81 (d, J = 7.06 Hz, 1 H), 4.74 (s, 2 H), 1.88 (d, J = 7.06 Hz, 3 H). UPLC-MS: 3.14 min, 491.0 [M + H]+, method 6. |
| 86 | 3-(1-(4-amino-3-(6-(hydroxymethyl)pyridin-3-yl)-1H-pyrazolo[3,4-d]pyrimidin-1-yl)ethyl)-4-phenyl-1H-isochromen-1-one | 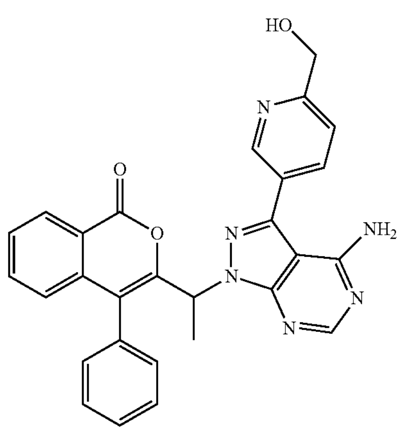 [SMILES: CC(c1oc(=O)c2ccccc2c1-c1ccccc1)n1nc(-c2ccc(CO)nc2)c2c(N)ncnc21] | D2a and (5-(4,4,5,5-tetramethyl-1,3,2-dioxa-borolan-2-yl)pyridin-2-yl)methanol | ¹H NMR (400 MHz, DMSO-d6) d ppm 8.78 (d, J = 1.76 Hz, 1 H), 8.18-8.39 (m, 3 H), 7.71-8.03 (m, 3 H), 7.60-7.67 (m, 1 H), 7.50-7.57 (m, 1 H), 7.33-7.50 (m, 3 H), 7.16 (d, J = 7.50 Hz, 1 H), 6.89 (d, J = 7.94 Hz, 1 H), 5.78 (q, J = 7.06 Hz, 1 H), 4.78 (s, 2 H), 1.87 (d, J = 7.06 Hz, 3 H). UPLC-MS: 3.26 min, 491.0 [M + H]+, method 6. |

| Ex. | Name | Structure | Reagents | UPLC-MS and ¹H NMR |
|---|---|---|---|---|
| 93 | 3-(1-(4-amino-3-(3-fluoro-4-isopropoxyphenyl)-1H-pyrazolo[3,4-d]pyrimidin-1-yl)ethyl)-4-phenyl-1H-isochromen-1-one | 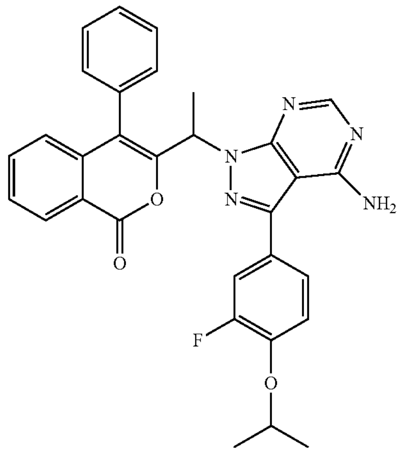 [SMILES: CC(C)Oc1ccc(-c2nn(C(C)c3oc(=O)c4ccccc4c3-c3ccccc3)c3ncnc(N)c23)cc1F] | D2a and 3-fluoro-4-isopropoxy-phenyl)boronic acid | ¹H NMR (400 MHz, DMSO-d6) δ ppm 8.16-8.28 (m, 1 H), 8.10 (s, 1 H), 7.70-7.84 (m, 1 H), 7.58-7.66 (m, 1 H), 7.49-7.57 (m, 1 H), 7.28-7.48 (m, 6 H), 7.10-7.19 (m, 1 H), 6.84-6.95 (m, 1 H), 5.58-5.81 (m, 1 H), 4.46-4.84 (m, 1 H), 1.75-1.96 (m, 3 H), 1.33 (d, J = 5.73 Hz, 6 H). UPLC-MS: 5.48 min, 536.0 [M + H]+, method 6 |
| 94 | 3-(1-(4-amino-3-(5-fluoropyridin-3-yl)-1H-pyrazolo[3,4-d]pyrimidin-1-yl)ethyl)-4-phenyl-1H-isochromen-1-one | 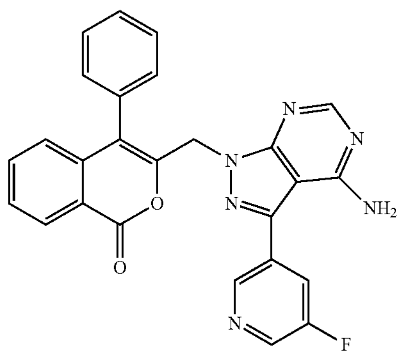 [SMILES: Nc1ncnc2c1c(-c1cncc(F)c1)nn2Cc1oc(=O)c2ccccc2c1-c1ccccc1] | D2a and (5-fluoro-pyridin-3-yl)boronic acid | ¹H NMR (400 MHz, DMSO-d6) d ppm 8.67 (s, 2 H), 8.17-8.27 (m, 1 H), 8.12 (s, 1 H), 7.85-7.93 (m, 1 H), 7.72-7.81 (m, 1 H), 7.59-7.69 (m, 1 H), 7.48-7.58 (m, 1 H), 7.31-7.45 (m, 3 H), 7.01-7.25 (m, 3 H), 6.83-6.95 (m, 1 H), 5.65-5.85 (m, 1 H), 1.78-1.94 (d, 3 H). UPLC-MS: 4.14 min, 479.0 [M + H]+, method 6 |
| 95 | 3-(1-(4-amino-3-(3-chloro-5-fluorophenyl)-1H-pyrazolo[3,4-d]pyrimidin-1-yl)ethyl)-4-phenyl-1H-isochromen-1-one | 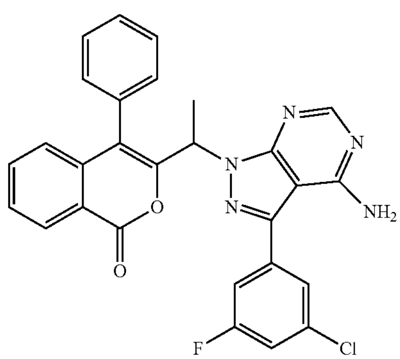 [SMILES: CC(c1oc(=O)c2ccccc2c1-c1ccccc1)n1nc(-c2cc(F)cc(Cl)c2)c2c(N)ncnc21] | D2a and (3-chloro-5-fluoro-phenyl)boronic acid | ¹H NMR (400 MHz, DMSO-d6) d ppm 8.28 (s, 1 H), 8.18-8.26 (m, 1 H), 7.73-7.82 (m, 1 H), 7.36-7.66 (m, 8 H), 7.16 (d, J = 7.50 Hz, 1 H), 6.89 (d, J = 7.94 Hz, 1 H), 5.65-5.89 (m, 2 H), 1.87 (d, J = 7.06 Hz, 3 H). UPLC-MS: 5.50 min, 511.9 [M + H]+, method 6. |
| 96 | 3-(1-(4-amino-3-(5-(methylsulfonyl)pyridin-3-yl)-1H-pyrazolo[3,4-d]pyrimidin-1-yl)ethyl)-4-phenyl-1H-isochromen-1-one | 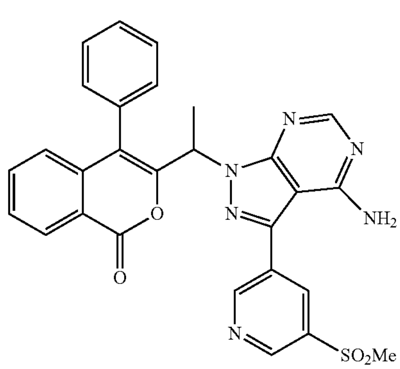 [SMILES: CC(c1oc(=O)c2ccccc2c1-c1ccccc1)n1nc(-c2cncc(S(C)(=O)=O)c2)c2c(N)ncnc21] | D2a and (5-(methyl-sulfonyl)pyridin-3-yl)boronic acid | ¹H NMR (400 MHz, DMSO-d6) δ ppm 9.15 (d, J = 2.21 Hz, 1 H), 9.09 (d, J = 1.76 Hz, 1 H), 8.42 (s, 1 H), 8.18-8.26 (m, 1 H), 8.15 (s, 1 H), 7.72-7.81 (m, 1 H), 7.59-7.68 (m, 1 H), 7.48-7.56 (m, 1 H), 7.35-7.47 (m, 3 H), 7.09-7.29 (m, 2 H), 6.79-6.94 (m, 1 H), 5.63-5.89 (m, 1 H), 3.39 (s, 3 H), 1.87 (d, J = 7.06 Hz, 3 H). UPLC-MS: 3.79 min, 539.0 [M + H]+, method 6 |

| Ex. | Name | Structure | Reagents | UPLC-MS and ¹H NMR |
|---|---|---|---|---|
| 97 | 3-(1-(4-amino-3-(6-(methylsulfonyl)pyridin-3-yl)-1H-pyrazolo[3,4-d]pyrimidin-1-yl)ethyl)-4-phenyl-1H-isochromen-1-one | 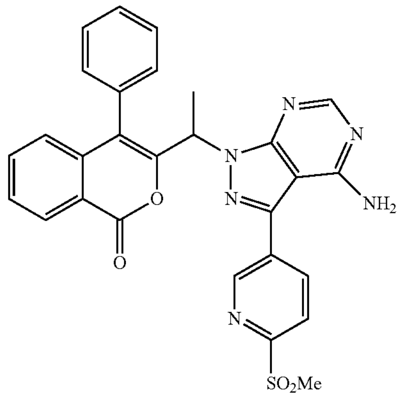 [SMILES: CC(c1oc(=O)c2ccccc2c1-c1ccccc1)n1nc(-c2ccc(S(C)(=O)=O)nc2)c2c(N)ncnc21] | D2 and (6-(methyl-sulfonyl)pyridin-3-yl)boronic acid | ¹H NMR (400 MHz, DMSO-d6) δ ppm 8.88-9.07 (m, 1 H), 8.29-8.38 (m, 1 H), 8.20-8.26 (m, 1 H), 8.15 (s, 2 H), 7.72-7.80 (m, 1 H), 7.59-7.66 (m, 1 H), 7.49-7.56 (m, 1 H), 7.33-7.46 (m, 3 H), 7.12-7.22 (m, 2 H), 6.85-6.92 (m, 1 H), 5.64-5.88 (m, 1 H), 1.87 (d, J = 7.06 Hz, 3 H). UPLC-MS: 3.95 min, 538.9 [M + H]+, method 6 |
| 98 | 3-(1-(4-amino-3-(5-fluoro-6-hydroxypyridin-3-yl)-1H-pyrazolo[3,4-d]pyrimidin-1-yl)ethyl)-4-phenyl-1H-isochromen-1-one | 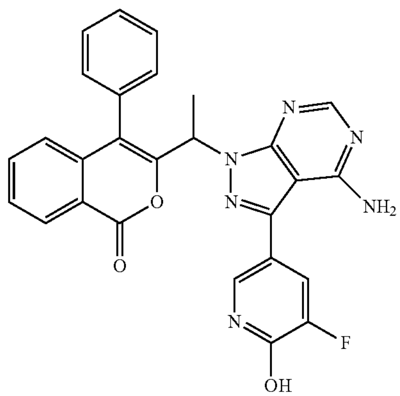 [SMILES: CC(c1oc(=O)c2ccccc2c1-c1ccccc1)n1nc(-c2cnc(O)c(F)c2)c2c(N)ncnc21] | D2a and (5-fluoro-6-hydroxy-pyridin-3-yl)boronic acid | ¹H NMR (400 MHz, DMSO-d6) δ ppm 11.70-12.55 (bs, 1 H), 8.18-8.26 (m, 1 H), 8.07 (s, 1 H), 7.70-7.82 (m, 1 H), 7.59-7.68 (m, 1 H), 7.53 (m, 2 H), 7.39 (m, 4 H), 7.01-7.21 (m, 3 H), 6.83-6.93 (m, 1 H), 5.63-5.72 (m, 1 H), 1.82 (d, J = 7.06 Hz, 3 H). UPLC-MS: 3.37 min, 495.0 [M + H]+, method 6 |
| 99 | 3-(1-(4-amino-3-(5-hydroxy-6-methylpyridin-3-yl)-1H-pyrazolo[3,4-d]pyrimidin-1-yl)ethyl)-4-phenyl-1H-isochromen-1-one | 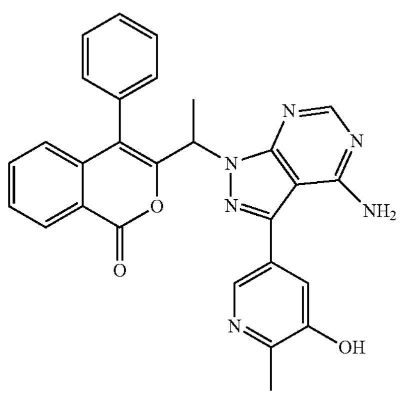 [SMILES: Cc1ncc(-c2nn(C(C)c3oc(=O)c4ccccc4c3-c3ccccc3)c3ncnc(N)c23)cc1O] | D2a and (5-methoxy-6-methylpyridin-3-yl)boronic acid | ¹H NMR (400 MHz, DMSO-d6) δ ppm 10.66-11.14 (m, 1 H), 8.28 (s, 1 H), 8.22 (d, J = 7.50 Hz, 1 H), 8.13 (s, 1 H), 7.71-7.82 (m, 1 H), 7.63 (t, J = 7.50 Hz, 2 H), 7.49-7.57 (m, 1 H), 7.36-7.48 (m, 3 H), 7.15 (d, J = 7.50 Hz, 2 H), 6.90 (d, J = 7.94 Hz, 1 H), 5.75 (q, J = 7.06 Hz, 1 H), 2.50 (s, 3 H), 1.85 (d, J = 7.06 Hz, 3 H). UPLC-MS: 3.17 min, 491 [M + H]+, method 6 |
| 100 | 3-(1-(4-amino-3-(5-(trifluoromethyl)pyridin-3-yl)-1H-pyrazolo[3,4-d]pyrimidin-1-yl)ethyl)-4-phenyl-1H-isochromen-1-one | 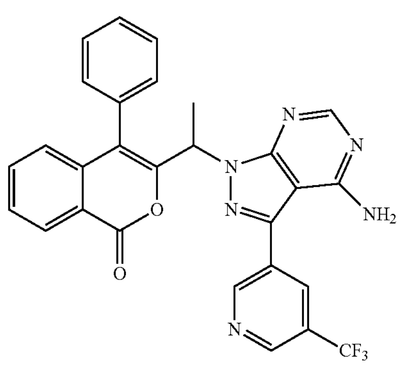 [SMILES: CC(c1oc(=O)c2ccccc2c1-c1ccccc1)n1nc(-c2cncc(C(F)(F)F)c2)c2c(N)ncnc21] | D2a and (5-(trifluoro-methyl)pyridin-3-yl)boronic acid | ¹H NMR (400 MHz, DMSO-d6) δ ppm 9.06 (s, 2 H), 8.26-8.32 (m, 1 H), 8.18-8.24 (m, 1 H), 8.14 (s, 1 H), 7.70-7.83 (m, 1 H), 7.58-7.66 (m, 1 H), 7.48-7.56 (m, 1 H), 7.33-7.47 (m, 3 H), 7.08-7.26 (m, 3 H), 6.83-6.93 (m, 1 H), 5.62-5.85 (m, 1 H), 1.87 (d, J = 7.06 Hz, 3 H). UPLC-MS: 4.83 min, 529.0 [M + H]+, method 6 |

-continued

| Ex. | Name | Structure | Reagents | UPLC-MS and ¹H NMR |
|---|---|---|---|---|
| 101 | 3-(1-(4-amino-3-(5-hydroxy-3-sulfur pentafluoride)-1H-pyrazolo[3,4-d]pyrimidin-1-yl)ethyl)-4-phenyl-1H-isochromen-1-one | 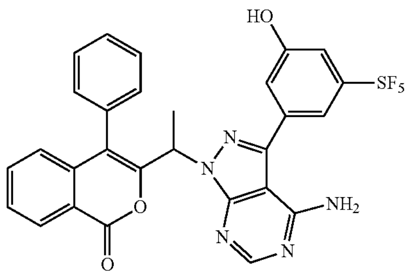 | D2a and 3-Methoxy-phenyl-sulphur penta-fluoride-5-boronic acid (Int. G17) | ¹H NMR (400 MHz, DMSO-d6) δ ppm 10.57 (s, 1 H), 8.22 (d, J = 7.06 Hz, 1 H), 8.13 (s, 1 H), 7.68-7.83 (m, 1 H), 7.58-7.65 (m, 1 H), 7.49-7.57 (m, 1 H), 7.35-7.48 (m, 4 H), 7.29 (d, J = 1.76 Hz, 2 H), 7.17 (d, J = 7.50 Hz, 1 H), 6.95-7.13 (m, 1 H), 6.89 (d, J = 7.94 Hz, 1 H), 5.60-5.87 (m, 1 H), 1.85 (d, J = 7.06 Hz, 3 H). UPLC-MS: 5.27 min, 601.9 [M + H]+, method 6 |
| 102 | 5-(4-amino-1-(1-(1-oxo-4-phenyl-1H-isochromen-3-yl)ethyl)-1H-pyrazolo[3,4-d]pyrimidin-3-yl)nicotinonitrile | 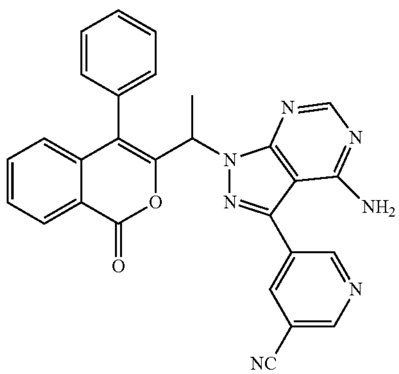 [SMILES: CC(c1oc(=O)c2ccccc2c1-c1ccccc1)n1nc(-c2cncc(C#N)c2)c2c(N)ncnc21] | Int. D2a and (5-cyano-pyridin-3-yl)boronic | ¹H NMR (400 MHz, DMSO-d6) δ ppm 1.86 (d, J = 7.28 Hz, 3 H), 5.72-5.81 (m, 1 H), 6.89 (d, J = 7.78 Hz, 1 H), 7.03-7.48 (m, 6 H), 7.49-7.56 (m, 1 H), 7.59-7.67 (m, 1 H), 7.77 (s, 1 H), 8.13 (s, 1 H), 8.22 (dd, J = 7.78, 1.00 Hz, 1 H), 8.45 (t, J = 2.01 Hz, 1 H), 9.03 (d, J = 2.01 Hz, 1 H), 9.10 (d, J = 2.01 Hz, 1 H). UPLC-MS: 4.10 min, 486.0 [M + H]+, method 6 |
| 113 | 3-(1-(4-amino-3-(3-amino-1H-indazol-5-yl)-1H-pyrazolo[3,4-d]pyrimidin-1-yl)ethyl)-4-phenyl-1H-isochromen-1-one | 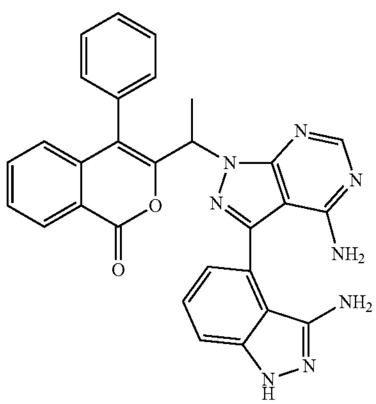 [SMILES: CC(c1oc(=O)c2ccccc2c1-c1ccccc1)n1nc(-c2cccc3[nH]nc(N)c23)c2c(N)ncnc21] | Int. D2a and 5-(4,4,5,5-tetramethyl-1,3,2-dioxa-borolan-2-yl)-1H-indazol-3-amine | ¹H NMR (400 MHz, DMSO-d₆) δ ppm 11.57-11.91 (bs, 1 H), 8.99-9.39 (bs, 2 H), 8.19-8.24 (m, 1 H), 8.09-8.13 (m, 1 H), 7.97-8.05 (m, 1 H), 7.73-7.81 (m, 1 H), 7.28-7.67 (m, 7 H), 7.11-7.18 (m, 1 H), 6.86-6.94 (m, 1 H), 5.61-5.83 (m, 1 H), 1.85 (d, J = 7.06 Hz, 3 H). UPLC-MS: 3.38 min, 515 [M + H]+, method 6 |
| 114 | 3-(1-(4-amino-3-(3-hydroxy-5-(trifluoromethoxy)phenyl)-1H-pyrazolo[3,4-d]pyrimidin-1-yl)ethyl)-4-phenyl-1H-isochromen-1-one | 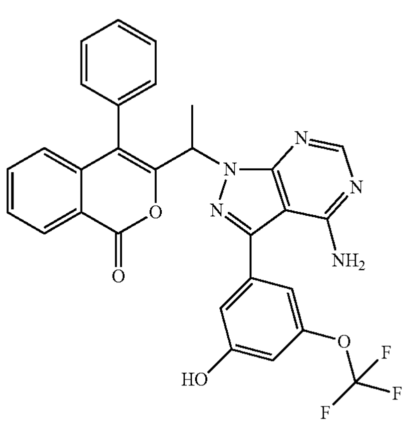 [SMILES: CC(c1oc(=O)c2ccccc2c1-c1ccccc1)n1nc(-c2cc(O)cc(OC(F)(F)F)c2)c2c(N)ncnc21] | Int. D2 and (3-hydroxy-5-(trifluoro-methoxy)phenyl) boronic acid | ¹H NMR (400 MHz, DMSO-d₆) δ ppm 10.35 (s, 1 H), 8.22 (d, J = 7.50 Hz, 1 H), 8.11 (s, 1 H), 7.77 (s, 1 H), 7.33-7.66 (m, 5 H), 7.16 (s, m H), 7.08 (s, 1 H), 6.97 (s, 1 H), 6.89 (d, J = 7.94 Hz, 1 H), 6.80 (m, 1 H), 5.73 (d, J = 7.06 Hz, 1 H), 1.84 (d, J = 7.06 Hz, 3 H). UPLC-MS: 5.11 min, 560 [M + H]+, method 6. |

-continued

| Ex. | Name | Structure | Reagents | UPLC-MS and $^1$H NMR |
|---|---|---|---|---|
| 121 | 3-(1-(4-amino-3-(3-fluoro-5-hydroxyphenyl)-1H-pyrazolo[3,4-d]pyrimidin-1-yl)ethyl)-4-(2-aminothiazol-5-yl)-1H-isochromen-1-one hydrochloride | 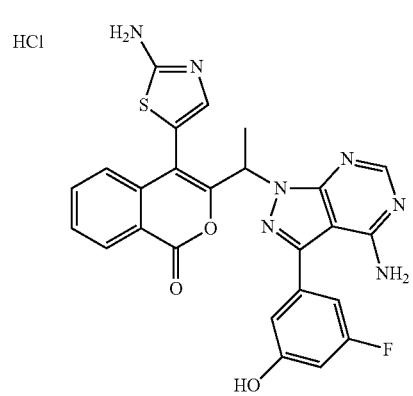 [SMILES: Cl ; CC(c1oc(=O)c2ccccc2c1-c1cnc(N)s1)n1nc(-c2cc(O)cc(F)c2)c2c(N)ncnc21] | Int. D18 and 3-fluoro-5-hydroxy-phenyl-boronic acid | $^1$H NMR (400 MHz, DMSO-d$_6$) δ ppm 10.35-10.13 (br.s., 2 H), 9.18-8.98 (br.s., 1 H), 8.36-6.63 (m, 11 H), 6.16-5.90 (m, 1 H), 1.04 (d, J = 6.17 Hz, 3 H). UPLC-MS: 1.81-2.26 min, 516 [M + H]+, method 6 |
| 128 | 3-(4-amino-1-((4-phenyl-1H-isochromen-3-yl)methyl)-1H-pyrazolo[3,4-d]pyrimidin-3-yl)-5-fluorophenol | 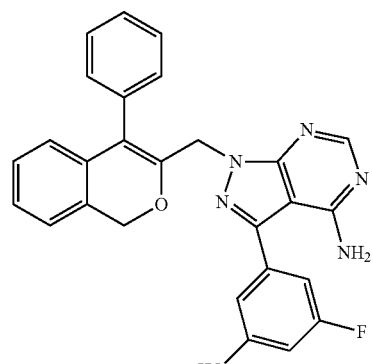 | Int. D20 and (3-fluoro-5-hydroxy-phenyl) boronic acid | 1H NMR (400 MHz, DMSO-d$_6$) δ ppm 10.32 (s, 1 H), 8.32 (s, 1 H), 7.33-7.58 (m, 5 H), 7.13-7.27 (m, 3 H), 6.90-6.95 (m, 1 H), 6.82-6.88 (m, 1 H), 6.61-6.70 (m, 1 H), 6.54-6.61 (m, 1 H), 5.02 (m, 4 H). UPLC-MS: 4.72 min, 466 [M + H]+, method 6 |
| 129 | 5-(4-amino-1-((4-phenyl-1H-isochromen-3-yl)methyl)-1H-pyrazolo[3,4-d]pyrimidin-3-yl)pyridin-3-ol | 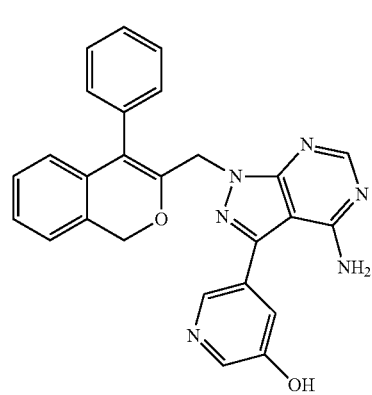 [SMILES: Nc1ncnc2c1c(-c1cncc(O)c1)nn2CC1=C(c2ccccc2)c2ccccc2CO1] | Int. D20 and 5-(1,5-dimethyl-2,4-dioxa-3-borabicyclo[3.1.0]hexan-3-yl)pyridin-3-ol | $^1$H NMR (400 MHz, DMSO-d$_6$) δ ppm 10.07-10.31 (m, 1 H), 8.29-8.36 (m, 1 H), 8.23-8.26 (m, 1 H), 8.17-8.22 (m, 1 H), 7.34-7.52 (m, 6 H), 7.07-7.28 (m, 3 H), 6.49-6.63 (m, 1 H), 5.02 (s, 4 H). UPLC-MS: 0.87 min, 449 [M + H]+, method 9. |

-continued

| Ex. | Name | Structure | Reagents | UPLC-MS and ¹H NMR |
|---|---|---|---|---|
| 131 | 3-(1-(4-amino-3-(3-fluoro-5-hydroxyphenyl)-1H-pyrazolo[3,4-d]pyrimidin-1-yl)ethyl)-4-(1-benzyl-1,2,3,6-tetrahydropyridin-4-yl)-1H-isochromen-1-one hydrochloride | 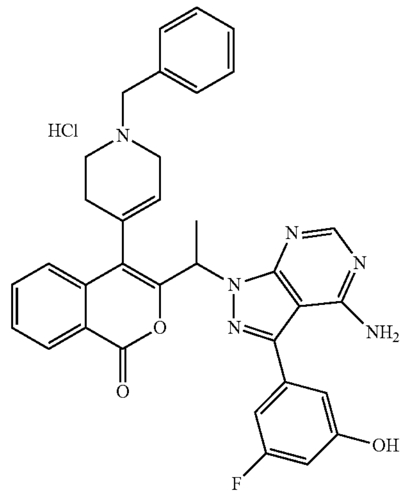 [SMILES: CC(c1oc(=O)c2ccccc2c1C1=CCN(Cc2ccccc2)CC1)n1nc(-c2cc(O)cc(F)c2)c2c(N)ncnc21 ; Cl] | Int. D21 and 3-fluoro-5-hydroxy-phenyl-boronic acid | ¹H NMR (400 MHz, DMSO-d$_6$) δ ppm 10.77-10.98 (m, 1H), 10.13-10.30 (m, 1H), 8.05-8.28 (m, 2H), 7.78-7.95 (m, 2H), 7.59-7.72 (m, 2H), 7.46-7.57 (m, 2H), 6.76-6.98 (m, 2H), 6.62-6.74 (m, 1H), 6.10-6.28 (m, 1H), 5.98-6.09 (m, 1H), 5.85-5.92 (m, 1H), 5.30-5.47 (m, 1H), 4.44-4.57 (m, 2H), 3.81-4.00 (m, 2H), 3.32-3.44 (m, 2H), 2.53-2.93 (m, 2H), 1.80-1.99 (m, 3H). UPLC-MS: 2.98 min, 589.0 [M + H]+, method 6 |
| 132 | 3-(1-(4-amino-3-(5-hydroxypyridin-3-yl)-1H-pyrazolo[3,4-d]pyrimidin-1-yl)ethyl)-4-(1-benzyl-1,2,3,6-tetrahydropyridin-4-yl)-1H-isochromen-1-one hydrochloride | 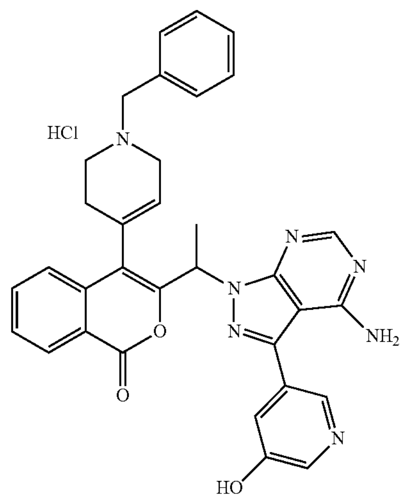 [SMILES: CC(c1oc(=O)c2ccccc2c1C1=CCN(Cc2ccccc2)CC1)n1nc(-c2cncc(O)c2)c2c(N)ncnc21 ; Cl] | Int. D21 and 5-(4,4,5,5-tetramethyl-1,3,2-dioxa-borolan-2-yl)pyridin-3-ol | ¹H NMR (400 MHz, DMSO-d$_6$) δ ppm 10.72-11.24 (m, 2H br), 8.33-8.47 (m, 2H), 8.21-8.30 (m, 1H), 8.06-8.20 (m, 1H), 7.79-7.95 (m, 2H), 7.59-7.75 (m, 3H), 7.37-7.58 (m, 3H), 6.17-6.36 (m, 1H), 6.00-6.12 (m, 1H), 5.38-5.41 (m, 1H), 4.40-4.60 (m, 2H), 3.91-3.97 (m, 1H), 3.50-3.55 (m, 1H), 3.27-3.46 (m, 2H), 2.76-3.03 (m, 2H), 2.53-2.68 (m, 1H), 1.82-1.99 (m, 3H).. UPLC-MS: 2.05 min, 572.0 [M + H]+, method 6. |
| 146 | 3-(1-(4-amino-3-(3-fluoro-5-hydroxyphenyl)-1H-pyrazolo[3,4-d]pyrimidin-1-yl)ethyl)-4-(1-(4-(dimethylamino)butanoyl)-1,2,3,6-tetrahydropyridin-4-yl)-1H-isochromen-1-one formate | 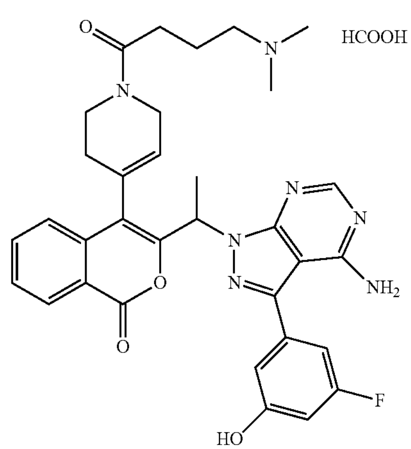 [SMILES: CC(c1oc(=O)c2ccccc2c1C1=CCN(C(=O)CCCN(C)C)CC1)n1nc(-c2cc(O)cc(F)c2)c2c(N)ncnc21 ; "HCOOH"] | Int. D25 and 3-fluoro-5-hydroxy-phenyl-boronic acid | ¹H NMR (600 MHz, DMSO-d6) δ ppm 1.67-1.78 (m, 2 H), 1.79-1.92 (m, 3 H), 2.03-2.47 (m, 12 H), 3.54-4.33 (m, 4 H), 5.80-6.32 (m, 2 H), 6.56-6.98 (m, 4 H), 7.30-7.49 (m, 1 H), 7.52-7.71 (m, 1 H), 7.76-7.92 (m, 1 H), 8.01-8.35 (m, 3 H). UPLC-MS: 2.57 min, 612.1 [M + H]+, method 6. |

-continued

| Ex. | Name | Structure | Reagents | UPLC-MS and ¹H NMR |
|---|---|---|---|---|
| 147 | 3-(1-(4-amino-3-(3-fluoro-5-hydroxyphenyl)-1H-pyrazolo[3,4-d]pyrimidin-1-yl)ethyl)-4-(1-(2-(dimethylamino)acetyl)-1,2,3,6-tetrahydropyridin-4-yl)-1H-isochromen-1-one formate | 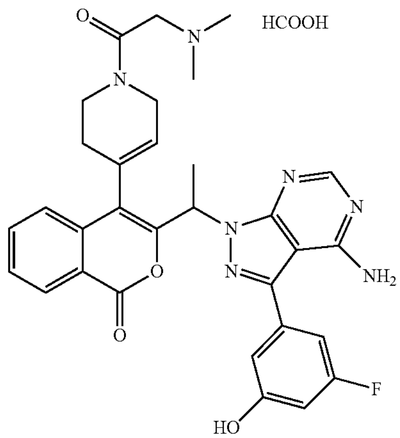 [SMILES: CC(c1oc(=O)c2ccccc2c1C1=CCN(C(=O)CN(C)C)CC1)n1nc(-c2cc(O)cc(F)c2)c2c(N)ncnc21 ; "HCOOH"] | Int. D26 and 3-fluoro-5-hydroxyphenylboronic acid | ¹H NMR (600 MHz, DMSO-d6) δ ppm 1.72-1.96 (m, 3 H), 2.09-2.46 (m, 8 H), 3.07-3.39 (m, 2 H), 3.69-3.96 (m, 2 H), 4.03-4.47 (m, 2 H), 5.97-6.28 (m, 2 H), 6.45-7.10 (m, 4 H), 7.35-7.51 (m, 1 H), 7.56-7.71 (m, 1 H), 7.79-7.95 (m, 1 H), 8.05-8.33 (m, 3 H). UPLC-MS: 2.45 min, 584.1 [M + H]+, method 6 |
| 148 | 3-(1-(4-amino-3-(3-fluoro-5-hydroxyphenyl)-1H-pyrazolo[3,4-d]pyrimidin-1-yl)ethyl)-4-(1-(1-methylpiperidine-4-carbonyl)-1,2,3,6-tetrahydropyridin-4-yl)-1H-isochromen-1-one formate | 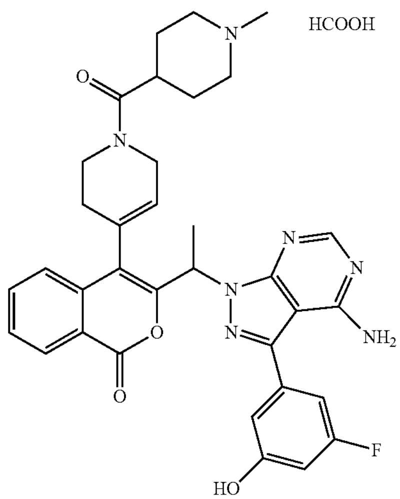 [SMILES: CC(c1oc(=O)c2ccccc2c1C1=CCN(C(=O)C2CCN(C)CC2)CC1)n1nc(-c2cc(O)cc(F)c2)c2c(N)ncnc21 ; "HCOOH"] | Int. D27 and 3-fluoro-5-hydroxyphenylboronic acid | ¹H NMR (600 MHz, DMSO-d6) δ ppm 8.08-8.28 (m, 3 H), 7.80-7.91 (m, 1 H), 7.56-7.72 (m, 1 H), 7.33-7.51 (m, 1 H), 6.79-6.96 (m, 2 H), 6.59-6.71 (m, 1 H), 6.15-6.32 (m, 1 H), 5.94-6.12 (m, 1 H), 5.18-5.41 (m, 1 H), 4.15-4.37 (m, 1 H), 3.52-4.12 (m, 4 H), 2.76-2.92 (m, 2 H), 2.54-2.71 (m, 1 H), 2.28-2.45 (m, 1 H), 2.20 (s, 3 H), 1.94-2.15 (m, 2 H), 1.87 (d, J = 7.23 Hz, 2 H), 1.81 (t, J = 7.23 Hz, 1 H), 1.54-1.74 (m, 3 H) UPLC-MS: 2.53 min, 624.1 [M + H]+, method 6. |
| 149 | 3-(1-(4-amino-3-(3-fluoro-5-hydroxyphenyl)-1H-pyrazolo[3,4-d]pyrimidin-1-yl)ethyl)-4-(1-(1-isopropylpiperidin-4-yl)-1,2,3,6-tetrahydropyridin-4-yl)-1H-isochromen-1-one dihydrochloride | 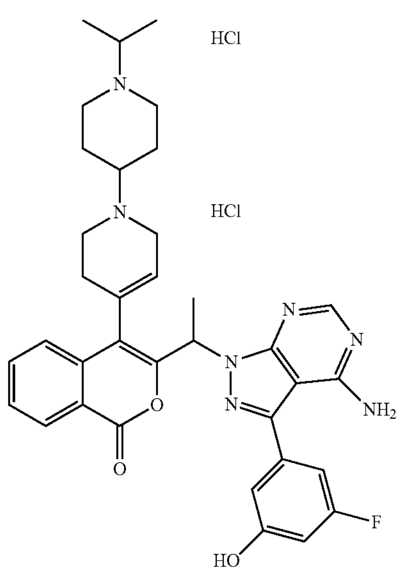 [SMILES: CC(C)N1CCC(N2CC=C(c3c(C(C)n4nc(-c5cc(O)cc(F)c5)c5c(N)ncnc54)oc(=O)c4ccccc34)CC2)CC1 ; Cl ; Cl] | Int. D24 and 3-fluoro-5-hydroxyphenylboronic acid | ¹H NMR (600 MHz, DMSO-d6) δ ppm 1.30 (m, 6 H), 1.72-2.10 (m, 3 H), 2.31-2.68 (m, 4 H), 2.91-3.20 (m, 3 H), 3.20-4.11 (m, 9 H), 6.00-6.63 (m, 2 H), 6.67-7.05 (m, 4 H), 7.53-8.23 (m, 4 H), 8.31-8.57 (m, 1 H), 10.17-10.98 (m, 2 H), 11.6-12.3 (m, 1 H). UPLC-MS: 3.97 min, 624.2 [M + H]+, method 11 |

| Ex. | Name | Structure | Reagents | UPLC-MS and ¹H NMR |
|---|---|---|---|---|
| 152 | 3-(1-(4-amino-3-(3-chloro-5-hydroxyphenyl)-1H-pyrazolo[3,4-d]pyrimidin-1-yl)ethyl)-4-(1,2,3,6-tetrahydropyridin-4-yl)-1H-isochromen-1-one formate | 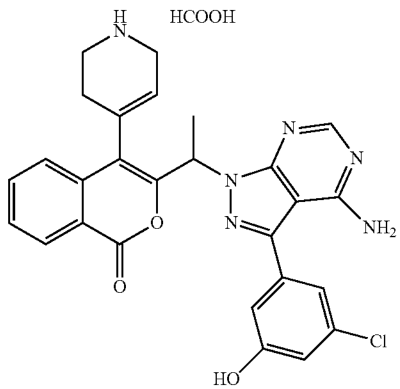 [SMILES: "HCOOH" ; CC(c1oc(=O)c2ccccc2c1C1=CCNCC1)n1nc(-c2cc(O)cc(Cl)c2)c2c(N)ncnc21] | Int. D14 and (3-chloro-5-hydroxyphenyl) boronic acid | ¹H NMR (600 MHz, DMSO-d6) δ ppm 6.81-8.40 (m, 11 H), 6.04-6.20 (m, 1 H), 5.96 (br.s., 1 H), 2.24-3.26 (m, 9 H), 1.79-1.95 (d, 3 H). UPLC-MS: min 2.59 min, 515.0 [M + H]+, method 6 |
| 153 | 3-(1-(4-amino-3-(3-hydroxy-5-(trifluoromethyl)phenyl)-1H-pyrazolo[3,4-d]pyrimidin-1-yl)ethyl)-4-(1,2,3,6-tetrahydropyridin-4-yl)-1H-isochromen-1-one formate | 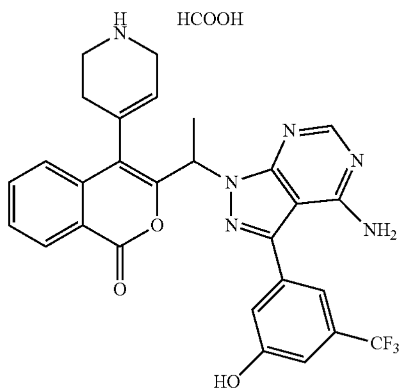 [SMILES: "HCOOH" ; CC(c1oc(=O)c2ccccc2c1C1=CCNCC1)n1nc(-c2cc(O)cc(C(F)(F)F)c2)c2c(N)ncnc21] | Int. D14 and (3-hydroxy-5-(trifluoromethyl)phenyl) boronic acid | 1H NMR (600 MHz, DMSO-d6) δ ppm 7.12-8.28 (m, 11 H), 6.58-7.09 (m, 1 H), 5.97 (br.s., 1 H), 2.30-3.31 (m, 9 H), 1.79-1.98 (d, 3 H). UPLC-MS: min 2.88 min, 549.0 [M + H]+, method 6 |
| 159 | 3-(1-(4-amino-3-(5-hydroxy-4-methylpyridin-3-yl)-1H-pyrazolo[3,4-d]pyrimidin-1-yl)ethyl)-4-phenyl-1H-isochromen-1-one | 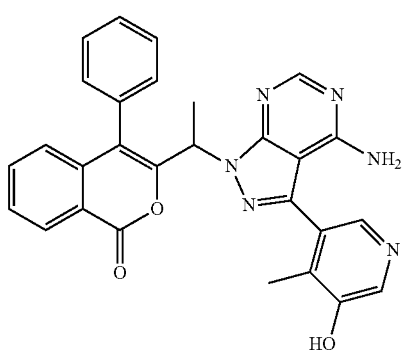 [SMILES: Cc1c(O)cncc1-c1nn(C(C)c2oc(=O)c3ccccc3c2-c2ccccc2)c2ncnc(N)c12] | Int. D2a and (5-methoxy-4-methylpyridin-3-yl)boronic acid (Intermediate G23) | 1H NMR (400 MHz, DMSO-$d_6$) δ ppm 1.85 (d, J = 7.03 Hz, 3 H), 2.25 (s, 3 H), 5.70-5.84 (m, 1 H), 6.92 (d, J = 7.78 Hz, 1 H), 7.21 (d, J = 7.28 Hz, 1 H), 7.40-7.53 (m, 3 H), 7.55-7.68 (m, 2 H), 7.75-7.82 (m, 1 H), 8.16-8.27 (m, 2 H), 8.40 (s, 2 H), 11.83 (br.s., 1 H). UPLC-MS: 3.30 min, 491.0 [M + H]+, method 6 |
| 160 | 3-(1-(4-amino-3-(5-hydroxy-2-methylpyridin-3-yl)-1H-pyrazolo[3,4-d]pyrimidin-1-yl)ethyl)-4-phenyl-1H-isochromen-1-one | 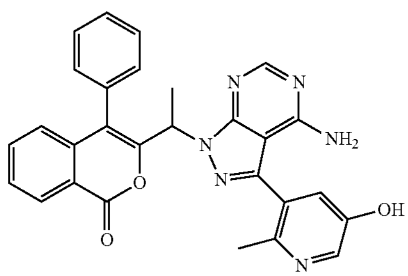 [SMILES: Cc1ncc(O)cc1-c1nn(C(C)c2oc(=O)c3ccccc3c2-c2ccccc2)c2ncnc(N)c12] | Int D2a and (5-methoxy-2-methylpyridin-3-yl)boronic acid (Intermediate G24) | 1H NMR (400 MHz, DMSO-$d_6$) δ ppm 1.82 (d, J = 7.03 Hz, 4 H), 2.32 (s, 4 H), 5.65-5.79 (m, 1 H), 6.91 (d, J = 8.03 Hz, 1 H), 7.10-7.67 (m, 7 H), 7.72-7.83(m, 1 H), 8.10 (s, 1 H), 8.14 (d, J = 2.76 Hz, 2 H), 8.21 (dd, J = 8.03, 1.00 Hz, 1 H), 9.98 (br.s., 1 H). UPLC-MS: 3.15 min, 491.1 [M + H]+, method 6. |

Example 72

4-(1-acetyl-1,2,3,6-tetrahydropyridin-4-yl)-3-(1-(4-amino-3-(3-fluoro-5-hydroxyphenyl)-1H-pyrazolo[3,4-d]pyrimidin-1-yl)ethyl)-1H-isochromen-1-one

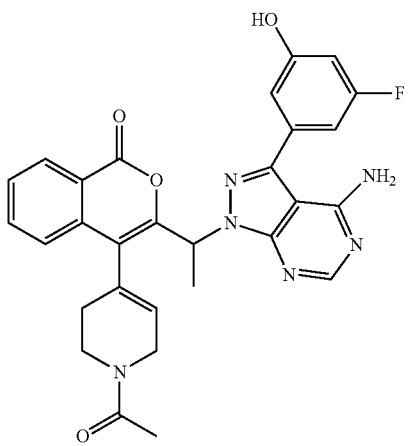 [SMILES: CC(=O)N1CC=C(c2c(C(C)n3nc(-c4cc(O)cc(F)c4)c4c(N)ncnc43)oc(=O)c3ccccc23)CC1]

The title compound was mane in a similar way as that or the compound of example 51 from 4-(1-acetyl-1,2,3,6-tetrahydropyridin-4-yl)-3-(1-(4-amino-3-iodo-1H-pyrazolo[3,4-d]pyrimidin-1-yl)ethyl)-1H-isochromen-1-one (Intermediate D12, 1.08 g, 1.941 mmol), (3-fluoro-5-hydroxyphenyl)boronic acid (0.605 g, 3.88 mmol), to give the title compound (456 mg, 43.5%) as a pale grey solid.

$^1$H NMR (400 MHz, DMSO-$d_6$) δ ppm 10.02-10.36 (s, 1 H), 8.12-8.33 (m, 2 H), 7.81-7.99 (m, 1 H), 7.57-7.70 (m, 1 H), 7.37-7.50 (m, 1 H), 6.80-6.96 (m, 2 H), 6.54-6.71 (m, 1 H), 6.18-6.31 (m, 1 H), 5.97-6.12 (m, 1 H), 5.16-5.33 (m, 1 H), 4.17-4.30 (m, 1 H), 4.04-4.15 (m, 1 H), 3.86-4.04 (m, 1 H), 3.48-3.82 (m, 2 H), 3.20 (s, 3 H), 2.01-2.05 (d, 3 H), 1.75-1.95 (m, 2 H). UPLC-MS: 3.13 min, 540.9 [M+H]+, method 6.

Example 73

3-(1-(4-amino-3-(3-fluoro-5-hydroxyphenyl)-1H-pyrazolo[3,4-d]pyrimidin-1-yl)ethyl)-4-(5-(pyrrolidin-1-ylmethyl)thiophen-2-yl)-1H-isochromen-1-one hydrochloride

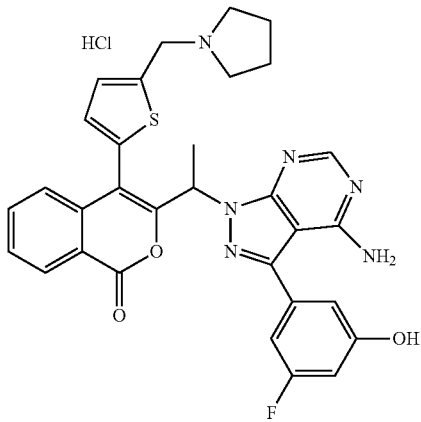 [SMILES: CC(c1oc(=O)c2ccccc2c1-c1ccc(CN2CCCC2)s1)n1nc(-c2cc(O)cc(F)c2)c2c(N)ncnc21 ; Cl]

The title compound was made in a similar way as that of the compound of example 67 from 5-(3-(1-(4-amino-3-(3-fluoro-5-hydroxyphenyl)-1H-pyrazolo[3,4-d]pyrimidin-1-yl)ethyl)-1-oxo-1H-isochromen-4-yl)thiophene-2-carbaldehyde (Intermediate F4, 57 mg, 0.108 mmol) and pyrrolidine (18.04 µl, 0.216 mmol), to give (prior to drying a small amount of 1M HCl aqueous was added) the title compound (37.8 mg, 56.5%) as whitish solid.

$^1$H NMR (400 MHz, DMSO-$d_6$) δ ppm 10.49 (br. s., 1 H), 10.25 (br. s., 1 H), 8.10-8.43 (m, 2 H), 7.79-7.90 (m, 1 H), 7.61-7.75 (m, 1 H), 7.41 (d, J=3.09 Hz, 1 H), 7.15 (d, J=7.94 Hz, 2 H), 6.91 (s, 1 H), 6.80-6.88 (m, 1 H), 6.69 (dt, J=11.03, 2.21 Hz, 1 H), 5.92 (d, J=7.06 Hz, 1 H), 4.61 (br. s., 2 H), 3.44 (m, 2 H), 3.10 (br. s., 2 H), 2.04 (m, 2 H), 1.70-1.95 (m, 7 H). UPLC-MS: 2.62 min, 582.9 [M+H]+, method 6.

Example 74

3-(1-(4-amino-3-(3-fluoro-5-hydroxyphenyl)-1H-pyrazolo[3,4-d]pyrimidin-1-yl)ethyl)-4-(5-((bis(2-hydroxyethyl)amino)methyl)thiophen-2-yl)-1H-isochromen-1-one, Formate

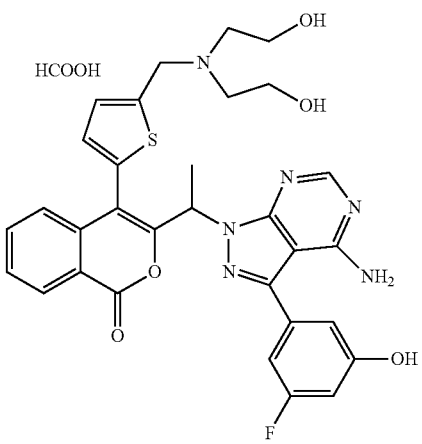 [SMILES: "HCOOH" ; CC(c1oc(=O)c2ccccc2c1-c1ccc(CN(CCO)CCO)s1)n1nc(-c2cc(O)cc(F)c2)c2c(N)ncnc21]

The title compound was made in a similar way as that of the compound of example 67 from 5-(3-(1-(4-amino-3-(3-fluoro-5-hydroxyphenyl)-1H-pyrazolo[3,4-d]pyrimidin-1-yl)ethyl)-1-oxo-1H-isochromen-4-yl)thiophene-2-carbaldehyde (Intermediate F4, 60 mg, 0.114 mmol) and 2,2'-azanediyldiethanol (23.92 mg, 0.227 mmol), to give the title compound (3 mg, 3.98%).

$^1$H NMR (400 MHz, DMSO-$d_6$) δ ppm 10.22 (s, 1 H), 9.68-10.01 (m, 1 H), 8.22 (d, J=7.94 Hz, 1 H), 8.14 (s, 1 H), 7.77-7.92 (m, 1 H), 7.66 (t, J=7.50 Hz, 1H), 7.46 (br. s., 1 H), 7.16 (d, J=7.94 Hz, 2 H), 6.91 (s, 1 H), 6.83 (d, J=8.82 Hz, 1 H), 6.67 (d, J=11.03 Hz, 1 H), 5.93 (d, J=7.06 Hz, 1 H), 5.38 (br. s., 2 H), 4.70 (br. s., 2 H), 3.82 (br. s., 4 H), 3.32 (s, 2 H), 1.85 (d, J=7.06 Hz, 3 H). UPLC-MS: 2.40 min, 616.9 [M+H]+, method 6.

Example 75

3-(1-(4-amino-3-(3-fluoro-5-hydroxyphenyl)-1H-pyrazolo[3,4-d]pyrimidin-1-yl)ethyl)-4-(5-(hydroxymethyl)thiophen-2-yl)-1H-isochromen-1-one

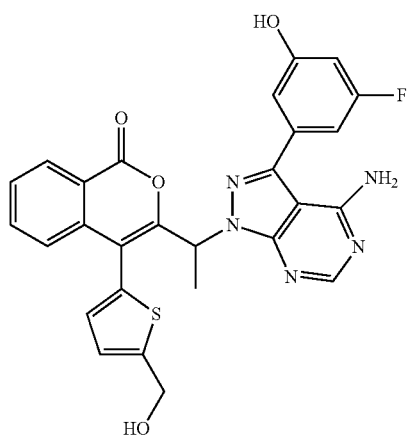 [SMILES: CC(c1oc(=O)c2ccccc2c1-c1ccc(CO)s1)n1nc(-c2cc(O)cc(F)c2)c2c(N)ncnc21]

The title compound was isolated during the experiment for producing example 74, in particular recovered during the final step of flash purification as second eluted compound (8.5 mg, 14.1%).

$^1$H NMR (400 MHz, DMSO-$d_6$) δ ppm 10.19 (s, 1 H), 8.14 (m, 2 H), 7.76-7.94 (m, 1 H), 7.47-7.71 (m, 1 H), 7.12-7.26 (m, 1 H), 7.00 (m, 2 H), 6.89-6.93 (m, 1 H), 6.79-6.87 (m, 1 H), 6.56-6.76 (m, 1 H), 5.76-6.09 (m, 1 H), 5.34-5.65 (m, 1 H), 4.52-4.78 (m, 2 H), 1.88 (d, J=7.06 Hz, 3 H). UPLC-MS: 3.43 min, 529.9 [M+H]+, method 6.

Example 76

3-(1-(4-amino-3-(3-fluoro-5-hydroxyphenyl)-1H-pyrazolo[3,4-d]pyrimidin-1-yl)ethyl)-4-(5-((4-(2-hydroxyethyl)piperazin-1-yl)methyl)thiophen-2-yl)-1H-isochromen-1-one hydrochloride

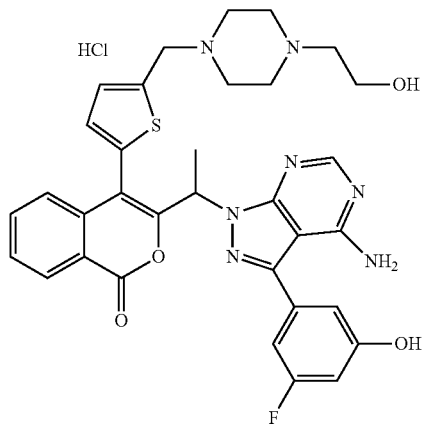 [SMILES: CC(c1oc(=O)c2ccccc2c1-c1ccc(CN2CCN(CCO)CC2)s1)n1nc(-c2cc(O)cc(F)c2)c2c(N)ncnc21 ; Cl]

The title compound was made in a similar way as that of the compound of example 67, from 5-(3-(1-(4-amino-3-(3-fluoro-5-hydroxyphenyl)-1H-pyrazolo[3,4-d]pyrimidin-1-yl)ethyl)-1-oxo-1H-isochromen-4-yl)thiophene-2-carbaldehyde (Intermediate F4, 60 mg, 0.114 mmol) and 2-(piperazin-1-yl)ethanol (29.6 mg, 0.227 mmol) to give the desired product (48.6 mg, 63.0%) as whitish solid.

$^1$H NMR (400 MHz, DMSO-$d_6$) δ ppm 9.85-10.43 (m, 1 H), 8.09-8.32 (m, 2 H), 7.78-7.91 (m, 1 H), 7.66 (t, J=7.50 Hz, 1 H), 7.20 (d, J=7.94 Hz, 2 H), 6.96-7.11 (m, 1 H), 6.81-6.96 (m, 2 H), 6.61-6.76 (m, 1 H), 5.85-6.04 (m, 1 H), 3.45-3.83 (m, 10 H), 3.21 (br. s., 4 H), 1.87 (d, J=7.06 Hz, 3 H). UPLC-MS: 2.66 min, 642.0 [M+H]+, method 6.

Example 76a (Enantiomer 1) and Example 76b (Enantiomer 2)

3-(1-(4-amino-3-(3-fluoro-5-hydroxyphenyl)-1H-pyrazolo[3,4-d]pyrimidin-1-yl)ethyl)-4-(5-((4-(2-hydroxyethyl)piperazin-1-yl)methyl)thiophen-2-yl)-1H-isochromen-1-one hydrochloride

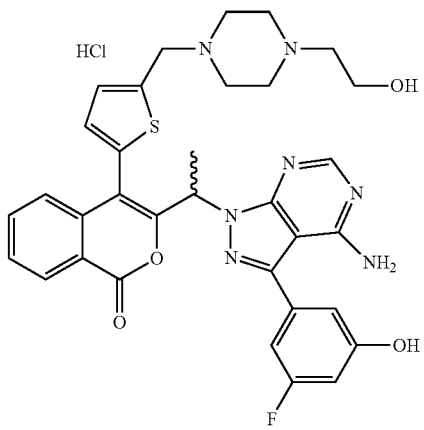

3-(1-(4-amino-3-(3-fluoro-5-hydroxyphenyl)-1H-pyrazolo[3,4-d]pyrimidin-1-yl)ethyl)-4-(5-(4-(2-hydroxyethyl)piperazin-1-yl)methyl)thiophen-2-yl)-1H-isochromen-1-one hydrochloride (example 76, 0.040 g) was dissolved in Ethanol/Methanol 1/1 (4 ml) and submitted to chiral resolution by Chiral preparative chromatography. Conditions: Column: Chiralpak AD-H (25×2.0 cm), 5um; Mobile phase: n-Hexane/(Ethanol+0.1% isopropylamine) 80/20% v/v; Flow rate: 17 ml/min; DAD detection: 220 nm; Loop: 300 μl; Injection: 3 mg (each injection).

The fractions containing the first eluted enantiomer were evaporated to dryness and purified by reverse phase flash chromatography on C18 cartridge ($H_2O$+0.1% HCOOH: $CH_3CN$+0.1% HCOOH=95:5 to 50:50); the residue was treated with 1.25M HCl in MeOH and evaporated to dryness to afford example 76a (first eluted enantiomer, 12 mg, 0.0168 mmol). Chiral HPLC (Method A16): Rt=12.1 min, ee>99%.

$^1$H NMR (500 MHz, DMSO-$d_6$) δ ppm 10.27 (br. s., 1 H), 8.25 (s, 1 H), 8.21 (d, 1 H), 7.81-7.86 (m, 1 H), 7.66 (t, 1 H), 6.94-7.52 (m, 5 H), 6.91 (s, 1 H), 6.85 (d, 1 H), 6.67-6.74 (m, 1 H), 5.96 (q, 1 H), 4.75-5.50 (m, 1 H), 3.56-4.22 (m, 10 H), 3.06-3.37 (m, 4 H), 1.87 (d, 3 H). UPLC-MS: 0.65 min, 642.2 [M+H]+, method 13.

The fractions containing the second eluted enantiomer were evaporated to dryness and purified by reverse phase flash chromatography on C18 cartridge (H$_2$O+0.1% HCOOH:CH$_3$CN+0.1% HCOOH=95:5 to 50:50); the residue was treated with 1.25M HCl in MeOH and evaporated to dryness to afford example 76b (second eluted enantiomer, 0.014 g, 0.0196 mmol). Chiral HPLC (Method A16): Rt=14.6 min, ee>99%.

$^1$H NMR (400 MHz, DMSO-d$_6$) δ ppm 10.26 (br. s., 1 H), 8.19-8.26 (m, 2 H), 7.81-7.86 (m, 1 H), 7.63-7.69 (m, 1 H), 6.94-7.52 (m, 5 H), 6.89-6.93 (m, 1 H), 6.82-6.88 (m, 1 H), 6.67-6.73 (m, 1 H), 5.96 (q, 1 H), 4.75-5. 55 (m, 1 H), 3.48-4.30 (m, 10 H), 3.07-3.36 (m, 4 H), 1.87 (d, 3 H). UPLC-MS: 0.65 min, 642.2 [M+H]+, method 13.

Example 77

4-((5-(3-(1-(4-amino-3-(3-fluoro-5-hydroxyphenyl)-1H-pyrazolo[3,4-d]pyrimidin-1-yl)ethyl)-1-oxo-1H-isochromen-4-yl)thiophen-2-yl)methyl)piperazin-2-one hydrochloride

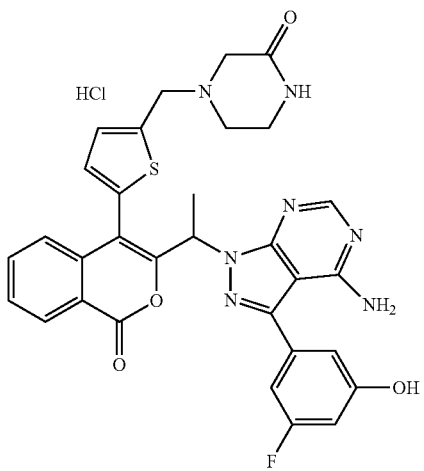 [SMILES: CC(c1oc(=O)c2ccccc2c1-c1ccc(CN2CCNC(=O)C2)s1)n1nc(-c2cc(O)cc(F)c2)c2c(N)ncnc21 ; Cl]

The title compound was made in a similar way as that of the compound of example 67, from 5-(3-(1-(4-amino-3-(3-fluoro-5-hydroxyphenyl)-1H-pyrazolo[3,4-d]pyrimidin-1-yl)ethyl)-1-oxo-1H-isochromen-4-yl)thiophene-2-carbaldehyde (Intermediate F4, 60 mg, 0.114 mmol) and piperazin-2-one (22.77 mg, 0.227 mmol) to give the desired product (29.8 mg, 40.4%) as whitish solid.

$^1$H NMR (400 MHz, DMSO-d$_6$) δ ppm 10.27 (br. s., 1 H), 8.15-8.59 (m, 3 H), 7.57-7.98 (m, 2 H), 7.41 (br. s., 1 H), 6.79-7.30 (m, 4 H), 6.54-6.75 (m, 1 H), 5.96 (q, J=7.06 Hz, 1 H), 4.59 (br. s., 2 H), 3.46 (br. s., 6 H), 1.87 (d, J=7.06 Hz, 3 H). UPLC-MS: 3.11 min, 612.0 [M+H]+, method 6.

Example 78

5-(3-(1-(4-amino-3-(3-fluoro-5-hydroxyphenyl)-1H-pyrazolo[3,4-d]pyrimidin-1-yl)ethyl)-1-oxo-1H-isochromen-4-yl)thiophene-2-carboxylic acid

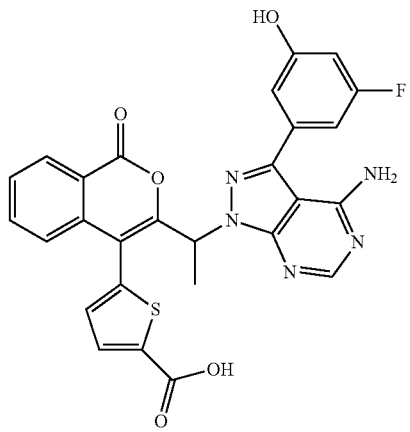 [SMILES: CC(c1oc(=O)c2ccccc2c1-c1ccc(C(=O)O)s1)n1nc(-c2cc(O)cc(F)c2)c2c(N)ncnc21]

5-(3-(1-(4-amino-3-(3-fluoro-5-hydroxyphenyl)-1H-pyrazolo[3,4-d]pyrimidin-1-yl)ethyl)-1-oxo-1H-isochromen-4-yl)thiophene-2-carbaldehyde (Intermediate F4, 19 mg, 0.036 mmol) was dissolved in 2-methyl-2-butene (300 μl, 2.83 mmol) and t-Butanol (0.5 ml), then a solution of NaClO$_2$ (32.6 mg, 0.360 mmol) and K$_2$H$_2$PO$_4$ (49.0 mg, 0.360 mmol) in 0.5 mL of water added and the mixture stirred at rt for 2 hrs. The reaction was quenched by the addition of 2M HCl$_{aqueous}$ (1 ml) and the crude purified via reverse phase chromatography using a Biotage C18 30 g SNAP with a gradient of water and acetonitrile to give the title compound (8 mg, 40.9%) as white solid.

$^1$H NMR (400 MHz, DMSO-d$_6$) δ ppm 12.87-13.46 (bs, 1 H), 9.96-10.54 (bs, 1 H), 8.17-8.27 (m, 1 H), 8.12 (s, 1 H), 7.77-7.87 (m, 1 H), 7.59-7.72 (m, 2 H), 7.13 (m, 4 H), 6.91 (s, 1 H), 6.79-6.86 (m, 1 H), 6.59-6.71 (m, 1 H), 5.75-6.06 (m, 1 H), 1.87 (d, J=7.06 Hz, 3 H). UPLC-MS: 3.52 min, 543.9 [M+H]+, method 6.

Example 79

3-(1-(4-amino-3-(3-fluoro-5-hydroxyphenyl)-1H-pyrazolo[3,4-d]pyrimidin-1-yl)ethyl)-4-benzyl-1H-isochromen-1-one

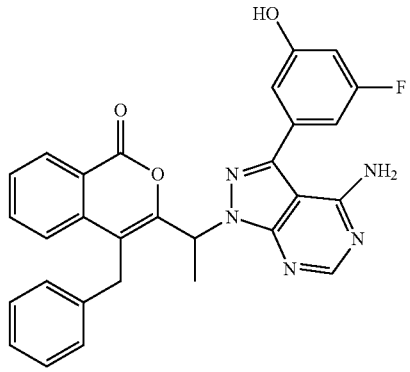 [SMILES: CC(c1oc(=O)c2ccccc2c1Cc1ccccc1)n1nc(-c2cc(O)cc(F)c2)c2c(N)ncnc21]

The title compound was made in a similar way as that of the compound of example 51 from 3-(1-(4-amino-3-iodo-1H-pyrazolo[3,4-d]pyrimidin-1-yl)ethyl)-4-benzyl-1H-isochromen-1-one (Intermediate D15, 45 mg, 0.086 mmol), (3-fluoro-5-hydroxyphenyl)boronic acid (26.8 mg, 0.172 mmol), to give the title compound (13 mg, 19.8%) as brown pale solid.

$^1$H NMR (400 MHz, DMSO-$d_6$) δ ppm 10.06 (s, 1 H), 8.14-8.27 (m, 2 H), 7.70-7.81 (m, 1 H), 7.38-7.63 (m, 2 H), 7.02-7.12 (m, 3 H), 6.89-6.98 (m, 2 H), 6.84-6.89 (m, 1 H), 6.75-6.82 (m, 1 H), 6.59-6.69 (m, 1 H), 6.21-6.45 (m, 1 H), 4.12-4.43 (m, 2 H), 1.68-1.96 (d, 3 H). UPLC-MS: 4.22 min, 507.9 [M+H]+, method 6.

Example 80

4-(1H-pyrazol-4-yl)-3-(1-(thieno[3,2-d]pyrimidin-4-ylamino)ethyl)-1H-isochromen-1-one hydrochloride

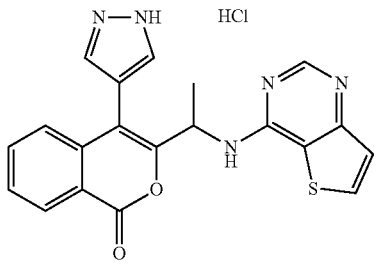 [SMILES: Cl ; CC(Nc1ncnc2ccsc12)c1oc(=O)c2ccccc2c1-c1cn[nH]c1]

3-(1-aminoethyl)-4-(1H-pyrazol-4-yl)-1H-isochromen-1-one dihydrochloride (Intermediate E4, 62 mg, 0.189 mmol), 4-chlorothieno[3,2-d]pyrimidine (45.1 mg, 0.264 mmol), TEA (0.092 ml, 0.661 mmol) were reacted in t-BuOH (1.1 ml) at 85° C. for 2 hrs and 90° C. for 4 hrs. The reaction was quenched by the addition of 1M HCl$_{aqueous}$ (2 ml) and purified via reverse phase chromatography using a Biotage C18 60 g SNAP with a gradient of water and acetonitrile to give the title compound (24 mg, 29.8%) as yellowish solid.

$^1$H NMR (400 MHz, DMSO-$d_6$) δ ppm 10.08 (br. s., 1 H), 8.81 (s, 1 H), 8.46 (d, J=5.29 Hz, 1 H), 8.19 (d, J=7.50 Hz, 1 H), 7.82 (m, 3 H), 7.62 (t, J=7.50 Hz, 1 H), 7.48 (m, 1 H), 7.22 (d, J=7.94 Hz, 1 H), 5.32 (t, J=6.84 Hz, 1 H), 1.60 (d, 3 H). UPLC-MS: 0.63 min, 390.0 [M+H]+, method 9

Example 81

4-(5-(morpholinomethyl)thiophen-2-yl)-3-(1-(thieno[3,2-d]pyrimidin-4-ylamino)ethyl)-1H-isochromen-1-one hydrochloride

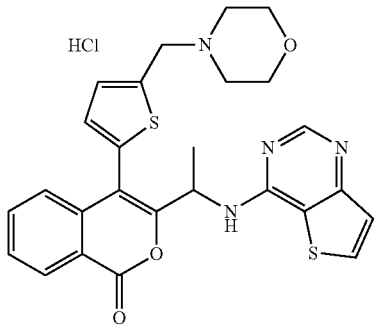 [SMILES: CC(Nc1ncnc2ccsc12)c1oc(=O)c2ccccc2c1-c1ccc(CN2CCOCC2)s1 ; Cl]

The title compound was made in a similar way as that of the compound of example 80, from 3-(1-aminoethyl)-4-(5-(morpholinomethyl)thiophen-2-yl)-1H-isochromen-1-one dihydrochloride (Intermediate E3, 80 mg, 0.180 mmol) and 4-chlorothieno[3,2-d]pyrimidine (43.1 mg, 0.253 mmol) to give the title compound (52 mg, 53.3%) as yellowish solid.

$^1$H NMR (400 MHz, DMSO-$d_6$) δ ppm 11.12-11.64 (bs, 1 H), 9.50-9.92 (bs, 1 H), 8.79 (br. s., 1 H), 8.38 (d, J=4.85 Hz, 1 H), 8.20 (d, J=7.94 Hz, 1 H), 7.84 (m, 1 H), 7.57-7.72 (m, 1 H), 7.39-7.56 (m, 2 H), 7.33 (m 1 H), 7.22 (d, J=7.94 Hz, 1 H), 5.27 (t, 1 H), 4.65 (br. s., 2 H), 3.68-4.13 (m, 4 H), 3.15 (m, 4 H), 1.62 (d, J=7.06 Hz, 3H). UPLC-MS: 6.38 min, 504.9 [M+H]+, method 8.

Example 82

4-amino-6-((1-(4-(5-(morpholinomethyl)thiophen-2-yl)-1-oxo-1H-isochromen-3-yl)ethyl)amino)pyrimidine-5-carbonitrile hydrochloride

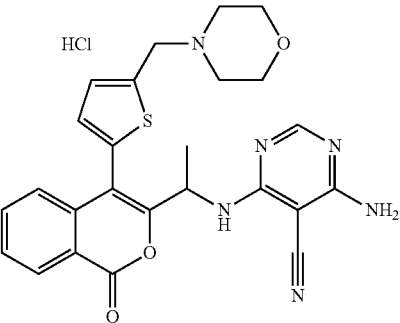 [SMILES: CC(Nc1ncnc(N)c1C#N)c1oc(=O)c2ccccc2c1-c1ccc(CN2CCOCC2)s1 ; Cl]

The title compound was made in a similar way as that of the compound of example 80, from 3-(1-aminoethyl)-4-(5-(morpholinomethyl)thiophen-2-yl)-1H-isochromen-1-one dihydrochloride (Intermediate E3, 60 mg, 0.135 mmol) and 4-amino-6-chloropyrimidine-5-carbonitrile (29.3 mg, 0.189 mmol) to give the title compound (4 mg, 5.6%) as yellowish solid.

$^1$H NMR (400 MHz, DMSO-$d_6$) δ ppm 11.24 (br. s., 1 H), 8.22 (d, J=7.94 Hz, 1 H), 8.14 (br. s., 1 H), 8.08 (s, 1 H), 7.83 (t, J=7.72 Hz, 1 H), 7.64 (t, J=7.50 Hz, 3 H), 7.49 (d, J=3.09 Hz, 1 H), 7.24 (d, J=3.53 Hz, 1 H), 7.17 (d, J=8.38 Hz, 1 H), 5.11 (t, J=6.84 Hz, 1 H), 4.63 (br. s., 2 H), 4.00 (d, J=11.91 Hz, 2 H), 3.78 (d, J=7.50 Hz, 2 H), 3.32 (d, J=11.91 Hz, 2 H), 3.12 (br. s., 2 H), 1.49 (d, J=7.06 Hz, 3 H). UPLC-MS: 1.87 min, 488.9 [M+H]+, method 6

Example 83

4-phenyl-3-(1-(pyrrolo[2,1-f][1,2,4]triazin-4-ylamino)ethyl)-1H-isochromen-1-one

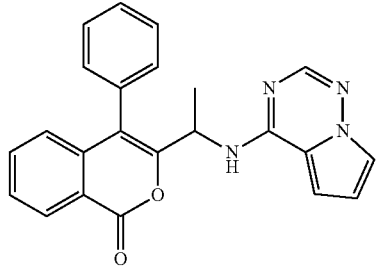 [SMILES: CC(Nc1ncnn2cccc12)c1oc(=O)c2ccccc2c1-c1ccccc1]

The title compound was made in a similar way as that of the compound of example 80, from 3-(1-aminoethyl)-4-phenyl-1H-isochromen-1-one hydrochloride (Intermediate E2, 50 mg, 0.166 mmol) and 4-chloropyrrolo[2,1-f][1,2,4]triazine (35.6 mg, 0.232 mmol) to give the title compound (50.3 mg, 79%) as whitish solid.

$^1$H NMR (400 MHz, DMSO-$d_6$) δ ppm 8.53 (d, J=6.62 Hz, 1 H), 8.20 (d, J=7.94 Hz, 1 H), 7.72-7.87 (m, 2 H), 7.45-7.66 (m, 6 H), 7.39 (d, J=7.06 Hz, 1 H), 7.04 (d, J=3.97 Hz, 1 H), 6.93 (d, J=8.38 Hz, 1 H), 6.47-6.69 (m, 1 H), 5.01 (t, J=7.06 Hz, 1 H), 1.52 (d, J=7.06 Hz, 3 H). UPLC-MS: 5.15 min, 383.0 [M+H]+, method 6.

Example 84

4-phenyl-3-(1-(pyrido[3,2-d]pyrimidin-4-ylamino)ethyl)-1H-isochromen-1-one

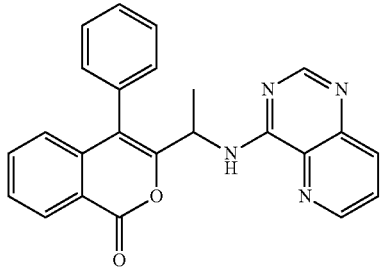 [SMILES: CC(Nc1ncnc2cccnc12)c1oc(=O)c2ccccc2c1-c1ccccc1]

The title compound was made in a similar way as that of the compound of example 80, from 3-(1-aminoethyl)-4-phenyl-1H-isochromen-1-one hydrochloride (Intermediate E2, 50 mg, 0.166 mmol) and 4-chloropyrido[3,2-d]pyrimidine (38.4 mg, 0.232 mmol) to give the desired product (2.2 mg, 3.4%).

$^1$H NMR (400 MHz, DMSO-$d_6$) δ ppm 8.81-9.08 (m, 2 H), 8.54 (s, 1 H), 8.10-8.24 (m, 2 H), 7.91 (dd, J=8.38, 3.97 Hz, 1 H), 7.71-7.80 (m, 1 H), 7.45-7.64 (m, 5 H), 7.41 (d, J=7.50 Hz, 1 H), 6.93 (d, J=7.94 Hz, 1 H), 5.11 (t, J=7.06 Hz, 1 H), 1.60 (d, J=7.06 Hz, 3 H). UPLC-MS: 4.13 min, 395.0 [M+H]+, method 6.

Example 87

N-(5-(4-amino-1-(1-(1-oxo-4-phenyl-1H-isochromen-3-yl)ethyl)-1H-pyrazolo[3,4-d]pyrimidin-3-yl)pyridin-3-yl)-4-fluorobenzenesulfonamide

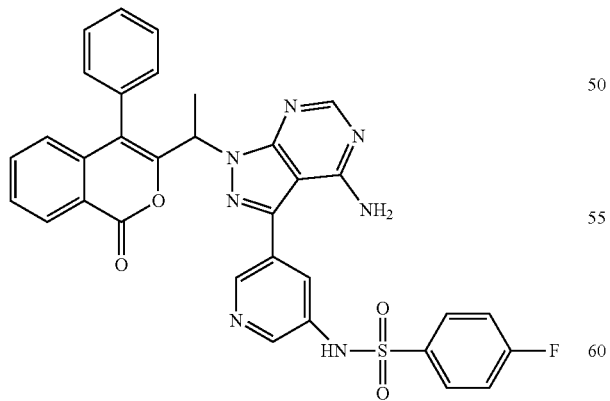

The title compound was made in a similar way as that of the compound of example 52 from 4-fluoro-N-(5-(trimethylstannyl)pyridin-3-yl)benzenesulfonamide (Intermediate G9, 98 mg, 0.236 mmol) and 3-(1-(4-amino-3-iodo-1H-pyrazolo[3, 4-d]pyrimidin-1-yl)ethyl)-4-phenyl-1H-isochromen-1-one (intermediate D2a, 60 mg, 0.118 mmol) affording the title compound (13 mg, 0.021 mmol, 17.4% yield) as white solid $^1$H NMR (400 MHz, DMSO-$d_6$) δ ppm 10.94 (br. s., 1 H), 8.50 (d, J=1.76 Hz, 1 H), 8.43 (d, J=2.21 Hz, 1 H), 8.17-8.27 (m, 2 H), 7.81-7.96 (m, 3 H), 7.73-7.80 (m, 3 H), 7.63 (m, 1 H), 7.48-7.58 (m, 1 H), 7.33-7.47 (m, 5 H), 7.12 (d, J=7.06 Hz, 1 H), 6.89 (d, J=8.38 Hz, 1 H), 5.77 (q, J=7.06 Hz, 1 H), 1.85 (d, J=7.06 Hz, 4 H). UPLC-MS: 1.13 min, 634 [M+H]+, method 9.

Example 88

3-(1-(4-amino-3-(5-aminopyridin-3-yl)-1H-pyrazolo[3,4-d]pyrimidin-1-yl)ethyl)-4-phenyl-1H-isochromen-1-one hydrochloride

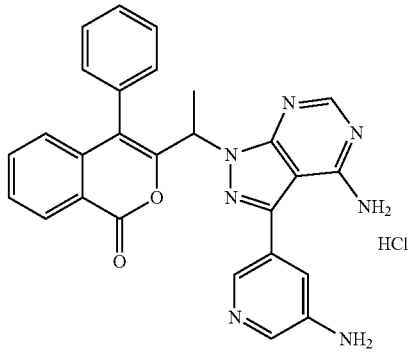 [SMILES: CC(c1oc(=O)c2ccccc2c1-c1ccccc1)n1nc(-c2cncc(N)c2)c2c(N)ncnc21 ; Cl]

The title compound was made in a similar way as that of the compound of example 52, from 3-(1-(4-amino-3-iodo-1H-pyrazolo[3,4-d]pyrimidin-1-yl)ethyl)-4-phenyl-1H-isochromen-1-one (intermediate D2a, 80 mg, 0.157 mmol) and tert-butyl 5-(trimethylstannyl)pyridin-3-ylcarbamate (Intermediate G10, 112 mg, 0.314 mmol) to give the title compound (14 mg, 0.029 mmol, 18.74% yield) as a white powder.

$^1$H NMR (400 MHz, DMSO-$d_6$) δ ppm 8.01-8.28 (m, 4 H), 7.76 (d, J=14.11 Hz, 2 H), 7.63 (m, 1 H), 7.53 (m, 1 H), 7.32-7.47 (m, 3 H), 7.14 (m, 1 H), 6.90 (d, J=7.94 Hz, 1 H), 6.47-6.80 (m, 1 H), 5.78 (d, J=7.06 Hz, 1 H), 1.85 (d, J=7.06 Hz, 3 H). UPLC-MS: 0.80 min, 476 [M+H]+, method 9.

Example 89

3-(1-(4-amino-3-(2-aminopyrimidin-4-yl)-1H-pyrazolo[3,4-d]pyrimidin-1-yl)ethyl)-4-phenyl-1H-isochromen-1-one hydrochloride

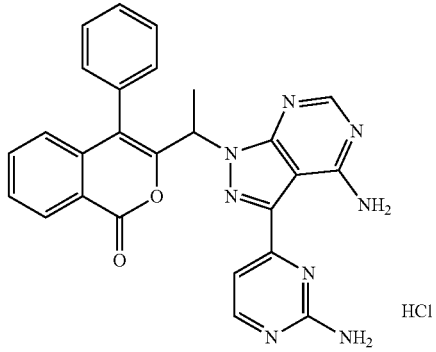 [SMILES: CC(c1oc(=O)c2ccccc2c1-c1ccccc1)n1nc(-c2ccnc(N)n2)c2c(N)ncnc21 ; Cl]

To a solution of triphenylphosphine (16.48 mg, 0.063 mmol) in dry dioxane (6 mL), 3-(1-(4-amino-3-iodo-1H-pyrazolo[3,4-d]pyrimidin-1-yl)ethyl)-4-phenyl-1H-isochromen-1-one (intermediate D2a, 80 mg, 0.157 mmol), copper (I) iodide (5.98 mg, 0.031 mmol), 4-trimethylstannyl-2-amino-bis(tertbutylcarbamate)-pyrimidine (Intermediate G11, 144 mg, 0.314 mmol), Bis(dibenzylideneacetone)palladium(0) (18.06 mg, 0.031 mmol) and lithium chloride (19.98 mg, 0.471 mmol) were added. Nitrogen was bubbled into solution for 10 min, solution was heated to 80° C. and stirred overnight. Solvent was removed under reduced pressure and product was purified by Biotage Si 10 g eluent with a gradient of DCM and ethanol affording a yellow solid. This compound was dissolved in 4M HCl in 1,4 dioxane and stirred for 8 hrs at room temperature. Solvent was removed and product was straightforward purified via reverse phase chromatography with a Biotage C18 10 g column (Phase A, water 95%, ACN 5%, formic acid 0.1%); (Phase B ACN 95%, water 5%, formic acid 0.1%) to give the title compound (6.6 mg, 7.5%) as a white powder.

$^1$H NMR (400 MHz, DMSO-d$_6$) δ ppm 8.51-8.71 (bs, 1 H), 8.39-8.49 (m, 1 H), 8.33 (s, 1 H), 8.22 (d, J=7.50 Hz, 1 H), 7.72-7.87 (m, 1 H), 7.59-7.70 (m, 2 H), 7.51-7.58 (m, 1 H), 7.31-7.50 (m, 4 H), 7.19 (d, J=7.06 Hz, 1 H), 6.91 (d, J=7.94 Hz, 1 H), 5.68-5.85 (m, 1 H), 4.27-4.39 (m, 1 H), 1.89 (d, J=7.06 Hz, 3 H). UPLC-MS: 3.91 min, 477 [M+H]+, method 6.

Example 90

3-(1-(4-amino-3-(6-hydroxypyrazin-2-yl)-1H-pyrazolo[3,4-d]pyrimidin-1-yl)ethyl)-4-phenyl-1H-isochromen-1-one

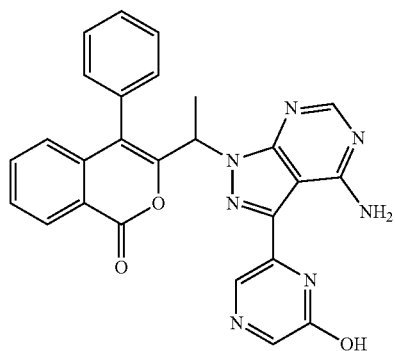 [SMILES: CC(c1oc(=O)c2ccccc2c1-c1ccccc1)n1nc(-c2cncc(O)n2)c2c(N)ncnc21]

The title compound was made in a similar way as that of the compound of example 89 from 3-(1-(4-amino-3-iodo-1H-pyrazolo[3,4-d]pyrimidin-1-yl)ethyl)-4-phenyl-1H-isochromen-1-one (intermediate D2a, 120 mg, 0.236 mmol) and 2-methoxy-6-(tributylstannyl)pyrazine (188 mg, 0.471 mmol) to give the title compound (25 mg, 36.8%) as a white powder.

$^1$H NMR (400 MHz, DMSO-d$_6$) δ ppm 8.85 (s, 1 H), 8.11-8.23 (m, 3 H), 7.86-7.96 (m, 1 H), 7.68-7.80 (m, 1 H), 7.56-7.63 (m, 1 H), 7.48-7.55 (m, 1 H), 7.33-7.46 (m, 3 H), 7.12-7.24 (m, 1 H), 6.80-6.91 (m, 1 H), 5.65-5.80 (m, 1 H), 1.78-1.97 (m, 3 H).

UPLC-MS: 4.08 min, 478 [M+H]+, method 6.

Example 91

3-(1-(4-amino-3-(5-hydroxypyridin-3-yl)-1H-pyrazolo[3,4-d]pyrimidin-1-yl)ethyl)-4-phenyl-1H-isochromen-1-one

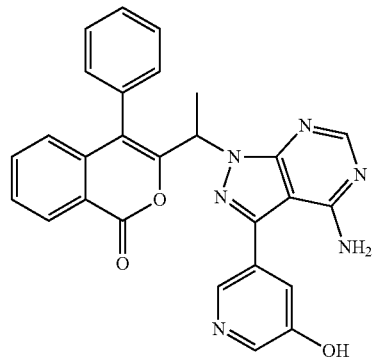 [SMILES: CC(c1oc(=O)c2ccccc2c1-c1ccccc1)n1nc(-c2cncc(O)c2)c2c(N)ncnc21]

The title compound was made in a similar way as that of the compound of example 89 from of 3-(1-(4-amino-3-iodo-1H-pyrazolo[3,4-d]pyrimidin-1-yl)ethyl)-4-phenyl-1H-isochromen-1-one (intermediate D2a, 804 mg, 1.579 mmol) and 3-methoxy-5-(tributylstannyl)pyridine (1257 mg, 3.16 mmol) at 120° C. overnight. Solvent was removed, and product was purified by Biotage Si 25 g with a gradient of DCM and EtOH affording a as yellow pale solid (500 mg). This material was dissolved in dry DCM (10 mL), 1M BBr$_3$ in DCM (24 ml) was added and the solution was stirred at room temperature for 48 hrs. Then, solution was cooled to 0° C. and dry ethanol (10 ml) was added. Solvent was evaporate and product was straightforward purified via reverse phase chromatography with a Biotage C18 SNAP column (Phase A, water 95%, ACN 5%, formic acid 0.1%); (Phase B ACN 95%, water 5%, formic acid 0.1%) affording the title compound as white solid. Then, product was dissolved in a mixture of DCM (100 ml) and EtOH (5 ml) and the solution was washed with saturated solution of aqueous NaHCO$_3$. aqueous phase was extracted with DCM (5×50 ml). Organic phases were collected, dried and solvent evaporated to dryness affording desired product affording the title compound (331 mg, 0.695 mmol, 68.4% yield) as a white solid.

$^1$H NMR (400 MHz, DMSO-d$_6$) δ ppm 8.21 (d, J=7.94 Hz, 1 H), 8.07 (s, 1 H), 7.75 (t, J=7.50 Hz, 2 H), 7.61 (t, J=7.50 Hz, 2 H), 7.51 (d, J=7.50 Hz, 1 H), 7.42 (m, 3 H), 7.12 (d, J=7.50 Hz, 1 H), 6.88 (d, J=7.94 Hz, 1 H), 6.67-6.83 (bs, 1 H), 5.69 (d, J=7.06 Hz, 1 H), 1.83 (d, J=7.06 Hz, 3 H). UPLC-MS: 3.40 min, 477 [M+H]+, method 6

Example 92

3-(1-(4-amino-3-(3-fluoro-5-hydroxyphenyl)-1H-pyrazolo[3,4-d]pyrimidin-1-yl)ethyl)-4-(8-methyl-8-azabicyclo[3.2.1]oct-2-en-3-yl)-1H-isochromen-1-one hydrochloride

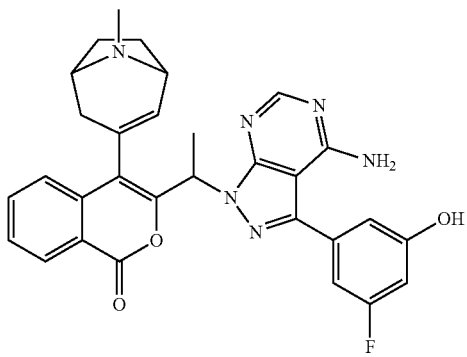 [SMILES: CC(c1oc(=O)c2ccccc2c1C1=CC2CCC(C1)N2C)n1nc(-c2cc(O)cc(F)c2)c2c(N)ncnc21]

Step a. Benzyl 3-(3-(1-(4-amino-3-(3-fluoro-5-methoxyphenyl)-1H-pyrazolo[3,4-d]pyrimidin-1-yl)ethyl)-1-oxo-1H-isochromen-4-yl)-8-azabicyclo[3.2.1]oct-2-ene-8-carboxylate

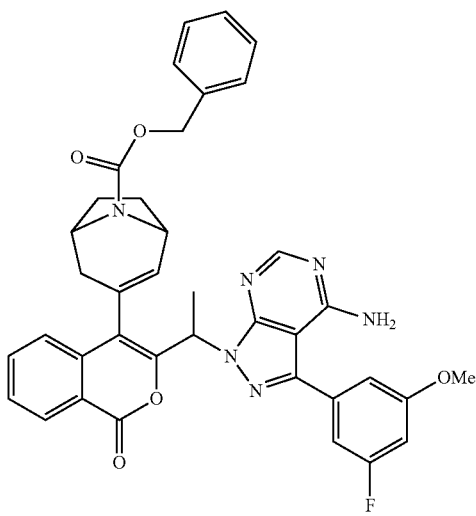 [SMILES: COc1cc(F)cc(-c2nn(C(C)c3oc(=O)c4ccccc4c3C3=CC4CCC(C3)N4C(=O)OCc3ccccc3)c3ncnc(N)c23)c1]

Title compound was prepared following the procedure described for the synthesis of Intermediate D1, from 3-(3-fluoro-5-methoxyphenyl)-1H-pyrazolo[3,4-d]pyrimidin-4-amine (Intermediate G1, 52.4 mg, 0.202 mmol) and benzyl 3-(3-(1-bromoethyl)-1-oxo-1H-isochromen-4-yl)-8-azabicyclo[3.2.1]oct-2-ene-8-carboxylate (Intermediate C40, 100 mg, 0.202 mmol) to give Benzyl 3-(3-(1-(4-amino-3-(3-fluoro-5-methoxyphenyl)-1H-pyrazolo[3,4-d]pyrimidin-1-yl)ethyl)-1-oxo-1H-isochromen-4-yl)-8-azabicyclo[3.2.1]oct-2-ene-8-carboxylate (125 mg, 0.186 mmol, 92% yield) as a yellow solid.

UPLC-MS: 1.28 min, 673 [M+H]+, method 9

Step b

To a solution of 3-(1-(4-amino-3-(3-fluoro-5-methoxyphenyl)-1H-pyrazolo[3,4-d]pyrimidin-1-yl)ethyl)-4-(8-azabicyclo[3.2.1]oct-2-en-3-yl)-1H-isochromen-1-one (80 mg, 0.149 mmol) in IPrOH (10 ml) and N aqueous HCl (1 ml), Pd/C 5% wet (10 mg, 0.149 mmol) was added. The resulting suspension was stripped under reduced pressure and the flask was filled with hydrogen (1 atm) for 10 min. Then, catalyst was filtered off and solvent was removed under reduced pressure. Crude compound was dissolved in dry DCM (5 ml), N-isopropyl-N-methylpropan-2-amine (0.023 ml, 0.149 mmol), trioxane (0.031 ml, 0.297 mmol) were added and the solution stirred at room temperature. After 30 min, sodiotriacetoxyborohydride (94 mg, 0.446 mmol) and acetic acid (0.026 ml, 0.446 mmol) were added and the reaction was stirred for further 1 h. Then, solvent was removed and the crude was purified was purified via reverse phase chromatography with a Biotage C18 SNAP column (Phase A, water 95%, ACN 5%, formic acid 0.1%); (Phase B ACN 95%, water 5%, formic acid 0.1%) affording 40 mg of white powder. This material was dissolved in DCM (3 ml) and 1 M BBr$_3$ in DCM (1.448 ml) was added and the solution was stirred for 4 hrs. Then, reaction was cooled to 0° C. and EtOH (1 ml) was added. Solvent was removed and the product was purified by C18 flash chromatography ((H$_2$O/ACN)) 95:5+0.1% HCOOH}:{(ACN/H$_2$O) 95:5+HCOOH 0.1%} from 100:0 to 0:100 affording the title compound (13 mg, 0.037 mmol, 31.2% yield) as a white solid.

$^1$H NMR (600 MHz, DMSO-d$_6$) δ ppm 10.06-10.65 (bs, 2 H), 6.61-8.42 (m, 11 H), 6.23-6.45 (m, 1 H), 5.85-6.12 (m, 1 H), 4.03-4.53 (m, 2 H), 1.79-3.31 (m, 9 H). UPLC-MS: 2.46 min, 539.1 [M+H]+, method 6.

Example 103

3-(1-(4-amino-3-(3-fluoro-5-hydroxyphenyl)-1H-pyrazolo[3,4-d]pyrimidin-1-yl)ethyl)-4-(4-aminocyclohex-1-en-1-yl)-1H-isochromen-1-one hydrochloride

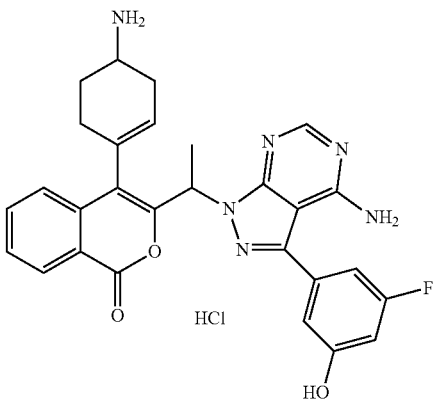 [SMILES: CC(c1oc(=O)c2ccccc2c1C1=CCC(N)CC1)n1nc(-c2cc(O)cc(F)c2)c2c(N)ncnc21 ; Cl]

To a solution of 3-(3-fluoro-5-methoxyphenyl)-1H-pyrazolo[3,4-d]pyrimidin-4-amine (Intermediate G1, 81 mg, 0.311 mmol) in dry DMF (4 ml), potassium carbonate (86 mg, 0.622 mmol) was added and the suspension was stirred for 10 min at room temperature. Then, benzyl (4-(3-(1-bromoethyl)-1-oxo-1H-isochromen-4-yl)cyclohex-3-en-1-yl)carbamate (intermediate C32, 150 mg, 0.311 mmol) was added and the solution was stirred at 60° C. for 2 hrs. Then, DMF was removed and the product was purified by Biotage Si 10 g with a gradient of DCM and EtOH. The recovered material (37 mg) was reacted with a 1 M boron tribromide in DCM (0.280 ml) in dry DCM (4 ml) for 18 hrs. Solvent was removed and the product was product was straightforward purified via reverse phase chromatography with a Biotage C18 SNAP column (Phase A, water 95%, ACN 5%, formic acid 0.1%); (Phase B ACN 95%, water 5%, formic acid 0.1%) to give the title compound (10 mg, 34.8% yield) as a white solid.

$^1$H NMR (400 MHz, DMSO-$d_6$) δ ppm 10.21 (m, 1 H), 6.55-8.44 (m, 13 H), 6.00-6.42 (m, 1 H), 5.94 (br s, 1 H), 1.66-2.84 (m, 10 H). UPLC-MS: 2.29 min, 513.0 [M+H]+, method 6.

Example 104

3-(1-(4-amino-3-(trifluoromethyl)-1H-pyrazolo[3,4-d]pyrimidin-1-yl)ethyl)-4-phenyl-1H-isochromen-1-one

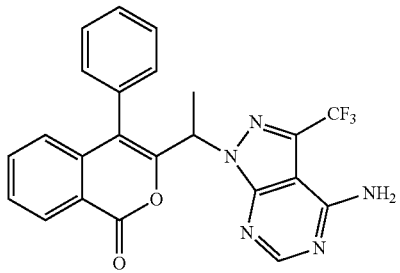 [SMILES: CC(c1oc(=O)c2ccccc2c1-c1ccccc1)n1nc(C(F)(F)F)c2c(N)ncnc21]

The title compound was made in a similar way as that of the compound of example 1 using 3-(trifluoromethyl)-1H-pyrazolo[3,4-d]pyrimidin-4-amine (Intermediate G16, 45 mg, 0.222 mmol) 3-(1-bromoethyl)-4-phenyl-1H-isochromen-1-one (intermediate C7, 72.9 mg, 0.222 mmol). to give the title compound (15 mg, 0.033 mmol, 15.0% yield) as white solid.

$^1$H NMR (400 MHz, DMSO-$d_6$) δ ppm 8.03-8.29 (m, 2 H), 7.77 (s, 1 H), 7.63 (s, 1 H), 7.48-7.55 (m, 1 H), 7.36-7.48 (m, 3 H), 7.14-7.21 (m, 1 H), 6.89 (d, J=7.94 Hz, 1 H), 5.59-5.88 (m, 1 H), 1.82 (d, J=7.06 Hz, 3 H). UPLC-MS: 4.79 min, 452.03 [M+H]+, method 6.

Example 105

3-(1-(4-amino-3-methyl-1H-pyrazolo[3,4-d]pyrimidin-1-yl)ethyl)-4-phenyl-1H-isochromen-1-one

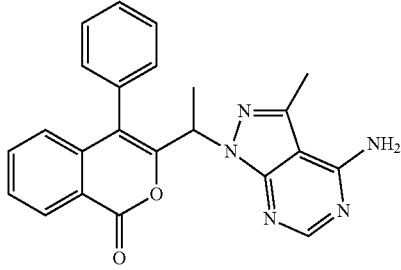 [SMILES: Cc1nn(C(C)c2oc(=O)c3ccccc3c2-c2ccccc2)c2ncnc(N)c12]

The title compound was made in a similar way as that of the compound of example 1, using 3-(1-bromoethyl)-4-phenyl-1H-isochromen-1-one (intermediate C7, 100 mg, 0.304 mmol) and 3-methyl-1H-pyrazolo[4,3-d]pyrimidin-7-amine (45.3 mg, 0.304 mmol) affording the title compound (20 mg, 16.6% yield) as a white powder.

$^1$H NMR (400 MHz, DMSO-$d_6$) δ ppm 8.22 (m, 3 H), 8.15 (s, 1 H), 7.72-7.82 (m, 1 H), 7.63 (m, 1 H), 7.52-7.58 (m, 1 H), 7.32-7.50 (m, 3 H), 7.06-7.13 (m, 1 H), 6.89 (d, J=8.38 Hz, 1 H), 5.48-5.71 (m, 1 H), 2.56 (s, 3 H), 1.78 (d, J=7.06 Hz, 3 H). UPLC-MS: 3.42 min, 398 [M+H]+, method 6

Example 106

3-(1-(4-amino-7H-pyrrolo[2,3-d]pyrimidin-7-yl)ethyl)-4-phenyl-1H-isochromen-1-one

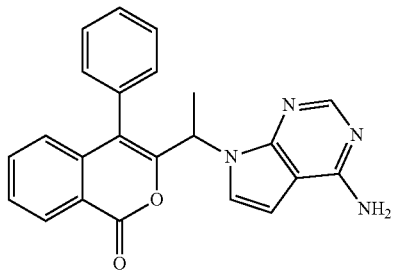 [SMILES: CC(c1oc(=O)c2ccccc2c1-c1ccccc1)n1ccc2c(N)ncnc21]

The title compound was made in a similar way as that of the compound of example 1 using 3-(1-bromoethyl)-4-phenyl-1H-isochromen-1-one (intermediate C7, 50 mg, 0.15 mmol), 7H-pyrrolo[2,3-d]pyrimidin-4-amine (30.6 mg, 0.23 mmol) to give the title compound (16 mg, 28%).

$^1$H NMR (400 MHz, methanol-$d_4$) δ ppm 8.30 (dd, J=7.94, 0.88 Hz, 1 H), 8.26 (s, 1 H), 7.93 (s, 1 H), 7.66-7.73 (m, 1 H), 7.57 (d, J=7.94 Hz, 2 H), 7.45 (d, J=3.53 Hz, 2 H), 7.37 (m, 2 H), 7.01 (dd, J=14.11, 7.94 Hz, 2 H), 6.64 (d, J=3.97 Hz, 1 H), 5.80 (q, J=7.06 Hz, 1 H), 1.78 (d, J=7.06 Hz, 3 H). UPLC-MS: 1.66 min, 383 [M+H]+, method 4.

Example 107

3-(1-(2,6-diamino-9H-purin-9-yl)ethyl)-4-phenyl-1H-isochromen-1-one

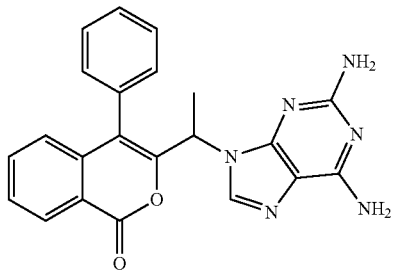 [SMILES: CC(c1oc(=O)c2ccccc2c1-c1ccccc1)n1cnc2c(N)nc(N)nc21]

The title compound was made in a similar way as that of the compound of example 1 from 3-(1-bromoethyl)-4-phenyl-1H-isochromen-1-one (intermediate C7, 50 mg, 0.15 mmol) and 9H-purine-2,6-diamine (34 mg, 0.23 mmol) to give the title compound (19 mg, 31%).

¹H NMR (400 MHz, DMSO-d₆) δ ppm 8.21 (d, J=7.50 Hz, 1 H), 7.94 (s, 1 H), 7.73-7.85 (m, 1 H), 7.49-7.70 (m, 5 H), 7.42 (d, J=7.06 Hz, 1 H), 6.94 (d, J=7.94 Hz, 1 H), 6.65 (br. s., 2 H), 5.57 (s, 2 H), 5.20 (q, J=7.35 Hz, 1 H), 1.74 (d, J=7.06 Hz, 3 H). UPLC-MS: 4.61 min, 399 [M+H]+, method 3.

Example 108

4-phenyl-3-(1-(thieno[2,3-d]pyrimidin-4-ylamino)ethyl)-1H-isochromen-1-one

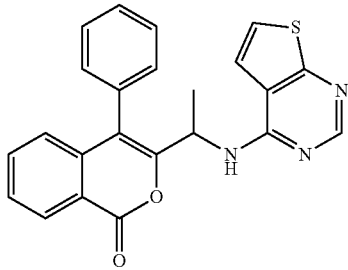 [SMILES: CC(Nc1ncnc2sccc12)c1oc(=O)c2ccccc2c1-c1ccccc1]

3-(1-aminoethyl)-4-phenyl-1H-isochromen-1-one hydrochloride (intermediate E2 50 mg, 0.166 mmol), 4-chlorothieno[2,3-d]pyrimidine (36.8 mg, 0.215 mmol), triethylamine (0.046 ml, 0.331 mmol) were reacted in 2-methylpropan-2-ol (1 ml) at 80° C. for 6 hrs and at 50° C. for 60 hrs. 4-Chlorothieno[2,3-d]pyrimidine (5.7 mg, 0.033 mmol), triethylamine (0.09 ml, 0.066 mmol) were added and the mixture reacted at 90° C. for 4 hrs. The crude was purified via reverse phase chromatography with a Biotage C18 30 g SNAP column (Phase A, water 95%, ACN 5%, formic acid 0.1%); Phase B ACN 95%, water 5%, formic acid 0.1%) to give the title compound (31 mg, 47%).

¹H NMR (400 MHz, DMSO-d₆) δ ppm 8.17-8.31 (m, 3 H), 7.73-7.82 (m, 2 H), 7.47-7.63 (m, 6 H), 7.39 (d, J=6.62 Hz, 1 H), 6.94 (d, J=7.94 Hz, 1 H), 5.02 (t, J=7.06 Hz, 1H), 1.54 (d, J=7.06 Hz, 3 H). UPLC-MS: 5.10 min, 400 [M+H]+, method 6.

Example 109

4-phenyl-3-(1-(thieno[3,2-d]pyrimidin-4-ylamino)ethyl)-1H-isochromen-1-one

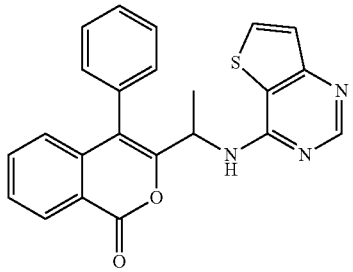 [SMILES: CC(Nc1ncnc2ccsc12)c1oc(=O)c2ccccc2c1-c1ccccc1]

3-(1-aminoethyl)-4-phenyl-1H-isochromen-1-one hydrochloride (intermediate E2, 50 mg, 0.166 mmol), 4-chlorothieno[3,2-d]pyrimidine (36.8 mg, 0.215 mmol), triethylamine (0.046 ml, 0.331 mmol) were reacted in 2-methylpropan-2-ol (1 ml) at 50° C. for 24 hrs and at 80° C. for 27 hrs. 4-Chlorothieno[2,3-d]pyrimidine (5.7 mg, 0.033 mmol), triethylamine (0.09 ml, 0.066 mmol) were added and the mixture reacted at 90° C. for 4 hrs. The crude was purified via reverse phase chromatography with a Biotage C18 30 g SNAP column (Phase A, water 95%, ACN 5%, formic acid 0.1%); Phase B ACN 95%, water 5%, formic acid 0.1%) to give the title compound (33 mg, 50%).

¹H NMR (400 MHz, DMSO-d₆) δ ppm 8.27-8.37 (m, 2 H), 8.17-8.24 (m, 1 H), 8.06-8.15 (m, 1 H), 7.68-7.83 (m, 1 H), 7.49-7.65 (m, 5 H), 7.28-7.45 (m, 2 H), 6.85-7.01 (m, 1 H), 4.84-5.09 (m, 1 H), 1.40-1.58 (m, 3 H). UPLC-MS: 3.84 min, 400 [M+H]+, method 6.

Example 110

2-amino-N-(1-(1-oxo-4-phenyl-1H-isochromen-3-yl)ethyl)pyrazolo[1,5-a]pyrimidine-3-carboxamide

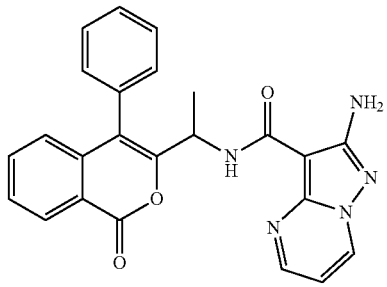 [SMILES: CC(NC(=O)c1c(N)nn2cccnc12)c1oc(=O)c2ccccc2c1-c1ccccc1]

3-(1-aminoethyl)-4-phenyl-1H-isochromen-1-one hydrochloride (intermediate E2, 50 mg, 0.166 mmol), 2-aminopyrazolo[1,5-a]pyrimidine-3-carboxylic acid (32.5 mg, 0.182 mmol), HOBt (30.4 mg, 0.199 mmol), HBTU (17.25 mg, 0.033 mmol) and DIPEA (61.0 µl, 0.349 mmol) were reacted in DCM (1 ml) at RT for 18 hrs. The crude was purified via reverse phase chromatography with a Biotage C18 30 g SNAP column (Phase A, water 95%, ACN 5%, formic acid 0.1%); Phase B ACN 95%, water 5%, formic acid 0.1%) to give the title compound (20 mg, 28%).

¹H NMR (400 MHz, DMSO-d₆) δ 8.86-8.97 (m, 1 H), 8.48-8.62 (m, 1 H), 8.19-8.31 (m, 1 H), 7.97-8.12 (m, 1 H), 7.72-7.83 (m, 1 H), 7.46-7.66 (m, 5 H), 7.34-7.45 (m, 1 H), 6.98-7.09 (m, 1 H), 6.85-6.96 (m, 1 H), 6.36 (s, 2 H), 4.70-5.02 (m, 1 H), 1.32-1.57 (d, 3 H). UPLC-MS: 4.29 min, 426 [M+H]+, method 6

Example 112

3-(1-(4-amino-3-(1H-indazol-4-yl)-1H-pyrazolo[3,4-d]pyrimidin-1-yl)ethyl)-4-phenyl-1H-isochromen-1-one

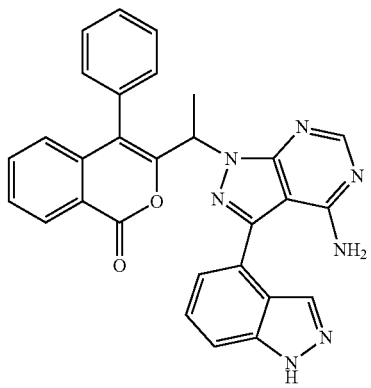 [SMILES: CC(c1oc(=O)c2ccccc2c1-c1ccccc1)n1nc(-c2cccc3[nH]ncc23)c2c(N)ncnc21]

The title compound was made in a similar way as that of the compound of example 52 from 3-(1-(4-amino-3-iodo-1H-pyrazolo[3,4-d]pyrimidin-1-yl)ethyl)-4-phenyl-1H-isochromen-1-one (intermediate D2a, 50 mg, 0.098 mmol), and 4-(trimethylstannyl)-1H-indazole (Intermediate G19, 41.4 mg, 0,147 mmol) to give the title compound (19 mg, 39%).

$^1$H NMR (400 MHz, DMSO-d$_6$) δ ppm 13.30 (s, 1 H), 8.13-8.27 (m, 2 H), 8.04-8.12 (m, 1 H), 7.70-7.79 (m, 1 H), 7.35-7.68 (m, 7 H), 7.25-7.34 (m, 1 H), 7.12-7.24 (m, 1 H), 6.82-6.96 (m, 1 H), 5.67-5.82 (m, 1 H), 1.68-1.97 (m, 3 H). UPLC-MS: 3.92 min, 500 [M+H]+, method 6

Example 115

3-(1-(6-amino-9H-purin-9-yl)ethyl)-4-(5-(morpholinomethyl)thiophen-2-yl)-1H-isochromen-1-one

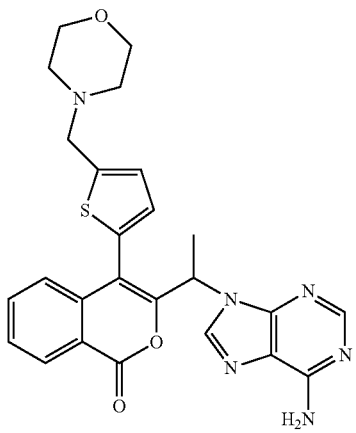 [SMILES: CC(c1oc(=O)c2ccccc2c1-c1ccc(CN2CCOCC2)s1)n1cnc2c(N)ncnc21]

3-(1-Bromoethyl)-4-(5-(morpholinomethyl)thiophen-2-yl)-1H-isochromen-1-one hydrobromide (intermediate C16, 52 mg, 0.113 mmol), N6,N6-bis(tert-Butoxycarbonyl)-adenine (74.1 mg, 0.221 mmol), K$_2$CO$_3$ (30.5 mg, 0.221 mmol) were reacted in DMF (0.5 ml) at 80° C. The crude was purified via reverse phase chromatography with a Biotage C18 30 g SNAP column (Phase A, water 95%, ACN 5%, formic acid 0.1%); Phase B ACN 95%, water 5%, formic acid 0.1%) and recovered material was then treated with HCl 37% before evaporation to give a crude that was further purified via reverse phase chromatography with a Biotage C18 12 g SNAP column (Phase A, water 95%, ACN 5%, formic acid 0.1%); Phase B ACN 95%, water 5%, formic acid 0.1%) to give the title compound (25 mg, 69%).

$^1$H NMR (400 MHz, DMSO-d$_6$) δ ppm 11.07-11.37 (bs, 1 H), 8.65 (s, 1 H), 8.31 (s, 2 H), 8.21 (d, J=7.50 Hz, 1 H), 7.95 (m, 1 H), 7.80-7.87 (m, 1 H), 7.62-7.72 (m, 1 H), 7.52 (d, J=2.65 Hz, 1 H), 7.29 (d, J=3.09 Hz, 1 H), 7.22 (d, J=7.94 Hz, 1 H), 5.68 (d, J=7.06 Hz, 1 H), 4.65 (s, 2 H), 4.01 (m, 4 H), 3.81 (m, 4 H), 3.28-3.40 (m, 4 H), 3.15 (m, 4 H), 1.92 (d, J=7.06 Hz, 3 H). UPLC-MS: 3.49 min, 489 [M+H]+, method 3.

Example 116

3-(1-(9H-purin-6-ylamino)ethyl)-4-(6-methoxypyridin-3-yl)-1H-isochromen-1-one

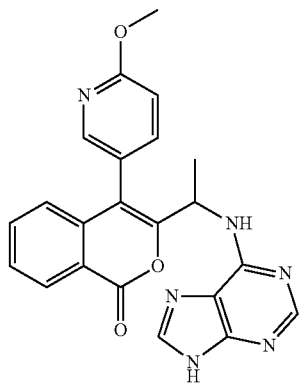 [SMILES: COc1ccc(-c2c(C(C)Nc3ncnc4[nH]cnc34)oc(=O)c3ccccc23)cn1]

The title compound was made in a similar way as that of the compound of example 21, from tert-Butyl 9-trityl-9H-purin-6-ylcarbamate (82 mg, 0.172 mmol) and 3-(1-bromoethyl)-4-(thiazol-5-yl)-1H-isochromen-1-one (intermediate C17, 100 mg, 0.194 mmol) to give the title compound (45 mg, 45.9%).

$^1$H NMR (400 MHz, DMSO-d$_6$) δ ppm 9.00-9.40 (bs, 1 H), 8.46 (br. s., 2 H), 8.14-8.35 (m, 2 H), 7.72-7.96 (m, 2 H), 7.63 (m, 1 H), 7.00 (m, 2 H), 5.08 (m, 1 H), 3.95 (s, 3 H), 1.42-1.73 (m, 3 H). UPLC-MS: 3.757 min, 415 [M+H]+, method 3

Example 117

3-(1-(9H-purin-6-ylamino)ethyl)-4-(thiazol-5-yl)-1H-isochromen-1-one

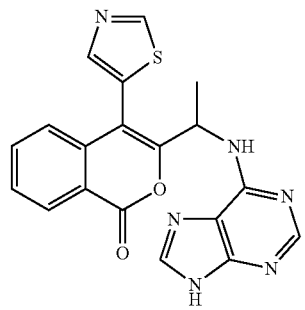 [SMILES: CC(Nc1ncnc2[nH]cnc12)c1oc(=O)c2ccccc2c1-c1cncs1]

The title compound was made in a similar way as that of the compound of example 21 from tert-Butyl 9-trityl-9H-purin-6-ylcarbamate (169 mg, 0.353 mmol) and 3-(1-bromoethyl)-4-(6-methoxypyridin-3-yl)-1H-isochromen-1-one (intermediate C12, 108 mg, 0.321 mmol) to give the title compound (12 mg, 17.7%).

$^1$H NMR (400 MHz, DMSO-d$_6$) δ ppm 9.55 (br. s., 1 H), 9.40 (s, 1 H), 8.45-8.64 (m, 2 H), 8.21 (d, J=7.50 Hz, 1 H), 8.11 (s, 1 H), 7.84 (t, J=7.72 Hz, 1 H), 7.65 (t, J=7.50 Hz, 1 H), 7.09 (d, J=7.94 Hz, 1 H), 5.16 (m, 1 H), 1.62 (d, J=7.06 Hz, 3 H). UPLC-MS: 4.14 min, 391 [M+H]+, method 7.

Example 122

3-(1-(9H-purin-6-ylamino)ethyl)-4-(1H-pyrazol-4-yl)-1H-isochromen-1-one

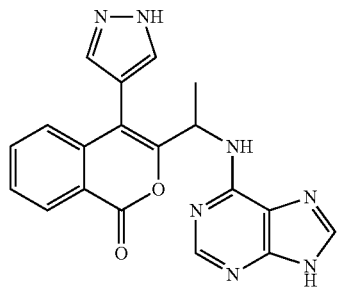 [SMILES: CC(Nc1ncnc2[nH]cnc12)c1oc(=O)c2ccccc2c1-c1cn[nH]c1]

The title compound was made in a similar way as that of the compound of example 43, from 3-(1-aminoethyl)-4-(1H-pyrazol-4-yl)-1H-isochromen-1-one dihydrochloride (intermediate E4, 50 mg, 0.152 mmol) 6-chloro-9H-purine (35.3 mg, 0.229 mmol) to give the title compound (19 mg, 30.4%).

$^1$H NMR (400 MHz, DMSO-d$_6$) δ ppm 9.13-9.44 (bs, 1 H), 8.52 (d, J=12.79 Hz, 2 H), 8.16 (d, J=7.50 Hz, 1 H), 7.73-7.88 (m, 3 H), 7.58 (m, 1 H), 7.19 (d, J=7.94 Hz, 1 H), 5.07-5.40 (m, 1 H), 1.54 (d, J=7.06 Hz, 3 H). UPLC-MS: 3.60 min, 374 [M+H]+, method 7.

Example 123

4-amino-6-((1-(1-oxo-4-(1H-pyrazol-4-yl)-1H-isochromen-3-yl)ethyl)amino)pyrimidine-5-carbonitrile hydrochloride

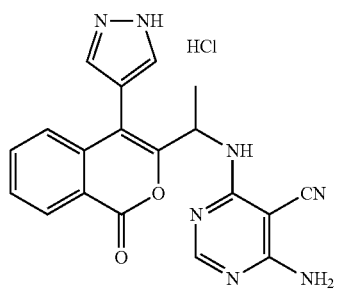 [SMILES: CC(Nc1ncnc(N)c1C#N)c1oc(=O)c2ccccc2c1-c1cn[nH]c1 ; Cl]

The title compound was made in a similar way as that of the compound of example 43, from 3-(1-aminoethyl)-4-(1 H-pyrazol-4-yl)-1H-isochromen-1-one dihydrochloride (intermediate E4, 50 mg, 0.152 mmol) 4-amino-6-bromopyrimidine-5-carbonitrile (39.4 mg, 0.198 mmol) to give the title compound (19 mg, 30.4%).

$^1$H NMR (400 MHz, DMSO-d$_6$) δ ppm 8.19 (d, J=7.06 Hz, 1 H), 8.01 (s, 1 H), 7.77 (m, 4 H), 7.60 (t, J=7.72 Hz, 1 H), 7.41 (br. s., 2 H), 7.20 (d, J=7.94 Hz, 1 H), 5.12 (t, J=6.84 Hz, 1 H), 1.44 (d, J=7.06 Hz, 3 H). UPLC-MS: 3.84 min, 374 [M+H]+, method 7.

Example 124

3-(1-(9H-purin-6-ylamino)ethyl)-4-(2-aminopyrimidin-5-yl)-1H-isochromen-1-one

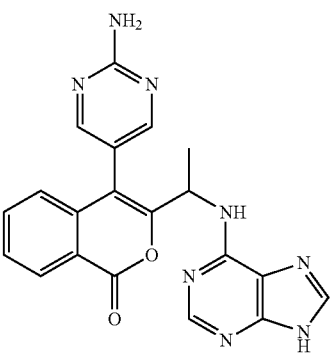 [SMILES: CC(Nc1ncnc2[nH]cnc12)c1oc(=O)c2ccccc2c1-c1cnc(N)nc1]

The title compound was made in a similar way as that of the compound of example 21 from tert-butyl 9-trityl-9H-purin-6-ylcarbamate (25.8 mg, 0.054 mmol) 4-(2-aminopyrimidin-5-yl)-3-(1-bromoethyl)-1H-isochromen-1-one (intermediate C34, 17 mg, 0.094 mmol) to give the title compound (7 mg, 35.6%).

$^1$H NMR (400 MHz, DMSO-d$_6$) δ ppm 9.18-9.44 (bs, 1 H), 8.29-8.55 (m, 4 H), 8.19 (d, J=7.94 Hz, 1 H), 7.81 (m, 1 H), 7.62 (m, 1 H), 6.81-7.43 (m, 3 H), 4.95-5.24 (m, 1 H), 1.60 (d, J=7.06 Hz, 3 H). UPLC-MS: 3.28 min, 401 [M+H]+, method 7.

Example 126

3-(1-(9H-purin-6-ylamino)ethyl)-4-(4-(piperazin-1-ylmethyl)phenyl)-1H-isochromen-1-one dihydrochloride

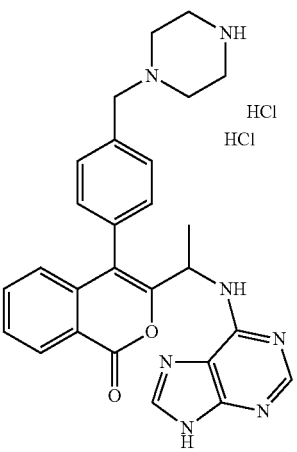 [SMILES: CC(Nc1ncnc2[nH]cnc12)c1oc(=O)c2ccccc2c1-c1ccc(CN2CCNCC2)cc1 ; Cl ; Cl]

The title compound was made in a similar way as that of the compound of example 21 from tert-butyl 9-trityl-9H-purin-6-ylcarbamate (130 mg, 0.273 mmol) tert-butyl 4-(4-(3-(1- bromoethyl)-1-oxo-1H-isochromen-4-yl)benzyl)piperazine-1-carboxylate (intermediate C35, 17 mg, 0.094 mmol) to give the title compound (22.8 mg, 17.7%).

1H NMR (400 MHz, DMSO-d6) δ ppm 8.98-9.32 (m, 1 H), 8.33 (br. s., 1 H), 8.22 (d, J=7.50 Hz, 1 H), 7.51-7.85 (m, 5 H), 7.45 (d, J=6.17 Hz, 1 H), 6.95 (d, J=7.94 Hz, 1 H), 4.86-5.25 (m, 1 H), 2.84-3.24 (m, 10 H), 1.56 (d, J=7.06 Hz, 3 H). UPLC-MS: 4.48 min, 482 [M+H]+, method 7.

Example 127

3-(1-(4-amino-1H-pyrazolo[3,4-d]pyrimidin-1-yl)ethyl)-4-(4-(piperazin-1-ylmethyl)phenyl)-1H-isochromen-1-one hydrochloride

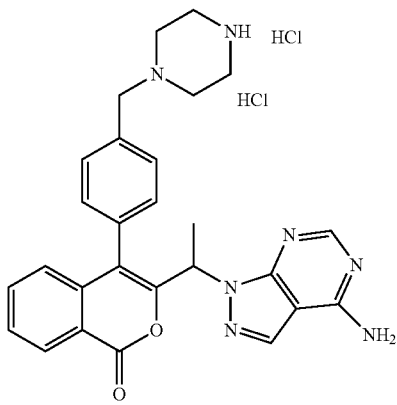 [SMILES: CC(c1oc(=O)c2ccccc2c1-c1ccc(CN2CCNCC2)cc1)n1ncc2c(N)ncnc21 ; Cl ; Cl]

tert-butyl 4-(4-(3-(1-bromoethyl)-1-oxo-1H-isochromen-4-yl)benzyl)piperazine-1-carboxylate (intermediate C35, 60 mg, 0.114 mmol), 1H-pyrazolo[3,4-d]pyrimidin-4-amine (30.7 mg, 0.228 mmol), and K$_2$CO$_3$ (31.4 mg, 0.228 mmol) were stirred in DMF (0.7 ml) at 80° C. for 3 hr. The reaction mixture was diluted with 1M HCl$_{aqueous}$ (1 ml) and purified via reverse phase chromatography with a Biotage C18 SNAP 60 g column (Phase A, water 95%, ACN 5%, formic acid 0.1%); Phase B ACN 95%, water 5%, formic acid 0.1%). The collected fractions were added with 37% HCl$_{aqueous}$ (1 ml) and concentrated to give the title compound (26 mg, 44%).

$^1$H NMR (400 MHz, DMSO-d$_6$) δ ppm 8.49 (br s, 0.5 H), 8.23-8.20 (m, 1H), 8.12 (br s, 0.5 H), 8.09 (br s, 1H), 8.01 (br s, 1H), 7.80-7.62 (m, 4H), 7.42-7.38 (m, 1.5H), 7.25-7.23 (m, 0.5 H) 6.90-6.88 (d, 1H), 5.65-5.55 (m, 1H), 2.54 (m, 3H), 1.81 (t, 3H). UPLC-MS: 3.78 min, 482 [M+H]+, method 3.

Example 130

3-(1-(4-amino-3-(3-fluoro-5-hydroxyphenyl)-1H-pyrazolo[3,4-d]pyrimidin-1-yl)ethyl)-4-(morpholinomethyl)-1H-isochromen-1-one

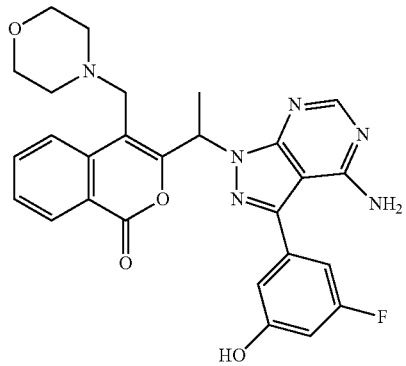 [SMILES: CC(c1oc(=O)c2ccccc2c1CN1CCOCC1)n1nc(-c2cc(O)cc(F)c2)c2c(N)ncnc21]

Step 1. 3-(1-(4-amino-3-(3-fluoro-5-methoxyphenyl)-1H-pyrazolo[3,4-d]pyrimidin-1-yl)ethyl)-4-(morpholinomethyl)-1H-isochromen-1-one

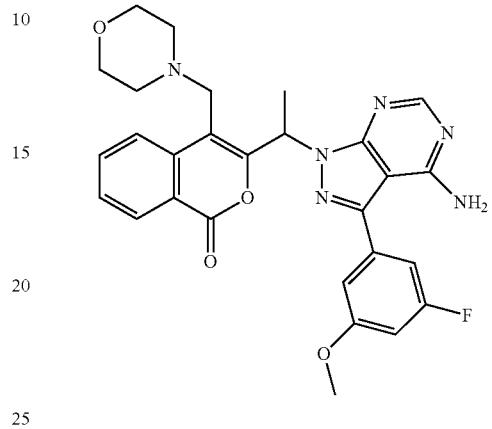

3-(3-Fluoro-5-methoxyphenyl)-1H-pyrazolo[3,4-d]pyrimidin-4-amine (intermediate G1, 0.135 g, 0.521 mmol) and potassium carbonate (0.206 g, 1.498 mmol) were mixed in DMF (5 ml) and stirred at r.t. for 10 min. Then a solution of 3-(1-bromoethyl)-4-(morpholinomethyl)-1H-isochromen-1-one hydrobromide (intermediate C48, 0.215 g, 0.496 mmol) in DMF (5 ml) was added and the mixture was heated at 70° C. for 3 hrs. The reaction was quenched by the addition of 1M HCl (2 ml) and the solvent was removed under vacuum. The crude was purified by reverse phase flash chromatography on C18 Biotage cartridge (H$_2$O:CH$_3$CN=80:20 to 100% CH$_3$CN, with 0.1% HCOOH) to afford 3-(1-(4-amino-3-(3-fluoro-5-methoxyphenyl)-1H-pyrazolo[3,4-d]pyrimidin-1-yl)ethyl)-4-(morpholinomethyl)-1H-isochromen-1-one (0.033 g).

UPLC-MS: 0.74 min, 531.4 [M+H]+, method 14.

Step 2

To a solution of 3-(1-(4-amino-3-(3-fluoro-5-methoxyphenyl)-1H-pyrazolo[3,4-d]pyrimidin-1-yl)ethyl)-4-(morpholinomethyl)-1H-isochromen-1-one (0.033 g) in dry DCM (2 ml), 1M BBr$_3$ in DCM (0.93 ml, 0.93 mmol) was added and the solution was stirred at room temperature for 2.5 hrs. The solution was cooled to 0° C. and ethanol (8 ml) was added. The solution was evaporate to dryness and crude was purified by flash chromatography in silica-NH cartridge (DCM to DCM:MeOH=90:10) affording title compound as a pale orange solid (5 mg).

$^1$H NMR (400 MHz, METHANOL-d$_4$) δ ppm 8.28 (s, 1 H), 8.23-8.27 (m, 1 H), 8.03 (d, 1 H), 7.80-7.85 (m, 1 H), 7.55-7.61 (m, 1 H), 6.90-6.93 (m, 1 H), 6.86-6.90 (m, 1 H), 6.63 (dt, 1 H), 6.54 (q, 1 H), 3.66-4.01 (m, 2 H), 3.49-3.56 (m, 4 H), 2.41-2.48 (m, 4 H), 1.98 (d, 3 H). UPLC-MS: 0.66 min, 517.4 [M+H]+, method 14.

Example 133 benzyl 4-(3-(1-(4-amino-3-(3-fluoro-5-hydroxyphenyl)-1H-pyrazolo[3,4-d]pyrimidin-1-yl)ethyl)-1-oxo-1H-isochromen-4-yl)-5,6-dihydropyridine-1(2H)-carboxylate

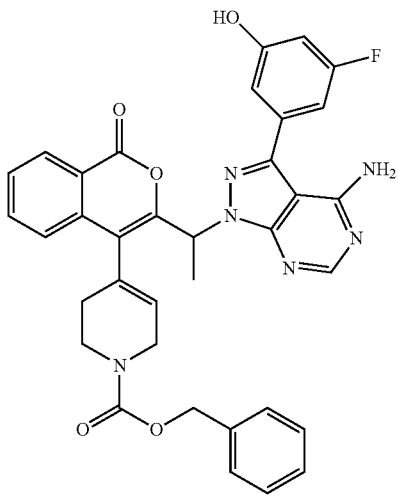 [SMILES: CC(c1oc(=O)c2ccccc2c1C1=CCN(C(=O)OCc2ccccc2)CC1)n1nc(-c2cc(O)cc(F)c2)c2c(N)ncnc21]

The title compound was made in a similar way as that of the compound of example 51, from benzyl 4-(3-(1-(4-amino-3-iodo-1H-pyrazolo[3,4-d]pyrimidin-1-yl)ethyl)-1-oxo-1H-isochromen-4-yl)-5,6-dihydropyridine-1(2H)-carboxylate (Intermediate D22, 334 mg, 0.515 mmol) and (3-fluoro-5-hydroxyphenyl)boronic acid (161 mg, 1.030 mmol to give the title compound (190 mg, 58.3%) as yellowish solid.

$^1$H NMR (400 MHz, DMSO-$d_6$) δ ppm 10.23 (br. s., 1 H), 8.02-8.50 (m, 3 H), 7.56-7.92 (m, 3 H), 7.38 (br. s., 1 H), 6.75-7.26 (m, 4 H), 6.57-6.73 (m, 1 H), 5.93 (q, J=7.06 Hz, 1 H), 4.56 (br. s., 2 H), 3.43 (br. s., 7 H), 1.84 (d, J=7.06 Hz, 3 H). UPLC-MS: 4.87 min, 633.0 [M+H]+, method 6

Example 134

3-(1-(4-amino-3-(3-fluoro-5-hydroxyphenyl)-1H-pyrazolo[3,4-d]pyrimidin-1-yl)ethyl)-4-(5-(piperazin-1-ylmethyl)thiophen-2-yl)-1H-isochromen-1-one dihydrochloride

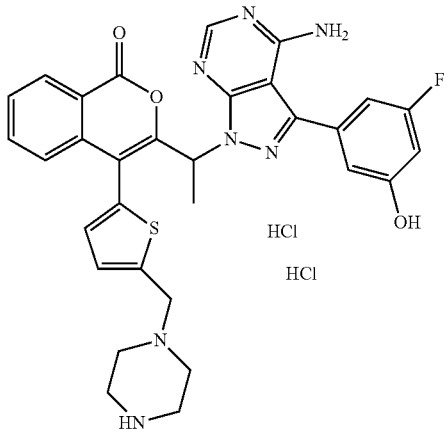 [SMILES: CC(c1oc(=O)c2ccccc2c1-c1ccc(CN2CCNCC2)s1)n1nc(-c2cc(O)cc(F)c2)c2c(N)ncnc21 ; Cl ; Cl]

Step a. benzyl 4-((5-(3-(1-(4-amino-3-(3-fluoro-5-methoxyphenyl)-1H-pyrazolo[3,4-d]pyrimidin-1-yl)ethyl)-1-oxo-1H-isochromen-4-yl)thiophen-2-yl)methyl)piperazine-1-carboxylate

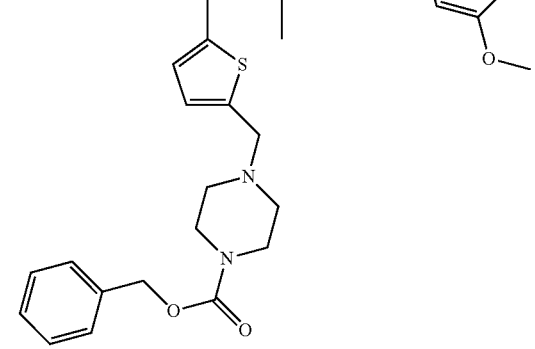

benzyl 4-((5-(3-(1-hydroxyethyl)-1-oxo-1H-isochromen-4-yl)thiophen-2-yl)methyl)piperazine-1-carboxylate (Intermediate B38, 903 mg, 1.790 mmol) was dissolved in 20 ml of dry then tribromophosphine 1M in DCM (2684 μl, 2.68 mmol) was slowly added. The mixture was stirred at r.t. The reaction was quenched by addition of 60 ml of NaHCO$_3$ sat. sol. and extracted with DCM (100 ml). Phases were separated to leave a milky organic phase. 30 ml of ACN were added and the solution became clear. The mixture was concentrated to dryness to leave an off white solid. In a separate 30 ml vial, 3-(3-fluoro-5-methoxyphenyl)-1H-pyrazolo[3,4-d]pyrimidin-4-amine (Intermediate G1, 510 mg, 1.969 mmol) and potassium carbonate (742 mg, 5.37 mmol) were suspended in 10 ml DMF and the mixture heated at 60 C for 15 min prior addition of the bromide dissolved in 5 ml of dry DMF. The reaction was stirred for a further hour at r.t. then the reaction was quenched with NaHCO$_3$aq (40 ml) and extracted with DCM (80 ml) then concentrated to leave a brown solid that was purified by chromatography eluting with DCM:MeOH to give benzyl 4-((5-(3-(1-(4-amino-3-(3-fluoro-5-methoxyphenyl)-1H-pyrazolo[3,4-d]pyrimidin-1-yl)ethyl)-1-oxo-1H-isochromen-4-yl)thiophen-2-yl)methyl)piperazine-1-carboxylate (460 mg, 0.617 mmol, 34.5% yield) as a brown solid.

UPLC-MS: 1.99 min, 746.09 [M+H]+, method 10

Step b

In a 250 ml round bottomed flask equipped with a magnetic stirrer benzyl 4-((5-(3-(1-(4-amino-3-(3-fluoro-5-methoxyphenyl)-1H-pyrazolo[3,4-d]pyrimidin-1-yl)ethyl)-1-oxo-1H-isochromen-4-yl)thiophen-2-yl)methyl)piperazine-1-carboxylate (460 mg, 0.617 mmol) was suspended in 20 ml of dry dichloromethane then 1M tribromoborane in DCM (5 ml) was added and the mixture was stirred overnight at r.t. MeOH (15 ml) and 1M HCl (5 ml) were added and the mixture was stirred for 30 min then organic solvents were evaporated and the crude was purified by reverse phase chromatography eluting with H$_2$O\MeCN\HCOOH 95:5:0.1% and MeCN\H$_2$O\HCOOH 95:5:0.1%, to give the title compound (254 mg, 0.379 mmol, 61.4% yield) as a whitish solid.

$^1$H NMR (600 MHz, DMSO-d6) δ ppm 8.16-8.29 (m, 2 H), 8.11 (s, 1 H), 7.75-7.91 (m, 1 H), 7.52-7.69 (m, 1 H), 7.15 (d, J=7.89 Hz, 1 H), 6.76-7.05 (m, 4 H), 6.66 (d, J=10.85 Hz, 1 H), 5.97 (q, J=7.13 Hz, 1 H), 3.67 (br. s., 2 H), 2.80 (br. s., 4 H), 2.41 (br. s., 4 H), 1.84 (d, J=7.23 Hz, 3 H). UPLC-MS: 1.32 min, 597.99 [M+H]+, method 10

Intermediate 135. 3-(1-(4-amino-3-(3-fluoro-5-hydroxyphenyl)-1H-pyrazolo[3,4-d]pyrimidin-1-yl)ethyl)-4-(5-((4-methyl)piperazin-1-yl)methyl)thiophen-2-yl)-1H-isochromen-1-one, dihydrochloride

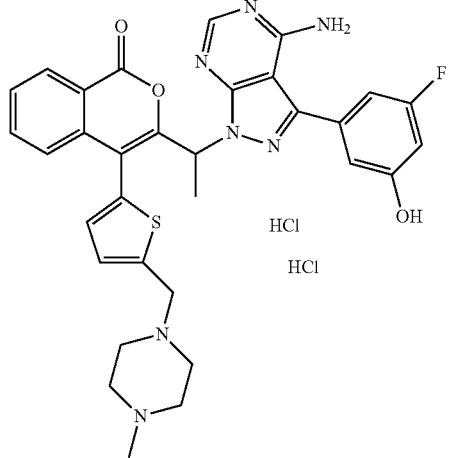 [SMILES: CC(c1oc(=O)c2ccccc2c1-c1ccc(CN2CCN(C)CC2)s1)n1nc(-c2cc(O)cc(F)c2)c2c(N)ncnc21 ; Cl ; Cl]

Step a, 3-(1-(4-amino-3-(3-fluoro-5-methoxyphenyl)-1H-pyrazolo[3,4-d]pyrimidin-1-yl)ethyl)-4-(5-((4-methylpiperazin-1-yl)methyl)thiophen-2-yl)-1H-isochromen-1-one

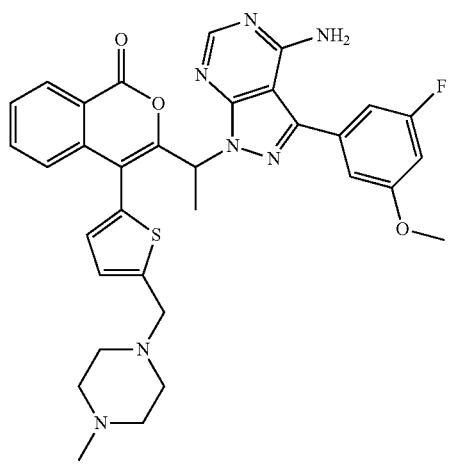 [SMILES: COc1cc(F)cc(-c2nn(C(C)c3oc(=O)c4ccccc4c3-c3ccc(CN4CCN(C)CC4)s3)c3ncnc(N)c23)c1]

The title compound was made in a similar way as that of the compound of example 134, step a, from 3-(1-hydroxyethyl)-4-(5-((4-methylpiperazin-1-yl)methyl)thiophen-2-yl)-1H-isochromen-1-one (Intermediate B39, 411 mg, 1.069 mmol), and 3-(3-fluoro-5-methoxyphenyl)-1H-pyrazolo[3,4-d]pyrimidin-4-amine (intermediate G1, 305 mg, 1.176 mmol) to give 3-(1-(4-amino-3-(3-fluoro-5-methoxyphenyl)-1H-pyrazolo[3,4-d]pyrimidin-1-yl)ethyl)-4-(5-((4-methylpiperazin-1-yl)methyl)thiophen-2-yl)-1H-isochromen-1-one (420 mg, 0.671 mmol, 62.8% yield) as a brown solid.

UPLC-MS: 1.52 min, 626.17 [M+H]+, method 10

Step b

The title compound was made in a similar way as that of the compound of example 134, step b, from 3-(1-(4-amino-3-(3-fluoro-5-methoxyphenyl)-1H-pyrazolo[3,4-d]pyrimidin-1-yl)ethyl)-4-(5-((4-methylpiperazin-1-yl)methyl)thiophen-2-yl)-1H-isochromen-1-one (410 mg, 0.655 mmol) to give the title compound (100 mg, 0.146 mmol, 22.29% yield) as a white solid.

$^1$H NMR (600 MHz, DMSO-d$_6$) δ ppm 10.17 (br. s., 1 H), 8.21 (dd, J=7.89, 0.66 Hz, 1 H), 8.13 (s, 1 H), 8.11 (s, 1 H), 7.78-7.87 (m, 1 H), 7.58-7.70 (m, 1 H), 7.15 (d, J=7.89 Hz, 1 H), 6.85-7.02 (m, 3 H), 6.83 (dd, J=8.88, 1.64 Hz, 1 H), 6.66 (dt, J=10.85, 2.30 Hz, 1 H), 5.96 (d, J=6.91 Hz, 1 H), 3.71 (br. s., 2 H), 3.29 (s, 3 H), 2.54-2.77 (m, 4 H), 2.39 (br. s., 4 H), 1.84 (d, J=6.91 Hz, 3 H). UPLC-MS: 1.29 min, 611.71 [M+H]+, method 10

Example 136

3-(1-(4-amino-3-(3-fluoro-5-hydroxyphenyl)-1H-pyrazolo[3,4-d]pyrimidin-1-yl)ethyl)-4-(5-(3-(dimethylamino)propyl)thiophen-2-yl)-1H-isochromen-1-one, Formate

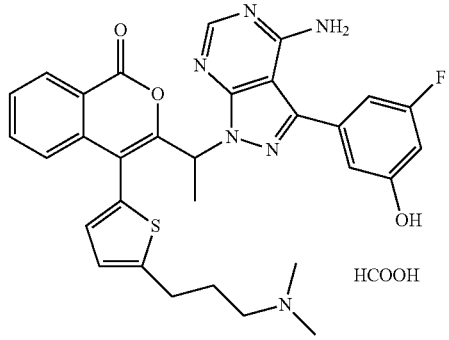 [SMILES: CC(c1oc(=O)c2ccccc2c1-c1ccc(CCCN(C)C)s1)n1nc(-c2cc(O)cc(F)c2)c2c(N)ncnc21 ; "HCOOH"]

223

Step a. 3-(1-(4-amino-3-(3-(benzyloxy)-5-fluorophenyl)-1H-pyrazolo[3,4-d]pyrimidin-1-yl)ethyl)-4-(5-(3-(dimethylamino)prop-1-en-1-yl)thiophen-2-yl)-1H-isochromen-1-one

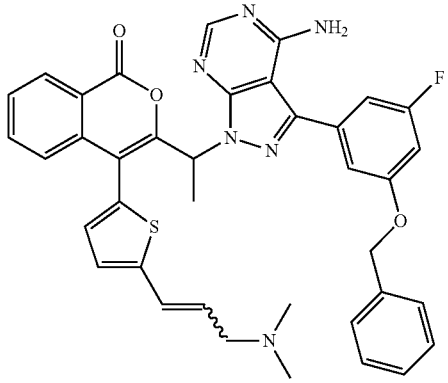 [SMILES: CC(c1oc(=O)c2ccccc2c1-c1ccc(C=CCN(C)C)s1)n1nc(-c2cc(F)cc(OCc3ccccc3)c2)c2c(N)ncnc21]

The title compound was made in a similar way as that of the compound of example 134, step a, from 4-(5-(3-(dimethylamino)prop-1-en-1-yl)thiophen-2-yl)-3-(1-hydroxyethyl)-1H-isochromen-1-one (Intermediate B40, 220 mg, 0,619 mmol), and 3-(3-(benzyloxy)-5-fluorophenyl)-1H-pyrazolo[3,4-d]pyrimidin-4-amine (Intermediate G18, 125 mg, 0.37 mmol) to give 3-(1-(4-amino-3-(3-(benzyloxy)-5-fluorophenyl)-1H-pyrazolo[3,4-d]pyrimidin-1-yl)ethyl)-4-(5-(3-(dimethylamino)prop-1-en-1-yl)thiophen-2-yl)-1H-isochromen-1-one (180 mg, 0,268 mmol, 43.2% yield) as a brown oil.

UPLC-MS: 1.86 min, 673.3 [M+H]+, method 10.

Step b 3-(1-(4-amino-3-(3-(benzyloxy)-5-fluorophenyl)-1H-pyrazolo[3,4-d]pyrimidin-1-yl)ethyl)-4-(5-(3-(dimethylamino)prop-1-en-1-yl)thiophen-2-yl)-1H-isochromen-1-one (180 mg, 0.268 mmol) was dissolved in 15 ml of EtOH then palladium on carbon 5% (28.5 mg, 0.268 mmol) was added, then under Ar atmosphere triethylsilane (2 ml, 12.52 mmol) was added. The mixture was filtered then the crude was concentrated and purified by reverse phase chromatography C18 30 g+12 g eluting with H₂O\MeCN\HCOOH 95:5:0.1% and MeCN\H₂O\HCOOH 95:5:0.1% to give the title compound (20 mg, 0.032 mmol, 11.85% yield) as a white solid.

$^1$H NMR (400 MHz, DMSO-$d_6$) δ ppm 8.17-8.29 (m, 3 H), 8.12 (s, 1 H), 7.71-7.87 (m, 2 H), 7.56-7.69 (m, 1 H), 7.37-7.56 (m, 1 H), 7.15 (d, J=8.38 Hz, 1 H), 6.76-6.94 (m, 4 H), 6.66 (d, J=10.58 Hz, 1 H), 5.96 (d, J=7.06 Hz, 1 H), 2.78 (t, J=7.28 Hz, 2 H), 2.28 (t, J=6.84 Hz, 2 H), 2.16 (s, 6 H), 1.84 (d, J=7.06 Hz, 3 H), 1.70 (t, 2 H). UPLC-MS: 0.81 min, 585.25 [M+H]+, method 9.

224

Example 137

3-(1-(4-amino-3-(3-fluoro-5-hydroxyphenyl)-1H-pyrazolo[3,4-d]pyrimidin-1-yl)ethyl)-4-(3-(3-(dimethylamino)propyl)phenyl)-1H-isochromen-1-one, Formic Acid

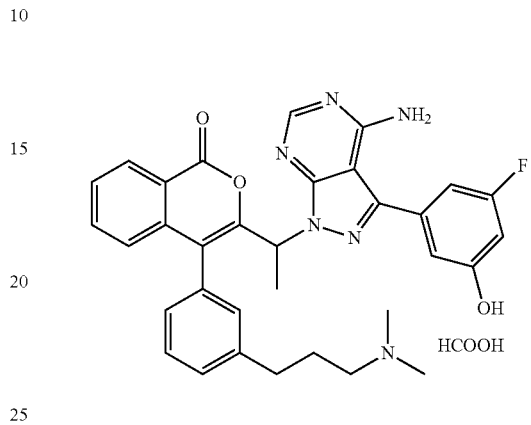

Step a. 3-(1-(4-amino-3-(3-fluoro-5-methoxyphenyl)-1H-pyrazolo[3,4-d]pyrimidin-1-yl)ethyl)-4-(5-((4-methylpiperazin-1-yl)methyl)thiophen-2-yl)-1H-isochromen-1-one

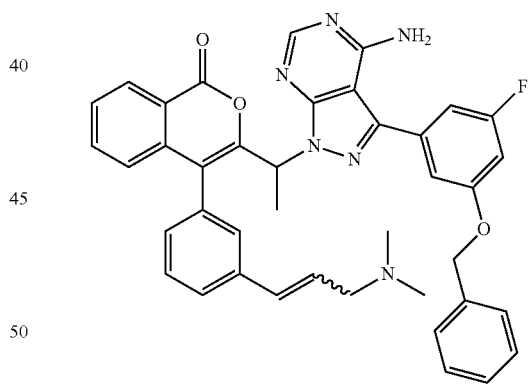

The title compound was made in a similar way as that of the compound of example 134, step a, from 4-(3-(3-(dimethylamino)prop-1-en-1-yl)phenyl)-3-(1-hydroxyethyl)-1H-isochromen-1-one (Intermediate B42, 280 mg, 0.801 mmol), and 3-(3-(benzyloxy)-5-fluorophenyl)-1H-pyrazolo[3,4-d]pyrimidin-4-amine (Intermediate G-18, 0.417 mmol, 140 mg) to give 3-(1-(4-amino-3-(3-fluoro-5-methoxyphenyl)-1H-pyrazolo[3,4-d]pyrimidin-1-yl)ethyl)-4-(5-((4-methylpiperazin-1-yl)methyl)thiophen-2-yl)-1H-isochromen-1-one (120 mg, 0.18 mmol, 43% yield) as a yellow oil.

UPLC-MS: 1.91 min, 667.27 [M+H]+, method 10

225

Step b

The title compound was made in a similar way as that of the compound of example 136, step b, from 3-(1-(4-amino-3-(3-(benzyloxy)-5-fluorophenyl)-1H-pyrazolo[3,4-d]pyrimidin-1-yl)ethyl)-4-(3-(3-(dimethylamino)prop-1-en-1-yl)phenyl)-1H-isochromen-1-one to give the title compound (120 mg, 0.18 mmol, 43.1% yield) as a white solid.

$^1$H NMR (400 MHz, DMSO-$d_6$) δ ppm 1.46-1.63 (m, 1 H), 1.70-1.88 (m, 4 H), 2.08 (br. s., 3 H), 2.14-2.25 (m, 4 H), 2.30-2.37 (m, 1 H), 2.40-2.48 (m, 1 H), 2.60-2.72 (m, 1 H), 5.74 (sxt, J=6.98 Hz, 1 H), 6.55-6.99 (m, 6 H), 7.13-7.86 (m, 6 H), 8.02-8.30 (m, 3 H). UPLC-MS: 1.37 min, 579.3 [M+H]+, method 10.

Examples 137a (enantiomer 1) and 137b (enantiomer 2)

3-(1-(4-amino-3-(3-fluoro-5-hydroxyphenyl)-1H-pyrazolo[3,4-d]pyrimidin-1-yl)ethyl)-4-(3-(3-(dimethylamino)propyl)phenyl)-1H-isochromen-1-one single enantiomers Racemate 3-(1-(4-amino-3-(3-fluoro-5-hydroxyphenyl)-1H-pyrazolo[3,4-d]pyrimidin-1-yl)ethyl)-4-(3-(3-(dimethylamino)propyl)phenyl)-1H-isochromen-1-one formate (example 137, 0.020 g, 0.860 mmol) was dissolved in 2 ml of Ethanol and submitted to chiral resolution by Chiral preparative chromatography. Conditions: Column: Chiralpak IC (25×2 cm), 5 um; Mobile phase: n-Hexane/(2-Propanol/Methanol 1/1+0.1% isopropylamine) 65/35v/v; Flow rate: 16 ml/min; DAD detection: 220 nm; Loop: 500 µl; Injection: 5 mg (each injection).

The fractions containing the first eluted enantiomer were evaporated to dryness to afford compound 137a (first eluted enantiomer, 6.8 mg, 0.0117 mmol). Chiral HPLC (Method A15): Rt=7.4 min, ee>99%.

$^1$H NMR (400 MHz, METHANOL-$d_4$) δ ppm 8.29-8.33 (m, 1 H), 8.05-8.08 (m, 1 H), 7.64-7.71 (m, 1 H), 7.55-7.61 (m, 1 H), 7.10-7.43 (m, 3 H), 6.87-6.97 (m, 2 H), 6.81-6.87 (m, 1 H), 6.60-6.70 (m, 2 H), 5.85-5.97 (m, 1 H), 2.24-2.73 (m, 10 H), 1.86-1.96 (m, 4 H), 1.61-1.71 (m, 1 H). UPLC-MS: 0.69 min, 579.4 [M+H]+, method 14.

The fractions containing the second eluted enantiomer were evaporated to dryness to afford compound 137b (second eluted enantiomer, 6.3 mg, 0.0109 mmol). Chiral HPLC (Method A15): Rt=8.4 min, ee=96.4%.

$^1$H NMR (400 MHz, METHANOL-$d_4$) δ ppm 8.28-8.33 (m, 1 H), 8.04-8.08 (m, 1 H), 7.63-7.71 (m, 1 H), 7.55-7.61 (m, 1 H), 7.10-7.42 (m, 3 H), 6.86-6.96 (m, 2 H), 6.79-6.86 (m, 1 H), 6.59-6.70 (m, 2 H), 5.85-5.97 (m, 1 H), 2.24-2.72 (m, 7 H), 2.17 (s, 3 H), 1.82-1.94 (m, 4 H), 1.57-1.67 (m, 1 H). UPLC-MS: 0.69 min, 579.4 [M+H]+, method 14.

226

Example 138

3-(1-(4-amino-3-(3-fluoro-5-hydroxyphenyl)-1H-pyrazolo[3,4-d]pyrimidin-1-yl)ethyl)-4-(4-(3-(dimethylamino)propyl)phenyl)-1H-isochromen-1-one, formate

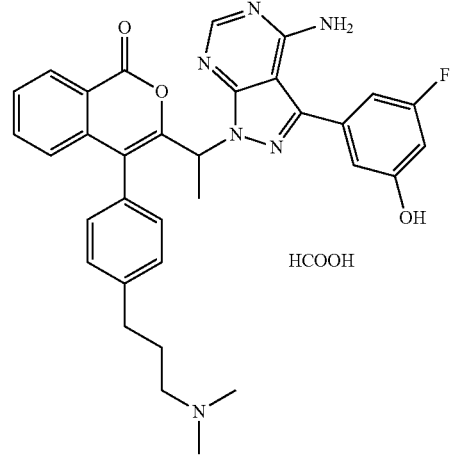 [SMILES: CC(c1oc(=O)c2ccccc2c1-c1ccc(CCCN(C)C)cc1)n1nc(-c2cc(O)cc(F)c2)c2c(N)ncnc21 ; "HCOOH"]

Step a. 3-(1-(4-amino-3-(3-(benzyloxy)-5-fluorophenyl)-1H-pyrazolo[3,4-d]pyrimidin-1-yl)ethyl)-4-(4-(3-(dimethylamino)prop-1-en-1-yl)phenyl)-1H-isochromen-1-one

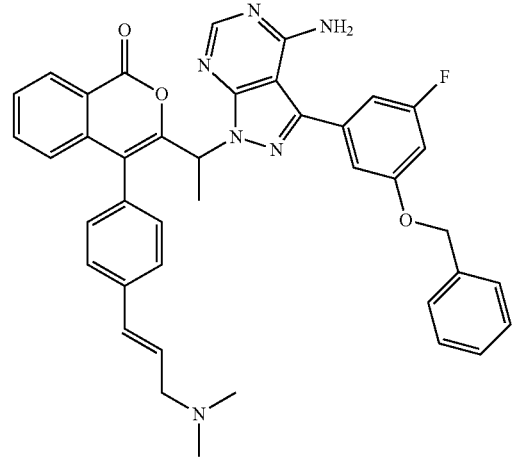 [SMILES: CC(c1oc(=O)c2ccccc2c1-c1ccc(/C=C/CN(C)C)cc1)n1nc(-c2cc(F)cc(OCc3ccccc3)c2)c2c(N)ncnc21]

The title compound was made in a similar way as that of the compound of example 134, step a, from 4-(4-(3-(dimethylamino)prop-1-en-1-yl)phenyl)-3-(1-hydroxyethyl)-1H-isochromen-1-one (intermediate B45, 220 mg, 0.630 mmol) and 3-(3-(benzyloxy)-5-fluorophenyl)-1H-pyrazolo[3,4-d]pyrimidin-4-amine (Intermediate G18, 0.63 mmol, 211 mg) to give 3-(1-(4-amino-3-(3-(benzyloxy)-5-fluorophenyl)-1H-pyrazolo[3,4-d]pyrimidin-1-yl)ethyl)-4-(4-(3-(dimethylamino)prop-1-en-1-yl)phenyl)-1H-isochromen-1-one (120 mg, 0.18 mmol, 43.1% yield) as a yellow oil.

UPLC-MS: 2.01 min, 667.21 [M+H]+, method 10

Step b

The title compound was made in a similar way as that of the compound of example 136, step b, from 3-(1-(4-amino-3-(3-(benzyloxy)-5-fluorophenyl)-1H-pyrazolo[3,4-d]pyrimidin-1-yl)ethyl)-4-(4-(3-(dimethylamino)prop-1-en-1-yl)phenyl)-1H-isochromen-1-one (162 mg, 0.243 mmol) to give the title compound (17 mg, 0.027 mmol, 11.20% yield) as a white solid.

1H NMR (600 MHz, DMSO-d6) δ ppm 10.03-10.35 (bs, 1 H), 8.22 (dd, J=7.89, 0.92 Hz, 1 H), 8.17 (s, 1 H), 8.07 (s, 1 H), 7.76 (t, 1 H), 7.62 (t, 1 H), 7.32 (dd, J=19.81, 1.83 Hz, 2 H), 7.12-7.20 (m, 1 H), 6.97 (m, 1 H), 6.86-6.92 (m, 2 H), 6.78-6.85 (m, 1 H), 6.61-6.68 (m, 1 H), 5.75 (d, J=6.97 Hz, 1 H), 2.61 (d, J=7.70 Hz, 2 H), 2.32 (m, 2 H), 2.20 (s, 6H, 3 H each), 1.82 (d, J=6.97 Hz, 3 H), 1.68-1.78 (m, 2 H). UPLC-MS: 1.35 min, 579.2 [M+H]+, method 10

Examples 138a (enantiomer 1) and 138b (enantiomer 2)

3-(1-(4-amino-3-(3-fluoro-5-hydroxyphenyl)-1H-pyrazolo[3,4-d]pyrimidin-1-yl)ethyl)-4-(4-(3-(dimethylamino)propyl)phenyl)-1H-isochromen-1-one single enantiomers

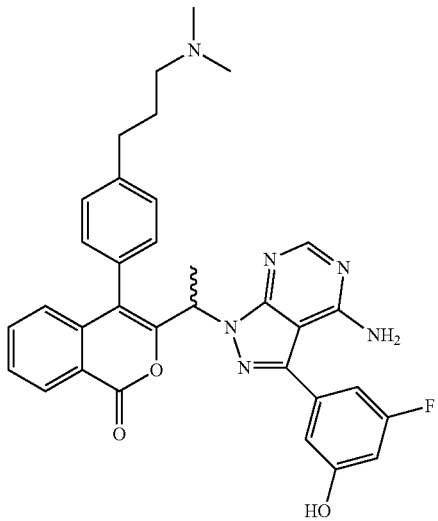 [SMILES: CC(c1oc(=O)c2ccccc2c1-c1ccc(CCCN(C)C)cc1)n1nc(-c2cc(O)cc(F)c2)c2c(N)ncnc21]

Racemate 3-(1-(4-amino-3-(3-fluoro-5-hydroxyphenyl)-1H-pyrazolo[3,4-d]pyrimidin-1-yl)ethyl)-4-(4-(3-(dimethylamino)propyl)phenyl)-1H-isochromen-1-one formate (example 138, 0.010 g, 0.016 mmol) was dissolved in Ethanol/Methanol 1/1 (3 ml) and submitted to chiral resolution by Chiral preparative chromatography. Conditions: Column: Chiralpak IC (25×2.0 cm), 5μ; Mobile phase: n-Hexane/(2-Propanol/Methanol 1/1+0.1% isopropylamine) 60/40% v/v; Flow rate: 16 ml/min; DAD detection: 220 nm; Loop: 1000 μl; Injection: 3.3 mg (each injection).

The fractions containing the first eluted enantiomer were evaporated to dryness to afford compound 138a (first eluted enantiomer, 3.1 mg, 0.005 mmol). Chiral HPLC (Method A15): Rt=7.3 min, ee>99%.

1H NMR (400 MHz, METHANOL-d4) δ ppm 8.27-8.32 (m, 1 H), 8.06 (s, 1 H), 7.63-7.69 (m, 1 H), 7.53-7.60 (m, 1 H), 7.28-7.33 (m, 1 H), 7.20-7.26 (m, 1 H), 7.04-7.09 (m, 1 H), 6.93 (d, 1 H), 6.88-6.90 (m, 1 H), 6.81-6.86 (m, 1 H), 6.74-6.78 (m, 1 H), 6.63 (dt, 1 H), 5.93 (q, 1 H), 2.57-2.68 (m, 4 H), 2.44 (s, 6 H), 1.81-1.94 (m, 5 H). UPLC-MS: 0.69 min, 579.5 [M+H]+, method 13.

The fractions containing the second eluted enantiomer were evaporated to dryness to afford compound 138b (second eluted enantiomer, 3.0 mg, 0.005 mmol). Chiral HPLC (Method A15): Rt=8.0 min, ee=93.2%.

1H NMR (400 MHz, METHANOL-d4) δ ppm 8.26-8.32 (m, 1 H), 8.06 (s, 1 H), 7.63-7.69 (m, 1 H), 7.53-7.60 (m, 1 H), 7.27-7.34 (m, 1 H), 7.20-7.26 (m, 1 H), 7.03-7.09 (m, 1 H), 6.93 (d, 1 H), 6.88-6.90 (m, 1 H), 6.81-6.86 (m, 1 H), 6.73-6.78 (m, 1 H), 6.63 (dt, 1 H), 5.92 (q, 1 H), 2.52-2.69 (m, 4 H), 2.41 (s, 6 H), 1.79-1.94 (m, 5 H). UPLC-MS: 0.69 min, 579.5 [M+H]+, method 13.

Example 139

3-(1-(4-amino-3-(3-fluoro-5-hydroxyphenyl)-1H-pyrazolo[3,4-d]pyrimidin-1-yl)ethyl)-4-(4-((4-methylpiperazin-1-yl)methyl)phenyl)-1H-isochromen-1-one, dihydrochloride

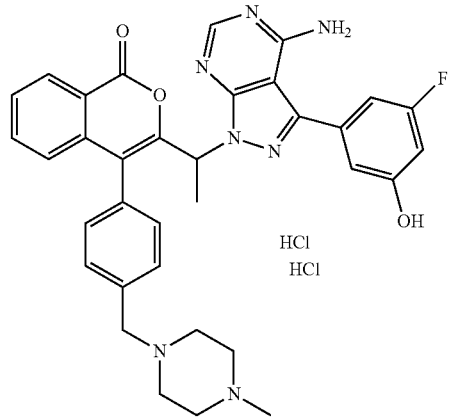 [SMILES: CC(c1oc(=O)c2ccccc2c1-c1ccc(CN2CCN(C)CC2)cc1)n1nc(-c2cc(O)cc(F)c2)c2c(N)ncnc21 ; Cl ; Cl]

Step a. 3-(1-(4-amino-3-(3-fluoro-5-methoxyphenyl)-1H-pyrazolo[3,4-d]pyrimidin-1-yl)ethyl)-4-(4-((4-methylpiperazin-1-yl)methyl)phenyl)-1H-isochromen-1-one

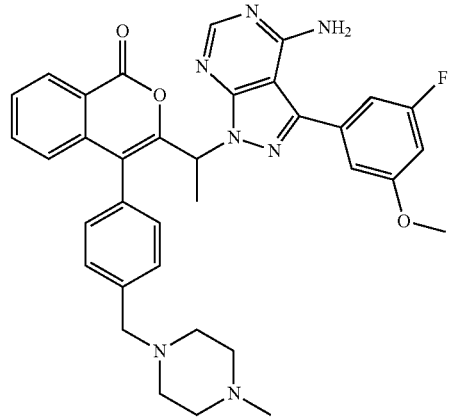 [SMILES: COc1cc(F)cc(-c2nn(C(C)c3oc(=O)c4ccccc4c3-c3ccc(CN4CCN(C)CC4)cc3)c3ncnc(N)c23)c1]

The title compound was made in a similar way as that of example 134, step a, from 3-(1-hydroxyethyl)-4-(4-((4-methylpiperazin-1-yl)methyl)phenyl)-1H-isochromen-1-one (Intermediate B46, 750 mg, 1.982 mmol) and 3-(3-fluoro-5-methoxyphenyl)-1H-pyrazolo[3,4-d]pyrimidin-4-amine (Intermediate G1, 565 mg, 2.18 mmol) to give 3-(1-(4-amino-3-(3-fluoro-5-methoxyphenyl)-1H-pyrazolo[3,4-d]pyrimidin-1-yl)ethyl)-4-(4-((4-methylpiperazin-1-yl)methyl)phenyl)-1H-isochromen-1-one (98 mg, 0.158 mmol, 7.98% yield) as a brown solid.

UPLC-MS: 1.53 min, 620.20 [M+H]+, method 10.

Step b

The title compound was made in a similar way as that of the compound of example 134, step b, from 3-(1-(4-amino-3-(3-fluoro-5-methoxyphenyl)-1H-pyrazolo[3,4-d]pyrimidin-1-yl)ethyl)-4-(4-((4-methylpiperazin-1-yl)methyl)phenyl)-1H-isochromen-1-one (98 mg, 0.158 mmol) to give the title compound (48 mg, 0.071 mmol, 44.7% yield) as a white solid
$^1$H NMR (600 MHz, DMSO-$d_6$) δ ppm 10.09-10.24 (bs, 1 H), 8.22 (dd, J=8.06, 0.82 Hz, 1 H), 8.04 (s, 1 H), 7.72-7.80 (m, 1 H), 7.59-7.66 (m, 1 H), 7.30-7.44 (m, 2 H), 7.22 (dd, J=7.89, 1.32 Hz, 1 H), 6.89 (d, J=1.97 Hz, 4 H), 6.62-6.70 (m, 1 H), 5.76 (d, J=7.23 Hz, 1 H), 3.29 (m, 4 H), 2.38-2.45 (m, 4 H), 1.81 (d, J=7.23 Hz, 3 H). UPLC-MS: 1.27 min, method 10.

Example 140

3-(1-(4-amino-3-(3-fluoro-5-hydroxyphenyl)-1H-pyrazolo[3,4-d]pyrimidin-1-yl)ethyl)-4-(4-(pyrrolidin-1-ylmethyl)phenyl)-1H-isochromen-1-one, hydrochloride

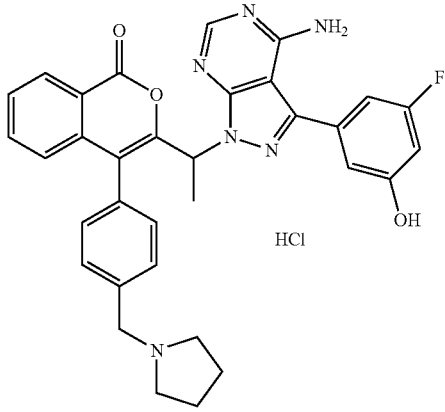 [SMILES: CC(c1oc(=O)c2ccccc2c1-c1ccc(CN2CCCC2)cc1)n1nc(-c2cc(O)cc(F)c2)c2c(N)ncnc21 ; Cl]

Step a. 3-(1-(4-amino-3-(3-fluoro-5-methoxyphenyl)-1H-pyrazolo[3,4-d]pyrimidin-1-yl)ethyl)-4-(4-(pyrrolidin-1-ylmethyl)phenyl)-1H-isochromen-1-one

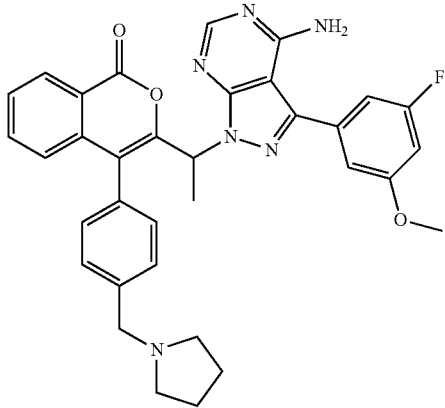 [SMILES: COc1cc(F)cc(-c2nn(C(C)c3oc(=O)c4ccccc4c3-c3ccc(CN4CCCC4)cc3)c3ncnc(N)c23)c1]

The title compound was made in a similar way as that of the example 134, step a, from 3-(1-hydroxyethyl)-4-(4-(pyrrolidin-1-ylmethyl)phenyl)-1H-isochromen-1-one (Intermediate B47, 380 mg, 1.088 mmol) and 3-(3-fluoro-5-methoxyphenyl)-1H-pyrazolo[3,4-d]pyrimidin-4-amine (Intermediate G1, 310 mg, 1.197 mmol) to give 3-(1-(4-amino-3-(3-fluoro-5-methoxyphenyl)-1H-pyrazolo[3,4-d]pyrimidin-1-yl)ethyl)-4-(4-(pyrrolidin-1-ylmethyl)phenyl)-1H-isochromen-1-one (170 mg, 0.288 mmol, 26.5% yield) as a brown solid.
UPLC-MS: 0.80 min, 591.25 [M+H]+, method 9

Step b

The title compound was made in a similar way as that of example 134, step b, from 3-(1-(4-amino-3-(3-fluoro-5-methoxyphenyl)-1H-pyrazolo[3,4-d]pyrimidin-1-yl)ethyl)-4-(4-(pyrrolidin-1-ylmethyl)phenyl)-1H-isochromen-1-one (170 mg, 0.288 mmol) to give the title compound (126 mg, 0.206 mmol, 71.4% yield) as a white solid.
$^1$H NMR (600 MHz, DMSO-$d_6$) δ ppm 10.21 (br. s., 2 H), 8.24 (dd, J=7.89, 0.99 Hz, 1 H), 8.03-8.17 (m, 2 H), 7.44-7.85 (m, 5 H), 7.22 (dd, J=7.73, 1.81 Hz, 1 H), 6.80-6.96 (m, 3 H), 6.68 (dt, J=10.85, 2.30 Hz, 1 H), 5.73 (q, J=7.13 Hz, 1 H), 4.40 (d, J=5.59 Hz, 2 H), 3.30 (m, 2 H), 3.10 (dd, J=10.69, 7.07 Hz, 2 H), 2.07 (br. s., 2 H), 1.88-2.00 (m, 2 H), 1.83 (d, J=6.91 Hz, 3 H). UPLC-MS: 1.23 min, 577.27 [M+H]+, method 10.

Example 141

3-(1-(4-amino-3-(3-fluoro-5-hydroxyphenyl)-1H-pyrazolo[3,4-d]pyrimidin-1-yl)ethyl)-4-(4-(piperidin-1-ylmethyl)phenyl)-1H-isochromen-1-one, hydrochloride

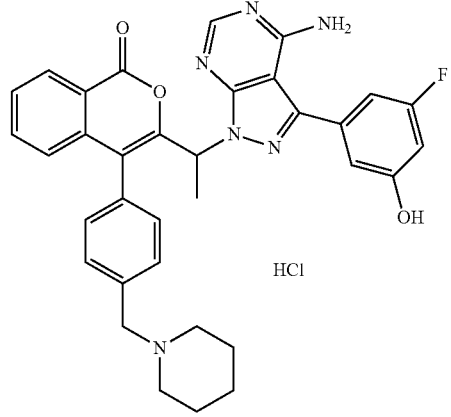 [SMILES: CC(c1oc(=O)c2ccccc2c1-c1ccc(CN2CCCCC2)cc1)n1nc(-c2cc(O)cc(F)c2)c2c(N)ncnc21 ; Cl]

Step a. 3-(1-(4-amino-3-(3-fluoro-5-methoxyphenyl)-1H-pyrazolo[3,4-d]pyrimidin-1-yl)ethyl)-4-(4-(piperidin-1-ylmethyl)phenyl)-1H-isochromen-1-one

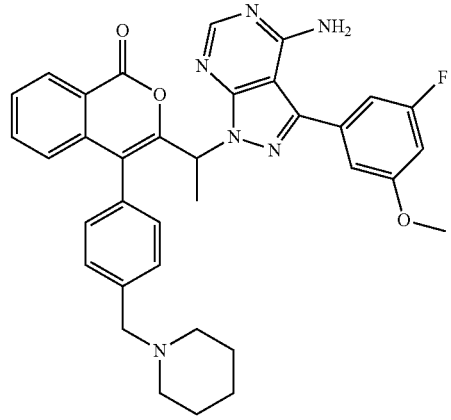 [SMILES: COc1cc(F)cc(-c2nn(C(C)c3oc(=O)c4ccccc4c3-c3ccc(CN4CCCCC4)cc3)c3ncnc(N)c23)c1]

The title compound was made in a similar way as that of the example 134, step a, from 3-(1-hydroxyethyl)-4-(4-(piperidin-1-ylmethyl)phenyl)-1H-isochromen-1-one (Intermediate B48, 720 mg, 1.981 mmol) and 3-(3-fluoro-5-methoxyphenyl)-1H-pyrazolo[3,4-d]pyrimidin-4-amine (Intermediate G1, 565 mg, 2.17 mmol) to give 3-(1-(4-amino-3-(3-fluoro-5-methoxyphenyl)-1H-pyrazolo[3,4-d]pyrimidin-1-yl)ethyl)-4-(4-(piperidin-1-ylmethyl)phenyl)-1H-isochromen-1-one (850 mg, 1.40 mmol, 71.0% yield) as a brown solid.

UPLC-MS: 1.53 min, 605.23 [M+H]+, method 10

Step b

The title compound was made in a similar way as that of the example 134, step b, from 3-(1-(4-amino-3-(3-fluoro-5-methoxyphenyl)-1H-pyrazolo[3,4-d]pyrimidin-1-yl)ethyl)-4-(4-(piperidin-1-ylmethyl)phenyl)-1H-isochromen-1-one (850 mg, 1.406 mmol) to give the title compound (420 mg, 0.67 mmol, 47.6% yield) as a white solid $^1$H NMR (600 MHz, DMSO-$d_6$) δ ppm 10.10-10.23 (m, 1 H), 8.24 (dd, J=7.89, 0.99 Hz, 1 H), 8.05 (s, 1 H), 7.77 (t, 1 H), 7.64 (t, 1 H), 7.31-7.60 (m, 3 H), 7.02-7.16 (m, 1 H), 6.86-6.94 (m, 2 H), 6.77-6.84 (m, 1 H), 6.66 (d, J=10.85 Hz, 1 H), 5.75 (d, J=6.91 Hz, 1 H), 3.72-4.21 (m, 2 H), 2.62-3.16 (m, 4 H), 1.82 (m, 9 H). UPLC-MS: 1.34 min, 591.17 [M+H]+, method 10.

Example 142

3-(1-(4-amino-3-(3-fluoro-5-hydroxyphenyl)-1H-pyrazolo[3,4-d]pyrimidin-1-yl)ethyl)-4-(3-((4-methylpiperazin-1-yl)methyl)phenyl)-1H-isochromen-1-one

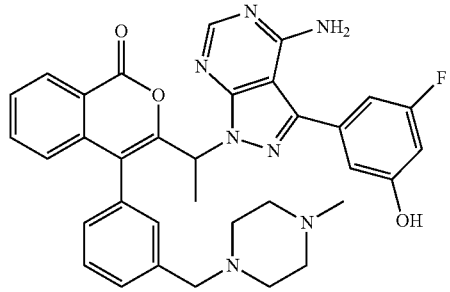 [SMILES: CC(c1oc(=O)c2ccccc2c1-c1cccc(CN2CCN(C)CC2)c1)n1nc(-c2cc(O)cc(F)c2)c2c(N)ncnc21]

Step a. 3-(1-(4-amino-3-(3-fluoro-5-methoxyphenyl)-1H-pyrazolo[3,4-d]pyrimidin-1-yl)ethyl)-4-(3-((4-methylpiperazin-1-yl)methyl)phenyl)-1H-isochromen-1-one

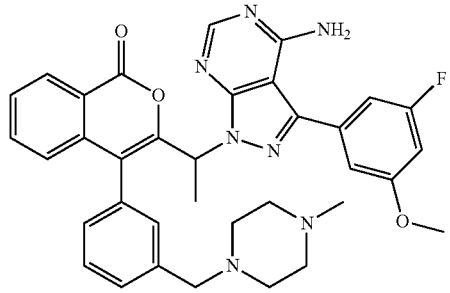 [SMILES: COc1cc(F)cc(-c2nn(C(C)c3oc(=O)c4ccccc4c3-c3cccc(CN4CCN(C)CC4)c3)c3ncnc(N)c23)c1]

The title compound was made in a similar way as that of the example 134, step a, from 3-(1-hydroxyethyl)-4-(3-((4-methylpiperazin-1-yl)methyl)phenyl)-1H-isochromen-1-one (Intermediate B49, 350 mg, 0.925 mmol) and 3-(3-fluoro-5-methoxyphenyl)-1H-pyrazolo[3,4-d]pyrimidin-4-amine (Intermediate G1, 264 mg, 1.017 mmol) to give 3-(1-(4-amino-3-(3-fluoro-5-methoxyphenyl)-1H-pyrazolo[3,4-d]pyrimidin-1-yl)ethyl)-4-(3-((4-methylpiperazin-1-yl)methyl)phenyl)-1H-isochromen-1-one (196 mg, 0.316 mmol, 34.2% yield) as a brown solid.

UPLC-MS: 0.82 min, 620.33 [M+H]+, method 9.

Step b

The title compound was made in a similar way as that of example 134, step b, from 3-(1-(4-amino-3-(3-fluoro-5-methoxyphenyl)-1H-pyrazolo[3,4-d]pyrimidin-1-yl)ethyl)-4-(3-((4-methylpiperazin-1-yl)methyl)phenyl)-1H-isochromen-1-one (196 mg, 0.316 mmol) to give the title compound (137 mg, 0.202 mmol, 63.8% yield) as a white solid.

$^1$H NMR (600 MHz, DMSO-$d_6$) δ ppm 10.20 (d, J=10.85 Hz, 1 H), 8.23 (ddd, J=7.89, 3.29, 0.99 Hz, 1 H), 8.15 (s, 1 H), 8.11 (s, 1 H), 7.73-7.82 (m, 1 H), 7.60-7.69 (m, 1 H), 7.23-7.57 (m, 4 H), 7.03 (d, J=6.91 Hz, 1 H), 6.86-6.94 (m, 2 H), 6.78-6.86 (m, 1 H), 6.68 (ddt, J=10.89, 6.54, 2.30, 2.30 Hz, 1 H), 5.61-5.87 (m, 1 H), 3.34 (br. s., 4 H), 2.52-3.20 (m, 9 H), 1.76-1.90 (m, 3 H). UPLC-MS: 2.78 min, 606.1 [M+H]+, method 9.

Example 143

3-(1-(4-amino-3-(3-fluoro-5-hydroxyphenyl)-1H-pyrazolo[3,4-d]pyrimidin-1-yl)ethyl)-4-(3-(piperidin-1-ylmethyl)phenyl)-1H-isochromen-1-one, Formate

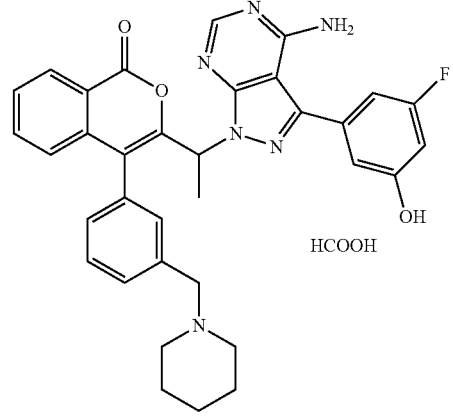 [SMILES: CC(c1oc(=O)c2ccccc2c1-c1cccc(CN2CCCCC2)c1)n1nc(-c2cc(O)cc(F)c2)c2c(N)ncnc21 ; "HCOOH"]

233

Step a. 3-(1-(4-amino-3-(3-(benzyloxy)-5-fluorophenyl)-1H-pyrazolo[3,4-d]pyrimidin-1-yl)ethyl)-4-(3-(piperidin-1-ylmethyl)phenyl)-1H-isochromen-1-one

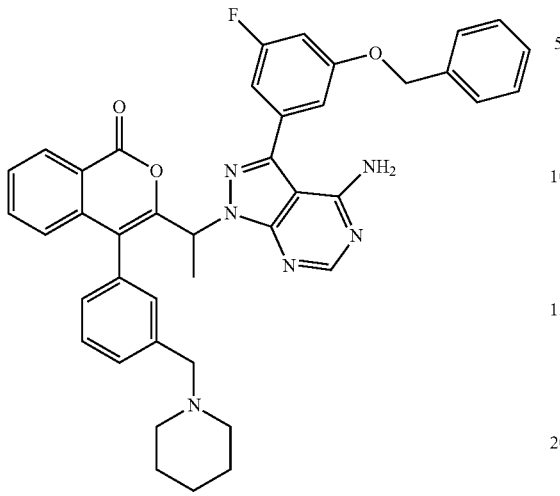

The title compound was made in a similar way as that of the compound of intermediate B37, from 3-(3-(1-(4-amino-3-(3-(benzyloxy)-5-fluorophenyl)-1H-pyrazolo[3,4-d]pyrimidin-1-yl)ethyl)-1-oxo-1H-isochromen-4-yl)benzaldehyde (Intermediate F6, 150 mg, 0.245 mmol), and piperidine (0.486 ml, 4.90 mmol) to give 3-(1-(4-amino-3-(3-(benzyloxy)-5-fluorophenyl)-1H-pyrazolo[3,4-d]pyrimidin-1-yl)ethyl)-4-(3-(piperidin-1-ylmethyl)phenyl)-1H-isochromen-1-one (103 mg, 0.151 mmol, 61.7% yield) as a whitish solid.

UPLC-MS: 2.08 min, 667.32 [M+H]+, method 10

Step b

The title compound was made in a similar way as that of the compound of example 136, step b, from 3-(1-(4-amino-3-(3-(benzyloxy)-5-fluorophenyl)-1H-pyrazolo[3,4-d]pyrimidin-1-yl)ethyl)-4-(3-(piperidin-1-ylmethyl)phenyl)-1H-isochromen-1-one (103 mg, 0.151 mmol) to give the title compound (13 mg, 13.5%) as a white solid.

$^1$H NMR (400 MHz, DMSO-$d_6$) δ ppm 8.15-8.35 (m, 3 H), 8.06 (d, J=4.41 Hz, 1 H), 7.76 (d, J=7.50 Hz, 1 H), 7.57-7.66 (m, 1 H), 7.39-7.51 (m, 1 H), 7.19-7.37 (m, 3 H), 6.74-7.06 (m, 5 H), 6.66 (d, J=11.03 Hz, 1 H), 5.56-5.83 (m, 1 H), 2.37 (m, 2 H), 2.18 (d, 3 H), 1.71-1.88 (m, 2 H), 1.18-1.65 (m, 8 H). UPLC-MS: 1.38 min, 591.30[M+H]+, method 10

Example 144

3-(1-(4-amino-3-(3-fluoro-5-hydroxyphenyl)-1H-pyrazolo[3,4-d]pyrimidin-1-yl)ethyl)-4-(2,2,6,6-tetramethyl-1,2,3,6-tetrahydropyridin-4-yl)-1H-isochromen-1-one hydrochloride

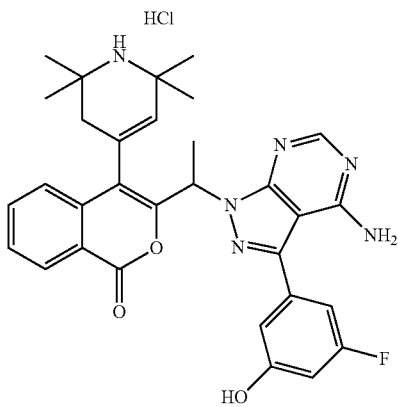 [SMILES: Cl ; CC(c1oc(=O)c2ccccc2c1C1=CC(C)(C)NC(C)(C)C1)n1nc(-c2cc(O)cc(F)c2)c2c(N)ncnc21]

234

Step a. 3-(1-(4-amino-3-(3-fluoro-5-methoxyphenyl)-1H-pyrazolo[3,4-d]pyrimidin-1-yl)ethyl)-4-(2,2,6,6-tetramethyl-1,2,3,6-tetrahydropyridin-4-yl)-1H-isochromen-1-one hydrochloride

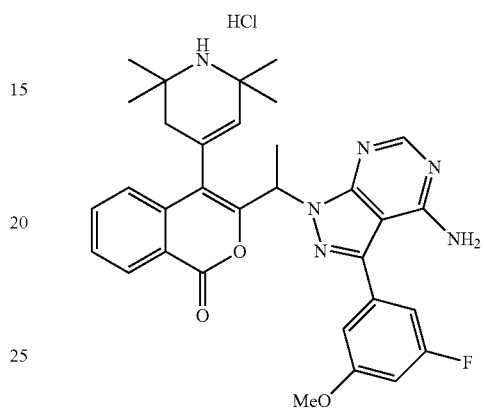

Title compound was prepared following the procedure reported for compound D1, 3-(1-bromoethyl)-4-(2,2,6,6-tetramethyl-1,2,3,6-tetrahydropyridin-4-yl)-1H-isochromen-1-one hydrobromide (Intermediate C39, 267 mg, 0.567 mmol) and Intermediate G1 (147 mg, 0.567 mmol) to give 3-(1-(4-amino-3-(3-fluoro-5-methoxyphenyl)-1H-pyrazolo[3,4-d]pyrimidin-1-yl)ethyl)-4-(2,2,6,6-tetramethyl-1,2,3,6-tetrahydropyridin-4-yl)-1H-isochromen-1-one hydrochloride (230 mg, 0.380 mmol, 67.1% yield) as a pale yellow powder.

UPLC-MS: 0.93 min, 568.7 [M+H]+, method 9

Step b

1M Boron tribromide in DCM (2.1 ml, 2.100 mmol) was added to a solution of 3-(1-(4-amino-3-(3-fluoro-5-methoxyphenyl)-1H-pyrazolo[3,4-d]pyrimidin-1-yl)ethyl)-4-(2,2,6,6-tetramethyl-1,2,3,6-tetrahydropyridin-4-yl)-1H-isochromen-1-one hydrochloride (226 mg, 0.373 mmol) in DCM (12 ml) and the resulting mixture was stirred at rt for 16 hrs. The suspension was slowly added at 0° C. to EtOH. The resulting mixture was concentrated under reduced pressure. Purification by RP-flash chromatography (Biotage 30 g C18 column, gradient elution from 100:0 to 60:40 A/B in 15 CV; A: water/MeCN 95/5+0.01% HCOOH, B: water/MeCN 5/95+0.01% HCOOH) yielded the title compound (168 mg, 0.284 mmol, 76% yield) as a pale yellow powder.

$^1$H NMR (600 MHz, DMSO-$d_6$) δ ppm 10.07-10.45 (bs, 1 H), 9.11-9.49 (m, 1 H), 8.43 (d, J=2.30 Hz, 1 H), 8.07-8.25 (m, 1 H), 7.55-8.01 (m, 3 H), 6.95 (dt, J=19.07, 1.64 Hz, 1 H), 6.66-6.90 (m, 2 H), 5.94-6.18 (m, 1 H), 2.94 (d, J=18.09 Hz, 1 H), 2.89 (m, 1 H), 1.87-2.06 (d, 3 H), 1.48-1.72 (m, 12 H). UPLC-MS: 2.69 min, 555.1 [M+H]+, method 6

Example 145

3-(1-(4-amino-3-(5-hydroxypyridin-3-yl)-1H-pyrazolo[3,4-d]pyrimidin-1-yl)ethyl)-4-(2,2,6,6-tetramethyl-1,2,3,6-tetrahydropyridin-4-yl)-1H-isochromen-1-one dihydrochloride

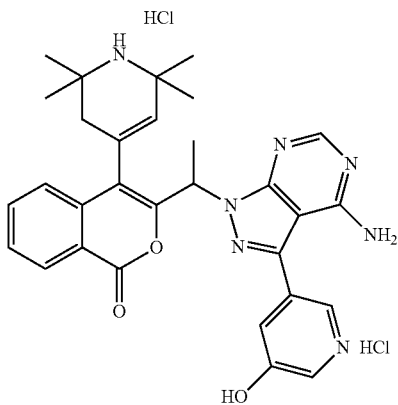 [SMILES: Cl ; CC(c1oc(=O)c2ccccc2c1C1=CC(C)(C)NC(C)(C)C1)n1nc(-c2cncc(O)c2)c2c(N)ncnc21 ; Cl]

Step a. 3-(1-(4-amino-3-(5-methoxypyridin-3-yl)-1H-pyrazolo[3,4-d]pyrimidin-1-yl)ethyl)-4-(2,2,6,6-tetramethyl-1,2,3,6-tetrahydropyridin-4-yl)-1H-isochromen-1-one hydrochloride

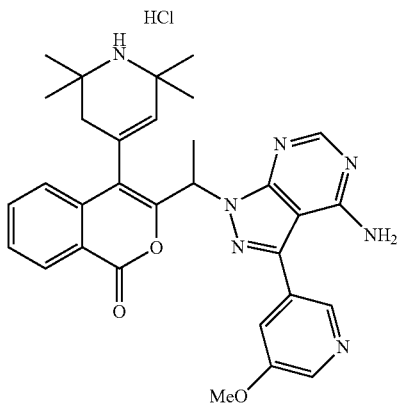 [SMILES: Cl ; COc1cncc(-c2nn(C(C)c3oc(=O)c4ccccc4c3C3=CC(C)(C)NC(C)(C)C3)c3ncnc(N)c23)c1]

The title compound was made in a similar way as that of intermediate D1, from 3-(1-bromoethyl)-4-(2,2,6,6-tetramethyl-1,2,3,6-tetrahydropyridin-4-yl)-1H-isochromen-1-one hydrobromide (Intermediate C39, 0.100 g, 0.212 mmol) and 3-(5-methoxypyridin-3-yl)-1H-pyrazolo[3,4-d]pyrimidin-4-amine (0.051 g, 0.212 mmol) to give 3-(1-(4-amino-3-(5-methoxypyridin-3-yl)-1H-pyrazolo[3,4-d]pyrimidin-1-yl)ethyl)-4-(2,2,6,6-tetramethyl-1,2,3,6-tetrahydropyridin-4-yl)-1H-isochromen-1-one hydrochloride (56.0 mg, 0.095 mmol, 44.9% yield) as a white powder.

UPLC-MS: 0.87 min, 551.8 [M+H]+, method 9.

Step b

Title compound was prepared following the procedure reported for compound Example 144, from 3-(1-(4-amino-3-(5-methoxypyridin-3-yl)-1H-pyrazolo[3,4-d]pyrimidin-1-yl)ethyl)-4-(2,2,6,6-tetramethyl-1,2,3,6-tetrahydropyridin-4-yl)-1H-isochromen-1-one hydrochloride (53.7 mg, 0.091 mmol) to give the title compound (17.6 mg, 0.029 mmol, 31.6% yield) as a white powder.

$^1$H NMR (600 MHz, DMSO-$d_6$) δ ppm 9.98-10.30 (bs, 1 H), 6.89-8.32 (m, 10 H), 5.88-6.13 (m, 2 H), 3.45 (m, 1 H), 2.96 (m, 1 H), 1.98 (d, J=7.23 Hz, 3 H), 0.98-1.60 (m, 12 H). UPLC-MS: 1.65 min, 538.1 [M+H]+, method 6.

Example 150

3-(1-(4-amino-3-(3-fluoro-5-hydroxyphenyl)-1H-pyrazolo[3,4-d]pyrimidin-1-yl)ethyl)-4-(1-(azetidine-3-carbonyl)-1,2,3,6-tetrahydropyridin-4-yl)-1H-isochromen-1-one formate

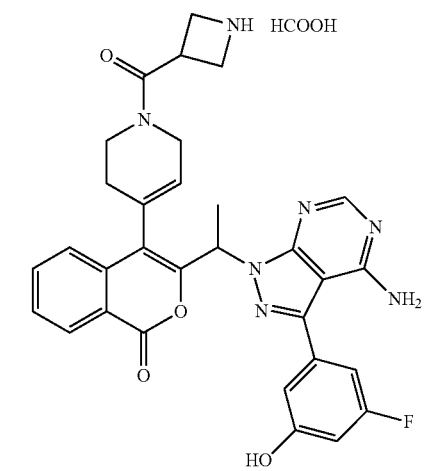 [SMILES: CC(c1oc(=O)c2ccccc2c1C1=CCN(C(=O)C2CNC2)CC1)n1nc(-c2cc(O)cc(F)c2)c2c(N)ncnc21 ; "HCOOH"]

Step a. tert-butyl 3-(4-(3-(1-(4-amino-3-(3-fluoro-5-hydroxyphenyl)-1H-pyrazolo[3,4-d]pyrimidin-1-yl)ethyl)-1-oxo-1H-isochromen-4-yl)-1,2,3,6-tetrahydropyridine-1-carbonyl)azetidine-1-carboxylate

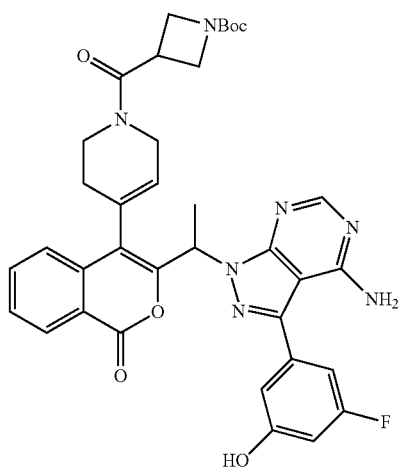 [SMILES: CC(c1oc(=O)c2ccccc2c1C1=CCN(C(=O)C2CN(C(=O)OC(C)(C)C)C2)CC1)n1nc(-c2cc(O)cc(F)c2)c2c(N)ncnc21]

The title compound was prepared following the procedure reported for Example 68, from tert-butyl 3-(4-(3-(1-(4-amino-3-iodo-1H-pyrazolo[3,4-d]pyrimidin-1-yl)ethyl)-1- oxo-1H-isochromen-4-yl)-1,2,3,6-tetrahydropyridine-1-carbonyl)azetidine-1-carboxylate (Intermediate D28, 0.251 g, 0.360 mmol), and 3-fluoro-5-hydroxyphenylboronic acid (0.112 g, 0.720 mmol) to give tert-butyl 3-(4-(3-(1-(4-amino-3-(3-fluoro-5-hydroxyphenyl)-1H-pyrazolo[3,4-d]pyrimidin-1-yl)ethyl)-1-oxo-1H-isochromen-4-yl)-1,2,3,6-tetrahydropyridine-1-carbonyl)azetidine-1-carboxylate (0.155 g, 0.227 mmol, 63.2% yield).

UPLC-MS: 1.03 min, 682.4 [M+H]+, method 9

Step b

4 M HCl in 1,4-dioxane (2 ml, 8.00 mmol) was added to a stirred solution of tert-butyl 3-(4-(3-(1-(4-amino-3-(3-fluoro-5-hydroxyphenyl)-1H-pyrazolo[3,4-d]pyrimidin-1-yl)ethyl)-1-oxo-1H-isochromen-4-yl)-1,2,3,6-tetrahydropyridine-1-carbonyl)azetidine-1-carboxylate (0.153 g, 0.224 mmol) in 1,4-dioxane (1 ml). After 1 h stirring at rt volatiles were removed under reduced pressure. Purification by RP flash chromatography (Biotage Isolera, 30 g C18 column, gradient elution from 100:0 to 80:20 A/B in 15 CV; A: water/MeCN 95/5+0.01% HCOOH, B: water/MeCN 5/95+0.01% HCOOH) yielded title compound (92.2 mg, 0.147 mmol, 65.5% yield) as a white powder.

$^1$H NMR (600 MHz, DMSO-$d_6$) δ ppm 6.65-8.34 (m, 11 H), 6.23 (m, 2 H), 3.30-4.29 (m, 11 H), 1.82 (d, 3 H). UPLC-MS: 2.36 min, 582.0 [M+H]+, method 6.

Example 151

3-(1-(4-amino-3-(3-fluoro-5-hydroxyphenyl)-1H-pyrazolo[3,4-d]pyrimidin-1-yl)ethyl)-4-(1-(1-methylazetidine-3-carbonyl)-1,2,3,6-tetrahydropyridin-4-yl)-1H-isochromen-1-one formate

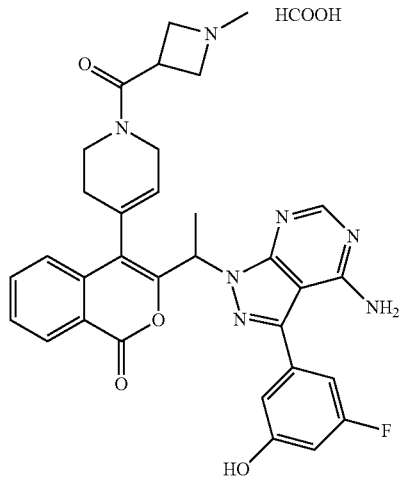 [SMILES: CC(c1oc(=O)c2ccccc2c1C1=CCN(C(=O)C2CN(C)C2)CC1)n1nc(-c2cc(O)cc(F)c2)c2c(N)ncnc21 ; "HCOOH"]

A mixture of 3-(1-(4-amino-3-(3-fluoro-5-hydroxyphenyl)-1H-pyrazolo[3,4-d]pyrimidin-1-yl)ethyl)-4-(1-(azetidine-3-carbonyl)-1,2,3,6-tetrahydropyridin-4-yl)-1H-isochromen-1-one formate (Example 150, 71.0 mg, 0.113 mmol), DIPEA (0.020 ml, 0.113 mmol), paraformaldehyde (69.3 mg, 2.30 mmol) and a spatula of Na$_2$SO$_4$ in DCM (2 ml) was stirred for 10 min at rt. Acetic acid (0.033 ml, 0.589 mmol) was then added followed by sodium triacetoxyhydroborate (82.2 mg, 0.387 mmol). After 6 hrs stirring at rt, volatiles were removed under reduced pressure. The residue was dissolved in DCM/EtOH 95:5 (10 ml) and washed with saturated sodium bicarbonate, then filtered on a phase separator and concentrated under reduced pressure. The residue was dissolved in DCM/MeOH 10:1 (1 ml), then formaldehyde (0.016 ml, 0.170 mmol) and AcOH (0.014 ml, 0.250 mmol) were added. After 5 min stirring, NaBH(OAc)$_3$ (25 mg, 0.118 mmol) was added. The resulting mixture was stirred for 30 min at rt, then it was concentrated under reduced pressure. Purification by RP flash chromatography (Biotage Isolera, 12 g C18 column, gradient elution from 100:0 to 60:40 A/B in 15 CV; A: water/MeCN 95/5+0.01% HCOOH, B: water/MeCN 5/95+0.01% HCOOH) yielded title compound (59.8 mg, 0.093 mmol, 82% yield) as a white solid.

$^1$H NMR (600 MHz, DMSO-$d_6$) δ ppm 1.90 (m, 3 H), 2.52 (t, J=5.59 Hz, 2 H), 2.75-4.56 (m, 12 H), 5.94-6.35 (m, 1 H), 6.62-6.74 (m, 1 H), 6.76-6.89 (m, 1 H), 6.89-7.01 (m, 1 H), 7.36-7.54 (m, 1 H), 7.57-7.69 (m, 1 H), 7.78-7.91 (m, 1 H), 8.04-8.84 (m, 2 H), 10.04-10.49 (m, 1 H). UPLC-MS: 2.41 min, 596.1 [M+H]+, method 6.

Example 154

3-(1-(4-amino-3-(3-chloro-5-hydroxyphenyl)-1H-pyrazolo[3,4-d]pyrimidin-1-yl)ethyl)-4-(1-methyl-1,2,3,6-tetrahydropyridin-4-yl)-1H-isochromen-1-one formate

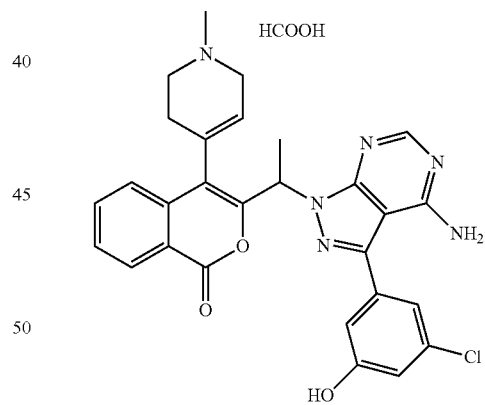

Title compound was prepared following the procedure reported for Example 151, from 3-(1-(4-amino-3-(3-chloro-5-hydroxyphenyl)-1H-pyrazolo[3,4-d]pyrimidin-1-yl)ethyl)-4-(1,2,3,6-tetrahydropyridin-4-yl)-1H-isochromen-1-one formate (Example 152, 200 mg, 0.357 mmol), to give the title compound (92.5 mg, 0.161 mmol, 45.1% yield) as a white powder.

$^1$H NMR (600 MHz, DMSO-$d_6$) δ ppm 6.81-8.40 (m, 11 H), 6.04-6.20 (m, 1 H), 5.96 (br. s., 1 H), 2.24-3.26 (m, 9 H), 1.79-1.95 (d, 3 H)

UPLC-MS: 2.60 min, 529.0 [M+H]+, method 6

Example 155

3-(1-(4-amino-3-(3-hydroxy-5-(trifluoromethyl)phenyl)-1H-pyrazolo[3,4-d]pyrimidin-1-yl)ethyl)-4-(1-methyl-1,2,3,6-tetrahydropyridin-4-yl)-1H-isochromen-1-one formate

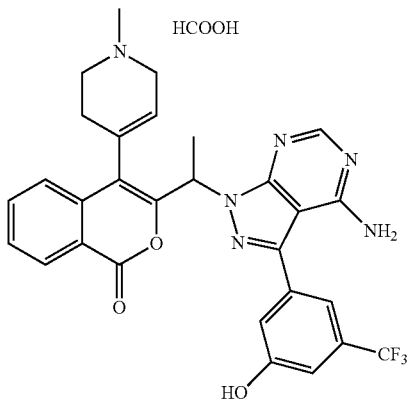 [SMILES: CC(c1oc(=O)c2ccccc2c1C1=CCN(C)CC1)n1nc(-c2cc(O)cc(C(F)(F)F)c2)c2c(N)ncnc21 ; "HCOOH"]

Title compound was synthesized following the procedure described for the preparation of Example 151, from 3-(1-(4-amino-3-(3-hydroxy-5-(trifluoromethyl)phenyl)-1H-pyrazolo[3,4-d]pyrimidin-1-yl)ethyl)-4-(1,2,3,6-tetrahydropyridin-4-yl)-1H-isochromen-1-one formate (Example 153, 215 mg, 0.362 mmol), to give the title compound (115 mg, 0.189 mmol, 52.3% yield) as a white powder.

$^1$H NMR (600 MHz, DMSO-$d_6$) δ ppm 7.12-8.28 (m, 11 H), 6.58-7.09 (m, 1 H), 5.97 (br. s., 1 H), 2.30-3.31 (m, 9 H), 1.79-1.98 (d, 3 H). UPLC-MS: 2.85 min, 563.1 [M+H]+, method 6

Example 156

3-(1-(4-amino-3-(3-fluoro-5-hydroxyphenyl)-1H-pyrazolo[3,4-d]pyrimidin-1-yl)ethyl)-4-(1-(azetidin-3-yl)-1,2,3,6-tetrahydropyridin-4-yl)-1H-isochromen-1-one dihydrochloride

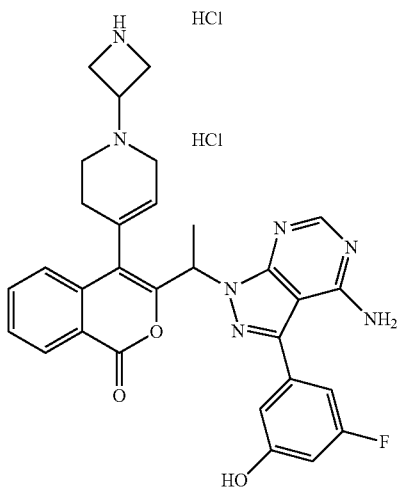 [SMILES: Cl ; CC(c1oc(=O)c2ccccc2c1C1=CCN(C2CNC2)CC1)n1nc(-c2cc(O)cc(F)c2)c2c(N)ncnc21 ; Cl]

Step a. 3-(1-(4-amino-3-(3-fluoro-5-hydroxyphenyl)-1H-pyrazolo[3,4-d]pyrimidin-1-yl)ethyl)-4-(1,2,3,6-tetrahydropyridin-4-yl)-1H-isochromen-1-one formate

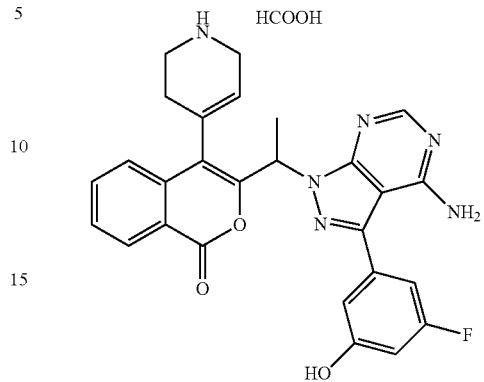

N$_2$ was bubbled for 5 min through a suspension of tert-butyl 4-(3-(1-(4-amino-3-iodo-1H-pyrazolo[3,4-d]pyrimidin-1-yl)ethyl)-1-oxo-1H-isochromen-4-yl)-5,6-dihydropyridine-1(2 H)-carboxylate (Intermediate D14, 735 mg, 1.197 mmol), 3-fluoro-5-hydroxyphenylboronic acid (0.28 g, 1.795 mmol), S-Phos-Pd-G2 (0.130 g, 0.179 mmol) and potassium phosphate (572 mg, 2.695 mmol) in THF/water 3:1 (8 ml). The mixture was heated at 85° C. for 1 hr by MW irradiation. A second run was performed in the same conditions on a mixture of reagents in the exact same amounts. The two reaction mixtures were combined and conc HCl (20 ml) was slowly added while stirring. Stirring went on at rt for 3 h, then volatiles were removed under reduced pressure. Purification by RP flash chromatography (Biotage Isolera, 60 g C18 column, gradient elution from 100:0 to 70:30 A/B in 15 CV; A: water/MeCN 95/5+0.01% HCOOH, B: water/MeCN 5/95+ 0.01% HCOOH) yielded 3-(1-(4-amino-3-(3-fluoro-5-hydroxyphenyl)-1H-pyrazolo[3,4-d]pyrimidin-1-yl)ethyl)-4-(1,2,3,6-tetrahydropyridin-4-yl)-1H-isochromen-1-one formate (0.990 g, 1.818 mmol, 76% yield) as a pale yellow powder.

UPLC-MS: 0.67 min, 499.2 [M+H]+, method 2 min

Step b. tert-butyl 3-(4-(3-(1-(4-amino-3-(3-fluoro-5-hydroxyphenyl)-1H-pyrazolo[3,4-d]pyrimidin-1-yl)ethyl)-1-oxo-1H-isochromen-4-yl)-5,6-dihydropyridin-1(2 H)-yl)azetidine-1-carboxylate formate

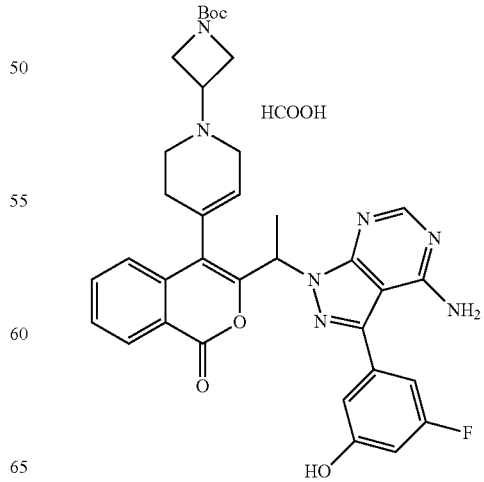

Compound was prepared following the procedure described for the synthesis of Intermediate D24, from 3-(1-(4-amino-3-(3-fluoro-5-hydroxyphenyl)-1H-pyrazolo[3,4-d]pyrimidin-1-yl)ethyl)-4-(1,2,3,6-tetrahydropyridin-4-yl)-1H-isochromen-1-one formate (300 mg, 0.551 mmol) and tert-butyl 3-oxoazetidine-1-carboxylate (236 mg, 1.379 mmol), to afford tert-butyl 3-(4-(3-(1-(4-amino-3-(3-fluoro-5-hydroxyphenyl)-1H-pyrazolo[3,4-d]pyrimidin-1-yl)ethyl)-1-oxo-1H-isochromen-4-yl)-5,6-dihydropyridin-1(2H)-yl)azetidine-1-carboxylate formate (74.4 mg, 0.106 mmol, 19.30% yield).

UPLC-MS: 0.85 min, 654.3 [M+H]+, method 9

Step c 4.0 M HCl in 1,4-dioxane (0.5 ml, 2.000 mmol) was added to a solution of tert-butyl 3-(4-(3-(1-(4-amino-3-(3-fluoro-5-hydroxyphenyl)-1H-pyrazolo[3,4-d]pyrimidin-1-yl)ethyl)-1-oxo-1H-isochromen-4-yl)-5,6-dihydropyridin-1(2H)-yl)azetidine-1-carboxylate formate (70 mg, 0.100 mmol) in 1,4-dioxane-methanol 3:1 (4 ml). The mixture was stirred for 6 hrs at rt, then volatiles were removed under reduced pressure. Purification by RP-flash chromatography (Biotage 30 g C18 column, gradient elution from 100:0 to 60:40 A/B in 15 CV; A: water/MeCN 95/5+0.01% HCOOH, B: water/MeCN 5/95+0.01% HCOOH) yielded title compound (57 mg, 0.091 mmol, 91% yield) as a white powder.

$^1$H NMR (600 MHz, DMSO-$d_6$) δ ppm 12.70-13.40 (br. s., 1 H), 10.32 (br. s., 1 H), 9.73 (br. s., 1 H), 9.22 (br. s., 1 H), 6.71-8.58 (m, 10 H), 5.95-6.37 (m, 2 H), 2.51-4.79 (m, 11 H), 1.76-2.04 (d, 3 H). UPLC-MS: 2.32 min, 554.1 [M+H]+, method 6

Example 157

3-(1-(4-amino-3-(3-fluoro-5-hydroxyphenyl)-1H-pyrazolo[3,4-d]pyrimidin-1-yl)ethyl)-4-(1-(1-(cyclopropylmethyl)azetidin-3-yl)-1,2,3,6-tetrahydropyridin-4-yl)-1H-isochromen-1-one dihydrochloride

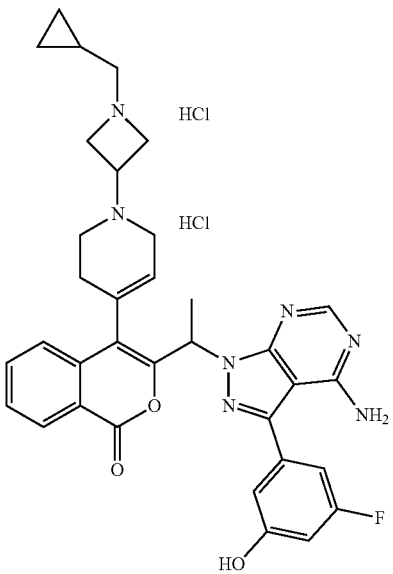 [SMILES: CC(c1oc(=O)c2ccccc2c1C1=CCN(C2CN(CC3CC3)C2)CC1)n1nc(-c2cc(O)cc(F)c2)c2c(N)ncnc21 ; Cl ; Cl]

Title compound was prepared following the procedure described for the synthesis of Intermediate D24, from 3-(1-(4-amino-3-(3-fluoro-5-hydroxyphenyl)-1H-pyrazolo[3,4-d]pyrimidin-1-yl)ethyl)-4-(1-(azetidin-3-yl)-1,2,3,6-tetrahydropyridin-4-yl)-1H-isochromen-1-one dihydrochloride (Example 156, 35 mg, 0.059 mmol) and cyclopropanecarbaldehyde (10.19 μl 0.136 mmol) to give the compound (33.8 mg, 0.050 mmol, 84% yield) as a white powder.

$^1$H NMR (600 MHz, DMSO-$d_6$) δ ppm 0.42 (br s, 2 H), 0.60 (br d, J=4.93 Hz, 2 H), 0.94-1.09 (m, 1 H), 1.95 (m, 3 H), 2.35-4.59 (m, 11 H), 4.62-4.96 (m, 2 H), 6.01-8.79 (m, 12 H), 10.08-10.63 (br, 1 H), 11.18-11.66 (br, 1 H), 12.98-13.61 (br, 1 H). UPLC-MS: 2.68 min, 608.2 [M+H]+, method 6

Example 158

3-(1-(4-amino-3-(3-fluoro-5-hydroxyphenyl)-1H-pyrazolo[3,4-d]pyrimidin-1-yl)ethyl)-4-(3-(dimethylamino)prop-1-yn-1-yl)-1H-isochromen-1-one hydrochloride

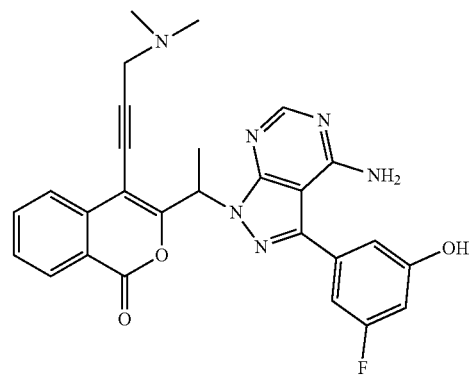 [SMILES: CC(c1oc(=O)c2ccccc2c1C#CCN(C)C)n1nc(-c2cc(O)cc(F)c2)c2c(N)ncnc21]

Step a. Benzyl (3-(3-(1-(4-amino-3-(3-fluoro-5-methoxyphenyl)-1H-pyrazolo[3,4-d]pyrimidin-1-yl)ethyl)-1-oxo-1H-isochromen-4-yl)prop-2-yn-1-yl)(methyl)carbamate

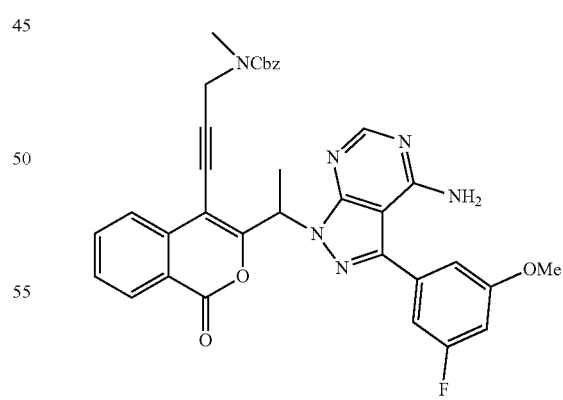

The title compound was prepared following the procedure described for the synthesis of Intermediate D1, from 3-(3-fluoro-5-methoxyphenyl)-1H-pyrazolo[3,4-d]pyrimidin-4-amine (Intermediate G1, 165 mg, 0.638 mmol) and benzyl (3-(3-(1-bromoethyl)-1-oxo-1H-isochromen-4-yl)prop-2-yn-1-yl)(methyl)carbamate (Intermediate C41, 290 mg, 0.638 mmol) to give Benzyl (3-(3-(1-(4-amino-3-(3-fluoro- 5-methoxyphenyl)-1H-pyrazolo[3,4-d]pyrimidin-1-yl) ethyl)-1-oxo-1H-isochromen-4-yl)prop-2-yn-1-yl)(methyl) carbamate (138 mg, 0.218 mmol, 34.2% yield) as yellow solid.

UPLC-MS: 1.27 min, 633 [M+H]+, method 9

Step b

To a solution of benzyl (3-(3-(1-(4-amino-3-(3-fluoro-5-methoxyphenyl)-1H-pyrazolo[3,4-d]pyrimidin-1-yl)ethyl)-1-oxo-1H-isochromen-4-yl)prop-2-yn-1-yl)(methyl)carbamate (100 mg, 0.158 mmol) in DCM (4 ml), 1M BBr$_3$ in DCM (3 ml, 10.50 mmol) was added and the reaction was stirred overnight. Then, the solution was cooled to 0° C. and stirred for 1 h. Then, EtOH (1 ml) was added and solvent was removed under reduced. The resulting material was reacted in DCM (4 ml) with trioxane (0.049 ml, 0.472 mmol), N-isopropyl-N-methylpropan-2-amine (18.14 mg, 0.157 mmol) for 30 min. Then, sodium triacetoxyborohydride (100 mg, 0.472 mmol) and acetic acid (28.4 mg, 0.472 mmol) were added and the reaction stirred for 1 h. Solvent was removed and crude was purified by C18 flash chromatography ((H$_2$O/ACN)) 95:5+0.1% HCOOH}:{(ACN/H$_2$O) 95:5+HCOOH 0.1%} from 100:0 to 0:100 affording the title compound (5 mg, 10.03 mmol, 6.37% yield) as a white solid.

$^1$H NMR (600 MHz, DMSO-d$_6$) δ ppm 10.34-10.50 (bs, 1 H), 10.13-10.27 (bs, 1 H), 8.26-8.31 (m, 1 H), 8.16-8.21 (m, 1 H), 7.89-8.03 (m, 2 H), 7.67-7.78 (m, 1 H), 6.90-6.95 (m, 1 H), 6.83-6.89 (m, 1 H), 6.66-6.76 (m, 1 H), 6.40-6.52 (m, 1 H), 4.35-4.55 (m, 2 H), 2.89-3.02 (m, 6 H), 1.92-1.98 (m, 3 H). UPLC-MS: 2.36 min, 499.2 [M+H]+, method 6

Example 161

3-(1-(4-amino-3-(5-hydroxy-6-(trifluoromethyl)pyridin-3-yl)-1H-pyrazolo[3,4-d]pyrimidin-1-yl)ethyl)-4-phenyl-1H-isochromen-1-one

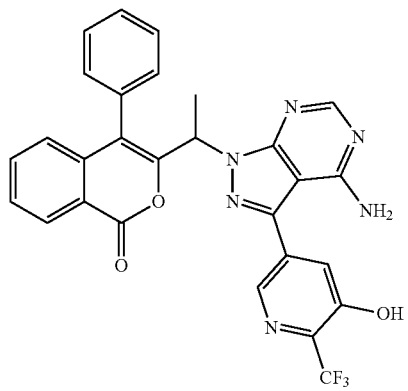 [SMILES: CC(c1oc(=O)c2ccccc2c1-c1ccccc1)n1nc(-c2cnc(C(F)(F)F)c(O)c2)c2c(N)ncnc21]

The title compound was made in a similar way as that of example 68, using 3-(1-(4-amino-3-iodo-1H-pyrazolo[3,4-d]

pyrimidin-1-yl)ethyl)-4-phenyl-1H-isochromen-1-one (intermediate D2a, 100 mg, 0.196 mmol) and (5-(benzyloxy)-6-(trifluoromethyl)pyridin-3-yl)boronic acid (Intermediate G25, 87 mg, 0.295 mmol). The resulting crude material was reacted in 2-Propanol (10 ml) with 1 N aqueous HCl (1 ml), palladium on carbon 5% wet (0.071 mmol) and hydrogen (1 atm). Then, catalyst was filtered off over celite pad and solvent was removed. Target product was purified by purified by C18 flash chromatography (Snap 30 g chromatography ((H$_2$O/ACN)) 95:5+0.1% HCOOH}:{(ACN/H$_2$O) 95:5+ HCOOH 0.1%} from 100:0 to 0:100 affording the title compound (20 mg, 0.037 mmol, 51.8% yield) as a white solid.

$^1$H NMR (400 MHz, DMSO-d$_6$) δ ppm 11.47 (br. s., 1 H), 6.52-8.35 (m, 14 H), 5.82 (d, J=7.06 Hz, 1 H), 1.83-1.99 (d, 3 H). UPLC-MS: 3.30 min, 545.1 [M+H]+, method 6.

Example 162

3-(1-(4-amino-3-(3-fluoro-5-hydroxyphenyl)-1H-pyrazolo[3,4-d]pyrimidin-1-yl)ethyl)-7-methyl-4-phenyl-1H-isochromen-1-one

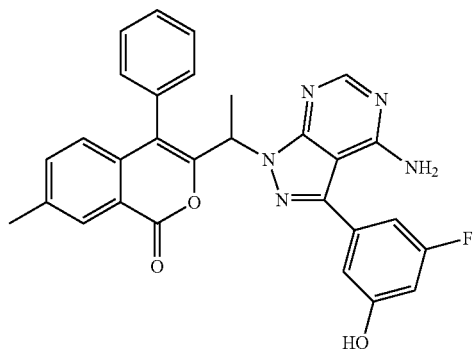 [SMILES: Cc1ccc2c(-c3ccccc3)c(C(C)n3nc(-c4cc(O)cc(F)c4)c4c(N)ncnc43)oc(=O)c2c1]

3-(1-(4-Amino-3-iodo-1H-pyrazolo[3,4-d]pyrimidin-1-yl)ethyl)-7-methyl-4-phenyl-1H-isochromen-1-one (intermediate D29, 0.100 g, 0.19 mmol), (3-fluoro-5-hydroxyphenyl)boronic acid (0.036 g, 0.229 mmol) and PPh$_3$ (0.030 g, 0.114 mmol) were dissolved in a mixture of DMF (10 ml), EtOH (4 ml) and water (4 ml); Na$_2$CO$_3$ (0.101 g, 0.95 mmol) was added and the mixture was degasses under nitrogen. Pd(OAc)$_2$ (0.009 g, 0.038 mmol) was added and the reaction was heated at 80° C. for 15 min. 1M HCl was added (pH≈2) and the mixture was partitioned between EtOAc and water. The organic phase was extracted with EtOAc and the combined organic layers were washed several times with brine and dried over sodium sulfate. The solvent was removed and the crude was purified by flash chromatography on Biotage silica gel cartridge (DCM to DCM:MeOH=97:3) to afford the title compound (0.023 g, 0.045 mmol, 24%).

$^1$H NMR (400 MHz, DMSO-d$_6$) δ ppm 10.19 (s, 1 H), 8.09 (s, 1 H), 8.03 (br. s, 1 H), 7.47-7.69 (m, 2 H), 7.30-7.47 (m, 3 H), 7.09-7.14 (m, 1 H), 6.89-6.92 (m, 1 H), 6.77-6.86 (m, 2

H), 6.66 (dt, 1 H), 6.00-8.00 (m, 2 H), 5.68-5.76 (m, 1 H), 2.42 (s, 3 H), 1.82 (d, 3 H). UPLC-MS: 1.10 min, 508.2 [M+H]+, method 13.

Example 163

3-(1-(4-amino-3-(3-fluoro-5-hydroxyphenyl)-1H-pyrazolo[3,4-d]pyrimidin-1-yl)ethyl)-7-chloro-4-phenyl-1H-isochromen-1-one

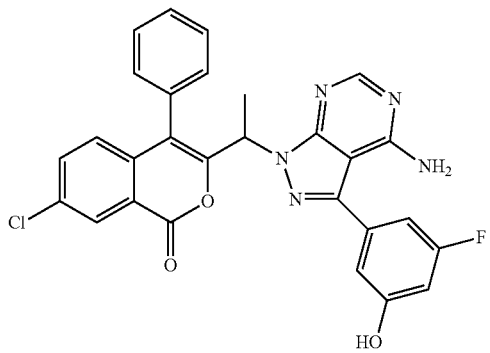 [SMILES: CC(c1oc(=O)c2cc(Cl)ccc2c1-c1ccccc1)n1nc(-c2cc(O)cc(F)c2)c2c(N)ncnc21]

The title compound was made in a similar way as that of the compound of example 162, from 3-(1-(4-amino-3-iodo-1H-pyrazolo[3,4-d]pyrimidin-1-yl)ethyl)-7-chloro-4-phenyl-1H-isochromen-1-one (intermediate D30, 0.100 g, 0.184 mmol) and (3-fluoro-5-hydroxyphenyl)boronic acid (0.034 g, 0.22 mmol) to provide title compound (0.05 g, 0.094 mmol, 51%).

$^1$H NMR (400 MHz, DMSO-$d_6$) δ ppm 10.21 (s, 1 H), 8.18 (d, 1 H), 8.10 (s, 1 H), 7.83 (dd, 1 H), 7.51-7.57 (m, 1 H), 7.37-7.49 (m, 3 H), 7.13-7.17 (m, 1 H), 6.86-6.95 (m, 2 H), 6.81-6.87 (m, 1 H), 6.67 (dt, 1 H), 6.00-8.50 (m, 2 H), 5.70-5.77 (m, 1 H), 1.83 (d, 3 H). UPLC-MS: 1.15 min, 527.9 [M+H]+, method 12.

Example 164

3-(1-(4-amino-3-(3-fluoro-5-hydroxyphenyl)-1H-pyrazolo[3,4-d]pyrimidin-1-yl)ethyl)-6-chloro-4-phenyl-1H-isochromen-1-one

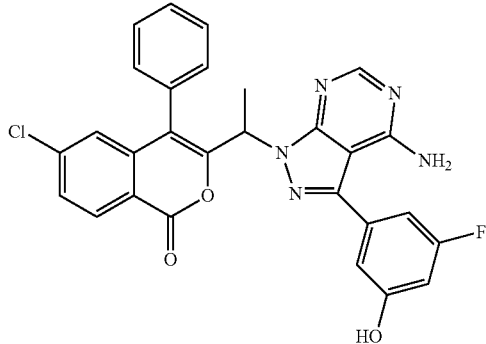 [SMILES: CC(c1oc(=O)c2ccc(Cl)cc2c1-c1ccccc1)n1nc(-c2cc(O)cc(F)c2)c2c(N)ncnc21]

The title compound was made in a similar way as that of example 162, from 3-(1-(4-Amino-3-iodo-1H-pyrazolo[3,4-d]pyrimidin-1-yl)ethyl)-6-chloro-4-phenyl-1H-isochromen-1-one (intermediate D31, 0.100 g, 0.184 mmol) and (3-fluoro-5-hydroxyphenyl)boronic acid (0.034 g, 0.221 mmol) to afford title compound as a white solid (0.023 g, 0.0463 mmol, 24%).

$^1$H NMR (400 MHz, DMSO-$d_6$) δ ppm 10.25 (br. s., 1 H), 8.22 (d, 1 H), 8.09 (s, 1 H), 7.68 (dd, 1 H), 7.51-7.58 (m, 1 H), 7.36-7.49 (m, 3 H), 7.13-7.18 (m, 1 H), 6.88-6.92 (m, 1 H), 6.80-6.85 (m, 1 H), 6.76 (d, 1 H), 6.63-6.69 (m, 1 H), 6.00-8.00 (m, 2 H), 5.68-5.76 (m, 1 H), 1.82 (d, 3 H). UPLC-MS: 1.17 min, 528.3 [M+H]+, method 14.

Example 165

3-(1-(4-amino-3-(3-fluoro-5-hydroxyphenyl)-1H-pyrazolo[3,4-d]pyrimidin-1-yl)ethyl)-6-fluoro-4-phenyl-1H-isochromen-1-one

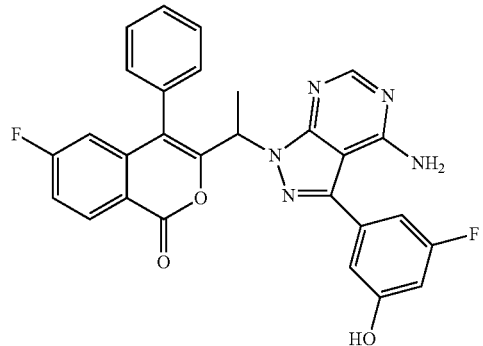 [SMILES: CC(c1oc(=O)c2ccc(F)cc2c1-c1ccccc1)n1nc(-c2cc(O)cc(F)c2)c2c(N)ncnc21]

In a sealed vial, a mixture of 3-(1-(4-amino-3-iodo-1H-pyrazolo[3,4-d]pyrimidin-1-yl)ethyl)-6-fluoro-4-phenyl-1H-isochromen-1-one (intermediate D32, 0.240 g, 0.455 mmol), (3-fluoro-5-hydroxyphenyl)boronic acid (0.156 g, 1 mmol) and K$_2$CO$_3$ (0.138 g, 1 mmol) in dioxane/H$_2$O 4:1 (10 ml) was degassed; Pd(dppf)Cl$_2$ (0.04 g, 0.054 mmol) was added and the reaction was heated at 120° C. for 4 hrs. 1M HCl was added (pH≈1) and the mixture was partitioned between EtOAc and water. The aqueous phase was extracted with EtOAc and the combined organic layers were washed with brine and dried over sodium sulfate. The solvent was removed and the crude was purified by flash chromatography on Biotage silica gel cartridge (cyclohexane:EtOAc=95:5 to =20:80) and then triturated with ACN to yield title compound as a white solid (0.08 g, 0.16 mmol).

$^1$H NMR (400 MHz, DMSO-$d_6$) δ ppm 10.19 (s, 1 H), 8.27-8.33 (m, 1 H), 8.09 (s, 1 H), 7.36-7.57 (m, 5 H), 7.13-7.18 (m, 1 H), 6.86-6.94 (m, 1 H), 6.80-6.86 (m, 1 H), 6.66 (dt, 1 H), 6.49 (dd, 1 H), 6.00-7.80 (m, 2 H), 5.66-5.78 (m, 1 H), 1.83 (d, 3 H). UPLC-MS: 1.08 min, 512.2 [M+H]+, method 13 W

Examples 166a (Enantiomer 1) and 166b (Enantiomer 2)

4-(1-acetyl-1,2,3,6-tetrahydropyridin-4-yl)-3-(1-(4-amino-3-(3-fluoro-5-hydroxyphenyl)-1H-pyrazolo[3,4-d]pyrimidin-1-yl)ethyl)-1H-isochromen-1-one single enantiomers

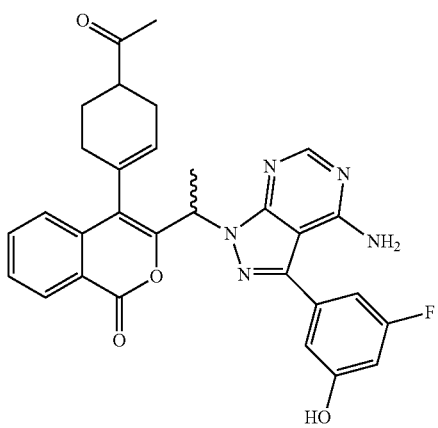 [SMILES: CC(=O)C1CC=C(c2c(C(C)n3nc(-c4cc(O)cc(F)c4)c4c(N)ncnc43)oc(=O)c3ccccc23)CC1]

Step 1. 4-(1-acetyl-1,2,3,6-tetrahydropyridin-4-yl)-3-(1-(4-amino-3-(3-((tert-butyldimethylsilyl)oxy)-5-fluorophenyl)-1H-pyrazolo[3,4-d]pyrimidin-1-yl)ethyl)-1H-isochromen-1-one (intermediate T.1)

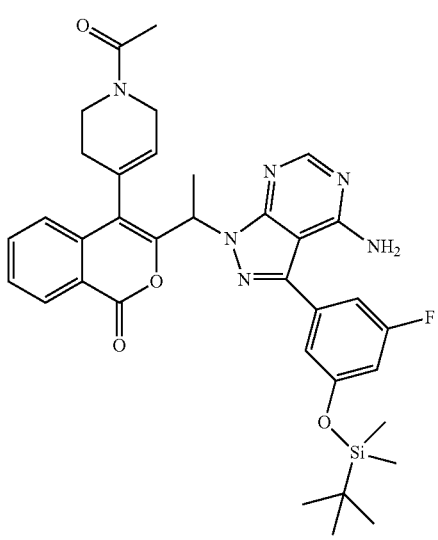 [SMILES: CC(=O)N1CC=C(c2c(C(C)n3nc(-c4cc(F)cc(O[Si](C)(C)C(C)(C)C)c4)c4c(N)ncnc43)oc(=O)c3ccccc23)CC1]

4-(1-acetyl-1,2,3,6-tetrahydropyridin-4-yl)-3-(1-(4-amino-3-(3-fluoro-5-hydroxyphenyl)-1H-pyrazolo[3,4-d]pyrimidin-1-yl)ethyl)-1H-isochromen-1-one (Example 72, 726 mg, 1.343 mmol) was dissolved in N,N-Dimethylformamide (7.5 ml), followed by the addition of TBDMSCl (405 mg, 2.69 mmol) and imidazole (366 mg, 5.37 mmol). The mixture stirred for 3 hrs at rt, then further 0.3 eq of TBDMSCl and imidazole were added to achieve full reaction completion The reaction was diluted with DCM (100 ml) and washed twice with 0.5M HCl$_{aqueous}$ (50 ml), filtered through a phase separator, and concentrated under reduced pressure. The residue was purified via flash chromatography on silica gel using a Biotage 100G SNAP with a gradient of DCM and EtOH to give the title compound (635 mg, 72.2%) as pinky foam.

UPLC-MS: 1.40 min, 655.0 [M+H]+, method 9

Step 2. 4-(1-acetyl-1,2,3,6-tetrahydropyridin-4-yl)-3-(1-(4-amino-3-(3-((tert-butyldimethylsilyl)oxy)-5-fluorophenyl)-1H-pyrazolo[3,4-d]pyrimidin-1-yl)ethyl)-1H-isochromen-1-one single enantiomers (T.2 and T.3)

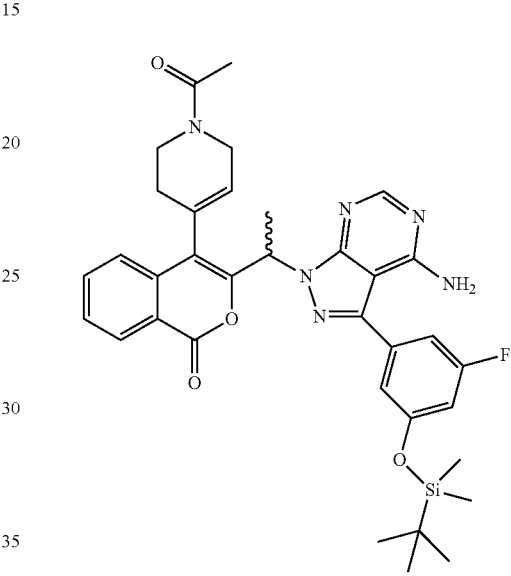

Racemate 4-(1-acetyl-1,2,3,6-tetrahydropyridin-4-yl)-3-(1-(4-amino-3-(3-((tert-butyldimethylsilyl)oxy)-5-fluorophenyl)-1H-pyrazolo[3,4-d]pyrimidin-1-yl)ethyl)-1H-isochromen-1-one (intermediate T.1, 0.759 g, 1.16 mmol) was dissolved in 14 ml Ethanol/Methanol 1/1+6 ml n-Hexane and submitted to chiral resolution by Chiral preparative chromatography. Conditions: Column: Chiralpak AS-H (25×2.0 cm), 5μ; Mobile phase: n-Hexane/(2-Propanol/Methanol 1/1+0.1% isopropylamine) 85/15% v/v; Flow rate: 17 ml/min; DAD detection: 220 nm; Loop: 700 μl; Injection: 26.6 mg/injection.

The fractions containing the first eluted enantiomer were evaporated to dryness to afford intermediate T.2 (first eluted enantiomer, 0.350 g, 0.535 mmol). Chiral HPLC (Method A10): Rt=13.6 min, ee>99%. UPLC-MS: 1.32 min, 655.5 [M+H]+, method 13.

The fractions containing the second eluted enantiomer were evaporated to dryness to afford intermediate T.3 (second eluted enantiomer, 0.365 g, 0.557 mmol). Chiral HPLC (Method A10): Rt=20.6 min, ee=>99%. UPLC-MS: 1.33 min, 655.5 [M+H]+, method 13.

Step 3. Examples 166a (Enantiomer 1): 4-(1-acetyl-1,2,3,6-tetrahydropyridin-4-yl)-3-(1-(4-amino-3-(3-fluoro-5-hydroxyphenyl)-1H-pyrazolo[3,4-d]pyrimidin-1-yl)ethyl)-1H-isochromen-1-one single enantiomer 4-(1-acetyl-1,2,3,6-tetrahydropyridin-4-yl)-3-(1-(4-amino-3-(3-((tert-butyldimethylsilyl)oxy)-5-fluorophenyl)-

1H-pyrazolo[3,4-d]pyrimidin-1-yl)ethyl)-1H-isochromen-1-one single enantiomer (intermediate T.2, first eluted enantiomer under the conditions described above, 0.350 g, 0.535 mmol) was dissolved in a solution of 1M HCl in EtOH (1.7 ml) and the mixture was stirred at RT overnight. The volatiles were removed under reduced pressure and the residue was purified by flash chromatography on silica gel cartridge (DCM to DCM:MeOH=95:5) to afford title compound as a yellow solid (0.270 g, 0.500 mmol, 93%). This compound proved to be the second eluted enantiomer under Chiral HPLC conditions of Method A11: Rt=15.8 min, ee=99.4%.

$^1$H NMR (500 MHz, DMSO-$d_6$) δ ppm 10.28 (br. s., 1 H), 8.27-8.54 (m, 1 H), 8.06-8.25 (m, 1 H), 7.80-7.96 (m, 1 H), 7.56-7.72 (m, 1 H), 7.37-7.52 (m, 1 H), 6.79-6.98 (m, 2 H), 6.65-6.75 (m, 1 H), 6.49-8.83 (m, 2 H), 6.07-6.35 (m, 1 H), 5.27-6.07 (m, 1 H), 3.53-4.33 (m, 4 H), 1.96-2.44 (m, 5 H), 1.62-1.94 (m, 3 H). UPLC-MS: 0.83 min, 541.3 [M+H]+, method 13.

Step 4. Examples 166b (Enantiomer 2) 4-(1-acetyl-1,2,3,6-tetrahydropyridin-4-yl)-3-(1-(4-amino-3-(3-fluoro-5-hydroxyphenyl)-1H-pyrazolo[3,4-d]pyrimidin-1-yl)ethyl)-1H-isochromen-1-one single enantiomer 4-(1-acetyl-1,2,3,6-tetrahydropyridin-4-yl)-3-(1-(4-amino-3-(3-((tert-butyldimethylsilyl)oxy)-5-fluorophenyl)-1H-pyrazolo[3,4-d]pyrimidin-1-yl)ethyl)-1H-isochromen-1-one single enantiomer (intermediate T.3, second eluted enantiomer under the conditions described above, 0.365 g, 0.557 mmol) was dissolved in a solution of 1M HCl in EtOH (1.78 mL) and the mixture was stirred at RT overnight. The volatiles were removed under reduced pressure and the residue was purified by flash chromatography on silica gel cartridge (DCM to DCM:MeOH=95:5) to afford title compound as a yellow solid (0.260 g, 0.481 mmol, 86%). This compound proved to be the first eluted enantiomer under Chiral HPLC conditions of Method A11: Rt=13.6 min, ee=99.6%.

$^1$H NMR (500 MHz, DMSO-$d_6$) δ ppm 10.28 (br. s., 1 H), 8.30-8.55 (m, 1 H), 8.12-8.24 (m, 1 H), 7.82-7.94 (m, 1 H), 7.57-7.71 (m, 1 H), 7.40-7.51 (m, 1 H), 6.80-6.97 (m, 2 H), 6.63-6.76 (m, 1 H), 6.49-8.83 (m, 2 H), 6.07-6.32 (m, 1 H), 5.26-6.06 (m, 1 H), 3.59-4.30 (m, 4 H), 1.94-2.48 (m, 5 H), 1.77-1.94 (m, 3 H). UPLC-MS: 0.83 min, 541.3 [M+H]+, method 13.

Examples 167a (Enantiomer 1) and 167b (Enantiomer 2)

3-(1-(4-amino-3-(3-fluoro-5-hydroxyphenyl)-1H-pyrazolo[3,4-d]pyrimidin-1-yl)ethyl)-4-(thiazol-5-yl)-1H-isochromen-1-one single enantiomers

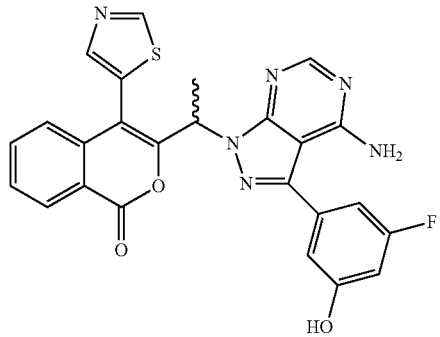 [SMILES: CC(c1oc(=O)c2ccccc2c1-c1cncs1)n1nc(-c2cc(O)cc(F)c2)c2c(N)ncnc21]

Step 1. 3-(1-(4-amino-3-(3-((tert-butyldimethylsilyl)oxy)-5-fluorophenyl)-1H-pyrazolo[3,4-d]pyrimidin-1-yl)ethyl)-4-(thiazol-5-yl)-1H-isochromen-1-one (intermediate R.1)

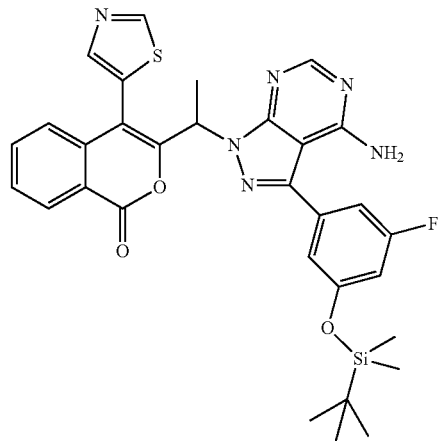 [SMILES: CC(c1oc(=O)c2ccccc2c1-c1cncs1)n1nc(-c2cc(F)cc(O[Si](C)(C)C(C)(C)C)c2)c2c(N)ncnc21]

To a solution of 3-(1-(4-amino-3-(3-fluoro-5-hydroxyphenyl)-1H-pyrazolo[3,4-d]pyrimidin-1-yl)ethyl)-4-(thiazol-5-yl)-1H-isochromen-1-one (260 mg, 0.519 mmol) in dry DMF (10 ml), IMIDAZOLE (0.137 ml, 2.078 mmol) and TBDM-SCl (0.270 ml, 1.558 mmol) were added and the solution stirred overnight. DMF was removed and residue was dissolved in DCM (50 mL) was washed with 0.5 N HCl aqueous solution. Organic phase was dried and solvent was removed. Crude was purified by silica gel flash chromatography (SNAP 25 g DCM:EtOH from 100:0 to 95:5) affording 3-(1-(4-amino-3-(3-((tert-butyldimethylsilyl)oxy)-5-fluorophenyl)-1H-pyrazolo[3,4-d]pyrimidin-1-yl)ethyl)-4-(thiazol-5-yl)-1H-isochromen-1-one (210 mg, 0.342 mmol, 65.8% yield) as a yellow pale solid.

UPLC-MS: 1.44 min, 615 [M+H]+, method 9.

Step 2. 3-(1-(4-amino-3-(3-((tert-butyldimethylsilyl)oxy)-5-fluorophenyl)-1H-pyrazolo[3,4-d]pyrimidin-1-yl)ethyl)-4-(thiazol-5-yl)-1H-isochromen-1-one single enantiomers (Intermediate R.2 and R.3)

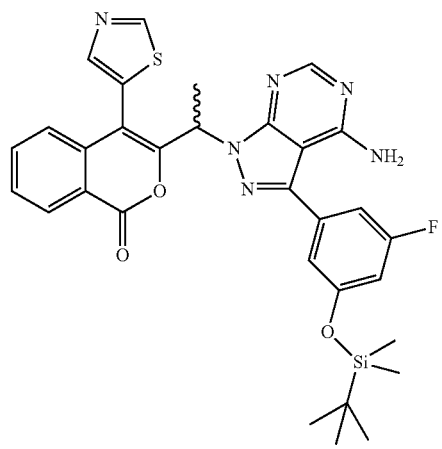 [SMILES: CC(c1oc(=O)c2ccccc2c1-c1cncs1)n1nc(-c2cc(F)cc(O[Si](C)(C)C(C)(C)C)c2)c2c(N)ncnc21]

Racemate 3-(1-(4-amino-3-(3-((tert-butyldimethylsilyl)oxy)-5-fluorophenyl)-1H-pyrazolo[3,4-d]pyrimidin-1-yl)ethyl)-4-(thiazol-5-yl)-1H-isochromen-1-one (intermediate R.1, 0.210 g, 0.34 mmol) was dissolved in EtOH (8 ml) and submitted to chiral resolution by Chiral preparative chromatography. Conditions: Column: Whelk O-1 (R,R) (25×2 cm), 10 um; Mobile phase: n-Hexane/(2-Propanol+0.1% isopropylamine) 40/60% v/v; Flow rate: 18 ml/min; DAD detection: 220 nm; Loop: 1000 μl; Injection: 26 mg (each injection).

The fractions containing the first eluted enantiomer were evaporated to dryness to afford intermediate R.2 (first eluted enantiomer, 0.084 g, 0.13 mmol). Chiral HPLC (Method A6): Rt=14.2 min, ee>99%.

UPLC-MS: 1.40 min, 615.4 [M+H]+, method 13

The fractions containing the second eluted enantiomer were evaporated to dryness to afford intermediate R.3 (second eluted enantiomer, 0.089 g, 0.14 mmol). Chiral HPLC (Method A6): Rt=18.8 min, ee=98.6%.

UPLC-MS: 1.41 min, 615.4 [M+H]+, method 13

Step 3. Example 167a 3-(1-(4-amino-3-(3-fluoro-5-hydroxyphenyl)-1H-pyrazolo[3,4-d]pyrimidin-1-yl)ethyl)-4-(thiazol-5-yl)-1H-isochromen-1-one single enantiomer 3-(1-(4-amino-3-(3-((tert-butyldimethylsilyl)oxy)-5-fluorophenyl)-1H-pyrazolo[3,4-d]pyrimidin-1-yl)ethyl)-4-(thiazol-5-yl)-1H-isochromen-1-one single enantiomer (intermediate R2, first eluted enantiomer under the conditions described above, 0.084 g, 0.13 mmol) was dissolved in a solution of 1M HCl in EtOH (0.416 ml) and the mixture was stirred at RT overnight. The volatiles were removed under reduced pressure and the residue was purified by flash chromatography on silica gel cartridge (DCM to DCM:MeOH=95:5) to afford title compound as a pale blue solid (0.043 g, 0.086 mmol, 66%). This compound proved to be the first eluted enantiomer under Chiral HPLC conditions of Method A7: Rt=16.0 min, ee>99%.

$^1$H NMR (400 MHz, DMSO-$d_6$) δ ppm 10.20 (s, 1 H), 9.29 (s, 1 H), 8.19-8.25 (m, 1 H), 8.14 (s, 1 H), 7.92 (br. s., 1 H), 7.80-7.86 (m, 1 H), 7.63-7.70 (m, 1 H), 7.04 (d, 1 H), 6.89-6.92 (m, 1 H), 6.81-6.86 (m, 1 H), 6.64-6.70 (m, 1 H), 5.86 (q, 1 H), 5.75-8.50 (m, 2 H), 1.86 (d, 3 H). UPLC-MS: 0.87 min, 501.3 [M+H]+, method 13

Step 4. Example 167b 3-(1-(4-amino-3-(3-fluoro-5-hydroxyphenyl)-1H-pyrazolo[3,4-d]pyrimidin-1-yl)ethyl)-4-(thiazol-5-yl)-1H-isochromen-1-one single enantiomer 3-(1-(4-amino-3-(3-((tert-butyldimethylsilyl)oxy)-5-fluorophenyl)-1H-pyrazolo[3,4-d]pyrimidin-1-yl)ethyl)-4-(thiazol-5-yl)-1H-isochromen-1-one single enantiomer (intermediate R.3, second eluted enantiomer under the conditions described above, 0.089 g, 0.14 mmol) was dissolved in a solution of 1M HCl in EtOH (0.5 ml) and the mixture was stirred at RT overnight. The volatiles were removed under reduced pressure and the residue was purified by flash chromatography on silica gel cartridge (DCM to DCM:MeOH=95:5) to afford title compound as a pale blue solid (0.048 g, 0.096 mmol, 74%). This compound proved to be the second eluted enantiomer under Chiral HPLC conditions of Method A7: Rt=20.1 min, ee=98.4%.

$^1$H NMR (400 MHz, DMSO-$d_6$) δ ppm 10.21 (s, 1 H), 9.29 (s, 1 H), 8.20-8.24 (m, 1 H), 8.15 (s, 1 H), 7.92 (br. s., 1 H), 7.79-7.86 (m, 1 H), 7.63-7.69 (m, 1 H), 7.04 (d, 1 H), 6.89-6.92 (m, 1 H), 6.80-6.86 (m, 1 H), 6.63-6.70 (m, 1 H), 5.87 (q, 1 H), 5.75-8.50 (m, 2 H), 1.86 (d, 3 H). UPLC-MS: 0.90 min, 501.2 [M+H]+, method 14

Examples 168a (Enantiomer 1) and 178b (Enantiomer 2)

3-(1-(4-amino-3-(5-hydroxypyridin-3-yl)-1H-pyrazolo[3,4-d]pyrimidin-1-yl)ethyl)-4-phenyl-1H-isochromen-1-one hydrochloride single enantiomers

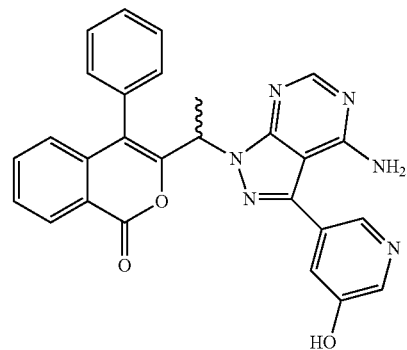 [SMILES: CC(c1oc(=O)c2ccccc2c1-c1ccccc1)n1nc(-c2cncc(O)c2)c2c(N)ncnc21]

Step 1. 3-(1-(4-amino-3-(5-((tert-butyldimethylsilyl)oxy)pyridin-3-yl)-1H-pyrazolo[3,4-d]pyrimidin-1-yl)ethyl)-4-phenyl-1H-isochromen-1-one (intermediate S.1)

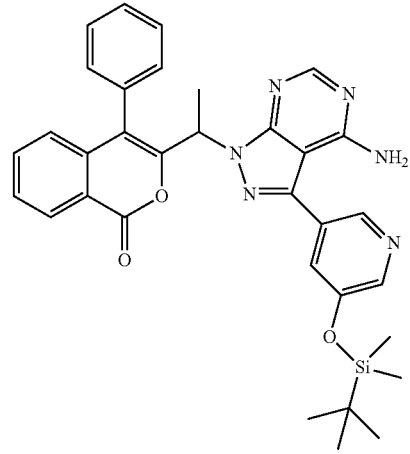 [SMILES: CC(c1oc(=O)c2ccccc2c1-c1ccccc1)n1nc(-c2cncc(O[Si](C)(C)C(C)(C)C)c2)c2c(N)ncnc21]

To a stirred mixture of 3-(1-(4-amino-3-(5-hydroxypyridin-3-yl)-1H-pyrazolo[3,4-d]pyrimidin-1-yl)ethyl)-4-phenyl-1H-isochromen-1-one (example 91, 0.260 g, 0.546 mmol) and imidazole (0.093 g, 1.36 mmol) in DMF (5.0 ml) TBDMSCl (0.206 g, 1.36 mmol) was added at RT and the mixture was stirred for 2 hrs. The mixture was partitioned between water and DCM, the aqueous phase was extracted with DCM and the combined organic layers were washed with brine and dried over sodium sulfate. The solvent was removed under reduced pressure. The residue was purified by flash chromatography on silica gel cartridge (DCM:MeOH=95:5 to 90:10) to afford 3-(1-(4-amino-3-(5-((tert-butyldimethylsilyl)oxy)pyridin-3-yl)-1H-pyrazolo[3,4-d]pyrimidin-1-yl)ethyl)-4-phenyl-1H-isochromen-1-one as a white solid (Intermediate S1, 0.178 g, 0.301 mmol, 55%).
UPLC-MS: 1.41 min, 591.4 [M+H]+, method 13

Step 2. 3-(1-(4-amino-3-(5-((tert-butyldimethylsilyl)oxy)pyridin-3-yl)-1H-pyrazolo[3,4-d]pyrimidin-1-yl)ethyl)-4-phenyl-1H-isochromen-1-one single enantiomers (Intermediate S.2 and S.3)

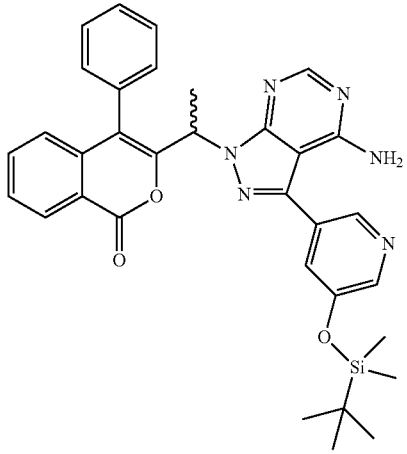 [SMILES: CC(c1oc(=O)c2ccccc2c1-c1ccccc1)n1nc(-c2cncc(O[Si](C)(C)C(C)(C)C)c2)c2c(N)ncnc21]

Racemate 3-(1-(4-amino-3-(5-((tert-butyldimethyl silyl)oxy)pyridin-3-yl)-1H-pyrazolo[3,4-d]pyrimidin-1-yl)ethyl)-4-phenyl-1H-isochromen-1-one (intermediate S.1, 0.178 g, 0.301 mmol) was dissolved in Ethanol/DCM 1/1 (7 ml) and submitted to chiral resolution by Chiral preparative chromatography. Conditions: Column: Whelk 01 (R,R) (25×2.11 cm), 10μ; Mobile phase: n-Hexane/(Ethanol+0.1% isopropylamine+10% DCM) 70/30% v/v; Flow rate: 17 ml/min; DAD detection: 220 nm; Loop: 500 μl; Injection: 13.5 mg/injection.

The fractions containing the first eluted enantiomer were evaporated to dryness to afford interemdiate S.2 (first eluted enantiomer, 0.070 g, 0.118 mmol). Chiral HPLC (Method A8): Rt=18.9 min, ee>99%. UPLC-MS: 1.43 min, 591.3 [M+H]+, method 16.

The fractions containing the second eluted enantiomer were evaporated to dryness to afford intermediate S.3 (second eluted enantiomer, 0.077 g, 0.130 mmol). Chiral HPLC (Method A8): Rt=21.9 min, ee=>99%. UPLC-MS: 1.43 min, 591.3 [M+H]+, method 16.

Step 3. Example 168a (Enantiomer 1): 3-(1-(4-amino-3-(5-hydroxypyridin-3-yl)-1H-pyrazolo[3,4-d]pyrimidin-1-yl)ethyl)-4-phenyl-1H-isochromen-1-one hydrochloride single enantiomer 3-(1-(4-amino-3-(5-((tert-butyldimethylsilyl)oxy)pyridin-3-yl)-1H-pyrazolo[3,4-d]pyrimidin-1-yl)ethyl)-4-phenyl-1H-isochromen-1-one single enantiomer (intermediate S.2, first eluted enantiomer under the conditions described above, 0.070 g, 0.118 mmol) was dissolved in a solution of 1M HCl in EtOH (0.38 mL) and the mixture was stirred at RT for 5 h. The volatiles were removed under reduced pressure and the residue was purified by flash chromatography on silica gel cartridge (DCM to DCM:MeOH=95:5) to afford title compound as a white solid (0.059 g, 0.115 mmol, 97%).

This compound proved to be the second eluted enantiomer under Chiral HPLC conditions of Method A9: Rt=15.4 min, ee>99%.

$^1$H NMR (400 MHz, DMSO-$d_6$) δ 11.36 (br. s., 1 H), 8.39-8.48 (m, 2 H), 8.20-8.29 (m, 2 H), 7.95 (br. s., 2 H), 7.74-7.86 (m, 2 H), 7.60-7.66 (m, 1 H), 7.50-7.57 (m, 1 H), 7.37-7.49 (m, 3 H), 7.11-7.18 (m, 1 H), 6.90 (d, 1 H), 5.79 (q, 1 H), 1.87 (d, 3 H). UPLC-MS: 0.82 min, 477.3 [M+H]+, method 13.

Step 4. Example 168b (Enantiomer 2): 3-(1-(4-amino-3-(5-hydroxypyridin-3-yl)-1H-pyrazolo[3,4-d]pyrimidin-1-yl)ethyl)-4-phenyl-1H-isochromen-1-one hydrochloride single enantiomer 3-(1-(4-amino-3-(5-((tert-butyldimethylsilyl)oxy)pyridin-3-yl)-1H-pyrazolo[3,4-d]pyrimidin-1-yl)ethyl)-4-phenyl-1H-isochromen-1-one single enantiomer (intermediate S.3, second eluted enantiomer under the conditions described above, 0.077 g, 0.130 mmol) was dissolved in a solution of HCl 1 M in EtOH (0.417 ml) and the mixture was stirred at RT for 5 hrs. The volatiles were removed under reduced pressure and the residue was purified by flash chromatography on silica gel cartridge (DCM to DCM:MeOH=95:5) to afford title compound as a white solid (0.034 g, 0.066 mmol, 51% yield). This compound proved to be the first eluted enantiomer under Chiral HPLC conditions of Method A9: Rt=13.2 min, ee=95.6%.

$^1$H NMR (400 MHz, DMSO-$d_6$) δ 11.47 (br. s., 1 H), 8.43-8.48 (m, 2 H), 8.28 (s, 1 H), 8.20-8.25 (m, 1 H), 8.04 (br. s., 2 H), 7.81-7.86 (m, 1 H), 7.74-7.81 (m, 1 H), 7.60-7.66 (m, 1 H), 7.50-7.57 (m, 1 H), 7.37-7.48 (m, 3 H), 7.11-7.18 (m, 1 H), 6.89 (d, 1 H), 5.80 (q, 1 H), 1.87 (d, 3 H). UPLC-MS: 0.82 min, 477.3 [M+H]+, method 13.

Example 169

3-(1-(4-amino-3-(3-fluoro-5-hydroxyphenyl)-1H-pyrazolo[3,4-d]pyrimidin-1-yl)ethyl)-4-(1-benzyl-1,2,5,6-tetrahydropyridin-3-yl)-1H-isochromen-1-one hydrochloride

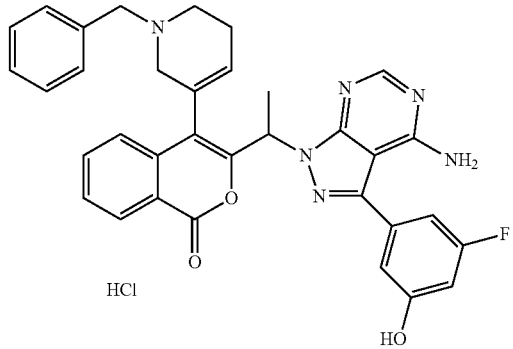 [SMILES: CC(c1oc(=O)c2ccccc2c1C1=CCCN(Cc2ccccc2)C1)n1nc(-c2cc(O)cc(F)c2)c2c(N)ncnc21 ; Cl]

The title compound was made in a similar way as that of example 162, from 3-(1-(4-Amino-3-iodo-1H-pyrazolo[3,4-d]pyrimidin-1-yl)ethyl)-4-(1-benzyl-1,2,5,6-tetrahydropyridin-3-yl)-1H-isochromen-1-one hydrochloride (intermediate D33, 1.828 g, 2.86 mmol), and (3-fluoro-5-hydroxyphenyl) boronic acid (0.890 g, 5.71 mmol) to provide title compound (1.3 g, 2.1 mmol, 71%).

¹H NMR (400 MHz, DMSO-d₆) δ ppm 10.11-11.75 (m, 2 H), 8.09-8.41 (m, 2 H), 7.57-8.06 (m, 5 H), 7.37-7.56 (m, 3 H), 7.03-8.55 (m, 2 H), 6.81-7.03 (m, 2 H), 6.63-6.76 (m, 1 H), 5.46-6.34 (m, 2 H), 4.32-4.68 (m, 2 H), 2.07-4.20 (m, 6 H), 1.78-1.98 (m, 3 H). UPLC-MS: 0.69 min, 589.5 [M+H]+, method 13

Example 169a (enantiomer 1) and Example 169b (enantiomer 2)

3-(1-(4-amino-3-(3-fluoro-5-hydroxyphenyl)-1H-pyrazolo[3,4-d]pyrimidin-1-yl)ethyl)-4-(1-benzyl-1,2,5,6-tetrahydropyridin-3-yl)-1H-isochromen-1-one hydrochloride single enantiomers Racemate 3-(1-(4-amino-3-(3-fluoro-5-hydroxyphenyl)-1H-pyrazolo[3,4-d]pyrimidin-1-yl)ethyl)-4-(1-benzyl-1,2,5,6-tetrahydropyridin-3-yl)-1H-isochromen-1-one hydrochloride (example 169, 0.25 g, 0.4 mmol) was dissolved in Ethanol (5 ml) and submitted to chiral resolution by Chiral preparative chromatography. Conditions: Column: Whelk 0-1 (R,R) (25×2 cm), 10 um; Mobile phase: n-Hexane/(Ethanol/Methanol 1/1+0.1% isopropylamine) 75/25% v/v; Flow rate: 18 ml/min; DAD detection: 220 nm; Loop: 500 µl; Injection: 25 mg (each injection).

The fractions containing the first eluted enantiomer were evaporated to dryness, 1.25M HCl in MeOH was added and the volatiles were removed under reduced pressure. The residue was purified by reverse phase flash chromatography on C18 cartridge (H₂O:CH₃CN=95:5 to 50:50, with 0.1% HCOOH); before drying 2 1N HCl (2 ml) were added and the volatiles were removed under reduced pressure to afford compound 169a as a white solid (first eluted enantiomer, 0.077 g, 0.0123 mmol). Chiral HPLC (Method A13): Rt=16.1 min, ee>99%.

¹H NMR (400 MHz, DMSO-d₆) δ ppm 10.12-12.00 (m, 2 H), 8.06-8.46 (m, 2 H), 7.58-8.03 (m, 5 H), 7.37-7.52 (m, 3 H), 7.00-8.55 (m, 2 H), 6.81-7.00 (m, 2 H), 6.66-6.76 (m, 1 H), 5.49-6.42 (m, 2 H), 4.32-4.68 (m, 2 H), 2.07-4.20 (m, 6 H), 1.80-1.98 (m, 3 H). UPLC-MS: 0.70 min, 589.5 [M+H]+, method 13.

The fractions containing the second eluted enantiomer were evaporated to dryness, 1.25M HCl in MeOH was added and the volatiles were removed under reduced pressure. The residue was purified by reverse phase flash chromatography on C18 cartridge (H₂O:CH₃CN=95:5 to 50:50, with 0.1% HCOOH); before drying 1N HCl (2 ml) were added and the volatiles were removed under reduced pressure to afford compound 169b as a white solid (second eluted enantiomer, 0.072 g, 0.115 mmol). Chiral HPLC (Method A13): Rt=19.0 min, ee=98.2%.

¹H NMR (400 MHz, DMSO-d₆) δ ppm 10.13-12.15 (m, 2 H), 8.06-8.48 (m, 2 H), 7.58-8.06 (m, 5 H), 7.37-7.51 (m, 3 H), 7.00-8.55 (m, 2 H), 6.81-7.00 (m, 2 H), 6.66-6.77 (m, 1 H), 5.50-6.45 (m, 2 H), 4.32-4.68 (m, 2 H), 2.09-4.23 (m, 6 H), 1.80-1.98 (m, 3 H). UPLC-MS: 0.66 min, 589.3 [M+H]+, method 14.

Example 170

3-(1-(4-amino-3-(3-fluoro-5-hydroxyphenyl)-1H-pyrazolo[3,4-d]pyrimidin-1-yl)ethyl)-4-(pyridin-2-yl)-1H-isochromen-1-one hydrochloride

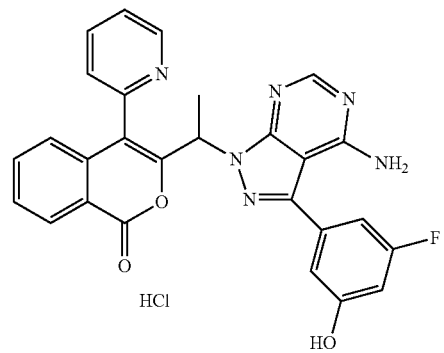 [SMILES: CC(c1oc(=O)c2ccccc2c1-c1ccccn1)n1nc(-c2cc(O)cc(F)c2)c2c(N)ncnc21 ; Cl]

The title compound was made in a similar way as that of example 162, from 3-(1-(4-Amino-3-iodo-1H-pyrazolo[3,4-d]pyrimidin-1-yl)ethyl)-4-(pyridin-2-yl)-1H-isochromen-1-one (intermediate D34), and (3-fluoro-5-hydroxyphenyl)boronic acid to provide the title compound.

¹H NMR (400 MHz, DMSO-d₆) δ ppm 10.29 (br. s., 1 H), 8.70 (br. s., 1 H), 8.19-8.29 (m, 2 H), 7.97 (br. s., 1 H), 7.74-7.84 (m, 1 H), 7.62-7.70 (m, 1 H), 7.43-7.60 (m, 2 H), 6.94 (d, 1 H), 6.89 (s, 1 H), 6.83 (d, 1 H), 6.71 (dt, 1 H), 6.50-8.60 (m, 2 H), 5.81-5.91 (m, 1 H), 1.87 (d, 3 H). UPLC-MS: 0.80 min, 495.0 [M+H]+, method 12.

Example 171

3-(1-(4-amino-3-(3-fluoro-5-hydroxyphenyl)-1H-pyrazolo[3,4-d]pyrimidin-1-yl)ethyl)-4-(1,2,5,6-tetrahydropyridin-3-yl)-1H-isochromen-1-one formate

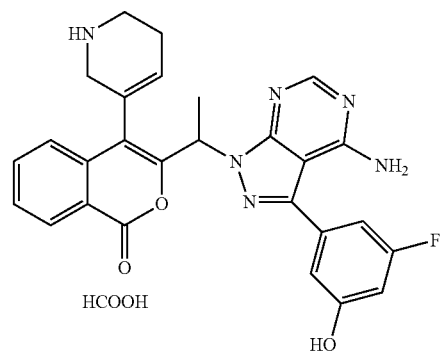 [SMILES: CC(c1oc(=O)c2ccccc2c1C1=CCCNC1)n1nc(-c2cc(O)cc(F)c2)c2c(N)ncnc21 ; "HCOOH"]

3-(1-(4-Amino-3-(3-fluoro-5-hydroxyphenyl)-1H-pyrazolo[3,4-d]pyrimidin-1-yl)ethyl)-4-(1-benzyl-1,2,5,6-tetrahydropyridin-3-yl)-1H-isochromen-1-one hydrochloride (example 169, 0.5 g, 0.799 mmol), was dissolved in DCM (3 ml) at 0° C.; DIPEA (0.395 ml, 2.262 mmol) and 1-chloroethyl carbonochloridate (0.651 ml, 6.03 mmol) were added at 0° C. under vigorous stirring and the reaction was stirred for 5 min at 0° C. and for 2 hrs at 60° C. The reaction was allowed to cool to RT and quenched with 5 ml of MeOH; the mixture was stirred for further 2.5 hrs at 60° C. and evaporated under reduced pressure to give a crude which was purified by reverse phase flash chromatography on C-18 cartridge (H$_2$O:CH$_3$CN=95:5 to 50:50, with 0.1% HCOOH) to afford title compound (0.068 g, 0.125 mmol, 16%).

$^1$H NMR (400 MHz, DMSO-d$_6$) δ ppm 10.18-10.30 (m, 1 H), 9.04-9.65 (m, 2 H), 8.25-8.31 (m, 1 H), 8.11-8.22 (m, 2 H), 7.83-7.94 (m, 1 H), 7.70-7.82 (m, 1 H), 7.60-7.70 (m, 1 H), 6.81-6.99 (m, 2 H), 6.62-6.75 (m, 1 H), 6.13-8.50 (m, 2 H), 5.55-6.29 (m, 2 H), 2.35-4.18 (m, 6 H), 1.80-1.95 (m, 3 H). UPLC-MS: 0.60 min, 499.4 [M+H]+, method 13

Example 172

3-(1-(4-amino-3-(3-fluoro-5-hydroxyphenyl)-1H-pyrazolo[3,4-d]pyrimidin-1-yl)ethyl)-4-(1-(1-methylpiperidin-4-yl)-1,2,5,6-tetrahydropyridin-3-yl)-1H-isochromen-1-one dihydrochloride

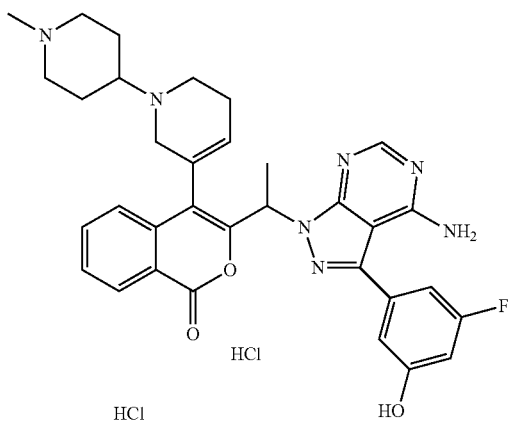 [SMILES: CC(c1oc(=O)c2ccccc2c1C1=CCCN(C2CCN(C)CC2)C1)n1nc(-c2cc(O)cc(F)c2)c2c(N)ncnc21 ; Cl ; Cl]

To a solution of 3-(1-(4-amino-3-(3-fluoro-5-hydroxyphenyl)-1H-pyrazolo[3,4-d]pyrimidin-1-yl)ethyl)-4-(1,2,5,6-tetrahydropyridin-3-yl)-1H-isochromen-1-one formate (example 171, 0.03 g, 0.055 mmol), 1-methylpiperidin-4-one (0.08 ml, 0.066 mmol) and DIPEA (0.009 ml, 0.055 mmol) in DCM (2 ml) dry Na$_2$SO$_4$ was added and the mixture stirred at RT for 10 min. AcOH (0.009 ml, 0.165 mmol) and sodium triacetoxyborohydride (0.023 g, 0.11 mmol) were added in this order and the reaction mixture was stirred for 3 hrs at RT. The reaction was quenched by the addition of 2M HCl (2 ml), the mixture was filtered and the filtrate was purified by reverse phase flash chromatography on Biotage C18 cartridge (water/MeCN 90/10+0.1% HCOOH to water/MeCN 5/95+0.01% HCOOH). Before drying 2M HCl (2 ml) was added and the mixture was dried under reduced pressure to afford title compound (0.025 g, 0.037 mmol, 68%).

$^1$H NMR (400 MHz, DMSO-d$_6$) δ ppm 8.58-10.68 (m, 2 H), 8.08-8.40 (m, 2 H), 7.81-7.99 (m, 1 H), 7.59-7.74 (m, 1 H), 7.43-7.55 (m, 1 H), 6.78-6.97 (m, 2 H), 6.56-6.73 (m, 1 H), 6.45-7.75 (m, 2 H), 6.09-6.29 (m, 1 H), 5.26-6.08 (m, 1 H), 2.54-3.29 (m, 13 H), 1.40-2.45 (m, 8 H). UPLC-MS: 0.89 min, 596.5 [M+H]+, method 15

Example 173

3-(1-(4-amino-3-(3-fluoro-5-hydroxyphenyl)-1H-pyrazolo[3,4-d]pyrimidin-1-yl)ethyl)-4-(1-(azetidin-3-yl)-1,2,5,6-tetrahydropyridin-3-yl)-1H-isochromen-1-one dihydrochloride

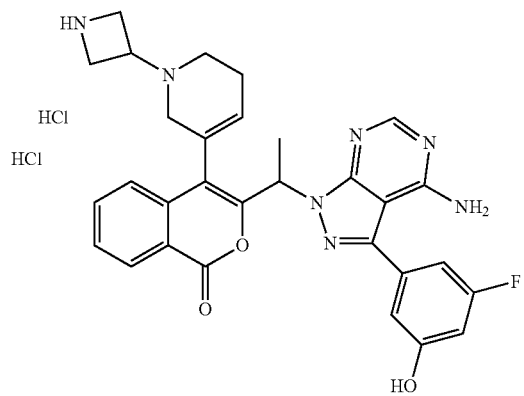 [SMILES: Cl ; Cl ; CC(c1oc(=O)c2ccccc2c1C1=CCCN(C2CNC2)C1)n1nc(-c2cc(O)cc(F)c2)c2c(N)ncnc21]

The title compound was made in a similar way as that of example 172 from 3-(1-(4-amino-3-(3-fluoro-5-hydroxyphenyl)-1H-pyrazolo[3,4-d]pyrimidin-1-yl)ethyl)-4-(1,2,5,6-tetrahydropyridin-3-yl)-1H-isochromen-1-one formate (example 171, 0.03 g, 0.055 mmol) and tert-butyl 3-oxoazetidine-1-carboxylate (0.019 g, 0.110 mmol) to give title compound (0.019 g, 0.030 mmol, 55%).

$^1$H NMR (400 MHz, METHANOL-d$_4$) δ ppm 8.43-8.56 (m, 1 H), 8.16-8.30 (m, 1 H), 7.82-7.95 (m, 1 H), 7.75-8.01 (m, 2 H), 7.52-7.72 (m, 1 H), 6.87-7.06 (m, 2 H), 6.64-6.80 (m, 1 H), 5.90-6.58 (m, 2 H), 3.30-4.90 (m, 9 H), 2.41-3.04 (m, 2 H), 1.92-2.22 (m, 3 H). UPLC-MS: 0.78 min, 554.4 [M+H]+, method 15

Example 174

3-(1-(4-amino-3-(3-fluoro-5-hydroxyphenyl)-1H-pyrazolo[3,4-d]pyrimidin-1-yl)ethyl)-4-(1-isopropyl-1,2,5,6-tetrahydropyridin-3-yl)-1H-isochromen-1-one hydrochloride

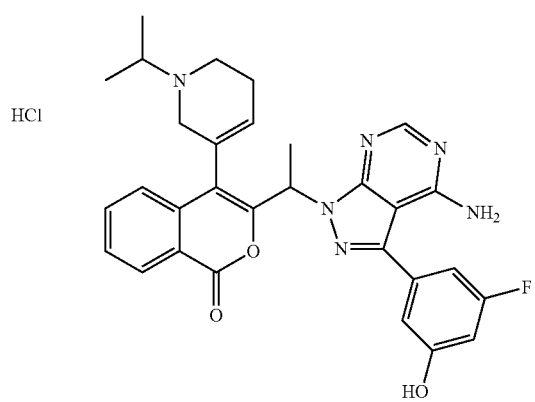 [SMILES: Cl ; CC(C)N1CCC=C(c2c(C(C)n3nc(-c4cc(O)cc(F)c4)c4c(N)ncnc43)oc(=O)c3ccccc23)C1]

The title compound was made in a similar way as that of example 172 from 3-(1-(4-amino-3-(3-fluoro-5-hydroxyphenyl)-1H-pyrazolo[3,4-d]pyrimidin-1-yl)ethyl)-4-(1,2,5,6-tetrahydropyridin-3-yl)-1H-isochromen-1-one formate (example 171, 0.061 g, 0.122 mmol) and acetone (0.010 mL, 0.134 mmol) to give title compound (2 mg, 0.003 mmol, 3%).

¹H NMR (400 MHz, METHANOL-d₄) δ ppm 8.13-8.53 (m, 2 H), 7.47-8.01 (m, 3 H), 6.85-7.04 (m, 2 H), 6.62-6.78 (m, 1 H), 5.72-6.48 (m, 2 H), 3.38-4.47 (m, 5 H), 2.36-3.09 (m, 2 H), 1.91-2.26 (m, 3 H), 1.38-1.69 (m, 6 H). UPLC-MS: 0.63 min, 541.5 [M+H]+, method 13

Example 175

3-(1-(4-amino-3-(5-hydroxypyridin-3-yl)-1H-pyrazolo[3,4-d]pyrimidin-1-yl)ethyl)-4-(1-methyl-1,2,3,6-tetrahydropyridin-4-yl)-1H-isochromen-1-one hydrochloride

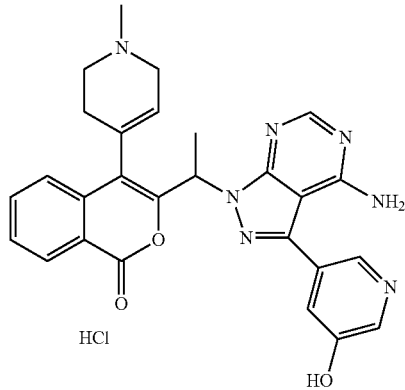 [SMILES: CC(c1oc(=O)c2ccccc2c1C1=CCN(C)CC1)n1nc(-c2cncc(O)c2)c2c(N)ncnc21 ; Cl]

The title compound was made in a similar way as that of example 162, from 3-(1-(4-amino-3-iodo-1H-pyrazolo[3,4-d]pyrimidin-1-yl)ethyl)-4-(1-methyl-1,2,3,6-tetrahydropyridin-4-yl)-1H-isochromen-1-one formic acid salt (intermediate D4, 0.050 g), and 5-(4,4,5,5-tetramethyl-1,3,2-dioxaborolan-2-yl)pyridin-3-ol (0.023 g, 0.104 mmol) to afford the title compound (0.014 g, 0.026 mmol).

¹H NMR (400 MHz, DMSO-d₆) δ ppm 11.03-11.70 (m, 2 H), 8.30-8.59 (m, 3 H), 8.10-8.24 (m, 1 H), 7.76-8.04 (m, 3 H), 7.72-8.29 (m, 2 H), 7.48-7.70 (m, 1 H), 5.44-6.47 (m, 2 H), 2.87-2.99 (m, 3 H), 2.44-4.08 (m, 6 H), 1.81-2.05 (m, 3 H). UPLC-MS: 0.42 min, 496.4 [M+H]+, method 13

Examples 176a (Enantiomer 1) and 176b (Enantiomer 2)

3-(1-(4-amino-3-(3-fluoro-5-hydroxyphenyl)-1H-pyrazolo[3,4-d]pyrimidin-1-yl)ethyl)-4-phenyl-1H-isochromen-1-one single enantiomers

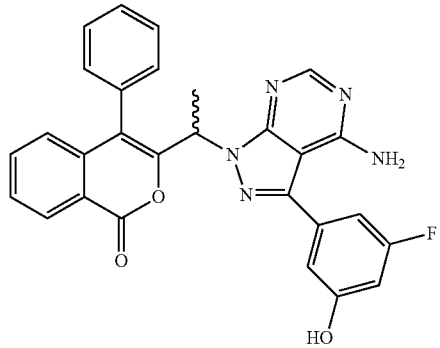 [SMILES: CC(c1oc(=O)c2ccccc2c1-c1ccccc1)n1nc(-c2cc(O)cc(F)c2)c2c(N)ncnc21]

Step 1. 3-(1-(4-amino-3-(3-((tert-butyldimethylsilyl)oxy)-5-fluorophenyl)-1H-pyrazolo[3,4-d]pyrimidin-1-yl)ethyl)-4-phenyl-1H-isochromen-1-one (intermediate Q.1)

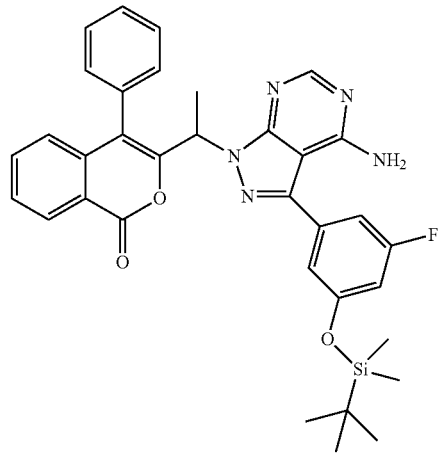 [SMILES: CC(c1oc(=O)c2ccccc2c1-c1ccccc1)n1nc(-c2cc(F)cc(O[Si](C)(C)C(C)(C)C)c2)c2c(N)ncnc21]

To a stirred mixture of 3-(1-(4-amino-3-(3-fluoro-5-hydroxyphenyl)-1H-pyrazolo[3,4-d]pyrimidin-1-yl)ethyl)-4-phenyl-1H-isochromen-1-one (example 40, 0.20 mmol) and imidazole (40.8 mg, 0.60 mmol) in DMF (1 ml) TBDMSCl (45.2 mg, 0.30 mmol) was added at RT and the mixture was stirred for 2 hrs. Additional imidazole (16 mg) and TBDMSCl (36 mg) were added and the mixture was stirred at the same temperature for further 2 hrs. Additional imidazole (27 mg) and TBDMSCl (121 mg) were added and the stirring was continued at room temperature overnight. The reaction mixture was diluted with DCM and washed with 0.5M HCl. The organic layer was dried over sodium sulfate, filtered and concentrated. The residue was purified by filtration on silica gel cartridge (DCM to DCM:MeOH=95:5) to afford 3-(1-(4-amino-3-(3-((tert-butyldimethylsilyl)oxy)-5-fluorophenyl)-1H-pyrazolo[3,4-d]pyrimidin-1-yl)ethyl)-4-phenyl-1H-isochromen-1-one (intermediate Q.1, 112 mg, 0.184 mmol, 92%).

UPLC-MS: 1.57 min, 608.4 [M+H]+, method 13

Step 2. 3-(1-(4-amino-3-(3-((tert-butyldimethylsilyl)oxy)-5-fluorophenyl)-1H-pyrazolo[3,4-d]pyrimidin-1-yl)ethyl)-4-phenyl-1H-isochromen-1-one single enantiomers (Intermediate Q.2 and Q.3)

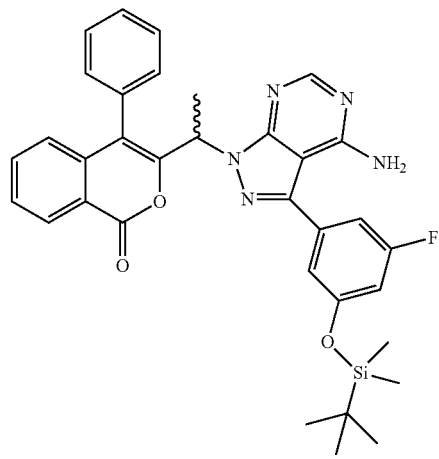 [SMILES: CC(c1oc(=O)c2ccccc2c1-c1ccccc1)n1nc(-c2cc(F)cc(O[Si](C)(C)C(C)(C)C)c2)c2c(N)ncnc21]

Racemate 3-(1-(4-amino-3-(3-((tert-butyldimethylsilyl)oxy)-5-fluorophenyl)-1H-pyrazolo[3,4-d]pyrimidin-1-yl)ethyl)-4-phenyl-1H-isochromen-1-one (intermediate Q.1, 0.124 g, 0.204 mmol) was dissolved in a mixture of DCM (5 ml) and Ethanol/Methanol 1/1 (6 ml) and submitted to chiral resolution by Chiral preparative chromatography. Conditions: Column: Chiralpak IC (25×2.0 cm), 5 μm; Mobile phase: n n-Hexane/(2-Propanol/Methanol 1/1+0.1% isopropylamine) 90/10% v/v; Flow rate: 17 ml/min; DAD detection: 220 nm; Loop: 500 μl; Injection: 5 mg/injection.

The fractions containing the first eluted enantiomer were evaporated to dryness to afford intermediate Q.2 (first eluted enantiomer, 40 mg, 0.066 mmol). Chiral HPLC (Method A4): Rt=15.7 min, ee>99%. UPLC-MS: 1.57 min, 608.4 [M+H]+, method 13

The fractions containing the second eluted enantiomer were evaporated to dryness to afford intermediate Q.3 (second eluted enantiomer, 38 mg, 0.063 mmol). Chiral HPLC (Method A4): Rt=17.8 min, ee=99%. UPLC-MS: 1.57 min, 608.4 [M+H]+, method 13

Step 3. Example 176a, 3-(1-(4-amino-3-(3-fluoro-5-hydroxyphenyl)-1H-pyrazolo[3,4-d]pyrimidin-1-yl)ethyl)-4-phenyl-1H-isochromen-1-one single enantiomer 3-(1-(4-amino-3-(3-((tert-butyldimethylsilyl)oxy)-5-fluorophenyl)-1H-pyrazolo[3,4-d]pyrimidin-1-yl)ethyl)-4-phenyl-1H-isochromen-1-one single enantiomer (intermediate Q.2, first eluted enantiomer under the conditions described above, 40 mg, 0.065 mmol) was dissolved in a solution of 1M HCl in EtOH (0.2 ml) and stirred at room temperature for 5 hrs. The volatiles were removed under reduced pressure and the residue was purified by flash chromatography on silica gel cartridge (DCM to DCM:MeOH=97:3) to afford title compound as a white solid (28 mg, 0.056 mmol, 87%). This compound proved to be the second eluted enantiomer under Chiral HPLC conditions of Method A5: Rt=12.0 min, ee=98.6%.

$^1$H NMR (400 MHz, DMSO-$d_6$) δ ppm 10.28 (br. s., 1 H), 8.19-8.26 (m, 2 H), 7.75-7.80 (m, 1 H), 7.61-7.66 (m, 1 H), 7.51-7.57 (m, 1 H), 7.37-7.48 (m, 3 H), 7.11-7.16 (m, 1 H), 6.87-6.92 (m, 2 H), 6.82-6.87 (m, 1 H), 6.70 (dt, 1 H), 6.0-8.5 (m, 2 H), 5.76 (q, 1 H), 1.85 (d, 3 H). UPLC-MS: 1.04 min, 494.3 [M+H]+, method 13.

Step 4. Example 176b, 3-(1-(4-amino-3-(3-fluoro-5-hydroxyphenyl)-1H-pyrazolo[3,4-d]pyrimidin-1-yl)ethyl)-4-phenyl-1H-isochromen-1-one single enantiomer 3-(1-(4-amino-3-(3-((tert-butyldimethylsilyl)oxy)-5-fluorophenyl)-1H-pyrazolo[3,4-d]pyrimidin-1-yl)ethyl)-4-phenyl-1H-isochromen-1-one single enantiomer (intermediate Q.3, second eluted enantiomer under the conditions described above, 0.038 g, 0.063 mmol) was dissolved in a solution of 1M HCl in EtOH (0.2 mL) and stirred at room temperature for 5 hrs. The volatiles were removed under reduced pressure and the residue was purified by flash chromatography on silica gel cartridge (DCM to DCM:MeOH=97:3) to afford title compound as a white solid (0.025 g, 0.05 mmol, 80%). This compound proved to be the first eluted enantiomer under Chiral HPLC conditions of Method A5: Rt=7.3 min, ee>99%.

$^1$H NMR (400 MHz, DMSO-$d_6$) δ ppm 10.24 (br. s., 1 H), 8.20-8.25 (m, 1 H), 8.16 (s, 1 H), 7.74-7.81 (m, 1 H), 7.60-7.66 (m, 1 H), 7.50-7.57 (m, 1 H), 7.35-7.48 (m, 3 H), 7.12-7.18 (m, 1 H), 6.87-6.93 (m, 2 H), 6.81-6.86 (m, 1 H), 6.68 (dt, 1 H), 6.00-8.50 (m, 2 H), 5.70-5.78 (m, 1 H), 1.84 (d, 3 H). UPLC-MS: 1.04 min, 494.3 [M+H]+, method 13.

Pharmacological Activity of the Compounds of the Present Invention.

In Vitro Determination of the PI3K Enzyme Inhibitory Activity in the Cell Free Assay.

Human recombinant proteins PI3Kα, P1Kβ, PI3Kγ and PI3Kδ were purchased from Millipore Ltd (Billerica, Mass.). Compounds were dissolved at 0.5 mM in DMSO and were tested at different concentrations for their activity against PI3Ks using the ADP-Glo™ Kinase Assay (Promega, Madison Wis.) according to the manufacturer's instructions.

Briefly, the kinase reactions were performed in 384-well white plates (Greiner Bio-One GmbH, Frickenhausen). Each well was loaded with 0.1 μl of test compounds and 2.5 μl of 2× reaction buffer (40 mM Tris pH7.5, 0.5 mM EGTA, 0.5 mM $Na_3VO_4$, 5 mM β-glycerophosphate, 0.1 mg/ml BSA, 1 mM DTT), containing 50 μM PI and PS substrates (L-α-phosphatidylinositol sodium salt and L-α-phosphatidyl-L-serine, Sigma-Aldrich, St. Louis Mo.) and the PI3K recombinant proteins (PI3Kγ 0.25 ng/μl, PI3Kδ 1 ng/μl, PI3Kα 0.125 ng/μl, PI3Kβ 1 ng/μl).

The reactions were started by adding 2.5 μl of 2×ATP solution to each well (final concentrations: PI3Kγ ATP 30 μM; PI3Kδ ATP 80 μM; PI3Kα ATP 50 μM; PI3β ATP 100 μM) and incubated for 60 min at room temperature. Subsequently, each kinase reaction was incubated for 40 min with 5 μl ADP-Glo™ Reagent, allowing depletion of unconsumed ATP. Then, the Kinase Detection Reagent (10 μl) was added in each well to convert ADP to ATP and to allow the newly synthesized ATP to be measured using a luciferase/luciferin reaction. Following 60 min incubation, the luminescence signal was measured using a Wallac EnVision® multilabel reader (PerkinElmer, Waltham Mass.). Curve fitting and IC50 calculation were carried out using a four-parameter logistic model in XLfit (IDBS, Guilford, UK) for Microsoft Excel (Microsoft, Redmont, Wash.). The results are provided below in Table 1.

TABLE 1

Results of the in vitro determination of the PI3K enzyme inhibitory activity in the cell free assay.

| Compound of Example N. | PI3K alpha inhibition | PI3K beta inhibition | PI3K delta inhibition | PI3K gamma inhibition |
|---|---|---|---|---|
| 1 | | + | ++ | ++ |
| 2 | | + | ++ | + |
| 21 | | | ++ | ++ |
| 3 | | + | ++ | + |
| 29 | | + | ++ | ++ |
| 30 | | + | ++ | ++ |
| 4 | | + | ++ | + |
| 31 | | | ++ | ++ |
| 13 | | | ++ | + |
| 10 | | | + | + |
| 14 | | | ++ | + |
| 32 | | | +++ | ++ |
| 5 | | | ++ | ++ |
| 22 | + | ++ | +++ | ++ |
| 22a | + | + | +++ | + |
| 22b | | | + | |
| Int D2 | + | ++ | +++ | ++ |
| Int D1 | | + | ++ | ++ |
| 6 | | | ++ | ++ |
| 33 | | | +++ | ++ |
| 37 | | | ++ | + |
| 7 | | | ++ | ++ |
| Int D3 | + | + | +++ | ++ |
| 40 | ++ | ++ | +++ | ++ |
| 41 | ++ | ++ | +++ | ++ |

TABLE 1-continued

Results of the in vitro determination of the PI3K enzyme inhibitory activity in the cell free assay.

| Compound of Example N. | PI3K alpha inhibition | PI3K beta inhibition | PI3K delta inhibition | PI3K gamma inhibition |
|---|---|---|---|---|
| 8 | | | ++ | ++ |
| 36 | | + | ++ | ++ |
| 34 | | + | ++ | ++ |
| 9 | | | ++ | ++ |
| 35 | | + | +++ | ++ |
| 42 | + | | +++ | ++ |
| 16 | | | ++ | ++ |
| 23 | + | ++ | +++ | + |
| 17 | | | ++ | + |
| 18 | | ++ | ++ | + |
| 19 | | | ++ | |
| 25 | | + | +++ | ++ |
| 20 | | | ++ | |
| 38 | | + | ++ | ++ |
| 26 | | | ++ | ++ |
| 39 | | + | ++ | ++ |
| 28 | | + | +++ | ++ |
| 43 | | | ++ | + |
| 29 | + | ++ | +++ | ++ |
| 44 | + | ++ | +++ | ++ |
| 45 | + | + | +++ | + |
| 46 | | ++ | +++ | ++ |
| 46a | ++ | ++ | +++ | ++ |
| 46b | + | ++ | ++ | + |
| 47 | + | + | ++ | ++ |
| 48 | | | +++ | ++ |
| 49a | ++ | ++ | +++ | ++ |
| 49b | | + | ++ | + |
| 53 | | | ++ | + |
| 54 | | | ++ | ++ |
| 55 | | | +++ | ++ |
| 56 | | | ++ | |
| 57 | | | ++ | ++ |
| 58 | | | ++ | ++ |
| 59 | ++ | ++ | +++ | ++ |
| 60 | ++ | ++ | +++ | ++ |
| 62 | ++ | ++ | +++ | ++ |
| 63 | ++ | ++ | +++ | ++ |
| 64 | ++ | ++ | +++ | ++ |
| 65 | ++ | ++ | +++ | ++ |
| 66 | ++ | ++ | +++ | ++ |
| 67 | ++ | ++ | +++ | ++ |
| 67a | ++ | ++ | +++ | ++ |
| 67b | | ++ | ++ | |
| 68 | ++ | ++ | +++ | ++ |
| 68a | | | ++ | |
| 68b | ++ | ++ | +++ | ++ |
| 70 | + | ++ | +++ | ++ |
| 71 | ++ | ++ | +++ | ++ |
| 72 | ++ | ++ | +++ | ++ |
| 73 | | ++ | +++ | + |
| 76a | | | ++ | |
| 76b | ++ | ++ | +++ | ++ |
| 78 | | + | +++ | ++ |
| 81 | | | ++ | + |
| 82 | | + | +++ | ++ |
| 83 | | | ++ | + |
| 84 | | | ++ | ++ |
| 85 | | | ++ | ++ |
| 86 | | | +++ | ++ |
| 87 | ++ | | ++ | ++ |
| 88 | | ++ | ++ | + |
| 89 | | | + | ++ |
| 90 | | | ++ | |
| 91 | ++ | ++ | +++ | ++ |
| 92 | ++ | ++ | ++ | + |
| 93 | | | ++ | ++ |
| 94 | | | ++ | ++ |
| 95 | | | + | |
| 96 | | | ++ | |
| 97 | | | +++ | + |
| 98 | | | ++ | |
| 99 | ++ | ++ | +++ | ++ |
| 100 | | | ++ | |
| 101 | | | ++ | |
| 102 | | | | ++ |
| 103 | ++ | ++ | +++ | + |
| 104 | | + | ++ | + |
| 105 | | ++ | +++ | ++ |
| 108 | | | ++ | |
| 109 | | | ++ | ++ |
| 110 | ++ | ++ | ++ | ++ |
| 111 | + | | ++ | ++ |
| 112 | | + | ++ | ++ |
| 113 | | | ++ | |
| 117 | ++ | + | +++ | ++ |
| 118 | ++ | + | ++ | + |
| 119 | + | + | ++ | ++ |
| 120 | ++ | ++ | +++ | ++ |
| 121 | + | ++ | ++ | ++ |
| 122 | ++ | ++ | +++ | ++ |
| 123 | ++ | ++ | ++ | ++ |
| 124 | + | + | ++ | + |
| 125 | | + | ++ | + |
| 126 | | | ++ | ++ |
| 127 | | | + | |
| 128 | + | ++ | ++ | ++ |
| 129 | ++ | ++ | ++ | + |
| 130 | ++ | ++ | +++ | ++ |
| 131 | | + | ++ | + |
| 135 | ++ | ++ | +++ | ++ |
| 136 | + | ++ | +++ | + |
| 137 | + | ++ | +++ | ++ |
| 137a | | + | ++ | |
| 137b | + | ++ | +++ | ++ |
| 138° | | | + | |
| 138b | + | + | +++ | ++ |
| 139 | + | + | +++ | + |
| 140 | + | ++ | +++ | + |
| 141 | + | ++ | +++ | + |
| 142 | + | + | +++ | + |
| 143 | | ++ | ++ | + |
| 144 | + | ++ | +++ | ++ |
| 145 | ++ | ++ | +++ | ++ |
| 146 | + | ++ | +++ | ++ |
| 147 | ++ | ++ | +++ | ++ |
| 148 | + | ++ | +++ | ++ |
| 149 | + | ++ | +++ | + |
| 151 | + | ++ | ++ | ++ |
| 152 | ++ | ++ | +++ | ++ |
| 153 | + | ++ | +++ | + |
| 154 | + | ++ | +++ | + |
| 155 | + | ++ | ++ | + |
| 156 | + | ++ | +++ | ++ |
| 157 | + | ++ | +++ | ++ |
| 158 | ++ | ++ | ++ | |
| 159 | | + | ++ | ++ |
| 160 | | ++ | +++ | ++ |
| 161 | + | + | +++ | + |
| 162 | + | | ++ | ++ |
| 163 | | | ++ | + |
| 164 | + | ++ | +++ | ++ |
| 165 | + | ++ | +++ | ++ |
| 166a | | | ++ | |
| 166b | + | ++ | +++ | ++ |
| 167a | ++ | ++ | +++ | ++ |
| 167b | + | ++ | +++ | ++ |
| 168a | ++ | ++ | +++ | ++ |
| 168b | | + | ++ | + |
| 169 | + | ++ | +++ | ++ |
| 169a | + | ++ | +++ | ++ |
| 169b | + | ++ | | |
| 170 | ++ | ++ | +++ | ++ |
| 171 | ++ | ++ | +++ | + |
| 172 | ++ | ++ | ++ | ++ |
| 173 | ++ | ++ | +++ | ++ |
| 174 | ++ | ++ | ++ | ++ |
| 175 | ++ | +++ | +++ | ++ |

TABLE 1-continued

Results of the in vitro determination of the PI3K enzyme inhibitory activity in the cell free assay.

| Compound of Example N. | PI3K alpha inhibition | PI3K beta inhibition | PI3K delta inhibition | PI3K gamma inhibition |
|---|---|---|---|---|
| 176a | + | + | +++ | + |
| 176b |  | + | ++ | ++ | wherein the compounds are classified in term of potency with respect to their inhibitory activity on PI3K-alfa, -beta, -gamma and -delta according to the following:

+++: IC50<10 nM
++: IC50 in the range 10-1000 nM
+: IC50>1000 nM

In Vitro Determination of the PI3K Enzyme Inhibitory Activity in the PBMCs Assay.

Human peripheral blood mononuclear cells (PBMCs) were purchased from Lonza (Basel, CH), washed and resuspended in RPMI 1640 medium (w/o Phenol Red) supplemented with 10% FBS, 2 mM glutamine, 100 U/ml penicillin and 100 µg/mL streptomycin (Life Technologies, Carlsbad Calif.). PBMCs were plated at a density of $10^5$ cells/well in 96-well plates coated with 6 µg/ml anti-human CD3 antibody (Biolegend, San Diego Calif.).

Cells were treated in RPMI (w/o Phenol Red) supplemented with 10% FBS with different concentrations of PI3K inhibitors ($10^{-12}$M-$10^{-5}$M, final DMSO concentration 0.2%), co-stimulated with 3 µg/ml anti-human CD28 antibody (BD Biosciences, San Jose Calif.) and incubated for 72 hours in an atmosphere of 95% air and 5% $CO_2$ at 37° C. Human IL-6 and IL-17 were measured in the supernatants using paired antibody quantitative ELISA kits (from Life Technologies, Carlsbad Calif. and R&D Systems, Minneapolis Minn. respectively) according to the manufacturer's instructions.

IC50 values were determined from concentration-response curves by nonlinear regression analysis using the Graph Pad Prism v.6 (GraphPad Software, La Jolla Calif.).

The compounds representative of the invention showed an IC50 lower than 1 µM with respect to the PI3K-delta subunit.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

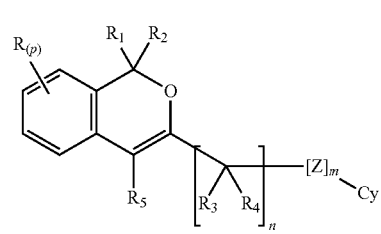

wherein:
each R, when present, is independently:
  $OR_6$;
  $SR_6$
  $S(O)_q$—$R_8$
  $NR_{10}R_{11}$
  halogen
  ($C_1$-$C_6$) alkyl;
  ($C_1$-$C_6$) haloalkyl;
  ($C_3$-$C_7$) cycloalkyl;
  ($C_5$-$C_7$) cycloalkenyl;
  ($C_2$-$C_6$) alkenyl;
  ($C_2$-$C_6$) alkynyl;
  substituted or unsubstituted aryl; or
  substituted or unsubstituted heteroaryl;
$R_1$ and $R_2$ are both H or together form an oxo group (=O);
$R_3$ and $R_4$, the same or different, in each occurrence are independently:
  H;
  ($C_1$-$C_6$) alkyl; or
  ($C_1$-$C_6$) haloalkyl;
$R_5$ is:
  ($C_1$-$C_6$) alkyl;
  ($C_1$-$C_6$) haloalkyl;
  ($C_1$-$C_6$) hydroxyalkyl;
  ($C_1$-$C_6$) aminoalkyl;
  ($C_3$-$C_7$) cycloalkyl;
  aryl ($C_1$-$C_3$) alkyl;
  ($C_5$-$C_7$)cycloalkenyl;
  ($C_2$-$C_6$) alkenyl;
  ($C_2$-$C_6$) alkynyl;
  ($C_2$-$C_6$) aminoalkynyl
  substituted or unsubstituted ($C_3$-$C_6$) heterocycloalkyl
  substituted or unsubstituted aryl; or
  substituted or unsubstituted heteroaryl;
$R_6$, $R_7$ and $R_{14}$ are the same or different and are at each occurrence independently:
  H;
  ($C_1$-$C_6$) alkyl;
  ($C_1$-$C_6$) haloalkyl;
  ($C_1$-$C_6$) hydroxyalkyl;
  ($C_1$-$C_6$) aminoalkyl;
  aryl($C_1$-$C_6$)alkyl
  ($C_1$-$C_6$) alkanoyl
  arylcarbonyl; or
  aryl ($C_2$-$C_4$) alkanoyl;
$R_8$ and $R_9$ are the same or different and are at each occurrence independently:
  ($C_1$-$C_6$) alkyl;
  ($C_1$-$C_6$) haloalkyl;
  ($C_1$-$C_6$) hydroxyalkyl;
  ($C_1$-$C_6$) aminoalkyl;

substituted or unsubstituted aryl;
substituted or unsubstituted heteroaryl; or
$NR_{12}R_{13}$;
$R_{10}$, $R_{11}$, $R_{12}$ and $R_{13}$ are the same or different and are at each occurrence independently selected from the group consisting of H, ($C_1$-$C_6$) aminoalkyl, ($C_1$-$C_6$) hydroxyalkyl and ($C_1$-$C_6$) alkyl, or taken together with the nitrogen atom they are linked to, either $R_{10}$ and $R_{11}$ or $R_{12}$ and $R_{13}$ form a 5 to 6 membered heterocyclic radical;
Z, when present, is an atom or a group each time independently selected from the group consisting of O, NH, C(O), NHC(O), C(O)NH, S, S(O), and S(O)$_2$;
m is zero or 1;
n is 1;
p is zero or an integer ranging from 1 to 3;
q is 1 or 2; and
Cy is
substituted or unsubstituted heteroaryl;
or a pharmaceutically acceptable salt thereof.

2. A compound or pharmaceutically acceptable salt according to claim 1, which is represented by formula (IA):

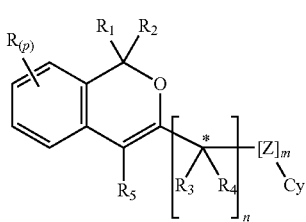

(IA)

wherein $R_3$ is as defined above except H, $R_4$ is H, and the absolute configuration of the chiral carbon (*) is (R).

3. A compound or pharmaceutically acceptable salt according to claim 1, which is represented by formula (IA):

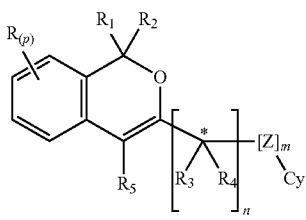

(IA)

wherein $R_3$ is as defined above except H, $R_4$ is H, and the absolute configuration of the chiral carbon (*) is (S).

4. A compound or pharmaceutically acceptable salt according to claim 1, which exists as a mixture of diastereoisomers.

5. A compound or pharmaceutically acceptable salt according to claim 1, wherein:
$R_3$ is H or ($C_1$-$C_6$) alkyl;
$R_4$ is H; and
$R_5$ is aryl (C1-C3) alkyl; ($C_5$-$C_7$) cycloalkenyl; ($C_2$-$C_6$) alkyny; ($C_2$-$C_6$) aminoalkynyl; substituted or unsubstituted ($C_3$-$C_6$) heterocycloalkyl; substituted or unsubstituted aryl; or substituted or unsubstituted heteroaryl.

6. A compound or pharmaceutically acceptable salt according to claim 1, wherein:
p is 0 or 1;
R is not present or is halogen or ($C_1$-$C_6$) alkyl;
$R_3$ is H, methyl, ethyl or propyl;
$R_4$ is H; and
$R_5$ is phenyl; phenylmethyl; 2-, 3- or 4-pyridinyl; 5-thiazolyl; 2-, 3-, 4- or 5-thienyl; 1H-pyrazol-4yl, 2-, 4-, 5- or 6- pyrimidinyl; cyclohexenyl; prop-1-ynyl; 1,2,3,6-tetrahydropyridin-4-yl; 1,2,5,6-tetrahydropyridin-3-yl; 8-azabicyclo[3.2.1]oct-2-en-3-yl; or 3,6-dihydro-2H-pyran-4-yl, optionally substituted by one or more groups selected from the group consisting of halogen, ($C_1$-$C_6$) alkyl, $OR_7$, —S(O)$_q$—$R_9$, —C(O)$NR_{10}R_{11}$, $COOR_{14}$, ($C_1$-$C_6$) hydroxyalkyl, substituted or unsubstituted ($C_1$-$C_6$) aminoalkyl, ($C_1$-$C_6$) alkanoyl, substituted or unsubstituted ($C_3$-$C_6$) heterocycloalkyl, aryl($C_1$-$C_6$)alkyl, heteroaryl($C_1$-$C_6$)alkyl, ($C_3$-$C_7$)cycloalkyl($C_1$-$C_6$)alkyl, and $NR_{10}R_{11}$.

7. A compound or pharmaceutically acceptable salt according to claim 1, wherein:
p is 0;
R is not present;
$R_3$ is H, methyl, ethyl or propyl;
$R_4$ is H; and
$R_5$ is phenyl; phenylmethyl; 2-, 3- or 4-pyridinyl; 5-thiazolyl; 2-, 3-, 4- or 5-thienyl; 1,2,3,6-tetrahydropyridin-4-yl; or 3,6-dihydro-2H-pyran-4-yl, optionally substituted by one or more groups selected from the group consisting of fluoro, bromo, methyl, methoxy, amino, dimethylamino, 4-morpholinosulfonyl, 4-(2-morpholinoethoxy), 4-morpholinomethyl and 4-piperazinomethyl; piperidin-1-ylmethyl, 4-methylpiperazine-1-carbonyl, (2-(dimethylamino)ethyl)-carbonyl, acetyl, phenylmethyl, phenylmethoxy-carbonyl, 4,4,5,5-tetramethyl-1,3-dioxolan-2-yl, pyrrolidin-1-ylmethyl, bis(2-hydroxyethyl)aminomethyl, hydroxymethyl, dimethylaminomethyl, (dimethylamino)propyl, 4-(2-hydroxyethyl)piperazin-1-yl)methyl piperazin-2-one-1-ylmethyl, cyclopropylmethyl, hydroxycarbonyl, or pyridin-4-ylmethyl.

8. A compound or pharmaceutically acceptable salt according to claim 1, wherein:
$R_3$ is H, methyl, ethyl or propyl;
$R_4$ is H;
$R_5$ is aryl ($C_1$-$C_3$) alkyl; substituted or unsubstituted ($C_3$-$C_6$) heterocycloalkyl; substituted or unsubstituted aryl or substituted or unsubstituted heteroaryl;
Z, when present, is an atom or a group selected from the group consisting of O, NH, C(O), NH—C(O), C(O)—NH, S, SO and SO$_2$;
CY is 7H-purin-7-yl; 9H-purin-9-yl; 9H-purin-6-yl; 1H-pyrazolo[3,4-d]pyrimidin-1-yl; 1H-pyrazolo[3,4-d]pyrimidin-4-yl; 2H-pyrazolo[3,4-d]pyrimidin-2-yl; 2-, 4-, 5- or 6-pyrimidinyl; 2-pyrazinyl; pyrrolo[2,3-d]pyrimidin-7-yl; pyrazolo[1,5-a]pyrimidin-3-yl; pyrido[3,2-d]pyrimidin-4-yl; pyrido[2,3-d]pyrimidin-8-yl-5-one; thieno[3,2-d]pyrimidin-4-yl; or thieno[2,3-d]pyrimidin-4-yl, which are all optionally substituted by one or more groups selected from the group consisting of halogen, ($C_1$-$C_6$) alkyl, ($C_1$-$C_6$) haloalkyl, CN, $NR_{10}R_{11}$, optionally substituted aryl, and optionally substituted heteroaryl selected from the group consisting of phenyl, 1H-indazol-4-yl, 1H-indazol-5-yl, 1H-indazol-6-yl, 2-, 3-, 4-, 5-, 6-pyridinyl, pyrazol-3-yl, pyrazol-4-yl, pyrazol-5-yl, pyrazin-2yl, pyrimidin-5-yl, pyridazin-4-yl and 2-, 4-, 5-thiazolyl.

9. A compound or pharmaceutically acceptable salt according to claim 1, wherein:
$R_1$ and $R_2$ together form an oxo group (═O);
$R_3$ is H, methyl or ethyl;

R₄ is H;

R₅ is phenyl; phenylmethyl; 2-, 3- or 4-pyridinyl; 5-thiazolyl; 2-, 3-, 4- or 5-thienyl; 1,2,3,6-tetrahydropyridin-4-yl; 3,6-dihydro-2H-pyran-4-yl; or 4-cyclohexenyl, which are all optionally substituted by one or more groups selected from the group consisting of fluoro, bromo, methyl, methoxy, dimethylamino, morpholinosulfonyl, morpholinoethoxy, morpholinomethyl and piperazinomethyl; 4-methylpiperazine-1-carbonyl, 4-(2-hydroxyethyl)piperazin-1-yl-methyl, piperazin-2-one-1-yl-methyl, or pyridin-4-ylmethyl;

Z, when present, is an atom or a group each time independently selected from O, NH, C(O), NH—C(O), C(O)—NH, S, SO, and SO₂;

CY is 7H-purin-7-yl; 9H-purin-9-yl; 9H-purin-6-yl; 1H-pyrazolo[3,4-d]pyrimidin-1-yl; 1H-pyrazolo[3,4-d]pyrimidin-4-yl; 2H-pyrazolo[3,4-d]pyrimidin-2-yl; and 2-, 4-, 5- or 6-pyrimidinyl; or 2-pyrazinyl which are all optionally substituted by one or more groups selected from the group consisting of Cl, Br, F, I, methyl, trifluoromethyl, CN; NH₂; NH—CH₃; N(CH₃)₂; 3-methyl-1H-indazol-5-yl, 1H-indazol-4-yl; 3-fluoro-5-hydroxyphenyl; 1-(3-fluoro-4-hydroxyphenyl); 6-, 5-, 4-hydroxypyridin-3-yl, 6-, 5-methoxypyridin-3-yl, 5-aminopyridin-3-yl, 5-fluoropyridin-3-yl, 5-fluoro-6-hydroxypyridin-3-yl 6-(methylsulfonyl)pyridin-3-yl, 5-hydroxy-6-methylpyridin-3-yl, 6-, 5-(hydroxymethyl)pyridin-3-yl, 2-aminothiazol-5-yl; 2-(acetamino)-(thiazol-5-yl), 2-aminopyrimidin-5-yl, 2-methoxypyrimidin-5-yl, 2-hydroxypyrimidin-5-yl, pyrazin-2-yl, 6-hydroxypyrazin-2-yl and 3-fluoro-4-isopropoxyphenyl.

10. A compound or pharmaceutically acceptable salt, which is an isochromene compound selected from the group consisting of:

3-((6-amino-9H-purin-9-yl)methyl)-4-phenyl-1H-isochromen-1-one;
3-((6-amino-9H-purin-9-yl)methyl)-4-(3-fluorophenyl)-1H-isochromen-1-one;
3-((6-amino-9H-purin-9-yl)methyl)-4-(2-fluorophenyl)-1H-isochromen-1-one;
3-((6-amino-9H-purin-9-yl)methyl)-4-m-tolyl-1H-isochromen-1-one;
3-(1-(6-amino-9H-purin-9-yl)ethyl)-4-phenyl-1H-isochromen-1-one;
3-(1-(6-amino-9H-purin-9-yl)ethyl)-4-m-tolyl-1H-isochromen-1-one;
3-(1-(6-amino-9H-purin-9-yl)ethyl)-4-(3-fluorophenyl)-1H-isochromen-1-one;
3-(1-(6-amino-9H-purin-9-yl)ethyl)-4-(3-(dimethylamino)phenyl)-1H-isochromen-1-one;
3-(1-(6-amino-9H-purin-9-yl)ethyl)-4-(3-(morpholinosulfonyp)phenyl)-1H-isochromen-1-one;
3-((9H-purin-6-ylthio)methyl)-4-phenyl-1H-isochromen-1-one;
3-((9H-purin-6-ylthio)methyl)-4-m-tolyl-1H-isochromen-1-one;
3-(1-(9H-purin-6-ylthio)ethyl)-4-m-tolyl-1H-isochromen-1-one;
3-(1-(9H-purin-6-ylthio)ethyl)-4-(3-fluorophenyl)-1H-isochromen-1-one;
3-(1-(4-amino-1H-pyrazolo[3,4-d]pyrimidin-1-yl)ethyl)-4-(6-methylpyridin-3-yl)-1H-isochromen-1-one;
3-(1-(4-amino-1H-pyrazolo[3,4-d]pyrimidin-1-yl)ethyl)-4-(3-(morpholinosulfonyl)phenyl)-1H-isochromen-1-one;
3-(1-(4-amino-1H-pyrazolo[3,4-d]pyrimidin-1-yl)ethyl)-4-phenyl-1H-isochromen-1-one;
3-(1-(4-amino-1H-pyrazolo[3,4-d]pyrimidin-1-yl)ethyl)-4-(thiazol-5-yl)-1H-isochromen-1-one;
3-(1-(4-amino-1H-pyrazolo[3,4-d]pyrimidin-1-yl)ethyl)-4-(2-methylpyridin-4-yl)-1H-isochromen-1-one;
3-(1-(4-amino-1H-pyrazolo[3,4-d]pyrimidin-1-yl)ethyl)-4-benzyl-1H-isochromen-1-one;
3((9H-purin-6-ylamino)methyl)-4-(3-fluorophenyl)-1H-isochromen-1-one;
3-(1-(9H-purin-6-ylamino)ethyl)-4-phenyl-1H-isochromen-1-one;
3-(1-(9H-purin-6-ylamino)ethyl)-4-(1,2,3,6-tetrahydropyridin-4-yl)-1H-isochromen-1-one;
3-(1-(9H-purin-6-ylamino)ethyl)-4-(3,6-dihydro-2H-pyran-4-yl)-1H-isochromen-1-one;
3-(1-(9H-purin-6-ylamino)propyl)-4-phenyl-1H-isochromen-1-one;
3-(1-(9H-purin-6-ylamino)ethyl)-4-(4-(2-morpholinoethoxy)phenyl)-1H-isochromen-1-one;
4-amino-8-(1-(1-oxo-4-phenyl-1H-isochromen-3-yl)ethyl)pyrido[2,3-d]pyrimidin-5(8H)-one;
3-(1-(9H-purin-6-ylamino)ethyl)-4-(5-(morpholinomethyl)thiophen-2-yl)-1H-isochromen-1-one;
3-((9H-purin-6-ylamino)methyl)-4-phenyl-1H-isochromen-1-one;
3-((9H-purin-6-ylamino)methyl)-4-(2-fluorophenyl)-1H-isochromen-1-one;
3-((9H-purin-6-ylamino)methyl)-4-m-tolyl-1H-isochromen-1-one;
3-(1-(9H-purin-6-ylamino)ethyl)-4-(3-fluorophenyl)-1H-isochromen-1-one;
3-(1-(9H-purin-6-ylamino)ethyl)-4-m-tolyl-1H-isochromen-1-one;
3-(1-(9H-purin-6-ylamino)ethyl)-4-(3-(dimethylamino)phenyl)-1H-isochromen-1-one;
3-((4-amino-3-(3-fluoro-5-hydroxyphenyl)-1H-pyrazolo[3,4-d]pyrimidin-1-yl)methyl)-4-phenyl-1H-isochromen-1-one;
3-((4-amino-3-(1H-indazol-5-yl)-1H-pyrazolo[3,4-d]pyrimidin-1-yl)methyl)-4-phenyl-1H-isochromen-1-one;
3-((4-amino-3-(3-methyl-1H-indazol-5-yl)-1H-pyrazolo[3,4-d]pyrimidin-1-yl)methyl)-4-phenyl-1H-isochromen-1-one;
3-((4-amino-3-(1H-indazol-6-yl)-1H-pyrazolo[3,4-d]pyrimidin-1-yl)methyl)-4-phenyl-1H-isochromen-1-one;
3-((4-amino-3-(3-fluoro-4-hydroxyphenyl)-1H-pyrazolo[3,4-d]pyrimidin-1-yl)methyl)-4-phenyl-1H-isochromen-1-one;
3-(1-(4-amino-3-(3-fluoro-5-hydroxyphenyl)-1H-pyrazolo[3,4-d]pyrimidin-1-yl)ethyl)-4-phenyl-1H-isochromen-1-one;
3-(1-(4-amino-3-(3-fluoro-5-hydroxyphenyl)-1H-pyrazolo[3,4-d]pyrimidin-1-;
3-(1-(4-amino-3-(1H-pyrazol-4-yl)-1H-pyrazolo[3,4-d]pyrimidin-1-yl)ethyl)-4-m-tolyl-1H-isochromen-1-one;
3-(1-(6-amino-9H-purin-9-yl)ethyl)-4-(6-methoxypyridin-3-yl)-1H-isochromen-1-one;
3-((4-amino-3-iodo-1H-pyrazolo[3,4-d]pyrimidin-1-yl)methyl)-4-phenyl-1H-isochromen-1-one;
3-(1-(4-amino-3-iodo-1H-pyrazolo[3,4-d]pyrimidin-1-yl)ethyl)-4-phenyl-1H-isochromen-1-one;
3-(1-(4-amino-3-iodo-1H-pyrazolo[3,4-d]pyrimidin-1-yl)ethyl)-4-m-tolyl-1H-isochromen-1-one;
3-(1-(1H-pyrazolo[3,4-d]pyrimidin-4-ylamino)ethyl)-4-phenyl-1H-isochromen-1-one;

4-amino-6-(1-(1-oxo-4-phenyl-1H-isochromen-3-yl)
ethylamino)pyrimidine-5-carbonitrile;
3-(1-(9H-purin-6-ylamino)ethyl)-4-(1-methyl-1,2,3,6-tetrahydropyridin-4-yl)-1H-isochromen-1-one;
3-(1-(4-amino-3-(3-fluoro-5-hydroxyphenyl)-1H-pyrazolo[3,4-d]pyrimidin-1-yl)ethyl)-4-(1-methyl-1,2,3,6-tetrahydropyridin-4-yl)-1H-isochromen-1-one;
3-(1-(4-amino-3-(3-fluoro-5-hydroxyphenyl)-1H-pyrazolo[3,4-d]pyrimidin-1-yl)ethyl)-4-(1-methyl-1,2,3,6-tetrahydropyridin-4-yl)-1H-isochromen-1-one single enantiomer 1;
3-(1-(4-amino-3-(3-fluoro-5-hydroxyphenyl)-1H-pyrazolo[3,4-d]pyrimidin-1-yl)ethyl)-4-(1-methyl-1,2,3,6-tetrahydropyridin-4-yl)-1H-isochromen-1-one single enantiomer 2;
3-(1-(9H-purin-6-ylamino)ethyl)-4-(4-(morpholinomethyl)phenyl)-1H-isochromen-1-one;
3-(1-(4-amino-3-(3-fluoro-5-hydroxyphenyl)-1H-pyrazolo[3,4-d]pyrimidin-1-yl)ethyl)-4-(4-(morpholinomethyl)phenyl)-1H-isochromen-1-one;
3-(1-(4-amino-3-(3-fluoro-5-hydroxyphenyl)-1H-pyrazolo[3,4-d]pyrimidin-1-yl)ethyl)-4-(5-(morpholinomethyl)thiophen-2-yl)-1H-isochromen-1-one;
3-(1-(4-amino-3-(3-fluoro-5-hydroxyphenyl)-1H-pyrazolo[3,4-d]pyrimidin-1-yl)ethyl)-4-(5-(morpholinomethyl)thiophen-2-yl)-1H-isochromen-1-one single enantiomer 1;
3-(1-(4-amino-3-(3-fluoro-5-hydroxyphenyl)-1H-pyrazolo[3,4-d]pyrimidin-1-yl)ethyl)-4-(5-(morpholinomethyl)thiophen-2-yl)-1H-isochromen-1-one single enantiomer 2;
3-(1-(9H-purin-6-ylamino)ethyl)-4-cyclohexenyl-1H-isochromen-1-one;
3-(1-(4-amino-3-(2-aminopyrimidin-5-yl)-1H-pyrazolo[3,4-d]pyrimidin-1-yl)ethyl)-4-phenyl-1H-isochromen-1-one;
3-(1-(4-amino-3-(pyrazin-2-yl)-1H-pyrazolo[3,4-d]pyrimidin-1-yl)ethyl)-4-phenyl-1H-isochromen-1-one;
3-(1-(4-amino-3-(pyridazin-4-yl)-1H-pyrazolo[3,4-d]pyrimidin-1-yl)ethyl)-4-phenyl-1H-isochromen-1-one;
3-(1-(4-amino-3-(pyridin-4-yl)-1H-pyrazolo[3,4-d]pyrimidin-1-yl)ethyl)-4-phenyl-1H-isochromen-1-one;
3-(1-(4-amino-3-(2-methoxypyrimidin-5-yl)-1H-pyrazolo[3,4-d]pyrimidin-1-yl)ethyl)-4-phenyl-1H-isochromen-1-one;
3-(1-(4-amino-3-(2-hydroxypyrimidin-5-yl)-1H-pyrazolo[3,4-d]pyrimidin-1-yl)ethyl)-4-phenyl-1H-isochromen-1-one;
3-(1-(4-amino-3-(5-methoxypyridin-3-yl)-1H-pyrazolo[3,4-d]pyrimidin-1-yl)ethyl)-4-phenyl-1H-isochromen-1-one;
3-(1-(4-amino-3-(pyridin-3-yl)-1H-pyrazolo[3,4-d]pyrimidin-1-yl)ethyl)-4-phenyl-;
3-(1-(4-amino-3-(2-aminothiazol-5-yl)-1H-pyrazolo[3,4-d]pyrimidin-1-yl)ethyl)-4-phenyl-1H-isochromen-1-one;
3-(1-(4-amino-3-(6-methoxypyridin-3-yl)-1H-pyrazolo[3,4-d]pyrimidin-1-yl)ethyl)-4-phenyl-1H-isochromen-1-one;
3-(1-(4-amino-3-(6-hydroxypyridin-3-yl)-1H-pyrazolo[3,4-d]pyrimidin-1-yl)ethyl)-4-phenyl-1H-isochromen-1-one;
N-(5-(4-amino-1-(1-(1-oxo-4-phenyl-1H-isochromen-3-yl)ethyl)-1H-pyrazolo[3,4-d]pyrimidin-3-yl)thiazol-2-yl)acetamide;
3-(1-(4-amino-3-(3-fluoro-5-hydroxyphenyl)-1H-pyrazolo[3,4-d]pyrimidin-1-yl)ethyl)-4-(1-methyl-1,2,5,6-tetrahydropyridin-3-yl)-1H-isochromen-1-one;
3-(1-(4-amino-3-(3-fluoro-5-hydroxyphenyl)-1H-pyrazolo[3,4-d]pyrimidin-1-yl)ethyl)-4-1,2,3,6-tetrahydropyridin-4-yl)-1H-isochromen-1-one;
3-(1-(4-amino-3-(3-fluoro-5-hydroxyphenyl)-1H-pyrazolo[3,4-d]pyrimidin-1-yl)ethyl)-4-(1-(pyridin-4-ylmethyl)-1,2,3,6-tetrahydropyridin-4-yl)-1H-isochromen-1-one;
3-(1-(4-amino-3-(3-fluoro-5-hydroxyphenyl)-1H-pyrazolo[3,4-d]pyrimidin-1-yl)ethyl)-4-(1-(cyclopropylmethyl)-1,2,3,6-tetrahydropyridin-4-yl)-1H-isochromen-1-one;
3-(1-(4-amino-3-(3-fluoro-5-hydroxyphenyl)-1H-pyrazolo[3,4-d]pyrimidin-1-yl)ethyl)-4-(3-((dimethylamino)methyl)phenyl)-1H-isochromen-1-one;
3-(1-(4-amino-3-(3-fluoro-5-hydroxyphenyl)-1H-pyrazolo[3,4-d]pyrimidin-1-yl)ethyl)-4-(3-((dimethylamino)methyl)phenyl)-1H-isochromen-1-one enantiomer 1;
3-(1-(4-amino-3-(3-fluoro-5-hydroxyphenyl)-1H-pyrazolo[3,4-d]pyrimidin-1-yl)ethyl)-4-(3-((dimethylamino)methyl)phenyl)-1H-isochromen-1-one enantiomer 2;
3-(1-(4-amino-3-(3-fluoro-5-hydroxyphenyl)-1H-pyrazolo[3,4-d]pyrimidin-1-yl)ethyl)-4-(5-(piperidin-1-ylmethyl)thiophen-2-yl)-1H-isochromen-1-one;
3-(1-(4-amino-3-(3-fluoro-5-hydroxyphenyl)-1H-pyrazolo[3,4-d]pyrimidin-1-yl)ethyl)-4-(5-(piperidin-1-ylmethyl)thiophen-2-yl)-1H-isochromen-1-one single enantiomer 1;
3-(1-(4-amino-3-(3-fluoro-5-hydroxyphenyl)-1H-pyrazolo[3,4-d]pyrimidin-1-yl)ethyl)-4-(5-(piperidin-1-ylmethyl)thiophen-2-yl)-1H-isochromen-1-one single enantiomer 2;
3-(1-(4-amino-3-(3-fluoro-5-hydroxyphenyl)-1H-pyrazolo[3,4-d]pyrimidin-1-yl)ethyl)-4-(4-(4-methylpiperazine-1-carbonyl)phenyl)-1H-isochromen-1-one;
3-(3-(1-(4-amino-3-(3-fluoro-5-hydroxyphenyl)-1H-pyrazolo[3,4-d]pyrimidin-1-yl)ethyl)-1-oxo-1H-isochromen-4-yl)-N-(2-(dimethylamino)ethyl)benzamide;
4-(1-acetyl-1,2,3,6-tetrahydropyridin-4-yl)-3-(1-(4-amino-3-(5-hydroxypyridin-3-yl)-1H-pyrazolo[3,4-d]pyrimidin-1-yl)ethyl)-1H-isochromen-1-one;
4-(1-acetyl-1,2,3,6-tetrahydropyridin-4-yl)-3-(1-(4-amino-3-(3-fluoro-5-hydroxyphenyl)-1H-pyrazolo[3,4-d]pyrimidin-1-yl)ethyl)-1H-isochromen-1-one;
3-(1-(4-amino-3-(3-fluoro-5-hydroxyphenyl)-1H-pyrazolo[3,4-d]pyrimidin-1-yl)ethyl)-4-(5-(pyrrolidin-1-ylmethyl)thiophen-2-yl)-1H-isocluomen-1-one;
3-(1-(4-amino-3-(3-fluoro-5-hydroxyphenyl)-1H-pyrazolo[3,4-d]pyrimidin-1-yl)ethyl)-4-(5-((bis(2-hydroxyethyl)amino)methyl)thiophen-2-yl)-1H-isochromen-1-one;
3-(1-(4-amino-3-(3-fluoro-5-hydroxyphenyl)-1H-pyrazolo[3,4-d]pyrimidin-1-yl)ethyl)-4-(5-(hydroxymethyl)thiophen-2-yl)-1H-isochromen-1-one;
3-(1-(4-amino-3-(3-fluoro-5-hydroxyphenyl)-1H-pyrazolo[3,4-d]pyrimidin-1-yl)ethyl)-4-(5-((4-(2-hydroxyethyl)piperazin-1-yl)methyl)thiophen-2-yl)-1H-isochromen-1-one;
3-(1-(4-amino-3-(3-fluoro-5-hydroxyphenyl)-1H-pyrazolo[3,4-d]pyrimidin-1-yl)ethyl)-4-(5-((4-(2-hydroxyethyl)piperazin-1-yl)methyl)thiophen-2-yl)-1H-isochromen-1-one single enantiomer 1;

3-(1-(4-amino-3-(3-fluoro-5-hydroxyphenyl)-1H-pyrazolo[3,4-d]pyrimidin-1-yl)ethyl)-4-(5-((4-(2-hydroxyethyl)piperazin-1-yl)methyl)thiophen-2-yl)-1H-isochromen-1-one single enantiomer 2;
4-((5-(3-(1-(4-amino-3-(3-fluoro-5-hydroxyphenyl)-1H-pyrazolo[3,4-d]pyrimidin-1-yl)ethyl)-1-oxo-1H-isochromen-4-yl)thiophen-2-yl)methyl)piperazin-2-one;
5-(3-(1-(4-amino-3-(3-fluoro-5-hydroxyphenyl)-1H-pyrazolo[3,4-d]pyrimidin-1-yl)ethyl)-1-oxo-1H-isochromen-4-yl)thiophene-2-carboxylic acid;
3-(1-(4-amino-3-(3-fluoro-5-hydroxyphenyl)-1H-pyrazolo[3,4-d]pyrimidin-1-yl)ethyl)-4-benzyl-1H-isochromen-1-one;
4-(1H-pyrazol-4-yl)-3-(1-(thieno[3,2-d]pyrimidin-4-ylamino)ethyl)-1H-isochromen-1-one;
4-(5-(morpholinomethyl)thiophen-2-yl)-3-(1-(thieno[3,2-d]pyrimidin-4-ylamino)ethyl)-1H-isochromen-1-one;
4-amino-6-((1-(4-(5-(morpholinomethyl)thiophen-2-yl)-1-oxo-1H-isochromen-3-yl)ethyl)amino)pyrimidine-5-carbonitrile;
4-phenyl-3-(1-(pyrrolo[2,1-f][1,2,4]triazin-4-ylamino)ethyl)-1H-isochromen-1-one;
4-phenyl-3-(1-(pyrido[3,2-d]pyrimidin-4-ylamino)ethyl)-1H-isochromen-1-one;
3-(1-(4-amino-3-(5-(hydroxymethyl)pyridin-3-yl)-1H-pyrazolo[3,4-d]pyrimidin-1-yl)ethyl)-4-phenyl-1H-isochromen-1-one;
3-(1-(4-amino-3-(6-(hydroxymethyl)pyridin-3-yl)-1H-pyrazolo[3,4-d]pyrimidin-1-yl)ethyl)-4-phenyl-1H-isochromen-1-one;
N-(5-(4-amino-1-(1-(1-oxo-4-phenyl-1H-isochromen-3-yl)ethyl)-1H-pyrazolo[3,4-d]pyrimidin-3-yl)pyridin-3-yl)-4-fluorobenzenesulfonamide;
3-(1-(4-amino-3-(5-aminopyridin-3-yl)-1H-pyrazolo[3,4-d]pyrimidin-1-yl)ethyl)-4-phenyl-1H-isochromen-1-one;
3-(1-(4-amino-3-(2-aminopyrimidin-4-yl)-1H-pyrazolo[3,4-d]pyrimidin-1-yl)ethyl)-4-phenyl-1H-isochromen-1-one;
3-(1-(4-amino-3-(6-hydroxypyrazin-2-yl)-1H-pyrazolo[3,4-d]pyrimidin-1-yl)ethyl)-4-phenyl-1H-isochromen-1-one;
3-(1-(4-amino-3-(5-hydroxypyridin-3-yl)-1H-pyrazolo[3,4-d]pyrimidin-1-yl)ethyl)-4-phenyl-1H-isochromen-1-one;
3-(1-(4-amino-3-(3-fluoro-5-hydroxyphenyl)-1H-pyrazolo[3,4-d]pyrimidin-1-yl)ethyl)-4-(8-methyl-8-azabicyclo[3.2.1]oct-2-en-3-yl)-1H-isochromen-1-one hydrochloride;
3-(1-(4-amino-3-(3-fluoro-4-isopropoxyphenyl)-1H-pyrazolo[3,4-d]pyrimidin-1-yl)ethyl)-4-phenyl-1H-isochromen-1-one;
3-(1-(4-amino-3-(5-fluoropyridin-3-yl)-1H-pyrazolo[3,4-d]pyrimidin-1-yl)ethyl)-4-phenyl-1H-isochromen-1-one;
3-(1-(4-amino-3-(3-chloro-5-fluorophenyl)-1H-pyrazolo[3,4-d]pyrimidin-1-yl)ethyl)-4-phenyl-1H-isochromen-1-one;
3-(1-(4-amino-3-(5-(methylsulfonyl)pyridin-3-yl)-1H-pyrazolo[3,4-d]pyrimidin-1-yl)ethyl)-4-phenyl-1H-isochromen-1-one;
3-(1-(4-amino-3-(6-(methylsulfonyl)pyridin-3-yl)-1H-pyrazolo[3,4-d]pyrimidin-1-yl)ethyl)-4-phenyl-1H-isochromen-1-one;
3-(1-(4-amino-3-(5-fluoro-6-hydroxypyridin-3-yl)-1H-pyrazolo[3,4-d]pyrimidin-1-yl)ethyl)-4-phenyl-1H-isochromen-1-one;
3-(1-(4-amino-3-(5-hydroxy-6-methylpyridin-3-yl)-1H-pyrazolo[3,4-d]pyrimidin-1-yl)ethyl)-4-phenyl-1H-isochromen-1-one;
3-(1-(4-amino-3-(5-(trifluoromethyl)pyridin-3-yl)-1H-pyrazolo[3,4-d]pyrimidin-1-yl)ethyl)-4-phenyl-1H-isochromen-1-one;
3-(1-(4-amino-3-(5-hydroxy-3-sulfur pentafluoride)-1H-pyrazolo[3,4-d]pyrimidin-1-yl)ethyl)-4-phenyl-1H-isochromen-1-one;
5-(4-amino-1-(1-(1-oxo-4-phenyl-1H-isochromen-3-yl)ethyl)-1H-pyrazolo[3,4-d]pyrimidin-3-yl)nicotinonitrile;
3-(1-(4-amino-3-(3-fluoro-5-hydroxyphenyl)-1H-pyrazolo[3,4-d]pyrimidin-1-yl)ethyl)-4-(4-aminocyclohex-1-en-1-yl)-1H-isochromen-1-one;
3-(1-(4-amino-3-(trifluoromethyl)-1H-pyrazolo[3,4-d]pyrimidin-1-yl)ethyl)-4-phenyl-1H-isochromen-1-one;
3-(1-(4-amino-3-methyl-1H-pyrazolo[3,4-d]pyrimidin-1-yl)ethyl)-4-phenyl-1H-isochromen-1-one;
3-(1-(4-amino-7H-pyrrolo[2,3-d]pyrimidin-7-yl)ethyl)-4-phenyl-1H-isochromen-1-one;
3-(1-(2,6-diamino-9H-purin-9-yl)ethyl)-4-phenyl-1H-isochromen-1-one;
4-phenyl-3-(1-(thieno[2,3-d]pyrimidin-4-ylamino)ethyl)-1H-isochromen-1-one;
4-phenyl-3-(1-(thieno[3,2-d]pyrimidin-4-ylamino)ethyl)-1H-isochromen-1-one;
2-amino-N-(1-(1-oxo-4-phenyl-1H-isochromen-3-yl)ethyl)pyrazolo[1,5-a]pyrimidine-3-carboxamide;
3-(1-(4-amino-3-(1H-pyrazol-3-yl)-1H-pyrazolo[3,4-d]pyrimidin-1-yl)ethyl)-4-phenyl-1H-isochromen-1-one;
3-(1-(4-amino-3-(1H-indazol-4-yl)-1H-pyrazolo[3,4-d]pyrimidin-1-yl)ethyl)-4-;
3-(1-(4-amino-3-(3-amino-1H-indazol-5-yl)-1H-pyrazolo[3,4-d]pyrimidin-1-yl)ethyl)-4-phenyl-1H-isochromen-1-one;
3-(1-(4-amino-3-(3-hydroxy-5-(trifluoromethoxy)phenyl)-1H-pyrazolo[3,4-d]pyrimidin-1-yl)ethyl)-4-phenyl-1H-isochromen-1-one;
3-(1-(6-amino-9H-purin-9-yl)ethyl)-4-(5-(morpholinomethyl)thiophen-2-yl)-1H-isochromen-1-one;
3-(1-(9H-purin-6-ylamino)ethyl)-4-(6-methoxypyridin-3-yl)-1H-isochromen-1-one;
3-(1-(9H-purin-6-ylamino)ethyl)-4-(thiazol-5-yl)-1H-isochromen-1-one;
3-(1-(4-amino-3-(3-fluoro-5-hydroxyphenyl)-2H-pyrazolo[3,4-d]pyrimidin-2-yl)ethyl)-4-phenyl-1H-isochromen-1-one;
3-(1-(4-amino-3-(3-fluoro-5-hydroxyphenyl)-1H-pyrazolo[3,4-d]pyrimidin-1-yl)ethyl)-4-(3-(dimethylamino)phenyl)-1H-isochromen-1-one;
3-(1-(4-amino-3-(3-fluoro-5-hydroxyphenyl)-1H-pyrazolo[3,4-d]pyrimidin-1-yl)ethyl)-4-(thiazol-5-yl)-1H-isochromen-1-one;
3-(1-(4-amino-3-(3-fluoro-5-hydroxyphenyl)-1H-pyrazolo[3,4-d]pyrimidin-1-yl)ethyl)-4-(2-aminothiazol-5-yl)-1H-isochromen-1-one;
3-(1-(9H-purin-6-ylamino)ethyl)-4-(1H-pyrazol-4-yl)-1H-isochromen-1-one;
4-amino-6-((1-(1-oxo-4-(1H-pyrazol-4-yl)-1H-isochromen-3-yl)ethyl)amino)pyrimidine-5-carbonitrile;
3-(1-(9H-purin-6-ylamino)ethyl)-4-(2-aminopyrimidin-5-yl)-1H-isochromen-1-one;
3-(1-(4-amino-3-(3-fluoro-5-hydroxyphenyl)-1H-pyrazolo[3,4-d]pyrimidin-1-yl)ethyl)-4-(4-(piperazin-1-ylmethyl)phenyl)-1H-isochromen-1-one;

3-(1-(9H-purin-6-ylamino)ethyl)-4-(4-(piperazin-1-ylmethyl)phenyl)-1H-isochromen-1-one;
3-(1-(4-amino-1H-pyrazolo[3,4-d]pyrimidin-1-yl)ethyl)-4-(4-(piperazin-1-ylmethyl)phenyl)-1H-isochromen-1-one;
3-(4-amino-1-((4-phenyl-1H-isochromen-3-yl)methyl)-1H-pyrazolo[3,4-d]pyrimidin-3-yl)-5-fluorophenol;
5-(4-amino-1-((4-phenyl-1H-isochromen-3-yl)methyl)-1H-pyrazolo[3,4-d]pyrimidin-3-yl)pyridin-3-ol;
3-(1-(4-amino-3-(3-fluoro-5-hydroxyphenyl)-1H-pyrazolo[3,4-d]pyrimidin-1-yl)ethyl)-4-(morpholinomethyl)-1H-isochromen-1-one;
3-(1-(4-amino-3-(3-fluoro-5-hydroxyphenyl)-1H-pyrazolo[3,4-d]pyrimidin-1-yl)ethyl)-4-(1-benzyl-1,2,3,6-tetrahydropyridin-4-yl)-1H-isochromen-1-one;
3-(1-(4-amino-3-(5-hydroxypyridin-3-yl)-1H-pyrazolo[3,4-d]pyrimidin-1-yl)ethyl)-4-(1-benzyl-1,2,3,6-tetrahydropyridin-4-yl)-1H-isochromen-1-one;
benzyl 4-(3-(1-(4-amino-3-(3-fluoro-5-hydroxyphenyl)-1H-pyrazolo[3,4-d]pyrimidin-1-yl)ethyl)-1-oxo-1H-isochromen-4-yl)-5,6-dihydropyridine-1(2H)-carboxylate;
3-(1-(4-amino-3-(3-fluoro-5-hydroxyphenyl)-1H-pyrazolo[3,4-d]pyrimidin-1-yl)ethyl)-4-(5-(piperazin-1-ylmethyl)thiophen-2-yl)-1H-isochromen-1-one;
3-(1-(4-amino-3-(3-fluoro-5-hydroxyphenyl)-1H-pyrazolo[3,4-d]pyrimidin-1-yl)ethyl)-4-(5-((4-methylpiperazin-1-yl)methyl)thiophen-2-yl)-1H-isochromen-1-one;
3-(1-(4-amino-3-(3-fluoro-5-hydroxyphenyl)-1H-pyrazolo[3,4-d]pyrimidin-1-yl)ethyl)-4-(5-(3-(dimethylamino)propyl)thiophen-2-yl)-1H-isochromen-1-one;
3-(1-(4-amino-3-(3-fluoro-5-hydroxyphenyl)-1H-pyrazolo[3,4-d]pyrimidin-1-yl)ethyl)-4-(3-(3-(dimethylamino)propyl)phenyl)-1H-isochromen-1-one;
3-(1-(4-amino-3-(3-fluoro-5-hydroxyphenyl)-1H-pyrazolo[3,4-d]pyrimidin-1-yl)ethyl)-4-(3-(3-(dimethylamino)propyl)phenyl)-1H-isochromen-1-one single enantiomer 1;
3-(1-(4-amino-3-(3-fluoro-5-hydroxyphenyl)-1H-pyrazolo[3,4-d]pyrimidin-1-yl)ethyl)-4-(3-(3-(dimethylamino)propyl)phenyl)-1H-isochromen-1-one single enantiomer 2;
3-(1-(4-amino-3-(3-fluoro-5-hydroxyphenyl)-1H-pyrazolo[3,4-d]pyrimidin-1-yl)ethyl)-4-(4-(3-(dimethylamino)propyl)phenyl)-1H-isochromen-1-one;
3-(1-(4-amino-3-(3-fluoro-5-hydroxyphenyl)-1H-pyrazolo[3,4-d]pyrimidin-1-yl)ethyl)-4-(4-(3-(dimethylamino)propyl)phenyl)-1H-isochromen-1-one single enantiomer 1;
3-(1-(4-amino-3-(3-fluoro-5-hydroxyphenyl)-1H-pyrazolo[3,4-d]pyrimidin-1-yl)ethyl)-4-(4-(3-(dimethylamino)propyl)phenyl)-1H-isochromen-1-one single enantiomer 2;
3-(1-(4-amino-3-(3-fluoro-5-hydroxyphenyl)-1H-pyrazolo[3,4-d]pyrimidin-1-yl)ethyl)-4-(4-((4-methylpiperazin-1-yl)methyl)phenyl)-1H-isochromen-1-one;
3-(1-(4-amino-3-(3-fluoro-5-hydroxyphenyl)-1H-pyrazolo[3,4-d]pyrimidin-1-yl)ethyl)-4-(4-(pyrrolidin-1-ylmethyl)phenyl)-1H-isochromen-1-one;
3-(1-(4-amino-3-(3-fluoro-5-hydroxyphenyl)-1H-pyrazolo[3,4-d]pyrimidin-1-yl)ethyl)-4-(4-(piperidin-1-ylmethyl)phenyl)-1H-isochromen-1-one;
3-(1-(4-amino-3-(3-fluoro-5-hydroxyphenyl)-1H-pyrazolo[3,4-d]pyrimidin-1-yl)ethyl)-4-(3-((4-methylpiperazin-1-yl)methyl)phenyl)-1H-isochromen-1-one;
3-(1-(4-amino-3-(3-fluoro-5-hydroxyphenyl)-1H-pyrazolo[3,4-d]pyrimidin-1-yl)ethyl)-4-(3-(piperidin-1-ylmethyl)phenyl)-1H-isochromen-1-one;
3-(1-(4-amino-3-(3-fluoro-5-hydroxyphenyl)-1H-pyrazolo[3,4-d]pyrimidin-1-yl)ethyl)-4-(2,2,6,6-tetramethyl-1,2,3,6-tetrahydropyridin-4-yl)-1H-isochromen-1-one;
3-(1-(4-amino-3-(5-hydroxypyridin-3-yl)-1H-pyrazolo[3,4-d]pyrimidin-1-yl)ethyl)-4-(2,2,6,6-tetramethyl-1,2,3,6-tetrahydropyridin-4-yl)-1H-isochromen-1-one;
3-(1-(4-amino-3-(3-fluoro-5-hydroxyphenyl)-1H-pyrazolo[3,4-d]pyrimidin-1-yl)ethyl)-4-(1-(4-(dimethylamino)butanoyl)-1,2,3,6-tetrahydropyridin-4-yl)-1H-isochromen-1;
3-(1-(4-amino-3-(3-fluoro-5-hydroxyphenyl)-1H-pyrazolo[3,4-d]pyrimidin-1-yl)ethyl)-4-(1-(2-(dimethylamino)acetyl)-1,2,3,6-tetrahydropyridin-4-yl)-1H-isochromen-1-one;
3-(1-(4-amino-3-(3-fluoro-5-hydroxyphenyl)-1H-pyrazolo[3,4-d]pyrimidin-1-yl)ethyl)-4-(1-(1-methylpiperidine-4-carbonyl)-1,2,3,6-tetrahydropyridin-4-yl)-1H-isochromen-1-one;
3-(1-(4-amino-3-(3-fluoro-5-hydroxyphenyl)-1H-pyrazolo[3,4-d]pyrimidin-1-yl)ethyl)-4-(1-(1-isopropylpiperidin-4-yl)-1,2,3,6-tetrahydropyridin-4-yl)-1H-isochromen-1-one;
3-(1-(4-amino-3-(3-fluoro-5-hydroxyphenyl)-1H-pyrazolo[3,4-d]pyrimidin-1-yl)ethyl)-4-(1-(azetidine-3-carbonyl)-1,2,3,6-tetrahydropyridin-4-yl)-1H-isochromen-1-one;
3-(1-(4-amino-3-(3-fluoro-5-hydroxyphenyl)-1H-pyrazolo[3,4-d]pyrimidin-1-yl)ethyl)-4-(1-(1-methylazetidine-3-carbonyl)-1,2,3,6-tetrahydropyridin-4-yl)-1H-isochromen-1-one;
3-(1-(4-amino-3-(3-chloro-5-hydroxyphenyl)-1H-pyrazolo[3,4-d]pyrimidin-1-yl)ethyl)-4-(1,2,3,6-tetrahydropyridin-4-yl)-1H-isochromen-1-one;
3-(1-(4-amino-3-(3-hydroxy-5-(trifluoromethyl)phenyl)-1H-pyrazolo[3,4-d]pyrimidin-1-yl)ethyl)-4-(1,2,3,6-tetrahydropyridin-4-yl)-1H-isochromen-1-one;
3-(1-(4-amino-3-(3-chloro-5-hydroxyphenyl)-1H-pyrazolo[3,4-d]pyrimidin-1-yl)ethyl)-4-(1-methyl-1,2,3,6-tetrahydropyridin-4-yl)-1H-isochromen-1-one;
3-(1-(4-amino-3-(3-hydroxy-5-(trifluoromethyl)phenyl)-1H-pyrazolo[3,4-d]pyrimidin-1-yl)ethyl)-4-(1-methyl-1,2,3,6-tetrahydropyridin-4-yl)-1H-isochromen-1-one;
3-(1-(4-amino-3-(3-fluoro-5-hydroxyphenyl)-1H-pyrazolo[3,4-d]pyrimidin-1-yl)ethyl)-4-(1-(azetidin-3-yl)-1,2,3,6-tetrahydropyridin-4-yl)-1H-isochromen-1-one;
3-(1-(4-amino-3-(3-fluoro-5-hydroxyphenyl)-1H-pyrazolo[3,4-d]pyrimidin-1-yl)ethyl)-4-(1-(1-(cyclopropylmethyl)azetidin-3-yl)-1,2,3,6-tetrahydropyridin-4-yl)-1H-isochromen-1-one;
3-(1-(4-amino-3-(3-fluoro-5-hydroxyphenyl)-1H-pyrazolo[3,4-d]pyrimidin-1-yl)ethyl)-4-(3-(dimethylamino)prop-1-yn-1-yl)-1H-isochromen-1-one;
3-(1-(4-amino-3-(5-hydroxy-4-methylpyridin-3-yl)-1H-pyrazolo[3,4-d]pyrimidin-1-yl)ethyl)-4-phenyl-1H-isochromen-1-one;
3-(1-(4-amino-3-(5-hydroxy-2-methylpyridin-3-yl)-1H-pyrazolo[3,4-d]pyrimidin-1-yl)ethyl)-4-phenyl-1H-isochromen-1-one;
3-(1-(4-amino-3-(5-hydroxy-6-(trifluoromethyl)pyridin-3-yl)-1H-pyrazolo[3,4-d]pyrimidin-1-yl)ethyl)-4-phenyl-1H-isochromen-1-one;

3-(1-(4-amino-3-(3-fluoro-5-hydroxyphenyl)-1H-pyrazolo[3,4-d]pyrimidin-1-yl)ethyl)-7-methyl-4-phenyl-1H-isochromen-1-one;

3-(1-(4-amino-3-(3-fluoro-5-hydroxyphenyl)-1H-pyrazolo[3,4-d]pyrimidin-1-yl)ethyl)-7-chloro-4-phenyl-1H-isochromen-1-one;

3-(1-(4-amino-3-(3-fluoro-5-hydroxyphenyl)-1H-pyrazolo[3,4-d]pyrimidin-1-yl)ethyl)-6-chloro-4-phenyl-1H-isochromen-1-one;

3-(1-(4-amino-3-(3-fluoro-5-hydroxyphenyl)-1H-pyrazolo[3,4-d]pyrimidin-1-yl)ethyl)-6-fluoro-4-phenyl-1H-isochromen-1-one;

4-(1-acetyl-1,2,3,6-tetrahydropyridin-4-yl)-3-(1-(4-amino-3-(3-fluoro-5-hydroxyphenyl)-1H-pyrazolo[3,4-d]pyrimidin-1-yl)ethyl)-1H-isochromen-1-one single enantiomer 1;

4-(1-acetyl-1,2,3,6-tetrahydropyridin-4-yl)-3-(1-(4-amino-3-(3-fluoro-5-hydroxyphenyl)-1H-pyrazolo[3,4-d]pyrimidin-1-yl)ethyl)-1H-isochromen-1-one single 2;

3-(1-(4-amino-3-(3-fluoro-5-hydroxyphenyl)-1H-pyrazolo[3,4-d]pyrimidin-1-yl)ethyl)-4-(thiazol-5-yl)-1H-isochromen-1-one single enantiomer 1;

3-(1-(4-amino-3-(3-fluoro-5-hydroxyphenyl)-1H-pyrazolo[3,4-d]pyrimidin-1-yl)ethyl)-4-(thiazol -5-yl)-1H-isochromen-1-one single enantiomer 2;

3-(1-(4-amino-3-(5-hydroxypyridin-3-yl)-1H-pyrazolo[3,4-d]pyrimidin-1-yl)ethyl)-4-phenyl-1H-isochromen-1-one single enantiomer 1;

3-(1-(4-amino-3-(5-hydroxypyridin-3-yl)-1H-pyrazolo[3,4-d]pyrimidin-1-yl)ethyl)-4-phenyl-1H-isochromen-1-one single enantiomer 2;

3-(1-(4-amino-3-(3-fluoro-5-hydroxyphenyl)-1H-pyrazolo[3,4-d]pyrimidin-1-yl)ethyl)-4-(1-benzyl-1,2,5,6-tetrahydropyridin-3-yl)-1H-isochromen-1-one;

3-(1-(4-amino-3-(3-fluoro-5-hydroxyphenyl)-1H-pyrazolo[3,4-d]pyrimidin-1-yl)ethyl)-4-(1-benzyl-1,2,5,6-tetrahydropyridin-3-yl)-1H-isochromen-1-one single enantiomer 1;

3-(1-(4-amino-3-(3-fluoro-5-hydroxyphenyl)-1H-pyrazolo[3,4-d]pyrimidin-1-yl)ethyl)-4-(1-benzyl-1,2,5,6-tetrahydropyridin-3-yl)-1H-isochromen-1-one single enantiomer 2;

3-(1-(4-amino-3-(3-fluoro-5-hydroxyphenyl)-1H-pyrazolo[3,4-d]pyrimidin-1-yl)ethyl)-4-(pyridin-2-yl)-1H-isochromen-1-one;

3-(1-(4-amino-3-(3-fluoro-5-hydroxyphenyl)-1H-pyrazolo[3,4-d]pyrimidin-1-yl)ethyl)-4-(1,2,5,6-tetrahydropyridin-3-yl)-1H-isochromen-1-one;

3-(1-(4-amino-3-(3-fluoro-5-hydroxyphenyl)-1H-pyrazolo[3,4-d]pyrimidin-1-yl)ethyl)-4-(1-(1-methylpiperidin-4-yl)-1,2,5,6-tetrahydropyridin-3-yl)-1H-isochromen-1-one;

3-(1-(4-amino-3-(3-fluoro-5-hydroxyphenyl)-1H-pyrazolo[3,4-d]pyrimidin-1-

3-(1-(4-amino-3-(3-fluoro-5-hydroxyphenyl)-1H-pyrazolo[3,4-d]pyrimidin-1-yl)ethyl)-4-(1-isopropyl-1,2,5,6-tetrahydropyridin-3-yl)-1H-isochromen-1-one;

3-(1-(4-amino-3-(5-hydroxypyridin-3-yl)-1H-pyrazolo[3,4-d]pyrimidin-1-yl)ethyl)-4-(1-methyl-1,2,3,6-tetrahydropyridin-4-yl)-1H-isochromen-1-one;

3-(1-(4-amino-3-(3-fluoro-5-hydroxyphenyl)-1H-pyrazolo[3,4-d]pyrimidin-1-yl)ethyl)-4-phenyl-1H-isochromen-1-one single enantiomer 1; and 3-(1-(4-amino-3-(3-fluoro-5-hydroxyphenyl)-1H-pyrazolo[3,4-d]pyrimidin-1-yl)ethyl)-4-phenyl-1H-isochromen-1-one single enantiomer 2;

or a pharmaceutically acceptable salt of said isochromene compound.

11. A pharmaceutical composition, comprising a compound or pharmaceutically acceptable salt according to claim 1, either alone or in combination with one or more active ingredients, in admixture with one or more pharmaceutically acceptable carriers or excipients.

12. A method for the treatment of a disorder associated with a PI3K enzyme mechanism, said method comprising administering an effective amount of a compound or pharmaceutically acceptable salt according to claim 1 to a subject in need thereof.

13. A method according to claim 12, wherein said disorder is a respiratory disease; viral infections; non-viral respiratory infections; allergic diseases; autoimmune diseases; inflammatory disorders; cardiovascular diseases; hematologic malignancies; neurodegenerative diseases; pancreatitis; multiorgan failure; kidney diseases; platelet aggregation; cancer; sperm motility; transplantation rejection; graft rejection; lung injuries; or pain.

14. A method according to claim 12, wherein said disorder is asthma, chronic obstructive pulmonary disease (COPD), or idiopathic pulmonary fibrosis (IPF).

15. A compound or pharmaceutically acceptable salt according to claim 1, wherein m is 1.

16. A compound or pharmaceutically acceptable salt according to claim 5, wherein m is 1.

17. A compound or pharmaceutically acceptable salt according to claim 6, wherein m is 1.

18. A compound or pharmaceutically acceptable salt according to claim 7, wherein m is 1.

19. A compound or pharmaceutically acceptable salt according to claim 8, wherein m is 1.

20. A compound or pharmaceutically acceptable salt according to claim 9, wherein m is 1.

* * * * *